United States Patent
Idkowiak-Baldys et al.

(10) Patent No.: US 9,597,274 B2
(45) Date of Patent: *Mar. 21, 2017

(54) PEPTIDES AND THEIR USE IN THE TREATMENT OF SKIN

(71) Applicant: Avon Products, Inc., Suffern, NY (US)

(72) Inventors: Jolanta Idkowiak-Baldys, Montebello, NY (US); John W. Lyga, Basking Ridge, NJ (US); Uma Santhanam, Tenafly, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,060

(22) Filed: Jun. 17, 2015

(65) Prior Publication Data

US 2016/0367463 A1 Dec. 22, 2016

(51) Int. Cl.

| A61K 38/04 | (2006.01) |
|---|---|
| C07K 7/00 | (2006.01) |
| A61K 8/64 | (2006.01) |
| A61Q 19/08 | (2006.01) |
| A61K 8/365 | (2006.01) |
| A61K 8/36 | (2006.01) |
| A61K 8/49 | (2006.01) |

(52) U.S. Cl.
CPC .................. *A61K 8/64* (2013.01); *A61K 8/36* (2013.01); *A61K 8/361* (2013.01); *A61K 8/365* (2013.01); *A61K 8/4926* (2013.01); *A61Q 19/08* (2013.01)

(58) Field of Classification Search
None
See application file for complete search history.

(56) References Cited

U.S. PATENT DOCUMENTS

| 7,737,119 | B2 * | 6/2010 | Dal Farra | A61K 8/64 424/401 |
|---|---|---|---|---|
| 9,056,889 | B2 * | 6/2015 | Chung | C07K 7/06 |

| 2003/0134780 | A1 | 7/2003 | Patt |
|---|---|---|---|
| 2007/0134262 | A1 | 6/2007 | Mattner et al. |
| 2009/0263402 | A1 | 10/2009 | Lee et al. |
| 2014/0105966 | A1 | 4/2014 | Bancel et al. |
| 2015/0148297 | A1 | 5/2015 | Majeed et al. |

FOREIGN PATENT DOCUMENTS

| WO | WO 98/06844 | * | 2/1998 |
|---|---|---|---|
| WO | 2014161863 A1 | | 10/2014 |

OTHER PUBLICATIONS

U.S. Appl. No. 14/844,095, filed Sep. 3, 2015, J. Idkowiak-Baldys.
U.S. Appl. No. 14/766,006, filed Aug 5, 2015, J. Idkowiak-Baldys.
U.S. Appl. No. 14/767,451, filed Aug 12, 2015, J. Idkowiak-Baldys.
U.S. Appl. No. 14/767,805, filed Aug 13, 2015, J. Idkowiak-Baldys.
Loffredo et al., Growth Differentiation Factor 11 Is a Circulating Factor that Reverses Age-Related Cardiac Hypertrophy. Cell, 2013, 153, 828-839.
Sinha et al., Restoring Systemic GDF11 Levels Reverses Age-Related Dysfunction in Mouse Skeletal Muscle, Science, 2014, 344:649-52.
Villeda et al., Young blood reverses age-related impairments in cognitive function and synaptic plasticity in mice. Nat. Med. 2014;20:659-63.
Chauhan et al., Modeling signaling pathways leading to wrinkle formation: Identification of the skin aging target. Indian J. Dermatol Venereol Leprol, Sep.-Oct. 2009, vol. 75, Issue 5.
Mooney et al., PeptideLocator: Prediction of Bioactive Peptides in Protein Sequences, Bioinformatices, 2013, pp. 1-7.
International Search Report to corresponding International Application No. PCT/US2016/023569 mailed Sep. 1, 2016.

* cited by examiner

*Primary Examiner* — Satyanarayana R Gudibande
(74) *Attorney, Agent, or Firm* — Brian P. McCloskey

(57) ABSTRACT

Peptides (and derivatives thereof), topical compositions, and methods of diminishing signs of aging and/or improving health of human integuments are provided. The peptides are derived from human Growth Differentiation Factor 11 (GDF-11).

5 Claims, No Drawings

PEPTIDES AND THEIR USE IN THE TREATMENT OF SKIN

SEQUENCE LISTING

The instant application contains a Sequence Listing which has been submitted electronically in ASCII format and is hereby incorporated by reference in its entirety. Said ASCII copy, created on Jun. 4, 2015, is named SC184U-US_SL.txt and is 462,174 bytes in size.

FIELD OF INVENTION

The present invention relates generally to peptides, in particular peptides derived from the Growth Differentiation Factor 11 (GDF-11) protein and topical formulations containing them, as well as associated methods for improving the health of skin and/or diminishing the dermatological signs of aging in human skin.

BACKGROUND

Growth factors are naturally occurring substances, usually proteins, that act as signaling molecules between cells. Their primary function is promoting cell differentiation and maturation. Growth factors play an important role in many functions, such as stimulating cell growth, proliferation, and wound healing. Many large classes, or superfamilies, of related growth factors are known.

Growth Differentiation Factor 11 (GDF-11) is a protein belonging to the transforming growth factor (TGF) superfamily (e.g., TGF-β), which encompasses a group of structurally-related proteins. Blood-derived GDF-11 was recently shown to be involved in reverting the aging phenotype in mice, including cardiac hypertrophy (see Loffredo et al., *Cell*, 2013, 153, 828-839), age-related sarcopenia (see Sinha et al., *Science,* 2014, 344:649-52), and decreased cognitive functions (see Villeda et al., *Nat. Med.* 2014; 20:659-63). Due to the many important roles growth factors play in maintaining healthy tissues, there has been some interest in using them in dermatological formulations. There are, however, drawbacks associated with the use of growth factors in topical formulations.

It is therefore an object of the invention to provide new peptides and derivatives thereof derived from GDF-11 and topical compositions containing them. It is also an object of the invention to provide methods for improving the health and/or appearance of skin, combatting signs of intrinsic and photoaging, and/or treating skin disorders. It is a further object of the invention to provide compositions and methods for treating, reversing, forestalling and/or ameliorating skin wrinkles and fine lines, tightening sagging skin, firming skin, and for treating hyperpigmentation and unwanted pigmentation with cosmetic compositions comprising effective amounts of a peptide of the invention.

The foregoing discussion is presented solely to provide a better understanding of the nature of the problems confronting the art and should not be construed in any way as an admission as to prior art.

SUMMARY OF THE INVENTION

In accordance with the foregoing objectives and others, the present invention provides active agents comprising peptides and topical formulations. The active agents are believed to be useful for improving one or more signs of dermatological aging when topically applied to human integuments (skin, lips, nails, hair, etc.), particularly skin. They are also contemplated to be useful in treating a variety of dermatological disorders and improving the overall health of skin. The peptides of the invention are derived from human growth factor GDF-11. In some embodiments, the active agents of the invention are capable of increasing collagen and/or HA production within skin cells and therefore will have a beneficial effect on reducing the appearance of aging on skin (e.g., diminishing the appearance of wrinkles and/or fine lines, tightening sagging skin, thickening thinning skin, evening skin tone, treating hyperpigmentation and unwanted pigmentation, etc.).

Because using the full length growth factor protein, GDF-11, may present challenges including, for example, delivery obstacles and possibly undesired activity, smaller peptide sequences (e.g., 3-11 or 3 or 4 or 5 or 6 or 7 or 8 or 9 or 10 or 11 amino acids) derived from the sequence of the full-length protein have been designed. These peptides, especially peptides similar or homologous to putative functional regions of the protein, are contemplated to have biological activity, including antiaging benefits in skin.

One aspect of the invention provides compositions for topical use comprising an active agent comprising one or more GDF-11-derived peptides or fragments or derivatives thereof (e.g., having from 3-11 consecutive amino acids from the GDF-11 sequence) including cyclic peptide fragments of the invention in a physiologically acceptable carrier. The active agent may be present in the composition in an amount between about 0.000001% to about 10% (e.g., 0.0001-1%) by weight of the composition. Peptides useful in the practice of the invention include, for example, those comprising 3 amino acids (SEQ ID NO: 2-375); 4 amino acids (SEQ ID NO: 376-767); 5 amino acids (SEQ ID NO:768-1161); 6 amino acids (SEQ ID NO: 1162-1556); 7 amino acids (SEQ ID NO: 1557-1951); 8 amino acids (SEQ ID NO: 1952-2346); 9 amino acids (SEQ ID NO: 2347-2741); 10 amino acids (SEQ ID NO: 2742-3136); 11 amino acids (SEQ ID NO: 3137-3531) or even larger fragments of GDF-11. In another aspect, methods are provided for ameliorating and/or preventing signs of human skin photoaging and intrinsic aging (e.g., diminishing the appearance of wrinkles and/or fine lines, tightening sagging skin, thickening thinning skin, evening skin tone, treating hyperpigmentation, etc.) comprising topically applying to the skin (e.g., skin of the face) a composition comprising, in a topically acceptable vehicle, one or more GDF-11-derived peptides of the invention.

These and other aspects of the present invention will become apparent to those skilled in the art after a reading of the following detailed description of the invention, including the illustrative embodiments and examples.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

All percentages given herein refer to the weight percentages of a particular component relative to the entire composition, including the vehicle, unless otherwise indicated. It will be understood that the sum of all weight % of individual components within a composition will not exceed 100%.

All terms used herein are intended to have their ordinary meaning unless otherwise provided. The phrases "physiologically acceptable," "topically acceptable," and "dermatologically acceptable" are used interchangeably and are intended to mean that a particular component is generally regarded as safe and non-toxic for application to a human integument (e.g., skin) at the levels employed. The term "prevent," as used herein, includes delaying, slowing or forestalling the onset of or progression of a particular sign of skin aging. The phrase "individual in need thereof" refers to a human that could benefit from improved dermal appearance or health, including males or females. In some embodiments, the individual in need thereof is a female. The term "skin" includes, without limitation, the lips, skin of the face, hands, arms, neck, scalp, and chest. The term "thin" skin includes, but is not limited to, skin that is prematurely thinned, and may be diagnosed as such by a dermatologist. In some embodiments, the thin skin is skin of a female under the age of 60; 50; 40; and/or skin of a pre-menopausal, peri-menopausal or post-menopausal female.

As used herein, the term "consisting essentially of" is intended to limit the invention to the specified materials or steps and those that do not materially affect the basic and novel characteristics of the claimed invention, as understood from a reading of this specification.

As used herein, a hydrocarbon, alkyl, alkenyl, alkynyl, aryl, aryl-alkyl, alkyl-aryl, heteroaryl, or combination of any of those will have from 1-30 carbon atoms, optionally substituted with O, N, S, unless otherwise specified. Any of the alkyl, alkenyl, and alkynyl groups disclosed herein, unless otherwise specified, may be straight-chained, branched, and/or cyclic. If the amount of an ingredient is not otherwise specified, it may be present in an amount from 0.00001-90% by weight.

The term "amino acid" is intended to include naturally occurring amino acids and non-proteinogenic amino acids as well as non-naturally occurring amino acids and includes any small molecule (MW<1,000 Daltons) having at least one carboxyl group and at least one primary or secondary amine group capable of forming peptide bonds. The term "peptide" is intended to include any molecule comprising at least two amino acids joined by a peptide bond and therefore includes di-peptides, tri-peptides, oligopeptides, and polypeptides having up to about 20 consecutive amino acid residues linked by peptide bonds. The term "peptide" also embraces structures having one or more linkers, spacers, or terminal groups which are not amino acids. It also includes cyclic peptides Peptides The peptides of the invention comprise, consist essentially of, or consist of amino acid sequences derived from the Growth Differentiation Factor 11 (GDF-11) protein. Consisting essentially of, as used herein, is intended to mean that additional amino acids may be present at either terminus provided they do not substantially impair the activity of the peptide. For example, in embodiments where a peptide "consists essentially of" SEQ ID NOs 2-3531, any additional amino acids may be excluded from the peptide if their inclusion produces a measurable improvement (e.g., greater than 50% reduction) of the beneficial activity, including, without limitation, upregulation of pro-collagen, collagen, elastin, fibronectin, and/or hyaluronic acid.

In one embodiment, the active agent comprises a peptide that comprises from 3-11 (e.g., 3, 4, 5, 6, 7, 8, 9, 10, or 11) consecutive amino acids derived from the sequence of Growth Differentiation Factor 11 (GDF-11) precursor [*Homo sapiens*], NCBI Reference Sequence Accession No.: NP_005802.1, shown in Table 1 (SEQ ID NO: 1).

TABLE 1

Sequence of GDF-11 Precursor [*Homo Sapiens*]

```
  1 mvlaaplllg flllalelrp rgeaaegpaa aaaaaaaaaa agvggerssr papsvapepd
 61 gcpvcvwrqh srelrlesik sqilsklrlk eapnisrevv kqllpkappl qqildlhdfq
121 gdalqpedfl eedeyhatte tvismaqetd pavqtdgspl cchfhfspkv mftkvlkaql
181 wvylrpvprp atvylqilrl kpltgegtag gggggrrhir irslkielhs rsghwqsidf
241 kqvlhswfrq pqsnwgiein afdpsgtdla vtslgpgaeg lhpfmelrvl entkrsrrnl
301 gldcdehsse srccrypltv dfeafgwdwi iapkrykany csgqceymfm qkyphthlvq
361 qanprgsagp cctptkmspi nmlyfndkqq iiygkipgmv vdrcgcs
```

In some embodiments, the active agent comprises a peptide which comprises, consists essentially of, or consists of any one or more of the 3-mer amino acid sequences (SEQ ID NO: 2-375) listed below in Table 2.

TABLE 2

| SEQ ID 2 | MVL |
|---|---|
| SEQ ID 3 | VLA |
| SEQ ID 4 | LAA |
| SEQ ID 5 | AAP |
| SEQ ID 6 | APL |
| SEQ ID 7 | PLL |
| SEQ ID 8 | LLL |
| SEQ ID 9 | LLG |
| SEQ ID 10 | LGF |
| SEQ ID 11 | GFL |
| SEQ ID 12 | FLL |
| SEQ ID 13 | LLA |
| SEQ ID 14 | LAL |

TABLE 2-continued

| | |
|---|---|
| SEQ ID 15 | ALE |
| SEQ ID 16 | LEL |
| SEQ ID 17 | ELR |
| SEQ ID 18 | LRP |
| SEQ ID 19 | RPR |
| SEQ ID 20 | PRG |
| SEQ ID 21 | RGE |
| SEQ ID 22 | GEA |
| SEQ ID 23 | EAA |
| SEQ ID 24 | AAE |
| SEQ ID 25 | AEG |
| SEQ ID 26 | EGP |
| SEQ ID 27 | GPA |
| SEQ ID 28 | PAA |
| SEQ ID 29 | AAA |
| SEQ ID 30 | AAG |
| SEQ ID 31 | AGV |
| SEQ ID 32 | GVG |
| SEQ ID 33 | VGG |
| SEQ ID 34 | GGE |
| SEQ ID 35 | GER |
| SEQ ID 36 | ERS |
| SEQ ID 37 | RSS |
| SEQ ID 38 | SSR |
| SEQ ID 39 | SRP |
| SEQ ID 40 | RPA |
| SEQ ID 41 | PAP |
| SEQ ID 42 | APS |
| SEQ ID 43 | PSV |
| SEQ ID 44 | SVA |
| SEQ ID 45 | VAP |
| SEQ ID 46 | APE |
| SEQ ID 47 | PEP |
| SEQ ID 48 | EPD |
| SEQ ID 49 | PDG |
| SEQ ID 50 | DGC |
| SEQ ID 51 | GCP |
| SEQ ID 52 | CPV |
| SEQ ID 53 | PVC |
| SEQ ID 54 | VCV |

TABLE 2-continued

| | |
|---|---|
| SEQ ID 55 | CVW |
| SEQ ID 56 | VWR |
| SEQ ID 57 | WRQ |
| SEQ ID 58 | RQH |
| SEQ ID 59 | QHS |
| SEQ ID 60 | HSR |
| SEQ ID 61 | SRE |
| SEQ ID 62 | REL |
| SEQ ID 63 | LRL |
| SEQ ID 64 | RLE |
| SEQ ID 65 | LES |
| SEQ ID 66 | ESI |
| SEQ ID 67 | SIK |
| SEQ ID 68 | IKS |
| SEQ ID 69 | KSQ |
| SEQ ID 70 | SQI |
| SEQ ID 71 | QIL |
| SEQ ID 72 | ILS |
| SEQ ID 73 | LSK |
| SEQ ID 74 | SKL |
| SEQ ID 75 | KLR |
| SEQ ID 76 | RLK |
| SEQ ID 77 | LKE |
| SEQ ID 78 | KEA |
| SEQ ID 79 | EAP |
| SEQ ID 80 | APN |
| SEQ ID 81 | PNI |
| SEQ ID 82 | NIS |
| SEQ ID 83 | ISR |
| SEQ ID 84 | REV |
| SEQ ID 85 | EVV |
| SEQ ID 86 | VVK |
| SEQ ID 87 | VKQ |
| SEQ ID 88 | KQL |
| SEQ ID 89 | QLL |
| SEQ ID 90 | LLP |
| SEQ ID 91 | LPK |
| SEQ ID 92 | PKA |
| SEQ ID 93 | KAP |
| SEQ ID 94 | APP |

TABLE 2-continued

| | |
|---|---|
| SEQ ID 95 | PPL |
| SEQ ID 96 | PLQ |
| SEQ ID 97 | LQQ |
| SEQ ID 98 | QQI |
| SEQ ID 99 | ILD |
| SEQ ID 100 | LDL |
| SEQ ID 101 | DLH |
| SEQ ID 102 | LHD |
| SEQ ID 103 | HDF |
| SEQ ID 104 | DFQ |
| SEQ ID 105 | FQG |
| SEQ ID 106 | QGD |
| SEQ ID 107 | GDA |
| SEQ ID 108 | DAL |
| SEQ ID 109 | ALQ |
| SEQ ID 110 | LQP |
| SEQ ID 111 | QPE |
| SEQ ID 112 | PED |
| SEQ ID 113 | EDF |
| SEQ ID 114 | DFL |
| SEQ ID 115 | FLE |
| SEQ ID 116 | LEE |
| SEQ ID 117 | EED |
| SEQ ID 118 | EDE |
| SEQ ID 119 | DEY |
| SEQ ID 120 | EYH |
| SEQ ID 121 | YHA |
| SEQ ID 122 | HAT |
| SEQ ID 123 | ATT |
| SEQ ID 124 | TTE |
| SEQ ID 125 | TET |
| SEQ ID 126 | ETV |
| SEQ ID 127 | TVI |
| SEQ ID 128 | VIS |
| SEQ ID 129 | ISM |
| SEQ ID 130 | SMA |
| SEQ ID 131 | MAQ |
| SEQ ID 132 | AQE |
| SEQ ID 133 | QET |
| SEQ ID 134 | ETD |

TABLE 2-continued

| | |
|---|---|
| SEQ ID 135 | TDP |
| SEQ ID 136 | DPA |
| SEQ ID 137 | PAV |
| SEQ ID 138 | AVQ |
| SEQ ID 139 | VQT |
| SEQ ID 140 | QTD |
| SEQ ID 141 | TDG |
| SEQ ID 142 | DGS |
| SEQ ID 143 | GSP |
| SEQ ID 144 | SPL |
| SEQ ID 145 | PLC |
| SEQ ID 146 | LCC |
| SEQ ID 147 | CCH |
| SEQ ID 148 | CHF |
| SEQ ID 149 | HFH |
| SEQ ID 150 | FHF |
| SEQ ID 151 | HFS |
| SEQ ID 152 | FSP |
| SEQ ID 153 | SPK |
| SEQ ID 154 | PKV |
| SEQ ID 155 | KVM |
| SEQ ID 156 | VMF |
| SEQ ID 157 | MFT |
| SEQ ID 158 | FTK |
| SEQ ID 159 | TKV |
| SEQ ID 160 | KVL |
| SEQ ID 161 | VLK |
| SEQ ID 162 | LKA |
| SEQ ID 163 | KAQ |
| SEQ ID 164 | AQL |
| SEQ ID 165 | QLW |
| SEQ ID 166 | LWV |
| SEQ ID 167 | WVY |
| SEQ ID 168 | VYL |
| SEQ ID 169 | YLR |
| SEQ ID 170 | RPV |
| SEQ ID 171 | PVP |
| SEQ ID 172 | VPR |
| SEQ ID 173 | PRP |
| SEQ ID 174 | PAT |

TABLE 2-continued

| | |
|---|---|
| SEQ ID 175 | ATV |
| SEQ ID 176 | TVY |
| SEQ ID 177 | YLQ |
| SEQ ID 178 | LQI |
| SEQ ID 179 | ILR |
| SEQ ID 180 | LKP |
| SEQ ID 181 | KPL |
| SEQ ID 182 | PLT |
| SEQ ID 183 | LTG |
| SEQ ID 184 | TGE |
| SEQ ID 185 | GEG |
| SEQ ID 186 | EGT |
| SEQ ID 187 | GTA |
| SEQ ID 188 | TAG |
| SEQ ID 189 | AGG |
| SEQ ID 190 | GGG |
| SEQ ID 191 | GGR |
| SEQ ID 192 | GRR |
| SEQ ID 193 | RRH |
| SEQ ID 194 | RHI |
| SEQ ID 195 | HIR |
| SEQ ID 196 | IRI |
| SEQ ID 197 | RIR |
| SEQ ID 198 | IRS |
| SEQ ID 199 | RSL |
| SEQ ID 200 | SLK |
| SEQ ID 201 | LKI |
| SEQ ID 202 | KIE |
| SEQ ID 203 | IEL |
| SEQ ID 204 | ELH |
| SEQ ID 205 | LHS |
| SEQ ID 206 | SRS |
| SEQ ID 207 | RSG |
| SEQ ID 208 | SGH |
| SEQ ID 209 | GHW |
| SEQ ID 210 | HWQ |
| SEQ ID 211 | WQS |
| SEQ ID 212 | QSI |
| SEQ ID 213 | SID |
| SEQ ID 214 | IDF |

TABLE 2-continued

| | |
|---|---|
| SEQ ID 215 | DFK |
| SEQ ID 216 | FKQ |
| SEQ ID 217 | KQV |
| SEQ ID 218 | QVL |
| SEQ ID 219 | VLH |
| SEQ ID 220 | HSW |
| SEQ ID 221 | SWF |
| SEQ ID 222 | WFR |
| SEQ ID 223 | FRQ |
| SEQ ID 224 | RQP |
| SEQ ID 225 | QPQ |
| SEQ ID 226 | PQS |
| SEQ ID 227 | QSN |
| SEQ ID 228 | SNW |
| SEQ ID 229 | NWG |
| SEQ ID 230 | WGI |
| SEQ ID 231 | GIE |
| SEQ ID 232 | IEI |
| SEQ ID 233 | EIN |
| SEQ ID 234 | INA |
| SEQ ID 235 | NAF |
| SEQ ID 236 | AFD |
| SEQ ID 237 | FDP |
| SEQ ID 238 | DPS |
| SEQ ID 239 | PSG |
| SEQ ID 240 | SGT |
| SEQ ID 241 | GTD |
| SEQ ID 242 | TDL |
| SEQ ID 243 | DLA |
| SEQ ID 244 | LAV |
| SEQ ID 245 | AVT |
| SEQ ID 246 | VTS |
| SEQ ID 247 | TSL |
| SEQ ID 248 | SLG |
| SEQ ID 249 | LGP |
| SEQ ID 250 | GPG |
| SEQ ID 251 | PGA |
| SEQ ID 252 | GAE |
| SEQ ID 253 | EGL |
| SEQ ID 254 | GLH |

TABLE 2-continued

| | |
|---|---|
| SEQ ID 255 | LHP |
| SEQ ID 256 | HPF |
| SEQ ID 257 | PFM |
| SEQ ID 258 | FME |
| SEQ ID 259 | MEL |
| SEQ ID 260 | LRV |
| SEQ ID 261 | RVL |
| SEQ ID 262 | VLE |
| SEQ ID 263 | LEN |
| SEQ ID 264 | ENT |
| SEQ ID 265 | NTK |
| SEQ ID 266 | TKR |
| SEQ ID 267 | KRS |
| SEQ ID 268 | RSR |
| SEQ ID 269 | SRR |
| SEQ ID 270 | RRN |
| SEQ ID 271 | RNL |
| SEQ ID 272 | NLG |
| SEQ ID 273 | LGL |
| SEQ ID 274 | GLD |
| SEQ ID 275 | LDC |
| SEQ ID 276 | DCD |
| SEQ ID 277 | CDE |
| SEQ ID 278 | DEH |
| SEQ ID 279 | EHS |
| SEQ ID 280 | HSS |
| SEQ ID 281 | SSE |
| SEQ ID 282 | SES |
| SEQ ID 283 | ESR |
| SEQ ID 284 | SRC |
| SEQ ID 285 | RCC |
| SEQ ID 286 | CCR |
| SEQ ID 287 | CRY |
| SEQ ID 288 | RYP |
| SEQ ID 289 | YPL |
| SEQ ID 290 | LTV |
| SEQ ID 291 | TVD |
| SEQ ID 292 | VDF |
| SEQ ID 293 | DFE |
| SEQ ID 294 | FEA |

TABLE 2-continued

| | |
|---|---|
| SEQ ID 295 | EAF |
| SEQ ID 296 | AFG |
| SEQ ID 297 | FGW |
| SEQ ID 298 | GWD |
| SEQ ID 299 | WDW |
| SEQ ID 300 | DWI |
| SEQ ID 301 | WII |
| SEQ ID 302 | IIA |
| SEQ ID 303 | IAP |
| SEQ ID 304 | APK |
| SEQ ID 305 | PKR |
| SEQ ID 306 | KRY |
| SEQ ID 307 | RYK |
| SEQ ID 308 | YKA |
| SEQ ID 309 | KAN |
| SEQ ID 310 | ANY |
| SEQ ID 311 | NYC |
| SEQ ID 312 | YCS |
| SEQ ID 313 | CSG |
| SEQ ID 314 | SGQ |
| SEQ ID 315 | GQC |
| SEQ ID 316 | QCE |
| SEQ ID 317 | CEY |
| SEQ ID 318 | EYM |
| SEQ ID 319 | YMF |
| SEQ ID 320 | MFM |
| SEQ ID 321 | FMQ |
| SEQ ID 322 | MQK |
| SEQ ID 323 | QKY |
| SEQ ID 324 | KYP |
| SEQ ID 325 | YPH |
| SEQ ID 326 | PHT |
| SEQ ID 327 | HTH |
| SEQ ID 328 | THL |
| SEQ ID 329 | HLV |
| SEQ ID 330 | LVQ |
| SEQ ID 331 | VQQ |
| SEQ ID 332 | QQA |
| SEQ ID 333 | QAN |
| SEQ ID 334 | ANP |

TABLE 2-continued

| | |
|---|---|
| SEQ ID 335 | NPR |
| SEQ ID 336 | RGS |
| SEQ ID 337 | GSA |
| SEQ ID 338 | SAG |
| SEQ ID 339 | AGP |
| SEQ ID 340 | GPC |
| SEQ ID 341 | PCC |
| SEQ ID 342 | CCT |
| SEQ ID 343 | CTP |
| SEQ ID 344 | TPT |
| SEQ ID 345 | PTK |
| SEQ ID 346 | TKM |
| SEQ ID 347 | KMS |
| SEQ ID 348 | MSP |
| SEQ ID 349 | SPI |
| SEQ ID 350 | PIN |
| SEQ ID 351 | INM |
| SEQ ID 352 | NML |
| SEQ ID 353 | MLY |
| SEQ ID 354 | LYF |
| SEQ ID 355 | YFN |
| SEQ ID 356 | FND |
| SEQ ID 357 | NDK |
| SEQ ID 358 | DKQ |
| SEQ ID 359 | KQQ |
| SEQ ID 360 | QII |
| SEQ ID 361 | IIY |
| SEQ ID 362 | IYG |
| SEQ ID 363 | YGK |
| SEQ ID 364 | GKI |
| SEQ ID 365 | KIP |
| SEQ ID 366 | IPG |
| SEQ ID 367 | PGM |
| SEQ ID 368 | GMV |
| SEQ ID 369 | MVV |
| SEQ ID 370 | VVD |
| SEQ ID 371 | VDR |
| SEQ ID 372 | DRC |
| SEQ ID 373 | RCG |
| SEQ ID 374 | CGC |
| SEQ ID 375 | GCS |

In some embodiments, the active agent comprises a peptide which comprises, consists essentially of, or consists of any one or more of the 4-mer amino acid sequences (SEQ ID NO: 376-767) listed below in Table 3.

TABLE 3

| | |
|---|---|
| SEQ ID 376 | MVLA |
| SEQ ID 377 | VLAA |
| SEQ ID 378 | LAAP |
| SEQ ID 379 | AAPL |
| SEQ ID 380 | APLL |
| SEQ ID 381 | PLLL |
| SEQ ID 382 | LLLG |
| SEQ ID 383 | LLGF |
| SEQ ID 384 | LGFL |
| SEQ ID 385 | GFLL |
| SEQ ID 386 | FLLL |
| SEQ ID 387 | LLLA |
| SEQ ID 388 | LLAL |
| SEQ ID 389 | LALE |
| SEQ ID 390 | ALEL |
| SEQ ID 391 | LELR |
| SEQ ID 392 | ELRP |
| SEQ ID 393 | LRPR |
| SEQ ID 394 | RPRG |
| SEQ ID 395 | PRGE |
| SEQ ID 396 | RGEA |
| SEQ ID 397 | GEAA |
| SEQ ID 398 | EAAE |
| SEQ ID 399 | AAEG |
| SEQ ID 400 | AEGP |
| SEQ ID 401 | EGPA |
| SEQ ID 402 | GPAA |
| SEQ ID 403 | PAAA |
| SEQ ID 404 | AAAA |
| SEQ ID 405 | AAAG |
| SEQ ID 406 | AAGV |
| SEQ ID 407 | AGVG |
| SEQ ID 408 | GVGG |

TABLE 3-continued

| | |
|---|---|
| SEQ ID 409 | VGGE |
| SEQ ID 410 | GGER |
| SEQ ID 411 | GERS |
| SEQ ID 412 | ERSS |
| SEQ ID 413 | RSSR |
| SEQ ID 414 | SSRP |
| SEQ ID 415 | SRPA |
| SEQ ID 416 | RPAP |
| SEQ ID 417 | PAPS |
| SEQ ID 418 | APSV |
| SEQ ID 419 | PSVA |
| SEQ ID 420 | SVAP |
| SEQ ID 421 | VAPE |
| SEQ ID 422 | APEP |
| SEQ ID 423 | PEPD |
| SEQ ID 424 | EPDG |
| SEQ ID 425 | PDGC |
| SEQ ID 426 | DGCP |
| SEQ ID 427 | GCPV |
| SEQ ID 428 | CPVC |
| SEQ ID 429 | PVCV |
| SEQ ID 430 | VCVW |
| SEQ ID 431 | CVWR |
| SEQ ID 432 | VWRQ |
| SEQ ID 433 | WRQH |
| SEQ ID 434 | RQHS |
| SEQ ID 435 | QHSR |
| SEQ ID 436 | HSRE |
| SEQ ID 437 | SREL |
| SEQ ID 438 | RELR |
| SEQ ID 439 | ELRL |
| SEQ ID 440 | LRLE |
| SEQ ID 441 | RLES |
| SEQ ID 442 | LESI |
| SEQ ID 443 | ESIK |
| SEQ ID 444 | SIKS |
| SEQ ID 445 | IKSQ |
| SEQ ID 446 | KSQI |
| SEQ ID 447 | SQIL |
| SEQ ID 448 | QILS |

TABLE 3-continued

| | |
|---|---|
| SEQ ID 449 | ILSK |
| SEQ ID 450 | LSKL |
| SEQ ID 451 | SKLR |
| SEQ ID 452 | KLRL |
| SEQ ID 453 | LRLK |
| SEQ ID 454 | RLKE |
| SEQ ID 455 | LKEA |
| SEQ ID 456 | KEAP |
| SEQ ID 457 | EAPN |
| SEQ ID 458 | APNI |
| SEQ ID 459 | PNIS |
| SEQ ID 460 | NISR |
| SEQ ID 461 | ISRE |
| SEQ ID 462 | SREV |
| SEQ ID 463 | REVV |
| SEQ ID 464 | EVVK |
| SEQ ID 465 | VVKQ |
| SEQ ID 466 | VKQL |
| SEQ ID 467 | KQLL |
| SEQ ID 468 | QLLP |
| SEQ ID 469 | LLPK |
| SEQ ID 470 | LPKA |
| SEQ ID 471 | PKAP |
| SEQ ID 472 | KAPP |
| SEQ ID 473 | APPL |
| SEQ ID 474 | PPLQ |
| SEQ ID 475 | PLQQ |
| SEQ ID 476 | LQQI |
| SEQ ID 477 | QQIL |
| SEQ ID 478 | QILD |
| SEQ ID 479 | ILDL |
| SEQ ID 480 | LDLH |
| SEQ ID 481 | DLHD |
| SEQ ID 482 | LHDF |
| SEQ ID 483 | HDFQ |
| SEQ ID 484 | DFQG |
| SEQ ID 485 | FQGD |
| SEQ ID 486 | QGDA |
| SEQ ID 487 | GDAL |
| SEQ ID 488 | DALQ |

TABLE 3-continued

| | |
|---|---|
| SEQ ID 489 | ALQP |
| SEQ ID 490 | LQPE |
| SEQ ID 491 | QPED |
| SEQ ID 492 | PEDF |
| SEQ ID 493 | EDFL |
| SEQ ID 494 | DFLE |
| SEQ ID 495 | FLEE |
| SEQ ID 496 | LEED |
| SEQ ID 497 | EEDE |
| SEQ ID 498 | EDEY |
| SEQ ID 499 | DEYH |
| SEQ ID 500 | EYHA |
| SEQ ID 501 | YHAT |
| SEQ ID 502 | HATT |
| SEQ ID 503 | ATTE |
| SEQ ID 504 | TTET |
| SEQ ID 505 | TETV |
| SEQ ID 506 | ETVI |
| SEQ ID 507 | TVIS |
| SEQ ID 508 | VISM |
| SEQ ID 509 | ISMA |
| SEQ ID 510 | SMAQ |
| SEQ ID 511 | MAQE |
| SEQ ID 512 | AQET |
| SEQ ID 513 | QETD |
| SEQ ID 514 | ETDP |
| SEQ ID 515 | TDPA |
| SEQ ID 516 | DPAV |
| SEQ ID 517 | PAVQ |
| SEQ ID 518 | AVQT |
| SEQ ID 519 | VQTD |
| SEQ ID 520 | QTDG |
| SEQ ID 521 | TDGS |
| SEQ ID 522 | DGSP |
| SEQ ID 523 | GSPL |
| SEQ ID 524 | SPLC |
| SEQ ID 525 | PLCC |
| SEQ ID 526 | LCCH |
| SEQ ID 527 | CCHF |
| SEQ ID 528 | CHFH |

TABLE 3-continued

| | |
|---|---|
| SEQ ID 529 | HFHF |
| SEQ ID 530 | FHFS |
| SEQ ID 531 | HFSP |
| SEQ ID 532 | FSPK |
| SEQ ID 533 | SPKV |
| SEQ ID 534 | PKVM |
| SEQ ID 535 | KVMF |
| SEQ ID 536 | VMFT |
| SEQ ID 537 | MFTK |
| SEQ ID 538 | FTKV |
| SEQ ID 539 | TKVL |
| SEQ ID 540 | KVLK |
| SEQ ID 541 | VLKA |
| SEQ ID 542 | LKAQ |
| SEQ ID 543 | KAQL |
| SEQ ID 544 | AQLW |
| SEQ ID 545 | QLWV |
| SEQ ID 546 | LWVY |
| SEQ ID 547 | WVYL |
| SEQ ID 548 | VYLR |
| SEQ ID 549 | YLRP |
| SEQ ID 550 | LRPV |
| SEQ ID 551 | RPVP |
| SEQ ID 552 | PVPR |
| SEQ ID 553 | VPRP |
| SEQ ID 554 | PRPA |
| SEQ ID 555 | RPAT |
| SEQ ID 556 | PATV |
| SEQ ID 557 | ATVY |
| SEQ ID 558 | TVYL |
| SEQ ID 559 | VYLQ |
| SEQ ID 560 | YLQI |
| SEQ ID 561 | LQIL |
| SEQ ID 562 | QILR |
| SEQ ID 563 | ILRL |
| SEQ ID 564 | RLKP |
| SEQ ID 565 | LKPL |
| SEQ ID 566 | KPLT |
| SEQ ID 567 | PLTG |
| SEQ ID 568 | LTGE |

TABLE 3-continued

| SEQ ID 569 | TGEG |
| --- | --- |
| SEQ ID 570 | GEGT |
| SEQ ID 571 | EGTA |
| SEQ ID 572 | GTAG |
| SEQ ID 573 | TAGG |
| SEQ ID 574 | AGGG |
| SEQ ID 575 | GGGG |
| SEQ ID 576 | GGGR |
| SEQ ID 577 | GGRR |
| SEQ ID 578 | GRRH |
| SEQ ID 579 | RRHI |
| SEQ ID 580 | RHIR |
| SEQ ID 581 | HIRI |
| SEQ ID 582 | IRIR |
| SEQ ID 583 | RIRS |
| SEQ ID 584 | IRSL |
| SEQ ID 585 | RSLK |
| SEQ ID 586 | SLKI |
| SEQ ID 587 | LKIE |
| SEQ ID 588 | KIEL |
| SEQ ID 589 | IELH |
| SEQ ID 590 | ELHS |
| SEQ ID 591 | LHSR |
| SEQ ID 592 | HSRS |
| SEQ ID 593 | SRSG |
| SEQ ID 594 | RSGH |
| SEQ ID 595 | SGHW |
| SEQ ID 596 | GHWQ |
| SEQ ID 597 | HWQS |
| SEQ ID 598 | WQSI |
| SEQ ID 599 | QSID |
| SEQ ID 600 | SIDF |
| SEQ ID 601 | IDFK |
| SEQ ID 602 | DFKQ |
| SEQ ID 603 | FKQV |
| SEQ ID 604 | KQVL |
| SEQ ID 605 | QVLH |
| SEQ ID 606 | VLHS |
| SEQ ID 607 | LHSW |
| SEQ ID 608 | HSWF |

TABLE 3-continued

| SEQ ID 609 | SWFR |
| --- | --- |
| SEQ ID 610 | WFRQ |
| SEQ ID 611 | FRQP |
| SEQ ID 612 | RQPQ |
| SEQ ID 613 | QPQS |
| SEQ ID 614 | PQSN |
| SEQ ID 615 | QSNW |
| SEQ ID 616 | SNWG |
| SEQ ID 617 | NWGI |
| SEQ ID 618 | WGIE |
| SEQ ID 619 | GIEI |
| SEQ ID 620 | IEIN |
| SEQ ID 621 | EINA |
| SEQ ID 622 | INAF |
| SEQ ID 623 | NAFD |
| SEQ ID 624 | AFDP |
| SEQ ID 625 | FDPS |
| SEQ ID 626 | DPSG |
| SEQ ID 627 | PSGT |
| SEQ ID 628 | SGTD |
| SEQ ID 629 | GTDL |
| SEQ ID 630 | TDLA |
| SEQ ID 631 | DLAV |
| SEQ ID 632 | LAVT |
| SEQ ID 633 | AVTS |
| SEQ ID 634 | VTSL |
| SEQ ID 635 | TSLG |
| SEQ ID 636 | SLGP |
| SEQ ID 637 | LGPG |
| SEQ ID 638 | GPGA |
| SEQ ID 639 | PGAE |
| SEQ ID 640 | GAEG |
| SEQ ID 641 | AEGL |
| SEQ ID 642 | EGLH |
| SEQ ID 643 | GLHP |
| SEQ ID 644 | LHPF |
| SEQ ID 645 | HPFM |
| SEQ ID 646 | PFME |
| SEQ ID 647 | FMEL |
| SEQ ID 648 | MELR |

TABLE 3-continued

| | |
|---|---|
| SEQ ID 649 | ELRV |
| SEQ ID 650 | LRVL |
| SEQ ID 651 | RVLE |
| SEQ ID 652 | VLEN |
| SEQ ID 653 | LENT |
| SEQ ID 654 | ENTK |
| SEQ ID 655 | NTKR |
| SEQ ID 656 | TKRS |
| SEQ ID 657 | KRSR |
| SEQ ID 658 | RSRR |
| SEQ ID 659 | SRRN |
| SEQ ID 660 | RRNL |
| SEQ ID 661 | RNLG |
| SEQ ID 662 | NLGL |
| SEQ ID 663 | LGLD |
| SEQ ID 664 | GLDC |
| SEQ ID 665 | LDCD |
| SEQ ID 666 | DCDE |
| SEQ ID 667 | CDEH |
| SEQ ID 668 | DEHS |
| SEQ ID 669 | EHSS |
| SEQ ID 670 | HSSE |
| SEQ ID 671 | SSES |
| SEQ ID 672 | SESR |
| SEQ ID 673 | ESRC |
| SEQ ID 674 | SRCC |
| SEQ ID 675 | RCCR |
| SEQ ID 676 | CCRY |
| SEQ ID 677 | CRYP |
| SEQ ID 678 | RYPL |
| SEQ ID 679 | YPLT |
| SEQ ID 680 | PLTV |
| SEQ ID 681 | LTVD |
| SEQ ID 682 | TVDF |
| SEQ ID 683 | VDFE |
| SEQ ID 684 | DFEA |
| SEQ ID 685 | FEAF |
| SEQ ID 686 | EAFG |
| SEQ ID 687 | AFGW |
| SEQ ID 688 | FGWD |

TABLE 3-continued

| | |
|---|---|
| SEQ ID 689 | GWDW |
| SEQ ID 690 | WDWI |
| SEQ ID 691 | DWII |
| SEQ ID 692 | WIIA |
| SEQ ID 693 | IIAP |
| SEQ ID 694 | IAPK |
| SEQ ID 695 | APKR |
| SEQ ID 696 | PKRY |
| SEQ ID 697 | KRYK |
| SEQ ID 698 | RYKA |
| SEQ ID 699 | YKAN |
| SEQ ID 700 | KANY |
| SEQ ID 701 | ANYC |
| SEQ ID 702 | NYCS |
| SEQ ID 703 | YCSG |
| SEQ ID 704 | CSGQ |
| SEQ ID 705 | SGQC |
| SEQ ID 706 | GQCE |
| SEQ ID 707 | QCEY |
| SEQ ID 708 | CEYM |
| SEQ ID 709 | EYMF |
| SEQ ID 710 | YMFM |
| SEQ ID 711 | MFMQ |
| SEQ ID 712 | FMQK |
| SEQ ID 713 | MQKY |
| SEQ ID 714 | QKYP |
| SEQ ID 715 | KYPH |
| SEQ ID 716 | YPHT |
| SEQ ID 717 | PHTH |
| SEQ ID 718 | HTHL |
| SEQ ID 719 | THLV |
| SEQ ID 720 | HLVQ |
| SEQ ID 721 | LVQQ |
| SEQ ID 722 | VQQA |
| SEQ ID 723 | QQAN |
| SEQ ID 724 | QANP |
| SEQ ID 725 | ANPR |
| SEQ ID 726 | NPRG |
| SEQ ID 727 | PRGS |
| SEQ ID 728 | RGSA |

TABLE 3-continued

| | |
|---|---|
| SEQ ID 729 | GSAG |
| SEQ ID 730 | SAGP |
| SEQ ID 731 | AGPC |
| SEQ ID 732 | GPCC |
| SEQ ID 733 | PCCT |
| SEQ ID 734 | CCTP |
| SEQ ID 735 | CTPT |
| SEQ ID 736 | TPTK |
| SEQ ID 737 | PTKM |
| SEQ ID 738 | TKMS |
| SEQ ID 739 | KMSP |
| SEQ ID 740 | MSPI |
| SEQ ID 741 | SPIN |
| SEQ ID 742 | PINM |
| SEQ ID 743 | INML |
| SEQ ID 744 | NMLY |
| SEQ ID 745 | MLYF |
| SEQ ID 746 | LYFN |
| SEQ ID 747 | YFND |
| SEQ ID 748 | FNDK |
| SEQ ID 749 | NDKQ |
| SEQ ID 750 | DKQQ |
| SEQ ID 751 | KQQI |
| SEQ ID 752 | QQII |
| SEQ ID 753 | QIIY |
| SEQ ID 754 | IIYG |
| SEQ ID 755 | IYGK |
| SEQ ID 756 | YGKI |
| SEQ ID 757 | GKIP |
| SEQ ID 758 | KIPG |
| SEQ ID 759 | IPGM |
| SEQ ID 760 | PGMV |
| SEQ ID 761 | GMVV |
| SEQ ID 762 | MVVD |
| SEQ ID 763 | VVDR |
| SEQ ID 764 | VDRC |
| SEQ ID 765 | DRCG |
| SEQ ID 766 | RCGC |
| SEQ ID 767 | CGCS |

In some embodiments, the active agent comprises a peptide which comprises, consists essentially of, or consists of any one or more of the 5-mer amino acid sequences (SEQ ID NO: 768-1161) listed below in Table 4.

TABLE 4

| | |
|---|---|
| SEQ ID 768 | MVLAA |
| SEQ ID 769 | VLAAP |
| SEQ ID 770 | LAAPL |
| SEQ ID 771 | AAPLL |
| SEQ ID 772 | APLLL |
| SEQ ID 773 | PLLLG |
| SEQ ID 774 | LLLGF |
| SEQ ID 775 | LLGFL |
| SEQ ID 776 | LGFLL |
| SEQ ID 777 | GFLLL |
| SEQ ID 778 | FLLLA |
| SEQ ID 779 | LLLAL |
| SEQ ID 780 | LLALE |
| SEQ ID 781 | LALEL |
| SEQ ID 782 | ALELR |
| SEQ ID 783 | LELRP |
| SEQ ID 784 | ELRPR |
| SEQ ID 785 | LRPRG |
| SEQ ID 786 | RPRGE |
| SEQ ID 787 | PRGEA |
| SEQ ID 788 | RGEAA |
| SEQ ID 789 | GEAAE |
| SEQ ID 790 | EAAEG |
| SEQ ID 791 | AAEGP |
| SEQ ID 792 | AEGPA |
| SEQ ID 793 | EGPAA |
| SEQ ID 794 | GPAAA |
| SEQ ID 795 | PAAAA |
| SEQ ID 796 | AAAAA |
| SEQ ID 797 | AAAAG |
| SEQ ID 798 | AAAGV |
| SEQ ID 799 | AAGVG |
| SEQ ID 800 | AGVGG |
| SEQ ID 801 | GVGGE |
| SEQ ID 802 | VGGER |
| SEQ ID 803 | GGERS |
| SEQ ID 804 | GERSS |

TABLE 4-continued

| SEQ ID | 805 | ERSSR |
| --- | --- | --- |
| SEQ ID | 806 | RSSRP |
| SEQ ID | 807 | SSRPA |
| SEQ ID | 808 | SRPAP |
| SEQ ID | 809 | RPAPS |
| SEQ ID | 810 | PAPSV |
| SEQ ID | 811 | APSVA |
| SEQ ID | 812 | PSVAP |
| SEQ ID | 813 | SVAPE |
| SEQ ID | 814 | VAPEP |
| SEQ ID | 815 | APEPD |
| SEQ ID | 816 | PEPDG |
| SEQ ID | 817 | EPDGC |
| SEQ ID | 818 | PDGCP |
| SEQ ID | 819 | DGCPV |
| SEQ ID | 820 | GCPVC |
| SEQ ID | 821 | CPVCV |
| SEQ ID | 822 | PVCVW |
| SEQ ID | 823 | VCVWR |
| SEQ ID | 824 | CVWRQ |
| SEQ ID | 825 | VWRQH |
| SEQ ID | 826 | WRQHS |
| SEQ ID | 827 | RQHSR |
| SEQ ID | 828 | QHSRE |
| SEQ ID | 829 | HSREL |
| SEQ ID | 830 | SRELR |
| SEQ ID | 831 | RELRL |
| SEQ ID | 832 | ELRLE |
| SEQ ID | 833 | LRLES |
| SEQ ID | 834 | RLESI |
| SEQ ID | 835 | LESIK |
| SEQ ID | 836 | ESIKS |
| SEQ ID | 837 | SIKSQ |
| SEQ ID | 838 | IKSQI |
| SEQ ID | 839 | KSQIL |
| SEQ ID | 840 | SQILS |
| SEQ ID | 841 | QILSK |
| SEQ ID | 842 | ILSKL |
| SEQ ID | 843 | LSKLR |
| SEQ ID | 844 | SKLRL |

TABLE 4-continued

| SEQ ID | 845 | KLRLK |
| --- | --- | --- |
| SEQ ID | 846 | LRLKE |
| SEQ ID | 847 | RLKEA |
| SEQ ID | 848 | LKEAP |
| SEQ ID | 849 | KEAPN |
| SEQ ID | 850 | EAPNI |
| SEQ ID | 851 | APNIS |
| SEQ ID | 852 | PNISR |
| SEQ ID | 853 | NISRE |
| SEQ ID | 854 | ISREV |
| SEQ ID | 855 | SREVV |
| SEQ ID | 856 | REVVK |
| SEQ ID | 857 | EVVKQ |
| SEQ ID | 858 | VVKQL |
| SEQ ID | 859 | VKQLL |
| SEQ ID | 860 | KQLLP |
| SEQ ID | 861 | QLLPK |
| SEQ ID | 862 | LLPKA |
| SEQ ID | 863 | LPKAP |
| SEQ ID | 864 | PKAPP |
| SEQ ID | 865 | KAPPL |
| SEQ ID | 866 | APPLQ |
| SEQ ID | 867 | PPLQQ |
| SEQ ID | 868 | PLQQI |
| SEQ ID | 869 | LQQIL |
| SEQ ID | 870 | QQILD |
| SEQ ID | 871 | QILDL |
| SEQ ID | 872 | ILDLH |
| SEQ ID | 873 | LDLHD |
| SEQ ID | 874 | DLHDF |
| SEQ ID | 875 | LHDFQ |
| SEQ ID | 876 | HDFQG |
| SEQ ID | 877 | DFQGD |
| SEQ ID | 878 | FQGDA |
| SEQ ID | 879 | QGDAL |
| SEQ ID | 880 | GDALQ |
| SEQ ID | 881 | DALQP |
| SEQ ID | 882 | ALQPE |
| SEQ ID | 883 | LQPED |
| SEQ ID | 884 | QPEDF |

TABLE 4-continued

| SEQ ID | 885 | PEDFL |
| --- | --- | --- |
| SEQ ID | 886 | EDFLE |
| SEQ ID | 887 | DFLEE |
| SEQ ID | 888 | FLEED |
| SEQ ID | 889 | LEEDE |
| SEQ ID | 890 | EEDEY |
| SEQ ID | 891 | EDEYH |
| SEQ ID | 892 | DEYHA |
| SEQ ID | 893 | EYHAT |
| SEQ ID | 894 | YHATT |
| SEQ ID | 895 | HATTE |
| SEQ ID | 896 | ATTET |
| SEQ ID | 897 | TTETV |
| SEQ ID | 898 | TETVI |
| SEQ ID | 899 | ETVIS |
| SEQ ID | 900 | TVISM |
| SEQ ID | 901 | VISMA |
| SEQ ID | 902 | ISMAQ |
| SEQ ID | 903 | SMAQE |
| SEQ ID | 904 | MAQET |
| SEQ ID | 905 | AQETD |
| SEQ ID | 906 | QETDP |
| SEQ ID | 907 | ETDPA |
| SEQ ID | 908 | TDPAV |
| SEQ ID | 909 | DPAVQ |
| SEQ ID | 910 | PAVQT |
| SEQ ID | 911 | AVQTD |
| SEQ ID | 912 | VQTDG |
| SEQ ID | 913 | QTDGS |
| SEQ ID | 914 | TDGSP |
| SEQ ID | 915 | DGSPL |
| SEQ ID | 916 | GSPLC |
| SEQ ID | 917 | SPLCC |
| SEQ ID | 918 | PLCCH |
| SEQ ID | 919 | LCCHF |
| SEQ ID | 920 | CCHFH |
| SEQ ID | 921 | CHFHF |
| SEQ ID | 922 | HFHFS |
| SEQ ID | 923 | FHFSP |
| SEQ ID | 924 | HFSPK |

TABLE 4-continued

| SEQ ID | 925 | FSPKV |
| --- | --- | --- |
| SEQ ID | 926 | SPKVM |
| SEQ ID | 927 | PKVMF |
| SEQ ID | 928 | KVMFT |
| SEQ ID | 929 | VMFTK |
| SEQ ID | 930 | MFTKV |
| SEQ ID | 931 | FTKVL |
| SEQ ID | 932 | TKVLK |
| SEQ ID | 933 | KVLKA |
| SEQ ID | 934 | VLKAQ |
| SEQ ID | 935 | LKAQL |
| SEQ ID | 936 | KAQLW |
| SEQ ID | 937 | AQLWV |
| SEQ ID | 938 | QLWVY |
| SEQ ID | 939 | LWVYL |
| SEQ ID | 940 | WVYLR |
| SEQ ID | 941 | VYLRP |
| SEQ ID | 942 | YLRPV |
| SEQ ID | 943 | LRPVP |
| SEQ ID | 944 | RPVPR |
| SEQ ID | 945 | PVPRP |
| SEQ ID | 946 | VPRPA |
| SEQ ID | 947 | PRPAT |
| SEQ ID | 948 | RPATV |
| SEQ ID | 949 | PATVY |
| SEQ ID | 950 | ATVYL |
| SEQ ID | 951 | TVYLQ |
| SEQ ID | 952 | VYLQI |
| SEQ ID | 953 | YLQIL |
| SEQ ID | 954 | LQILR |
| SEQ ID | 955 | QILRL |
| SEQ ID | 956 | ILRLK |
| SEQ ID | 957 | LRLKP |
| SEQ ID | 958 | RLKPL |
| SEQ ID | 959 | LKPLT |
| SEQ ID | 960 | KPLTG |
| SEQ ID | 961 | PLTGE |
| SEQ ID | 962 | LTGEG |
| SEQ ID | 963 | TGEGT |
| SEQ ID | 964 | GEGTA |

TABLE 4-continued

| SEQ ID | 965 | EGTAG |
| --- | --- | --- |
| SEQ ID | 966 | GTAGG |
| SEQ ID | 967 | TAGGG |
| SEQ ID | 968 | AGGGG |
| SEQ ID | 969 | GGGGG |
| SEQ ID | 970 | GGGGR |
| SEQ ID | 971 | GGGRR |
| SEQ ID | 972 | GGRRH |
| SEQ ID | 973 | GRRHI |
| SEQ ID | 974 | RRHIR |
| SEQ ID | 975 | RHIRI |
| SEQ ID | 976 | HIRIR |
| SEQ ID | 977 | IRIRS |
| SEQ ID | 978 | RIRSL |
| SEQ ID | 979 | IRSLK |
| SEQ ID | 980 | RSLKI |
| SEQ ID | 981 | SLKIE |
| SEQ ID | 982 | LKIEL |
| SEQ ID | 983 | KIELH |
| SEQ ID | 984 | IELHS |
| SEQ ID | 985 | ELHSR |
| SEQ ID | 986 | LHSRS |
| SEQ ID | 987 | HSRSG |
| SEQ ID | 988 | SRSGH |
| SEQ ID | 989 | RSGHW |
| SEQ ID | 990 | SGHWQ |
| SEQ ID | 991 | GHWQS |
| SEQ ID | 992 | HWQSI |
| SEQ ID | 993 | WQSID |
| SEQ ID | 994 | QSIDF |
| SEQ ID | 995 | SIDFK |
| SEQ ID | 996 | IDFKQ |
| SEQ ID | 997 | DFKQV |
| SEQ ID | 998 | FKQVL |
| SEQ ID | 999 | KQVLH |
| SEQ ID | 1000 | QVLHS |
| SEQ ID | 1001 | VLHSW |
| SEQ ID | 1002 | LHSWF |
| SEQ ID | 1003 | HSWFR |
| SEQ ID | 1004 | SWFRQ |
| SEQ ID | 1005 | WFRQP |
| SEQ ID | 1006 | FRQPQ |
| SEQ ID | 1007 | RQPQS |
| SEQ ID | 1008 | QPQSN |
| SEQ ID | 1009 | PQSNW |
| SEQ ID | 1010 | QSNWG |
| SEQ ID | 1011 | SNWGI |
| SEQ ID | 1012 | NWGIE |
| SEQ ID | 1013 | WGIEI |
| SEQ ID | 1014 | GIEIN |
| SEQ ID | 1015 | IEINA |
| SEQ ID | 1016 | EINAF |
| SEQ ID | 1017 | INAFD |
| SEQ ID | 1018 | NAFDP |
| SEQ ID | 1019 | AFDPS |
| SEQ ID | 1020 | FDPSG |
| SEQ ID | 1021 | DPSGT |
| SEQ ID | 1022 | PSGTD |
| SEQ ID | 1023 | SGTDL |
| SEQ ID | 1024 | GTDLA |
| SEQ ID | 1025 | TDLAV |
| SEQ ID | 1026 | DLAVT |
| SEQ ID | 1027 | LAVTS |
| SEQ ID | 1028 | AVTSL |
| SEQ ID | 1029 | VTSLG |
| SEQ ID | 1030 | TSLGP |
| SEQ ID | 1031 | SLGPG |
| SEQ ID | 1032 | LGPGA |
| SEQ ID | 1033 | GPGAE |
| SEQ ID | 1034 | PGAEG |
| SEQ ID | 1035 | GAEGL |
| SEQ ID | 1036 | AEGLH |
| SEQ ID | 1037 | EGLHP |
| SEQ ID | 1038 | GLHPF |
| SEQ ID | 1039 | LHPFM |
| SEQ ID | 1040 | HPFME |
| SEQ ID | 1041 | PFMEL |
| SEQ ID | 1042 | FMELR |
| SEQ ID | 1043 | MELRV |
| SEQ ID | 1044 | ELRVL |

TABLE 4-continued

| SEQ ID | 1045 | LRVLE |
| --- | --- | --- |
| SEQ ID | 1046 | RVLEN |
| SEQ ID | 1047 | VLENT |
| SEQ ID | 1048 | LENTK |
| SEQ ID | 1049 | ENTKR |
| SEQ ID | 1050 | NTKRS |
| SEQ ID | 1051 | TKRSR |
| SEQ ID | 1052 | KRSRR |
| SEQ ID | 1053 | RSRRN |
| SEQ ID | 1054 | SRRNL |
| SEQ ID | 1055 | RRNLG |
| SEQ ID | 1056 | RNLGL |
| SEQ ID | 1057 | NLGLD |
| SEQ ID | 1058 | LGLDC |
| SEQ ID | 1059 | GLDCD |
| SEQ ID | 1060 | LDCDE |
| SEQ ID | 1061 | DCDEH |
| SEQ ID | 1062 | CDEHS |
| SEQ ID | 1063 | DEHSS |
| SEQ ID | 1064 | EHSSE |
| SEQ ID | 1065 | HSSES |
| SEQ ID | 1066 | SSESR |
| SEQ ID | 1067 | SESRC |
| SEQ ID | 1068 | ESRCC |
| SEQ ID | 1069 | SRCCR |
| SEQ ID | 1070 | RCCRY |
| SEQ ID | 1071 | CCRYP |
| SEQ ID | 1072 | CRYPL |
| SEQ ID | 1073 | RYPLT |
| SEQ ID | 1074 | YPLTV |
| SEQ ID | 1075 | PLTVD |
| SEQ ID | 1076 | LTVDF |
| SEQ ID | 1077 | TVDFE |
| SEQ ID | 1078 | VDFEA |
| SEQ ID | 1079 | DFEAF |
| SEQ ID | 1080 | FEAFG |
| SEQ ID | 1081 | EAFGW |
| SEQ ID | 1082 | AFGWD |
| SEQ ID | 1083 | FGWDW |
| SEQ ID | 1084 | GWDWI |

TABLE 4-continued

| SEQ ID | 1085 | WDWII |
| --- | --- | --- |
| SEQ ID | 1086 | DWIIA |
| SEQ ID | 1087 | WIIAP |
| SEQ ID | 1088 | IIAPK |
| SEQ ID | 1089 | IAPKR |
| SEQ ID | 1090 | APKRY |
| SEQ ID | 1091 | PKRYK |
| SEQ ID | 1092 | KRYKA |
| SEQ ID | 1093 | RYKAN |
| SEQ ID | 1094 | YKANY |
| SEQ ID | 1095 | KANYC |
| SEQ ID | 1096 | ANYCS |
| SEQ ID | 1097 | NYCSG |
| SEQ ID | 1098 | YCSGQ |
| SEQ ID | 1099 | CSGQC |
| SEQ ID | 1100 | SGQCE |
| SEQ ID | 1101 | GQCEY |
| SEQ ID | 1102 | QCEYM |
| SEQ ID | 1103 | CEYMF |
| SEQ ID | 1104 | EYMFM |
| SEQ ID | 1105 | YMFMQ |
| SEQ ID | 1106 | MFMQK |
| SEQ ID | 1107 | FMQKY |
| SEQ ID | 1108 | MQKYP |
| SEQ ID | 1109 | QKYPH |
| SEQ ID | 1110 | KYPHT |
| SEQ ID | 1111 | YPHTH |
| SEQ ID | 1112 | PHTHL |
| SEQ ID | 1113 | HTHLV |
| SEQ ID | 1114 | THLVQ |
| SEQ ID | 1115 | HLVQQ |
| SEQ ID | 1116 | LVQQA |
| SEQ ID | 1117 | VQQAN |
| SEQ ID | 1118 | QQANP |
| SEQ ID | 1119 | QANPR |
| SEQ ID | 1120 | ANPRG |
| SEQ ID | 1121 | NPRGS |
| SEQ ID | 1122 | PRGSA |
| SEQ ID | 1123 | RGSAG |
| SEQ ID | 1124 | GSAGP |

TABLE 4-continued

| | | |
|---|---|---|
| SEQ ID | 1125 | SAGPC |
| SEQ ID | 1126 | AGPCC |
| SEQ ID | 1127 | GPCCT |
| SEQ ID | 1128 | PCCTP |
| SEQ ID | 1129 | CCTPT |
| SEQ ID | 1130 | CTPTK |
| SEQ ID | 1131 | TPTKM |
| SEQ ID | 1132 | PTKMS |
| SEQ ID | 1133 | TKMSP |
| SEQ ID | 1134 | KMSPI |
| SEQ ID | 1135 | MSPIN |
| SEQ ID | 1136 | SPINM |
| SEQ ID | 1137 | PINML |
| SEQ ID | 1138 | INMLY |
| SEQ ID | 1139 | NMLYF |
| SEQ ID | 1140 | MLYFN |
| SEQ ID | 1141 | LYFND |
| SEQ ID | 1142 | YFNDK |
| SEQ ID | 1143 | FNDKQ |
| SEQ ID | 1144 | NDKQQ |
| SEQ ID | 1145 | DKQQI |
| SEQ ID | 1146 | KQQII |
| SEQ ID | 1147 | QQIIY |
| SEQ ID | 1148 | QIIYG |
| SEQ ID | 1149 | IIYGK |
| SEQ ID | 1150 | IYGKI |
| SEQ ID | 1151 | YGKIP |
| SEQ ID | 1152 | GKIPG |
| SEQ ID | 1153 | KIPGM |
| SEQ ID | 1154 | IPGMV |
| SEQ ID | 1155 | PGMVV |
| SEQ ID | 1156 | GMVVD |
| SEQ ID | 1157 | MVVDR |
| SEQ ID | 1158 | VVDRC |
| SEQ ID | 1159 | VDRCG |
| SEQ ID | 1160 | DRCGC |
| SEQ ID | 1161 | RCGCS |

In some embodiments, the active agent comprises a peptide which comprises, consists essentially of, or consists of any one or more of the 6-mer amino acid sequences (SEQ ID NO: 1162-1556) listed below in Table 5.

TABLE 5

| | | |
|---|---|---|
| SEQ ID | 1162 | MVLAAP |
| SEQ ID | 1163 | VLAAPL |
| SEQ ID | 1164 | LAAPLL |
| SEQ ID | 1165 | AAPLLL |
| SEQ ID | 1166 | APLLLG |
| SEQ ID | 1167 | PLLLGF |
| SEQ ID | 1168 | LLLGFL |
| SEQ ID | 1169 | LLGFLL |
| SEQ ID | 1170 | LGFLLL |
| SEQ ID | 1171 | GFLLLA |
| SEQ ID | 1172 | FLLLAL |
| SEQ ID | 1173 | LLLALE |
| SEQ ID | 1174 | LLALEL |
| SEQ ID | 1175 | LALELR |
| SEQ ID | 1176 | ALELRP |
| SEQ ID | 1177 | LELRPR |
| SEQ ID | 1178 | ELRPRG |
| SEQ ID | 1179 | LRPRGE |
| SEQ ID | 1180 | RPRGEA |
| SEQ ID | 1181 | PRGEAA |
| SEQ ID | 1182 | RGEAAE |
| SEQ ID | 1183 | GEAAEG |
| SEQ ID | 1184 | EAAEGP |
| SEQ ID | 1185 | AAEGPA |
| SEQ ID | 1186 | AEGPAA |
| SEQ ID | 1187 | EGPAAA |
| SEQ ID | 1188 | GPAAAA |
| SEQ ID | 1189 | PAAAAA |
| SEQ ID | 1190 | AAAAAA |
| SEQ ID | 1191 | AAAAAG |
| SEQ ID | 1192 | AAAAGV |
| SEQ ID | 1193 | AAAGVG |
| SEQ ID | 1194 | AAGVGG |
| SEQ ID | 1195 | AGVGGE |
| SEQ ID | 1196 | GVGGER |
| SEQ ID | 1197 | VGGERS |
| SEQ ID | 1198 | GGERSS |
| SEQ ID | 1199 | GERSSR |
| SEQ ID | 1200 | ERSSRP |
| SEQ ID | 1201 | RSSRPA |

TABLE 5-continued

| | |
|---|---|
| SEQ ID 1202 | SSRPAP |
| SEQ ID 1203 | SRPAPS |
| SEQ ID 1204 | RPAPSV |
| SEQ ID 1205 | PAPSVA |
| SEQ ID 1206 | APSVAP |
| SEQ ID 1207 | PSVAPE |
| SEQ ID 1208 | SVAPEP |
| SEQ ID 1209 | VAPEPD |
| SEQ ID 1210 | APEPDG |
| SEQ ID 1211 | PEPDGC |
| SEQ ID 1212 | EPDGCP |
| SEQ ID 1213 | PDGCPV |
| SEQ ID 1214 | DGCPVC |
| SEQ ID 1215 | GCPVCV |
| SEQ ID 1216 | CPVCVW |
| SEQ ID 1217 | PVCVWR |
| SEQ ID 1218 | VCVWRQ |
| SEQ ID 1219 | CVWRQH |
| SEQ ID 1220 | VWRQHS |
| SEQ ID 1221 | WRQHSR |
| SEQ ID 1222 | RQHSRE |
| SEQ ID 1223 | QHSREL |
| SEQ ID 1224 | HSRELR |
| SEQ ID 1225 | SRELRL |
| SEQ ID 1226 | RELRLE |
| SEQ ID 1227 | ELRLES |
| SEQ ID 1228 | LRLESI |
| SEQ ID 1229 | RLESIK |
| SEQ ID 1230 | LESIKS |
| SEQ ID 1231 | ESIKSQ |
| SEQ ID 1232 | SIKSQI |
| SEQ ID 1233 | IKSQIL |
| SEQ ID 1234 | KSQILS |
| SEQ ID 1235 | SQILSK |
| SEQ ID 1236 | QILSKL |
| SEQ ID 1237 | ILSKLR |
| SEQ ID 1238 | LSKLRL |
| SEQ ID 1239 | SKLRLK |
| SEQ ID 1240 | KLRLKE |
| SEQ ID 1241 | LRLKEA |

TABLE 5-continued

| | |
|---|---|
| SEQ ID 1242 | RLKEAP |
| SEQ ID 1243 | LKEAPN |
| SEQ ID 1244 | KEAPNI |
| SEQ ID 1245 | EAPNIS |
| SEQ ID 1246 | APNISR |
| SEQ ID 1247 | PNISRE |
| SEQ ID 1248 | NISREV |
| SEQ ID 1249 | ISREVV |
| SEQ ID 1250 | SREVVK |
| SEQ ID 1251 | REVVKQ |
| SEQ ID 1252 | EVVKQL |
| SEQ ID 1253 | VVKQLL |
| SEQ ID 1254 | VKQLLP |
| SEQ ID 1255 | KQLLPK |
| SEQ ID 1256 | QLLPKA |
| SEQ ID 1257 | LLPKAP |
| SEQ ID 1258 | LPKAPP |
| SEQ ID 1259 | PKAPPL |
| SEQ ID 1260 | KAPPLQ |
| SEQ ID 1261 | APPLQQ |
| SEQ ID 1262 | PPLQQI |
| SEQ ID 1263 | PLQQIL |
| SEQ ID 1264 | LQQILD |
| SEQ ID 1265 | QQILDL |
| SEQ ID 1266 | QILDLH |
| SEQ ID 1267 | ILDLHD |
| SEQ ID 1268 | LDLHDF |
| SEQ ID 1269 | DLHDFQ |
| SEQ ID 1270 | LHDFQG |
| SEQ ID 1271 | HDFQGD |
| SEQ ID 1272 | DFQGDA |
| SEQ ID 1273 | FQGDAL |
| SEQ ID 1274 | QGDALQ |
| SEQ ID 1275 | GDALQP |
| SEQ ID 1276 | DALQPE |
| SEQ ID 1277 | ALQPED |
| SEQ ID 1278 | LQPEDF |
| SEQ ID 1279 | QPEDFL |
| SEQ ID 1280 | PEDFLE |
| SEQ ID 1281 | EDFLEE |

TABLE 5-continued

| | |
|---|---|
| SEQ ID 1282 | DFLEED |
| SEQ ID 1283 | FLEEDE |
| SEQ ID 1284 | LEEDEY |
| SEQ ID 1285 | EEDEYH |
| SEQ ID 1286 | EDEYHA |
| SEQ ID 1287 | DEYHAT |
| SEQ ID 1288 | EYHATT |
| SEQ ID 1289 | YHATTE |
| SEQ ID 1290 | HATTET |
| SEQ ID 1291 | ATTETV |
| SEQ ID 1292 | TTETVI |
| SEQ ID 1293 | TETVIS |
| SEQ ID 1294 | ETVISM |
| SEQ ID 1295 | TVISMA |
| SEQ ID 1296 | VISMAQ |
| SEQ ID 1297 | ISMAQE |
| SEQ ID 1298 | SMAQET |
| SEQ ID 1299 | MAQETD |
| SEQ ID 1300 | AQETDP |
| SEQ ID 1301 | QETDPA |
| SEQ ID 1302 | ETDPAV |
| SEQ ID 1303 | TDPAVQ |
| SEQ ID 1304 | DPAVQT |
| SEQ ID 1305 | PAVQTD |
| SEQ ID 1306 | AVQTDG |
| SEQ ID 1307 | VQTDGS |
| SEQ ID 1308 | QTDGSP |
| SEQ ID 1309 | TDGSPL |
| SEQ ID 1310 | DGSPLC |
| SEQ ID 1311 | GSPLCC |
| SEQ ID 1312 | SPLCCH |
| SEQ ID 1313 | PLCCHF |
| SEQ ID 1314 | LCCHFH |
| SEQ ID 1315 | CCHFHF |
| SEQ ID 1316 | CHFHFS |
| SEQ ID 1317 | HFHFSP |
| SEQ ID 1318 | FHFSPK |
| SEQ ID 1319 | HFSPKV |
| SEQ ID 1320 | FSPKVM |
| SEQ ID 1321 | SPKVMF |

TABLE 5-continued

| | |
|---|---|
| SEQ ID 1322 | PKVMFT |
| SEQ ID 1323 | KVMFTK |
| SEQ ID 1324 | VMFTKV |
| SEQ ID 1325 | MFTKVL |
| SEQ ID 1326 | FTKVLK |
| SEQ ID 1327 | TKVLKA |
| SEQ ID 1328 | KVLKAQ |
| SEQ ID 1329 | VLKAQL |
| SEQ ID 1330 | LKAQLW |
| SEQ ID 1331 | KAQLWV |
| SEQ ID 1332 | AQLWVY |
| SEQ ID 1333 | QLWVYL |
| SEQ ID 1334 | LWVYLR |
| SEQ ID 1335 | WVYLRP |
| SEQ ID 1336 | VYLRPV |
| SEQ ID 1337 | YLRPVP |
| SEQ ID 1338 | LRPVPR |
| SEQ ID 1339 | RPVPRP |
| SEQ ID 1340 | PVPRPA |
| SEQ ID 1341 | VPRPAT |
| SEQ ID 1342 | PRPATV |
| SEQ ID 1343 | RPATVY |
| SEQ ID 1344 | PATVYL |
| SEQ ID 1345 | ATVYLQ |
| SEQ ID 1346 | TVYLQI |
| SEQ ID 1347 | VYLQIL |
| SEQ ID 1348 | YLQILR |
| SEQ ID 1349 | LQILRL |
| SEQ ID 1350 | QILRLK |
| SEQ ID 1351 | ILRLKP |
| SEQ ID 1352 | LRLKPL |
| SEQ ID 1353 | RLKPLT |
| SEQ ID 1354 | LKPLTG |
| SEQ ID 1355 | KPLTGE |
| SEQ ID 1356 | PLTGEG |
| SEQ ID 1357 | LTGEGT |
| SEQ ID 1358 | TGEGTA |
| SEQ ID 1359 | GEGTAG |
| SEQ ID 1360 | EGTAGG |
| SEQ ID 1361 | GTAGGG |

TABLE 5-continued

| | |
|---|---|
| SEQ ID 1362 | TAGGGG |
| SEQ ID 1363 | AGGGGG |
| SEQ ID 1364 | GGGGGG |
| SEQ ID 1365 | GGGGGR |
| SEQ ID 1366 | GGGGRR |
| SEQ ID 1367 | GGGRRH |
| SEQ ID 1368 | GGRRHI |
| SEQ ID 1369 | GRRHIR |
| SEQ ID 1370 | RRHIRI |
| SEQ ID 1371 | RHIRIR |
| SEQ ID 1372 | HIRIRS |
| SEQ ID 1373 | IRIRSL |
| SEQ ID 1374 | RIRSLK |
| SEQ ID 1375 | IRSLKI |
| SEQ ID 1376 | RSLKIE |
| SEQ ID 1377 | SLKIEL |
| SEQ ID 1378 | LKIELH |
| SEQ ID 1379 | KIELHS |
| SEQ ID 1380 | IELHSR |
| SEQ ID 1381 | ELHSRS |
| SEQ ID 1382 | LHSRSG |
| SEQ ID 1383 | HSRSGH |
| SEQ ID 1384 | SRSGHW |
| SEQ ID 1385 | RSGHWQ |
| SEQ ID 1386 | SGHWQS |
| SEQ ID 1387 | GHWQSI |
| SEQ ID 1388 | HWQSID |
| SEQ ID 1389 | WQSIDF |
| SEQ ID 1390 | QSIDFK |
| SEQ ID 1391 | SIDFKQ |
| SEQ ID 1392 | IDFKQV |
| SEQ ID 1393 | DFKQVL |
| SEQ ID 1394 | FKQVLH |
| SEQ ID 1395 | KQVLHS |
| SEQ ID 1396 | QVLHSW |
| SEQ ID 1397 | VLHSWF |
| SEQ ID 1398 | LHSWFR |
| SEQ ID 1399 | HSWFRQ |
| SEQ ID 1400 | SWFRQP |
| SEQ ID 1401 | WFRQPQ |

TABLE 5-continued

| | |
|---|---|
| SEQ ID 1402 | FRQPQS |
| SEQ ID 1403 | RQPQSN |
| SEQ ID 1404 | QPQSNW |
| SEQ ID 1405 | PQSNWG |
| SEQ ID 1406 | QSNWGI |
| SEQ ID 1407 | SNWGIE |
| SEQ ID 1408 | NWGIEI |
| SEQ ID 1409 | WGIEIN |
| SEQ ID 1410 | GIEINA |
| SEQ ID 1411 | IEINAF |
| SEQ ID 1412 | EINAFD |
| SEQ ID 1413 | INAFDP |
| SEQ ID 1414 | NAFDPS |
| SEQ ID 1415 | AFDPSG |
| SEQ ID 1416 | FDPSGT |
| SEQ ID 1417 | DPSGTD |
| SEQ ID 1418 | PSGTDL |
| SEQ ID 1419 | SGTDLA |
| SEQ ID 1420 | GTDLAV |
| SEQ ID 1421 | TDLAVT |
| SEQ ID 1422 | DLAVTS |
| SEQ ID 1423 | LAVTSL |
| SEQ ID 1424 | AVTSLG |
| SEQ ID 1425 | VTSLGP |
| SEQ ID 1426 | TSLGPG |
| SEQ ID 1427 | SLGPGA |
| SEQ ID 1428 | LGPGAE |
| SEQ ID 1429 | GPGAEG |
| SEQ ID 1430 | PGAEGL |
| SEQ ID 1431 | GAEGLH |
| SEQ ID 1432 | AEGLHP |
| SEQ ID 1433 | EGLHPF |
| SEQ ID 1434 | GLHPFM |
| SEQ ID 1435 | LHPFME |
| SEQ ID 1436 | HPFMEL |
| SEQ ID 1437 | PFMELR |
| SEQ ID 1438 | FMELRV |
| SEQ ID 1439 | MELRVL |
| SEQ ID 1440 | ELRVLE |
| SEQ ID 1441 | LRVLEN |

TABLE 5-continued

| | |
|---|---|
| SEQ ID 1442 | RVLENT |
| SEQ ID 1443 | VLENTK |
| SEQ ID 1444 | LENTKR |
| SEQ ID 1445 | ENTKRS |
| SEQ ID 1446 | NTKRSR |
| SEQ ID 1447 | TKRSRR |
| SEQ ID 1448 | KRSRRN |
| SEQ ID 1449 | RSRRNL |
| SEQ ID 1450 | SRRNLG |
| SEQ ID 1451 | RRNLGL |
| SEQ ID 1452 | RNLGLD |
| SEQ ID 1453 | NLGLDC |
| SEQ ID 1454 | LGLDCD |
| SEQ ID 1455 | GLDCDE |
| SEQ ID 1456 | LDCDEH |
| SEQ ID 1457 | DCDEHS |
| SEQ ID 1458 | CDEHSS |
| SEQ ID 1459 | DEHSSE |
| SEQ ID 1460 | EHSSES |
| SEQ ID 1461 | HSSESR |
| SEQ ID 1462 | SSESRC |
| SEQ ID 1463 | SESRCC |
| SEQ ID 1464 | ESRCCR |
| SEQ ID 1465 | SRCCRY |
| SEQ ID 1466 | RCCRYP |
| SEQ ID 1467 | CCRYPL |
| SEQ ID 1468 | CRYPLT |
| SEQ ID 1469 | RYPLTV |
| SEQ ID 1470 | YPLTVD |
| SEQ ID 1471 | PLTVDF |
| SEQ ID 1472 | LTVDFE |
| SEQ ID 1473 | TVDFEA |
| SEQ ID 1474 | VDFEAF |
| SEQ ID 1475 | DFEAFG |
| SEQ ID 1476 | FEAFGW |
| SEQ ID 1477 | EAFGWD |
| SEQ ID 1478 | AFGWDW |
| SEQ ID 1479 | FGWDWI |
| SEQ ID 1480 | GWDWII |
| SEQ ID 1481 | WDWIIA |

TABLE 5-continued

| | |
|---|---|
| SEQ ID 1482 | DWIIAP |
| SEQ ID 1483 | WIIAPK |
| SEQ ID 1484 | IIAPKR |
| SEQ ID 1485 | IAPKRY |
| SEQ ID 1486 | APKRYK |
| SEQ ID 1487 | PKRYKA |
| SEQ ID 1488 | KRYKAN |
| SEQ ID 1489 | RYKANY |
| SEQ ID 1490 | YKANYC |
| SEQ ID 1491 | KANYCS |
| SEQ ID 1492 | ANYCSG |
| SEQ ID 1493 | NYCSGQ |
| SEQ ID 1494 | YCSGQC |
| SEQ ID 1495 | CSGQCE |
| SEQ ID 1496 | SGQCEY |
| SEQ ID 1497 | GQCEYM |
| SEQ ID 1498 | QCEYMF |
| SEQ ID 1499 | CEYMFM |
| SEQ ID 1500 | EYMFMQ |
| SEQ ID 1501 | YMFMQK |
| SEQ ID 1502 | MFMQKY |
| SEQ ID 1503 | FMQKYP |
| SEQ ID 1504 | MQKYPH |
| SEQ ID 1505 | QKYPHT |
| SEQ ID 1506 | KYPHTH |
| SEQ ID 1507 | YPHTHL |
| SEQ ID 1508 | PHTHLV |
| SEQ ID 1509 | HTHLVQ |
| SEQ ID 1510 | THLVQQ |
| SEQ ID 1511 | HLVQQA |
| SEQ ID 1512 | LVQQAN |
| SEQ ID 1513 | VQQANP |
| SEQ ID 1514 | QQANPR |
| SEQ ID 1515 | QANPRG |
| SEQ ID 1516 | ANPRGS |
| SEQ ID 1517 | NPRGSA |
| SEQ ID 1518 | PRGSAG |
| SEQ ID 1519 | RGSAGP |
| SEQ ID 1520 | GSAGPC |
| SEQ ID 1521 | SAGPCC |

TABLE 5-continued

| SEQ ID 1522 | AGPCCT |
| --- | --- |
| SEQ ID 1523 | GPCCTP |
| SEQ ID 1524 | PCCTPT |
| SEQ ID 1525 | CCTPTK |
| SEQ ID 1526 | CTPTKM |
| SEQ ID 1527 | TPTKMS |
| SEQ ID 1528 | PTKMSP |
| SEQ ID 1529 | TKMSPI |
| SEQ ID 1530 | KMSPIN |
| SEQ ID 1531 | MSPINM |
| SEQ ID 1532 | SPINML |
| SEQ ID 1533 | PINMLY |
| SEQ ID 1534 | INMLYF |
| SEQ ID 1535 | NMLYFN |
| SEQ ID 1536 | MLYFND |
| SEQ ID 1537 | LYFNDK |
| SEQ ID 1538 | YFNDKQ |
| SEQ ID 1539 | FNDKQQ |
| SEQ ID 1540 | NDKQQI |
| SEQ ID 1541 | DKQQII |
| SEQ ID 1542 | KQQIIY |
| SEQ ID 1543 | QQIIYG |
| SEQ ID 1544 | QIIYGK |
| SEQ ID 1545 | IIYGKI |
| SEQ ID 1546 | IYGKIP |
| SEQ ID 1547 | YGKIPG |
| SEQ ID 1548 | GKIPGM |
| SEQ ID 1549 | KIPGMV |
| SEQ ID 1550 | IPGMVV |
| SEQ ID 1551 | PGMVVD |
| SEQ ID 1552 | GMVVDR |
| SEQ ID 1553 | MVVDRC |
| SEQ ID 1554 | VVDRCG |
| SEQ ID 1555 | VDRCGC |
| SEQ ID 1556 | DRCGCS |

In some embodiments, the active agent comprises a peptide which comprises, consists essentially of, or consists of any one or more of the 7-mer amino acid sequences (SEQ ID NO: 1557-1951) listed below in Table 6.

TABLE 6

| SEQ ID 1557 | MVLAAPL |
| --- | --- |
| SEQ ID 1558 | VLAAPLL |
| SEQ ID 1559 | LAAPLLL |
| SEQ ID 1560 | AAPLLLG |
| SEQ ID 1561 | APLLLGF |
| SEQ ID 1562 | PLLLGFL |
| SEQ ID 1563 | LLLGFLL |
| SEQ ID 1564 | LLGFLLL |
| SEQ ID 1565 | LGFLLLA |
| SEQ ID 1566 | GFLLLAL |
| SEQ ID 1567 | FLLLALE |
| SEQ ID 1568 | LLLALEL |
| SEQ ID 1569 | LLALELR |
| SEQ ID 1570 | LALELRP |
| SEQ ID 1571 | ALELRPR |
| SEQ ID 1572 | LELRPRG |
| SEQ ID 1573 | ELRPRGE |
| SEQ ID 1574 | LRPRGEA |
| SEQ ID 1575 | RPRGEAA |
| SEQ ID 1576 | PRGEAAE |
| SEQ ID 1577 | RGEAAEG |
| SEQ ID 1578 | GEAAEGP |
| SEQ ID 1579 | EAAEGPA |
| SEQ ID 1580 | AAEGPAA |
| SEQ ID 1581 | AEGPAAA |
| SEQ ID 1582 | EGPAAAA |
| SEQ ID 1583 | GPAAAAA |
| SEQ ID 1584 | PAAAAAA |
| SEQ ID 1585 | AAAAAAA |
| SEQ ID 1586 | AAAAAAG |
| SEQ ID 1587 | AAAAAGV |
| SEQ ID 1588 | AAAAGVG |
| SEQ ID 1589 | AAAGVGG |
| SEQ ID 1590 | AAGVGGE |
| SEQ ID 1591 | AGVGGER |
| SEQ ID 1592 | GVGGERS |
| SEQ ID 1593 | VGGERSS |
| SEQ ID 1594 | GGERSSR |
| SEQ ID 1595 | GERSSRP |
| SEQ ID 1596 | ERSSRPA |

TABLE 6-continued

| | |
|---|---|
| SEQ ID 1597 | RSSRPAP |
| SEQ ID 1598 | SSRPAPS |
| SEQ ID 1599 | SRPAPSV |
| SEQ ID 1600 | RPAPSVA |
| SEQ ID 1601 | PAPSVAP |
| SEQ ID 1602 | APSVAPE |
| SEQ ID 1603 | PSVAPEP |
| SEQ ID 1604 | SVAPEPD |
| SEQ ID 1605 | VAPEPDG |
| SEQ ID 1606 | APEPDGC |
| SEQ ID 1607 | PEPDGCP |
| SEQ ID 1608 | EPDGCPV |
| SEQ ID 1609 | PDGCPVC |
| SEQ ID 1610 | DGCPVCV |
| SEQ ID 1611 | GCPVCVW |
| SEQ ID 1612 | CPVCVWR |
| SEQ ID 1613 | PVCVWRQ |
| SEQ ID 1614 | VCVWRQH |
| SEQ ID 1615 | CVWRQHS |
| SEQ ID 1616 | VWRQHSR |
| SEQ ID 1617 | WRQHSRE |
| SEQ ID 1618 | RQHSREL |
| SEQ ID 1619 | QHSRELR |
| SEQ ID 1620 | HSRELRL |
| SEQ ID 1621 | SRELRLE |
| SEQ ID 1622 | RELRLES |
| SEQ ID 1623 | ELRLESI |
| SEQ ID 1624 | LRLESIK |
| SEQ ID 1625 | RLESIKS |
| SEQ ID 1626 | LESIKSQ |
| SEQ ID 1627 | ESIKSQI |
| SEQ ID 1628 | SIKSQIL |
| SEQ ID 1629 | IKSQILS |
| SEQ ID 1630 | KSQILSK |
| SEQ ID 1631 | SQILSKL |
| SEQ ID 1632 | QILSKLR |
| SEQ ID 1633 | ILSKLRL |
| SEQ ID 1634 | LSKLRLK |
| SEQ ID 1635 | SKLRLKE |
| SEQ ID 1636 | KLRLKEA |
| SEQ ID 1637 | LRLKEAP |
| SEQ ID 1638 | RLKEAPN |
| SEQ ID 1639 | LKEAPNI |
| SEQ ID 1640 | KEAPNIS |
| SEQ ID 1641 | EAPNISR |
| SEQ ID 1642 | APNISRE |
| SEQ ID 1643 | PNISREV |
| SEQ ID 1644 | NISREVV |
| SEQ ID 1645 | ISREVVK |
| SEQ ID 1646 | SREVVKQ |
| SEQ ID 1647 | REVVKQL |
| SEQ ID 1648 | EVVKQLL |
| SEQ ID 1649 | VVKQLLP |
| SEQ ID 1650 | VKQLLPK |
| SEQ ID 1651 | KQLLPKA |
| SEQ ID 1652 | QLLPKAP |
| SEQ ID 1653 | LLPKAPP |
| SEQ ID 1654 | LPKAPPL |
| SEQ ID 1655 | PKAPPLQ |
| SEQ ID 1656 | KAPPLQQ |
| SEQ ID 1657 | APPLQQI |
| SEQ ID 1658 | PPLQQIL |
| SEQ ID 1659 | PLQQILD |
| SEQ ID 1660 | LQQILDL |
| SEQ ID 1661 | QQILDLH |
| SEQ ID 1662 | QILDLHD |
| SEQ ID 1663 | ILDLHDF |
| SEQ ID 1664 | LDLHDFQ |
| SEQ ID 1665 | DLHDFQG |
| SEQ ID 1666 | LHDFQGD |
| SEQ ID 1667 | HDFQGDA |
| SEQ ID 1668 | DFQGDAL |
| SEQ ID 1669 | FQGDALQ |
| SEQ ID 1670 | QGDALQP |
| SEQ ID 1671 | GDALQPE |
| SEQ ID 1672 | DALQPED |
| SEQ ID 1673 | ALQPEDF |
| SEQ ID 1674 | LQPEDFL |
| SEQ ID 1675 | QPEDFLE |
| SEQ ID 1676 | PEDFLEE |

TABLE 6-continued

| SEQ ID | Sequence |
|---|---|
| SEQ ID 1677 | EDFLEED |
| SEQ ID 1678 | DFLEEDE |
| SEQ ID 1679 | FLEEDEY |
| SEQ ID 1680 | LEEDEYH |
| SEQ ID 1681 | EEDEYHA |
| SEQ ID 1682 | EDEYHAT |
| SEQ ID 1683 | DEYHATT |
| SEQ ID 1684 | EYHATTE |
| SEQ ID 1685 | YHATTET |
| SEQ ID 1686 | HATTETV |
| SEQ ID 1687 | ATTETVI |
| SEQ ID 1688 | TTETVIS |
| SEQ ID 1689 | TETVISM |
| SEQ ID 1690 | ETVISMA |
| SEQ ID 1691 | TVISMAQ |
| SEQ ID 1692 | VISMAQE |
| SEQ ID 1693 | ISMAQET |
| SEQ ID 1694 | SMAQETD |
| SEQ ID 1695 | MAQETDP |
| SEQ ID 1696 | AQETDPA |
| SEQ ID 1697 | QETDPAV |
| SEQ ID 1698 | ETDPAVQ |
| SEQ ID 1699 | TDPAVQT |
| SEQ ID 1700 | DPAVQTD |
| SEQ ID 1701 | PAVQTDG |
| SEQ ID 1702 | AVQTDGS |
| SEQ ID 1703 | VQTDGSP |
| SEQ ID 1704 | QTDGSPL |
| SEQ ID 1705 | TDGSPLC |
| SEQ ID 1706 | DGSPLCC |
| SEQ ID 1707 | GSPLCCH |
| SEQ ID 1708 | SPLCCHF |
| SEQ ID 1709 | PLCCHFH |
| SEQ ID 1710 | LCCHFHF |
| SEQ ID 1711 | CCHFHFS |
| SEQ ID 1712 | CHFHFSP |
| SEQ ID 1713 | HFHFSPK |
| SEQ ID 1714 | FHFSPKV |
| SEQ ID 1715 | HFSPKVM |
| SEQ ID 1716 | FSPKVMF |
| SEQ ID 1717 | SPKVMFT |
| SEQ ID 1718 | PKVMFTK |
| SEQ ID 1719 | KVMFTKV |
| SEQ ID 1720 | VMFTKVL |
| SEQ ID 1721 | MFTKVLK |
| SEQ ID 1722 | FTKVLKA |
| SEQ ID 1723 | TKVLKAQ |
| SEQ ID 1724 | KVLKAQL |
| SEQ ID 1725 | VLKAQLW |
| SEQ ID 1726 | LKAQLWV |
| SEQ ID 1727 | KAQLWVY |
| SEQ ID 1728 | AQLWVYL |
| SEQ ID 1729 | QLWVYLR |
| SEQ ID 1730 | LWVYLRP |
| SEQ ID 1731 | WVYLRPV |
| SEQ ID 1732 | VYLRPVP |
| SEQ ID 1733 | YLRPVPR |
| SEQ ID 1734 | LRPVPRP |
| SEQ ID 1735 | RPVPRPA |
| SEQ ID 1736 | PVPRPAT |
| SEQ ID 1737 | VPRPATV |
| SEQ ID 1738 | PRPATVY |
| SEQ ID 1739 | RPATVYL |
| SEQ ID 1740 | PATVYLQ |
| SEQ ID 1741 | ATVYLQI |
| SEQ ID 1742 | TVYLQIL |
| SEQ ID 1743 | VYLQILR |
| SEQ ID 1744 | YLQILRL |
| SEQ ID 1745 | LQILRLK |
| SEQ ID 1746 | QILRLKP |
| SEQ ID 1747 | ILRLKPL |
| SEQ ID 1748 | LRLKPLT |
| SEQ ID 1749 | RLKPLTG |
| SEQ ID 1750 | LKPLTGE |
| SEQ ID 1751 | KPLTGEG |
| SEQ ID 1752 | PLTGEGT |
| SEQ ID 1753 | LTGEGTA |
| SEQ ID 1754 | TGEGTAG |
| SEQ ID 1755 | GEGTAGG |
| SEQ ID 1756 | EGTAGGG |

TABLE 6-continued

| | |
|---|---|
| SEQ ID 1757 | GTAGGGG |
| SEQ ID 1758 | TAGGGGG |
| SEQ ID 1759 | AGGGGGG |
| SEQ ID 1760 | GGGGGGR |
| SEQ ID 1761 | GGGGGRR |
| SEQ ID 1762 | GGGGRRH |
| SEQ ID 1763 | GGGRRHI |
| SEQ ID 1764 | GGRRHIR |
| SEQ ID 1765 | GRRHIRI |
| SEQ ID 1766 | RRHIRIR |
| SEQ ID 1767 | RHIRIRS |
| SEQ ID 1768 | HIRIRSL |
| SEQ ID 1769 | IRIRSLK |
| SEQ ID 1770 | RIRSLKI |
| SEQ ID 1771 | IRSLKIE |
| SEQ ID 1772 | RSLKIEL |
| SEQ ID 1773 | SLKIELH |
| SEQ ID 1774 | LKIELHS |
| SEQ ID 1775 | KIELHSR |
| SEQ ID 1776 | IELHSRS |
| SEQ ID 1777 | ELHSRSG |
| SEQ ID 1778 | LHSRSGH |
| SEQ ID 1779 | HSRSGHW |
| SEQ ID 1780 | SRSGHWQ |
| SEQ ID 1781 | RSGHWQS |
| SEQ ID 1782 | SGHWQSI |
| SEQ ID 1783 | GHWQSID |
| SEQ ID 1784 | HWQSIDF |
| SEQ ID 1785 | WQSIDFK |
| SEQ ID 1786 | QSIDFKQ |
| SEQ ID 1787 | SIDFKQV |
| SEQ ID 1788 | IDFKQVL |
| SEQ ID 1789 | DFKQVLH |
| SEQ ID 1790 | FKQVLHS |
| SEQ ID 1791 | KQVLHSW |
| SEQ ID 1792 | QVLHSWF |
| SEQ ID 1793 | VLHSWFR |
| SEQ ID 1794 | LHSWFRQ |
| SEQ ID 1795 | HSWFRQP |
| SEQ ID 1796 | SWFRQPQ |
| SEQ ID 1797 | WFRQPQS |
| SEQ ID 1798 | FRQPQSN |
| SEQ ID 1799 | RQPQSNW |
| SEQ ID 1800 | QPQSNWG |
| SEQ ID 1801 | PQSNWGI |
| SEQ ID 1802 | QSNWGIE |
| SEQ ID 1803 | SNWGIEI |
| SEQ ID 1804 | NWGIEIN |
| SEQ ID 1805 | WGIEINA |
| SEQ ID 1806 | GIEINAF |
| SEQ ID 1807 | IEINAFD |
| SEQ ID 1808 | EINAFDP |
| SEQ ID 1809 | INAFDPS |
| SEQ ID 1810 | NAFDPSG |
| SEQ ID 1811 | AFDPSGT |
| SEQ ID 1812 | FDPSGTD |
| SEQ ID 1813 | DPSGTDL |
| SEQ ID 1814 | PSGTDLA |
| SEQ ID 1815 | SGTDLAV |
| SEQ ID 1816 | GTDLAVT |
| SEQ ID 1817 | TDLAVTS |
| SEQ ID 1818 | DLAVTSL |
| SEQ ID 1819 | LAVTSLG |
| SEQ ID 1820 | AVTSLGP |
| SEQ ID 1821 | VTSLGPG |
| SEQ ID 1822 | TSLGPGA |
| SEQ ID 1823 | SLGPGAE |
| SEQ ID 1824 | LGPGAEG |
| SEQ ID 1825 | GPGAEGL |
| SEQ ID 1826 | PGAEGLH |
| SEQ ID 1827 | GAEGLHP |
| SEQ ID 1828 | AEGLHPF |
| SEQ ID 1829 | EGLHPFM |
| SEQ ID 1830 | GLHPFME |
| SEQ ID 1831 | LHPFMEL |
| SEQ ID 1832 | HPFMELR |
| SEQ ID 1833 | PFMELRV |
| SEQ ID 1834 | FMELRVL |
| SEQ ID 1835 | MELRVLE |
| SEQ ID 1836 | ELRVLEN |

TABLE 6-continued

| | |
|---|---|
| SEQ ID 1837 | LRVLENT |
| SEQ ID 1838 | RVLENTK |
| SEQ ID 1839 | VLENTKR |
| SEQ ID 1840 | LENTKRS |
| SEQ ID 1841 | ENTKRSR |
| SEQ ID 1842 | NTKRSRR |
| SEQ ID 1843 | TKRSRRN |
| SEQ ID 1844 | KRSRRNL |
| SEQ ID 1845 | RSRRNLG |
| SEQ ID 1846 | SRRNLGL |
| SEQ ID 1847 | RRNLGLD |
| SEQ ID 1848 | RNLGLDC |
| SEQ ID 1849 | NLGLDCD |
| SEQ ID 1850 | LGLDCDE |
| SEQ ID 1851 | GLDCDEH |
| SEQ ID 1852 | LDCDEHS |
| SEQ ID 1853 | DCDEHSS |
| SEQ ID 1854 | CDEHSSE |
| SEQ ID 1855 | DEHSSES |
| SEQ ID 1856 | EHSSESR |
| SEQ ID 1857 | HSSESRC |
| SEQ ID 1858 | SSESRCC |
| SEQ ID 1859 | SESRCCR |
| SEQ ID 1860 | ESRCCRY |
| SEQ ID 1861 | SRCCRYP |
| SEQ ID 1862 | RCCRYPL |
| SEQ ID 1863 | CCRYPLT |
| SEQ ID 1864 | CRYPLTV |
| SEQ ID 1865 | RYPLTVD |
| SEQ ID 1866 | YPLTVDF |
| SEQ ID 1867 | PLTVDFE |
| SEQ ID 1868 | LTVDFEA |
| SEQ ID 1869 | TVDFEAF |
| SEQ ID 1870 | VDFEAFG |
| SEQ ID 1871 | DFEAFGW |
| SEQ ID 1872 | FEAFGWD |
| SEQ ID 1873 | EAFGWDW |
| SEQ ID 1874 | AFGWDWI |
| SEQ ID 1875 | FGWDWII |
| SEQ ID 1876 | GWDWIIA |

TABLE 6-continued

| | |
|---|---|
| SEQ ID 1877 | WDWIIAP |
| SEQ ID 1878 | DWIIAPK |
| SEQ ID 1879 | WIIAPKR |
| SEQ ID 1880 | IIAPKRY |
| SEQ ID 1881 | IAPKRYK |
| SEQ ID 1882 | APKRYKA |
| SEQ ID 1883 | PKRYKAN |
| SEQ ID 1884 | KRYKANY |
| SEQ ID 1885 | RYKANYC |
| SEQ ID 1886 | YKANYCS |
| SEQ ID 1887 | KANYCSG |
| SEQ ID 1888 | ANYCSGQ |
| SEQ ID 1889 | NYCSGQC |
| SEQ ID 1890 | YCSGQCE |
| SEQ ID 1891 | CSGQCEY |
| SEQ ID 1892 | SGQCEYM |
| SEQ ID 1893 | GQCEYMF |
| SEQ ID 1894 | QCEYMFM |
| SEQ ID 1895 | CEYMFMQ |
| SEQ ID 1896 | EYMFMQK |
| SEQ ID 1897 | YMFMQKY |
| SEQ ID 1898 | MFMQKYP |
| SEQ ID 1899 | FMQKYPH |
| SEQ ID 1900 | MQKYPHT |
| SEQ ID 1901 | QKYPHTH |
| SEQ ID 1902 | KYPHTHL |
| SEQ ID 1903 | YPHTHLV |
| SEQ ID 1904 | PHTHLVQ |
| SEQ ID 1905 | HTHLVQQ |
| SEQ ID 1906 | THLVQQA |
| SEQ ID 1907 | HLVQQAN |
| SEQ ID 1908 | LVQQANP |
| SEQ ID 1909 | VQQANPR |
| SEQ ID 1910 | QQANPRG |
| SEQ ID 1911 | QANPRGS |
| SEQ ID 1912 | ANPRGSA |
| SEQ ID 1913 | NPRGSAG |
| SEQ ID 1914 | PRGSAGP |
| SEQ ID 1915 | RGSAGPC |
| SEQ ID 1916 | GSAGPCC |

TABLE 6-continued

| SEQ ID 1917 | SAGPCCT |
|---|---|
| SEQ ID 1918 | AGPCCTP |
| SEQ ID 1919 | GPCCTPT |
| SEQ ID 1920 | PCCTPTK |
| SEQ ID 1921 | CCTPTKM |
| SEQ ID 1922 | CTPTKMS |
| SEQ ID 1923 | TPTKMSP |
| SEQ ID 1924 | PTKMSPI |
| SEQ ID 1925 | TKMSPIN |
| SEQ ID 1926 | KMSPINM |
| SEQ ID 1927 | MSPINML |
| SEQ ID 1928 | SPINMLY |
| SEQ ID 1929 | PINMLYF |
| SEQ ID 1930 | INMLYFN |
| SEQ ID 1931 | NMLYFND |
| SEQ ID 1932 | MLYFNDK |
| SEQ ID 1933 | LYFNDKQ |
| SEQ ID 1934 | YFNDKQQ |
| SEQ ID 1935 | FNDKQQI |
| SEQ ID 1936 | NDKQQII |
| SEQ ID 1937 | DKQQIIY |
| SEQ ID 1938 | KQQIIYG |
| SEQ ID 1939 | QQIIYGK |
| SEQ ID 1940 | QIIYGKI |
| SEQ ID 1941 | IIYGKIP |
| SEQ ID 1942 | IYGKIPG |
| SEQ ID 1943 | YGKIPGM |
| SEQ ID 1944 | GKIPGMV |
| SEQ ID 1945 | KIPGMVV |
| SEQ ID 1946 | IPGMVVD |
| SEQ ID 1947 | PGMVVDR |
| SEQ ID 1948 | GMVVDRC |
| SEQ ID 1949 | MVVDRCG |
| SEQ ID 1950 | VVDRCGC |
| SEQ ID 1951 | VDRCGCS |

In some embodiments, the active agent comprises a peptide which comprises, consists essentially of, or consists of any one or more of the 8-mer amino acid sequences (SEQ ID NO: 1952-2346) listed below in Table 7.

TABLE 7

| SEQ ID 1952 | MVLAAPLL |
|---|---|
| SEQ ID 1953 | VLAAPLLL |
| SEQ ID 1954 | LAAPLLLG |
| SEQ ID 1955 | AAPLLLGF |
| SEQ ID 1956 | APLLLGFL |
| SEQ ID 1957 | PLLLGFLL |
| SEQ ID 1958 | LLLGFLLL |
| SEQ ID 1959 | LLGFLLLA |
| SEQ ID 1960 | LGFLLLAL |
| SEQ ID 1961 | GFLLLALE |
| SEQ ID 1962 | FLLLALEL |
| SEQ ID 1963 | LLLALELR |
| SEQ ID 1964 | LLALELRP |
| SEQ ID 1965 | LALELRPR |
| SEQ ID 1966 | ALELRPRG |
| SEQ ID 1967 | LELRPRGE |
| SEQ ID 1968 | ELRPRGEA |
| SEQ ID 1969 | LRPRGEAA |
| SEQ ID 1970 | RPRGEAAE |
| SEQ ID 1971 | PRGEAAEG |
| SEQ ID 1972 | RGEAAEGP |
| SEQ ID 1973 | GEAAEGPA |
| SEQ ID 1974 | EAAEGPAA |
| SEQ ID 1975 | AAEGPAAA |
| SEQ ID 1976 | AEGPAAAA |
| SEQ ID 1977 | EGPAAAAA |
| SEQ ID 1978 | GPAAAAAA |
| SEQ ID 1979 | PAAAAAAA |
| SEQ ID 1980 | AAAAAAAA |
| SEQ ID 1981 | AAAAAAAG |
| SEQ ID 1982 | AAAAAAGV |
| SEQ ID 1983 | AAAAAGVG |
| SEQ ID 1984 | AAAAGVGG |
| SEQ ID 1985 | AAAGVGGE |
| SEQ ID 1986 | AAGVGGER |
| SEQ ID 1987 | AGVGGERS |
| SEQ ID 1988 | GVGGERSS |
| SEQ ID 1989 | VGGERSSR |
| SEQ ID 1990 | GGERSSRP |
| SEQ ID 1991 | GERSSRPA |

TABLE 7-continued

| SEQ ID 1992 | ERSSRPAP |
| SEQ ID 1993 | RSSRPAPS |
| SEQ ID 1994 | SSRPAPSV |
| SEQ ID 1995 | SRPAPSVA |
| SEQ ID 1996 | RPAPSVAP |
| SEQ ID 1997 | PAPSVAPE |
| SEQ ID 1998 | APSVAPEP |
| SEQ ID 1999 | PSVAPEPD |
| SEQ ID 2000 | SVAPEPDG |
| SEQ ID 2001 | VAPEPDGC |
| SEQ ID 2002 | APEPDGCP |
| SEQ ID 2003 | PEPDGCPV |
| SEQ ID 2004 | EPDGCPVC |
| SEQ ID 2005 | PDGCPVCV |
| SEQ ID 2006 | DGCPVCVW |
| SEQ ID 2007 | GCPVCVWR |
| SEQ ID 2008 | CPVCVWRQ |
| SEQ ID 2009 | PVCVWRQH |
| SEQ ID 2010 | VCVWRQHS |
| SEQ ID 2011 | CVWRQHSR |
| SEQ ID 2012 | VWRQHSRE |
| SEQ ID 2013 | WRQHSREL |
| SEQ ID 2014 | RQHSRELR |
| SEQ ID 2015 | QHSRELRL |
| SEQ ID 2016 | HSRELRLE |
| SEQ ID 2017 | SRELRLES |
| SEQ ID 2018 | RELRLESI |
| SEQ ID 2019 | ELRLESIK |
| SEQ ID 2020 | LRLESIKS |
| SEQ ID 2021 | RLESIKSQ |
| SEQ ID 2022 | LESIKSQI |
| SEQ ID 2023 | ESIKSQIL |
| SEQ ID 2024 | SIKSQILS |
| SEQ ID 2025 | IKSQILSK |
| SEQ ID 2026 | KSQILSKL |
| SEQ ID 2027 | SQILSKLR |
| SEQ ID 2028 | QILSKLRL |
| SEQ ID 2029 | ILSKLRLK |
| SEQ ID 2030 | LSKLRLKE |
| SEQ ID 2031 | SKLRLKEA |
| SEQ ID 2032 | KLRLKEAP |
| SEQ ID 2033 | LRLKEAPN |
| SEQ ID 2034 | RLKEAPNI |
| SEQ ID 2035 | LKEAPNIS |
| SEQ ID 2036 | KEAPNISR |
| SEQ ID 2037 | EAPNISRE |
| SEQ ID 2038 | APNISREV |
| SEQ ID 2039 | PNISREVV |
| SEQ ID 2040 | NISREVVK |
| SEQ ID 2041 | ISREVVKQ |
| SEQ ID 2042 | SREVVKQL |
| SEQ ID 2043 | REVVKQLL |
| SEQ ID 2044 | EVVKQLLP |
| SEQ ID 2045 | VVKQLLPK |
| SEQ ID 2046 | VKQLLPKA |
| SEQ ID 2047 | KQLLPKAP |
| SEQ ID 2048 | QLLPKAPP |
| SEQ ID 2049 | LLPKAPPL |
| SEQ ID 2050 | LPKAPPLQ |
| SEQ ID 2051 | PKAPPLQQ |
| SEQ ID 2052 | KAPPLQQI |
| SEQ ID 2053 | APPLQQIL |
| SEQ ID 2054 | PPLQQILD |
| SEQ ID 2055 | PLQQILDL |
| SEQ ID 2056 | LQQILDLH |
| SEQ ID 2057 | QQILDLHD |
| SEQ ID 2058 | QILDLHDF |
| SEQ ID 2059 | ILDLHDFQ |
| SEQ ID 2060 | LDLHDFQG |
| SEQ ID 2061 | DLHDFQGD |
| SEQ ID 2062 | LHDFQGDA |
| SEQ ID 2063 | HDFQGDAL |
| SEQ ID 2064 | DFQGDALQ |
| SEQ ID 2065 | FQGDALQP |
| SEQ ID 2066 | QGDALQPE |
| SEQ ID 2067 | GDALQPED |
| SEQ ID 2068 | DALQPEDF |
| SEQ ID 2069 | ALQPEDFL |
| SEQ ID 2070 | LQPEDFLE |
| SEQ ID 2071 | QPEDFLEE |

TABLE 7-continued

| | |
|---|---|
| SEQ ID 2072 | PEDFLEED |
| SEQ ID 2073 | EDFLEEDE |
| SEQ ID 2074 | DFLEEDEY |
| SEQ ID 2075 | FLEEDEYH |
| SEQ ID 2076 | LEEDEYHA |
| SEQ ID 2077 | EEDEYHAT |
| SEQ ID 2078 | EDEYHATT |
| SEQ ID 2079 | DEYHATTE |
| SEQ ID 2080 | EYHATTET |
| SEQ ID 2081 | YHATTETV |
| SEQ ID 2082 | HATTETVI |
| SEQ ID 2083 | ATTETVIS |
| SEQ ID 2084 | TTETVISM |
| SEQ ID 2085 | TETVISMA |
| SEQ ID 2086 | ETVISMAQ |
| SEQ ID 2087 | TVISMAQE |
| SEQ ID 2088 | VISMAQET |
| SEQ ID 2089 | ISMAQETD |
| SEQ ID 2090 | SMAQETDP |
| SEQ ID 2091 | MAQETDPA |
| SEQ ID 2092 | AQETDPAV |
| SEQ ID 2093 | QETDPAVQ |
| SEQ ID 2094 | ETDPAVQT |
| SEQ ID 2095 | TDPAVQTD |
| SEQ ID 2096 | DPAVQTDG |
| SEQ ID 2097 | PAVQTDGS |
| SEQ ID 2098 | AVQTDGSP |
| SEQ ID 2099 | VQTDGSPL |
| SEQ ID 2100 | QTDGSPLC |
| SEQ ID 2101 | TDGSPLCC |
| SEQ ID 2102 | DGSPLCCH |
| SEQ ID 2103 | GSPLCCHF |
| SEQ ID 2104 | SPLCCHFH |
| SEQ ID 2105 | PLCCHFHF |
| SEQ ID 2106 | LCCHFHFS |
| SEQ ID 2107 | CCHFHFSP |
| SEQ ID 2108 | CHFHFSPK |
| SEQ ID 2109 | HFHFSPKV |
| SEQ ID 2110 | FHFSPKVM |
| SEQ ID 2111 | HFSPKVMF |
| SEQ ID 2112 | FSPKVMFT |
| SEQ ID 2113 | SPKVMFTK |
| SEQ ID 2114 | PKVMFTKV |
| SEQ ID 2115 | KVMFTKVL |
| SEQ ID 2116 | VMFTKVLK |
| SEQ ID 2117 | MFTKVLKA |
| SEQ ID 2118 | FTKVLKAQ |
| SEQ ID 2119 | TKVLKAQL |
| SEQ ID 2120 | KVLKAQLW |
| SEQ ID 2121 | VLKAQLWV |
| SEQ ID 2122 | LKAQLWVY |
| SEQ ID 2123 | KAQLWVYL |
| SEQ ID 2124 | AQLWVYLR |
| SEQ ID 2125 | QLWVYLRP |
| SEQ ID 2126 | LWVYLRPV |
| SEQ ID 2127 | WVYLRPVP |
| SEQ ID 2128 | VYLRPVPR |
| SEQ ID 2129 | YLRPVPRP |
| SEQ ID 2130 | LRPVPRPA |
| SEQ ID 2131 | RPVPRPAT |
| SEQ ID 2132 | PVPRPATV |
| SEQ ID 2133 | VPRPATVY |
| SEQ ID 2134 | PRPATVYL |
| SEQ ID 2135 | RPATVYLQ |
| SEQ ID 2136 | PATVYLQI |
| SEQ ID 2137 | ATVYLQIL |
| SEQ ID 2138 | TVYLQILR |
| SEQ ID 2139 | VYLQILRL |
| SEQ ID 2140 | YLQILRLK |
| SEQ ID 2141 | LQILRLKP |
| SEQ ID 2142 | QILRLKPL |
| SEQ ID 2143 | ILRLKPLT |
| SEQ ID 2144 | LRLKPLTG |
| SEQ ID 2145 | RLKPLTGE |
| SEQ ID 2146 | LKPLTGEG |
| SEQ ID 2147 | KPLTGEGT |
| SEQ ID 2148 | PLTGEGTA |
| SEQ ID 2149 | LTGEGTAG |
| SEQ ID 2150 | TGEGTAGG |
| SEQ ID 2151 | GEGTAGGG |

TABLE 7-continued

| | |
|---|---|
| SEQ ID 2152 | EGTAGGGG |
| SEQ ID 2153 | GTAGGGGG |
| SEQ ID 2154 | TAGGGGGG |
| SEQ ID 2155 | AGGGGGGR |
| SEQ ID 2156 | GGGGGGRR |
| SEQ ID 2157 | GGGGGRRH |
| SEQ ID 2158 | GGGGRRHI |
| SEQ ID 2159 | GGGRRHIR |
| SEQ ID 2160 | GGRRHIRI |
| SEQ ID 2161 | GRRHIRIR |
| SEQ ID 2162 | RRHIRIRS |
| SEQ ID 2163 | RHIRIRSL |
| SEQ ID 2164 | HIRIRSLK |
| SEQ ID 2165 | IRIRSLKI |
| SEQ ID 2166 | RIRSLKIE |
| SEQ ID 2167 | IRSLKIEL |
| SEQ ID 2168 | RSLKIELH |
| SEQ ID 2169 | SLKIELHS |
| SEQ ID 2170 | LKIELHSR |
| SEQ ID 2171 | KIELHSRS |
| SEQ ID 2172 | IELHSRSG |
| SEQ ID 2173 | ELHSRSGH |
| SEQ ID 2174 | LHSRSGHW |
| SEQ ID 2175 | HSRSGHWQ |
| SEQ ID 2176 | SRSGHWQS |
| SEQ ID 2177 | RSGHWQSI |
| SEQ ID 2178 | SGHWQSID |
| SEQ ID 2179 | GHWQSIDF |
| SEQ ID 2180 | HWQSIDFK |
| SEQ ID 2181 | WQSIDFKQ |
| SEQ ID 2182 | QSIDFKQV |
| SEQ ID 2183 | SIDFKQVL |
| SEQ ID 2184 | IDFKQVLH |
| SEQ ID 2185 | DFKQVLHS |
| SEQ ID 2186 | FKQVLHSW |
| SEQ ID 2187 | KQVLHSWF |
| SEQ ID 2188 | QVLHSWFR |
| SEQ ID 2189 | VLHSWFRQ |
| SEQ ID 2190 | LHSWFRQP |
| SEQ ID 2191 | HSWFRQPQ |

TABLE 7-continued

| | |
|---|---|
| SEQ ID 2192 | SWFRQPQS |
| SEQ ID 2193 | WFRQPQSN |
| SEQ ID 2194 | FRQPQSNW |
| SEQ ID 2195 | RQPQSNWG |
| SEQ ID 2196 | QPQSNWGI |
| SEQ ID 2197 | PQSNWGIE |
| SEQ ID 2198 | QSNWGIEI |
| SEQ ID 2199 | SNWGIEIN |
| SEQ ID 2200 | NWGIEINA |
| SEQ ID 2201 | WGIEINAF |
| SEQ ID 2202 | GIEINAFD |
| SEQ ID 2203 | IEINAFDP |
| SEQ ID 2204 | EINAFDPS |
| SEQ ID 2205 | INAFDPSG |
| SEQ ID 2206 | NAFDPSGT |
| SEQ ID 2207 | AFDPSGTD |
| SEQ ID 2208 | FDPSGTDL |
| SEQ ID 2209 | DPSGTDLA |
| SEQ ID 2210 | PSGTDLAV |
| SEQ ID 2211 | SGTDLAVT |
| SEQ ID 2212 | GTDLAVTS |
| SEQ ID 2213 | TDLAVTSL |
| SEQ ID 2214 | DLAVTSLG |
| SEQ ID 2215 | LAVTSLGP |
| SEQ ID 2216 | AVTSLGPG |
| SEQ ID 2217 | VTSLGPGA |
| SEQ ID 2218 | TSLGPGAE |
| SEQ ID 2219 | SLGPGAEG |
| SEQ ID 2220 | LGPGAEGL |
| SEQ ID 2221 | GPGAEGLH |
| SEQ ID 2222 | PGAEGLHP |
| SEQ ID 2223 | GAEGLHPF |
| SEQ ID 2224 | AEGLHPFM |
| SEQ ID 2225 | EGLHPFME |
| SEQ ID 2226 | GLHPFMEL |
| SEQ ID 2227 | LHPFMELR |
| SEQ ID 2228 | HPFMELRV |
| SEQ ID 2229 | PFMELRVL |
| SEQ ID 2230 | FMELRVLE |
| SEQ ID 2231 | MELRVLEN |

TABLE 7-continued

| | |
|---|---|
| SEQ ID 2232 | ELRVLENT |
| SEQ ID 2233 | LRVLENTK |
| SEQ ID 2234 | RVLENTKR |
| SEQ ID 2235 | VLENTKRS |
| SEQ ID 2236 | LENTKRSR |
| SEQ ID 2237 | ENTKRSRR |
| SEQ ID 2238 | NTKRSRRN |
| SEQ ID 2239 | TKRSRRNL |
| SEQ ID 2240 | KRSRRNLG |
| SEQ ID 2241 | RSRRNLGL |
| SEQ ID 2242 | SRRNLGLD |
| SEQ ID 2243 | RRNLGLDC |
| SEQ ID 2244 | RNLGLDCD |
| SEQ ID 2245 | NLGLDCDE |
| SEQ ID 2246 | LGLDCDEH |
| SEQ ID 2247 | GLDCDEHS |
| SEQ ID 2248 | LDCDEHSS |
| SEQ ID 2249 | DCDEHSSE |
| SEQ ID 2250 | CDEHSSES |
| SEQ ID 2251 | DEHSSESR |
| SEQ ID 2252 | EHSSESRC |
| SEQ ID 2253 | HSSESRCC |
| SEQ ID 2254 | SSESRCCR |
| SEQ ID 2255 | SESRCCRY |
| SEQ ID 2256 | ESRCCRYP |
| SEQ ID 2257 | SRCCRYPL |
| SEQ ID 2258 | RCCRYPLT |
| SEQ ID 2259 | CCRYPLTV |
| SEQ ID 2260 | CRYPLTVD |
| SEQ ID 2261 | RYPLTVDF |
| SEQ ID 2262 | YPLTVDFE |
| SEQ ID 2263 | PLTVDFEA |
| SEQ ID 2264 | LTVDFEAF |
| SEQ ID 2265 | TVDFEAFG |
| SEQ ID 2266 | VDFEAFGW |
| SEQ ID 2267 | DFEAFGWD |
| SEQ ID 2268 | FEAFGWDW |
| SEQ ID 2269 | EAFGWDWI |
| SEQ ID 2270 | AFGWDWII |
| SEQ ID 2271 | FGWDWIIA |

TABLE 7-continued

| | |
|---|---|
| SEQ ID 2272 | GWDWIIAP |
| SEQ ID 2273 | WDWIIAPK |
| SEQ ID 2274 | DWIIAPKR |
| SEQ ID 2275 | WIIAPKRY |
| SEQ ID 2276 | IIAPKRYK |
| SEQ ID 2277 | IAPKRYKA |
| SEQ ID 2278 | APKRYKAN |
| SEQ ID 2279 | PKRYKANY |
| SEQ ID 2280 | KRYKANYC |
| SEQ ID 2281 | RYKANYCS |
| SEQ ID 2282 | YKANYCSG |
| SEQ ID 2283 | KANYCSGQ |
| SEQ ID 2284 | ANYCSGQC |
| SEQ ID 2285 | NYCSGQCE |
| SEQ ID 2286 | YCSGQCEY |
| SEQ ID 2287 | CSGQCEYM |
| SEQ ID 2288 | SGQCEYMF |
| SEQ ID 2289 | GQCEYMFM |
| SEQ ID 2290 | QCEYMFMQ |
| SEQ ID 2291 | CEYMFMQK |
| SEQ ID 2292 | EYMFMQKY |
| SEQ ID 2293 | YMFMQKYP |
| SEQ ID 2294 | MFMQKYPH |
| SEQ ID 2295 | FMQKYPHT |
| SEQ ID 2296 | MQKYPHTH |
| SEQ ID 2297 | QKYPHTHL |
| SEQ ID 2298 | KYPHTHLV |
| SEQ ID 2299 | YPHTHLVQ |
| SEQ ID 2300 | PHTHLVQQ |
| SEQ ID 2301 | HTHLVQQA |
| SEQ ID 2302 | THLVQQAN |
| SEQ ID 2303 | HLVQQANP |
| SEQ ID 2304 | LVQQANPR |
| SEQ ID 2305 | VQQANPRG |
| SEQ ID 2306 | QQANPRGS |
| SEQ ID 2307 | QANPRGSA |
| SEQ ID 2308 | ANPRGSAG |
| SEQ ID 2309 | NPRGSAGP |
| SEQ ID 2310 | PRGSAGPC |
| SEQ ID 2311 | RGSAGPCC |

TABLE 7-continued

| | |
|---|---|
| SEQ ID 2312 | GSAGPCCT |
| SEQ ID 2313 | SAGPCCTP |
| SEQ ID 2314 | AGPCCTPT |
| SEQ ID 2315 | GPCCTPTK |
| SEQ ID 2316 | PCCTPTKM |
| SEQ ID 2317 | CCTPTKMS |
| SEQ ID 2318 | CTPTKMSP |
| SEQ ID 2319 | TPTKMSPI |
| SEQ ID 2320 | PTKMSPIN |
| SEQ ID 2321 | TKMSPINM |
| SEQ ID 2322 | KMSPINML |
| SEQ ID 2323 | MSPINMLY |
| SEQ ID 2324 | SPINMLYF |
| SEQ ID 2325 | PINMLYFN |
| SEQ ID 2326 | INMLYFND |
| SEQ ID 2327 | NMLYFNDK |
| SEQ ID 2328 | MLYFNDKQ |
| SEQ ID 2329 | LYFNDKQQ |
| SEQ ID 2330 | YFNDKQQI |
| SEQ ID 2331 | FNDKQQII |
| SEQ ID 2332 | NDKQQIIY |
| SEQ ID 2333 | DKQQIIYG |
| SEQ ID 2334 | KQQIIYGK |
| SEQ ID 2335 | QQIIYGKI |
| SEQ ID 2336 | QIIYGKIP |
| SEQ ID 2337 | IIYGKIPG |
| SEQ ID 2338 | IYGKIPGM |
| SEQ ID 2339 | YGKIPGMV |
| SEQ ID 2340 | GKIPGMVV |
| SEQ ID 2341 | KIPGMVVD |
| SEQ ID 2342 | IPGMVVDR |
| SEQ ID 2343 | PGMVVDRC |
| SEQ ID 2344 | GMVVDRCG |
| SEQ ID 2345 | MVVDRCGC |
| SEQ ID 2346 | VVDRCGCS |

In some embodiments, the active agent comprises a peptide which comprises, consists essentially of, or consists of any one or more of the 9-mer amino acid sequences (SEQ ID NO: 2347-2741) listed below in Table 8.

TABLE 8

| | |
|---|---|
| SEQ ID 2347 | MVLAAPLLL |
| SEQ ID 2348 | VLAAPLLLG |
| SEQ ID 2349 | LAAPLLLGF |
| SEQ ID 2350 | AAPLLLGFL |
| SEQ ID 2351 | APLLLGFLL |
| SEQ ID 2352 | PLLLGFLLL |
| SEQ ID 2353 | LLLGFLLLA |
| SEQ ID 2354 | LLGFLLLAL |
| SEQ ID 2355 | LGFLLLALE |
| SEQ ID 2356 | GFLLLALEL |
| SEQ ID 2357 | FLLLALELR |
| SEQ ID 2358 | LLLALELRP |
| SEQ ID 2359 | LLALELRPR |
| SEQ ID 2360 | LALELRPRG |
| SEQ ID 2361 | ALELRPRGE |
| SEQ ID 2362 | LELRPRGEA |
| SEQ ID 2363 | ELRPRGEAA |
| SEQ ID 2364 | LRPRGEAAE |
| SEQ ID 2365 | RPRGEAAEG |
| SEQ ID 2366 | PRGEAAEGP |
| SEQ ID 2367 | RGEAAEGPA |
| SEQ ID 2368 | GEAAEGPAA |
| SEQ ID 2369 | EAAEGPAAA |
| SEQ ID 2370 | AAEGPAAAA |
| SEQ ID 2371 | AEGPAAAAA |
| SEQ ID 2372 | EGPAAAAAA |
| SEQ ID 2373 | GPAAAAAAA |
| SEQ ID 2374 | PAAAAAAAA |
| SEQ ID 2375 | AAAAAAAAA |
| SEQ ID 2376 | AAAAAAAAG |
| SEQ ID 2377 | AAAAAAAGV |
| SEQ ID 2378 | AAAAAAGVG |
| SEQ ID 2379 | AAAAAGVGG |
| SEQ ID 2380 | AAAAGVGGE |
| SEQ ID 2381 | AAAGVGGER |
| SEQ ID 2382 | AAGVGGERS |
| SEQ ID 2383 | AGVGGERSS |
| SEQ ID 2384 | GVGGERSSR |
| SEQ ID 2385 | VGGERSSRP |
| SEQ ID 2386 | GGERSSRPA |

TABLE 8-continued

| | |
|---|---|
| SEQ ID 2387 | GERSSRPAP |
| SEQ ID 2388 | ERSSRPAPS |
| SEQ ID 2389 | RSSRPAPSV |
| SEQ ID 2390 | SSRPAPSVA |
| SEQ ID 2391 | SRPAPSVAP |
| SEQ ID 2392 | RPAPSVAPE |
| SEQ ID 2393 | PAPSVAPEP |
| SEQ ID 2394 | APSVAPEPD |
| SEQ ID 2395 | PSVAPEPDG |
| SEQ ID 2396 | SVAPEPDGC |
| SEQ ID 2397 | VAPEPDGCP |
| SEQ ID 2398 | APEPDGCPV |
| SEQ ID 2399 | PEPDGCPVC |
| SEQ ID 2400 | EPDGCPVCV |
| SEQ ID 2401 | PDGCPVCVW |
| SEQ ID 2402 | DGCPVCVWR |
| SEQ ID 2403 | GCPVCVWRQ |
| SEQ ID 2404 | CPVCVWRQH |
| SEQ ID 2405 | PVCVWRQHS |
| SEQ ID 2406 | VCVWRQHSR |
| SEQ ID 2407 | CVWRQHSRE |
| SEQ ID 2408 | VWRQHSREL |
| SEQ ID 2409 | WRQHSRELR |
| SEQ ID 2410 | RQHSRELRL |
| SEQ ID 2411 | QHSRELRLE |
| SEQ ID 2412 | HSRELRLES |
| SEQ ID 2413 | SRELRLESI |
| SEQ ID 2414 | RELRLESIK |
| SEQ ID 2415 | ELRLESIKS |
| SEQ ID 2416 | LRLESIKSQ |
| SEQ ID 2417 | RLESIKSQI |
| SEQ ID 2418 | LESIKSQIL |
| SEQ ID 2419 | ESIKSQILS |
| SEQ ID 2420 | SIKSQILSK |
| SEQ ID 2421 | IKSQILSKL |
| SEQ ID 2422 | KSQILSKLR |
| SEQ ID 2423 | SQILSKLRL |
| SEQ ID 2424 | QILSKLRLK |
| SEQ ID 2425 | ILSKLRLKE |
| SEQ ID 2426 | LSKLRLKEA |
| SEQ ID 2427 | SKLRLKEAP |
| SEQ ID 2428 | KLRLKEAPN |
| SEQ ID 2429 | LRLKEAPNI |
| SEQ ID 2430 | RLKEAPNIS |
| SEQ ID 2431 | LKEAPNISR |
| SEQ ID 2432 | KEAPNISRE |
| SEQ ID 2433 | EAPNISREV |
| SEQ ID 2434 | APNISREVV |
| SEQ ID 2435 | PNISREVVK |
| SEQ ID 2436 | NISREVVKQ |
| SEQ ID 2437 | ISREVVKQL |
| SEQ ID 2438 | SREVVKQLL |
| SEQ ID 2439 | REVVKQLLP |
| SEQ ID 2440 | EVVKQLLPK |
| SEQ ID 2441 | VVKQLLPKA |
| SEQ ID 2442 | VKQLLPKAP |
| SEQ ID 2443 | KQLLPKAPP |
| SEQ ID 2444 | QLLPKAPPL |
| SEQ ID 2445 | LLPKAPPLQ |
| SEQ ID 2446 | LPKAPPLQQ |
| SEQ ID 2447 | PKAPPLQQI |
| SEQ ID 2448 | KAPPLQQIL |
| SEQ ID 2449 | APPLQQILD |
| SEQ ID 2450 | PPLQQILDL |
| SEQ ID 2451 | PLQQILDLH |
| SEQ ID 2452 | LQQILDLHD |
| SEQ ID 2453 | QQILDLHDF |
| SEQ ID 2454 | QILDLHDFQ |
| SEQ ID 2455 | ILDLHDFQG |
| SEQ ID 2456 | LDLHDFQGD |
| SEQ ID 2457 | DLHDFQGDA |
| SEQ ID 2458 | LHDFQGDAL |
| SEQ ID 2459 | HDFQGDALQ |
| SEQ ID 2460 | DFQGDALQP |
| SEQ ID 2461 | FQGDALQPE |
| SEQ ID 2462 | QGDALQPED |
| SEQ ID 2463 | GDALQPEDF |
| SEQ ID 2464 | DALQPEDFL |
| SEQ ID 2465 | ALQPEDFLE |
| SEQ ID 2466 | LQPEDFLEE |

TABLE 8-continued

| | |
|---|---|
| SEQ ID 2467 | QPEDFLEED |
| SEQ ID 2468 | PEDFLEEDE |
| SEQ ID 2469 | EDFLEEDEY |
| SEQ ID 2470 | DFLEEDEYH |
| SEQ ID 2471 | FLEEDEYHA |
| SEQ ID 2472 | LEEDEYHAT |
| SEQ ID 2473 | EEDEYHATT |
| SEQ ID 2474 | EDEYHATTE |
| SEQ ID 2475 | DEYHATTET |
| SEQ ID 2476 | EYHATTETV |
| SEQ ID 2477 | YHATTETVI |
| SEQ ID 2478 | HATTETVIS |
| SEQ ID 2479 | ATTETVISM |
| SEQ ID 2480 | TTETVISMA |
| SEQ ID 2481 | TETVISMAQ |
| SEQ ID 2482 | ETVISMAQE |
| SEQ ID 2483 | TVISMAQET |
| SEQ ID 2484 | VISMAQETD |
| SEQ ID 2485 | ISMAQETDP |
| SEQ ID 2486 | SMAQETDPA |
| SEQ ID 2487 | MAQETDPAV |
| SEQ ID 2488 | AQETDPAVQ |
| SEQ ID 2489 | QETDPAVQT |
| SEQ ID 2490 | ETDPAVQTD |
| SEQ ID 2491 | TDPAVQTDG |
| SEQ ID 2492 | DPAVQTDGS |
| SEQ ID 2493 | PAVQTDGSP |
| SEQ ID 2494 | AVQTDGSPL |
| SEQ ID 2495 | VQTDGSPLC |
| SEQ ID 2496 | QTDGSPLCC |
| SEQ ID 2497 | TDGSPLCCH |
| SEQ ID 2498 | DGSPLCCHF |
| SEQ ID 2499 | GSPLCCHFH |
| SEQ ID 2500 | SPLCCHFHF |
| SEQ ID 2501 | PLCCHFHFS |
| SEQ ID 2502 | LCCHFHFSP |
| SEQ ID 2503 | CCHFHFSPK |
| SEQ ID 2504 | CHFHFSPKV |
| SEQ ID 2505 | HFHFSPKVM |
| SEQ ID 2506 | FHFSPKVMF |
| SEQ ID 2507 | HFSPKVMFT |
| SEQ ID 2508 | FSPKVMFTK |
| SEQ ID 2509 | SPKVMFTKV |
| SEQ ID 2510 | PKVMFTKVL |
| SEQ ID 2511 | KVMFTKVLK |
| SEQ ID 2512 | VMFTKVLKA |
| SEQ ID 2513 | MFTKVLKAQ |
| SEQ ID 2514 | FTKVLKAQL |
| SEQ ID 2515 | TKVLKAQLW |
| SEQ ID 2516 | KVLKAQLWV |
| SEQ ID 2517 | VLKAQLWVY |
| SEQ ID 2518 | LKAQLWVYL |
| SEQ ID 2519 | KAQLWVYLR |
| SEQ ID 2520 | AQLWVYLRP |
| SEQ ID 2521 | QLWVYLRPV |
| SEQ ID 2522 | LWVYLRPVP |
| SEQ ID 2523 | WVYLRPVPR |
| SEQ ID 2524 | VYLRPVPRP |
| SEQ ID 2525 | YLRPVPRPA |
| SEQ ID 2526 | LRPVPRPAT |
| SEQ ID 2527 | RPVPRPATV |
| SEQ ID 2528 | PVPRPATVY |
| SEQ ID 2529 | VPRPATVYL |
| SEQ ID 2530 | PRPATVYLQ |
| SEQ ID 2531 | RPATVYLQI |
| SEQ ID 2532 | PATVYLQIL |
| SEQ ID 2533 | ATVYLQILR |
| SEQ ID 2534 | TVYLQILRL |
| SEQ ID 2535 | VYLQILRLK |
| SEQ ID 2536 | YLQILRLKP |
| SEQ ID 2537 | LQILRLKPL |
| SEQ ID 2538 | QILRLKPLT |
| SEQ ID 2539 | ILRLKPLTG |
| SEQ ID 2540 | LRLKPLTGE |
| SEQ ID 2541 | RLKPLTGEG |
| SEQ ID 2542 | LKPLTGEGT |
| SEQ ID 2543 | KPLTGEGTA |
| SEQ ID 2544 | PLTGEGTAG |
| SEQ ID 2545 | LTGEGTAGG |
| SEQ ID 2546 | TGEGTAGGG |

TABLE 8-continued

| | |
|---|---|
| SEQ ID 2547 | GEGTAGGGG |
| SEQ ID 2548 | EGTAGGGGG |
| SEQ ID 2549 | GTAGGGGGG |
| SEQ ID 2550 | TAGGGGGGR |
| SEQ ID 2551 | AGGGGGGRR |
| SEQ ID 2552 | GGGGGGRRH |
| SEQ ID 2553 | GGGGGRRHI |
| SEQ ID 2554 | GGGGRRHIR |
| SEQ ID 2555 | GGGRRHIRI |
| SEQ ID 2556 | GGRRHIRIR |
| SEQ ID 2557 | GRRHIRIRS |
| SEQ ID 2558 | RRHIRIRSL |
| SEQ ID 2559 | RHIRIRSLK |
| SEQ ID 2560 | HIRIRSLKI |
| SEQ ID 2561 | IRIRSLKIE |
| SEQ ID 2562 | RIRSLKIEL |
| SEQ ID 2563 | IRSLKIELH |
| SEQ ID 2564 | RSLKIELHS |
| SEQ ID 2565 | SLKIELHSR |
| SEQ ID 2566 | LKIELHSRS |
| SEQ ID 2567 | KIELHSRSG |
| SEQ ID 2568 | IELHSRSGH |
| SEQ ID 2569 | ELHSRSGHW |
| SEQ ID 2570 | LHSRSGHWQ |
| SEQ ID 2571 | HSRSGHWQS |
| SEQ ID 2572 | SRSGHWQSI |
| SEQ ID 2573 | RSGHWQSID |
| SEQ ID 2574 | SGHWQSIDF |
| SEQ ID 2575 | GHWQSIDFK |
| SEQ ID 2576 | HWQSIDFKQ |
| SEQ ID 2577 | WQSIDFKQV |
| SEQ ID 2578 | QSIDFKQVL |
| SEQ ID 2579 | SIDFKQVLH |
| SEQ ID 2580 | IDFKQVLHS |
| SEQ ID 2581 | DFKQVLHSW |
| SEQ ID 2582 | FKQVLHSWF |
| SEQ ID 2583 | KQVLHSWFR |
| SEQ ID 2584 | QVLHSWFRQ |
| SEQ ID 2585 | VLHSWFRQP |
| SEQ ID 2586 | LHSWFRQPQ |
| SEQ ID 2587 | HSWFRQPQS |
| SEQ ID 2588 | SWFRQPQSN |
| SEQ ID 2589 | WFRQPQSNW |
| SEQ ID 2590 | FRQPQSNWG |
| SEQ ID 2591 | RQPQSNWGI |
| SEQ ID 2592 | QPQSNWGIE |
| SEQ ID 2593 | PQSNWGIEI |
| SEQ ID 2594 | QSNWGIEIN |
| SEQ ID 2595 | SNWGIEINA |
| SEQ ID 2596 | NWGIEINAF |
| SEQ ID 2597 | WGIEINAFD |
| SEQ ID 2598 | GIEINAFDP |
| SEQ ID 2599 | IEINAFDPS |
| SEQ ID 2600 | EINAFDPSG |
| SEQ ID 2601 | INAFDPSGT |
| SEQ ID 2602 | NAFDPSGTD |
| SEQ ID 2603 | AFDPSGTDL |
| SEQ ID 2604 | FDPSGTDLA |
| SEQ ID 2605 | DPSGTDLAV |
| SEQ ID 2606 | PSGTDLAVT |
| SEQ ID 2607 | SGTDLAVTS |
| SEQ ID 2608 | GTDLAVTSL |
| SEQ ID 2609 | TDLAVTSLG |
| SEQ ID 2610 | DLAVTSLGP |
| SEQ ID 2611 | LAVTSLGPG |
| SEQ ID 2612 | AVTSLGPGA |
| SEQ ID 2613 | VTSLGPGAE |
| SEQ ID 2614 | TSLGPGAEG |
| SEQ ID 2615 | SLGPGAEGL |
| SEQ ID 2616 | LGPGAEGLH |
| SEQ ID 2617 | GPGAEGLHP |
| SEQ ID 2618 | PGAEGLHPF |
| SEQ ID 2619 | GAEGLHPFM |
| SEQ ID 2620 | AEGLHPFME |
| SEQ ID 2621 | EGLHPFMEL |
| SEQ ID 2622 | GLHPFMELR |
| SEQ ID 2623 | LHPFMELRV |
| SEQ ID 2624 | HPFMELRVL |
| SEQ ID 2625 | PFMELRVLE |
| SEQ ID 2626 | FMELRVLEN |

TABLE 8-continued

| | |
|---|---|
| SEQ ID 2627 | MELRVLENT |
| SEQ ID 2628 | ELRVLENTK |
| SEQ ID 2629 | LRVLENTKR |
| SEQ ID 2630 | RVLENTKRS |
| SEQ ID 2631 | VLENTKRSR |
| SEQ ID 2632 | LENTKRSRR |
| SEQ ID 2633 | ENTKRSRRN |
| SEQ ID 2634 | NTKRSRRNL |
| SEQ ID 2635 | TKRSRRNLG |
| SEQ ID 2636 | KRSRRNLGL |
| SEQ ID 2637 | RSRRNLGLD |
| SEQ ID 2638 | SRRNLGLDC |
| SEQ ID 2639 | RRNLGLDCD |
| SEQ ID 2640 | RNLGLDCDE |
| SEQ ID 2641 | NLGLDCDEH |
| SEQ ID 2642 | LGLDCDEHS |
| SEQ ID 2643 | GLDCDEHSS |
| SEQ ID 2644 | LDCDEHSSE |
| SEQ ID 2645 | DCDEHSSES |
| SEQ ID 2646 | CDEHSSESR |
| SEQ ID 2647 | DEHSSESRC |
| SEQ ID 2648 | EHSSESRCC |
| SEQ ID 2649 | HSSESRCCR |
| SEQ ID 2650 | SSESRCCRY |
| SEQ ID 2651 | SESRCCRYP |
| SEQ ID 2652 | ESRCCRYPL |
| SEQ ID 2653 | SRCCRYPLT |
| SEQ ID 2654 | RCCRYPLTV |
| SEQ ID 2655 | CCRYPLTVD |
| SEQ ID 2656 | CRYPLTVDF |
| SEQ ID 2657 | RYPLTVDFE |
| SEQ ID 2658 | YPLTVDFEA |
| SEQ ID 2659 | PLTVDFEAF |
| SEQ ID 2660 | LTVDFEAFG |
| SEQ ID 2661 | TVDFEAFGW |
| SEQ ID 2662 | VDFEAFGWD |
| SEQ ID 2663 | DFEAFGWDW |
| SEQ ID 2664 | FEAFGWDWI |
| SEQ ID 2665 | EAFGWDWII |
| SEQ ID 2666 | AFGWDWIIA |
| SEQ ID 2667 | FGWDWIIAP |
| SEQ ID 2668 | GWDWIIAPK |
| SEQ ID 2669 | WDWIIAPKR |
| SEQ ID 2670 | DWIIAPKRY |
| SEQ ID 2671 | WIIAPKRYK |
| SEQ ID 2672 | IIAPKRYKA |
| SEQ ID 2673 | IAPKRYKAN |
| SEQ ID 2674 | APKRYKANY |
| SEQ ID 2675 | PKRYKANYC |
| SEQ ID 2676 | KRYKANYCS |
| SEQ ID 2677 | RYKANYCSG |
| SEQ ID 2678 | YKANYCSGQ |
| SEQ ID 2679 | KANYCSGQC |
| SEQ ID 2680 | ANYCSGQCE |
| SEQ ID 2681 | NYCSGQCEY |
| SEQ ID 2682 | YCSGQCEYM |
| SEQ ID 2683 | CSGQCEYMF |
| SEQ ID 2684 | SGQCEYMFM |
| SEQ ID 2685 | GQCEYMFMQ |
| SEQ ID 2686 | QCEYMFMQK |
| SEQ ID 2687 | CEYMFMQKY |
| SEQ ID 2688 | EYMFMQKYP |
| SEQ ID 2689 | YMFMQKYPH |
| SEQ ID 2690 | MFMQKYPHT |
| SEQ ID 2691 | FMQKYPHTH |
| SEQ ID 2692 | MQKYPHTHL |
| SEQ ID 2693 | QKYPHTHLV |
| SEQ ID 2694 | KYPHTHLVQ |
| SEQ ID 2695 | YPHTHLVQQ |
| SEQ ID 2696 | PHTHLVQQA |
| SEQ ID 2697 | HTHLVQQAN |
| SEQ ID 2698 | THLVQQANP |
| SEQ ID 2699 | HLVQQANPR |
| SEQ ID 2700 | LVQQANPRG |
| SEQ ID 2701 | VQQANPRGS |
| SEQ ID 2702 | QQANPRGSA |
| SEQ ID 2703 | QANPRGSAG |
| SEQ ID 2704 | ANPRGSAGP |
| SEQ ID 2705 | NPRGSAGPC |
| SEQ ID 2706 | PRGSAGPCC |

TABLE 8-continued

| SEQ ID | Sequence |
|---|---|
| SEQ ID 2707 | RGSAGPCCT |
| SEQ ID 2708 | GSAGPCCTP |
| SEQ ID 2709 | SAGPCCTPT |
| SEQ ID 2710 | AGPCCTPTK |
| SEQ ID 2711 | GPCCTPTKM |
| SEQ ID 2712 | PCCTPTKMS |
| SEQ ID 2713 | CCTPTKMSP |
| SEQ ID 2714 | CTPTKMSPI |
| SEQ ID 2715 | TPTKMSPIN |
| SEQ ID 2716 | PTKMSPINM |
| SEQ ID 2717 | TKMSPINML |
| SEQ ID 2718 | KMSPINMLY |
| SEQ ID 2719 | MSPINMLYF |
| SEQ ID 2720 | SPINMLYFN |
| SEQ ID 2721 | PINMLYFND |
| SEQ ID 2722 | INMLYFNDK |
| SEQ ID 2723 | NMLYFNDKQ |
| SEQ ID 2724 | MLYFNDKQQ |
| SEQ ID 2725 | LYFNDKQQI |
| SEQ ID 2726 | YFNDKQQII |
| SEQ ID 2727 | FNDKQQIIY |
| SEQ ID 2728 | NDKQQIIYG |
| SEQ ID 2729 | DKQQIIYGK |
| SEQ ID 2730 | KQQIIYGKI |
| SEQ ID 2731 | QQIIYGKIP |
| SEQ ID 2732 | QIIYGKIPG |
| SEQ ID 2733 | IIYGKIPGM |
| SEQ ID 2734 | IYGKIPGMV |
| SEQ ID 2735 | YGKIPGMVV |
| SEQ ID 2736 | GKIPGMVVD |
| SEQ ID 2737 | KIPGMVVDR |
| SEQ ID 2738 | IPGMVVDRC |
| SEQ ID 2739 | PGMVVDRCG |
| SEQ ID 2740 | GMVVDRCGC |
| SEQ ID 2741 | MVVDRCGCS |

In some embodiments, the active agent comprises a peptide which comprises, consists essentially of, or consists of any one or more of the 10-mer amino acid sequences (SEQ ID NO: 2742-3136) listed below in Table 9.

TABLE 9

| SEQ ID | Sequence |
|---|---|
| SEQ ID 2742 | MVLAAPLLLG |
| SEQ ID 2743 | VLAAPLLLGF |
| SEQ ID 2744 | LAAPLLLGFL |
| SEQ ID 2745 | AAPLLLGFLL |
| SEQ ID 2746 | APLLLGFLLL |
| SEQ ID 2747 | PLLLGFLLLA |
| SEQ ID 2748 | LLLGFLLLAL |
| SEQ ID 2749 | LLGFLLLALE |
| SEQ ID 2750 | LGFLLLALEL |
| SEQ ID 2751 | GFLLLALELR |
| SEQ ID 2752 | FLLLALELRP |
| SEQ ID 2753 | LLLALELRPR |
| SEQ ID 2754 | LLALELRPRG |
| SEQ ID 2755 | LALELRPRGE |
| SEQ ID 2756 | ALELRPRGEA |
| SEQ ID 2757 | LELRPRGEAA |
| SEQ ID 2758 | ELRPRGEAAE |
| SEQ ID 2759 | LRPRGEAAEG |
| SEQ ID 2760 | RPRGEAAEGP |
| SEQ ID 2761 | PRGEAAEGPA |
| SEQ ID 2762 | RGEAAEGPAA |
| SEQ ID 2763 | GEAAEGPAAA |
| SEQ ID 2764 | EAAEGPAAAA |
| SEQ ID 2765 | AAEGPAAAAA |
| SEQ ID 2766 | AEGPAAAAAA |
| SEQ ID 2767 | EGPAAAAAAA |
| SEQ ID 2768 | GPAAAAAAAA |
| SEQ ID 2769 | PAAAAAAAAA |
| SEQ ID 2770 | AAAAAAAAAA |
| SEQ ID 2771 | AAAAAAAAAG |
| SEQ ID 2772 | AAAAAAAAGV |
| SEQ ID 2773 | AAAAAAAGVG |
| SEQ ID 2774 | AAAAAAGVGG |
| SEQ ID 2775 | AAAAAGVGGE |
| SEQ ID 2776 | AAAAGVGGER |
| SEQ ID 2777 | AAAGVGGERS |
| SEQ ID 2778 | AAGVGGERSS |
| SEQ ID 2779 | AGVGGERSSR |
| SEQ ID 2780 | GVGGERSSRP |
| SEQ ID 2781 | VGGERSSRPA |

TABLE 9-continued

| | |
|---|---|
| SEQ ID 2782 | GGERSSRPAP |
| SEQ ID 2783 | GERSSRPAPS |
| SEQ ID 2784 | ERSSRPAPSV |
| SEQ ID 2785 | RSSRPAPSVA |
| SEQ ID 2786 | SSRPAPSVAP |
| SEQ ID 2787 | SRPAPSVAPE |
| SEQ ID 2788 | RPAPSVAPEP |
| SEQ ID 2789 | PAPSVAPEPD |
| SEQ ID 2790 | APSVAPEPDG |
| SEQ ID 2791 | PSVAPEPDGC |
| SEQ ID 2792 | SVAPEPDGCP |
| SEQ ID 2793 | VAPEPDGCPV |
| SEQ ID 2794 | APEPDGCPVC |
| SEQ ID 2795 | PEPDGCPVCV |
| SEQ ID 2796 | EPDGCPVCVW |
| SEQ ID 2797 | PDGCPVCVWR |
| SEQ ID 2798 | DGCPVCVWRQ |
| SEQ ID 2799 | GCPVCVWRQH |
| SEQ ID 2800 | CPVCVWRQHS |
| SEQ ID 2801 | PVCVWRQHSR |
| SEQ ID 2802 | VCVWRQHSRE |
| SEQ ID 2803 | CVWRQHSREL |
| SEQ ID 2804 | VWRQHSRELR |
| SEQ ID 2805 | WRQHSRELRL |
| SEQ ID 2806 | RQHSRELRLE |
| SEQ ID 2807 | QHSRELRLES |
| SEQ ID 2808 | HSRELRLESI |
| SEQ ID 2809 | SRELRLESIK |
| SEQ ID 2810 | RELRLESIKS |
| SEQ ID 2811 | ELRLESIKSQ |
| SEQ ID 2812 | LRLESIKSQI |
| SEQ ID 2813 | RLESIKSQIL |
| SEQ ID 2814 | LESIKSQILS |
| SEQ ID 2815 | ESIKSQILSK |
| SEQ ID 2816 | SIKSQILSKL |
| SEQ ID 2817 | IKSQILSKLR |
| SEQ ID 2818 | KSQILSKLRL |
| SEQ ID 2819 | SQILSKLRLK |
| SEQ ID 2820 | QILSKLRLKE |
| SEQ ID 2821 | ILSKLRLKEA |
| SEQ ID 2822 | LSKLRLKEAP |
| SEQ ID 2823 | SKLRLKEAPN |
| SEQ ID 2824 | KLRLKEAPNI |
| SEQ ID 2825 | LRLKEAPNIS |
| SEQ ID 2826 | RLKEAPNISR |
| SEQ ID 2827 | LKEAPNISRE |
| SEQ ID 2828 | KEAPNISREV |
| SEQ ID 2829 | EAPNISREVV |
| SEQ ID 2830 | APNISREVVK |
| SEQ ID 2831 | PNISREVVKQ |
| SEQ ID 2832 | NISREVVKQL |
| SEQ ID 2833 | ISREVVKQLL |
| SEQ ID 2834 | SREVVKQLLP |
| SEQ ID 2835 | REVVKQLLPK |
| SEQ ID 2836 | EVVKQLLPKA |
| SEQ ID 2837 | VVKQLLPKAP |
| SEQ ID 2838 | VKQLLPKAPP |
| SEQ ID 2839 | KQLLPKAPPL |
| SEQ ID 2840 | QLLPKAPPLQ |
| SEQ ID 2841 | LLPKAPPLQQ |
| SEQ ID 2842 | LPKAPPLQQI |
| SEQ ID 2843 | PKAPPLQQIL |
| SEQ ID 2844 | KAPPLQQILD |
| SEQ ID 2845 | APPLQQILDL |
| SEQ ID 2846 | PPLQQILDLH |
| SEQ ID 2847 | PLQQILDLHD |
| SEQ ID 2848 | LQQILDLHDF |
| SEQ ID 2849 | QQILDLHDFQ |
| SEQ ID 2850 | QILDLHDFQG |
| SEQ ID 2851 | ILDLHDFQGD |
| SEQ ID 2852 | LDLHDFQGDA |
| SEQ ID 2853 | DLHDFQGDAL |
| SEQ ID 2854 | LHDFQGDALQ |
| SEQ ID 2855 | HDFQGDALQP |
| SEQ ID 2856 | DFQGDALQPE |
| SEQ ID 2857 | FQGDALQPED |
| SEQ ID 2858 | QGDALQPEDF |
| SEQ ID 2859 | GDALQPEDFL |
| SEQ ID 2860 | DALQPEDFLE |
| SEQ ID 2861 | ALQPEDFLEE |

TABLE 9-continued

| | |
|---|---|
| SEQ ID 2862 | LQPEDFLEED |
| SEQ ID 2863 | QPEDFLEEDE |
| SEQ ID 2864 | PEDFLEEDEY |
| SEQ ID 2865 | EDFLEEDEYH |
| SEQ ID 2866 | DFLEEDEYHA |
| SEQ ID 2867 | FLEEDEYHAT |
| SEQ ID 2868 | LEEDEYHATT |
| SEQ ID 2869 | EEDEYHATTE |
| SEQ ID 2870 | EDEYHATTET |
| SEQ ID 2871 | DEYHATTETV |
| SEQ ID 2872 | EYHATTETVI |
| SEQ ID 2873 | YHATTETVIS |
| SEQ ID 2874 | HATTETVISM |
| SEQ ID 2875 | ATTETVISMA |
| SEQ ID 2876 | TTETVISMAQ |
| SEQ ID 2877 | TETVISMAQE |
| SEQ ID 2878 | ETVISMAQET |
| SEQ ID 2879 | TVISMAQETD |
| SEQ ID 2880 | VISMAQETDP |
| SEQ ID 2881 | ISMAQETDPA |
| SEQ ID 2882 | SMAQETDPAV |
| SEQ ID 2883 | MAQETDPAVQ |
| SEQ ID 2884 | AQETDPAVQT |
| SEQ ID 2885 | QETDPAVQTD |
| SEQ ID 2886 | ETDPAVQTDG |
| SEQ ID 2887 | TDPAVQTDGS |
| SEQ ID 2888 | DPAVQTDGSP |
| SEQ ID 2889 | PAVQTDGSPL |
| SEQ ID 2890 | AVQTDGSPLC |
| SEQ ID 2891 | VQTDGSPLCC |
| SEQ ID 2892 | QTDGSPLCCH |
| SEQ ID 2893 | TDGSPLCCHF |
| SEQ ID 2894 | DGSPLCCHFH |
| SEQ ID 2895 | GSPLCCHFHF |
| SEQ ID 2896 | SPLCCHFHFS |
| SEQ ID 2897 | PLCCHFHFSP |
| SEQ ID 2898 | LCCHFHFSPK |
| SEQ ID 2899 | CCHFHFSPKV |
| SEQ ID 2900 | CHFHFSPKVM |
| SEQ ID 2901 | HFHFSPKVMF |
| SEQ ID 2902 | FHFSPKVMFT |
| SEQ ID 2903 | HFSPKVMFTK |
| SEQ ID 2904 | FSPKVMFTKV |
| SEQ ID 2905 | SPKVMFTKVL |
| SEQ ID 2906 | PKVMFTKVLK |
| SEQ ID 2907 | KVMFTKVLKA |
| SEQ ID 2908 | VMFTKVLKAQ |
| SEQ ID 2909 | MFTKVLKAQL |
| SEQ ID 2910 | FTKVLKAQLW |
| SEQ ID 2911 | TKVLKAQLWV |
| SEQ ID 2912 | KVLKAQLWVY |
| SEQ ID 2913 | VLKAQLWVYL |
| SEQ ID 2914 | LKAQLWVYLR |
| SEQ ID 2915 | KAQLWVYLRP |
| SEQ ID 2916 | AQLWVYLRPV |
| SEQ ID 2917 | QLWVYLRPVP |
| SEQ ID 2918 | LWVYLRPVPR |
| SEQ ID 2919 | WVYLRPVPRP |
| SEQ ID 2920 | VYLRPVPRPA |
| SEQ ID 2921 | YLRPVPRPAT |
| SEQ ID 2922 | LRPVPRPATV |
| SEQ ID 2923 | RPVPRPATVY |
| SEQ ID 2924 | PVPRPATVYL |
| SEQ ID 2925 | VPRPATVYLQ |
| SEQ ID 2926 | PRPATVYLQI |
| SEQ ID 2927 | RPATVYLQIL |
| SEQ ID 2928 | PATVYLQILR |
| SEQ ID 2929 | ATVYLQILRL |
| SEQ ID 2930 | TVYLQILRLK |
| SEQ ID 2931 | VYLQILRLKP |
| SEQ ID 2932 | YLQILRLKPL |
| SEQ ID 2933 | LQILRLKPLT |
| SEQ ID 2934 | QILRLKPLTG |
| SEQ ID 2935 | ILRLKPLTGE |
| SEQ ID 2936 | LRLKPLTGEG |
| SEQ ID 2937 | RLKPLTGEGT |
| SEQ ID 2938 | LKPLTGEGTA |
| SEQ ID 2939 | KPLTGEGTAG |
| SEQ ID 2940 | PLTGEGTAGG |
| SEQ ID 2941 | LTGEGTAGGG |

TABLE 9-continued

| SEQ ID 2942 | TGEGTAGGGG |
| SEQ ID 2943 | GEGTAGGGGG |
| SEQ ID 2944 | EGTAGGGGGG |
| SEQ ID 2945 | GTAGGGGGGR |
| SEQ ID 2946 | TAGGGGGGRR |
| SEQ ID 2947 | AGGGGGGRRH |
| SEQ ID 2948 | GGGGGGRRHI |
| SEQ ID 2949 | GGGGGRRHIR |
| SEQ ID 2950 | GGGGRRHIRI |
| SEQ ID 2951 | GGGRRHIRIR |
| SEQ ID 2952 | GGRRHIRIRS |
| SEQ ID 2953 | GRRHIRIRSL |
| SEQ ID 2954 | RRHIRIRSLK |
| SEQ ID 2955 | RHIRIRSLKI |
| SEQ ID 2956 | HIRIRSLKIE |
| SEQ ID 2957 | IRIRSLKIEL |
| SEQ ID 2958 | RIRSLKIELH |
| SEQ ID 2959 | IRSLKIELHS |
| SEQ ID 2960 | RSLKIELHSR |
| SEQ ID 2961 | SLKIELHSRS |
| SEQ ID 2962 | LKIELHSRSG |
| SEQ ID 2963 | KIELHSRSGH |
| SEQ ID 2964 | IELHSRSGHW |
| SEQ ID 2965 | ELHSRSGHWQ |
| SEQ ID 2966 | LHSRSGHWQS |
| SEQ ID 2967 | HSRSGHWQSI |
| SEQ ID 2968 | SRSGHWQSID |
| SEQ ID 2969 | RSGHWQSIDF |
| SEQ ID 2970 | SGHWQSIDFK |
| SEQ ID 2971 | GHWQSIDFKQ |
| SEQ ID 2972 | HWQSIDFKQV |
| SEQ ID 2973 | WQSIDFKQVL |
| SEQ ID 2974 | QSIDFKQVLH |
| SEQ ID 2975 | SIDFKQVLHS |
| SEQ ID 2976 | IDFKQVLHSW |
| SEQ ID 2977 | DFKQVLHSWF |
| SEQ ID 2978 | FKQVLHSWFR |
| SEQ ID 2979 | KQVLHSWFRQ |
| SEQ ID 2980 | QVLHSWFRQP |
| SEQ ID 2981 | VLHSWFRQPQ |
| SEQ ID 2982 | LHSWFRQPQS |
| SEQ ID 2983 | HSWFRQPQSN |
| SEQ ID 2984 | SWFRQPQSNW |
| SEQ ID 2985 | WFRQPQSNWG |
| SEQ ID 2986 | FRQPQSNWGI |
| SEQ ID 2987 | RQPQSNWGIE |
| SEQ ID 2988 | QPQSNWGIEI |
| SEQ ID 2989 | PQSNWGIEIN |
| SEQ ID 2990 | QSNWGIEINA |
| SEQ ID 2991 | SNWGIEINAF |
| SEQ ID 2992 | NWGIEINAFD |
| SEQ ID 2993 | WGIEINAFDP |
| SEQ ID 2994 | GIEINAFDPS |
| SEQ ID 2995 | IEINAFDPSG |
| SEQ ID 2996 | EINAFDPSGT |
| SEQ ID 2997 | INAFDPSGTD |
| SEQ ID 2998 | NAFDPSGTDL |
| SEQ ID 2999 | AFDPSGTDLA |
| SEQ ID 3000 | FDPSGTDLAV |
| SEQ ID 3001 | DPSGTDLAVT |
| SEQ ID 3002 | PSGTDLAVTS |
| SEQ ID 3003 | SGTDLAVTSL |
| SEQ ID 3004 | GTDLAVTSLG |
| SEQ ID 3005 | TDLAVTSLGP |
| SEQ ID 3006 | DLAVTSLGPG |
| SEQ ID 3007 | LAVTSLGPGA |
| SEQ ID 3008 | AVTSLGPGAE |
| SEQ ID 3009 | VTSLGPGAEG |
| SEQ ID 3010 | TSLGPGAEGL |
| SEQ ID 3011 | SLGPGAEGLH |
| SEQ ID 3012 | LGPGAEGLHP |
| SEQ ID 3013 | GPGAEGLHPF |
| SEQ ID 3014 | PGAEGLHPFM |
| SEQ ID 3015 | GAEGLHPFME |
| SEQ ID 3016 | AEGLHPFMEL |
| SEQ ID 3017 | EGLHPFMELR |
| SEQ ID 3018 | GLHPFMELRV |
| SEQ ID 3019 | LHPFMELRVL |
| SEQ ID 3020 | HPFMELRVLE |
| SEQ ID 3021 | PFMELRVLEN |

TABLE 9-continued

| | |
|---|---|
| SEQ ID 3022 | FMELRVLENT |
| SEQ ID 3023 | MELRVLENTK |
| SEQ ID 3024 | ELRVLENTKR |
| SEQ ID 3025 | LRVLENTKRS |
| SEQ ID 3026 | RVLENTKRSR |
| SEQ ID 3027 | VLENTKRSRR |
| SEQ ID 3028 | LENTKRSRRN |
| SEQ ID 3029 | ENTKRSRRNL |
| SEQ ID 3030 | NTKRSRRNLG |
| SEQ ID 3031 | TKRSRRNLGL |
| SEQ ID 3032 | KRSRRNLGLD |
| SEQ ID 3033 | RSRRNLGLDC |
| SEQ ID 3034 | SRRNLGLDCD |
| SEQ ID 3035 | RRNLGLDCDE |
| SEQ ID 3036 | RNLGLDCDEH |
| SEQ ID 3037 | NLGLDCDEHS |
| SEQ ID 3038 | LGLDCDEHSS |
| SEQ ID 3039 | GLDCDEHSSE |
| SEQ ID 3040 | LDCDEHSSES |
| SEQ ID 3041 | DCDEHSSESR |
| SEQ ID 3042 | CDEHSSESRC |
| SEQ ID 3043 | DEHSSESRCC |
| SEQ ID 3044 | EHSSESRCCR |
| SEQ ID 3045 | HSSESRCCRY |
| SEQ ID 3046 | SSESRCCRYP |
| SEQ ID 3047 | SESRCCRYPL |
| SEQ ID 3048 | ESRCCRYPLT |
| SEQ ID 3049 | SRCCRYPLTV |
| SEQ ID 3050 | RCCRYPLTVD |
| SEQ ID 3051 | CCRYPLTVDF |
| SEQ ID 3052 | CRYPLTVDFE |
| SEQ ID 3053 | RYPLTVDFEA |
| SEQ ID 3054 | YPLTVDFEAF |
| SEQ ID 3055 | PLTVDFEAFG |
| SEQ ID 3056 | LTVDFEAFGW |
| SEQ ID 3057 | TVDFEAFGWD |
| SEQ ID 3058 | VDFEAFGWDW |
| SEQ ID 3059 | DFEAFGWDWI |
| SEQ ID 3060 | FEAFGWDWII |
| SEQ ID 3061 | EAFGWDWIIA |

TABLE 9-continued

| | |
|---|---|
| SEQ ID 3062 | AFGWDWIIAP |
| SEQ ID 3063 | FGWDWIIAPK |
| SEQ ID 3064 | GWDWIIAPKR |
| SEQ ID 3065 | WDWIIAPKRY |
| SEQ ID 3066 | DWIIAPKRYK |
| SEQ ID 3067 | WIIAPKRYKA |
| SEQ ID 3068 | IIAPKRYKAN |
| SEQ ID 3069 | IAPKRYKANY |
| SEQ ID 3070 | APKRYKANYC |
| SEQ ID 3071 | PKRYKANYCS |
| SEQ ID 3072 | KRYKANYCSG |
| SEQ ID 3073 | RYKANYCSGQ |
| SEQ ID 3074 | YKANYCSGQC |
| SEQ ID 3075 | KANYCSGQCE |
| SEQ ID 3076 | ANYCSGQCEY |
| SEQ ID 3077 | NYCSGQCEYM |
| SEQ ID 3078 | YCSGQCEYMF |
| SEQ ID 3079 | CSGQCEYMFM |
| SEQ ID 3080 | SGQCEYMFMQ |
| SEQ ID 3081 | GQCEYMFMQK |
| SEQ ID 3082 | QCEYMFMQKY |
| SEQ ID 3083 | CEYMFMQKYP |
| SEQ ID 3084 | EYMFMQKYPH |
| SEQ ID 3085 | YMFMQKYPHT |
| SEQ ID 3086 | MFMQKYPHTH |
| SEQ ID 3087 | FMQKYPHTHL |
| SEQ ID 3088 | MQKYPHTHLV |
| SEQ ID 3089 | QKYPHTHLVQ |
| SEQ ID 3090 | KYPHTHLVQQ |
| SEQ ID 3091 | YPHTHLVQQA |
| SEQ ID 3092 | PHTHLVQQAN |
| SEQ ID 3093 | HTHLVQQANP |
| SEQ ID 3094 | THLVQQANPR |
| SEQ ID 3095 | HLVQQANPRG |
| SEQ ID 3096 | LVQQANPRGS |
| SEQ ID 3097 | VQQANPRGSA |
| SEQ ID 3098 | QQANPRGSAG |
| SEQ ID 3099 | QANPRGSAGP |
| SEQ ID 3100 | ANPRGSAGPC |
| SEQ ID 3101 | NPRGSAGPCC |

TABLE 9-continued

| | |
|---|---|
| SEQ ID 3102 | PRGSAGPCCT |
| SEQ ID 3103 | RGSAGPCCTP |
| SEQ ID 3104 | GSAGPCCTPT |
| SEQ ID 3105 | SAGPCCTPTK |
| SEQ ID 3106 | AGPCCTPTKM |
| SEQ ID 3107 | GPCCTPTKMS |
| SEQ ID 3108 | PCCTPTKMSP |
| SEQ ID 3109 | CCTPTKMSPI |
| SEQ ID 3110 | CTPTKMSPIN |
| SEQ ID 3111 | TPTKMSPINM |
| SEQ ID 3112 | PTKMSPINML |
| SEQ ID 3113 | TKMSPINMLY |
| SEQ ID 3114 | KMSPINMLYF |
| SEQ ID 3115 | MSPINMLYFN |
| SEQ ID 3116 | SPINMLYFND |
| SEQ ID 3117 | PINMLYFNDK |
| SEQ ID 3118 | INMLYFNDKQ |
| SEQ ID 3119 | NMLYFNDKQQ |
| SEQ ID 3120 | MLYFNDKQQI |
| SEQ ID 3121 | LYFNDKQQII |
| SEQ ID 3122 | YFNDKQQIIY |
| SEQ ID 3123 | FNDKQQIIYG |
| SEQ ID 3124 | NDKQQIIYGK |
| SEQ ID 3125 | DKQQIIYGKI |
| SEQ ID 3126 | KQQIIYGKIP |
| SEQ ID 3127 | QQIIYGKIPG |
| SEQ ID 3128 | QIIYGKIPGM |
| SEQ ID 3129 | IIYGKIPGMV |
| SEQ ID 3130 | IYGKIPGMVV |
| SEQ ID 3131 | YGKIPGMVVD |
| SEQ ID 3132 | GKIPGMVVDR |
| SEQ ID 3133 | KIPGMVVDRC |
| SEQ ID 3134 | IPGMVVDRCG |
| SEQ ID 3135 | PGMVVDRCGC |
| SEQ ID 3136 | GMVVDRCGCS |

In some embodiments, the active agent comprises a peptide which comprises, consists essentially of, or consists of any one or more of the 11-mer amino acid sequences (SEQ ID NO: 3137-3531) listed below in Table 10.

TABLE 10

| | |
|---|---|
| SEQ ID 3137 | MVLAAPLLLGF |
| SEQ ID 3138 | VLAAPLLLGFL |
| SEQ ID 3139 | LAAPLLLGFLL |
| SEQ ID 3140 | AAPLLLGFLLL |
| SEQ ID 3141 | APLLLGFLLLA |
| SEQ ID 3142 | PLLLGFLLLAL |
| SEQ ID 3143 | LLLGFLLLALE |
| SEQ ID 3144 | LLGFLLLALEL |
| SEQ ID 3145 | LGFLLLALELR |
| SEQ ID 3146 | GFLLLALELRP |
| SEQ ID 3147 | FLLLALELRPR |
| SEQ ID 3148 | LLLALELRPRG |
| SEQ ID 3149 | LLALELRPRGE |
| SEQ ID 3150 | LALELRPRGEA |
| SEQ ID 3151 | ALELRPRGEAA |
| SEQ ID 3152 | LELRPRGEAAE |
| SEQ ID 3153 | ELRPRGEAAEG |
| SEQ ID 3154 | LRPRGEAAEGP |
| SEQ ID 3155 | RPRGEAAEGPA |
| SEQ ID 3156 | PRGEAAEGPAA |
| SEQ ID 3157 | RGEAAEGPAAA |
| SEQ ID 3158 | GEAAEGPAAAA |
| SEQ ID 3159 | EAAEGPAAAAA |
| SEQ ID 3160 | AAEGPAAAAAA |
| SEQ ID 3161 | AEGPAAAAAAA |
| SEQ ID 3162 | EGPAAAAAAAA |
| SEQ ID 3163 | GPAAAAAAAAA |
| SEQ ID 3164 | PAAAAAAAAAA |
| SEQ ID 3165 | AAAAAAAAAAA |
| SEQ ID 3166 | AAAAAAAAAAG |
| SEQ ID 3167 | AAAAAAAAAGV |
| SEQ ID 3168 | AAAAAAAAGVG |
| SEQ ID 3169 | AAAAAAAGVGG |
| SEQ ID 3170 | AAAAAAGVGGE |
| SEQ ID 3171 | AAAAAGVGGER |
| SEQ ID 3172 | AAAAGVGGERS |
| SEQ ID 3173 | AAAGVGGERSS |
| SEQ ID 3174 | AAGVGGERSSR |
| SEQ ID 3175 | AGVGGERSSRP |
| SEQ ID 3176 | GVGGERSSRPA |

TABLE 10-continued

| SEQ ID 3177 | VGGERSSRPAP |
| SEQ ID 3178 | GGERSSRPAPS |
| SEQ ID 3179 | GERSSRPAPSV |
| SEQ ID 3180 | ERSSRPAPSVA |
| SEQ ID 3181 | RSSRPAPSVAP |
| SEQ ID 3182 | SSRPAPSVAPE |
| SEQ ID 3183 | SRPAPSVAPEP |
| SEQ ID 3184 | RPAPSVAPEPD |
| SEQ ID 3185 | PAPSVAPEPDG |
| SEQ ID 3186 | APSVAPEPDGC |
| SEQ ID 3187 | PSVAPEPDGCP |
| SEQ ID 3188 | SVAPEPDGCPV |
| SEQ ID 3189 | VAPEPDGCPVC |
| SEQ ID 3190 | APEPDGCPVCV |
| SEQ ID 3191 | PEPDGCPVCVW |
| SEQ ID 3192 | EPDGCPVCVWR |
| SEQ ID 3193 | PDGCPVCVWRQ |
| SEQ ID 3194 | DGCPVCVWRQH |
| SEQ ID 3195 | GCPVCVWRQHS |
| SEQ ID 3196 | CPVCVWRQHSR |
| SEQ ID 3197 | PVCVWRQHSRE |
| SEQ ID 3198 | VCVWRQHSREL |
| SEQ ID 3199 | CVWRQHSRELR |
| SEQ ID 3200 | VWRQHSRELRL |
| SEQ ID 3201 | WRQHSRELRLE |
| SEQ ID 3202 | RQHSRELRLES |
| SEQ ID 3203 | QHSRELRLESI |
| SEQ ID 3204 | HSRELRLESIK |
| SEQ ID 3205 | SRELRLESIKS |
| SEQ ID 3206 | RELRLESIKSQ |
| SEQ ID 3207 | ELRLESIKSQI |
| SEQ ID 3208 | LRLESIKSQIL |
| SEQ ID 3209 | RLESIKSQILS |
| SEQ ID 3210 | LESIKSQILSK |
| SEQ ID 3211 | ESIKSQILSKL |
| SEQ ID 3212 | SIKSQILSKLR |
| SEQ ID 3213 | IKSQILSKLRL |
| SEQ ID 3214 | KSQILSKLRLK |
| SEQ ID 3215 | SQILSKLRLKE |
| SEQ ID 3216 | QILSKLRLKEA |

TABLE 10-continued

| SEQ ID 3217 | ILSKLRLKEAP |
| SEQ ID 3218 | LSKLRLKEAPN |
| SEQ ID 3219 | SKLRLKEAPNI |
| SEQ ID 3220 | KLRLKEAPNIS |
| SEQ ID 3221 | LRLKEAPNISR |
| SEQ ID 3222 | RLKEAPNISRE |
| SEQ ID 3223 | LKEAPNISREV |
| SEQ ID 3224 | KEAPNISREVV |
| SEQ ID 3225 | EAPNISREVVK |
| SEQ ID 3226 | APNISREVVKQ |
| SEQ ID 3227 | PNISREVVKQL |
| SEQ ID 3228 | NISREVVKQLL |
| SEQ ID 3229 | ISREVVKQLLP |
| SEQ ID 3230 | SREVVKQLLPK |
| SEQ ID 3231 | REVVKQLLPKA |
| SEQ ID 3232 | EVVKQLLPKAP |
| SEQ ID 3233 | VVKQLLPKAPP |
| SEQ ID 3234 | VKQLLPKAPPL |
| SEQ ID 3235 | KQLLPKAPPLQ |
| SEQ ID 3236 | QLLPKAPPLQQ |
| SEQ ID 3237 | LLPKAPPLQQI |
| SEQ ID 3238 | LPKAPPLQQIL |
| SEQ ID 3239 | PKAPPLQQILD |
| SEQ ID 3240 | KAPPLQQILDL |
| SEQ ID 3241 | APPLQQILDLH |
| SEQ ID 3242 | PPLQQILDLHD |
| SEQ ID 3243 | PLQQILDLHDF |
| SEQ ID 3244 | LQQILDLHDFQ |
| SEQ ID 3245 | QQILDLHDFQG |
| SEQ ID 3246 | QILDLHDFQGD |
| SEQ ID 3247 | ILDLHDFQGDA |
| SEQ ID 3248 | LDLHDFQGDAL |
| SEQ ID 3249 | DLHDFQGDALQ |
| SEQ ID 3250 | LHDFQGDALQP |
| SEQ ID 3251 | HDFQGDALQPE |
| SEQ ID 3252 | DFQGDALQPED |
| SEQ ID 3253 | FQGDALQPEDF |
| SEQ ID 3254 | QGDALQPEDFL |
| SEQ ID 3255 | GDALQPEDFLE |
| SEQ ID 3256 | DALQPEDFLEE |

TABLE 10-continued

| | |
|---|---|
| SEQ ID 3257 | ALQPEDFLEED |
| SEQ ID 3258 | LQPEDFLEEDE |
| SEQ ID 3259 | QPEDFLEEDEY |
| SEQ ID 3260 | PEDFLEEDEYH |
| SEQ ID 3261 | EDFLEEDEYHA |
| SEQ ID 3262 | DFLEEDEYHAT |
| SEQ ID 3263 | FLEEDEYHATT |
| SEQ ID 3264 | LEEDEYHATTE |
| SEQ ID 3265 | EEDEYHATTET |
| SEQ ID 3266 | EDEYHATTETV |
| SEQ ID 3267 | DEYHATTETVI |
| SEQ ID 3268 | EYHATTETVIS |
| SEQ ID 3269 | YHATTETVISM |
| SEQ ID 3270 | HATTETVISMA |
| SEQ ID 3271 | ATTETVISMAQ |
| SEQ ID 3272 | TTETVISMAQE |
| SEQ ID 3273 | TETVISMAQET |
| SEQ ID 3274 | ETVISMAQETD |
| SEQ ID 3275 | TVISMAQETDP |
| SEQ ID 3276 | VISMAQETDPA |
| SEQ ID 3277 | ISMAQETDPAV |
| SEQ ID 3278 | SMAQETDPAVQ |
| SEQ ID 3279 | MAQETDPAVQT |
| SEQ ID 3280 | AQETDPAVQTD |
| SEQ ID 3281 | QETDPAVQTDG |
| SEQ ID 3282 | ETDPAVQTDGS |
| SEQ ID 3283 | TDPAVQTDGSP |
| SEQ ID 3284 | DPAVQTDGSPL |
| SEQ ID 3285 | PAVQTDGSPLC |
| SEQ ID 3286 | AVQTDGSPLCC |
| SEQ ID 3287 | VQTDGSPLCCH |
| SEQ ID 3288 | QTDGSPLCCHF |
| SEQ ID 3289 | TDGSPLCCHFH |
| SEQ ID 3290 | DGSPLCCHFHF |
| SEQ ID 3291 | GSPLCCHFHFS |
| SEQ ID 3292 | SPLCCHFHFSP |
| SEQ ID 3293 | PLCCHFHFSPK |
| SEQ ID 3294 | LCCHFHFSPKV |
| SEQ ID 3295 | CCHFHFSPKVM |
| SEQ ID 3296 | CHFHFSPKVMF |
| SEQ ID 3297 | HFHFSPKVMFT |
| SEQ ID 3298 | FHFSPKVMFTK |
| SEQ ID 3299 | HFSPKVMFTKV |
| SEQ ID 3300 | FSPKVMFTKVL |
| SEQ ID 3301 | SPKVMFTKVLK |
| SEQ ID 3302 | PKVMFTKVLKA |
| SEQ ID 3303 | KVMFTKVLKAQ |
| SEQ ID 3304 | VMFTKVLKAQL |
| SEQ ID 3305 | MFTKVLKAQLW |
| SEQ ID 3306 | FTKVLKAQLWV |
| SEQ ID 3307 | TKVLKAQLWVY |
| SEQ ID 3308 | KVLKAQLWVYL |
| SEQ ID 3309 | VLKAQLWVYLR |
| SEQ ID 3310 | LKAQLWVYLRP |
| SEQ ID 3311 | KAQLWVYLRPV |
| SEQ ID 3312 | AQLWVYLRPVP |
| SEQ ID 3313 | QLWVYLRPVPR |
| SEQ ID 3314 | LWVYLRPVPRP |
| SEQ ID 3315 | WVYLRPVPRPA |
| SEQ ID 3316 | VYLRPVPRPAT |
| SEQ ID 3317 | YLRPVPRPATV |
| SEQ ID 3318 | LRPVPRPATVY |
| SEQ ID 3319 | RPVPRPATVYL |
| SEQ ID 3320 | PVPRPATVYLQ |
| SEQ ID 3321 | VPRPATVYLQI |
| SEQ ID 3322 | PRPATVYLQIL |
| SEQ ID 3323 | RPATVYLQILR |
| SEQ ID 3324 | PATVYLQILRL |
| SEQ ID 3325 | ATVYLQILRLK |
| SEQ ID 3326 | TVYLQILRLKP |
| SEQ ID 3327 | VYLQILRLKPL |
| SEQ ID 3328 | YLQILRLKPLT |
| SEQ ID 3329 | LQILRLKPLTG |
| SEQ ID 3330 | QILRLKPLTGE |
| SEQ ID 3331 | ILRLKPLTGEG |
| SEQ ID 3332 | LRLKPLTGEGT |
| SEQ ID 3333 | RLKPLTGEGTA |
| SEQ ID 3334 | LKPLTGEGTAG |
| SEQ ID 3335 | KPLTGEGTAGG |
| SEQ ID 3336 | PLTGEGTAGGG |

TABLE 10-continued

| | |
|---|---|
| SEQ ID 3337 | LTGEGTAGGGG |
| SEQ ID 3338 | TGEGTAGGGGG |
| SEQ ID 3339 | GEGTAGGGGGG |
| SEQ ID 3340 | EGTAGGGGGGR |
| SEQ ID 3341 | GTAGGGGGGRR |
| SEQ ID 3342 | TAGGGGGGRRH |
| SEQ ID 3343 | AGGGGGGRRHI |
| SEQ ID 3344 | GGGGGGRRHIR |
| SEQ ID 3345 | GGGGGRRHIRI |
| SEQ ID 3346 | GGGGRRHIRIR |
| SEQ ID 3347 | GGGRRHIRIRS |
| SEQ ID 3348 | GGRRHIRIRSL |
| SEQ ID 3349 | GRRHIRIRSLK |
| SEQ ID 3350 | RRHIRIRSLKI |
| SEQ ID 3351 | RHIRIRSLKIE |
| SEQ ID 3352 | HIRIRSLKIEL |
| SEQ ID 3353 | IRIRSLKIELH |
| SEQ ID 3354 | RIRSLKIELHS |
| SEQ ID 3355 | IRSLKIELHSR |
| SEQ ID 3356 | RSLKIELHSRS |
| SEQ ID 3357 | SLKIELHSRSG |
| SEQ ID 3358 | LKIELHSRSGH |
| SEQ ID 3359 | KIELHSRSGHW |
| SEQ ID 3360 | IELHSRSGHWQ |
| SEQ ID 3361 | ELHSRSGHWQS |
| SEQ ID 3362 | LHSRSGHWQSI |
| SEQ ID 3363 | HSRSGHWQSID |
| SEQ ID 3364 | SRSGHWQSIDF |
| SEQ ID 3365 | RSGHWQSIDFK |
| SEQ ID 3366 | SGHWQSIDFKQ |
| SEQ ID 3367 | GHWQSIDFKQV |
| SEQ ID 3368 | HWQSIDFKQVL |
| SEQ ID 3369 | WQSIDFKQVLH |
| SEQ ID 3370 | QSIDFKQVLHS |
| SEQ ID 3371 | SIDFKQVLHSW |
| SEQ ID 3372 | IDFKQVLHSWF |
| SEQ ID 3373 | DFKQVLHSWFR |
| SEQ ID 3374 | FKQVLHSWFRQ |
| SEQ ID 3375 | KQVLHSWFRQP |
| SEQ ID 3376 | QVLHSWFRQPQ |

TABLE 10-continued

| | |
|---|---|
| SEQ ID 3377 | VLHSWFRQPQS |
| SEQ ID 3378 | LHSWFRQPQSN |
| SEQ ID 3379 | HSWFRQPQSNW |
| SEQ ID 3380 | SWFRQPQSNWG |
| SEQ ID 3381 | WFRQPQSNWGI |
| SEQ ID 3382 | FRQPQSNWGIE |
| SEQ ID 3383 | RQPQSNWGIEI |
| SEQ ID 3384 | QPQSNWGIEIN |
| SEQ ID 3385 | PQSNWGIEINA |
| SEQ ID 3386 | QSNWGIEINAF |
| SEQ ID 3387 | SNWGIEINAFD |
| SEQ ID 3388 | NWGIEINAFDP |
| SEQ ID 3389 | WGIEINAFDPS |
| SEQ ID 3390 | GIEINAFDPSG |
| SEQ ID 3391 | IEINAFDPSGT |
| SEQ ID 3392 | EINAFDPSGTD |
| SEQ ID 3393 | INAFDPSGTDL |
| SEQ ID 3394 | NAFDPSGTDLA |
| SEQ ID 3395 | AFDPSGTDLAV |
| SEQ ID 3396 | FDPSGTDLAVT |
| SEQ ID 3397 | DPSGTDLAVTS |
| SEQ ID 3398 | PSGTDLAVTSL |
| SEQ ID 3399 | SGTDLAVTSLG |
| SEQ ID 3400 | GTDLAVTSLGP |
| SEQ ID 3401 | TDLAVTSLGPG |
| SEQ ID 3402 | DLAVTSLGPGA |
| SEQ ID 3403 | LAVTSLGPGAE |
| SEQ ID 3404 | AVTSLGPGAEG |
| SEQ ID 3405 | VTSLGPGAEGL |
| SEQ ID 3406 | TSLGPGAEGLH |
| SEQ ID 3407 | SLGPGAEGLHP |
| SEQ ID 3408 | LGPGAEGLHPF |
| SEQ ID 3409 | GPGAEGLHPFM |
| SEQ ID 3410 | PGAEGLHPFME |
| SEQ ID 3411 | GAEGLHPFMEL |
| SEQ ID 3412 | AEGLHPFMELR |
| SEQ ID 3413 | EGLHPFMELRV |
| SEQ ID 3414 | GLHPFMELRVL |
| SEQ ID 3415 | LHPFMELRVLE |
| SEQ ID 3416 | HPFMELRVLEN |

TABLE 10-continued

| | |
|---|---|
| SEQ ID 3417 | PFMELRVLENT |
| SEQ ID 3418 | FMELRVLENTK |
| SEQ ID 3419 | MELRVLENTKR |
| SEQ ID 3420 | ELRVLENTKRS |
| SEQ ID 3421 | LRVLENTKRSR |
| SEQ ID 3422 | RVLENTKRSRR |
| SEQ ID 3423 | VLENTKRSRRN |
| SEQ ID 3424 | LENTKRSRRNL |
| SEQ ID 3425 | ENTKRSRRNLG |
| SEQ ID 3426 | NTKRSRRNLGL |
| SEQ ID 3427 | TKRSRRNLGLD |
| SEQ ID 3428 | KRSRRNLGLDC |
| SEQ ID 3429 | RSRRNLGLDCD |
| SEQ ID 3430 | SRRNLGLDCDE |
| SEQ ID 3431 | RRNLGLDCDEH |
| SEQ ID 3432 | RNLGLDCDEHS |
| SEQ ID 3433 | NLGLDCDEHSS |
| SEQ ID 3434 | LGLDCDEHSSE |
| SEQ ID 3435 | GLDCDEHSSES |
| SEQ ID 3436 | LDCDEHSSESR |
| SEQ ID 3437 | DCDEHSSESRC |
| SEQ ID 3438 | CDEHSSESRCC |
| SEQ ID 3439 | DEHSSESRCCR |
| SEQ ID 3440 | EHSSESRCCRY |
| SEQ ID 3441 | HSSESRCCRYP |
| SEQ ID 3442 | SSESRCCRYPL |
| SEQ ID 3443 | SESRCCRYPLT |
| SEQ ID 3444 | ESRCCRYPLTV |
| SEQ ID 3445 | SRCCRYPLTVD |
| SEQ ID 3446 | RCCRYPLTVDF |
| SEQ ID 3447 | CCRYPLTVDFE |
| SEQ ID 3448 | CRYPLTVDFEA |
| SEQ ID 3449 | RYPLTVDFEAF |
| SEQ ID 3450 | YPLTVDFEAFG |
| SEQ ID 3451 | PLTVDFEAFGW |
| SEQ ID 3452 | LTVDFEAFGWD |
| SEQ ID 3453 | TVDFEAFGWDW |
| SEQ ID 3454 | VDFEAFGWDWI |
| SEQ ID 3455 | DFEAFGWDWII |
| SEQ ID 3456 | FEAFGWDWIIA |
| SEQ ID 3457 | EAFGWDWIIAP |
| SEQ ID 3458 | AFGWDWIIAPK |
| SEQ ID 3459 | FGWDWIIAPKR |
| SEQ ID 3460 | GWDWIIAPKRY |
| SEQ ID 3461 | WDWIIAPKRYK |
| SEQ ID 3462 | DWIIAPKRYKA |
| SEQ ID 3463 | WIIAPKRYKAN |
| SEQ ID 3464 | IIAPKRYKANY |
| SEQ ID 3465 | IAPKRYKANYC |
| SEQ ID 3466 | APKRYKANYCS |
| SEQ ID 3467 | PKRYKANYCSG |
| SEQ ID 3468 | KRYKANYCSGQ |
| SEQ ID 3469 | RYKANYCSGQC |
| SEQ ID 3470 | YKANYCSGQCE |
| SEQ ID 3471 | KANYCSGQCEY |
| SEQ ID 3472 | ANYCSGQCEYM |
| SEQ ID 3473 | NYCSGQCEYMF |
| SEQ ID 3474 | YCSGQCEYMFM |
| SEQ ID 3475 | CSGQCEYMFMQ |
| SEQ ID 3476 | SGQCEYMFMQK |
| SEQ ID 3477 | GQCEYMFMQKY |
| SEQ ID 3478 | QCEYMFMQKYP |
| SEQ ID 3479 | CEYMFMQKYPH |
| SEQ ID 3480 | EYMFMQKYPHT |
| SEQ ID 3481 | YMFMQKYPHTH |
| SEQ ID 3482 | MFMQKYPHTHL |
| SEQ ID 3483 | FMQKYPHTHLV |
| SEQ ID 3484 | MQKYPHTHLVQ |
| SEQ ID 3485 | QKYPHTHLVQQ |
| SEQ ID 3486 | KYPHTHLVQQA |
| SEQ ID 3487 | YPHTHLVQQAN |
| SEQ ID 3488 | PHTHLVQQANP |
| SEQ ID 3489 | HTHLVQQANPR |
| SEQ ID 3490 | THLVQQANPRG |
| SEQ ID 3491 | HLVQQANPRGS |
| SEQ ID 3492 | LVQQANPRGSA |
| SEQ ID 3493 | VQQANPRGSAG |
| SEQ ID 3494 | QQANPRGSAGP |
| SEQ ID 3495 | QANPRGSAGPC |
| SEQ ID 3496 | ANPRGSAGPCC |

TABLE 10-continued

| | |
|---|---|
| SEQ ID 3497 | NPRGSAGPCCT |
| SEQ ID 3498 | PRGSAGPCCTP |
| SEQ ID 3499 | RGSAGPCCTPT |
| SEQ ID 3500 | GSAGPCCTPTK |
| SEQ ID 3501 | SAGPCCTPTKM |
| SEQ ID 3502 | AGPCCTPTKMS |
| SEQ ID 3503 | GPCCTPTKMSP |
| SEQ ID 3504 | PCCTPTKMSPI |
| SEQ ID 3505 | CCTPTKMSPIN |
| SEQ ID 3506 | CTPTKMSPINM |
| SEQ ID 3507 | TPTKMSPINML |
| SEQ ID 3508 | PTKMSPINMLY |
| SEQ ID 3509 | TKMSPINMLYF |
| SEQ ID 3510 | KMSPINMLYFN |
| SEQ ID 3511 | MSPINMLYFND |
| SEQ ID 3512 | SPINMLYFNDK |
| SEQ ID 3513 | PINMLYFNDKQ |
| SEQ ID 3514 | INMLYFNDKQQ |
| SEQ ID 3515 | NMLYFNDKQQI |
| SEQ ID 3516 | MLYFNDKQQII |
| SEQ ID 3517 | LYFNDKQQIIY |
| SEQ ID 3518 | YFNDKQQIIYG |
| SEQ ID 3519 | FNDKQQIIYGK |
| SEQ ID 3520 | NDKQQIIYGKI |
| SEQ ID 3521 | DKQQIIYGKIP |
| SEQ ID 3522 | KQQIIYGKIPG |
| SEQ ID 3523 | QQIIYGKIPGM |
| SEQ ID 3524 | QIIYGKIPGMV |
| SEQ ID 3525 | IIYGKIPGMVV |
| SEQ ID 3526 | IYGKIPGMVVD |
| SEQ ID 3527 | YGKIPGMVVDR |
| SEQ ID 3528 | GKIPGMVVDRC |
| SEQ ID 3529 | KIPGMVVDRCG |
| SEQ ID 3530 | IPGMVVDRCGC |
| SEQ ID 3531 | PGMVVDRCGCS |

One aspect of the invention provides an active agent comprising a peptide comprising an amino acid sequence derived from GDF-11 having the following sequence:

(SEQ ID NO: 1193)
AAAGVG (Ala-Ala-Ala-Gly-Val-Gly).

Another aspect of the invention provides an active agent comprising a peptide comprising an amino acid sequence derived from GDF-11 having the following sequence:

(SEQ ID NO: 1581)
AEGPAAA (Ala-Glu-Gly-Pro-Ala-Ala-Ala)

Yet another aspect of the invention provides an active agent comprising a peptide comprising an amino acid sequence derived from GDF-11 having the following sequence:

(SEQ ID NO: 3338)
TGEGTAGGGGG (Thr-Gly-Glu-Gly-

Thr-Ala-Gly-Gly-Gly-Gly-Gly).

In some embodiments, the peptides may comprise one, two, three or more conservative substitutions of amino acids. As used herein, a "conservative substitution" is one in which substitution of one amino acid for another does not impair the function of the peptide, including substitution of an amino acid having a side chain of a certain nature (e.g., acidic, basic, aromatic, aliphatic uncharged, non-polar uncharged, hydrophilic uncharged) by another amino acid having a side chain of the same nature. Examples of conservative substitutions are shown below in Table 11.

TABLE 11

| Conservative Substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In some embodiments, the peptides may comprise one, two, three or more (e.g., one, two, three, etc.) non-natural and/or non-proteinogenic amino acids substituted or in place a comparable number of amino acids in SEQ ID NOs. 2-3531. In some embodiments, the peptides of the invention may comprise modified variants of SEQ ID NOs 2-3531 wherein at least one of the amino acids is replaced by the "D" (dextrorotary) analogue of the natural "L" optical isomer found in SEQ ID Nos 2-3531. In another embodiment, at least one (e.g., one, two, three, etc.) of the amino acids found in SEQ ID Nos. 2-2531 are replaced with a non-naturally occurring and/or non-proteogenic amino acid according to Formulas (III) or (IV) as detailed below.

In one embodiment, the peptide sequence will comprise at least three consecutive alanine residues. In one embodiment, the peptide sequence will comprise at least three consecutive glycine residues.

The peptides of the invention can be modified to improve the lipophilicity, stability, or to enhance penetration through the stratum corneum. In some embodiments, the peptides are modified with a fatty acid chain (e.g., $C_{6-22}$), such as palmitoyl. In some embodiments, at least one of the nitrogen atoms in the amide bonds between adjacent amino acids may be methylated to improve metabolic stability. The peptides may also be phosphorylated, for example by forming one or more phosphoserine, phosphothreonine and/or phosphotyrosine residues.

In some embodiments, the modified peptides will have the structure according to Formula (I):

$$R_1\text{-}\Omega\text{-}R_2 \quad (I)$$

where $\Omega$ represents a peptide of the invention (e.g., comprising any of SEQ ID 2-3531) and $R_1$ and $R_2$ are independently either absent or are selected from hydrogen or $C_{1-26}$ ($C_{1-6}$ or $C_{6-12}$ or $C_{12-18}$ or $C_{18-22}$) hydrocarbons, optionally substituted with a group $X_1$ or with 1-20 (or 1-10 or 1-6 or 1-3) heteroatoms selected from halogen (e.g., fluorine), oxygen, nitrogen, phosphorous, sulfur, silicon and combinations thereof (more typically, oxygen and nitrogen). In some embodiments, one of $R_1$ and $R_2$ is a $C_{1-26}$ hydrocarbon. In some embodiments, only one of $R_1$ and $R_2$ is a $C_{1-26}$ hydrocarbon. In some embodiments, one of $R_1$ and $R_2$ is a $C_{1-26}$ hydrocarbon selected from the group consisting of alkyl, alkenyl, alkynyl, aryl, alkyl-aryl (e.g., benzyl), and aryl-alkyl optionally substituted with halogen (e.g., fluorine), oxygen, nitrogen, phosphorous, sulfur, and combinations thereof, in various embodiments comprising heteroatoms selected from halogen (e.g., fluorine), oxygen, nitrogen, phosphorous, sulfur, and combinations thereof, in various embodiments comprising from 1-10 or 1-6 or 1-3 heteroatoms. In some embodiments, $R_1$ and/or $R_2$ may comprise a group of the form R—(C=O)—, where R is a $C_{1-25}$ hydrocarbon as described above. In one embodiment, $R_1$ and/or $R_2$ may comprise an acyl group, for example, one having the form $CH_3$—$(CH_3)_n$-(C=O)— where "n" is an integer from 0-25 (e.g., zero or from 7-17). In one embodiment, $R_1$ and/or $R_2$ may comprise an acetyl group of the form $CH_3$—(C=O)—. In one embodiment, $R_1$ and/or $R_2$ may comprise a palmitoyl group of the form $CH_3$—$(CH_3)_{14}$—(C=O)—. $R_1$ and/or $R_2$ may be attached to a nitrogen atom on the peptide so thereby form an amide bond of the form $\Omega$-NH—(C=O)—R, formed, for example, through the reaction of an acid of the form R—(C=O)—OH (or activated derivative of the acid) with a nitrogen atom on the N-terminal amino group of the peptide or a nitrogen atom on a side chain (e.g., lysine) of the peptide. In some embodiments, $R_1$ and/or $R_2$ may be attached to the peptide through an amide bond of the form $\Omega$-(C=O)—NH—R, formed, for example, by reaction of an amine of the form R—NH with the carboxyl terminus of the peptide or on a carboxyl-containing side chain (e.g., aspartic acid or glutamic acid). In some embodiments, $R_1$ and/or $R_2$ may be attached to the peptide through an ester bond of the form $\Omega$-(C=O)—O—R, formed, for example, through the reaction of an alcohol of the form R—OH with the carboxyl terminus of the peptide or carboxyl side chain (e.g., aspartic acid or glutamic acid). In some embodiments, $R_1$ and/or $R_2$ may be attached to the peptide through an ester bond of the form $\Omega$-O—(C=O)—R, formed, for example, by the reaction of an acid of the form R—(C=O)—OH with a hydroxyl group on an amino acid side chain (e.g., serine or threonine). In any case where an acid is reacted, the acid may first be activated according to conventional practice by first converting it to an anhydride, acid halide, or activated ester, such as an N-hydroxysuccinimide ester, etc. It is also contemplated that $R_1$ and/or $R_2$ may be attached to the peptide through thioester bonds of the form $\Omega$-S—(C=O)—R, thioether bonds of the form $\Omega$-S—R, ether bonds of the form $\Omega$-O—R, and amines of the form of the form $\Omega$-$NR^N$—R, to name but a few non-limiting examples. In various embodiments, R may be branched (e.g., ethylhexyl), cyclic, or straight chained. R and $R^N$ may be, without limitation methyl, ethyl, propyl, butyl, pentyl, hexyl, heptyl, octyl, nonyl, decyl, undecyl, dodecyl, or $C_{13}$, or $C_{14}$, or $C_{15}$, or $C_{16}$, or $C_{17}$, or $C_{18}$, or $C_{19}$, or $C_{20}$, or $C_{21}$, or $C_{22}$, or $C_{23}$, or $C_{24}$, or $C_{25}$, or $C_{26}$ alkyl, akenyl, or akynyl, etc, optionally substituted with a group $X_1$ or heteroatoms selected from halogen (e.g., fluorine), oxygen, nitrogen, phosphorous, sulfur, silicon, and combinations thereof, in various embodiments comprising from 1-10 or 1-6 or 1-3 heteroatoms. Any of the groups R, $R_1$, $R_2$ and $R^N$ may be further substituted with from 1-3 groups $X_1$ where $X_1$ is selected independently at each occurrence from hydrogen, —F; —Cl; —Br; —I; —OH, —OR*; —$NH_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —$CO_2$H; —$CO_2$—; —$CO_2$R*; —(C=O)—S—R*; —O—(C=O)—H; —O—(C=O)—R*; —S—(C=O)—R*; —(C=O)—$NH_2$; —(C=O)—N(R*)$_2$; —(C=O)—$NHNH_2$; —O—(C=O)—$NHNH_2$; —(C=S)—$NH_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —$SO_2$—R*; —O—S(=O)$_2$—R*; —S(=O)$_2$—OR*; —N(R*)—$SO_2$—R*; —$SO_2$—N(R*)$_2$; —O—$SO_3$—R*; —O—S(=O)$_2$—OR*; —O—S(=O)—OR*; —O—S(=O)—R*; —S(=O)—OR*; —S(=O)—OR*; —S(=O)—R*; —NO; —$NO_2$; —$NO_3$; —O—NO; —O—$NO_2$; —$N_3$; —$N_2$—R*; —N($C_2H_4$); —Si(R*)$_3$; —$CF_3$; —O—$CF_3$; —$PR^*_2$; —O—P(=O)(OR*)$_2$; —P(=O)(OR*)$_2$, $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical. R* is a $C_{1-10}$ hydrocarbon, such as methyl, ethyl, propyl, butyl, pentyl, hexyl, benzyl, phenyl, etc. Any two of R, R*, $R^N$, $R_1$, and $R_2$ may together form a 3-8 membered, optionally heterocyclic ring.

In some embodiments, $R_1$ or $R_2$ is attached covalently to the terminal carboxyl group. In some embodiments, $R_1$ and/or $R_2$ is attached to the terminal amino group. In some embodiments, $R_1$ and/or $R_2$ is attached to a side chain having a nitrogen, oxygen, or sulfur atom.

In some embodiments, $R_1$ and/or $R_2$ promotes adhesion to or penetration of an integument. In some embodiments, $R_1$ and/or $R_2$ comprise biotin, a beta-keto ester, or a polyarginine sequence (e.g., having 3-15 arginines).

The peptide can be pegylated to enhance water-solubility. In some embodiments, $R_1$ and/or $R_2$ have the form —(OCH$_2$CH$_2$)y-Z or —(CH$_2$CH$_2$O)y-Z, where "y" is an integer from 1-20 (or from 1-10 or from 1-6 or from 1-3) and Z is H, $R_3$, $X_1$, or $R_4$—$X_1$, where $R_3$ and $R_4$ are independently branched, straight chained, or cyclic $C_{1-6}$ hydrocarbons (e.g., methyl, ethyl, propyl, methylene, —(CH$_2$)$_n$— (n=1-6), etc.). In some embodiments, $R_1$ and/or $R_2$ comprise mini-PEG (i.e., 11-amino-3,6,9-trioxaundecanoic acid).

The peptides $\Omega$ of the invention can be modified to improve stability or function by incorporating one or more additional amino acids to either or both ends of SEQ ID NO: 2-3531 according to Formula (II):

$$\Psi_1\text{-}\Phi\text{-}\Psi_2 \quad (II)$$

where $\Phi$ represents a peptide of the invention (e.g., a peptide comprising any of SEQ ID NO: 2-3531) and $\Psi_1$ and $\Psi_2$ are independently either absent or are selected from hydrogen, an amino acid, a non-natural amino acid, a non-proteinogenic amino acid, a di- or tri-peptide, or combinations thereof. Suitable amino acids include without limitation, Alanine, Cysteine, Aspartic acid, Glutamic acid, Phenylalanine, Glycine, Histidine, Isoleucine, Lysine, Leucine, Methionine, Asparagine, Pyrrolysine, Proline, Glutamine, Arginine, Serine, Threonine, Selenocysteine, Valine, Tryptophan, and Tyrosine. Each of the foregoing (except glycine) may be in the "L" or "D" optical isomeric configurations. The non-natural amino acid or non-proteinogenic amino acids may be, for example, a dextrorotary "D" optical isomer of a naturally occurring L-amino acid. The non-natural amino acid or non-proteinogenic amino acids may, for example, have the structure of formula (III) or (IV):

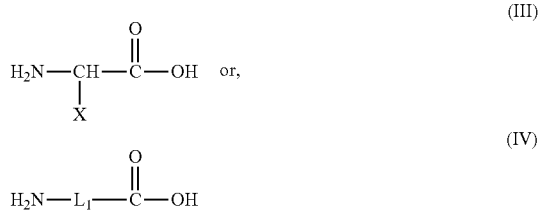

where X is selected from $X_1$, $C_{1-26}$ ($C_{1-6}$ or $C_{6-12}$ or $C_{12-18}$ or $C_{18-22}$) hydrocarbons, optionally substituted with a group $X_1$ or with from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof. In some embodiments, X is ethyl, propyl, butyl, pentyl, hexyl, heptyl, octyl, nonyl, decyl, undecyl, dodecyl. In some embodiments, X is $C_{1-12}$ or $C_{26}$ alkyl, akenyl, akynyl, aryl, aryl-alkyl, alkyl-aryl, alkyl-aryl-alkyl, heteroaryl, alkyl-heteroaryl, heteroaryl-alkyl, alkyl-heteroaryl-alkyl, etc., optionally substituted with $X_1$, or with 1-20 (or 1-10 or 1-6 or 1-3) heteroatoms selected from halogen (e.g., fluorine), oxygen, nitrogen, phosphorous, sulfur, and combinations thereof. In some embodiments, X comprises a fused ring system having two, three, or more 5- or 6-membered rings. $L_1$ is a hydrocarbon spacer comprising from 1-20 carbon atoms and optionally substituted with a group $X_1$ or from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof. In some embodiments, $L_1$ will have the form —$(CH_3)p$- where "p" is an integer from 1-20 or from 1-10 or from 1-6. In some embodiments, $L_1$ will comprise from 1-6 oxo or oxa groups. In one embodiment, the amino acid of formula (IV) is aminoethanoic acid, aminopropionic acid, aminobutyric acid, aminovaleric acid, aminocaproic acid, aminoenanthic acid, aminocaprylic acid, amino pelargonicacid, or aminocapric acid. In one embodiment, $\Psi_1$ and/or $\Psi_2$ comprises lysyl-aminovaleric acid or aminovaleric acid-lysyl. In some embodiments either terminus may be functionalized with an amino acid of the form $H_2N$—$(CH_2)_q$—$CO_2H$ where "q" is an integer from 1-10, including amino valeric acid. In some embodiments, a lysine-amino valeric acid group is added at either terminus through a peptide bond. In some embodiments, $\Psi_1$ and/or $\Psi_2$ comprise oligomers having 2-16 or 2-8 or 2-6 or 2-4 amino acids, for example, naturally occurring amino acids. The peptides can also be cyclized.

The peptides of formula (II) may further be modified according to formula (I) such that they have the form of formula (V):

wherein, any of $R_1$, $R_2$, $\Psi_1$, and $\Psi_2$ may be absent but are otherwise defined as above.

Peptides of the invention may have one or more additional amino acids joined to the amino and/or carboxy terminus via peptide bonds. For example, polyarginine (n=2-15) may be beneficially used to enhance penetration of the peptide into skin. In some embodiments, the peptides will comprise a hydrocarbon chain on the amino and/or carboxyl terminus, including, without limitation, $C_{1-24}$ or $C_{6-18}$ or $C_{12-18}$ aliphatic hydrocarbons, which may be straight chained or branched or cyclic. In some embodiments, the peptides include the reaction product of a peptide with a fatty acid or fatty alcohol. A fatty acid or alcohol, as used herein, contains 6-26 carbon atoms. For example, the N-terminus may be reacted with a $C_{6-24}$ fatty acid (e.g., palmitic acid) to form an amide bond. The carboxyl terminus may be reacted with a $C_{6-24}$ fatty alcohol (e.g., cetyl alcohol) to form an ester. These fatty derivatives may improve the lipophilicity of the peptide.

Topically acceptable salts and prodrugs (collectively "derivatives") of the peptides of the invention are also suitable. Salts will typically be acid addition salts formed by the reaction of the peptide with an inorganic or an organic acid. Inorganic acids include mineral acids such as HCl and $H_2SO_4$, and the like. Organic acids include citric, benzoic, tartaric, malic, maleic, succinic, acetic, and propionic acid. The peptides may exist in zwitterionic form. Prodrugs include any esters or amides that hydrolyze in vivo to yield the peptide. Examples of suitable prodrugs can be found in the book entitled "Prodrugs and Targeted Delivery: Towards Better ADME Properties," Volume 47 (2011), published by WILEY-VCH Verlag & Co, which is herein incorporated by reference in its entirety. In one embodiment, the prodrug is formed by reacting the peptide with glyoxylic acid to produce peptidyl-α-hydroxylglycine derivatives having improved stability. In other embodiment the prodrugs may include terminal N-acetyl derivatives, side chain N-acetyl derivatives, N-hydroxy methylation or N-phthalidation of its N-terminus and/or side chain.

It is within the skill in the art to prepare peptides using, for example, conventional protection and activation chemistry. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), tert-butoxycarbonyl (t-Boc), and 9-flourenylmethloxycarbonyl (FMOC). The carboxyl group may be protected by forming an acid or base labile ester such as a methyl, ethyl, benzyl, or trimethylsilyl esters. After protection, the first and second amino acids are reacted in a suitable solvent such as water or DMF in the presence of an in situ activating agent such as N,N'-dicyclohexylcarbodiimide (DCCI), diisopropylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as tert-butyl or benzyl for OH and SH; methyl, ethyl, tert-butyl or benzyl for carboxyl groups, and 2,2,5,7,8-pentamethylchroman-6-sulphonyl for the $NHC(NH_2)$=NH functionality of Arg. Following the coupling reaction, selective deprotection of the amino group of the first amino acid is accomplished by acid hydrolysis under conditions that do not remove the carboxyl protecting group of the second amino acid. The procedure is repeated with additional amino protected amino acids. Solid phase synthesis, such as the well-known Merrifield method, is especially useful for synthesizing the peptides of the invention. Lysine-amino valeric acid (K-ava) derivatives are described in U.S. Pat. No. 8,551,956, the disclosure of which is hereby incorporated by reference.

Topical Compositions

The compositions according to the invention may be formulated in a variety of forms for topical application and will typically comprise from about 0.000001% by weight to about 20% by weight of the peptide. More typically, the peptide will comprise from about 0.00001% by weight to about 10% by weight, and more preferably from about 0.00001% by weight to about 5% by weight of the composition. In one embodiment, the active peptide or a fragment or derivative thereof will comprise from about 0.001% by weight to about 1% by weight or from about 0.001% by weight or to about 0.1% by weight of the composition. The compositions may comprise an effective amount of the peptide, by which is meant an amount sufficient to stimulate production of collagen in the skin. In other embodiments, the amount of peptide or derivative thereof will be sufficient to diminish the appearance of dermatological signs of aging in a given area of skin when topically applied thereto daily for a period of at least eight weeks.

The peptides of the invention (e.g., comprising any of SEQ ID NOs: 2-3531) are provided in physiologically acceptable vehicles or carriers. The vehicle may be either hydrophobic or hydrophilic. Suitable, hydrophobic carriers include, for example, waxy non-ionic substances commonly used in cosmetics, such as esters and ethers of fatty alcohols and of fatty acids, with carbon chain length from $C_4$ to $C_{22}$, typically from $C_8$ to $C_{18}$, or from $C_{12}$ to $C_{18}$.

Examples of fatty hydrophobic carriers include isopropyl myristate, isopropyl palmitate, octyl palmitate, isopropyl lanolate, acetylated lanolin alcohol, the benzoate of $C_{12}$-$C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, isopropyl isostearate, and the like.

Suitable hydrophilic carriers may comprise, for example, water, lower alcohols ($C_{1-6}$) such as ethanol, mixtures of ethanol and water, glycols, and alkoxylated glycols commonly used in cosmetics, including ethylene glycol, diethylene glycol, triethylene glycol, propylene glycol, dipropylene glycol, and the like.

The topically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, or a gellant, typically in an amount from about 0.001% to about 5% by weight.

The topically acceptable vehicle may include water; vegetable oils; mineral oils; ester oils; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 50% to about 99% by weight of the composition. In some embodiments, the compositions are anhydrous.

In one embodiment of the invention, the compositions may include one or more additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few. The amounts of these various ingredients are those conventionally used in the cosmetic field to achieve their intended purpose, and range individually or collectively typically from about 0.001 wt % to about 20 wt % by weight of the composition. The nature of these ingredients and their amounts must be compatible with the production and function of the compositions of the disclosure.

Exemplary anti-aging components include, without limitation, botanicals (e.g., *Butea frondosa* extract, *Tiliacora triandra* extract, *Portulaca oleracea*, *Melicope elleryana*, etc.); phytol; phytonic acid; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA) in amounts effective to stabilize the retinoid (e.g., 0.0001%-5%). The composition may include from 0.001-10% by weight phytol.

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one embodiment, the composition comprises thiodipropionic acid or a mono- or diester thereof such as dilauryl thiodipropionic acid. Antioxidants may comprise, individually or collectively, from about 0.001% to about 10% (w/w), or from about 0.01% to about 5% (w/w) of the total weight of the composition.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, and vegetable gums such as xanthan gum; gelling agents, such as ester-terminated polyester amides; structuring agents; metal chelating agents such as EDTA or salts thereof; fillers and powders, colorants, pH adjusters (citric acid, ethanolamine, sodium hydroxide, etc.); film formers, moisturizers, minerals, viscosity and/or rheology modifiers, anti-acne agents, anti-inflammatories, depigmenting agents, pharmaceutical agents, surfactants, botanicals, sunscreens, insect repellents, skin cooling compounds, skin protectants, conditioners, lubricants, fragrances, excipients, preservatives, stabilizers, emulsifiers, and mixtures thereof. The foregoing may individually or collectively comprise from about 0.0001% to about 20% by weight of the composition.

Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute individually or in the aggregate, from about 0.01% to about 20% of the total weight of the composition.

A sunscreen may be included to protect the skin from damaging ultraviolet rays. The sunscreen may provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, homosalate, oxybenzone, octocrylene, titanium dioxide, zinc oxide, or any mixtures thereof. The sunscreen may be present from about 1 wt % to about 30 wt % of the total weight of the composition.

In one embodiment, the topical composition will have a pH range from 1 to 13, with a pH in the range of from 2 to 12 being typical. In some embodiment, the composition will have a pH in the range of from 3.5 to 7 or from 7-10.5. In some embodiments, the pH will be in the range of 3-4, or 4-5, or 5-6, or 6-7, or 7-8, or 8-9, or 9-10, or 10-11, or 11-12. Suitable pH adjusters such as sodium hydroxide, citric acid and triethanolamine may be added to bring the pH within the desired range.

Another embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

The compositions may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. The composition is typically formulated as a lotion, cream, ointment, serum, or gel.

Methods of Treatment

The invention also provides a method for ameliorating and/or preventing signs of human skin photo- and intrinsic aging comprising topically applying the compositions of the invention. The compositions of the invention are preferably applied to affected skin areas once or twice daily for as long as is necessary to achieve desired anti-aging results. In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

In some embodiments, methods for enhancing the production of pro-collagen, collagen and/or HA in human skin comprise topically applying to an area of the skin in need thereof (e.g., sagging skin, thinning skin, skin suffering from wrinkles and fine lines, etc.) a topical composition comprising a topically acceptable vehicle, and an effective amount of a peptide of the invention (e.g., comprising any of SEQ ID NOs: 2-3531), for a time sufficient to enhance the levels of pro-collagen, collagen, and/or HA in the dermis. The treatment may be at least once or twice daily and may last for a period of at least four weeks, typically at least eight weeks, twelve weeks, or longer.

In another aspect of the invention, the compositions are applied topically to improve the aesthetic appearance of human skin. The method comprises topically applying to an area of the skin in need thereof a composition comprising an effective amount of a peptide of the invention (e.g., comprising any of SEQ ID NOs: 2-3531) for a time sufficient to improve the aesthetic appearance of said human skin. The composition may optionally further comprise a retinoid (e.g., from 0.0001-5%) and/or an alpha-hydroxy acid (e.g., glycolic acid) (e.g., from 0.0001-25%) and/or a beta-hydroxy acid (e.g., salicylic acid or a derivative) (e.g., from 0.0001-15%).

The improvement in aesthetic appearance of human skin may be an improvement of any attribute or characteristic of skin, including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;

(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

As used herein, "aesthetic improvement" may be measured by evaluation of before and after pictures by panels of dermatologists, or by other objective measures known in the art.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition comprising a peptide of the invention (e.g., comprising any of SEQ ID NOs: 2-3531), for a time sufficient to reduce the visibility, number, or depth of said wrinkles and/or fine lines. The treatment may be a least once or twice daily and may last for a period of at least four weeks, typically at least eight weeks, twelve weeks, or longer. The composition may optionally further comprise a retinoid (e.g., retinol or retinol palmitate) and/or an alpha-hydroxy acid (e.g., glycolic acid) and/or a beta-hydroxy acid (e.g., salicylic acid or derivative) in amounts effective to improve the appearance of skin. In some embodiments, methods reduce the severity of, reduce the number of, or prevent or forestall the onset of, wrinkles or fine lines on human skin. The composition may be topically applied to an area of the skin in need thereof (e.g., directly to wrinkled skin), an effective amount (e.g., 0.000001%-1% by weight, w/w) of a peptide of the invention (e.g., comprising any of SEQ ID NOs: 2-3531) in combination with an effective amount (e.g., 0.01%-5% by weight, w/w) of retinol and/or an effective amount (e.g., 0.001%-20% by weight, w/w) of an alpha-hydroxy acid (e.g., glycolic acid) and/or a beta-hydroxy acid (e.g., salicylic acid). The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

Topically application of a composition comprising a peptide comprising any of SEQ ID NOs: 2-3531, typically in a physiologically acceptable vehicle, over an affected area of skin may remediate, reverse, reduce, ameliorate, or prevent dermatological signs of aging. Generally, the improvement in the condition and/or appearance of skin is selected from the group consisting of: reducing dermatological signs of chronological aging, photo-aging, hormonal aging, and/or actinic aging; preventing and/or reducing the appearance of lines or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

It is also contemplated that the compositions of the invention will be useful for treating thin skin by topically applying the composition comprising the active peptides (e.g., comprising any of SEQ ID NOs: 2-3531) to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention comprising active peptides (e.g., comprising any of SEQ ID NOs: 2-3531) are applied to human skin to reduce sebum production or improve the appearance of skin affected by cellulite, and/or reduce unwanted lipogenesis or increase lipolysis. In this embodiment, the peptides of the invention can be formulated in topically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

In certain embodiments, the compositions described herein comprising active peptides (e.g., comprising any of SEQ ID NOs: 2-3531) can be used to treat and/or prevent hyper-pigmentation of skin and/or of the hair, for example, to lighten skin or hair. In some embodiments, the compositions are topically applied to the skin or hair, for example to an area of hyper-pigmented skin or hair. Hyper-pigmentation includes any coloration of an individual's skin or hair that is darker than desired by the individual and that is caused by melanocytes. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, for example, skin tanned due to UV exposure. Hyper-pigmented hair includes any shade of hair that is darker than desired.

Treating hyper-pigmentation or hyper-pigmented skin/ hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be effective in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In some embodiments, the compositions of the invention are used in a rotational, alternating, or sequential treatment regimen comprising topical application of the compositions of the invention for a first period of time (e.g., at least once daily for at least one day), followed by a second period of time in which at least one additional treatment modality is administered for at least one additional day following said first period of time. The second treatment modality may comprise topical application of any skin benefit agent, such as a retinoid (e.g., retinol), phytol, antioxidants (e.g., ascorbic acid or TDPA or esters thereof), botanicals, such as *Tiliacora triandra*, niacinamide, vitamins such as Vitamin E and Vitamin E acetate, salicylic acid, salicylates and derivatives thereof, moisturizers, emollients, etc.

In another embodiment, the peptides of the invention (e.g., comprising any of SEQ ID NOs: 2-3531) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms (including lyophilized powders of the peptide suitable for reconstitution with water). Pharmaceutical compositions may also be in the form of creams, serums, etc., or formulated for injection. Pharmaceutical dosage forms will typically include from about 0.1 mg to about 200 mg, or from about 1 mg to about 100 mg of the peptides of the invention.

Solid dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

The following example illustrates a specific aspect of the instant description. The example should not be construed as limiting, as the example merely provides specific understanding and practice of the embodiments and its various aspects.

Example 1

The peptides of the invention were synthesized by GenScript (Piscataway, N.J.).

Human dermal fibroblast cells were grown in a 96 well plate in DMEM media (available from Corning, N.Y.) supplemented with 10% Fetal Bovine Serum (FBS) and L-glutamine ($0.07 \times 10^5$ cells/plate). After reaching about 75% confluence, cells were transferred into DMEM media without FBS and incubated for 4-6 hours. Next, cells were treated with a peptide at 0.00001%, 0.0001%, 0.001% final concentration in DMEM media without FBS for 48 h. After treatment, the media were collected and cell viability was measured using MTT. The amount of collagen secreted was tested in the media using HTRF human pro-collagen I kit (available from Cisbio Inc., Bedford, Mass.). The amount of secreted Hyaluronic Acid (HA) was tested in the media using HA Elisa kit (available from Corgenix, Broomfield, Colo.).

The results are summarized in Table 12 below as percent change of pro-collagen I and/or HA production relative to vehicle control (peptide concentrations provided in parentheses) using the following keys:

Pro-Collagen I Increase Key: 0: <10%, +: 10-30%, ++: 30-50%, +++: 50-70%, ++++: >70%

HA Increase Key: 0: <20%, +: 20-50%, ++: 50-90%, +++: 90-150%, ++++: >150%

TABLE 12

| Peptide Sequence | Increase in Pro-Collagen I Production | Increase in HA Production |
|---|---|---|
| GDALQPE (SEQ ID NO: 1671) | 0 | 0 |
| QPED (SEQ ID NO: 491) | 0 | 0 |
| LRLK (SEQ ID NO: 453) | 0 | +(0.001%) |
| MVV (SEQ ID NO: 369) | 0 | +(0.0001%) |

TABLE 12-continued

| Peptide Sequence | Increase in Pro-Collagen I Production | Increase in HA Production |
|---|---|---|
| LENTKRS (SEQ ID NO: 1840) | 0 | 0 |
| QILSKLRL (SEQ ID NO: 2028) | +(0.001%) | N/A |

As shown in Table 12, peptides of the invention effectively increase pro-collagen I and/or hyaluronic acid production in human dermal fibroblast cells.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

The invention claimed is:

1. A method for diminishing the appearance of dermatological signs of aging comprising topically applying to the skin in need thereof a composition comprising, in a topically acceptable vehicle, an active agent comprising a GDF-11 peptide fragment consisting of the sequence LRLK (SEQ ID NO: 453), MVV (SEQ ID NO: 369), or QILSKLRL (SEQ ID NO: 2028), and/or $C_{1-24}$ aliphatic derivatives thereof.

2. The method according to claim 1, wherein said dermatological signs of aging include fine lines and/or wrinkles.

3. The method according to claim 1, wherein said active agent increases collagen production in skin.

4. The method according to claim 1, wherein said active agent increases hyaluronic acid production in skin.

5. The method according to claim 1, wherein said composition is applied at least once daily for at least eight weeks.

\* \* \* \* \*

SEQUENCE LISTING

```
<160> NUMBER OF SEQ ID NOS: 3531

<210> SEQ ID NO 1
<211> LENGTH: 407
<212> TYPE: PRT
<213> ORGANISM: Homo sapiens

<400> SEQUENCE: 1

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
```

-continued

```
                275                 280                 285
        Val Leu Glu Asn Thr Lys Arg Ser Arg Arg Asn Leu Gly Leu Asp Cys
            290                 295                 300
        Asp Glu His Ser Ser Glu Ser Arg Cys Cys Arg Tyr Pro Leu Thr Val
        305                 310                 315                 320
        Asp Phe Glu Ala Phe Gly Trp Asp Trp Ile Ile Ala Pro Lys Arg Tyr
                        325                 330                 335
        Lys Ala Asn Tyr Cys Ser Gly Gln Cys Glu Tyr Met Phe Met Gln Lys
                    340                 345                 350
        Tyr Pro His Thr His Leu Val Gln Gln Ala Asn Pro Arg Gly Ser Ala
                355                 360                 365
        Gly Pro Cys Cys Thr Pro Thr Lys Met Ser Pro Ile Asn Met Leu Tyr
            370                 375                 380
        Phe Asn Asp Lys Gln Gln Ile Ile Tyr Gly Lys Ile Pro Gly Met Val
        385                 390                 395                 400
        Val Asp Arg Cys Gly Cys Ser
                        405

<210> SEQ ID NO 2
<211> LENGTH: 3
<212> TYPE: PRT
<213> ORGANISM: Homo sapiens

<400> SEQUENCE: 2

Met Val Leu
1

<210> SEQ ID NO 3
<211> LENGTH: 3
<212> TYPE: PRT
<213> ORGANISM: Homo sapiens

<400> SEQUENCE: 3

Val Leu Ala
1

<210> SEQ ID NO 4
<211> LENGTH: 3
<212> TYPE: PRT
<213> ORGANISM: Homo sapiens

<400> SEQUENCE: 4

Leu Ala Ala
1

<210> SEQ ID NO 5
<211> LENGTH: 3
<212> TYPE: PRT
<213> ORGANISM: Homo sapiens

<400> SEQUENCE: 5

Ala Ala Pro
1

<210> SEQ ID NO 6
<211> LENGTH: 3
<212> TYPE: PRT
<213> ORGANISM: Homo sapiens

<400> SEQUENCE: 6

Ala Pro Leu
```

```
<210> SEQ ID NO 7
<211> LENGTH: 3
<212> TYPE: PRT
<213> ORGANISM: Homo sapiens

<400> SEQUENCE: 7

Pro Leu Leu
1

<210> SEQ ID NO 8
<211> LENGTH: 3
<212> TYPE: PRT
<213> ORGANISM: Homo sapiens

<400> SEQUENCE: 8

Leu Leu Leu
1

<210> SEQ ID NO 9
<211> LENGTH: 3
<212> TYPE: PRT
<213> ORGANISM: Homo sapiens

<400> SEQUENCE: 9

Leu Leu Gly
1

<210> SEQ ID NO 10
<211> LENGTH: 3
<212> TYPE: PRT
<213> ORGANISM: Homo sapiens

<400> SEQUENCE: 10

Leu Gly Phe
1

<210> SEQ ID NO 11
<211> LENGTH: 3
<212> TYPE: PRT
<213> ORGANISM: Homo sapiens

<400> SEQUENCE: 11

Gly Phe Leu
1

<210> SEQ ID NO 12
<211> LENGTH: 3
<212> TYPE: PRT
<213> ORGANISM: Homo sapiens

<400> SEQUENCE: 12

Phe Leu Leu
1

<210> SEQ ID NO 13
<211> LENGTH: 3
<212> TYPE: PRT
<213> ORGANISM: Homo sapiens

<400> SEQUENCE: 13

Leu Leu Ala
1
```

```
<210> SEQ ID NO 14
<211> LENGTH: 3
<212> TYPE: PRT
<213> ORGANISM: Homo sapiens

<400> SEQUENCE: 14

Leu Ala Leu
1

<210> SEQ ID NO 15
<211> LENGTH: 3
<212> TYPE: PRT
<213> ORGANISM: Homo sapiens

<400> SEQUENCE: 15

Ala Leu Glu
1

<210> SEQ ID NO 16
<211> LENGTH: 3
<212> TYPE: PRT
<213> ORGANISM: Homo sapiens

<400> SEQUENCE: 16

Leu Glu Leu
1

<210> SEQ ID NO 17
<211> LENGTH: 3
<212> TYPE: PRT
<213> ORGANISM: Homo sapiens

<400> SEQUENCE: 17

Glu Leu Arg
1

<210> SEQ ID NO 18
<211> LENGTH: 3
<212> TYPE: PRT
<213> ORGANISM: Homo sapiens

<400> SEQUENCE: 18

Leu Arg Pro
1

<210> SEQ ID NO 19
<211> LENGTH: 3
<212> TYPE: PRT
<213> ORGANISM: Homo sapiens

<400> SEQUENCE: 19

Arg Pro Arg
1

<210> SEQ ID NO 20
<211> LENGTH: 3
<212> TYPE: PRT
<213> ORGANISM: Homo sapiens

<400> SEQUENCE: 20

Pro Arg Gly
1

<210> SEQ ID NO 21
```

```
<211> LENGTH: 3
<212> TYPE: PRT
<213> ORGANISM: Homo sapiens

<400> SEQUENCE: 21

Arg Gly Glu
1

<210> SEQ ID NO 22
<211> LENGTH: 3
<212> TYPE: PRT
<213> ORGANISM: Homo sapiens

<400> SEQUENCE: 22

Gly Glu Ala
1

<210> SEQ ID NO 23
<211> LENGTH: 3
<212> TYPE: PRT
<213> ORGANISM: Homo sapiens

<400> SEQUENCE: 23

Glu Ala Ala
1

<210> SEQ ID NO 24
<211> LENGTH: 3
<212> TYPE: PRT
<213> ORGANISM: Homo sapiens

<400> SEQUENCE: 24

Ala Ala Glu
1

<210> SEQ ID NO 25
<211> LENGTH: 3
<212> TYPE: PRT
<213> ORGANISM: Homo sapiens

<400> SEQUENCE: 25

Ala Glu Gly
1

<210> SEQ ID NO 26
<211> LENGTH: 3
<212> TYPE: PRT
<213> ORGANISM: Homo sapiens

<400> SEQUENCE: 26

Glu Gly Pro
1

<210> SEQ ID NO 27
<211> LENGTH: 3
<212> TYPE: PRT
<213> ORGANISM: Homo sapiens

<400> SEQUENCE: 27

Gly Pro Ala
1

<210> SEQ ID NO 28
<211> LENGTH: 3
<212> TYPE: PRT
```

```
<213> ORGANISM: Homo sapiens

<400> SEQUENCE: 28

Pro Ala Ala
1

<210> SEQ ID NO 29
<211> LENGTH: 3
<212> TYPE: PRT
<213> ORGANISM: Homo sapiens

<400> SEQUENCE: 29

Ala Ala Ala
1

<210> SEQ ID NO 30
<211> LENGTH: 3
<212> TYPE: PRT
<213> ORGANISM: Homo sapiens

<400> SEQUENCE: 30

Ala Ala Gly
1

<210> SEQ ID NO 31
<211> LENGTH: 3
<212> TYPE: PRT
<213> ORGANISM: Homo sapiens

<400> SEQUENCE: 31

Ala Gly Val
1

<210> SEQ ID NO 32
<211> LENGTH: 3
<212> TYPE: PRT
<213> ORGANISM: Homo sapiens

<400> SEQUENCE: 32

Gly Val Gly
1

<210> SEQ ID NO 33
<211> LENGTH: 3
<212> TYPE: PRT
<213> ORGANISM: Homo sapiens

<400> SEQUENCE: 33

Val Gly Gly
1

<210> SEQ ID NO 34
<211> LENGTH: 3
<212> TYPE: PRT
<213> ORGANISM: Homo sapiens

<400> SEQUENCE: 34

Gly Gly Glu
1

<210> SEQ ID NO 35
<211> LENGTH: 3
<212> TYPE: PRT
<213> ORGANISM: Homo sapiens
```

```
<400> SEQUENCE: 35

Gly Glu Arg
1

<210> SEQ ID NO 36
<211> LENGTH: 3
<212> TYPE: PRT
<213> ORGANISM: Homo sapiens

<400> SEQUENCE: 36

Glu Arg Ser
1

<210> SEQ ID NO 37
<211> LENGTH: 3
<212> TYPE: PRT
<213> ORGANISM: Homo sapiens

<400> SEQUENCE: 37

Arg Ser Ser
1

<210> SEQ ID NO 38
<211> LENGTH: 3
<212> TYPE: PRT
<213> ORGANISM: Homo sapiens

<400> SEQUENCE: 38

Ser Ser Arg
1

<210> SEQ ID NO 39
<211> LENGTH: 3
<212> TYPE: PRT
<213> ORGANISM: Homo sapiens

<400> SEQUENCE: 39

Ser Arg Pro
1

<210> SEQ ID NO 40
<211> LENGTH: 3
<212> TYPE: PRT
<213> ORGANISM: Homo sapiens

<400> SEQUENCE: 40

Arg Pro Ala
1

<210> SEQ ID NO 41
<211> LENGTH: 3
<212> TYPE: PRT
<213> ORGANISM: Homo sapiens

<400> SEQUENCE: 41

Pro Ala Pro
1

<210> SEQ ID NO 42
<211> LENGTH: 3
<212> TYPE: PRT
<213> ORGANISM: Homo sapiens

<400> SEQUENCE: 42
```

Ala Pro Ser
1

<210> SEQ ID NO 43
<211> LENGTH: 3
<212> TYPE: PRT
<213> ORGANISM: Homo sapiens

<400> SEQUENCE: 43

Pro Ser Val
1

<210> SEQ ID NO 44
<211> LENGTH: 3
<212> TYPE: PRT
<213> ORGANISM: Homo sapiens

<400> SEQUENCE: 44

Ser Val Ala
1

<210> SEQ ID NO 45
<211> LENGTH: 3
<212> TYPE: PRT
<213> ORGANISM: Homo sapiens

<400> SEQUENCE: 45

Val Ala Pro
1

<210> SEQ ID NO 46
<211> LENGTH: 3
<212> TYPE: PRT
<213> ORGANISM: Homo sapiens

<400> SEQUENCE: 46

Ala Pro Glu
1

<210> SEQ ID NO 47
<211> LENGTH: 3
<212> TYPE: PRT
<213> ORGANISM: Homo sapiens

<400> SEQUENCE: 47

Pro Glu Pro
1

<210> SEQ ID NO 48
<211> LENGTH: 3
<212> TYPE: PRT
<213> ORGANISM: Homo sapiens

<400> SEQUENCE: 48

Glu Pro Asp
1

<210> SEQ ID NO 49
<211> LENGTH: 3
<212> TYPE: PRT
<213> ORGANISM: Homo sapiens

<400> SEQUENCE: 49

Pro Asp Gly
1

<210> SEQ ID NO 50
<211> LENGTH: 3
<212> TYPE: PRT
<213> ORGANISM: Homo sapiens

<400> SEQUENCE: 50

Asp Gly Cys
1

<210> SEQ ID NO 51
<211> LENGTH: 3
<212> TYPE: PRT
<213> ORGANISM: Homo sapiens

<400> SEQUENCE: 51

Gly Cys Pro
1

<210> SEQ ID NO 52
<211> LENGTH: 3
<212> TYPE: PRT
<213> ORGANISM: Homo sapiens

<400> SEQUENCE: 52

Cys Pro Val
1

<210> SEQ ID NO 53
<211> LENGTH: 3
<212> TYPE: PRT
<213> ORGANISM: Homo sapiens

<400> SEQUENCE: 53

Pro Val Cys
1

<210> SEQ ID NO 54
<211> LENGTH: 3
<212> TYPE: PRT
<213> ORGANISM: Homo sapiens

<400> SEQUENCE: 54

Val Cys Val
1

<210> SEQ ID NO 55
<211> LENGTH: 3
<212> TYPE: PRT
<213> ORGANISM: Homo sapiens

<400> SEQUENCE: 55

Cys Val Trp
1

<210> SEQ ID NO 56
<211> LENGTH: 3
<212> TYPE: PRT
<213> ORGANISM: Homo sapiens

<400> SEQUENCE: 56

Val Trp Arg
1

```
<210> SEQ ID NO 57
<211> LENGTH: 3
<212> TYPE: PRT
<213> ORGANISM: Homo sapiens

<400> SEQUENCE: 57

Trp Arg Gln
1

<210> SEQ ID NO 58
<211> LENGTH: 3
<212> TYPE: PRT
<213> ORGANISM: Homo sapiens

<400> SEQUENCE: 58

Arg Gln His
1

<210> SEQ ID NO 59
<211> LENGTH: 3
<212> TYPE: PRT
<213> ORGANISM: Homo sapiens

<400> SEQUENCE: 59

Gln His Ser
1

<210> SEQ ID NO 60
<211> LENGTH: 3
<212> TYPE: PRT
<213> ORGANISM: Homo sapiens

<400> SEQUENCE: 60

His Ser Arg
1

<210> SEQ ID NO 61
<211> LENGTH: 3
<212> TYPE: PRT
<213> ORGANISM: Homo sapiens

<400> SEQUENCE: 61

Ser Arg Glu
1

<210> SEQ ID NO 62
<211> LENGTH: 3
<212> TYPE: PRT
<213> ORGANISM: Homo sapiens

<400> SEQUENCE: 62

Arg Glu Leu
1

<210> SEQ ID NO 63
<211> LENGTH: 3
<212> TYPE: PRT
<213> ORGANISM: Homo sapiens

<400> SEQUENCE: 63

Leu Arg Leu
1

<210> SEQ ID NO 64
<211> LENGTH: 3
```

<212> TYPE: PRT
<213> ORGANISM: Homo sapiens

<400> SEQUENCE: 64

Arg Leu Glu
1

<210> SEQ ID NO 65
<211> LENGTH: 3
<212> TYPE: PRT
<213> ORGANISM: Homo sapiens

<400> SEQUENCE: 65

Leu Glu Ser
1

<210> SEQ ID NO 66
<211> LENGTH: 3
<212> TYPE: PRT
<213> ORGANISM: Homo sapiens

<400> SEQUENCE: 66

Glu Ser Ile
1

<210> SEQ ID NO 67
<211> LENGTH: 3
<212> TYPE: PRT
<213> ORGANISM: Homo sapiens

<400> SEQUENCE: 67

Ser Ile Lys
1

<210> SEQ ID NO 68
<211> LENGTH: 3
<212> TYPE: PRT
<213> ORGANISM: Homo sapiens

<400> SEQUENCE: 68

Ile Lys Ser
1

<210> SEQ ID NO 69
<211> LENGTH: 3
<212> TYPE: PRT
<213> ORGANISM: Homo sapiens

<400> SEQUENCE: 69

Lys Ser Gln
1

<210> SEQ ID NO 70
<211> LENGTH: 3
<212> TYPE: PRT
<213> ORGANISM: Homo sapiens

<400> SEQUENCE: 70

Ser Gln Ile
1

<210> SEQ ID NO 71
<211> LENGTH: 3
<212> TYPE: PRT
<213> ORGANISM: Homo sapiens

```
<400> SEQUENCE: 71

Gln Ile Leu
1

<210> SEQ ID NO 72
<211> LENGTH: 3
<212> TYPE: PRT
<213> ORGANISM: Homo sapiens

<400> SEQUENCE: 72

Ile Leu Ser
1

<210> SEQ ID NO 73
<211> LENGTH: 3
<212> TYPE: PRT
<213> ORGANISM: Homo sapiens

<400> SEQUENCE: 73

Leu Ser Lys
1

<210> SEQ ID NO 74
<211> LENGTH: 3
<212> TYPE: PRT
<213> ORGANISM: Homo sapiens

<400> SEQUENCE: 74

Ser Lys Leu
1

<210> SEQ ID NO 75
<211> LENGTH: 3
<212> TYPE: PRT
<213> ORGANISM: Homo sapiens

<400> SEQUENCE: 75

Lys Leu Arg
1

<210> SEQ ID NO 76
<211> LENGTH: 3
<212> TYPE: PRT
<213> ORGANISM: Homo sapiens

<400> SEQUENCE: 76

Arg Leu Lys
1

<210> SEQ ID NO 77
<211> LENGTH: 3
<212> TYPE: PRT
<213> ORGANISM: Homo sapiens

<400> SEQUENCE: 77

Leu Lys Glu
1

<210> SEQ ID NO 78
<211> LENGTH: 3
<212> TYPE: PRT
<213> ORGANISM: Homo sapiens

<400> SEQUENCE: 78
```

Lys Glu Ala
1

<210> SEQ ID NO 79
<211> LENGTH: 3
<212> TYPE: PRT
<213> ORGANISM: Homo sapiens

<400> SEQUENCE: 79

Glu Ala Pro
1

<210> SEQ ID NO 80
<211> LENGTH: 3
<212> TYPE: PRT
<213> ORGANISM: Homo sapiens

<400> SEQUENCE: 80

Ala Pro Asn
1

<210> SEQ ID NO 81
<211> LENGTH: 3
<212> TYPE: PRT
<213> ORGANISM: Homo sapiens

<400> SEQUENCE: 81

Pro Asn Ile
1

<210> SEQ ID NO 82
<211> LENGTH: 3
<212> TYPE: PRT
<213> ORGANISM: Homo sapiens

<400> SEQUENCE: 82

Asn Ile Ser
1

<210> SEQ ID NO 83
<211> LENGTH: 3
<212> TYPE: PRT
<213> ORGANISM: Homo sapiens

<400> SEQUENCE: 83

Ile Ser Arg
1

<210> SEQ ID NO 84
<211> LENGTH: 3
<212> TYPE: PRT
<213> ORGANISM: Homo sapiens

<400> SEQUENCE: 84

Arg Glu Val
1

<210> SEQ ID NO 85
<211> LENGTH: 3
<212> TYPE: PRT
<213> ORGANISM: Homo sapiens

<400> SEQUENCE: 85

Glu Val Val

<210> SEQ ID NO 86
<211> LENGTH: 3
<212> TYPE: PRT
<213> ORGANISM: Homo sapiens

<400> SEQUENCE: 86

Val Val Lys
1

<210> SEQ ID NO 87
<211> LENGTH: 3
<212> TYPE: PRT
<213> ORGANISM: Homo sapiens

<400> SEQUENCE: 87

Val Lys Gln
1

<210> SEQ ID NO 88
<211> LENGTH: 3
<212> TYPE: PRT
<213> ORGANISM: Homo sapiens

<400> SEQUENCE: 88

Lys Gln Leu
1

<210> SEQ ID NO 89
<211> LENGTH: 3
<212> TYPE: PRT
<213> ORGANISM: Homo sapiens

<400> SEQUENCE: 89

Gln Leu Leu
1

<210> SEQ ID NO 90
<211> LENGTH: 3
<212> TYPE: PRT
<213> ORGANISM: Homo sapiens

<400> SEQUENCE: 90

Leu Leu Pro
1

<210> SEQ ID NO 91
<211> LENGTH: 3
<212> TYPE: PRT
<213> ORGANISM: Homo sapiens

<400> SEQUENCE: 91

Leu Pro Lys
1

<210> SEQ ID NO 92
<211> LENGTH: 3
<212> TYPE: PRT
<213> ORGANISM: Homo sapiens

<400> SEQUENCE: 92

Pro Lys Ala
1

```
<210> SEQ ID NO 93
<211> LENGTH: 3
<212> TYPE: PRT
<213> ORGANISM: Homo sapiens

<400> SEQUENCE: 93

Lys Ala Pro
1

<210> SEQ ID NO 94
<211> LENGTH: 3
<212> TYPE: PRT
<213> ORGANISM: Homo sapiens

<400> SEQUENCE: 94

Ala Pro Pro
1

<210> SEQ ID NO 95
<211> LENGTH: 3
<212> TYPE: PRT
<213> ORGANISM: Homo sapiens

<400> SEQUENCE: 95

Pro Pro Leu
1

<210> SEQ ID NO 96
<211> LENGTH: 3
<212> TYPE: PRT
<213> ORGANISM: Homo sapiens

<400> SEQUENCE: 96

Pro Leu Gln
1

<210> SEQ ID NO 97
<211> LENGTH: 3
<212> TYPE: PRT
<213> ORGANISM: Homo sapiens

<400> SEQUENCE: 97

Leu Gln Gln
1

<210> SEQ ID NO 98
<211> LENGTH: 3
<212> TYPE: PRT
<213> ORGANISM: Homo sapiens

<400> SEQUENCE: 98

Gln Gln Ile
1

<210> SEQ ID NO 99
<211> LENGTH: 3
<212> TYPE: PRT
<213> ORGANISM: Homo sapiens

<400> SEQUENCE: 99

Ile Leu Asp
1

<210> SEQ ID NO 100
```

```
<210> SEQ ID NO 100
<211> LENGTH: 3
<212> TYPE: PRT
<213> ORGANISM: Homo sapiens

<400> SEQUENCE: 100

Leu Asp Leu
1

<210> SEQ ID NO 101
<211> LENGTH: 3
<212> TYPE: PRT
<213> ORGANISM: Homo sapiens

<400> SEQUENCE: 101

Asp Leu His
1

<210> SEQ ID NO 102
<211> LENGTH: 3
<212> TYPE: PRT
<213> ORGANISM: Homo sapiens

<400> SEQUENCE: 102

Leu His Asp
1

<210> SEQ ID NO 103
<211> LENGTH: 3
<212> TYPE: PRT
<213> ORGANISM: Homo sapiens

<400> SEQUENCE: 103

His Asp Phe
1

<210> SEQ ID NO 104
<211> LENGTH: 3
<212> TYPE: PRT
<213> ORGANISM: Homo sapiens

<400> SEQUENCE: 104

Asp Phe Gln
1

<210> SEQ ID NO 105
<211> LENGTH: 3
<212> TYPE: PRT
<213> ORGANISM: Homo sapiens

<400> SEQUENCE: 105

Phe Gln Gly
1

<210> SEQ ID NO 106
<211> LENGTH: 3
<212> TYPE: PRT
<213> ORGANISM: Homo sapiens

<400> SEQUENCE: 106

Gln Gly Asp
1

<210> SEQ ID NO 107
<211> LENGTH: 3
<212> TYPE: PRT
```

<213> ORGANISM: Homo sapiens

<400> SEQUENCE: 107

Gly Asp Ala
1

<210> SEQ ID NO 108
<211> LENGTH: 3
<212> TYPE: PRT
<213> ORGANISM: Homo sapiens

<400> SEQUENCE: 108

Asp Ala Leu
1

<210> SEQ ID NO 109
<211> LENGTH: 3
<212> TYPE: PRT
<213> ORGANISM: Homo sapiens

<400> SEQUENCE: 109

Ala Leu Gln
1

<210> SEQ ID NO 110
<211> LENGTH: 3
<212> TYPE: PRT
<213> ORGANISM: Homo sapiens

<400> SEQUENCE: 110

Leu Gln Pro
1

<210> SEQ ID NO 111
<211> LENGTH: 3
<212> TYPE: PRT
<213> ORGANISM: Homo sapiens

<400> SEQUENCE: 111

Gln Pro Glu
1

<210> SEQ ID NO 112
<211> LENGTH: 3
<212> TYPE: PRT
<213> ORGANISM: Homo sapiens

<400> SEQUENCE: 112

Pro Glu Asp
1

<210> SEQ ID NO 113
<211> LENGTH: 3
<212> TYPE: PRT
<213> ORGANISM: Homo sapiens

<400> SEQUENCE: 113

Glu Asp Phe
1

<210> SEQ ID NO 114
<211> LENGTH: 3
<212> TYPE: PRT
<213> ORGANISM: Homo sapiens

```
<400> SEQUENCE: 114

Asp Phe Leu
1

<210> SEQ ID NO 115
<211> LENGTH: 3
<212> TYPE: PRT
<213> ORGANISM: Homo sapiens

<400> SEQUENCE: 115

Phe Leu Glu
1

<210> SEQ ID NO 116
<211> LENGTH: 3
<212> TYPE: PRT
<213> ORGANISM: Homo sapiens

<400> SEQUENCE: 116

Leu Glu Glu
1

<210> SEQ ID NO 117
<211> LENGTH: 3
<212> TYPE: PRT
<213> ORGANISM: Homo sapiens

<400> SEQUENCE: 117

Glu Glu Asp
1

<210> SEQ ID NO 118
<211> LENGTH: 3
<212> TYPE: PRT
<213> ORGANISM: Homo sapiens

<400> SEQUENCE: 118

Glu Asp Glu
1

<210> SEQ ID NO 119
<211> LENGTH: 3
<212> TYPE: PRT
<213> ORGANISM: Homo sapiens

<400> SEQUENCE: 119

Asp Glu Tyr
1

<210> SEQ ID NO 120
<211> LENGTH: 3
<212> TYPE: PRT
<213> ORGANISM: Homo sapiens

<400> SEQUENCE: 120

Glu Tyr His
1

<210> SEQ ID NO 121
<211> LENGTH: 3
<212> TYPE: PRT
<213> ORGANISM: Homo sapiens

<400> SEQUENCE: 121
```

Tyr His Ala
1

<210> SEQ ID NO 122
<211> LENGTH: 3
<212> TYPE: PRT
<213> ORGANISM: Homo sapiens

<400> SEQUENCE: 122

His Ala Thr
1

<210> SEQ ID NO 123
<211> LENGTH: 3
<212> TYPE: PRT
<213> ORGANISM: Homo sapiens

<400> SEQUENCE: 123

Ala Thr Thr
1

<210> SEQ ID NO 124
<211> LENGTH: 3
<212> TYPE: PRT
<213> ORGANISM: Homo sapiens

<400> SEQUENCE: 124

Thr Thr Glu
1

<210> SEQ ID NO 125
<211> LENGTH: 3
<212> TYPE: PRT
<213> ORGANISM: Homo sapiens

<400> SEQUENCE: 125

Thr Glu Thr
1

<210> SEQ ID NO 126
<211> LENGTH: 3
<212> TYPE: PRT
<213> ORGANISM: Homo sapiens

<400> SEQUENCE: 126

Glu Thr Val
1

<210> SEQ ID NO 127
<211> LENGTH: 3
<212> TYPE: PRT
<213> ORGANISM: Homo sapiens

<400> SEQUENCE: 127

Thr Val Ile
1

<210> SEQ ID NO 128
<211> LENGTH: 3
<212> TYPE: PRT
<213> ORGANISM: Homo sapiens

<400> SEQUENCE: 128

Val Ile Ser
1

<210> SEQ ID NO 129
<211> LENGTH: 3
<212> TYPE: PRT
<213> ORGANISM: Homo sapiens

<400> SEQUENCE: 129

Ile Ser Met
1

<210> SEQ ID NO 130
<211> LENGTH: 3
<212> TYPE: PRT
<213> ORGANISM: Homo sapiens

<400> SEQUENCE: 130

Ser Met Ala
1

<210> SEQ ID NO 131
<211> LENGTH: 3
<212> TYPE: PRT
<213> ORGANISM: Homo sapiens

<400> SEQUENCE: 131

Met Ala Gln
1

<210> SEQ ID NO 132
<211> LENGTH: 3
<212> TYPE: PRT
<213> ORGANISM: Homo sapiens

<400> SEQUENCE: 132

Ala Gln Glu
1

<210> SEQ ID NO 133
<211> LENGTH: 3
<212> TYPE: PRT
<213> ORGANISM: Homo sapiens

<400> SEQUENCE: 133

Gln Glu Thr
1

<210> SEQ ID NO 134
<211> LENGTH: 3
<212> TYPE: PRT
<213> ORGANISM: Homo sapiens

<400> SEQUENCE: 134

Glu Thr Asp
1

<210> SEQ ID NO 135
<211> LENGTH: 3
<212> TYPE: PRT
<213> ORGANISM: Homo sapiens

<400> SEQUENCE: 135

Thr Asp Pro
1

<210> SEQ ID NO 136
<211> LENGTH: 3
<212> TYPE: PRT
<213> ORGANISM: Homo sapiens

<400> SEQUENCE: 136

Asp Pro Ala
1

<210> SEQ ID NO 137
<211> LENGTH: 3
<212> TYPE: PRT
<213> ORGANISM: Homo sapiens

<400> SEQUENCE: 137

Pro Ala Val
1

<210> SEQ ID NO 138
<211> LENGTH: 3
<212> TYPE: PRT
<213> ORGANISM: Homo sapiens

<400> SEQUENCE: 138

Ala Val Gln
1

<210> SEQ ID NO 139
<211> LENGTH: 3
<212> TYPE: PRT
<213> ORGANISM: Homo sapiens

<400> SEQUENCE: 139

Val Gln Thr
1

<210> SEQ ID NO 140
<211> LENGTH: 3
<212> TYPE: PRT
<213> ORGANISM: Homo sapiens

<400> SEQUENCE: 140

Gln Thr Asp
1

<210> SEQ ID NO 141
<211> LENGTH: 3
<212> TYPE: PRT
<213> ORGANISM: Homo sapiens

<400> SEQUENCE: 141

Thr Asp Gly
1

<210> SEQ ID NO 142
<211> LENGTH: 3
<212> TYPE: PRT
<213> ORGANISM: Homo sapiens

<400> SEQUENCE: 142

Asp Gly Ser
1

<210> SEQ ID NO 143
<211> LENGTH: 3

```
<212> TYPE: PRT
<213> ORGANISM: Homo sapiens

<400> SEQUENCE: 143

Gly Ser Pro
1

<210> SEQ ID NO 144
<211> LENGTH: 3
<212> TYPE: PRT
<213> ORGANISM: Homo sapiens

<400> SEQUENCE: 144

Ser Pro Leu
1

<210> SEQ ID NO 145
<211> LENGTH: 3
<212> TYPE: PRT
<213> ORGANISM: Homo sapiens

<400> SEQUENCE: 145

Pro Leu Cys
1

<210> SEQ ID NO 146
<211> LENGTH: 3
<212> TYPE: PRT
<213> ORGANISM: Homo sapiens

<400> SEQUENCE: 146

Leu Cys Cys
1

<210> SEQ ID NO 147
<211> LENGTH: 3
<212> TYPE: PRT
<213> ORGANISM: Homo sapiens

<400> SEQUENCE: 147

Cys Cys His
1

<210> SEQ ID NO 148
<211> LENGTH: 3
<212> TYPE: PRT
<213> ORGANISM: Homo sapiens

<400> SEQUENCE: 148

Cys His Phe
1

<210> SEQ ID NO 149
<211> LENGTH: 3
<212> TYPE: PRT
<213> ORGANISM: Homo sapiens

<400> SEQUENCE: 149

His Phe His
1

<210> SEQ ID NO 150
<211> LENGTH: 3
<212> TYPE: PRT
<213> ORGANISM: Homo sapiens
```

<400> SEQUENCE: 150

Phe His Phe
1

<210> SEQ ID NO 151
<211> LENGTH: 3
<212> TYPE: PRT
<213> ORGANISM: Homo sapiens

<400> SEQUENCE: 151

His Phe Ser
1

<210> SEQ ID NO 152
<211> LENGTH: 3
<212> TYPE: PRT
<213> ORGANISM: Homo sapiens

<400> SEQUENCE: 152

Phe Ser Pro
1

<210> SEQ ID NO 153
<211> LENGTH: 3
<212> TYPE: PRT
<213> ORGANISM: Homo sapiens

<400> SEQUENCE: 153

Ser Pro Lys
1

<210> SEQ ID NO 154
<211> LENGTH: 3
<212> TYPE: PRT
<213> ORGANISM: Homo sapiens

<400> SEQUENCE: 154

Pro Lys Val
1

<210> SEQ ID NO 155
<211> LENGTH: 3
<212> TYPE: PRT
<213> ORGANISM: Homo sapiens

<400> SEQUENCE: 155

Lys Val Met
1

<210> SEQ ID NO 156
<211> LENGTH: 3
<212> TYPE: PRT
<213> ORGANISM: Homo sapiens

<400> SEQUENCE: 156

Val Met Phe
1

<210> SEQ ID NO 157
<211> LENGTH: 3
<212> TYPE: PRT
<213> ORGANISM: Homo sapiens

<400> SEQUENCE: 157

Met Phe Thr
1

<210> SEQ ID NO 158
<211> LENGTH: 3
<212> TYPE: PRT
<213> ORGANISM: Homo sapiens

<400> SEQUENCE: 158

Phe Thr Lys
1

<210> SEQ ID NO 159
<211> LENGTH: 3
<212> TYPE: PRT
<213> ORGANISM: Homo sapiens

<400> SEQUENCE: 159

Thr Lys Val
1

<210> SEQ ID NO 160
<211> LENGTH: 3
<212> TYPE: PRT
<213> ORGANISM: Homo sapiens

<400> SEQUENCE: 160

Lys Val Leu
1

<210> SEQ ID NO 161
<211> LENGTH: 3
<212> TYPE: PRT
<213> ORGANISM: Homo sapiens

<400> SEQUENCE: 161

Val Leu Lys
1

<210> SEQ ID NO 162
<211> LENGTH: 3
<212> TYPE: PRT
<213> ORGANISM: Homo sapiens

<400> SEQUENCE: 162

Leu Lys Ala
1

<210> SEQ ID NO 163
<211> LENGTH: 3
<212> TYPE: PRT
<213> ORGANISM: Homo sapiens

<400> SEQUENCE: 163

Lys Ala Gln
1

<210> SEQ ID NO 164
<211> LENGTH: 3
<212> TYPE: PRT
<213> ORGANISM: Homo sapiens

<400> SEQUENCE: 164

Ala Gln Leu

<210> SEQ ID NO 165
<211> LENGTH: 3
<212> TYPE: PRT
<213> ORGANISM: Homo sapiens

<400> SEQUENCE: 165

Gln Leu Trp
1

<210> SEQ ID NO 166
<211> LENGTH: 3
<212> TYPE: PRT
<213> ORGANISM: Homo sapiens

<400> SEQUENCE: 166

Leu Trp Val
1

<210> SEQ ID NO 167
<211> LENGTH: 3
<212> TYPE: PRT
<213> ORGANISM: Homo sapiens

<400> SEQUENCE: 167

Trp Val Tyr
1

<210> SEQ ID NO 168
<211> LENGTH: 3
<212> TYPE: PRT
<213> ORGANISM: Homo sapiens

<400> SEQUENCE: 168

Val Tyr Leu
1

<210> SEQ ID NO 169
<211> LENGTH: 3
<212> TYPE: PRT
<213> ORGANISM: Homo sapiens

<400> SEQUENCE: 169

Tyr Leu Arg
1

<210> SEQ ID NO 170
<211> LENGTH: 3
<212> TYPE: PRT
<213> ORGANISM: Homo sapiens

<400> SEQUENCE: 170

Arg Pro Val
1

<210> SEQ ID NO 171
<211> LENGTH: 3
<212> TYPE: PRT
<213> ORGANISM: Homo sapiens

<400> SEQUENCE: 171

Pro Val Pro
1

```
<210> SEQ ID NO 172
<211> LENGTH: 3
<212> TYPE: PRT
<213> ORGANISM: Homo sapiens

<400> SEQUENCE: 172

Val Pro Arg
1

<210> SEQ ID NO 173
<211> LENGTH: 3
<212> TYPE: PRT
<213> ORGANISM: Homo sapiens

<400> SEQUENCE: 173

Pro Arg Pro
1

<210> SEQ ID NO 174
<211> LENGTH: 3
<212> TYPE: PRT
<213> ORGANISM: Homo sapiens

<400> SEQUENCE: 174

Pro Ala Thr
1

<210> SEQ ID NO 175
<211> LENGTH: 3
<212> TYPE: PRT
<213> ORGANISM: Homo sapiens

<400> SEQUENCE: 175

Ala Thr Val
1

<210> SEQ ID NO 176
<211> LENGTH: 3
<212> TYPE: PRT
<213> ORGANISM: Homo sapiens

<400> SEQUENCE: 176

Thr Val Tyr
1

<210> SEQ ID NO 177
<211> LENGTH: 3
<212> TYPE: PRT
<213> ORGANISM: Homo sapiens

<400> SEQUENCE: 177

Tyr Leu Gln
1

<210> SEQ ID NO 178
<211> LENGTH: 3
<212> TYPE: PRT
<213> ORGANISM: Homo sapiens

<400> SEQUENCE: 178

Leu Gln Ile
1

<210> SEQ ID NO 179
```

```
<211> LENGTH: 3
<212> TYPE: PRT
<213> ORGANISM: Homo sapiens

<400> SEQUENCE: 179

Ile Leu Arg
1

<210> SEQ ID NO 180
<211> LENGTH: 3
<212> TYPE: PRT
<213> ORGANISM: Homo sapiens

<400> SEQUENCE: 180

Leu Lys Pro
1

<210> SEQ ID NO 181
<211> LENGTH: 3
<212> TYPE: PRT
<213> ORGANISM: Homo sapiens

<400> SEQUENCE: 181

Lys Pro Leu
1

<210> SEQ ID NO 182
<211> LENGTH: 3
<212> TYPE: PRT
<213> ORGANISM: Homo sapiens

<400> SEQUENCE: 182

Pro Leu Thr
1

<210> SEQ ID NO 183
<211> LENGTH: 3
<212> TYPE: PRT
<213> ORGANISM: Homo sapiens

<400> SEQUENCE: 183

Leu Thr Gly
1

<210> SEQ ID NO 184
<211> LENGTH: 3
<212> TYPE: PRT
<213> ORGANISM: Homo sapiens

<400> SEQUENCE: 184

Thr Gly Glu
1

<210> SEQ ID NO 185
<211> LENGTH: 3
<212> TYPE: PRT
<213> ORGANISM: Homo sapiens

<400> SEQUENCE: 185

Gly Glu Gly
1

<210> SEQ ID NO 186
<211> LENGTH: 3
<212> TYPE: PRT
```

<213> ORGANISM: Homo sapiens

<400> SEQUENCE: 186

Glu Gly Thr
1

<210> SEQ ID NO 187
<211> LENGTH: 3
<212> TYPE: PRT
<213> ORGANISM: Homo sapiens

<400> SEQUENCE: 187

Gly Thr Ala
1

<210> SEQ ID NO 188
<211> LENGTH: 3
<212> TYPE: PRT
<213> ORGANISM: Homo sapiens

<400> SEQUENCE: 188

Thr Ala Gly
1

<210> SEQ ID NO 189
<211> LENGTH: 3
<212> TYPE: PRT
<213> ORGANISM: Homo sapiens

<400> SEQUENCE: 189

Ala Gly Gly
1

<210> SEQ ID NO 190
<211> LENGTH: 3
<212> TYPE: PRT
<213> ORGANISM: Homo sapiens

<400> SEQUENCE: 190

Gly Gly Gly
1

<210> SEQ ID NO 191
<211> LENGTH: 3
<212> TYPE: PRT
<213> ORGANISM: Homo sapiens

<400> SEQUENCE: 191

Gly Gly Arg
1

<210> SEQ ID NO 192
<211> LENGTH: 3
<212> TYPE: PRT
<213> ORGANISM: Homo sapiens

<400> SEQUENCE: 192

Gly Arg Arg
1

<210> SEQ ID NO 193
<211> LENGTH: 3
<212> TYPE: PRT
<213> ORGANISM: Homo sapiens

```
<400> SEQUENCE: 193

Arg Arg His
1

<210> SEQ ID NO 194
<211> LENGTH: 3
<212> TYPE: PRT
<213> ORGANISM: Homo sapiens

<400> SEQUENCE: 194

Arg His Ile
1

<210> SEQ ID NO 195
<211> LENGTH: 3
<212> TYPE: PRT
<213> ORGANISM: Homo sapiens

<400> SEQUENCE: 195

His Ile Arg
1

<210> SEQ ID NO 196
<211> LENGTH: 3
<212> TYPE: PRT
<213> ORGANISM: Homo sapiens

<400> SEQUENCE: 196

Ile Arg Ile
1

<210> SEQ ID NO 197
<211> LENGTH: 3
<212> TYPE: PRT
<213> ORGANISM: Homo sapiens

<400> SEQUENCE: 197

Arg Ile Arg
1

<210> SEQ ID NO 198
<211> LENGTH: 3
<212> TYPE: PRT
<213> ORGANISM: Homo sapiens

<400> SEQUENCE: 198

Ile Arg Ser
1

<210> SEQ ID NO 199
<211> LENGTH: 3
<212> TYPE: PRT
<213> ORGANISM: Homo sapiens

<400> SEQUENCE: 199

Arg Ser Leu
1

<210> SEQ ID NO 200
<211> LENGTH: 3
<212> TYPE: PRT
<213> ORGANISM: Homo sapiens

<400> SEQUENCE: 200
```

```
Ser Leu Lys
1

<210> SEQ ID NO 201
<211> LENGTH: 3
<212> TYPE: PRT
<213> ORGANISM: Homo sapiens

<400> SEQUENCE: 201

Leu Lys Ile
1

<210> SEQ ID NO 202
<211> LENGTH: 3
<212> TYPE: PRT
<213> ORGANISM: Homo sapiens

<400> SEQUENCE: 202

Lys Ile Glu
1

<210> SEQ ID NO 203
<211> LENGTH: 3
<212> TYPE: PRT
<213> ORGANISM: Homo sapiens

<400> SEQUENCE: 203

Ile Glu Leu
1

<210> SEQ ID NO 204
<211> LENGTH: 3
<212> TYPE: PRT
<213> ORGANISM: Homo sapiens

<400> SEQUENCE: 204

Glu Leu His
1

<210> SEQ ID NO 205
<211> LENGTH: 3
<212> TYPE: PRT
<213> ORGANISM: Homo sapiens

<400> SEQUENCE: 205

Leu His Ser
1

<210> SEQ ID NO 206
<211> LENGTH: 3
<212> TYPE: PRT
<213> ORGANISM: Homo sapiens

<400> SEQUENCE: 206

Ser Arg Ser
1

<210> SEQ ID NO 207
<211> LENGTH: 3
<212> TYPE: PRT
<213> ORGANISM: Homo sapiens

<400> SEQUENCE: 207

Arg Ser Gly
1
```

```
<210> SEQ ID NO 208
<211> LENGTH: 3
<212> TYPE: PRT
<213> ORGANISM: Homo sapiens

<400> SEQUENCE: 208

Ser Gly His
1

<210> SEQ ID NO 209
<211> LENGTH: 3
<212> TYPE: PRT
<213> ORGANISM: Homo sapiens

<400> SEQUENCE: 209

Gly His Trp
1

<210> SEQ ID NO 210
<211> LENGTH: 3
<212> TYPE: PRT
<213> ORGANISM: Homo sapiens

<400> SEQUENCE: 210

His Trp Gln
1

<210> SEQ ID NO 211
<211> LENGTH: 3
<212> TYPE: PRT
<213> ORGANISM: Homo sapiens

<400> SEQUENCE: 211

Trp Gln Ser
1

<210> SEQ ID NO 212
<211> LENGTH: 3
<212> TYPE: PRT
<213> ORGANISM: Homo sapiens

<400> SEQUENCE: 212

Gln Ser Ile
1

<210> SEQ ID NO 213
<211> LENGTH: 3
<212> TYPE: PRT
<213> ORGANISM: Homo sapiens

<400> SEQUENCE: 213

Ser Ile Asp
1

<210> SEQ ID NO 214
<211> LENGTH: 3
<212> TYPE: PRT
<213> ORGANISM: Homo sapiens

<400> SEQUENCE: 214

Ile Asp Phe
1
```

<210> SEQ ID NO 215
<211> LENGTH: 3
<212> TYPE: PRT
<213> ORGANISM: Homo sapiens

<400> SEQUENCE: 215

Asp Phe Lys
1

<210> SEQ ID NO 216
<211> LENGTH: 3
<212> TYPE: PRT
<213> ORGANISM: Homo sapiens

<400> SEQUENCE: 216

Phe Lys Gln
1

<210> SEQ ID NO 217
<211> LENGTH: 3
<212> TYPE: PRT
<213> ORGANISM: Homo sapiens

<400> SEQUENCE: 217

Lys Gln Val
1

<210> SEQ ID NO 218
<211> LENGTH: 3
<212> TYPE: PRT
<213> ORGANISM: Homo sapiens

<400> SEQUENCE: 218

Gln Val Leu
1

<210> SEQ ID NO 219
<211> LENGTH: 3
<212> TYPE: PRT
<213> ORGANISM: Homo sapiens

<400> SEQUENCE: 219

Val Leu His
1

<210> SEQ ID NO 220
<211> LENGTH: 3
<212> TYPE: PRT
<213> ORGANISM: Homo sapiens

<400> SEQUENCE: 220

His Ser Trp
1

<210> SEQ ID NO 221
<211> LENGTH: 3
<212> TYPE: PRT
<213> ORGANISM: Homo sapiens

<400> SEQUENCE: 221

Ser Trp Phe
1

<210> SEQ ID NO 222
<211> LENGTH: 3

```
<212> TYPE: PRT
<213> ORGANISM: Homo sapiens

<400> SEQUENCE: 222

Trp Phe Arg
1

<210> SEQ ID NO 223
<211> LENGTH: 3
<212> TYPE: PRT
<213> ORGANISM: Homo sapiens

<400> SEQUENCE: 223

Phe Arg Gln
1

<210> SEQ ID NO 224
<211> LENGTH: 3
<212> TYPE: PRT
<213> ORGANISM: Homo sapiens

<400> SEQUENCE: 224

Arg Gln Pro
1

<210> SEQ ID NO 225
<211> LENGTH: 3
<212> TYPE: PRT
<213> ORGANISM: Homo sapiens

<400> SEQUENCE: 225

Gln Pro Gln
1

<210> SEQ ID NO 226
<211> LENGTH: 3
<212> TYPE: PRT
<213> ORGANISM: Homo sapiens

<400> SEQUENCE: 226

Pro Gln Ser
1

<210> SEQ ID NO 227
<211> LENGTH: 3
<212> TYPE: PRT
<213> ORGANISM: Homo sapiens

<400> SEQUENCE: 227

Gln Ser Asn
1

<210> SEQ ID NO 228
<211> LENGTH: 3
<212> TYPE: PRT
<213> ORGANISM: Homo sapiens

<400> SEQUENCE: 228

Ser Asn Trp
1

<210> SEQ ID NO 229
<211> LENGTH: 3
<212> TYPE: PRT
<213> ORGANISM: Homo sapiens
```

<400> SEQUENCE: 229

Asn Trp Gly
1

<210> SEQ ID NO 230
<211> LENGTH: 3
<212> TYPE: PRT
<213> ORGANISM: Homo sapiens

<400> SEQUENCE: 230

Trp Gly Ile
1

<210> SEQ ID NO 231
<211> LENGTH: 3
<212> TYPE: PRT
<213> ORGANISM: Homo sapiens

<400> SEQUENCE: 231

Gly Ile Glu
1

<210> SEQ ID NO 232
<211> LENGTH: 3
<212> TYPE: PRT
<213> ORGANISM: Homo sapiens

<400> SEQUENCE: 232

Ile Glu Ile
1

<210> SEQ ID NO 233
<211> LENGTH: 3
<212> TYPE: PRT
<213> ORGANISM: Homo sapiens

<400> SEQUENCE: 233

Glu Ile Asn
1

<210> SEQ ID NO 234
<211> LENGTH: 3
<212> TYPE: PRT
<213> ORGANISM: Homo sapiens

<400> SEQUENCE: 234

Ile Asn Ala
1

<210> SEQ ID NO 235
<211> LENGTH: 3
<212> TYPE: PRT
<213> ORGANISM: Homo sapiens

<400> SEQUENCE: 235

Asn Ala Phe
1

<210> SEQ ID NO 236
<211> LENGTH: 3
<212> TYPE: PRT
<213> ORGANISM: Homo sapiens

<400> SEQUENCE: 236

Ala Phe Asp
1

<210> SEQ ID NO 237
<211> LENGTH: 3
<212> TYPE: PRT
<213> ORGANISM: Homo sapiens

<400> SEQUENCE: 237

Phe Asp Pro
1

<210> SEQ ID NO 238
<211> LENGTH: 3
<212> TYPE: PRT
<213> ORGANISM: Homo sapiens

<400> SEQUENCE: 238

Asp Pro Ser
1

<210> SEQ ID NO 239
<211> LENGTH: 3
<212> TYPE: PRT
<213> ORGANISM: Homo sapiens

<400> SEQUENCE: 239

Pro Ser Gly
1

<210> SEQ ID NO 240
<211> LENGTH: 3
<212> TYPE: PRT
<213> ORGANISM: Homo sapiens

<400> SEQUENCE: 240

Ser Gly Thr
1

<210> SEQ ID NO 241
<211> LENGTH: 3
<212> TYPE: PRT
<213> ORGANISM: Homo sapiens

<400> SEQUENCE: 241

Gly Thr Asp
1

<210> SEQ ID NO 242
<211> LENGTH: 3
<212> TYPE: PRT
<213> ORGANISM: Homo sapiens

<400> SEQUENCE: 242

Thr Asp Leu
1

<210> SEQ ID NO 243
<211> LENGTH: 3
<212> TYPE: PRT
<213> ORGANISM: Homo sapiens

<400> SEQUENCE: 243

Asp Leu Ala

-continued

```
<210> SEQ ID NO 244
<211> LENGTH: 3
<212> TYPE: PRT
<213> ORGANISM: Homo sapiens

<400> SEQUENCE: 244

Leu Ala Val
1

<210> SEQ ID NO 245
<211> LENGTH: 3
<212> TYPE: PRT
<213> ORGANISM: Homo sapiens

<400> SEQUENCE: 245

Ala Val Thr
1

<210> SEQ ID NO 246
<211> LENGTH: 3
<212> TYPE: PRT
<213> ORGANISM: Homo sapiens

<400> SEQUENCE: 246

Val Thr Ser
1

<210> SEQ ID NO 247
<211> LENGTH: 3
<212> TYPE: PRT
<213> ORGANISM: Homo sapiens

<400> SEQUENCE: 247

Thr Ser Leu
1

<210> SEQ ID NO 248
<211> LENGTH: 3
<212> TYPE: PRT
<213> ORGANISM: Homo sapiens

<400> SEQUENCE: 248

Ser Leu Gly
1

<210> SEQ ID NO 249
<211> LENGTH: 3
<212> TYPE: PRT
<213> ORGANISM: Homo sapiens

<400> SEQUENCE: 249

Leu Gly Pro
1

<210> SEQ ID NO 250
<211> LENGTH: 3
<212> TYPE: PRT
<213> ORGANISM: Homo sapiens

<400> SEQUENCE: 250

Gly Pro Gly
1
```

<210> SEQ ID NO 251
<211> LENGTH: 3
<212> TYPE: PRT
<213> ORGANISM: Homo sapiens

<400> SEQUENCE: 251

Pro Gly Ala
1

<210> SEQ ID NO 252
<211> LENGTH: 3
<212> TYPE: PRT
<213> ORGANISM: Homo sapiens

<400> SEQUENCE: 252

Gly Ala Glu
1

<210> SEQ ID NO 253
<211> LENGTH: 3
<212> TYPE: PRT
<213> ORGANISM: Homo sapiens

<400> SEQUENCE: 253

Glu Gly Leu
1

<210> SEQ ID NO 254
<211> LENGTH: 3
<212> TYPE: PRT
<213> ORGANISM: Homo sapiens

<400> SEQUENCE: 254

Gly Leu His
1

<210> SEQ ID NO 255
<211> LENGTH: 3
<212> TYPE: PRT
<213> ORGANISM: Homo sapiens

<400> SEQUENCE: 255

Leu His Pro
1

<210> SEQ ID NO 256
<211> LENGTH: 3
<212> TYPE: PRT
<213> ORGANISM: Homo sapiens

<400> SEQUENCE: 256

His Pro Phe
1

<210> SEQ ID NO 257
<211> LENGTH: 3
<212> TYPE: PRT
<213> ORGANISM: Homo sapiens

<400> SEQUENCE: 257

Pro Phe Met
1

<210> SEQ ID NO 258

```
<211> LENGTH: 3
<212> TYPE: PRT
<213> ORGANISM: Homo sapiens

<400> SEQUENCE: 258

Phe Met Glu
1

<210> SEQ ID NO 259
<211> LENGTH: 3
<212> TYPE: PRT
<213> ORGANISM: Homo sapiens

<400> SEQUENCE: 259

Met Glu Leu
1

<210> SEQ ID NO 260
<211> LENGTH: 3
<212> TYPE: PRT
<213> ORGANISM: Homo sapiens

<400> SEQUENCE: 260

Leu Arg Val
1

<210> SEQ ID NO 261
<211> LENGTH: 3
<212> TYPE: PRT
<213> ORGANISM: Homo sapiens

<400> SEQUENCE: 261

Arg Val Leu
1

<210> SEQ ID NO 262
<211> LENGTH: 3
<212> TYPE: PRT
<213> ORGANISM: Homo sapiens

<400> SEQUENCE: 262

Val Leu Glu
1

<210> SEQ ID NO 263
<211> LENGTH: 3
<212> TYPE: PRT
<213> ORGANISM: Homo sapiens

<400> SEQUENCE: 263

Leu Glu Asn
1

<210> SEQ ID NO 264
<211> LENGTH: 3
<212> TYPE: PRT
<213> ORGANISM: Homo sapiens

<400> SEQUENCE: 264

Glu Asn Thr
1

<210> SEQ ID NO 265
<211> LENGTH: 3
<212> TYPE: PRT
```

<213> ORGANISM: Homo sapiens

<400> SEQUENCE: 265

Asn Thr Lys
1

<210> SEQ ID NO 266
<211> LENGTH: 3
<212> TYPE: PRT
<213> ORGANISM: Homo sapiens

<400> SEQUENCE: 266

Thr Lys Arg
1

<210> SEQ ID NO 267
<211> LENGTH: 3
<212> TYPE: PRT
<213> ORGANISM: Homo sapiens

<400> SEQUENCE: 267

Lys Arg Ser
1

<210> SEQ ID NO 268
<211> LENGTH: 3
<212> TYPE: PRT
<213> ORGANISM: Homo sapiens

<400> SEQUENCE: 268

Arg Ser Arg
1

<210> SEQ ID NO 269
<211> LENGTH: 3
<212> TYPE: PRT
<213> ORGANISM: Homo sapiens

<400> SEQUENCE: 269

Ser Arg Arg
1

<210> SEQ ID NO 270
<211> LENGTH: 3
<212> TYPE: PRT
<213> ORGANISM: Homo sapiens

<400> SEQUENCE: 270

Arg Arg Asn
1

<210> SEQ ID NO 271
<211> LENGTH: 3
<212> TYPE: PRT
<213> ORGANISM: Homo sapiens

<400> SEQUENCE: 271

Arg Asn Leu
1

<210> SEQ ID NO 272
<211> LENGTH: 3
<212> TYPE: PRT
<213> ORGANISM: Homo sapiens

```
<400> SEQUENCE: 272

Asn Leu Gly
1

<210> SEQ ID NO 273
<211> LENGTH: 3
<212> TYPE: PRT
<213> ORGANISM: Homo sapiens

<400> SEQUENCE: 273

Leu Gly Leu
1

<210> SEQ ID NO 274
<211> LENGTH: 3
<212> TYPE: PRT
<213> ORGANISM: Homo sapiens

<400> SEQUENCE: 274

Gly Leu Asp
1

<210> SEQ ID NO 275
<211> LENGTH: 3
<212> TYPE: PRT
<213> ORGANISM: Homo sapiens

<400> SEQUENCE: 275

Leu Asp Cys
1

<210> SEQ ID NO 276
<211> LENGTH: 3
<212> TYPE: PRT
<213> ORGANISM: Homo sapiens

<400> SEQUENCE: 276

Asp Cys Asp
1

<210> SEQ ID NO 277
<211> LENGTH: 3
<212> TYPE: PRT
<213> ORGANISM: Homo sapiens

<400> SEQUENCE: 277

Cys Asp Glu
1

<210> SEQ ID NO 278
<211> LENGTH: 3
<212> TYPE: PRT
<213> ORGANISM: Homo sapiens

<400> SEQUENCE: 278

Asp Glu His
1

<210> SEQ ID NO 279
<211> LENGTH: 3
<212> TYPE: PRT
<213> ORGANISM: Homo sapiens

<400> SEQUENCE: 279
```

Glu His Ser
1

<210> SEQ ID NO 280
<211> LENGTH: 3
<212> TYPE: PRT
<213> ORGANISM: Homo sapiens

<400> SEQUENCE: 280

His Ser Ser
1

<210> SEQ ID NO 281
<211> LENGTH: 3
<212> TYPE: PRT
<213> ORGANISM: Homo sapiens

<400> SEQUENCE: 281

Ser Ser Glu
1

<210> SEQ ID NO 282
<211> LENGTH: 3
<212> TYPE: PRT
<213> ORGANISM: Homo sapiens

<400> SEQUENCE: 282

Ser Glu Ser
1

<210> SEQ ID NO 283
<211> LENGTH: 3
<212> TYPE: PRT
<213> ORGANISM: Homo sapiens

<400> SEQUENCE: 283

Glu Ser Arg
1

<210> SEQ ID NO 284
<211> LENGTH: 3
<212> TYPE: PRT
<213> ORGANISM: Homo sapiens

<400> SEQUENCE: 284

Ser Arg Cys
1

<210> SEQ ID NO 285
<211> LENGTH: 3
<212> TYPE: PRT
<213> ORGANISM: Homo sapiens

<400> SEQUENCE: 285

Arg Cys Cys
1

<210> SEQ ID NO 286
<211> LENGTH: 3
<212> TYPE: PRT
<213> ORGANISM: Homo sapiens

<400> SEQUENCE: 286

Cys Cys Arg
1

```
<210> SEQ ID NO 287
<211> LENGTH: 3
<212> TYPE: PRT
<213> ORGANISM: Homo sapiens

<400> SEQUENCE: 287

Cys Arg Tyr
1

<210> SEQ ID NO 288
<211> LENGTH: 3
<212> TYPE: PRT
<213> ORGANISM: Homo sapiens

<400> SEQUENCE: 288

Arg Tyr Pro
1

<210> SEQ ID NO 289
<211> LENGTH: 3
<212> TYPE: PRT
<213> ORGANISM: Homo sapiens

<400> SEQUENCE: 289

Tyr Pro Leu
1

<210> SEQ ID NO 290
<211> LENGTH: 3
<212> TYPE: PRT
<213> ORGANISM: Homo sapiens

<400> SEQUENCE: 290

Leu Thr Val
1

<210> SEQ ID NO 291
<211> LENGTH: 3
<212> TYPE: PRT
<213> ORGANISM: Homo sapiens

<400> SEQUENCE: 291

Thr Val Asp
1

<210> SEQ ID NO 292
<211> LENGTH: 3
<212> TYPE: PRT
<213> ORGANISM: Homo sapiens

<400> SEQUENCE: 292

Val Asp Phe
1

<210> SEQ ID NO 293
<211> LENGTH: 3
<212> TYPE: PRT
<213> ORGANISM: Homo sapiens

<400> SEQUENCE: 293

Asp Phe Glu
1
```

```
<210> SEQ ID NO 294
<211> LENGTH: 3
<212> TYPE: PRT
<213> ORGANISM: Homo sapiens

<400> SEQUENCE: 294

Phe Glu Ala
1

<210> SEQ ID NO 295
<211> LENGTH: 3
<212> TYPE: PRT
<213> ORGANISM: Homo sapiens

<400> SEQUENCE: 295

Glu Ala Phe
1

<210> SEQ ID NO 296
<211> LENGTH: 3
<212> TYPE: PRT
<213> ORGANISM: Homo sapiens

<400> SEQUENCE: 296

Ala Phe Gly
1

<210> SEQ ID NO 297
<211> LENGTH: 3
<212> TYPE: PRT
<213> ORGANISM: Homo sapiens

<400> SEQUENCE: 297

Phe Gly Trp
1

<210> SEQ ID NO 298
<211> LENGTH: 3
<212> TYPE: PRT
<213> ORGANISM: Homo sapiens

<400> SEQUENCE: 298

Gly Trp Asp
1

<210> SEQ ID NO 299
<211> LENGTH: 3
<212> TYPE: PRT
<213> ORGANISM: Homo sapiens

<400> SEQUENCE: 299

Trp Asp Trp
1

<210> SEQ ID NO 300
<211> LENGTH: 3
<212> TYPE: PRT
<213> ORGANISM: Homo sapiens

<400> SEQUENCE: 300

Asp Trp Ile
1

<210> SEQ ID NO 301
<211> LENGTH: 3
```

```
<212> TYPE: PRT
<213> ORGANISM: Homo sapiens

<400> SEQUENCE: 301

Trp Ile Ile
1

<210> SEQ ID NO 302
<211> LENGTH: 3
<212> TYPE: PRT
<213> ORGANISM: Homo sapiens

<400> SEQUENCE: 302

Ile Ile Ala
1

<210> SEQ ID NO 303
<211> LENGTH: 3
<212> TYPE: PRT
<213> ORGANISM: Homo sapiens

<400> SEQUENCE: 303

Ile Ala Pro
1

<210> SEQ ID NO 304
<211> LENGTH: 3
<212> TYPE: PRT
<213> ORGANISM: Homo sapiens

<400> SEQUENCE: 304

Ala Pro Lys
1

<210> SEQ ID NO 305
<211> LENGTH: 3
<212> TYPE: PRT
<213> ORGANISM: Homo sapiens

<400> SEQUENCE: 305

Pro Lys Arg
1

<210> SEQ ID NO 306
<211> LENGTH: 3
<212> TYPE: PRT
<213> ORGANISM: Homo sapiens

<400> SEQUENCE: 306

Lys Arg Tyr
1

<210> SEQ ID NO 307
<211> LENGTH: 3
<212> TYPE: PRT
<213> ORGANISM: Homo sapiens

<400> SEQUENCE: 307

Arg Tyr Lys
1

<210> SEQ ID NO 308
<211> LENGTH: 3
<212> TYPE: PRT
<213> ORGANISM: Homo sapiens
```

<400> SEQUENCE: 308

Tyr Lys Ala
1

<210> SEQ ID NO 309
<211> LENGTH: 3
<212> TYPE: PRT
<213> ORGANISM: Homo sapiens

<400> SEQUENCE: 309

Lys Ala Asn
1

<210> SEQ ID NO 310
<211> LENGTH: 3
<212> TYPE: PRT
<213> ORGANISM: Homo sapiens

<400> SEQUENCE: 310

Ala Asn Tyr
1

<210> SEQ ID NO 311
<211> LENGTH: 3
<212> TYPE: PRT
<213> ORGANISM: Homo sapiens

<400> SEQUENCE: 311

Asn Tyr Cys
1

<210> SEQ ID NO 312
<211> LENGTH: 3
<212> TYPE: PRT
<213> ORGANISM: Homo sapiens

<400> SEQUENCE: 312

Tyr Cys Ser
1

<210> SEQ ID NO 313
<211> LENGTH: 3
<212> TYPE: PRT
<213> ORGANISM: Homo sapiens

<400> SEQUENCE: 313

Cys Ser Gly
1

<210> SEQ ID NO 314
<211> LENGTH: 3
<212> TYPE: PRT
<213> ORGANISM: Homo sapiens

<400> SEQUENCE: 314

Ser Gly Gln
1

<210> SEQ ID NO 315
<211> LENGTH: 3
<212> TYPE: PRT
<213> ORGANISM: Homo sapiens

<400> SEQUENCE: 315

Gly Gln Cys
1

<210> SEQ ID NO 316
<211> LENGTH: 3
<212> TYPE: PRT
<213> ORGANISM: Homo sapiens

<400> SEQUENCE: 316

Gln Cys Glu
1

<210> SEQ ID NO 317
<211> LENGTH: 3
<212> TYPE: PRT
<213> ORGANISM: Homo sapiens

<400> SEQUENCE: 317

Cys Glu Tyr
1

<210> SEQ ID NO 318
<211> LENGTH: 3
<212> TYPE: PRT
<213> ORGANISM: Homo sapiens

<400> SEQUENCE: 318

Glu Tyr Met
1

<210> SEQ ID NO 319
<211> LENGTH: 3
<212> TYPE: PRT
<213> ORGANISM: Homo sapiens

<400> SEQUENCE: 319

Tyr Met Phe
1

<210> SEQ ID NO 320
<211> LENGTH: 3
<212> TYPE: PRT
<213> ORGANISM: Homo sapiens

<400> SEQUENCE: 320

Met Phe Met
1

<210> SEQ ID NO 321
<211> LENGTH: 3
<212> TYPE: PRT
<213> ORGANISM: Homo sapiens

<400> SEQUENCE: 321

Phe Met Gln
1

<210> SEQ ID NO 322
<211> LENGTH: 3
<212> TYPE: PRT
<213> ORGANISM: Homo sapiens

<400> SEQUENCE: 322

Met Gln Lys

```
<210> SEQ ID NO 323
<211> LENGTH: 3
<212> TYPE: PRT
<213> ORGANISM: Homo sapiens

<400> SEQUENCE: 323

Gln Lys Tyr
1

<210> SEQ ID NO 324
<211> LENGTH: 3
<212> TYPE: PRT
<213> ORGANISM: Homo sapiens

<400> SEQUENCE: 324

Lys Tyr Pro
1

<210> SEQ ID NO 325
<211> LENGTH: 3
<212> TYPE: PRT
<213> ORGANISM: Homo sapiens

<400> SEQUENCE: 325

Tyr Pro His
1

<210> SEQ ID NO 326
<211> LENGTH: 3
<212> TYPE: PRT
<213> ORGANISM: Homo sapiens

<400> SEQUENCE: 326

Pro His Thr
1

<210> SEQ ID NO 327
<211> LENGTH: 3
<212> TYPE: PRT
<213> ORGANISM: Homo sapiens

<400> SEQUENCE: 327

His Thr His
1

<210> SEQ ID NO 328
<211> LENGTH: 3
<212> TYPE: PRT
<213> ORGANISM: Homo sapiens

<400> SEQUENCE: 328

Thr His Leu
1

<210> SEQ ID NO 329
<211> LENGTH: 3
<212> TYPE: PRT
<213> ORGANISM: Homo sapiens

<400> SEQUENCE: 329

His Leu Val
1
```

<210> SEQ ID NO 330
<211> LENGTH: 3
<212> TYPE: PRT
<213> ORGANISM: Homo sapiens

<400> SEQUENCE: 330

Leu Val Gln
1

<210> SEQ ID NO 331
<211> LENGTH: 3
<212> TYPE: PRT
<213> ORGANISM: Homo sapiens

<400> SEQUENCE: 331

Val Gln Gln
1

<210> SEQ ID NO 332
<211> LENGTH: 3
<212> TYPE: PRT
<213> ORGANISM: Homo sapiens

<400> SEQUENCE: 332

Gln Gln Ala
1

<210> SEQ ID NO 333
<211> LENGTH: 3
<212> TYPE: PRT
<213> ORGANISM: Homo sapiens

<400> SEQUENCE: 333

Gln Ala Asn
1

<210> SEQ ID NO 334
<211> LENGTH: 3
<212> TYPE: PRT
<213> ORGANISM: Homo sapiens

<400> SEQUENCE: 334

Ala Asn Pro
1

<210> SEQ ID NO 335
<211> LENGTH: 3
<212> TYPE: PRT
<213> ORGANISM: Homo sapiens

<400> SEQUENCE: 335

Asn Pro Arg
1

<210> SEQ ID NO 336
<211> LENGTH: 3
<212> TYPE: PRT
<213> ORGANISM: Homo sapiens

<400> SEQUENCE: 336

Arg Gly Ser
1

<210> SEQ ID NO 337

```
<210> SEQ ID NO 337
<211> LENGTH: 3
<212> TYPE: PRT
<213> ORGANISM: Homo sapiens

<400> SEQUENCE: 337

Gly Ser Ala
1

<210> SEQ ID NO 338
<211> LENGTH: 3
<212> TYPE: PRT
<213> ORGANISM: Homo sapiens

<400> SEQUENCE: 338

Ser Ala Gly
1

<210> SEQ ID NO 339
<211> LENGTH: 3
<212> TYPE: PRT
<213> ORGANISM: Homo sapiens

<400> SEQUENCE: 339

Ala Gly Pro
1

<210> SEQ ID NO 340
<211> LENGTH: 3
<212> TYPE: PRT
<213> ORGANISM: Homo sapiens

<400> SEQUENCE: 340

Gly Pro Cys
1

<210> SEQ ID NO 341
<211> LENGTH: 3
<212> TYPE: PRT
<213> ORGANISM: Homo sapiens

<400> SEQUENCE: 341

Pro Cys Cys
1

<210> SEQ ID NO 342
<211> LENGTH: 3
<212> TYPE: PRT
<213> ORGANISM: Homo sapiens

<400> SEQUENCE: 342

Cys Cys Thr
1

<210> SEQ ID NO 343
<211> LENGTH: 3
<212> TYPE: PRT
<213> ORGANISM: Homo sapiens

<400> SEQUENCE: 343

Cys Thr Pro
1

<210> SEQ ID NO 344
<211> LENGTH: 3
<212> TYPE: PRT
```

<213> ORGANISM: Homo sapiens

<400> SEQUENCE: 344

Thr Pro Thr
1

<210> SEQ ID NO 345
<211> LENGTH: 3
<212> TYPE: PRT
<213> ORGANISM: Homo sapiens

<400> SEQUENCE: 345

Pro Thr Lys
1

<210> SEQ ID NO 346
<211> LENGTH: 3
<212> TYPE: PRT
<213> ORGANISM: Homo sapiens

<400> SEQUENCE: 346

Thr Lys Met
1

<210> SEQ ID NO 347
<211> LENGTH: 3
<212> TYPE: PRT
<213> ORGANISM: Homo sapiens

<400> SEQUENCE: 347

Lys Met Ser
1

<210> SEQ ID NO 348
<211> LENGTH: 3
<212> TYPE: PRT
<213> ORGANISM: Homo sapiens

<400> SEQUENCE: 348

Met Ser Pro
1

<210> SEQ ID NO 349
<211> LENGTH: 3
<212> TYPE: PRT
<213> ORGANISM: Homo sapiens

<400> SEQUENCE: 349

Ser Pro Ile
1

<210> SEQ ID NO 350
<211> LENGTH: 3
<212> TYPE: PRT
<213> ORGANISM: Homo sapiens

<400> SEQUENCE: 350

Pro Ile Asn
1

<210> SEQ ID NO 351
<211> LENGTH: 3
<212> TYPE: PRT
<213> ORGANISM: Homo sapiens

```
<400> SEQUENCE: 351

Ile Asn Met
1

<210> SEQ ID NO 352
<211> LENGTH: 3
<212> TYPE: PRT
<213> ORGANISM: Homo sapiens

<400> SEQUENCE: 352

Asn Met Leu
1

<210> SEQ ID NO 353
<211> LENGTH: 3
<212> TYPE: PRT
<213> ORGANISM: Homo sapiens

<400> SEQUENCE: 353

Met Leu Tyr
1

<210> SEQ ID NO 354
<211> LENGTH: 3
<212> TYPE: PRT
<213> ORGANISM: Homo sapiens

<400> SEQUENCE: 354

Leu Tyr Phe
1

<210> SEQ ID NO 355
<211> LENGTH: 3
<212> TYPE: PRT
<213> ORGANISM: Homo sapiens

<400> SEQUENCE: 355

Tyr Phe Asn
1

<210> SEQ ID NO 356
<211> LENGTH: 3
<212> TYPE: PRT
<213> ORGANISM: Homo sapiens

<400> SEQUENCE: 356

Phe Asn Asp
1

<210> SEQ ID NO 357
<211> LENGTH: 3
<212> TYPE: PRT
<213> ORGANISM: Homo sapiens

<400> SEQUENCE: 357

Asn Asp Lys
1

<210> SEQ ID NO 358
<211> LENGTH: 3
<212> TYPE: PRT
<213> ORGANISM: Homo sapiens

<400> SEQUENCE: 358
```

Asp Lys Gln
1

<210> SEQ ID NO 359
<211> LENGTH: 3
<212> TYPE: PRT
<213> ORGANISM: Homo sapiens

<400> SEQUENCE: 359

Lys Gln Gln
1

<210> SEQ ID NO 360
<211> LENGTH: 3
<212> TYPE: PRT
<213> ORGANISM: Homo sapiens

<400> SEQUENCE: 360

Gln Ile Ile
1

<210> SEQ ID NO 361
<211> LENGTH: 3
<212> TYPE: PRT
<213> ORGANISM: Homo sapiens

<400> SEQUENCE: 361

Ile Ile Tyr
1

<210> SEQ ID NO 362
<211> LENGTH: 3
<212> TYPE: PRT
<213> ORGANISM: Homo sapiens

<400> SEQUENCE: 362

Ile Tyr Gly
1

<210> SEQ ID NO 363
<211> LENGTH: 3
<212> TYPE: PRT
<213> ORGANISM: Homo sapiens

<400> SEQUENCE: 363

Tyr Gly Lys
1

<210> SEQ ID NO 364
<211> LENGTH: 3
<212> TYPE: PRT
<213> ORGANISM: Homo sapiens

<400> SEQUENCE: 364

Gly Lys Ile
1

<210> SEQ ID NO 365
<211> LENGTH: 3
<212> TYPE: PRT
<213> ORGANISM: Homo sapiens

<400> SEQUENCE: 365

Lys Ile Pro
1

<210> SEQ ID NO 366
<211> LENGTH: 3
<212> TYPE: PRT
<213> ORGANISM: Homo sapiens

<400> SEQUENCE: 366

Ile Pro Gly
1

<210> SEQ ID NO 367
<211> LENGTH: 3
<212> TYPE: PRT
<213> ORGANISM: Homo sapiens

<400> SEQUENCE: 367

Pro Gly Met
1

<210> SEQ ID NO 368
<211> LENGTH: 3
<212> TYPE: PRT
<213> ORGANISM: Homo sapiens

<400> SEQUENCE: 368

Gly Met Val
1

<210> SEQ ID NO 369
<211> LENGTH: 3
<212> TYPE: PRT
<213> ORGANISM: Homo sapiens

<400> SEQUENCE: 369

Met Val Val
1

<210> SEQ ID NO 370
<211> LENGTH: 3
<212> TYPE: PRT
<213> ORGANISM: Homo sapiens

<400> SEQUENCE: 370

Val Val Asp
1

<210> SEQ ID NO 371
<211> LENGTH: 3
<212> TYPE: PRT
<213> ORGANISM: Homo sapiens

<400> SEQUENCE: 371

Val Asp Arg
1

<210> SEQ ID NO 372
<211> LENGTH: 3
<212> TYPE: PRT
<213> ORGANISM: Homo sapiens

<400> SEQUENCE: 372

Asp Arg Cys
1

```
<210> SEQ ID NO 373
<211> LENGTH: 3
<212> TYPE: PRT
<213> ORGANISM: Homo sapiens

<400> SEQUENCE: 373

Arg Cys Gly
1

<210> SEQ ID NO 374
<211> LENGTH: 3
<212> TYPE: PRT
<213> ORGANISM: Homo sapiens

<400> SEQUENCE: 374

Cys Gly Cys
1

<210> SEQ ID NO 375
<211> LENGTH: 3
<212> TYPE: PRT
<213> ORGANISM: Homo sapiens

<400> SEQUENCE: 375

Gly Cys Ser
1

<210> SEQ ID NO 376
<211> LENGTH: 4
<212> TYPE: PRT
<213> ORGANISM: Homo sapiens

<400> SEQUENCE: 376

Met Val Leu Ala
1

<210> SEQ ID NO 377
<211> LENGTH: 4
<212> TYPE: PRT
<213> ORGANISM: Homo sapiens

<400> SEQUENCE: 377

Val Leu Ala Ala
1

<210> SEQ ID NO 378
<211> LENGTH: 4
<212> TYPE: PRT
<213> ORGANISM: Homo sapiens

<400> SEQUENCE: 378

Leu Ala Ala Pro
1

<210> SEQ ID NO 379
<211> LENGTH: 4
<212> TYPE: PRT
<213> ORGANISM: Homo sapiens

<400> SEQUENCE: 379

Ala Ala Pro Leu
1

<210> SEQ ID NO 380
<211> LENGTH: 4
```

```
<212> TYPE: PRT
<213> ORGANISM: Homo sapiens

<400> SEQUENCE: 380

Ala Pro Leu Leu
1

<210> SEQ ID NO 381
<211> LENGTH: 4
<212> TYPE: PRT
<213> ORGANISM: Homo sapiens

<400> SEQUENCE: 381

Pro Leu Leu Leu
1

<210> SEQ ID NO 382
<211> LENGTH: 4
<212> TYPE: PRT
<213> ORGANISM: Homo sapiens

<400> SEQUENCE: 382

Leu Leu Leu Gly
1

<210> SEQ ID NO 383
<211> LENGTH: 4
<212> TYPE: PRT
<213> ORGANISM: Homo sapiens

<400> SEQUENCE: 383

Leu Leu Gly Phe
1

<210> SEQ ID NO 384
<211> LENGTH: 4
<212> TYPE: PRT
<213> ORGANISM: Homo sapiens

<400> SEQUENCE: 384

Leu Gly Phe Leu
1

<210> SEQ ID NO 385
<211> LENGTH: 4
<212> TYPE: PRT
<213> ORGANISM: Homo sapiens

<400> SEQUENCE: 385

Gly Phe Leu Leu
1

<210> SEQ ID NO 386
<211> LENGTH: 4
<212> TYPE: PRT
<213> ORGANISM: Homo sapiens

<400> SEQUENCE: 386

Phe Leu Leu Leu
1

<210> SEQ ID NO 387
<211> LENGTH: 4
<212> TYPE: PRT
<213> ORGANISM: Homo sapiens
```

<400> SEQUENCE: 387

Leu Leu Leu Ala
1

<210> SEQ ID NO 388
<211> LENGTH: 4
<212> TYPE: PRT
<213> ORGANISM: Homo sapiens

<400> SEQUENCE: 388

Leu Leu Ala Leu
1

<210> SEQ ID NO 389
<211> LENGTH: 4
<212> TYPE: PRT
<213> ORGANISM: Homo sapiens

<400> SEQUENCE: 389

Leu Ala Leu Glu
1

<210> SEQ ID NO 390
<211> LENGTH: 4
<212> TYPE: PRT
<213> ORGANISM: Homo sapiens

<400> SEQUENCE: 390

Ala Leu Glu Leu
1

<210> SEQ ID NO 391
<211> LENGTH: 4
<212> TYPE: PRT
<213> ORGANISM: Homo sapiens

<400> SEQUENCE: 391

Leu Glu Leu Arg
1

<210> SEQ ID NO 392
<211> LENGTH: 4
<212> TYPE: PRT
<213> ORGANISM: Homo sapiens

<400> SEQUENCE: 392

Glu Leu Arg Pro
1

<210> SEQ ID NO 393
<211> LENGTH: 4
<212> TYPE: PRT
<213> ORGANISM: Homo sapiens

<400> SEQUENCE: 393

Leu Arg Pro Arg
1

<210> SEQ ID NO 394
<211> LENGTH: 4
<212> TYPE: PRT
<213> ORGANISM: Homo sapiens

<400> SEQUENCE: 394

Arg Pro Arg Gly
1

<210> SEQ ID NO 395
<211> LENGTH: 4
<212> TYPE: PRT
<213> ORGANISM: Homo sapiens

<400> SEQUENCE: 395

Pro Arg Gly Glu
1

<210> SEQ ID NO 396
<211> LENGTH: 4
<212> TYPE: PRT
<213> ORGANISM: Homo sapiens

<400> SEQUENCE: 396

Arg Gly Glu Ala
1

<210> SEQ ID NO 397
<211> LENGTH: 4
<212> TYPE: PRT
<213> ORGANISM: Homo sapiens

<400> SEQUENCE: 397

Gly Glu Ala Ala
1

<210> SEQ ID NO 398
<211> LENGTH: 4
<212> TYPE: PRT
<213> ORGANISM: Homo sapiens

<400> SEQUENCE: 398

Glu Ala Ala Glu
1

<210> SEQ ID NO 399
<211> LENGTH: 4
<212> TYPE: PRT
<213> ORGANISM: Homo sapiens

<400> SEQUENCE: 399

Ala Ala Glu Gly
1

<210> SEQ ID NO 400
<211> LENGTH: 4
<212> TYPE: PRT
<213> ORGANISM: Homo sapiens

<400> SEQUENCE: 400

Ala Glu Gly Pro
1

<210> SEQ ID NO 401
<211> LENGTH: 4
<212> TYPE: PRT
<213> ORGANISM: Homo sapiens

<400> SEQUENCE: 401

Glu Gly Pro Ala

```
<210> SEQ ID NO 402
<211> LENGTH: 4
<212> TYPE: PRT
<213> ORGANISM: Homo sapiens

<400> SEQUENCE: 402

Gly Pro Ala Ala
1

<210> SEQ ID NO 403
<211> LENGTH: 4
<212> TYPE: PRT
<213> ORGANISM: Homo sapiens

<400> SEQUENCE: 403

Pro Ala Ala Ala
1

<210> SEQ ID NO 404
<211> LENGTH: 4
<212> TYPE: PRT
<213> ORGANISM: Homo sapiens

<400> SEQUENCE: 404

Ala Ala Ala Ala
1

<210> SEQ ID NO 405
<211> LENGTH: 4
<212> TYPE: PRT
<213> ORGANISM: Homo sapiens

<400> SEQUENCE: 405

Ala Ala Ala Gly
1

<210> SEQ ID NO 406
<211> LENGTH: 4
<212> TYPE: PRT
<213> ORGANISM: Homo sapiens

<400> SEQUENCE: 406

Ala Ala Gly Val
1

<210> SEQ ID NO 407
<211> LENGTH: 4
<212> TYPE: PRT
<213> ORGANISM: Homo sapiens

<400> SEQUENCE: 407

Ala Gly Val Gly
1

<210> SEQ ID NO 408
<211> LENGTH: 4
<212> TYPE: PRT
<213> ORGANISM: Homo sapiens

<400> SEQUENCE: 408

Gly Val Gly Gly
1
```

<210> SEQ ID NO 409
<211> LENGTH: 4
<212> TYPE: PRT
<213> ORGANISM: Homo sapiens

<400> SEQUENCE: 409

Val Gly Gly Glu
1

<210> SEQ ID NO 410
<211> LENGTH: 4
<212> TYPE: PRT
<213> ORGANISM: Homo sapiens

<400> SEQUENCE: 410

Gly Gly Glu Arg
1

<210> SEQ ID NO 411
<211> LENGTH: 4
<212> TYPE: PRT
<213> ORGANISM: Homo sapiens

<400> SEQUENCE: 411

Gly Glu Arg Ser
1

<210> SEQ ID NO 412
<211> LENGTH: 4
<212> TYPE: PRT
<213> ORGANISM: Homo sapiens

<400> SEQUENCE: 412

Glu Arg Ser Ser
1

<210> SEQ ID NO 413
<211> LENGTH: 4
<212> TYPE: PRT
<213> ORGANISM: Homo sapiens

<400> SEQUENCE: 413

Arg Ser Ser Arg
1

<210> SEQ ID NO 414
<211> LENGTH: 4
<212> TYPE: PRT
<213> ORGANISM: Homo sapiens

<400> SEQUENCE: 414

Ser Ser Arg Pro
1

<210> SEQ ID NO 415
<211> LENGTH: 4
<212> TYPE: PRT
<213> ORGANISM: Homo sapiens

<400> SEQUENCE: 415

Ser Arg Pro Ala
1

<210> SEQ ID NO 416

```
<211> LENGTH: 4
<212> TYPE: PRT
<213> ORGANISM: Homo sapiens

<400> SEQUENCE: 416

Arg Pro Ala Pro
1

<210> SEQ ID NO 417
<211> LENGTH: 4
<212> TYPE: PRT
<213> ORGANISM: Homo sapiens

<400> SEQUENCE: 417

Pro Ala Pro Ser
1

<210> SEQ ID NO 418
<211> LENGTH: 4
<212> TYPE: PRT
<213> ORGANISM: Homo sapiens

<400> SEQUENCE: 418

Ala Pro Ser Val
1

<210> SEQ ID NO 419
<211> LENGTH: 4
<212> TYPE: PRT
<213> ORGANISM: Homo sapiens

<400> SEQUENCE: 419

Pro Ser Val Ala
1

<210> SEQ ID NO 420
<211> LENGTH: 4
<212> TYPE: PRT
<213> ORGANISM: Homo sapiens

<400> SEQUENCE: 420

Ser Val Ala Pro
1

<210> SEQ ID NO 421
<211> LENGTH: 4
<212> TYPE: PRT
<213> ORGANISM: Homo sapiens

<400> SEQUENCE: 421

Val Ala Pro Glu
1

<210> SEQ ID NO 422
<211> LENGTH: 4
<212> TYPE: PRT
<213> ORGANISM: Homo sapiens

<400> SEQUENCE: 422

Ala Pro Glu Pro
1

<210> SEQ ID NO 423
<211> LENGTH: 4
<212> TYPE: PRT
```

```
<213> ORGANISM: Homo sapiens

<400> SEQUENCE: 423

Pro Glu Pro Asp
1

<210> SEQ ID NO 424
<211> LENGTH: 4
<212> TYPE: PRT
<213> ORGANISM: Homo sapiens

<400> SEQUENCE: 424

Glu Pro Asp Gly
1

<210> SEQ ID NO 425
<211> LENGTH: 4
<212> TYPE: PRT
<213> ORGANISM: Homo sapiens

<400> SEQUENCE: 425

Pro Asp Gly Cys
1

<210> SEQ ID NO 426
<211> LENGTH: 4
<212> TYPE: PRT
<213> ORGANISM: Homo sapiens

<400> SEQUENCE: 426

Asp Gly Cys Pro
1

<210> SEQ ID NO 427
<211> LENGTH: 4
<212> TYPE: PRT
<213> ORGANISM: Homo sapiens

<400> SEQUENCE: 427

Gly Cys Pro Val
1

<210> SEQ ID NO 428
<211> LENGTH: 4
<212> TYPE: PRT
<213> ORGANISM: Homo sapiens

<400> SEQUENCE: 428

Cys Pro Val Cys
1

<210> SEQ ID NO 429
<211> LENGTH: 4
<212> TYPE: PRT
<213> ORGANISM: Homo sapiens

<400> SEQUENCE: 429

Pro Val Cys Val
1

<210> SEQ ID NO 430
<211> LENGTH: 4
<212> TYPE: PRT
<213> ORGANISM: Homo sapiens
```

```
<400> SEQUENCE: 430

Val Cys Val Trp
1

<210> SEQ ID NO 431
<211> LENGTH: 4
<212> TYPE: PRT
<213> ORGANISM: Homo sapiens

<400> SEQUENCE: 431

Cys Val Trp Arg
1

<210> SEQ ID NO 432
<211> LENGTH: 4
<212> TYPE: PRT
<213> ORGANISM: Homo sapiens

<400> SEQUENCE: 432

Val Trp Arg Gln
1

<210> SEQ ID NO 433
<211> LENGTH: 4
<212> TYPE: PRT
<213> ORGANISM: Homo sapiens

<400> SEQUENCE: 433

Trp Arg Gln His
1

<210> SEQ ID NO 434
<211> LENGTH: 4
<212> TYPE: PRT
<213> ORGANISM: Homo sapiens

<400> SEQUENCE: 434

Arg Gln His Ser
1

<210> SEQ ID NO 435
<211> LENGTH: 4
<212> TYPE: PRT
<213> ORGANISM: Homo sapiens

<400> SEQUENCE: 435

Gln His Ser Arg
1

<210> SEQ ID NO 436
<211> LENGTH: 4
<212> TYPE: PRT
<213> ORGANISM: Homo sapiens

<400> SEQUENCE: 436

His Ser Arg Glu
1

<210> SEQ ID NO 437
<211> LENGTH: 4
<212> TYPE: PRT
<213> ORGANISM: Homo sapiens

<400> SEQUENCE: 437
```

Ser Arg Glu Leu
1

<210> SEQ ID NO 438
<211> LENGTH: 4
<212> TYPE: PRT
<213> ORGANISM: Homo sapiens

<400> SEQUENCE: 438

Arg Glu Leu Arg
1

<210> SEQ ID NO 439
<211> LENGTH: 4
<212> TYPE: PRT
<213> ORGANISM: Homo sapiens

<400> SEQUENCE: 439

Glu Leu Arg Leu
1

<210> SEQ ID NO 440
<211> LENGTH: 4
<212> TYPE: PRT
<213> ORGANISM: Homo sapiens

<400> SEQUENCE: 440

Leu Arg Leu Glu
1

<210> SEQ ID NO 441
<211> LENGTH: 4
<212> TYPE: PRT
<213> ORGANISM: Homo sapiens

<400> SEQUENCE: 441

Arg Leu Glu Ser
1

<210> SEQ ID NO 442
<211> LENGTH: 4
<212> TYPE: PRT
<213> ORGANISM: Homo sapiens

<400> SEQUENCE: 442

Leu Glu Ser Ile
1

<210> SEQ ID NO 443
<211> LENGTH: 4
<212> TYPE: PRT
<213> ORGANISM: Homo sapiens

<400> SEQUENCE: 443

Glu Ser Ile Lys
1

<210> SEQ ID NO 444
<211> LENGTH: 4
<212> TYPE: PRT
<213> ORGANISM: Homo sapiens

<400> SEQUENCE: 444

Ser Ile Lys Ser
1

```
<210> SEQ ID NO 445
<211> LENGTH: 4
<212> TYPE: PRT
<213> ORGANISM: Homo sapiens

<400> SEQUENCE: 445

Ile Lys Ser Gln
1

<210> SEQ ID NO 446
<211> LENGTH: 4
<212> TYPE: PRT
<213> ORGANISM: Homo sapiens

<400> SEQUENCE: 446

Lys Ser Gln Ile
1

<210> SEQ ID NO 447
<211> LENGTH: 4
<212> TYPE: PRT
<213> ORGANISM: Homo sapiens

<400> SEQUENCE: 447

Ser Gln Ile Leu
1

<210> SEQ ID NO 448
<211> LENGTH: 4
<212> TYPE: PRT
<213> ORGANISM: Homo sapiens

<400> SEQUENCE: 448

Gln Ile Leu Ser
1

<210> SEQ ID NO 449
<211> LENGTH: 4
<212> TYPE: PRT
<213> ORGANISM: Homo sapiens

<400> SEQUENCE: 449

Ile Leu Ser Lys
1

<210> SEQ ID NO 450
<211> LENGTH: 4
<212> TYPE: PRT
<213> ORGANISM: Homo sapiens

<400> SEQUENCE: 450

Leu Ser Lys Leu
1

<210> SEQ ID NO 451
<211> LENGTH: 4
<212> TYPE: PRT
<213> ORGANISM: Homo sapiens

<400> SEQUENCE: 451

Ser Lys Leu Arg
1
```

```
<210> SEQ ID NO 452
<211> LENGTH: 4
<212> TYPE: PRT
<213> ORGANISM: Homo sapiens

<400> SEQUENCE: 452

Lys Leu Arg Leu
1

<210> SEQ ID NO 453
<211> LENGTH: 4
<212> TYPE: PRT
<213> ORGANISM: Homo sapiens

<400> SEQUENCE: 453

Leu Arg Leu Lys
1

<210> SEQ ID NO 454
<211> LENGTH: 4
<212> TYPE: PRT
<213> ORGANISM: Homo sapiens

<400> SEQUENCE: 454

Arg Leu Lys Glu
1

<210> SEQ ID NO 455
<211> LENGTH: 4
<212> TYPE: PRT
<213> ORGANISM: Homo sapiens

<400> SEQUENCE: 455

Leu Lys Glu Ala
1

<210> SEQ ID NO 456
<211> LENGTH: 4
<212> TYPE: PRT
<213> ORGANISM: Homo sapiens

<400> SEQUENCE: 456

Lys Glu Ala Pro
1

<210> SEQ ID NO 457
<211> LENGTH: 4
<212> TYPE: PRT
<213> ORGANISM: Homo sapiens

<400> SEQUENCE: 457

Glu Ala Pro Asn
1

<210> SEQ ID NO 458
<211> LENGTH: 4
<212> TYPE: PRT
<213> ORGANISM: Homo sapiens

<400> SEQUENCE: 458

Ala Pro Asn Ile
1

<210> SEQ ID NO 459
<211> LENGTH: 4
```

```
<212> TYPE: PRT
<213> ORGANISM: Homo sapiens

<400> SEQUENCE: 459

Pro Asn Ile Ser
1

<210> SEQ ID NO 460
<211> LENGTH: 4
<212> TYPE: PRT
<213> ORGANISM: Homo sapiens

<400> SEQUENCE: 460

Asn Ile Ser Arg
1

<210> SEQ ID NO 461
<211> LENGTH: 4
<212> TYPE: PRT
<213> ORGANISM: Homo sapiens

<400> SEQUENCE: 461

Ile Ser Arg Glu
1

<210> SEQ ID NO 462
<211> LENGTH: 4
<212> TYPE: PRT
<213> ORGANISM: Homo sapiens

<400> SEQUENCE: 462

Ser Arg Glu Val
1

<210> SEQ ID NO 463
<211> LENGTH: 4
<212> TYPE: PRT
<213> ORGANISM: Homo sapiens

<400> SEQUENCE: 463

Arg Glu Val Val
1

<210> SEQ ID NO 464
<211> LENGTH: 4
<212> TYPE: PRT
<213> ORGANISM: Homo sapiens

<400> SEQUENCE: 464

Glu Val Val Lys
1

<210> SEQ ID NO 465
<211> LENGTH: 4
<212> TYPE: PRT
<213> ORGANISM: Homo sapiens

<400> SEQUENCE: 465

Val Val Lys Gln
1

<210> SEQ ID NO 466
<211> LENGTH: 4
<212> TYPE: PRT
<213> ORGANISM: Homo sapiens
```

```
<400> SEQUENCE: 466

Val Lys Gln Leu
1

<210> SEQ ID NO 467
<211> LENGTH: 4
<212> TYPE: PRT
<213> ORGANISM: Homo sapiens

<400> SEQUENCE: 467

Lys Gln Leu Leu
1

<210> SEQ ID NO 468
<211> LENGTH: 4
<212> TYPE: PRT
<213> ORGANISM: Homo sapiens

<400> SEQUENCE: 468

Gln Leu Leu Pro
1

<210> SEQ ID NO 469
<211> LENGTH: 4
<212> TYPE: PRT
<213> ORGANISM: Homo sapiens

<400> SEQUENCE: 469

Leu Leu Pro Lys
1

<210> SEQ ID NO 470
<211> LENGTH: 4
<212> TYPE: PRT
<213> ORGANISM: Homo sapiens

<400> SEQUENCE: 470

Leu Pro Lys Ala
1

<210> SEQ ID NO 471
<211> LENGTH: 4
<212> TYPE: PRT
<213> ORGANISM: Homo sapiens

<400> SEQUENCE: 471

Pro Lys Ala Pro
1

<210> SEQ ID NO 472
<211> LENGTH: 4
<212> TYPE: PRT
<213> ORGANISM: Homo sapiens

<400> SEQUENCE: 472

Lys Ala Pro Pro
1

<210> SEQ ID NO 473
<211> LENGTH: 4
<212> TYPE: PRT
<213> ORGANISM: Homo sapiens

<400> SEQUENCE: 473
```

```
Ala Pro Pro Leu
1

<210> SEQ ID NO 474
<211> LENGTH: 4
<212> TYPE: PRT
<213> ORGANISM: Homo sapiens

<400> SEQUENCE: 474

Pro Pro Leu Gln
1

<210> SEQ ID NO 475
<211> LENGTH: 4
<212> TYPE: PRT
<213> ORGANISM: Homo sapiens

<400> SEQUENCE: 475

Pro Leu Gln Gln
1

<210> SEQ ID NO 476
<211> LENGTH: 4
<212> TYPE: PRT
<213> ORGANISM: Homo sapiens

<400> SEQUENCE: 476

Leu Gln Gln Ile
1

<210> SEQ ID NO 477
<211> LENGTH: 4
<212> TYPE: PRT
<213> ORGANISM: Homo sapiens

<400> SEQUENCE: 477

Gln Gln Ile Leu
1

<210> SEQ ID NO 478
<211> LENGTH: 4
<212> TYPE: PRT
<213> ORGANISM: Homo sapiens

<400> SEQUENCE: 478

Gln Ile Leu Asp
1

<210> SEQ ID NO 479
<211> LENGTH: 4
<212> TYPE: PRT
<213> ORGANISM: Homo sapiens

<400> SEQUENCE: 479

Ile Leu Asp Leu
1

<210> SEQ ID NO 480
<211> LENGTH: 4
<212> TYPE: PRT
<213> ORGANISM: Homo sapiens

<400> SEQUENCE: 480

Leu Asp Leu His
```

```
<210> SEQ ID NO 481
<211> LENGTH: 4
<212> TYPE: PRT
<213> ORGANISM: Homo sapiens

<400> SEQUENCE: 481

Asp Leu His Asp
1

<210> SEQ ID NO 482
<211> LENGTH: 4
<212> TYPE: PRT
<213> ORGANISM: Homo sapiens

<400> SEQUENCE: 482

Leu His Asp Phe
1

<210> SEQ ID NO 483
<211> LENGTH: 4
<212> TYPE: PRT
<213> ORGANISM: Homo sapiens

<400> SEQUENCE: 483

His Asp Phe Gln
1

<210> SEQ ID NO 484
<211> LENGTH: 4
<212> TYPE: PRT
<213> ORGANISM: Homo sapiens

<400> SEQUENCE: 484

Asp Phe Gln Gly
1

<210> SEQ ID NO 485
<211> LENGTH: 4
<212> TYPE: PRT
<213> ORGANISM: Homo sapiens

<400> SEQUENCE: 485

Phe Gln Gly Asp
1

<210> SEQ ID NO 486
<211> LENGTH: 4
<212> TYPE: PRT
<213> ORGANISM: Homo sapiens

<400> SEQUENCE: 486

Gln Gly Asp Ala
1

<210> SEQ ID NO 487
<211> LENGTH: 4
<212> TYPE: PRT
<213> ORGANISM: Homo sapiens

<400> SEQUENCE: 487

Gly Asp Ala Leu
1
```

<210> SEQ ID NO 488
<211> LENGTH: 4
<212> TYPE: PRT
<213> ORGANISM: Homo sapiens

<400> SEQUENCE: 488

Asp Ala Leu Gln
1

<210> SEQ ID NO 489
<211> LENGTH: 4
<212> TYPE: PRT
<213> ORGANISM: Homo sapiens

<400> SEQUENCE: 489

Ala Leu Gln Pro
1

<210> SEQ ID NO 490
<211> LENGTH: 4
<212> TYPE: PRT
<213> ORGANISM: Homo sapiens

<400> SEQUENCE: 490

Leu Gln Pro Glu
1

<210> SEQ ID NO 491
<211> LENGTH: 4
<212> TYPE: PRT
<213> ORGANISM: Homo sapiens

<400> SEQUENCE: 491

Gln Pro Glu Asp
1

<210> SEQ ID NO 492
<211> LENGTH: 4
<212> TYPE: PRT
<213> ORGANISM: Homo sapiens

<400> SEQUENCE: 492

Pro Glu Asp Phe
1

<210> SEQ ID NO 493
<211> LENGTH: 4
<212> TYPE: PRT
<213> ORGANISM: Homo sapiens

<400> SEQUENCE: 493

Glu Asp Phe Leu
1

<210> SEQ ID NO 494
<211> LENGTH: 4
<212> TYPE: PRT
<213> ORGANISM: Homo sapiens

<400> SEQUENCE: 494

Asp Phe Leu Glu
1

<210> SEQ ID NO 495

```
<211> LENGTH: 4
<212> TYPE: PRT
<213> ORGANISM: Homo sapiens

<400> SEQUENCE: 495

Phe Leu Glu Glu
1

<210> SEQ ID NO 496
<211> LENGTH: 4
<212> TYPE: PRT
<213> ORGANISM: Homo sapiens

<400> SEQUENCE: 496

Leu Glu Glu Asp
1

<210> SEQ ID NO 497
<211> LENGTH: 4
<212> TYPE: PRT
<213> ORGANISM: Homo sapiens

<400> SEQUENCE: 497

Glu Glu Asp Glu
1

<210> SEQ ID NO 498
<211> LENGTH: 4
<212> TYPE: PRT
<213> ORGANISM: Homo sapiens

<400> SEQUENCE: 498

Glu Asp Glu Tyr
1

<210> SEQ ID NO 499
<211> LENGTH: 4
<212> TYPE: PRT
<213> ORGANISM: Homo sapiens

<400> SEQUENCE: 499

Asp Glu Tyr His
1

<210> SEQ ID NO 500
<211> LENGTH: 4
<212> TYPE: PRT
<213> ORGANISM: Homo sapiens

<400> SEQUENCE: 500

Glu Tyr His Ala
1

<210> SEQ ID NO 501
<211> LENGTH: 4
<212> TYPE: PRT
<213> ORGANISM: Homo sapiens

<400> SEQUENCE: 501

Tyr His Ala Thr
1

<210> SEQ ID NO 502
<211> LENGTH: 4
<212> TYPE: PRT
```

<213> ORGANISM: Homo sapiens

<400> SEQUENCE: 502

His Ala Thr Thr
1

<210> SEQ ID NO 503
<211> LENGTH: 4
<212> TYPE: PRT
<213> ORGANISM: Homo sapiens

<400> SEQUENCE: 503

Ala Thr Thr Glu
1

<210> SEQ ID NO 504
<211> LENGTH: 4
<212> TYPE: PRT
<213> ORGANISM: Homo sapiens

<400> SEQUENCE: 504

Thr Thr Glu Thr
1

<210> SEQ ID NO 505
<211> LENGTH: 4
<212> TYPE: PRT
<213> ORGANISM: Homo sapiens

<400> SEQUENCE: 505

Thr Glu Thr Val
1

<210> SEQ ID NO 506
<211> LENGTH: 4
<212> TYPE: PRT
<213> ORGANISM: Homo sapiens

<400> SEQUENCE: 506

Glu Thr Val Ile
1

<210> SEQ ID NO 507
<211> LENGTH: 4
<212> TYPE: PRT
<213> ORGANISM: Homo sapiens

<400> SEQUENCE: 507

Thr Val Ile Ser
1

<210> SEQ ID NO 508
<211> LENGTH: 4
<212> TYPE: PRT
<213> ORGANISM: Homo sapiens

<400> SEQUENCE: 508

Val Ile Ser Met
1

<210> SEQ ID NO 509
<211> LENGTH: 4
<212> TYPE: PRT
<213> ORGANISM: Homo sapiens

```
<400> SEQUENCE: 509

Ile Ser Met Ala
1

<210> SEQ ID NO 510
<211> LENGTH: 4
<212> TYPE: PRT
<213> ORGANISM: Homo sapiens

<400> SEQUENCE: 510

Ser Met Ala Gln
1

<210> SEQ ID NO 511
<211> LENGTH: 4
<212> TYPE: PRT
<213> ORGANISM: Homo sapiens

<400> SEQUENCE: 511

Met Ala Gln Glu
1

<210> SEQ ID NO 512
<211> LENGTH: 4
<212> TYPE: PRT
<213> ORGANISM: Homo sapiens

<400> SEQUENCE: 512

Ala Gln Glu Thr
1

<210> SEQ ID NO 513
<211> LENGTH: 4
<212> TYPE: PRT
<213> ORGANISM: Homo sapiens

<400> SEQUENCE: 513

Gln Glu Thr Asp
1

<210> SEQ ID NO 514
<211> LENGTH: 4
<212> TYPE: PRT
<213> ORGANISM: Homo sapiens

<400> SEQUENCE: 514

Glu Thr Asp Pro
1

<210> SEQ ID NO 515
<211> LENGTH: 4
<212> TYPE: PRT
<213> ORGANISM: Homo sapiens

<400> SEQUENCE: 515

Thr Asp Pro Ala
1

<210> SEQ ID NO 516
<211> LENGTH: 4
<212> TYPE: PRT
<213> ORGANISM: Homo sapiens

<400> SEQUENCE: 516
```

Asp Pro Ala Val
1

<210> SEQ ID NO 517
<211> LENGTH: 4
<212> TYPE: PRT
<213> ORGANISM: Homo sapiens

<400> SEQUENCE: 517

Pro Ala Val Gln
1

<210> SEQ ID NO 518
<211> LENGTH: 4
<212> TYPE: PRT
<213> ORGANISM: Homo sapiens

<400> SEQUENCE: 518

Ala Val Gln Thr
1

<210> SEQ ID NO 519
<211> LENGTH: 4
<212> TYPE: PRT
<213> ORGANISM: Homo sapiens

<400> SEQUENCE: 519

Val Gln Thr Asp
1

<210> SEQ ID NO 520
<211> LENGTH: 4
<212> TYPE: PRT
<213> ORGANISM: Homo sapiens

<400> SEQUENCE: 520

Gln Thr Asp Gly
1

<210> SEQ ID NO 521
<211> LENGTH: 4
<212> TYPE: PRT
<213> ORGANISM: Homo sapiens

<400> SEQUENCE: 521

Thr Asp Gly Ser
1

<210> SEQ ID NO 522
<211> LENGTH: 4
<212> TYPE: PRT
<213> ORGANISM: Homo sapiens

<400> SEQUENCE: 522

Asp Gly Ser Pro
1

<210> SEQ ID NO 523
<211> LENGTH: 4
<212> TYPE: PRT
<213> ORGANISM: Homo sapiens

<400> SEQUENCE: 523

Gly Ser Pro Leu
1

<210> SEQ ID NO 524
<211> LENGTH: 4
<212> TYPE: PRT
<213> ORGANISM: Homo sapiens

<400> SEQUENCE: 524

Ser Pro Leu Cys
1

<210> SEQ ID NO 525
<211> LENGTH: 4
<212> TYPE: PRT
<213> ORGANISM: Homo sapiens

<400> SEQUENCE: 525

Pro Leu Cys Cys
1

<210> SEQ ID NO 526
<211> LENGTH: 4
<212> TYPE: PRT
<213> ORGANISM: Homo sapiens

<400> SEQUENCE: 526

Leu Cys Cys His
1

<210> SEQ ID NO 527
<211> LENGTH: 4
<212> TYPE: PRT
<213> ORGANISM: Homo sapiens

<400> SEQUENCE: 527

Cys Cys His Phe
1

<210> SEQ ID NO 528
<211> LENGTH: 4
<212> TYPE: PRT
<213> ORGANISM: Homo sapiens

<400> SEQUENCE: 528

Cys His Phe His
1

<210> SEQ ID NO 529
<211> LENGTH: 4
<212> TYPE: PRT
<213> ORGANISM: Homo sapiens

<400> SEQUENCE: 529

His Phe His Phe
1

<210> SEQ ID NO 530
<211> LENGTH: 4
<212> TYPE: PRT
<213> ORGANISM: Homo sapiens

<400> SEQUENCE: 530

Phe His Phe Ser
1

```
<210> SEQ ID NO 531
<211> LENGTH: 4
<212> TYPE: PRT
<213> ORGANISM: Homo sapiens

<400> SEQUENCE: 531

His Phe Ser Pro
1

<210> SEQ ID NO 532
<211> LENGTH: 4
<212> TYPE: PRT
<213> ORGANISM: Homo sapiens

<400> SEQUENCE: 532

Phe Ser Pro Lys
1

<210> SEQ ID NO 533
<211> LENGTH: 4
<212> TYPE: PRT
<213> ORGANISM: Homo sapiens

<400> SEQUENCE: 533

Ser Pro Lys Val
1

<210> SEQ ID NO 534
<211> LENGTH: 4
<212> TYPE: PRT
<213> ORGANISM: Homo sapiens

<400> SEQUENCE: 534

Pro Lys Val Met
1

<210> SEQ ID NO 535
<211> LENGTH: 4
<212> TYPE: PRT
<213> ORGANISM: Homo sapiens

<400> SEQUENCE: 535

Lys Val Met Phe
1

<210> SEQ ID NO 536
<211> LENGTH: 4
<212> TYPE: PRT
<213> ORGANISM: Homo sapiens

<400> SEQUENCE: 536

Val Met Phe Thr
1

<210> SEQ ID NO 537
<211> LENGTH: 4
<212> TYPE: PRT
<213> ORGANISM: Homo sapiens

<400> SEQUENCE: 537

Met Phe Thr Lys
1

<210> SEQ ID NO 538
<211> LENGTH: 4
```

<212> TYPE: PRT
<213> ORGANISM: Homo sapiens

<400> SEQUENCE: 538

Phe Thr Lys Val
1

<210> SEQ ID NO 539
<211> LENGTH: 4
<212> TYPE: PRT
<213> ORGANISM: Homo sapiens

<400> SEQUENCE: 539

Thr Lys Val Leu
1

<210> SEQ ID NO 540
<211> LENGTH: 4
<212> TYPE: PRT
<213> ORGANISM: Homo sapiens

<400> SEQUENCE: 540

Lys Val Leu Lys
1

<210> SEQ ID NO 541
<211> LENGTH: 4
<212> TYPE: PRT
<213> ORGANISM: Homo sapiens

<400> SEQUENCE: 541

Val Leu Lys Ala
1

<210> SEQ ID NO 542
<211> LENGTH: 4
<212> TYPE: PRT
<213> ORGANISM: Homo sapiens

<400> SEQUENCE: 542

Leu Lys Ala Gln
1

<210> SEQ ID NO 543
<211> LENGTH: 4
<212> TYPE: PRT
<213> ORGANISM: Homo sapiens

<400> SEQUENCE: 543

Lys Ala Gln Leu
1

<210> SEQ ID NO 544
<211> LENGTH: 4
<212> TYPE: PRT
<213> ORGANISM: Homo sapiens

<400> SEQUENCE: 544

Ala Gln Leu Trp
1

<210> SEQ ID NO 545
<211> LENGTH: 4
<212> TYPE: PRT
<213> ORGANISM: Homo sapiens -continued

<400> SEQUENCE: 545

Gln Leu Trp Val
1

<210> SEQ ID NO 546
<211> LENGTH: 4
<212> TYPE: PRT
<213> ORGANISM: Homo sapiens

<400> SEQUENCE: 546

Leu Trp Val Tyr
1

<210> SEQ ID NO 547
<211> LENGTH: 4
<212> TYPE: PRT
<213> ORGANISM: Homo sapiens

<400> SEQUENCE: 547

Trp Val Tyr Leu
1

<210> SEQ ID NO 548
<211> LENGTH: 4
<212> TYPE: PRT
<213> ORGANISM: Homo sapiens

<400> SEQUENCE: 548

Val Tyr Leu Arg
1

<210> SEQ ID NO 549
<211> LENGTH: 4
<212> TYPE: PRT
<213> ORGANISM: Homo sapiens

<400> SEQUENCE: 549

Tyr Leu Arg Pro
1

<210> SEQ ID NO 550
<211> LENGTH: 4
<212> TYPE: PRT
<213> ORGANISM: Homo sapiens

<400> SEQUENCE: 550

Leu Arg Pro Val
1

<210> SEQ ID NO 551
<211> LENGTH: 4
<212> TYPE: PRT
<213> ORGANISM: Homo sapiens

<400> SEQUENCE: 551

Arg Pro Val Pro
1

<210> SEQ ID NO 552
<211> LENGTH: 4
<212> TYPE: PRT
<213> ORGANISM: Homo sapiens

<400> SEQUENCE: 552

Pro Val Pro Arg
1

<210> SEQ ID NO 553
<211> LENGTH: 4
<212> TYPE: PRT
<213> ORGANISM: Homo sapiens

<400> SEQUENCE: 553

Val Pro Arg Pro
1

<210> SEQ ID NO 554
<211> LENGTH: 4
<212> TYPE: PRT
<213> ORGANISM: Homo sapiens

<400> SEQUENCE: 554

Pro Arg Pro Ala
1

<210> SEQ ID NO 555
<211> LENGTH: 4
<212> TYPE: PRT
<213> ORGANISM: Homo sapiens

<400> SEQUENCE: 555

Arg Pro Ala Thr
1

<210> SEQ ID NO 556
<211> LENGTH: 4
<212> TYPE: PRT
<213> ORGANISM: Homo sapiens

<400> SEQUENCE: 556

Pro Ala Thr Val
1

<210> SEQ ID NO 557
<211> LENGTH: 4
<212> TYPE: PRT
<213> ORGANISM: Homo sapiens

<400> SEQUENCE: 557

Ala Thr Val Tyr
1

<210> SEQ ID NO 558
<211> LENGTH: 4
<212> TYPE: PRT
<213> ORGANISM: Homo sapiens

<400> SEQUENCE: 558

Thr Val Tyr Leu
1

<210> SEQ ID NO 559
<211> LENGTH: 4
<212> TYPE: PRT
<213> ORGANISM: Homo sapiens

<400> SEQUENCE: 559

Val Tyr Leu Gln

<210> SEQ ID NO 560
<211> LENGTH: 4
<212> TYPE: PRT
<213> ORGANISM: Homo sapiens

<400> SEQUENCE: 560

Tyr Leu Gln Ile
1

<210> SEQ ID NO 561
<211> LENGTH: 4
<212> TYPE: PRT
<213> ORGANISM: Homo sapiens

<400> SEQUENCE: 561

Leu Gln Ile Leu
1

<210> SEQ ID NO 562
<211> LENGTH: 4
<212> TYPE: PRT
<213> ORGANISM: Homo sapiens

<400> SEQUENCE: 562

Gln Ile Leu Arg
1

<210> SEQ ID NO 563
<211> LENGTH: 4
<212> TYPE: PRT
<213> ORGANISM: Homo sapiens

<400> SEQUENCE: 563

Ile Leu Arg Leu
1

<210> SEQ ID NO 564
<211> LENGTH: 4
<212> TYPE: PRT
<213> ORGANISM: Homo sapiens

<400> SEQUENCE: 564

Arg Leu Lys Pro
1

<210> SEQ ID NO 565
<211> LENGTH: 4
<212> TYPE: PRT
<213> ORGANISM: Homo sapiens

<400> SEQUENCE: 565

Leu Lys Pro Leu
1

<210> SEQ ID NO 566
<211> LENGTH: 4
<212> TYPE: PRT
<213> ORGANISM: Homo sapiens

<400> SEQUENCE: 566

Lys Pro Leu Thr
1

<210> SEQ ID NO 567
<211> LENGTH: 4
<212> TYPE: PRT
<213> ORGANISM: Homo sapiens

<400> SEQUENCE: 567

Pro Leu Thr Gly
1

<210> SEQ ID NO 568
<211> LENGTH: 4
<212> TYPE: PRT
<213> ORGANISM: Homo sapiens

<400> SEQUENCE: 568

Leu Thr Gly Glu
1

<210> SEQ ID NO 569
<211> LENGTH: 4
<212> TYPE: PRT
<213> ORGANISM: Homo sapiens

<400> SEQUENCE: 569

Thr Gly Glu Gly
1

<210> SEQ ID NO 570
<211> LENGTH: 4
<212> TYPE: PRT
<213> ORGANISM: Homo sapiens

<400> SEQUENCE: 570

Gly Glu Gly Thr
1

<210> SEQ ID NO 571
<211> LENGTH: 4
<212> TYPE: PRT
<213> ORGANISM: Homo sapiens

<400> SEQUENCE: 571

Glu Gly Thr Ala
1

<210> SEQ ID NO 572
<211> LENGTH: 4
<212> TYPE: PRT
<213> ORGANISM: Homo sapiens

<400> SEQUENCE: 572

Gly Thr Ala Gly
1

<210> SEQ ID NO 573
<211> LENGTH: 4
<212> TYPE: PRT
<213> ORGANISM: Homo sapiens

<400> SEQUENCE: 573

Thr Ala Gly Gly
1

<210> SEQ ID NO 574

```
<210> SEQ ID NO 574
<211> LENGTH: 4
<212> TYPE: PRT
<213> ORGANISM: Homo sapiens

<400> SEQUENCE: 574

Ala Gly Gly Gly
1

<210> SEQ ID NO 575
<211> LENGTH: 4
<212> TYPE: PRT
<213> ORGANISM: Homo sapiens

<400> SEQUENCE: 575

Gly Gly Gly Gly
1

<210> SEQ ID NO 576
<211> LENGTH: 4
<212> TYPE: PRT
<213> ORGANISM: Homo sapiens

<400> SEQUENCE: 576

Gly Gly Gly Arg
1

<210> SEQ ID NO 577
<211> LENGTH: 4
<212> TYPE: PRT
<213> ORGANISM: Homo sapiens

<400> SEQUENCE: 577

Gly Gly Arg Arg
1

<210> SEQ ID NO 578
<211> LENGTH: 4
<212> TYPE: PRT
<213> ORGANISM: Homo sapiens

<400> SEQUENCE: 578

Gly Arg Arg His
1

<210> SEQ ID NO 579
<211> LENGTH: 4
<212> TYPE: PRT
<213> ORGANISM: Homo sapiens

<400> SEQUENCE: 579

Arg Arg His Ile
1

<210> SEQ ID NO 580
<211> LENGTH: 4
<212> TYPE: PRT
<213> ORGANISM: Homo sapiens

<400> SEQUENCE: 580

Arg His Ile Arg
1

<210> SEQ ID NO 581
<211> LENGTH: 4
<212> TYPE: PRT
```

<213> ORGANISM: Homo sapiens

<400> SEQUENCE: 581

His Ile Arg Ile
1

<210> SEQ ID NO 582
<211> LENGTH: 4
<212> TYPE: PRT
<213> ORGANISM: Homo sapiens

<400> SEQUENCE: 582

Ile Arg Ile Arg
1

<210> SEQ ID NO 583
<211> LENGTH: 4
<212> TYPE: PRT
<213> ORGANISM: Homo sapiens

<400> SEQUENCE: 583

Arg Ile Arg Ser
1

<210> SEQ ID NO 584
<211> LENGTH: 4
<212> TYPE: PRT
<213> ORGANISM: Homo sapiens

<400> SEQUENCE: 584

Ile Arg Ser Leu
1

<210> SEQ ID NO 585
<211> LENGTH: 4
<212> TYPE: PRT
<213> ORGANISM: Homo sapiens

<400> SEQUENCE: 585

Arg Ser Leu Lys
1

<210> SEQ ID NO 586
<211> LENGTH: 4
<212> TYPE: PRT
<213> ORGANISM: Homo sapiens

<400> SEQUENCE: 586

Ser Leu Lys Ile
1

<210> SEQ ID NO 587
<211> LENGTH: 4
<212> TYPE: PRT
<213> ORGANISM: Homo sapiens

<400> SEQUENCE: 587

Leu Lys Ile Glu
1

<210> SEQ ID NO 588
<211> LENGTH: 4
<212> TYPE: PRT
<213> ORGANISM: Homo sapiens

<400> SEQUENCE: 588

Lys Ile Glu Leu
1

<210> SEQ ID NO 589
<211> LENGTH: 4
<212> TYPE: PRT
<213> ORGANISM: Homo sapiens

<400> SEQUENCE: 589

Ile Glu Leu His
1

<210> SEQ ID NO 590
<211> LENGTH: 4
<212> TYPE: PRT
<213> ORGANISM: Homo sapiens

<400> SEQUENCE: 590

Glu Leu His Ser
1

<210> SEQ ID NO 591
<211> LENGTH: 4
<212> TYPE: PRT
<213> ORGANISM: Homo sapiens

<400> SEQUENCE: 591

Leu His Ser Arg
1

<210> SEQ ID NO 592
<211> LENGTH: 4
<212> TYPE: PRT
<213> ORGANISM: Homo sapiens

<400> SEQUENCE: 592

His Ser Arg Ser
1

<210> SEQ ID NO 593
<211> LENGTH: 4
<212> TYPE: PRT
<213> ORGANISM: Homo sapiens

<400> SEQUENCE: 593

Ser Arg Ser Gly
1

<210> SEQ ID NO 594
<211> LENGTH: 4
<212> TYPE: PRT
<213> ORGANISM: Homo sapiens

<400> SEQUENCE: 594

Arg Ser Gly His
1

<210> SEQ ID NO 595
<211> LENGTH: 4
<212> TYPE: PRT
<213> ORGANISM: Homo sapiens

<400> SEQUENCE: 595

Ser Gly His Trp
1

<210> SEQ ID NO 596
<211> LENGTH: 4
<212> TYPE: PRT
<213> ORGANISM: Homo sapiens

<400> SEQUENCE: 596

Gly His Trp Gln
1

<210> SEQ ID NO 597
<211> LENGTH: 4
<212> TYPE: PRT
<213> ORGANISM: Homo sapiens

<400> SEQUENCE: 597

His Trp Gln Ser
1

<210> SEQ ID NO 598
<211> LENGTH: 4
<212> TYPE: PRT
<213> ORGANISM: Homo sapiens

<400> SEQUENCE: 598

Trp Gln Ser Ile
1

<210> SEQ ID NO 599
<211> LENGTH: 4
<212> TYPE: PRT
<213> ORGANISM: Homo sapiens

<400> SEQUENCE: 599

Gln Ser Ile Asp
1

<210> SEQ ID NO 600
<211> LENGTH: 4
<212> TYPE: PRT
<213> ORGANISM: Homo sapiens

<400> SEQUENCE: 600

Ser Ile Asp Phe
1

<210> SEQ ID NO 601
<211> LENGTH: 4
<212> TYPE: PRT
<213> ORGANISM: Homo sapiens

<400> SEQUENCE: 601

Ile Asp Phe Lys
1

<210> SEQ ID NO 602
<211> LENGTH: 4
<212> TYPE: PRT
<213> ORGANISM: Homo sapiens

<400> SEQUENCE: 602

Asp Phe Lys Gln
1

<210> SEQ ID NO 603
<211> LENGTH: 4
<212> TYPE: PRT
<213> ORGANISM: Homo sapiens

<400> SEQUENCE: 603

Phe Lys Gln Val
1

<210> SEQ ID NO 604
<211> LENGTH: 4
<212> TYPE: PRT
<213> ORGANISM: Homo sapiens

<400> SEQUENCE: 604

Lys Gln Val Leu
1

<210> SEQ ID NO 605
<211> LENGTH: 4
<212> TYPE: PRT
<213> ORGANISM: Homo sapiens

<400> SEQUENCE: 605

Gln Val Leu His
1

<210> SEQ ID NO 606
<211> LENGTH: 4
<212> TYPE: PRT
<213> ORGANISM: Homo sapiens

<400> SEQUENCE: 606

Val Leu His Ser
1

<210> SEQ ID NO 607
<211> LENGTH: 4
<212> TYPE: PRT
<213> ORGANISM: Homo sapiens

<400> SEQUENCE: 607

Leu His Ser Trp
1

<210> SEQ ID NO 608
<211> LENGTH: 4
<212> TYPE: PRT
<213> ORGANISM: Homo sapiens

<400> SEQUENCE: 608

His Ser Trp Phe
1

<210> SEQ ID NO 609
<211> LENGTH: 4
<212> TYPE: PRT
<213> ORGANISM: Homo sapiens

<400> SEQUENCE: 609

Ser Trp Phe Arg
1

```
<210> SEQ ID NO 610
<211> LENGTH: 4
<212> TYPE: PRT
<213> ORGANISM: Homo sapiens

<400> SEQUENCE: 610

Trp Phe Arg Gln
1

<210> SEQ ID NO 611
<211> LENGTH: 4
<212> TYPE: PRT
<213> ORGANISM: Homo sapiens

<400> SEQUENCE: 611

Phe Arg Gln Pro
1

<210> SEQ ID NO 612
<211> LENGTH: 4
<212> TYPE: PRT
<213> ORGANISM: Homo sapiens

<400> SEQUENCE: 612

Arg Gln Pro Gln
1

<210> SEQ ID NO 613
<211> LENGTH: 4
<212> TYPE: PRT
<213> ORGANISM: Homo sapiens

<400> SEQUENCE: 613

Gln Pro Gln Ser
1

<210> SEQ ID NO 614
<211> LENGTH: 4
<212> TYPE: PRT
<213> ORGANISM: Homo sapiens

<400> SEQUENCE: 614

Pro Gln Ser Asn
1

<210> SEQ ID NO 615
<211> LENGTH: 4
<212> TYPE: PRT
<213> ORGANISM: Homo sapiens

<400> SEQUENCE: 615

Gln Ser Asn Trp
1

<210> SEQ ID NO 616
<211> LENGTH: 4
<212> TYPE: PRT
<213> ORGANISM: Homo sapiens

<400> SEQUENCE: 616

Ser Asn Trp Gly
1

<210> SEQ ID NO 617
<211> LENGTH: 4
```

```
<212> TYPE: PRT
<213> ORGANISM: Homo sapiens

<400> SEQUENCE: 617

Asn Trp Gly Ile
1

<210> SEQ ID NO 618
<211> LENGTH: 4
<212> TYPE: PRT
<213> ORGANISM: Homo sapiens

<400> SEQUENCE: 618

Trp Gly Ile Glu
1

<210> SEQ ID NO 619
<211> LENGTH: 4
<212> TYPE: PRT
<213> ORGANISM: Homo sapiens

<400> SEQUENCE: 619

Gly Ile Glu Ile
1

<210> SEQ ID NO 620
<211> LENGTH: 4
<212> TYPE: PRT
<213> ORGANISM: Homo sapiens

<400> SEQUENCE: 620

Ile Glu Ile Asn
1

<210> SEQ ID NO 621
<211> LENGTH: 4
<212> TYPE: PRT
<213> ORGANISM: Homo sapiens

<400> SEQUENCE: 621

Glu Ile Asn Ala
1

<210> SEQ ID NO 622
<211> LENGTH: 4
<212> TYPE: PRT
<213> ORGANISM: Homo sapiens

<400> SEQUENCE: 622

Ile Asn Ala Phe
1

<210> SEQ ID NO 623
<211> LENGTH: 4
<212> TYPE: PRT
<213> ORGANISM: Homo sapiens

<400> SEQUENCE: 623

Asn Ala Phe Asp
1

<210> SEQ ID NO 624
<211> LENGTH: 4
<212> TYPE: PRT
<213> ORGANISM: Homo sapiens
```

<400> SEQUENCE: 624

Ala Phe Asp Pro
1

<210> SEQ ID NO 625
<211> LENGTH: 4
<212> TYPE: PRT
<213> ORGANISM: Homo sapiens

<400> SEQUENCE: 625

Phe Asp Pro Ser
1

<210> SEQ ID NO 626
<211> LENGTH: 4
<212> TYPE: PRT
<213> ORGANISM: Homo sapiens

<400> SEQUENCE: 626

Asp Pro Ser Gly
1

<210> SEQ ID NO 627
<211> LENGTH: 4
<212> TYPE: PRT
<213> ORGANISM: Homo sapiens

<400> SEQUENCE: 627

Pro Ser Gly Thr
1

<210> SEQ ID NO 628
<211> LENGTH: 4
<212> TYPE: PRT
<213> ORGANISM: Homo sapiens

<400> SEQUENCE: 628

Ser Gly Thr Asp
1

<210> SEQ ID NO 629
<211> LENGTH: 4
<212> TYPE: PRT
<213> ORGANISM: Homo sapiens

<400> SEQUENCE: 629

Gly Thr Asp Leu
1

<210> SEQ ID NO 630
<211> LENGTH: 4
<212> TYPE: PRT
<213> ORGANISM: Homo sapiens

<400> SEQUENCE: 630

Thr Asp Leu Ala
1

<210> SEQ ID NO 631
<211> LENGTH: 4
<212> TYPE: PRT
<213> ORGANISM: Homo sapiens

<400> SEQUENCE: 631

Asp Leu Ala Val
1

<210> SEQ ID NO 632
<211> LENGTH: 4
<212> TYPE: PRT
<213> ORGANISM: Homo sapiens

<400> SEQUENCE: 632

Leu Ala Val Thr
1

<210> SEQ ID NO 633
<211> LENGTH: 4
<212> TYPE: PRT
<213> ORGANISM: Homo sapiens

<400> SEQUENCE: 633

Ala Val Thr Ser
1

<210> SEQ ID NO 634
<211> LENGTH: 4
<212> TYPE: PRT
<213> ORGANISM: Homo sapiens

<400> SEQUENCE: 634

Val Thr Ser Leu
1

<210> SEQ ID NO 635
<211> LENGTH: 4
<212> TYPE: PRT
<213> ORGANISM: Homo sapiens

<400> SEQUENCE: 635

Thr Ser Leu Gly
1

<210> SEQ ID NO 636
<211> LENGTH: 4
<212> TYPE: PRT
<213> ORGANISM: Homo sapiens

<400> SEQUENCE: 636

Ser Leu Gly Pro
1

<210> SEQ ID NO 637
<211> LENGTH: 4
<212> TYPE: PRT
<213> ORGANISM: Homo sapiens

<400> SEQUENCE: 637

Leu Gly Pro Gly
1

<210> SEQ ID NO 638
<211> LENGTH: 4
<212> TYPE: PRT
<213> ORGANISM: Homo sapiens

<400> SEQUENCE: 638

Gly Pro Gly Ala

```
<210> SEQ ID NO 639
<211> LENGTH: 4
<212> TYPE: PRT
<213> ORGANISM: Homo sapiens

<400> SEQUENCE: 639

Pro Gly Ala Glu
1

<210> SEQ ID NO 640
<211> LENGTH: 4
<212> TYPE: PRT
<213> ORGANISM: Homo sapiens

<400> SEQUENCE: 640

Gly Ala Glu Gly
1

<210> SEQ ID NO 641
<211> LENGTH: 4
<212> TYPE: PRT
<213> ORGANISM: Homo sapiens

<400> SEQUENCE: 641

Ala Glu Gly Leu
1

<210> SEQ ID NO 642
<211> LENGTH: 4
<212> TYPE: PRT
<213> ORGANISM: Homo sapiens

<400> SEQUENCE: 642

Glu Gly Leu His
1

<210> SEQ ID NO 643
<211> LENGTH: 4
<212> TYPE: PRT
<213> ORGANISM: Homo sapiens

<400> SEQUENCE: 643

Gly Leu His Pro
1

<210> SEQ ID NO 644
<211> LENGTH: 4
<212> TYPE: PRT
<213> ORGANISM: Homo sapiens

<400> SEQUENCE: 644

Leu His Pro Phe
1

<210> SEQ ID NO 645
<211> LENGTH: 4
<212> TYPE: PRT
<213> ORGANISM: Homo sapiens

<400> SEQUENCE: 645

His Pro Phe Met
1
```

```
<210> SEQ ID NO 646
<211> LENGTH: 4
<212> TYPE: PRT
<213> ORGANISM: Homo sapiens

<400> SEQUENCE: 646

Pro Phe Met Glu
1

<210> SEQ ID NO 647
<211> LENGTH: 4
<212> TYPE: PRT
<213> ORGANISM: Homo sapiens

<400> SEQUENCE: 647

Phe Met Glu Leu
1

<210> SEQ ID NO 648
<211> LENGTH: 4
<212> TYPE: PRT
<213> ORGANISM: Homo sapiens

<400> SEQUENCE: 648

Met Glu Leu Arg
1

<210> SEQ ID NO 649
<211> LENGTH: 4
<212> TYPE: PRT
<213> ORGANISM: Homo sapiens

<400> SEQUENCE: 649

Glu Leu Arg Val
1

<210> SEQ ID NO 650
<211> LENGTH: 4
<212> TYPE: PRT
<213> ORGANISM: Homo sapiens

<400> SEQUENCE: 650

Leu Arg Val Leu
1

<210> SEQ ID NO 651
<211> LENGTH: 4
<212> TYPE: PRT
<213> ORGANISM: Homo sapiens

<400> SEQUENCE: 651

Arg Val Leu Glu
1

<210> SEQ ID NO 652
<211> LENGTH: 4
<212> TYPE: PRT
<213> ORGANISM: Homo sapiens

<400> SEQUENCE: 652

Val Leu Glu Asn
1

<210> SEQ ID NO 653
```

```
<211> LENGTH: 4
<212> TYPE: PRT
<213> ORGANISM: Homo sapiens

<400> SEQUENCE: 653

Leu Glu Asn Thr
1

<210> SEQ ID NO 654
<211> LENGTH: 4
<212> TYPE: PRT
<213> ORGANISM: Homo sapiens

<400> SEQUENCE: 654

Glu Asn Thr Lys
1

<210> SEQ ID NO 655
<211> LENGTH: 4
<212> TYPE: PRT
<213> ORGANISM: Homo sapiens

<400> SEQUENCE: 655

Asn Thr Lys Arg
1

<210> SEQ ID NO 656
<211> LENGTH: 4
<212> TYPE: PRT
<213> ORGANISM: Homo sapiens

<400> SEQUENCE: 656

Thr Lys Arg Ser
1

<210> SEQ ID NO 657
<211> LENGTH: 4
<212> TYPE: PRT
<213> ORGANISM: Homo sapiens

<400> SEQUENCE: 657

Lys Arg Ser Arg
1

<210> SEQ ID NO 658
<211> LENGTH: 4
<212> TYPE: PRT
<213> ORGANISM: Homo sapiens

<400> SEQUENCE: 658

Arg Ser Arg Arg
1

<210> SEQ ID NO 659
<211> LENGTH: 4
<212> TYPE: PRT
<213> ORGANISM: Homo sapiens

<400> SEQUENCE: 659

Ser Arg Arg Asn
1

<210> SEQ ID NO 660
<211> LENGTH: 4
<212> TYPE: PRT
```

<213> ORGANISM: Homo sapiens

<400> SEQUENCE: 660

Arg Arg Asn Leu
1

<210> SEQ ID NO 661
<211> LENGTH: 4
<212> TYPE: PRT
<213> ORGANISM: Homo sapiens

<400> SEQUENCE: 661

Arg Asn Leu Gly
1

<210> SEQ ID NO 662
<211> LENGTH: 4
<212> TYPE: PRT
<213> ORGANISM: Homo sapiens

<400> SEQUENCE: 662

Asn Leu Gly Leu
1

<210> SEQ ID NO 663
<211> LENGTH: 4
<212> TYPE: PRT
<213> ORGANISM: Homo sapiens

<400> SEQUENCE: 663

Leu Gly Leu Asp
1

<210> SEQ ID NO 664
<211> LENGTH: 4
<212> TYPE: PRT
<213> ORGANISM: Homo sapiens

<400> SEQUENCE: 664

Gly Leu Asp Cys
1

<210> SEQ ID NO 665
<211> LENGTH: 4
<212> TYPE: PRT
<213> ORGANISM: Homo sapiens

<400> SEQUENCE: 665

Leu Asp Cys Asp
1

<210> SEQ ID NO 666
<211> LENGTH: 4
<212> TYPE: PRT
<213> ORGANISM: Homo sapiens

<400> SEQUENCE: 666

Asp Cys Asp Glu
1

<210> SEQ ID NO 667
<211> LENGTH: 4
<212> TYPE: PRT
<213> ORGANISM: Homo sapiens

<400> SEQUENCE: 667

Cys Asp Glu His
1

<210> SEQ ID NO 668
<211> LENGTH: 4
<212> TYPE: PRT
<213> ORGANISM: Homo sapiens

<400> SEQUENCE: 668

Asp Glu His Ser
1

<210> SEQ ID NO 669
<211> LENGTH: 4
<212> TYPE: PRT
<213> ORGANISM: Homo sapiens

<400> SEQUENCE: 669

Glu His Ser Ser
1

<210> SEQ ID NO 670
<211> LENGTH: 4
<212> TYPE: PRT
<213> ORGANISM: Homo sapiens

<400> SEQUENCE: 670

His Ser Ser Glu
1

<210> SEQ ID NO 671
<211> LENGTH: 4
<212> TYPE: PRT
<213> ORGANISM: Homo sapiens

<400> SEQUENCE: 671

Ser Ser Glu Ser
1

<210> SEQ ID NO 672
<211> LENGTH: 4
<212> TYPE: PRT
<213> ORGANISM: Homo sapiens

<400> SEQUENCE: 672

Ser Glu Ser Arg
1

<210> SEQ ID NO 673
<211> LENGTH: 4
<212> TYPE: PRT
<213> ORGANISM: Homo sapiens

<400> SEQUENCE: 673

Glu Ser Arg Cys
1

<210> SEQ ID NO 674
<211> LENGTH: 4
<212> TYPE: PRT
<213> ORGANISM: Homo sapiens

<400> SEQUENCE: 674

Ser Arg Cys Cys
1

<210> SEQ ID NO 675
<211> LENGTH: 4
<212> TYPE: PRT
<213> ORGANISM: Homo sapiens

<400> SEQUENCE: 675

Arg Cys Cys Arg
1

<210> SEQ ID NO 676
<211> LENGTH: 4
<212> TYPE: PRT
<213> ORGANISM: Homo sapiens

<400> SEQUENCE: 676

Cys Cys Arg Tyr
1

<210> SEQ ID NO 677
<211> LENGTH: 4
<212> TYPE: PRT
<213> ORGANISM: Homo sapiens

<400> SEQUENCE: 677

Cys Arg Tyr Pro
1

<210> SEQ ID NO 678
<211> LENGTH: 4
<212> TYPE: PRT
<213> ORGANISM: Homo sapiens

<400> SEQUENCE: 678

Arg Tyr Pro Leu
1

<210> SEQ ID NO 679
<211> LENGTH: 4
<212> TYPE: PRT
<213> ORGANISM: Homo sapiens

<400> SEQUENCE: 679

Tyr Pro Leu Thr
1

<210> SEQ ID NO 680
<211> LENGTH: 4
<212> TYPE: PRT
<213> ORGANISM: Homo sapiens

<400> SEQUENCE: 680

Pro Leu Thr Val
1

<210> SEQ ID NO 681
<211> LENGTH: 4
<212> TYPE: PRT
<213> ORGANISM: Homo sapiens

<400> SEQUENCE: 681

Leu Thr Val Asp
1

<210> SEQ ID NO 682
<211> LENGTH: 4
<212> TYPE: PRT
<213> ORGANISM: Homo sapiens

<400> SEQUENCE: 682

Thr Val Asp Phe
1

<210> SEQ ID NO 683
<211> LENGTH: 4
<212> TYPE: PRT
<213> ORGANISM: Homo sapiens

<400> SEQUENCE: 683

Val Asp Phe Glu
1

<210> SEQ ID NO 684
<211> LENGTH: 4
<212> TYPE: PRT
<213> ORGANISM: Homo sapiens

<400> SEQUENCE: 684

Asp Phe Glu Ala
1

<210> SEQ ID NO 685
<211> LENGTH: 4
<212> TYPE: PRT
<213> ORGANISM: Homo sapiens

<400> SEQUENCE: 685

Phe Glu Ala Phe
1

<210> SEQ ID NO 686
<211> LENGTH: 4
<212> TYPE: PRT
<213> ORGANISM: Homo sapiens

<400> SEQUENCE: 686

Glu Ala Phe Gly
1

<210> SEQ ID NO 687
<211> LENGTH: 4
<212> TYPE: PRT
<213> ORGANISM: Homo sapiens

<400> SEQUENCE: 687

Ala Phe Gly Trp
1

<210> SEQ ID NO 688
<211> LENGTH: 4
<212> TYPE: PRT
<213> ORGANISM: Homo sapiens

<400> SEQUENCE: 688

Phe Gly Trp Asp
1

```
<210> SEQ ID NO 689
<211> LENGTH: 4
<212> TYPE: PRT
<213> ORGANISM: Homo sapiens

<400> SEQUENCE: 689

Gly Trp Asp Trp
1

<210> SEQ ID NO 690
<211> LENGTH: 4
<212> TYPE: PRT
<213> ORGANISM: Homo sapiens

<400> SEQUENCE: 690

Trp Asp Trp Ile
1

<210> SEQ ID NO 691
<211> LENGTH: 4
<212> TYPE: PRT
<213> ORGANISM: Homo sapiens

<400> SEQUENCE: 691

Asp Trp Ile Ile
1

<210> SEQ ID NO 692
<211> LENGTH: 4
<212> TYPE: PRT
<213> ORGANISM: Homo sapiens

<400> SEQUENCE: 692

Trp Ile Ile Ala
1

<210> SEQ ID NO 693
<211> LENGTH: 4
<212> TYPE: PRT
<213> ORGANISM: Homo sapiens

<400> SEQUENCE: 693

Ile Ile Ala Pro
1

<210> SEQ ID NO 694
<211> LENGTH: 4
<212> TYPE: PRT
<213> ORGANISM: Homo sapiens

<400> SEQUENCE: 694

Ile Ala Pro Lys
1

<210> SEQ ID NO 695
<211> LENGTH: 4
<212> TYPE: PRT
<213> ORGANISM: Homo sapiens

<400> SEQUENCE: 695

Ala Pro Lys Arg
1

<210> SEQ ID NO 696
<211> LENGTH: 4
```

```
<212> TYPE: PRT
<213> ORGANISM: Homo sapiens

<400> SEQUENCE: 696

Pro Lys Arg Tyr
1

<210> SEQ ID NO 697
<211> LENGTH: 4
<212> TYPE: PRT
<213> ORGANISM: Homo sapiens

<400> SEQUENCE: 697

Lys Arg Tyr Lys
1

<210> SEQ ID NO 698
<211> LENGTH: 4
<212> TYPE: PRT
<213> ORGANISM: Homo sapiens

<400> SEQUENCE: 698

Arg Tyr Lys Ala
1

<210> SEQ ID NO 699
<211> LENGTH: 4
<212> TYPE: PRT
<213> ORGANISM: Homo sapiens

<400> SEQUENCE: 699

Tyr Lys Ala Asn
1

<210> SEQ ID NO 700
<211> LENGTH: 4
<212> TYPE: PRT
<213> ORGANISM: Homo sapiens

<400> SEQUENCE: 700

Lys Ala Asn Tyr
1

<210> SEQ ID NO 701
<211> LENGTH: 4
<212> TYPE: PRT
<213> ORGANISM: Homo sapiens

<400> SEQUENCE: 701

Ala Asn Tyr Cys
1

<210> SEQ ID NO 702
<211> LENGTH: 4
<212> TYPE: PRT
<213> ORGANISM: Homo sapiens

<400> SEQUENCE: 702

Asn Tyr Cys Ser
1

<210> SEQ ID NO 703
<211> LENGTH: 4
<212> TYPE: PRT
<213> ORGANISM: Homo sapiens
```

<400> SEQUENCE: 703

Tyr Cys Ser Gly
1

<210> SEQ ID NO 704
<211> LENGTH: 4
<212> TYPE: PRT
<213> ORGANISM: Homo sapiens

<400> SEQUENCE: 704

Cys Ser Gly Gln
1

<210> SEQ ID NO 705
<211> LENGTH: 4
<212> TYPE: PRT
<213> ORGANISM: Homo sapiens

<400> SEQUENCE: 705

Ser Gly Gln Cys
1

<210> SEQ ID NO 706
<211> LENGTH: 4
<212> TYPE: PRT
<213> ORGANISM: Homo sapiens

<400> SEQUENCE: 706

Gly Gln Cys Glu
1

<210> SEQ ID NO 707
<211> LENGTH: 4
<212> TYPE: PRT
<213> ORGANISM: Homo sapiens

<400> SEQUENCE: 707

Gln Cys Glu Tyr
1

<210> SEQ ID NO 708
<211> LENGTH: 4
<212> TYPE: PRT
<213> ORGANISM: Homo sapiens

<400> SEQUENCE: 708

Cys Glu Tyr Met
1

<210> SEQ ID NO 709
<211> LENGTH: 4
<212> TYPE: PRT
<213> ORGANISM: Homo sapiens

<400> SEQUENCE: 709

Glu Tyr Met Phe
1

<210> SEQ ID NO 710
<211> LENGTH: 4
<212> TYPE: PRT
<213> ORGANISM: Homo sapiens

<400> SEQUENCE: 710

Tyr Met Phe Met
1

<210> SEQ ID NO 711
<211> LENGTH: 4
<212> TYPE: PRT
<213> ORGANISM: Homo sapiens

<400> SEQUENCE: 711

Met Phe Met Gln
1

<210> SEQ ID NO 712
<211> LENGTH: 4
<212> TYPE: PRT
<213> ORGANISM: Homo sapiens

<400> SEQUENCE: 712

Phe Met Gln Lys
1

<210> SEQ ID NO 713
<211> LENGTH: 4
<212> TYPE: PRT
<213> ORGANISM: Homo sapiens

<400> SEQUENCE: 713

Met Gln Lys Tyr
1

<210> SEQ ID NO 714
<211> LENGTH: 4
<212> TYPE: PRT
<213> ORGANISM: Homo sapiens

<400> SEQUENCE: 714

Gln Lys Tyr Pro
1

<210> SEQ ID NO 715
<211> LENGTH: 4
<212> TYPE: PRT
<213> ORGANISM: Homo sapiens

<400> SEQUENCE: 715

Lys Tyr Pro His
1

<210> SEQ ID NO 716
<211> LENGTH: 4
<212> TYPE: PRT
<213> ORGANISM: Homo sapiens

<400> SEQUENCE: 716

Tyr Pro His Thr
1

<210> SEQ ID NO 717
<211> LENGTH: 4
<212> TYPE: PRT
<213> ORGANISM: Homo sapiens

<400> SEQUENCE: 717

Pro His Thr His

<210> SEQ ID NO 718
<211> LENGTH: 4
<212> TYPE: PRT
<213> ORGANISM: Homo sapiens

<400> SEQUENCE: 718

His Thr His Leu
1

<210> SEQ ID NO 719
<211> LENGTH: 4
<212> TYPE: PRT
<213> ORGANISM: Homo sapiens

<400> SEQUENCE: 719

Thr His Leu Val
1

<210> SEQ ID NO 720
<211> LENGTH: 4
<212> TYPE: PRT
<213> ORGANISM: Homo sapiens

<400> SEQUENCE: 720

His Leu Val Gln
1

<210> SEQ ID NO 721
<211> LENGTH: 4
<212> TYPE: PRT
<213> ORGANISM: Homo sapiens

<400> SEQUENCE: 721

Leu Val Gln Gln
1

<210> SEQ ID NO 722
<211> LENGTH: 4
<212> TYPE: PRT
<213> ORGANISM: Homo sapiens

<400> SEQUENCE: 722

Val Gln Gln Ala
1

<210> SEQ ID NO 723
<211> LENGTH: 4
<212> TYPE: PRT
<213> ORGANISM: Homo sapiens

<400> SEQUENCE: 723

Gln Gln Ala Asn
1

<210> SEQ ID NO 724
<211> LENGTH: 4
<212> TYPE: PRT
<213> ORGANISM: Homo sapiens

<400> SEQUENCE: 724

Gln Ala Asn Pro
1

<210> SEQ ID NO 725
<211> LENGTH: 4
<212> TYPE: PRT
<213> ORGANISM: Homo sapiens

<400> SEQUENCE: 725

Ala Asn Pro Arg
1

<210> SEQ ID NO 726
<211> LENGTH: 4
<212> TYPE: PRT
<213> ORGANISM: Homo sapiens

<400> SEQUENCE: 726

Asn Pro Arg Gly
1

<210> SEQ ID NO 727
<211> LENGTH: 4
<212> TYPE: PRT
<213> ORGANISM: Homo sapiens

<400> SEQUENCE: 727

Pro Arg Gly Ser
1

<210> SEQ ID NO 728
<211> LENGTH: 4
<212> TYPE: PRT
<213> ORGANISM: Homo sapiens

<400> SEQUENCE: 728

Arg Gly Ser Ala
1

<210> SEQ ID NO 729
<211> LENGTH: 4
<212> TYPE: PRT
<213> ORGANISM: Homo sapiens

<400> SEQUENCE: 729

Gly Ser Ala Gly
1

<210> SEQ ID NO 730
<211> LENGTH: 4
<212> TYPE: PRT
<213> ORGANISM: Homo sapiens

<400> SEQUENCE: 730

Ser Ala Gly Pro
1

<210> SEQ ID NO 731
<211> LENGTH: 4
<212> TYPE: PRT
<213> ORGANISM: Homo sapiens

<400> SEQUENCE: 731

Ala Gly Pro Cys
1

<210> SEQ ID NO 732

<210> SEQ ID NO 732
<211> LENGTH: 4
<212> TYPE: PRT
<213> ORGANISM: Homo sapiens

<400> SEQUENCE: 732

Gly Pro Cys Cys
1

<210> SEQ ID NO 733
<211> LENGTH: 4
<212> TYPE: PRT
<213> ORGANISM: Homo sapiens

<400> SEQUENCE: 733

Pro Cys Cys Thr
1

<210> SEQ ID NO 734
<211> LENGTH: 4
<212> TYPE: PRT
<213> ORGANISM: Homo sapiens

<400> SEQUENCE: 734

Cys Cys Thr Pro
1

<210> SEQ ID NO 735
<211> LENGTH: 4
<212> TYPE: PRT
<213> ORGANISM: Homo sapiens

<400> SEQUENCE: 735

Cys Thr Pro Thr
1

<210> SEQ ID NO 736
<211> LENGTH: 4
<212> TYPE: PRT
<213> ORGANISM: Homo sapiens

<400> SEQUENCE: 736

Thr Pro Thr Lys
1

<210> SEQ ID NO 737
<211> LENGTH: 4
<212> TYPE: PRT
<213> ORGANISM: Homo sapiens

<400> SEQUENCE: 737

Pro Thr Lys Met
1

<210> SEQ ID NO 738
<211> LENGTH: 4
<212> TYPE: PRT
<213> ORGANISM: Homo sapiens

<400> SEQUENCE: 738

Thr Lys Met Ser
1

<210> SEQ ID NO 739
<211> LENGTH: 4
<212> TYPE: PRT

<213> ORGANISM: Homo sapiens

<400> SEQUENCE: 739

Lys Met Ser Pro
1

<210> SEQ ID NO 740
<211> LENGTH: 4
<212> TYPE: PRT
<213> ORGANISM: Homo sapiens

<400> SEQUENCE: 740

Met Ser Pro Ile
1

<210> SEQ ID NO 741
<211> LENGTH: 4
<212> TYPE: PRT
<213> ORGANISM: Homo sapiens

<400> SEQUENCE: 741

Ser Pro Ile Asn
1

<210> SEQ ID NO 742
<211> LENGTH: 4
<212> TYPE: PRT
<213> ORGANISM: Homo sapiens

<400> SEQUENCE: 742

Pro Ile Asn Met
1

<210> SEQ ID NO 743
<211> LENGTH: 4
<212> TYPE: PRT
<213> ORGANISM: Homo sapiens

<400> SEQUENCE: 743

Ile Asn Met Leu
1

<210> SEQ ID NO 744
<211> LENGTH: 4
<212> TYPE: PRT
<213> ORGANISM: Homo sapiens

<400> SEQUENCE: 744

Asn Met Leu Tyr
1

<210> SEQ ID NO 745
<211> LENGTH: 4
<212> TYPE: PRT
<213> ORGANISM: Homo sapiens

<400> SEQUENCE: 745

Met Leu Tyr Phe
1

<210> SEQ ID NO 746
<211> LENGTH: 4
<212> TYPE: PRT
<213> ORGANISM: Homo sapiens

```
<400> SEQUENCE: 746

Leu Tyr Phe Asn
1

<210> SEQ ID NO 747
<211> LENGTH: 4
<212> TYPE: PRT
<213> ORGANISM: Homo sapiens

<400> SEQUENCE: 747

Tyr Phe Asn Asp
1

<210> SEQ ID NO 748
<211> LENGTH: 4
<212> TYPE: PRT
<213> ORGANISM: Homo sapiens

<400> SEQUENCE: 748

Phe Asn Asp Lys
1

<210> SEQ ID NO 749
<211> LENGTH: 4
<212> TYPE: PRT
<213> ORGANISM: Homo sapiens

<400> SEQUENCE: 749

Asn Asp Lys Gln
1

<210> SEQ ID NO 750
<211> LENGTH: 4
<212> TYPE: PRT
<213> ORGANISM: Homo sapiens

<400> SEQUENCE: 750

Asp Lys Gln Gln
1

<210> SEQ ID NO 751
<211> LENGTH: 4
<212> TYPE: PRT
<213> ORGANISM: Homo sapiens

<400> SEQUENCE: 751

Lys Gln Gln Ile
1

<210> SEQ ID NO 752
<211> LENGTH: 4
<212> TYPE: PRT
<213> ORGANISM: Homo sapiens

<400> SEQUENCE: 752

Gln Gln Ile Ile
1

<210> SEQ ID NO 753
<211> LENGTH: 4
<212> TYPE: PRT
<213> ORGANISM: Homo sapiens

<400> SEQUENCE: 753
```

Gln Ile Ile Tyr
1

<210> SEQ ID NO 754
<211> LENGTH: 4
<212> TYPE: PRT
<213> ORGANISM: Homo sapiens

<400> SEQUENCE: 754

Ile Ile Tyr Gly
1

<210> SEQ ID NO 755
<211> LENGTH: 4
<212> TYPE: PRT
<213> ORGANISM: Homo sapiens

<400> SEQUENCE: 755

Ile Tyr Gly Lys
1

<210> SEQ ID NO 756
<211> LENGTH: 4
<212> TYPE: PRT
<213> ORGANISM: Homo sapiens

<400> SEQUENCE: 756

Tyr Gly Lys Ile
1

<210> SEQ ID NO 757
<211> LENGTH: 4
<212> TYPE: PRT
<213> ORGANISM: Homo sapiens

<400> SEQUENCE: 757

Gly Lys Ile Pro
1

<210> SEQ ID NO 758
<211> LENGTH: 4
<212> TYPE: PRT
<213> ORGANISM: Homo sapiens

<400> SEQUENCE: 758

Lys Ile Pro Gly
1

<210> SEQ ID NO 759
<211> LENGTH: 4
<212> TYPE: PRT
<213> ORGANISM: Homo sapiens

<400> SEQUENCE: 759

Ile Pro Gly Met
1

<210> SEQ ID NO 760
<211> LENGTH: 4
<212> TYPE: PRT
<213> ORGANISM: Homo sapiens

<400> SEQUENCE: 760

Pro Gly Met Val
1

```
<210> SEQ ID NO 761
<211> LENGTH: 4
<212> TYPE: PRT
<213> ORGANISM: Homo sapiens

<400> SEQUENCE: 761

Gly Met Val Val
1

<210> SEQ ID NO 762
<211> LENGTH: 4
<212> TYPE: PRT
<213> ORGANISM: Homo sapiens

<400> SEQUENCE: 762

Met Val Val Asp
1

<210> SEQ ID NO 763
<211> LENGTH: 4
<212> TYPE: PRT
<213> ORGANISM: Homo sapiens

<400> SEQUENCE: 763

Val Val Asp Arg
1

<210> SEQ ID NO 764
<211> LENGTH: 4
<212> TYPE: PRT
<213> ORGANISM: Homo sapiens

<400> SEQUENCE: 764

Val Asp Arg Cys
1

<210> SEQ ID NO 765
<211> LENGTH: 4
<212> TYPE: PRT
<213> ORGANISM: Homo sapiens

<400> SEQUENCE: 765

Asp Arg Cys Gly
1

<210> SEQ ID NO 766
<211> LENGTH: 4
<212> TYPE: PRT
<213> ORGANISM: Homo sapiens

<400> SEQUENCE: 766

Arg Cys Gly Cys
1

<210> SEQ ID NO 767
<211> LENGTH: 4
<212> TYPE: PRT
<213> ORGANISM: Homo sapiens

<400> SEQUENCE: 767

Cys Gly Cys Ser
1
```

<210> SEQ ID NO 768
<211> LENGTH: 5
<212> TYPE: PRT
<213> ORGANISM: Homo sapiens

<400> SEQUENCE: 768

Met Val Leu Ala Ala
1               5

<210> SEQ ID NO 769
<211> LENGTH: 5
<212> TYPE: PRT
<213> ORGANISM: Homo sapiens

<400> SEQUENCE: 769

Val Leu Ala Ala Pro
1               5

<210> SEQ ID NO 770
<211> LENGTH: 5
<212> TYPE: PRT
<213> ORGANISM: Homo sapiens

<400> SEQUENCE: 770

Leu Ala Ala Pro Leu
1               5

<210> SEQ ID NO 771
<211> LENGTH: 5
<212> TYPE: PRT
<213> ORGANISM: Homo sapiens

<400> SEQUENCE: 771

Ala Ala Pro Leu Leu
1               5

<210> SEQ ID NO 772
<211> LENGTH: 5
<212> TYPE: PRT
<213> ORGANISM: Homo sapiens

<400> SEQUENCE: 772

Ala Pro Leu Leu Leu
1               5

<210> SEQ ID NO 773
<211> LENGTH: 5
<212> TYPE: PRT
<213> ORGANISM: Homo sapiens

<400> SEQUENCE: 773

Pro Leu Leu Leu Gly
1               5

<210> SEQ ID NO 774
<211> LENGTH: 5
<212> TYPE: PRT
<213> ORGANISM: Homo sapiens

<400> SEQUENCE: 774

Leu Leu Leu Gly Phe
1               5

<210> SEQ ID NO 775
<211> LENGTH: 5

```
<212> TYPE: PRT
<213> ORGANISM: Homo sapiens

<400> SEQUENCE: 775

Leu Leu Gly Phe Leu
1               5

<210> SEQ ID NO 776
<211> LENGTH: 5
<212> TYPE: PRT
<213> ORGANISM: Homo sapiens

<400> SEQUENCE: 776

Leu Gly Phe Leu Leu
1               5

<210> SEQ ID NO 777
<211> LENGTH: 5
<212> TYPE: PRT
<213> ORGANISM: Homo sapiens

<400> SEQUENCE: 777

Gly Phe Leu Leu Leu
1               5

<210> SEQ ID NO 778
<211> LENGTH: 5
<212> TYPE: PRT
<213> ORGANISM: Homo sapiens

<400> SEQUENCE: 778

Phe Leu Leu Leu Ala
1               5

<210> SEQ ID NO 779
<211> LENGTH: 5
<212> TYPE: PRT
<213> ORGANISM: Homo sapiens

<400> SEQUENCE: 779

Leu Leu Leu Ala Leu
1               5

<210> SEQ ID NO 780
<211> LENGTH: 5
<212> TYPE: PRT
<213> ORGANISM: Homo sapiens

<400> SEQUENCE: 780

Leu Leu Ala Leu Glu
1               5

<210> SEQ ID NO 781
<211> LENGTH: 5
<212> TYPE: PRT
<213> ORGANISM: Homo sapiens

<400> SEQUENCE: 781

Leu Ala Leu Glu Leu
1               5

<210> SEQ ID NO 782
<211> LENGTH: 5
<212> TYPE: PRT
<213> ORGANISM: Homo sapiens
```

<400> SEQUENCE: 782

Ala Leu Glu Leu Arg
1               5

<210> SEQ ID NO 783
<211> LENGTH: 5
<212> TYPE: PRT
<213> ORGANISM: Homo sapiens

<400> SEQUENCE: 783

Leu Glu Leu Arg Pro
1               5

<210> SEQ ID NO 784
<211> LENGTH: 5
<212> TYPE: PRT
<213> ORGANISM: Homo sapiens

<400> SEQUENCE: 784

Glu Leu Arg Pro Arg
1               5

<210> SEQ ID NO 785
<211> LENGTH: 5
<212> TYPE: PRT
<213> ORGANISM: Homo sapiens

<400> SEQUENCE: 785

Leu Arg Pro Arg Gly
1               5

<210> SEQ ID NO 786
<211> LENGTH: 5
<212> TYPE: PRT
<213> ORGANISM: Homo sapiens

<400> SEQUENCE: 786

Arg Pro Arg Gly Glu
1               5

<210> SEQ ID NO 787
<211> LENGTH: 5
<212> TYPE: PRT
<213> ORGANISM: Homo sapiens

<400> SEQUENCE: 787

Pro Arg Gly Glu Ala
1               5

<210> SEQ ID NO 788
<211> LENGTH: 5
<212> TYPE: PRT
<213> ORGANISM: Homo sapiens

<400> SEQUENCE: 788

Arg Gly Glu Ala Ala
1               5

<210> SEQ ID NO 789
<211> LENGTH: 5
<212> TYPE: PRT
<213> ORGANISM: Homo sapiens

<400> SEQUENCE: 789

```
Gly Glu Ala Ala Glu
1               5

<210> SEQ ID NO 790
<211> LENGTH: 5
<212> TYPE: PRT
<213> ORGANISM: Homo sapiens

<400> SEQUENCE: 790

Glu Ala Ala Glu Gly
1               5

<210> SEQ ID NO 791
<211> LENGTH: 5
<212> TYPE: PRT
<213> ORGANISM: Homo sapiens

<400> SEQUENCE: 791

Ala Ala Glu Gly Pro
1               5

<210> SEQ ID NO 792
<211> LENGTH: 5
<212> TYPE: PRT
<213> ORGANISM: Homo sapiens

<400> SEQUENCE: 792

Ala Glu Gly Pro Ala
1               5

<210> SEQ ID NO 793
<211> LENGTH: 5
<212> TYPE: PRT
<213> ORGANISM: Homo sapiens

<400> SEQUENCE: 793

Glu Gly Pro Ala Ala
1               5

<210> SEQ ID NO 794
<211> LENGTH: 5
<212> TYPE: PRT
<213> ORGANISM: Homo sapiens

<400> SEQUENCE: 794

Gly Pro Ala Ala Ala
1               5

<210> SEQ ID NO 795
<211> LENGTH: 5
<212> TYPE: PRT
<213> ORGANISM: Homo sapiens

<400> SEQUENCE: 795

Pro Ala Ala Ala Ala
1               5

<210> SEQ ID NO 796
<211> LENGTH: 5
<212> TYPE: PRT
<213> ORGANISM: Homo sapiens

<400> SEQUENCE: 796

Ala Ala Ala Ala Ala
```

```
1               5

<210> SEQ ID NO 797
<211> LENGTH: 5
<212> TYPE: PRT
<213> ORGANISM: Homo sapiens

<400> SEQUENCE: 797

Ala Ala Ala Ala Gly
1               5

<210> SEQ ID NO 798
<211> LENGTH: 5
<212> TYPE: PRT
<213> ORGANISM: Homo sapiens

<400> SEQUENCE: 798

Ala Ala Ala Gly Val
1               5

<210> SEQ ID NO 799
<211> LENGTH: 5
<212> TYPE: PRT
<213> ORGANISM: Homo sapiens

<400> SEQUENCE: 799

Ala Ala Gly Val Gly
1               5

<210> SEQ ID NO 800
<211> LENGTH: 5
<212> TYPE: PRT
<213> ORGANISM: Homo sapiens

<400> SEQUENCE: 800

Ala Gly Val Gly Gly
1               5

<210> SEQ ID NO 801
<211> LENGTH: 5
<212> TYPE: PRT
<213> ORGANISM: Homo sapiens

<400> SEQUENCE: 801

Gly Val Gly Gly Glu
1               5

<210> SEQ ID NO 802
<211> LENGTH: 5
<212> TYPE: PRT
<213> ORGANISM: Homo sapiens

<400> SEQUENCE: 802

Val Gly Gly Glu Arg
1               5

<210> SEQ ID NO 803
<211> LENGTH: 5
<212> TYPE: PRT
<213> ORGANISM: Homo sapiens

<400> SEQUENCE: 803

Gly Gly Glu Arg Ser
1               5
```

<210> SEQ ID NO 804
<211> LENGTH: 5
<212> TYPE: PRT
<213> ORGANISM: Homo sapiens

<400> SEQUENCE: 804

Gly Glu Arg Ser Ser
1               5

<210> SEQ ID NO 805
<211> LENGTH: 5
<212> TYPE: PRT
<213> ORGANISM: Homo sapiens

<400> SEQUENCE: 805

Glu Arg Ser Ser Arg
1               5

<210> SEQ ID NO 806
<211> LENGTH: 5
<212> TYPE: PRT
<213> ORGANISM: Homo sapiens

<400> SEQUENCE: 806

Arg Ser Ser Arg Pro
1               5

<210> SEQ ID NO 807
<211> LENGTH: 5
<212> TYPE: PRT
<213> ORGANISM: Homo sapiens

<400> SEQUENCE: 807

Ser Ser Arg Pro Ala
1               5

<210> SEQ ID NO 808
<211> LENGTH: 5
<212> TYPE: PRT
<213> ORGANISM: Homo sapiens

<400> SEQUENCE: 808

Ser Arg Pro Ala Pro
1               5

<210> SEQ ID NO 809
<211> LENGTH: 5
<212> TYPE: PRT
<213> ORGANISM: Homo sapiens

<400> SEQUENCE: 809

Arg Pro Ala Pro Ser
1               5

<210> SEQ ID NO 810
<211> LENGTH: 5
<212> TYPE: PRT
<213> ORGANISM: Homo sapiens

<400> SEQUENCE: 810

Pro Ala Pro Ser Val
1               5

<210> SEQ ID NO 811

```
<211> LENGTH: 5
<212> TYPE: PRT
<213> ORGANISM: Homo sapiens

<400> SEQUENCE: 811

Ala Pro Ser Val Ala
1               5

<210> SEQ ID NO 812
<211> LENGTH: 5
<212> TYPE: PRT
<213> ORGANISM: Homo sapiens

<400> SEQUENCE: 812

Pro Ser Val Ala Pro
1               5

<210> SEQ ID NO 813
<211> LENGTH: 5
<212> TYPE: PRT
<213> ORGANISM: Homo sapiens

<400> SEQUENCE: 813

Ser Val Ala Pro Glu
1               5

<210> SEQ ID NO 814
<211> LENGTH: 5
<212> TYPE: PRT
<213> ORGANISM: Homo sapiens

<400> SEQUENCE: 814

Val Ala Pro Glu Pro
1               5

<210> SEQ ID NO 815
<211> LENGTH: 5
<212> TYPE: PRT
<213> ORGANISM: Homo sapiens

<400> SEQUENCE: 815

Ala Pro Glu Pro Asp
1               5

<210> SEQ ID NO 816
<211> LENGTH: 5
<212> TYPE: PRT
<213> ORGANISM: Homo sapiens

<400> SEQUENCE: 816

Pro Glu Pro Asp Gly
1               5

<210> SEQ ID NO 817
<211> LENGTH: 5
<212> TYPE: PRT
<213> ORGANISM: Homo sapiens

<400> SEQUENCE: 817

Glu Pro Asp Gly Cys
1               5

<210> SEQ ID NO 818
<211> LENGTH: 5
<212> TYPE: PRT
```

```
<213> ORGANISM: Homo sapiens

<400> SEQUENCE: 818

Pro Asp Gly Cys Pro
1               5

<210> SEQ ID NO 819
<211> LENGTH: 5
<212> TYPE: PRT
<213> ORGANISM: Homo sapiens

<400> SEQUENCE: 819

Asp Gly Cys Pro Val
1               5

<210> SEQ ID NO 820
<211> LENGTH: 5
<212> TYPE: PRT
<213> ORGANISM: Homo sapiens

<400> SEQUENCE: 820

Gly Cys Pro Val Cys
1               5

<210> SEQ ID NO 821
<211> LENGTH: 5
<212> TYPE: PRT
<213> ORGANISM: Homo sapiens

<400> SEQUENCE: 821

Cys Pro Val Cys Val
1               5

<210> SEQ ID NO 822
<211> LENGTH: 5
<212> TYPE: PRT
<213> ORGANISM: Homo sapiens

<400> SEQUENCE: 822

Pro Val Cys Val Trp
1               5

<210> SEQ ID NO 823
<211> LENGTH: 5
<212> TYPE: PRT
<213> ORGANISM: Homo sapiens

<400> SEQUENCE: 823

Val Cys Val Trp Arg
1               5

<210> SEQ ID NO 824
<211> LENGTH: 5
<212> TYPE: PRT
<213> ORGANISM: Homo sapiens

<400> SEQUENCE: 824

Cys Val Trp Arg Gln
1               5

<210> SEQ ID NO 825
<211> LENGTH: 5
<212> TYPE: PRT
<213> ORGANISM: Homo sapiens
```

<400> SEQUENCE: 825

Val Trp Arg Gln His
1               5

<210> SEQ ID NO 826
<211> LENGTH: 5
<212> TYPE: PRT
<213> ORGANISM: Homo sapiens

<400> SEQUENCE: 826

Trp Arg Gln His Ser
1               5

<210> SEQ ID NO 827
<211> LENGTH: 5
<212> TYPE: PRT
<213> ORGANISM: Homo sapiens

<400> SEQUENCE: 827

Arg Gln His Ser Arg
1               5

<210> SEQ ID NO 828
<211> LENGTH: 5
<212> TYPE: PRT
<213> ORGANISM: Homo sapiens

<400> SEQUENCE: 828

Gln His Ser Arg Glu
1               5

<210> SEQ ID NO 829
<211> LENGTH: 5
<212> TYPE: PRT
<213> ORGANISM: Homo sapiens

<400> SEQUENCE: 829

His Ser Arg Glu Leu
1               5

<210> SEQ ID NO 830
<211> LENGTH: 5
<212> TYPE: PRT
<213> ORGANISM: Homo sapiens

<400> SEQUENCE: 830

Ser Arg Glu Leu Arg
1               5

<210> SEQ ID NO 831
<211> LENGTH: 5
<212> TYPE: PRT
<213> ORGANISM: Homo sapiens

<400> SEQUENCE: 831

Arg Glu Leu Arg Leu
1               5

<210> SEQ ID NO 832
<211> LENGTH: 5
<212> TYPE: PRT
<213> ORGANISM: Homo sapiens

<400> SEQUENCE: 832

```
Glu Leu Arg Leu Glu
1               5

<210> SEQ ID NO 833
<211> LENGTH: 5
<212> TYPE: PRT
<213> ORGANISM: Homo sapiens

<400> SEQUENCE: 833

Leu Arg Leu Glu Ser
1               5

<210> SEQ ID NO 834
<211> LENGTH: 5
<212> TYPE: PRT
<213> ORGANISM: Homo sapiens

<400> SEQUENCE: 834

Arg Leu Glu Ser Ile
1               5

<210> SEQ ID NO 835
<211> LENGTH: 5
<212> TYPE: PRT
<213> ORGANISM: Homo sapiens

<400> SEQUENCE: 835

Leu Glu Ser Ile Lys
1               5

<210> SEQ ID NO 836
<211> LENGTH: 5
<212> TYPE: PRT
<213> ORGANISM: Homo sapiens

<400> SEQUENCE: 836

Glu Ser Ile Lys Ser
1               5

<210> SEQ ID NO 837
<211> LENGTH: 5
<212> TYPE: PRT
<213> ORGANISM: Homo sapiens

<400> SEQUENCE: 837

Ser Ile Lys Ser Gln
1               5

<210> SEQ ID NO 838
<211> LENGTH: 5
<212> TYPE: PRT
<213> ORGANISM: Homo sapiens

<400> SEQUENCE: 838

Ile Lys Ser Gln Ile
1               5

<210> SEQ ID NO 839
<211> LENGTH: 5
<212> TYPE: PRT
<213> ORGANISM: Homo sapiens

<400> SEQUENCE: 839

Lys Ser Gln Ile Leu
1               5
```

<210> SEQ ID NO 840
<211> LENGTH: 5
<212> TYPE: PRT
<213> ORGANISM: Homo sapiens

<400> SEQUENCE: 840

Ser Gln Ile Leu Ser
1               5

<210> SEQ ID NO 841
<211> LENGTH: 5
<212> TYPE: PRT
<213> ORGANISM: Homo sapiens

<400> SEQUENCE: 841

Gln Ile Leu Ser Lys
1               5

<210> SEQ ID NO 842
<211> LENGTH: 5
<212> TYPE: PRT
<213> ORGANISM: Homo sapiens

<400> SEQUENCE: 842

Ile Leu Ser Lys Leu
1               5

<210> SEQ ID NO 843
<211> LENGTH: 5
<212> TYPE: PRT
<213> ORGANISM: Homo sapiens

<400> SEQUENCE: 843

Leu Ser Lys Leu Arg
1               5

<210> SEQ ID NO 844
<211> LENGTH: 5
<212> TYPE: PRT
<213> ORGANISM: Homo sapiens

<400> SEQUENCE: 844

Ser Lys Leu Arg Leu
1               5

<210> SEQ ID NO 845
<211> LENGTH: 5
<212> TYPE: PRT
<213> ORGANISM: Homo sapiens

<400> SEQUENCE: 845

Lys Leu Arg Leu Lys
1               5

<210> SEQ ID NO 846
<211> LENGTH: 5
<212> TYPE: PRT
<213> ORGANISM: Homo sapiens

<400> SEQUENCE: 846

Leu Arg Leu Lys Glu
1               5

<210> SEQ ID NO 847
<211> LENGTH: 5
<212> TYPE: PRT
<213> ORGANISM: Homo sapiens

<400> SEQUENCE: 847

Arg Leu Lys Glu Ala
1               5

<210> SEQ ID NO 848
<211> LENGTH: 5
<212> TYPE: PRT
<213> ORGANISM: Homo sapiens

<400> SEQUENCE: 848

Leu Lys Glu Ala Pro
1               5

<210> SEQ ID NO 849
<211> LENGTH: 5
<212> TYPE: PRT
<213> ORGANISM: Homo sapiens

<400> SEQUENCE: 849

Lys Glu Ala Pro Asn
1               5

<210> SEQ ID NO 850
<211> LENGTH: 5
<212> TYPE: PRT
<213> ORGANISM: Homo sapiens

<400> SEQUENCE: 850

Glu Ala Pro Asn Ile
1               5

<210> SEQ ID NO 851
<211> LENGTH: 5
<212> TYPE: PRT
<213> ORGANISM: Homo sapiens

<400> SEQUENCE: 851

Ala Pro Asn Ile Ser
1               5

<210> SEQ ID NO 852
<211> LENGTH: 5
<212> TYPE: PRT
<213> ORGANISM: Homo sapiens

<400> SEQUENCE: 852

Pro Asn Ile Ser Arg
1               5

<210> SEQ ID NO 853
<211> LENGTH: 5
<212> TYPE: PRT
<213> ORGANISM: Homo sapiens

<400> SEQUENCE: 853

Asn Ile Ser Arg Glu
1               5

<210> SEQ ID NO 854
<211> LENGTH: 5

```
<212> TYPE: PRT
<213> ORGANISM: Homo sapiens

<400> SEQUENCE: 854

Ile Ser Arg Glu Val
1               5

<210> SEQ ID NO 855
<211> LENGTH: 5
<212> TYPE: PRT
<213> ORGANISM: Homo sapiens

<400> SEQUENCE: 855

Ser Arg Glu Val Val
1               5

<210> SEQ ID NO 856
<211> LENGTH: 5
<212> TYPE: PRT
<213> ORGANISM: Homo sapiens

<400> SEQUENCE: 856

Arg Glu Val Val Lys
1               5

<210> SEQ ID NO 857
<211> LENGTH: 5
<212> TYPE: PRT
<213> ORGANISM: Homo sapiens

<400> SEQUENCE: 857

Glu Val Val Lys Gln
1               5

<210> SEQ ID NO 858
<211> LENGTH: 5
<212> TYPE: PRT
<213> ORGANISM: Homo sapiens

<400> SEQUENCE: 858

Val Val Lys Gln Leu
1               5

<210> SEQ ID NO 859
<211> LENGTH: 5
<212> TYPE: PRT
<213> ORGANISM: Homo sapiens

<400> SEQUENCE: 859

Val Lys Gln Leu Leu
1               5

<210> SEQ ID NO 860
<211> LENGTH: 5
<212> TYPE: PRT
<213> ORGANISM: Homo sapiens

<400> SEQUENCE: 860

Lys Gln Leu Leu Pro
1               5

<210> SEQ ID NO 861
<211> LENGTH: 5
<212> TYPE: PRT
<213> ORGANISM: Homo sapiens
```

<400> SEQUENCE: 861

Gln Leu Leu Pro Lys
1               5

<210> SEQ ID NO 862
<211> LENGTH: 5
<212> TYPE: PRT
<213> ORGANISM: Homo sapiens

<400> SEQUENCE: 862

Leu Leu Pro Lys Ala
1               5

<210> SEQ ID NO 863
<211> LENGTH: 5
<212> TYPE: PRT
<213> ORGANISM: Homo sapiens

<400> SEQUENCE: 863

Leu Pro Lys Ala Pro
1               5

<210> SEQ ID NO 864
<211> LENGTH: 5
<212> TYPE: PRT
<213> ORGANISM: Homo sapiens

<400> SEQUENCE: 864

Pro Lys Ala Pro Pro
1               5

<210> SEQ ID NO 865
<211> LENGTH: 5
<212> TYPE: PRT
<213> ORGANISM: Homo sapiens

<400> SEQUENCE: 865

Lys Ala Pro Pro Leu
1               5

<210> SEQ ID NO 866
<211> LENGTH: 5
<212> TYPE: PRT
<213> ORGANISM: Homo sapiens

<400> SEQUENCE: 866

Ala Pro Pro Leu Gln
1               5

<210> SEQ ID NO 867
<211> LENGTH: 5
<212> TYPE: PRT
<213> ORGANISM: Homo sapiens

<400> SEQUENCE: 867

Pro Pro Leu Gln Gln
1               5

<210> SEQ ID NO 868
<211> LENGTH: 5
<212> TYPE: PRT
<213> ORGANISM: Homo sapiens

<400> SEQUENCE: 868

Pro Leu Gln Gln Ile
1               5

<210> SEQ ID NO 869
<211> LENGTH: 5
<212> TYPE: PRT
<213> ORGANISM: Homo sapiens

<400> SEQUENCE: 869

Leu Gln Gln Ile Leu
1               5

<210> SEQ ID NO 870
<211> LENGTH: 5
<212> TYPE: PRT
<213> ORGANISM: Homo sapiens

<400> SEQUENCE: 870

Gln Gln Ile Leu Asp
1               5

<210> SEQ ID NO 871
<211> LENGTH: 5
<212> TYPE: PRT
<213> ORGANISM: Homo sapiens

<400> SEQUENCE: 871

Gln Ile Leu Asp Leu
1               5

<210> SEQ ID NO 872
<211> LENGTH: 5
<212> TYPE: PRT
<213> ORGANISM: Homo sapiens

<400> SEQUENCE: 872

Ile Leu Asp Leu His
1               5

<210> SEQ ID NO 873
<211> LENGTH: 5
<212> TYPE: PRT
<213> ORGANISM: Homo sapiens

<400> SEQUENCE: 873

Leu Asp Leu His Asp
1               5

<210> SEQ ID NO 874
<211> LENGTH: 5
<212> TYPE: PRT
<213> ORGANISM: Homo sapiens

<400> SEQUENCE: 874

Asp Leu His Asp Phe
1               5

<210> SEQ ID NO 875
<211> LENGTH: 5
<212> TYPE: PRT
<213> ORGANISM: Homo sapiens

<400> SEQUENCE: 875

Leu His Asp Phe Gln 1               5

<210> SEQ ID NO 876
<211> LENGTH: 5
<212> TYPE: PRT
<213> ORGANISM: Homo sapiens

<400> SEQUENCE: 876

His Asp Phe Gln Gly
1               5

<210> SEQ ID NO 877
<211> LENGTH: 5
<212> TYPE: PRT
<213> ORGANISM: Homo sapiens

<400> SEQUENCE: 877

Asp Phe Gln Gly Asp
1               5

<210> SEQ ID NO 878
<211> LENGTH: 5
<212> TYPE: PRT
<213> ORGANISM: Homo sapiens

<400> SEQUENCE: 878

Phe Gln Gly Asp Ala
1               5

<210> SEQ ID NO 879
<211> LENGTH: 5
<212> TYPE: PRT
<213> ORGANISM: Homo sapiens

<400> SEQUENCE: 879

Gln Gly Asp Ala Leu
1               5

<210> SEQ ID NO 880
<211> LENGTH: 5
<212> TYPE: PRT
<213> ORGANISM: Homo sapiens

<400> SEQUENCE: 880

Gly Asp Ala Leu Gln
1               5

<210> SEQ ID NO 881
<211> LENGTH: 5
<212> TYPE: PRT
<213> ORGANISM: Homo sapiens

<400> SEQUENCE: 881

Asp Ala Leu Gln Pro
1               5

<210> SEQ ID NO 882
<211> LENGTH: 5
<212> TYPE: PRT
<213> ORGANISM: Homo sapiens

<400> SEQUENCE: 882

Ala Leu Gln Pro Glu
1               5

<210> SEQ ID NO 883
<211> LENGTH: 5
<212> TYPE: PRT
<213> ORGANISM: Homo sapiens

<400> SEQUENCE: 883

Leu Gln Pro Glu Asp
1               5

<210> SEQ ID NO 884
<211> LENGTH: 5
<212> TYPE: PRT
<213> ORGANISM: Homo sapiens

<400> SEQUENCE: 884

Gln Pro Glu Asp Phe
1               5

<210> SEQ ID NO 885
<211> LENGTH: 5
<212> TYPE: PRT
<213> ORGANISM: Homo sapiens

<400> SEQUENCE: 885

Pro Glu Asp Phe Leu
1               5

<210> SEQ ID NO 886
<211> LENGTH: 5
<212> TYPE: PRT
<213> ORGANISM: Homo sapiens

<400> SEQUENCE: 886

Glu Asp Phe Leu Glu
1               5

<210> SEQ ID NO 887
<211> LENGTH: 5
<212> TYPE: PRT
<213> ORGANISM: Homo sapiens

<400> SEQUENCE: 887

Asp Phe Leu Glu Glu
1               5

<210> SEQ ID NO 888
<211> LENGTH: 5
<212> TYPE: PRT
<213> ORGANISM: Homo sapiens

<400> SEQUENCE: 888

Phe Leu Glu Glu Asp
1               5

<210> SEQ ID NO 889
<211> LENGTH: 5
<212> TYPE: PRT
<213> ORGANISM: Homo sapiens

<400> SEQUENCE: 889

Leu Glu Glu Asp Glu
1               5

<210> SEQ ID NO 890

```
<211> LENGTH: 5
<212> TYPE: PRT
<213> ORGANISM: Homo sapiens

<400> SEQUENCE: 890

Glu Glu Asp Glu Tyr
1               5

<210> SEQ ID NO 891
<211> LENGTH: 5
<212> TYPE: PRT
<213> ORGANISM: Homo sapiens

<400> SEQUENCE: 891

Glu Asp Glu Tyr His
1               5

<210> SEQ ID NO 892
<211> LENGTH: 5
<212> TYPE: PRT
<213> ORGANISM: Homo sapiens

<400> SEQUENCE: 892

Asp Glu Tyr His Ala
1               5

<210> SEQ ID NO 893
<211> LENGTH: 5
<212> TYPE: PRT
<213> ORGANISM: Homo sapiens

<400> SEQUENCE: 893

Glu Tyr His Ala Thr
1               5

<210> SEQ ID NO 894
<211> LENGTH: 5
<212> TYPE: PRT
<213> ORGANISM: Homo sapiens

<400> SEQUENCE: 894

Tyr His Ala Thr Thr
1               5

<210> SEQ ID NO 895
<211> LENGTH: 5
<212> TYPE: PRT
<213> ORGANISM: Homo sapiens

<400> SEQUENCE: 895

His Ala Thr Thr Glu
1               5

<210> SEQ ID NO 896
<211> LENGTH: 5
<212> TYPE: PRT
<213> ORGANISM: Homo sapiens

<400> SEQUENCE: 896

Ala Thr Thr Glu Thr
1               5

<210> SEQ ID NO 897
<211> LENGTH: 5
<212> TYPE: PRT
```

<213> ORGANISM: Homo sapiens

<400> SEQUENCE: 897

Thr Thr Glu Thr Val
1               5

<210> SEQ ID NO 898
<211> LENGTH: 5
<212> TYPE: PRT
<213> ORGANISM: Homo sapiens

<400> SEQUENCE: 898

Thr Glu Thr Val Ile
1               5

<210> SEQ ID NO 899
<211> LENGTH: 5
<212> TYPE: PRT
<213> ORGANISM: Homo sapiens

<400> SEQUENCE: 899

Glu Thr Val Ile Ser
1               5

<210> SEQ ID NO 900
<211> LENGTH: 5
<212> TYPE: PRT
<213> ORGANISM: Homo sapiens

<400> SEQUENCE: 900

Thr Val Ile Ser Met
1               5

<210> SEQ ID NO 901
<211> LENGTH: 5
<212> TYPE: PRT
<213> ORGANISM: Homo sapiens

<400> SEQUENCE: 901

Val Ile Ser Met Ala
1               5

<210> SEQ ID NO 902
<211> LENGTH: 5
<212> TYPE: PRT
<213> ORGANISM: Homo sapiens

<400> SEQUENCE: 902

Ile Ser Met Ala Gln
1               5

<210> SEQ ID NO 903
<211> LENGTH: 5
<212> TYPE: PRT
<213> ORGANISM: Homo sapiens

<400> SEQUENCE: 903

Ser Met Ala Gln Glu
1               5

<210> SEQ ID NO 904
<211> LENGTH: 5
<212> TYPE: PRT
<213> ORGANISM: Homo sapiens

<400> SEQUENCE: 904

Met Ala Gln Glu Thr
1               5

<210> SEQ ID NO 905
<211> LENGTH: 5
<212> TYPE: PRT
<213> ORGANISM: Homo sapiens

<400> SEQUENCE: 905

Ala Gln Glu Thr Asp
1               5

<210> SEQ ID NO 906
<211> LENGTH: 5
<212> TYPE: PRT
<213> ORGANISM: Homo sapiens

<400> SEQUENCE: 906

Gln Glu Thr Asp Pro
1               5

<210> SEQ ID NO 907
<211> LENGTH: 5
<212> TYPE: PRT
<213> ORGANISM: Homo sapiens

<400> SEQUENCE: 907

Glu Thr Asp Pro Ala
1               5

<210> SEQ ID NO 908
<211> LENGTH: 5
<212> TYPE: PRT
<213> ORGANISM: Homo sapiens

<400> SEQUENCE: 908

Thr Asp Pro Ala Val
1               5

<210> SEQ ID NO 909
<211> LENGTH: 5
<212> TYPE: PRT
<213> ORGANISM: Homo sapiens

<400> SEQUENCE: 909

Asp Pro Ala Val Gln
1               5

<210> SEQ ID NO 910
<211> LENGTH: 5
<212> TYPE: PRT
<213> ORGANISM: Homo sapiens

<400> SEQUENCE: 910

Pro Ala Val Gln Thr
1               5

<210> SEQ ID NO 911
<211> LENGTH: 5
<212> TYPE: PRT
<213> ORGANISM: Homo sapiens

<400> SEQUENCE: 911

Ala Val Gln Thr Asp
1               5

<210> SEQ ID NO 912
<211> LENGTH: 5
<212> TYPE: PRT
<213> ORGANISM: Homo sapiens

<400> SEQUENCE: 912

Val Gln Thr Asp Gly
1               5

<210> SEQ ID NO 913
<211> LENGTH: 5
<212> TYPE: PRT
<213> ORGANISM: Homo sapiens

<400> SEQUENCE: 913

Gln Thr Asp Gly Ser
1               5

<210> SEQ ID NO 914
<211> LENGTH: 5
<212> TYPE: PRT
<213> ORGANISM: Homo sapiens

<400> SEQUENCE: 914

Thr Asp Gly Ser Pro
1               5

<210> SEQ ID NO 915
<211> LENGTH: 5
<212> TYPE: PRT
<213> ORGANISM: Homo sapiens

<400> SEQUENCE: 915

Asp Gly Ser Pro Leu
1               5

<210> SEQ ID NO 916
<211> LENGTH: 5
<212> TYPE: PRT
<213> ORGANISM: Homo sapiens

<400> SEQUENCE: 916

Gly Ser Pro Leu Cys
1               5

<210> SEQ ID NO 917
<211> LENGTH: 5
<212> TYPE: PRT
<213> ORGANISM: Homo sapiens

<400> SEQUENCE: 917

Ser Pro Leu Cys Cys
1               5

<210> SEQ ID NO 918
<211> LENGTH: 5
<212> TYPE: PRT
<213> ORGANISM: Homo sapiens

<400> SEQUENCE: 918

Pro Leu Cys Cys His
1               5

<210> SEQ ID NO 919
<211> LENGTH: 5
<212> TYPE: PRT
<213> ORGANISM: Homo sapiens

<400> SEQUENCE: 919

Leu Cys Cys His Phe
1               5

<210> SEQ ID NO 920
<211> LENGTH: 5
<212> TYPE: PRT
<213> ORGANISM: Homo sapiens

<400> SEQUENCE: 920

Cys Cys His Phe His
1               5

<210> SEQ ID NO 921
<211> LENGTH: 5
<212> TYPE: PRT
<213> ORGANISM: Homo sapiens

<400> SEQUENCE: 921

Cys His Phe His Phe
1               5

<210> SEQ ID NO 922
<211> LENGTH: 5
<212> TYPE: PRT
<213> ORGANISM: Homo sapiens

<400> SEQUENCE: 922

His Phe His Phe Ser
1               5

<210> SEQ ID NO 923
<211> LENGTH: 5
<212> TYPE: PRT
<213> ORGANISM: Homo sapiens

<400> SEQUENCE: 923

Phe His Phe Ser Pro
1               5

<210> SEQ ID NO 924
<211> LENGTH: 5
<212> TYPE: PRT
<213> ORGANISM: Homo sapiens

<400> SEQUENCE: 924

His Phe Ser Pro Lys
1               5

<210> SEQ ID NO 925
<211> LENGTH: 5
<212> TYPE: PRT
<213> ORGANISM: Homo sapiens

<400> SEQUENCE: 925

Phe Ser Pro Lys Val
1               5

<210> SEQ ID NO 926
<211> LENGTH: 5
<212> TYPE: PRT
<213> ORGANISM: Homo sapiens

<400> SEQUENCE: 926

Ser Pro Lys Val Met
1               5

<210> SEQ ID NO 927
<211> LENGTH: 5
<212> TYPE: PRT
<213> ORGANISM: Homo sapiens

<400> SEQUENCE: 927

Pro Lys Val Met Phe
1               5

<210> SEQ ID NO 928
<211> LENGTH: 5
<212> TYPE: PRT
<213> ORGANISM: Homo sapiens

<400> SEQUENCE: 928

Lys Val Met Phe Thr
1               5

<210> SEQ ID NO 929
<211> LENGTH: 5
<212> TYPE: PRT
<213> ORGANISM: Homo sapiens

<400> SEQUENCE: 929

Val Met Phe Thr Lys
1               5

<210> SEQ ID NO 930
<211> LENGTH: 5
<212> TYPE: PRT
<213> ORGANISM: Homo sapiens

<400> SEQUENCE: 930

Met Phe Thr Lys Val
1               5

<210> SEQ ID NO 931
<211> LENGTH: 5
<212> TYPE: PRT
<213> ORGANISM: Homo sapiens

<400> SEQUENCE: 931

Phe Thr Lys Val Leu
1               5

<210> SEQ ID NO 932
<211> LENGTH: 5
<212> TYPE: PRT
<213> ORGANISM: Homo sapiens

<400> SEQUENCE: 932

Thr Lys Val Leu Lys
1               5

<210> SEQ ID NO 933
<211> LENGTH: 5

```
<212> TYPE: PRT
<213> ORGANISM: Homo sapiens

<400> SEQUENCE: 933

Lys Val Leu Lys Ala
1               5

<210> SEQ ID NO 934
<211> LENGTH: 5
<212> TYPE: PRT
<213> ORGANISM: Homo sapiens

<400> SEQUENCE: 934

Val Leu Lys Ala Gln
1               5

<210> SEQ ID NO 935
<211> LENGTH: 5
<212> TYPE: PRT
<213> ORGANISM: Homo sapiens

<400> SEQUENCE: 935

Leu Lys Ala Gln Leu
1               5

<210> SEQ ID NO 936
<211> LENGTH: 5
<212> TYPE: PRT
<213> ORGANISM: Homo sapiens

<400> SEQUENCE: 936

Lys Ala Gln Leu Trp
1               5

<210> SEQ ID NO 937
<211> LENGTH: 5
<212> TYPE: PRT
<213> ORGANISM: Homo sapiens

<400> SEQUENCE: 937

Ala Gln Leu Trp Val
1               5

<210> SEQ ID NO 938
<211> LENGTH: 5
<212> TYPE: PRT
<213> ORGANISM: Homo sapiens

<400> SEQUENCE: 938

Gln Leu Trp Val Tyr
1               5

<210> SEQ ID NO 939
<211> LENGTH: 5
<212> TYPE: PRT
<213> ORGANISM: Homo sapiens

<400> SEQUENCE: 939

Leu Trp Val Tyr Leu
1               5

<210> SEQ ID NO 940
<211> LENGTH: 5
<212> TYPE: PRT
<213> ORGANISM: Homo sapiens
```

<400> SEQUENCE: 940

Trp Val Tyr Leu Arg
1               5

<210> SEQ ID NO 941
<211> LENGTH: 5
<212> TYPE: PRT
<213> ORGANISM: Homo sapiens

<400> SEQUENCE: 941

Val Tyr Leu Arg Pro
1               5

<210> SEQ ID NO 942
<211> LENGTH: 5
<212> TYPE: PRT
<213> ORGANISM: Homo sapiens

<400> SEQUENCE: 942

Tyr Leu Arg Pro Val
1               5

<210> SEQ ID NO 943
<211> LENGTH: 5
<212> TYPE: PRT
<213> ORGANISM: Homo sapiens

<400> SEQUENCE: 943

Leu Arg Pro Val Pro
1               5

<210> SEQ ID NO 944
<211> LENGTH: 5
<212> TYPE: PRT
<213> ORGANISM: Homo sapiens

<400> SEQUENCE: 944

Arg Pro Val Pro Arg
1               5

<210> SEQ ID NO 945
<211> LENGTH: 5
<212> TYPE: PRT
<213> ORGANISM: Homo sapiens

<400> SEQUENCE: 945

Pro Val Pro Arg Pro
1               5

<210> SEQ ID NO 946
<211> LENGTH: 5
<212> TYPE: PRT
<213> ORGANISM: Homo sapiens

<400> SEQUENCE: 946

Val Pro Arg Pro Ala
1               5

<210> SEQ ID NO 947
<211> LENGTH: 5
<212> TYPE: PRT
<213> ORGANISM: Homo sapiens

<400> SEQUENCE: 947

Pro Arg Pro Ala Thr
1               5

<210> SEQ ID NO 948
<211> LENGTH: 5
<212> TYPE: PRT
<213> ORGANISM: Homo sapiens

<400> SEQUENCE: 948

Arg Pro Ala Thr Val
1               5

<210> SEQ ID NO 949
<211> LENGTH: 5
<212> TYPE: PRT
<213> ORGANISM: Homo sapiens

<400> SEQUENCE: 949

Pro Ala Thr Val Tyr
1               5

<210> SEQ ID NO 950
<211> LENGTH: 5
<212> TYPE: PRT
<213> ORGANISM: Homo sapiens

<400> SEQUENCE: 950

Ala Thr Val Tyr Leu
1               5

<210> SEQ ID NO 951
<211> LENGTH: 5
<212> TYPE: PRT
<213> ORGANISM: Homo sapiens

<400> SEQUENCE: 951

Thr Val Tyr Leu Gln
1               5

<210> SEQ ID NO 952
<211> LENGTH: 5
<212> TYPE: PRT
<213> ORGANISM: Homo sapiens

<400> SEQUENCE: 952

Val Tyr Leu Gln Ile
1               5

<210> SEQ ID NO 953
<211> LENGTH: 5
<212> TYPE: PRT
<213> ORGANISM: Homo sapiens

<400> SEQUENCE: 953

Tyr Leu Gln Ile Leu
1               5

<210> SEQ ID NO 954
<211> LENGTH: 5
<212> TYPE: PRT
<213> ORGANISM: Homo sapiens

<400> SEQUENCE: 954

Leu Gln Ile Leu Arg

```
<210> SEQ ID NO 955
<211> LENGTH: 5
<212> TYPE: PRT
<213> ORGANISM: Homo sapiens

<400> SEQUENCE: 955

Gln Ile Leu Arg Leu
1               5

<210> SEQ ID NO 956
<211> LENGTH: 5
<212> TYPE: PRT
<213> ORGANISM: Homo sapiens

<400> SEQUENCE: 956

Ile Leu Arg Leu Lys
1               5

<210> SEQ ID NO 957
<211> LENGTH: 5
<212> TYPE: PRT
<213> ORGANISM: Homo sapiens

<400> SEQUENCE: 957

Leu Arg Leu Lys Pro
1               5

<210> SEQ ID NO 958
<211> LENGTH: 5
<212> TYPE: PRT
<213> ORGANISM: Homo sapiens

<400> SEQUENCE: 958

Arg Leu Lys Pro Leu
1               5

<210> SEQ ID NO 959
<211> LENGTH: 5
<212> TYPE: PRT
<213> ORGANISM: Homo sapiens

<400> SEQUENCE: 959

Leu Lys Pro Leu Thr
1               5

<210> SEQ ID NO 960
<211> LENGTH: 5
<212> TYPE: PRT
<213> ORGANISM: Homo sapiens

<400> SEQUENCE: 960

Lys Pro Leu Thr Gly
1               5

<210> SEQ ID NO 961
<211> LENGTH: 5
<212> TYPE: PRT
<213> ORGANISM: Homo sapiens

<400> SEQUENCE: 961

Pro Leu Thr Gly Glu
1               5
```

<210> SEQ ID NO 962
<211> LENGTH: 5
<212> TYPE: PRT
<213> ORGANISM: Homo sapiens

<400> SEQUENCE: 962

Leu Thr Gly Glu Gly
1               5

<210> SEQ ID NO 963
<211> LENGTH: 5
<212> TYPE: PRT
<213> ORGANISM: Homo sapiens

<400> SEQUENCE: 963

Thr Gly Glu Gly Thr
1               5

<210> SEQ ID NO 964
<211> LENGTH: 5
<212> TYPE: PRT
<213> ORGANISM: Homo sapiens

<400> SEQUENCE: 964

Gly Glu Gly Thr Ala
1               5

<210> SEQ ID NO 965
<211> LENGTH: 5
<212> TYPE: PRT
<213> ORGANISM: Homo sapiens

<400> SEQUENCE: 965

Glu Gly Thr Ala Gly
1               5

<210> SEQ ID NO 966
<211> LENGTH: 5
<212> TYPE: PRT
<213> ORGANISM: Homo sapiens

<400> SEQUENCE: 966

Gly Thr Ala Gly Gly
1               5

<210> SEQ ID NO 967
<211> LENGTH: 5
<212> TYPE: PRT
<213> ORGANISM: Homo sapiens

<400> SEQUENCE: 967

Thr Ala Gly Gly Gly
1               5

<210> SEQ ID NO 968
<211> LENGTH: 5
<212> TYPE: PRT
<213> ORGANISM: Homo sapiens

<400> SEQUENCE: 968

Ala Gly Gly Gly Gly
1               5

<210> SEQ ID NO 969

```
<211> LENGTH: 5
<212> TYPE: PRT
<213> ORGANISM: Homo sapiens

<400> SEQUENCE: 969

Gly Gly Gly Gly Gly
1               5

<210> SEQ ID NO 970
<211> LENGTH: 5
<212> TYPE: PRT
<213> ORGANISM: Homo sapiens

<400> SEQUENCE: 970

Gly Gly Gly Gly Arg
1               5

<210> SEQ ID NO 971
<211> LENGTH: 5
<212> TYPE: PRT
<213> ORGANISM: Homo sapiens

<400> SEQUENCE: 971

Gly Gly Gly Arg Arg
1               5

<210> SEQ ID NO 972
<211> LENGTH: 5
<212> TYPE: PRT
<213> ORGANISM: Homo sapiens

<400> SEQUENCE: 972

Gly Gly Arg Arg His
1               5

<210> SEQ ID NO 973
<211> LENGTH: 5
<212> TYPE: PRT
<213> ORGANISM: Homo sapiens

<400> SEQUENCE: 973

Gly Arg Arg His Ile
1               5

<210> SEQ ID NO 974
<211> LENGTH: 5
<212> TYPE: PRT
<213> ORGANISM: Homo sapiens

<400> SEQUENCE: 974

Arg Arg His Ile Arg
1               5

<210> SEQ ID NO 975
<211> LENGTH: 5
<212> TYPE: PRT
<213> ORGANISM: Homo sapiens

<400> SEQUENCE: 975

Arg His Ile Arg Ile
1               5

<210> SEQ ID NO 976
<211> LENGTH: 5
<212> TYPE: PRT
```

<213> ORGANISM: Homo sapiens

<400> SEQUENCE: 976

His Ile Arg Ile Arg
1               5

<210> SEQ ID NO 977
<211> LENGTH: 5
<212> TYPE: PRT
<213> ORGANISM: Homo sapiens

<400> SEQUENCE: 977

Ile Arg Ile Arg Ser
1               5

<210> SEQ ID NO 978
<211> LENGTH: 5
<212> TYPE: PRT
<213> ORGANISM: Homo sapiens

<400> SEQUENCE: 978

Arg Ile Arg Ser Leu
1               5

<210> SEQ ID NO 979
<211> LENGTH: 5
<212> TYPE: PRT
<213> ORGANISM: Homo sapiens

<400> SEQUENCE: 979

Ile Arg Ser Leu Lys
1               5

<210> SEQ ID NO 980
<211> LENGTH: 5
<212> TYPE: PRT
<213> ORGANISM: Homo sapiens

<400> SEQUENCE: 980

Arg Ser Leu Lys Ile
1               5

<210> SEQ ID NO 981
<211> LENGTH: 5
<212> TYPE: PRT
<213> ORGANISM: Homo sapiens

<400> SEQUENCE: 981

Ser Leu Lys Ile Glu
1               5

<210> SEQ ID NO 982
<211> LENGTH: 5
<212> TYPE: PRT
<213> ORGANISM: Homo sapiens

<400> SEQUENCE: 982

Leu Lys Ile Glu Leu
1               5

<210> SEQ ID NO 983
<211> LENGTH: 5
<212> TYPE: PRT
<213> ORGANISM: Homo sapiens

<400> SEQUENCE: 983

Lys Ile Glu Leu His
1               5

<210> SEQ ID NO 984
<211> LENGTH: 5
<212> TYPE: PRT
<213> ORGANISM: Homo sapiens

<400> SEQUENCE: 984

Ile Glu Leu His Ser
1               5

<210> SEQ ID NO 985
<211> LENGTH: 5
<212> TYPE: PRT
<213> ORGANISM: Homo sapiens

<400> SEQUENCE: 985

Glu Leu His Ser Arg
1               5

<210> SEQ ID NO 986
<211> LENGTH: 5
<212> TYPE: PRT
<213> ORGANISM: Homo sapiens

<400> SEQUENCE: 986

Leu His Ser Arg Ser
1               5

<210> SEQ ID NO 987
<211> LENGTH: 5
<212> TYPE: PRT
<213> ORGANISM: Homo sapiens

<400> SEQUENCE: 987

His Ser Arg Ser Gly
1               5

<210> SEQ ID NO 988
<211> LENGTH: 5
<212> TYPE: PRT
<213> ORGANISM: Homo sapiens

<400> SEQUENCE: 988

Ser Arg Ser Gly His
1               5

<210> SEQ ID NO 989
<211> LENGTH: 5
<212> TYPE: PRT
<213> ORGANISM: Homo sapiens

<400> SEQUENCE: 989

Arg Ser Gly His Trp
1               5

<210> SEQ ID NO 990
<211> LENGTH: 5
<212> TYPE: PRT
<213> ORGANISM: Homo sapiens

<400> SEQUENCE: 990

```
Ser Gly His Trp Gln
1               5

<210> SEQ ID NO 991
<211> LENGTH: 5
<212> TYPE: PRT
<213> ORGANISM: Homo sapiens

<400> SEQUENCE: 991

Gly His Trp Gln Ser
1               5

<210> SEQ ID NO 992
<211> LENGTH: 5
<212> TYPE: PRT
<213> ORGANISM: Homo sapiens

<400> SEQUENCE: 992

His Trp Gln Ser Ile
1               5

<210> SEQ ID NO 993
<211> LENGTH: 5
<212> TYPE: PRT
<213> ORGANISM: Homo sapiens

<400> SEQUENCE: 993

Trp Gln Ser Ile Asp
1               5

<210> SEQ ID NO 994
<211> LENGTH: 5
<212> TYPE: PRT
<213> ORGANISM: Homo sapiens

<400> SEQUENCE: 994

Gln Ser Ile Asp Phe
1               5

<210> SEQ ID NO 995
<211> LENGTH: 5
<212> TYPE: PRT
<213> ORGANISM: Homo sapiens

<400> SEQUENCE: 995

Ser Ile Asp Phe Lys
1               5

<210> SEQ ID NO 996
<211> LENGTH: 5
<212> TYPE: PRT
<213> ORGANISM: Homo sapiens

<400> SEQUENCE: 996

Ile Asp Phe Lys Gln
1               5

<210> SEQ ID NO 997
<211> LENGTH: 5
<212> TYPE: PRT
<213> ORGANISM: Homo sapiens

<400> SEQUENCE: 997

Asp Phe Lys Gln Val
1               5
```

<210> SEQ ID NO 998
<211> LENGTH: 5
<212> TYPE: PRT
<213> ORGANISM: Homo sapiens

<400> SEQUENCE: 998

Phe Lys Gln Val Leu
1               5

<210> SEQ ID NO 999
<211> LENGTH: 5
<212> TYPE: PRT
<213> ORGANISM: Homo sapiens

<400> SEQUENCE: 999

Lys Gln Val Leu His
1               5

<210> SEQ ID NO 1000
<211> LENGTH: 5
<212> TYPE: PRT
<213> ORGANISM: Homo sapiens

<400> SEQUENCE: 1000

Gln Val Leu His Ser
1               5

<210> SEQ ID NO 1001
<211> LENGTH: 5
<212> TYPE: PRT
<213> ORGANISM: Homo sapiens

<400> SEQUENCE: 1001

Val Leu His Ser Trp
1               5

<210> SEQ ID NO 1002
<211> LENGTH: 5
<212> TYPE: PRT
<213> ORGANISM: Homo sapiens

<400> SEQUENCE: 1002

Leu His Ser Trp Phe
1               5

<210> SEQ ID NO 1003
<211> LENGTH: 5
<212> TYPE: PRT
<213> ORGANISM: Homo sapiens

<400> SEQUENCE: 1003

His Ser Trp Phe Arg
1               5

<210> SEQ ID NO 1004
<211> LENGTH: 5
<212> TYPE: PRT
<213> ORGANISM: Homo sapiens

<400> SEQUENCE: 1004

Ser Trp Phe Arg Gln
1               5

```
<210> SEQ ID NO 1005
<211> LENGTH: 5
<212> TYPE: PRT
<213> ORGANISM: Homo sapiens

<400> SEQUENCE: 1005

Trp Phe Arg Gln Pro
1               5

<210> SEQ ID NO 1006
<211> LENGTH: 5
<212> TYPE: PRT
<213> ORGANISM: Homo sapiens

<400> SEQUENCE: 1006

Phe Arg Gln Pro Gln
1               5

<210> SEQ ID NO 1007
<211> LENGTH: 5
<212> TYPE: PRT
<213> ORGANISM: Homo sapiens

<400> SEQUENCE: 1007

Arg Gln Pro Gln Ser
1               5

<210> SEQ ID NO 1008
<211> LENGTH: 5
<212> TYPE: PRT
<213> ORGANISM: Homo sapiens

<400> SEQUENCE: 1008

Gln Pro Gln Ser Asn
1               5

<210> SEQ ID NO 1009
<211> LENGTH: 5
<212> TYPE: PRT
<213> ORGANISM: Homo sapiens

<400> SEQUENCE: 1009

Pro Gln Ser Asn Trp
1               5

<210> SEQ ID NO 1010
<211> LENGTH: 5
<212> TYPE: PRT
<213> ORGANISM: Homo sapiens

<400> SEQUENCE: 1010

Gln Ser Asn Trp Gly
1               5

<210> SEQ ID NO 1011
<211> LENGTH: 5
<212> TYPE: PRT
<213> ORGANISM: Homo sapiens

<400> SEQUENCE: 1011

Ser Asn Trp Gly Ile
1               5

<210> SEQ ID NO 1012
<211> LENGTH: 5
```

```
<212> TYPE: PRT
<213> ORGANISM: Homo sapiens

<400> SEQUENCE: 1012

Asn Trp Gly Ile Glu
1               5

<210> SEQ ID NO 1013
<211> LENGTH: 5
<212> TYPE: PRT
<213> ORGANISM: Homo sapiens

<400> SEQUENCE: 1013

Trp Gly Ile Glu Ile
1               5

<210> SEQ ID NO 1014
<211> LENGTH: 5
<212> TYPE: PRT
<213> ORGANISM: Homo sapiens

<400> SEQUENCE: 1014

Gly Ile Glu Ile Asn
1               5

<210> SEQ ID NO 1015
<211> LENGTH: 5
<212> TYPE: PRT
<213> ORGANISM: Homo sapiens

<400> SEQUENCE: 1015

Ile Glu Ile Asn Ala
1               5

<210> SEQ ID NO 1016
<211> LENGTH: 5
<212> TYPE: PRT
<213> ORGANISM: Homo sapiens

<400> SEQUENCE: 1016

Glu Ile Asn Ala Phe
1               5

<210> SEQ ID NO 1017
<211> LENGTH: 5
<212> TYPE: PRT
<213> ORGANISM: Homo sapiens

<400> SEQUENCE: 1017

Ile Asn Ala Phe Asp
1               5

<210> SEQ ID NO 1018
<211> LENGTH: 5
<212> TYPE: PRT
<213> ORGANISM: Homo sapiens

<400> SEQUENCE: 1018

Asn Ala Phe Asp Pro
1               5

<210> SEQ ID NO 1019
<211> LENGTH: 5
<212> TYPE: PRT
<213> ORGANISM: Homo sapiens
```

<400> SEQUENCE: 1019

Ala Phe Asp Pro Ser
1               5

<210> SEQ ID NO 1020
<211> LENGTH: 5
<212> TYPE: PRT
<213> ORGANISM: Homo sapiens

<400> SEQUENCE: 1020

Phe Asp Pro Ser Gly
1               5

<210> SEQ ID NO 1021
<211> LENGTH: 5
<212> TYPE: PRT
<213> ORGANISM: Homo sapiens

<400> SEQUENCE: 1021

Asp Pro Ser Gly Thr
1               5

<210> SEQ ID NO 1022
<211> LENGTH: 5
<212> TYPE: PRT
<213> ORGANISM: Homo sapiens

<400> SEQUENCE: 1022

Pro Ser Gly Thr Asp
1               5

<210> SEQ ID NO 1023
<211> LENGTH: 5
<212> TYPE: PRT
<213> ORGANISM: Homo sapiens

<400> SEQUENCE: 1023

Ser Gly Thr Asp Leu
1               5

<210> SEQ ID NO 1024
<211> LENGTH: 5
<212> TYPE: PRT
<213> ORGANISM: Homo sapiens

<400> SEQUENCE: 1024

Gly Thr Asp Leu Ala
1               5

<210> SEQ ID NO 1025
<211> LENGTH: 5
<212> TYPE: PRT
<213> ORGANISM: Homo sapiens

<400> SEQUENCE: 1025

Thr Asp Leu Ala Val
1               5

<210> SEQ ID NO 1026
<211> LENGTH: 5
<212> TYPE: PRT
<213> ORGANISM: Homo sapiens

<400> SEQUENCE: 1026

Asp Leu Ala Val Thr
1               5

<210> SEQ ID NO 1027
<211> LENGTH: 5
<212> TYPE: PRT
<213> ORGANISM: Homo sapiens

<400> SEQUENCE: 1027

Leu Ala Val Thr Ser
1               5

<210> SEQ ID NO 1028
<211> LENGTH: 5
<212> TYPE: PRT
<213> ORGANISM: Homo sapiens

<400> SEQUENCE: 1028

Ala Val Thr Ser Leu
1               5

<210> SEQ ID NO 1029
<211> LENGTH: 5
<212> TYPE: PRT
<213> ORGANISM: Homo sapiens

<400> SEQUENCE: 1029

Val Thr Ser Leu Gly
1               5

<210> SEQ ID NO 1030
<211> LENGTH: 5
<212> TYPE: PRT
<213> ORGANISM: Homo sapiens

<400> SEQUENCE: 1030

Thr Ser Leu Gly Pro
1               5

<210> SEQ ID NO 1031
<211> LENGTH: 5
<212> TYPE: PRT
<213> ORGANISM: Homo sapiens

<400> SEQUENCE: 1031

Ser Leu Gly Pro Gly
1               5

<210> SEQ ID NO 1032
<211> LENGTH: 5
<212> TYPE: PRT
<213> ORGANISM: Homo sapiens

<400> SEQUENCE: 1032

Leu Gly Pro Gly Ala
1               5

<210> SEQ ID NO 1033
<211> LENGTH: 5
<212> TYPE: PRT
<213> ORGANISM: Homo sapiens

<400> SEQUENCE: 1033

Gly Pro Gly Ala Glu 1   5

<210> SEQ ID NO 1034
<211> LENGTH: 5
<212> TYPE: PRT
<213> ORGANISM: Homo sapiens

<400> SEQUENCE: 1034

Pro Gly Ala Glu Gly
1               5

<210> SEQ ID NO 1035
<211> LENGTH: 5
<212> TYPE: PRT
<213> ORGANISM: Homo sapiens

<400> SEQUENCE: 1035

Gly Ala Glu Gly Leu
1               5

<210> SEQ ID NO 1036
<211> LENGTH: 5
<212> TYPE: PRT
<213> ORGANISM: Homo sapiens

<400> SEQUENCE: 1036

Ala Glu Gly Leu His
1               5

<210> SEQ ID NO 1037
<211> LENGTH: 5
<212> TYPE: PRT
<213> ORGANISM: Homo sapiens

<400> SEQUENCE: 1037

Glu Gly Leu His Pro
1               5

<210> SEQ ID NO 1038
<211> LENGTH: 5
<212> TYPE: PRT
<213> ORGANISM: Homo sapiens

<400> SEQUENCE: 1038

Gly Leu His Pro Phe
1               5

<210> SEQ ID NO 1039
<211> LENGTH: 5
<212> TYPE: PRT
<213> ORGANISM: Homo sapiens

<400> SEQUENCE: 1039

Leu His Pro Phe Met
1               5

<210> SEQ ID NO 1040
<211> LENGTH: 5
<212> TYPE: PRT
<213> ORGANISM: Homo sapiens

<400> SEQUENCE: 1040

His Pro Phe Met Glu
1               5

<210> SEQ ID NO 1041
<211> LENGTH: 5
<212> TYPE: PRT
<213> ORGANISM: Homo sapiens

<400> SEQUENCE: 1041

Pro Phe Met Glu Leu
1               5

<210> SEQ ID NO 1042
<211> LENGTH: 5
<212> TYPE: PRT
<213> ORGANISM: Homo sapiens

<400> SEQUENCE: 1042

Phe Met Glu Leu Arg
1               5

<210> SEQ ID NO 1043
<211> LENGTH: 5
<212> TYPE: PRT
<213> ORGANISM: Homo sapiens

<400> SEQUENCE: 1043

Met Glu Leu Arg Val
1               5

<210> SEQ ID NO 1044
<211> LENGTH: 5
<212> TYPE: PRT
<213> ORGANISM: Homo sapiens

<400> SEQUENCE: 1044

Glu Leu Arg Val Leu
1               5

<210> SEQ ID NO 1045
<211> LENGTH: 5
<212> TYPE: PRT
<213> ORGANISM: Homo sapiens

<400> SEQUENCE: 1045

Leu Arg Val Leu Glu
1               5

<210> SEQ ID NO 1046
<211> LENGTH: 5
<212> TYPE: PRT
<213> ORGANISM: Homo sapiens

<400> SEQUENCE: 1046

Arg Val Leu Glu Asn
1               5

<210> SEQ ID NO 1047
<211> LENGTH: 5
<212> TYPE: PRT
<213> ORGANISM: Homo sapiens

<400> SEQUENCE: 1047

Val Leu Glu Asn Thr
1               5

<210> SEQ ID NO 1048

```
<211> LENGTH: 5
<212> TYPE: PRT
<213> ORGANISM: Homo sapiens

<400> SEQUENCE: 1048

Leu Glu Asn Thr Lys
1               5

<210> SEQ ID NO 1049
<211> LENGTH: 5
<212> TYPE: PRT
<213> ORGANISM: Homo sapiens

<400> SEQUENCE: 1049

Glu Asn Thr Lys Arg
1               5

<210> SEQ ID NO 1050
<211> LENGTH: 5
<212> TYPE: PRT
<213> ORGANISM: Homo sapiens

<400> SEQUENCE: 1050

Asn Thr Lys Arg Ser
1               5

<210> SEQ ID NO 1051
<211> LENGTH: 5
<212> TYPE: PRT
<213> ORGANISM: Homo sapiens

<400> SEQUENCE: 1051

Thr Lys Arg Ser Arg
1               5

<210> SEQ ID NO 1052
<211> LENGTH: 5
<212> TYPE: PRT
<213> ORGANISM: Homo sapiens

<400> SEQUENCE: 1052

Lys Arg Ser Arg Arg
1               5

<210> SEQ ID NO 1053
<211> LENGTH: 5
<212> TYPE: PRT
<213> ORGANISM: Homo sapiens

<400> SEQUENCE: 1053

Arg Ser Arg Arg Asn
1               5

<210> SEQ ID NO 1054
<211> LENGTH: 5
<212> TYPE: PRT
<213> ORGANISM: Homo sapiens

<400> SEQUENCE: 1054

Ser Arg Arg Asn Leu
1               5

<210> SEQ ID NO 1055
<211> LENGTH: 5
<212> TYPE: PRT
```

<213> ORGANISM: Homo sapiens

<400> SEQUENCE: 1055

Arg Arg Asn Leu Gly
1               5

<210> SEQ ID NO 1056
<211> LENGTH: 5
<212> TYPE: PRT
<213> ORGANISM: Homo sapiens

<400> SEQUENCE: 1056

Arg Asn Leu Gly Leu
1               5

<210> SEQ ID NO 1057
<211> LENGTH: 5
<212> TYPE: PRT
<213> ORGANISM: Homo sapiens

<400> SEQUENCE: 1057

Asn Leu Gly Leu Asp
1               5

<210> SEQ ID NO 1058
<211> LENGTH: 5
<212> TYPE: PRT
<213> ORGANISM: Homo sapiens

<400> SEQUENCE: 1058

Leu Gly Leu Asp Cys
1               5

<210> SEQ ID NO 1059
<211> LENGTH: 5
<212> TYPE: PRT
<213> ORGANISM: Homo sapiens

<400> SEQUENCE: 1059

Gly Leu Asp Cys Asp
1               5

<210> SEQ ID NO 1060
<211> LENGTH: 5
<212> TYPE: PRT
<213> ORGANISM: Homo sapiens

<400> SEQUENCE: 1060

Leu Asp Cys Asp Glu
1               5

<210> SEQ ID NO 1061
<211> LENGTH: 5
<212> TYPE: PRT
<213> ORGANISM: Homo sapiens

<400> SEQUENCE: 1061

Asp Cys Asp Glu His
1               5

<210> SEQ ID NO 1062
<211> LENGTH: 5
<212> TYPE: PRT
<213> ORGANISM: Homo sapiens

```
<400> SEQUENCE: 1062

Cys Asp Glu His Ser
1               5

<210> SEQ ID NO 1063
<211> LENGTH: 5
<212> TYPE: PRT
<213> ORGANISM: Homo sapiens

<400> SEQUENCE: 1063

Asp Glu His Ser Ser
1               5

<210> SEQ ID NO 1064
<211> LENGTH: 5
<212> TYPE: PRT
<213> ORGANISM: Homo sapiens

<400> SEQUENCE: 1064

Glu His Ser Ser Glu
1               5

<210> SEQ ID NO 1065
<211> LENGTH: 5
<212> TYPE: PRT
<213> ORGANISM: Homo sapiens

<400> SEQUENCE: 1065

His Ser Ser Glu Ser
1               5

<210> SEQ ID NO 1066
<211> LENGTH: 5
<212> TYPE: PRT
<213> ORGANISM: Homo sapiens

<400> SEQUENCE: 1066

Ser Ser Glu Ser Arg
1               5

<210> SEQ ID NO 1067
<211> LENGTH: 5
<212> TYPE: PRT
<213> ORGANISM: Homo sapiens

<400> SEQUENCE: 1067

Ser Glu Ser Arg Cys
1               5

<210> SEQ ID NO 1068
<211> LENGTH: 5
<212> TYPE: PRT
<213> ORGANISM: Homo sapiens

<400> SEQUENCE: 1068

Glu Ser Arg Cys Cys
1               5

<210> SEQ ID NO 1069
<211> LENGTH: 5
<212> TYPE: PRT
<213> ORGANISM: Homo sapiens

<400> SEQUENCE: 1069
```

```
Ser Arg Cys Cys Arg
1               5

<210> SEQ ID NO 1070
<211> LENGTH: 5
<212> TYPE: PRT
<213> ORGANISM: Homo sapiens

<400> SEQUENCE: 1070

Arg Cys Cys Arg Tyr
1               5

<210> SEQ ID NO 1071
<211> LENGTH: 5
<212> TYPE: PRT
<213> ORGANISM: Homo sapiens

<400> SEQUENCE: 1071

Cys Cys Arg Tyr Pro
1               5

<210> SEQ ID NO 1072
<211> LENGTH: 5
<212> TYPE: PRT
<213> ORGANISM: Homo sapiens

<400> SEQUENCE: 1072

Cys Arg Tyr Pro Leu
1               5

<210> SEQ ID NO 1073
<211> LENGTH: 5
<212> TYPE: PRT
<213> ORGANISM: Homo sapiens

<400> SEQUENCE: 1073

Arg Tyr Pro Leu Thr
1               5

<210> SEQ ID NO 1074
<211> LENGTH: 5
<212> TYPE: PRT
<213> ORGANISM: Homo sapiens

<400> SEQUENCE: 1074

Tyr Pro Leu Thr Val
1               5

<210> SEQ ID NO 1075
<211> LENGTH: 5
<212> TYPE: PRT
<213> ORGANISM: Homo sapiens

<400> SEQUENCE: 1075

Pro Leu Thr Val Asp
1               5

<210> SEQ ID NO 1076
<211> LENGTH: 5
<212> TYPE: PRT
<213> ORGANISM: Homo sapiens

<400> SEQUENCE: 1076

Leu Thr Val Asp Phe
1               5
```

<210> SEQ ID NO 1077
<211> LENGTH: 5
<212> TYPE: PRT
<213> ORGANISM: Homo sapiens

<400> SEQUENCE: 1077

Thr Val Asp Phe Glu
1               5

<210> SEQ ID NO 1078
<211> LENGTH: 5
<212> TYPE: PRT
<213> ORGANISM: Homo sapiens

<400> SEQUENCE: 1078

Val Asp Phe Glu Ala
1               5

<210> SEQ ID NO 1079
<211> LENGTH: 5
<212> TYPE: PRT
<213> ORGANISM: Homo sapiens

<400> SEQUENCE: 1079

Asp Phe Glu Ala Phe
1               5

<210> SEQ ID NO 1080
<211> LENGTH: 5
<212> TYPE: PRT
<213> ORGANISM: Homo sapiens

<400> SEQUENCE: 1080

Phe Glu Ala Phe Gly
1               5

<210> SEQ ID NO 1081
<211> LENGTH: 5
<212> TYPE: PRT
<213> ORGANISM: Homo sapiens

<400> SEQUENCE: 1081

Glu Ala Phe Gly Trp
1               5

<210> SEQ ID NO 1082
<211> LENGTH: 5
<212> TYPE: PRT
<213> ORGANISM: Homo sapiens

<400> SEQUENCE: 1082

Ala Phe Gly Trp Asp
1               5

<210> SEQ ID NO 1083
<211> LENGTH: 5
<212> TYPE: PRT
<213> ORGANISM: Homo sapiens

<400> SEQUENCE: 1083

Phe Gly Trp Asp Trp
1               5

```
<210> SEQ ID NO 1084
<211> LENGTH: 5
<212> TYPE: PRT
<213> ORGANISM: Homo sapiens

<400> SEQUENCE: 1084

Gly Trp Asp Trp Ile
1               5

<210> SEQ ID NO 1085
<211> LENGTH: 5
<212> TYPE: PRT
<213> ORGANISM: Homo sapiens

<400> SEQUENCE: 1085

Trp Asp Trp Ile Ile
1               5

<210> SEQ ID NO 1086
<211> LENGTH: 5
<212> TYPE: PRT
<213> ORGANISM: Homo sapiens

<400> SEQUENCE: 1086

Asp Trp Ile Ile Ala
1               5

<210> SEQ ID NO 1087
<211> LENGTH: 5
<212> TYPE: PRT
<213> ORGANISM: Homo sapiens

<400> SEQUENCE: 1087

Trp Ile Ile Ala Pro
1               5

<210> SEQ ID NO 1088
<211> LENGTH: 5
<212> TYPE: PRT
<213> ORGANISM: Homo sapiens

<400> SEQUENCE: 1088

Ile Ile Ala Pro Lys
1               5

<210> SEQ ID NO 1089
<211> LENGTH: 5
<212> TYPE: PRT
<213> ORGANISM: Homo sapiens

<400> SEQUENCE: 1089

Ile Ala Pro Lys Arg
1               5

<210> SEQ ID NO 1090
<211> LENGTH: 5
<212> TYPE: PRT
<213> ORGANISM: Homo sapiens

<400> SEQUENCE: 1090

Ala Pro Lys Arg Tyr
1               5

<210> SEQ ID NO 1091
<211> LENGTH: 5
```

<212> TYPE: PRT
<213> ORGANISM: Homo sapiens

<400> SEQUENCE: 1091

Pro Lys Arg Tyr Lys
1               5

<210> SEQ ID NO 1092
<211> LENGTH: 5
<212> TYPE: PRT
<213> ORGANISM: Homo sapiens

<400> SEQUENCE: 1092

Lys Arg Tyr Lys Ala
1               5

<210> SEQ ID NO 1093
<211> LENGTH: 5
<212> TYPE: PRT
<213> ORGANISM: Homo sapiens

<400> SEQUENCE: 1093

Arg Tyr Lys Ala Asn
1               5

<210> SEQ ID NO 1094
<211> LENGTH: 5
<212> TYPE: PRT
<213> ORGANISM: Homo sapiens

<400> SEQUENCE: 1094

Tyr Lys Ala Asn Tyr
1               5

<210> SEQ ID NO 1095
<211> LENGTH: 5
<212> TYPE: PRT
<213> ORGANISM: Homo sapiens

<400> SEQUENCE: 1095

Lys Ala Asn Tyr Cys
1               5

<210> SEQ ID NO 1096
<211> LENGTH: 5
<212> TYPE: PRT
<213> ORGANISM: Homo sapiens

<400> SEQUENCE: 1096

Ala Asn Tyr Cys Ser
1               5

<210> SEQ ID NO 1097
<211> LENGTH: 5
<212> TYPE: PRT
<213> ORGANISM: Homo sapiens

<400> SEQUENCE: 1097

Asn Tyr Cys Ser Gly
1               5

<210> SEQ ID NO 1098
<211> LENGTH: 5
<212> TYPE: PRT
<213> ORGANISM: Homo sapiens

<400> SEQUENCE: 1098

Tyr Cys Ser Gly Gln
1               5

<210> SEQ ID NO 1099
<211> LENGTH: 5
<212> TYPE: PRT
<213> ORGANISM: Homo sapiens

<400> SEQUENCE: 1099

Cys Ser Gly Gln Cys
1               5

<210> SEQ ID NO 1100
<211> LENGTH: 5
<212> TYPE: PRT
<213> ORGANISM: Homo sapiens

<400> SEQUENCE: 1100

Ser Gly Gln Cys Glu
1               5

<210> SEQ ID NO 1101
<211> LENGTH: 5
<212> TYPE: PRT
<213> ORGANISM: Homo sapiens

<400> SEQUENCE: 1101

Gly Gln Cys Glu Tyr
1               5

<210> SEQ ID NO 1102
<211> LENGTH: 5
<212> TYPE: PRT
<213> ORGANISM: Homo sapiens

<400> SEQUENCE: 1102

Gln Cys Glu Tyr Met
1               5

<210> SEQ ID NO 1103
<211> LENGTH: 5
<212> TYPE: PRT
<213> ORGANISM: Homo sapiens

<400> SEQUENCE: 1103

Cys Glu Tyr Met Phe
1               5

<210> SEQ ID NO 1104
<211> LENGTH: 5
<212> TYPE: PRT
<213> ORGANISM: Homo sapiens

<400> SEQUENCE: 1104

Glu Tyr Met Phe Met
1               5

<210> SEQ ID NO 1105
<211> LENGTH: 5
<212> TYPE: PRT
<213> ORGANISM: Homo sapiens

<400> SEQUENCE: 1105

Tyr Met Phe Met Gln
1               5

<210> SEQ ID NO 1106
<211> LENGTH: 5
<212> TYPE: PRT
<213> ORGANISM: Homo sapiens

<400> SEQUENCE: 1106

Met Phe Met Gln Lys
1               5

<210> SEQ ID NO 1107
<211> LENGTH: 5
<212> TYPE: PRT
<213> ORGANISM: Homo sapiens

<400> SEQUENCE: 1107

Phe Met Gln Lys Tyr
1               5

<210> SEQ ID NO 1108
<211> LENGTH: 5
<212> TYPE: PRT
<213> ORGANISM: Homo sapiens

<400> SEQUENCE: 1108

Met Gln Lys Tyr Pro
1               5

<210> SEQ ID NO 1109
<211> LENGTH: 5
<212> TYPE: PRT
<213> ORGANISM: Homo sapiens

<400> SEQUENCE: 1109

Gln Lys Tyr Pro His
1               5

<210> SEQ ID NO 1110
<211> LENGTH: 5
<212> TYPE: PRT
<213> ORGANISM: Homo sapiens

<400> SEQUENCE: 1110

Lys Tyr Pro His Thr
1               5

<210> SEQ ID NO 1111
<211> LENGTH: 5
<212> TYPE: PRT
<213> ORGANISM: Homo sapiens

<400> SEQUENCE: 1111

Tyr Pro His Thr His
1               5

<210> SEQ ID NO 1112
<211> LENGTH: 5
<212> TYPE: PRT
<213> ORGANISM: Homo sapiens

<400> SEQUENCE: 1112

Pro His Thr His Leu

```
1               5

<210> SEQ ID NO 1113
<211> LENGTH: 5
<212> TYPE: PRT
<213> ORGANISM: Homo sapiens

<400> SEQUENCE: 1113

His Thr His Leu Val
1               5

<210> SEQ ID NO 1114
<211> LENGTH: 5
<212> TYPE: PRT
<213> ORGANISM: Homo sapiens

<400> SEQUENCE: 1114

Thr His Leu Val Gln
1               5

<210> SEQ ID NO 1115
<211> LENGTH: 5
<212> TYPE: PRT
<213> ORGANISM: Homo sapiens

<400> SEQUENCE: 1115

His Leu Val Gln Gln
1               5

<210> SEQ ID NO 1116
<211> LENGTH: 5
<212> TYPE: PRT
<213> ORGANISM: Homo sapiens

<400> SEQUENCE: 1116

Leu Val Gln Gln Ala
1               5

<210> SEQ ID NO 1117
<211> LENGTH: 5
<212> TYPE: PRT
<213> ORGANISM: Homo sapiens

<400> SEQUENCE: 1117

Val Gln Gln Ala Asn
1               5

<210> SEQ ID NO 1118
<211> LENGTH: 5
<212> TYPE: PRT
<213> ORGANISM: Homo sapiens

<400> SEQUENCE: 1118

Gln Gln Ala Asn Pro
1               5

<210> SEQ ID NO 1119
<211> LENGTH: 5
<212> TYPE: PRT
<213> ORGANISM: Homo sapiens

<400> SEQUENCE: 1119

Gln Ala Asn Pro Arg
1               5
```

```
<210> SEQ ID NO 1120
<211> LENGTH: 5
<212> TYPE: PRT
<213> ORGANISM: Homo sapiens

<400> SEQUENCE: 1120

Ala Asn Pro Arg Gly
1               5

<210> SEQ ID NO 1121
<211> LENGTH: 5
<212> TYPE: PRT
<213> ORGANISM: Homo sapiens

<400> SEQUENCE: 1121

Asn Pro Arg Gly Ser
1               5

<210> SEQ ID NO 1122
<211> LENGTH: 5
<212> TYPE: PRT
<213> ORGANISM: Homo sapiens

<400> SEQUENCE: 1122

Pro Arg Gly Ser Ala
1               5

<210> SEQ ID NO 1123
<211> LENGTH: 5
<212> TYPE: PRT
<213> ORGANISM: Homo sapiens

<400> SEQUENCE: 1123

Arg Gly Ser Ala Gly
1               5

<210> SEQ ID NO 1124
<211> LENGTH: 5
<212> TYPE: PRT
<213> ORGANISM: Homo sapiens

<400> SEQUENCE: 1124

Gly Ser Ala Gly Pro
1               5

<210> SEQ ID NO 1125
<211> LENGTH: 5
<212> TYPE: PRT
<213> ORGANISM: Homo sapiens

<400> SEQUENCE: 1125

Ser Ala Gly Pro Cys
1               5

<210> SEQ ID NO 1126
<211> LENGTH: 5
<212> TYPE: PRT
<213> ORGANISM: Homo sapiens

<400> SEQUENCE: 1126

Ala Gly Pro Cys Cys
1               5

<210> SEQ ID NO 1127
```

```
<211> LENGTH: 5
<212> TYPE: PRT
<213> ORGANISM: Homo sapiens

<400> SEQUENCE: 1127

Gly Pro Cys Cys Thr
1               5

<210> SEQ ID NO 1128
<211> LENGTH: 5
<212> TYPE: PRT
<213> ORGANISM: Homo sapiens

<400> SEQUENCE: 1128

Pro Cys Cys Thr Pro
1               5

<210> SEQ ID NO 1129
<211> LENGTH: 5
<212> TYPE: PRT
<213> ORGANISM: Homo sapiens

<400> SEQUENCE: 1129

Cys Cys Thr Pro Thr
1               5

<210> SEQ ID NO 1130
<211> LENGTH: 5
<212> TYPE: PRT
<213> ORGANISM: Homo sapiens

<400> SEQUENCE: 1130

Cys Thr Pro Thr Lys
1               5

<210> SEQ ID NO 1131
<211> LENGTH: 5
<212> TYPE: PRT
<213> ORGANISM: Homo sapiens

<400> SEQUENCE: 1131

Thr Pro Thr Lys Met
1               5

<210> SEQ ID NO 1132
<211> LENGTH: 5
<212> TYPE: PRT
<213> ORGANISM: Homo sapiens

<400> SEQUENCE: 1132

Pro Thr Lys Met Ser
1               5

<210> SEQ ID NO 1133
<211> LENGTH: 5
<212> TYPE: PRT
<213> ORGANISM: Homo sapiens

<400> SEQUENCE: 1133

Thr Lys Met Ser Pro
1               5

<210> SEQ ID NO 1134
<211> LENGTH: 5
<212> TYPE: PRT
```

<213> ORGANISM: Homo sapiens

<400> SEQUENCE: 1134

Lys Met Ser Pro Ile
1               5

<210> SEQ ID NO 1135
<211> LENGTH: 5
<212> TYPE: PRT
<213> ORGANISM: Homo sapiens

<400> SEQUENCE: 1135

Met Ser Pro Ile Asn
1               5

<210> SEQ ID NO 1136
<211> LENGTH: 5
<212> TYPE: PRT
<213> ORGANISM: Homo sapiens

<400> SEQUENCE: 1136

Ser Pro Ile Asn Met
1               5

<210> SEQ ID NO 1137
<211> LENGTH: 5
<212> TYPE: PRT
<213> ORGANISM: Homo sapiens

<400> SEQUENCE: 1137

Pro Ile Asn Met Leu
1               5

<210> SEQ ID NO 1138
<211> LENGTH: 5
<212> TYPE: PRT
<213> ORGANISM: Homo sapiens

<400> SEQUENCE: 1138

Ile Asn Met Leu Tyr
1               5

<210> SEQ ID NO 1139
<211> LENGTH: 5
<212> TYPE: PRT
<213> ORGANISM: Homo sapiens

<400> SEQUENCE: 1139

Asn Met Leu Tyr Phe
1               5

<210> SEQ ID NO 1140
<211> LENGTH: 5
<212> TYPE: PRT
<213> ORGANISM: Homo sapiens

<400> SEQUENCE: 1140

Met Leu Tyr Phe Asn
1               5

<210> SEQ ID NO 1141
<211> LENGTH: 5
<212> TYPE: PRT
<213> ORGANISM: Homo sapiens

```
<400> SEQUENCE: 1141

Leu Tyr Phe Asn Asp
1               5

<210> SEQ ID NO 1142
<211> LENGTH: 5
<212> TYPE: PRT
<213> ORGANISM: Homo sapiens

<400> SEQUENCE: 1142

Tyr Phe Asn Asp Lys
1               5

<210> SEQ ID NO 1143
<211> LENGTH: 5
<212> TYPE: PRT
<213> ORGANISM: Homo sapiens

<400> SEQUENCE: 1143

Phe Asn Asp Lys Gln
1               5

<210> SEQ ID NO 1144
<211> LENGTH: 5
<212> TYPE: PRT
<213> ORGANISM: Homo sapiens

<400> SEQUENCE: 1144

Asn Asp Lys Gln Gln
1               5

<210> SEQ ID NO 1145
<211> LENGTH: 5
<212> TYPE: PRT
<213> ORGANISM: Homo sapiens

<400> SEQUENCE: 1145

Asp Lys Gln Gln Ile
1               5

<210> SEQ ID NO 1146
<211> LENGTH: 5
<212> TYPE: PRT
<213> ORGANISM: Homo sapiens

<400> SEQUENCE: 1146

Lys Gln Gln Ile Ile
1               5

<210> SEQ ID NO 1147
<211> LENGTH: 5
<212> TYPE: PRT
<213> ORGANISM: Homo sapiens

<400> SEQUENCE: 1147

Gln Gln Ile Ile Tyr
1               5

<210> SEQ ID NO 1148
<211> LENGTH: 5
<212> TYPE: PRT
<213> ORGANISM: Homo sapiens

<400> SEQUENCE: 1148
```

```
Gln Ile Ile Tyr Gly
1               5

<210> SEQ ID NO 1149
<211> LENGTH: 5
<212> TYPE: PRT
<213> ORGANISM: Homo sapiens

<400> SEQUENCE: 1149

Ile Ile Tyr Gly Lys
1               5

<210> SEQ ID NO 1150
<211> LENGTH: 5
<212> TYPE: PRT
<213> ORGANISM: Homo sapiens

<400> SEQUENCE: 1150

Ile Tyr Gly Lys Ile
1               5

<210> SEQ ID NO 1151
<211> LENGTH: 5
<212> TYPE: PRT
<213> ORGANISM: Homo sapiens

<400> SEQUENCE: 1151

Tyr Gly Lys Ile Pro
1               5

<210> SEQ ID NO 1152
<211> LENGTH: 5
<212> TYPE: PRT
<213> ORGANISM: Homo sapiens

<400> SEQUENCE: 1152

Gly Lys Ile Pro Gly
1               5

<210> SEQ ID NO 1153
<211> LENGTH: 5
<212> TYPE: PRT
<213> ORGANISM: Homo sapiens

<400> SEQUENCE: 1153

Lys Ile Pro Gly Met
1               5

<210> SEQ ID NO 1154
<211> LENGTH: 5
<212> TYPE: PRT
<213> ORGANISM: Homo sapiens

<400> SEQUENCE: 1154

Ile Pro Gly Met Val
1               5

<210> SEQ ID NO 1155
<211> LENGTH: 5
<212> TYPE: PRT
<213> ORGANISM: Homo sapiens

<400> SEQUENCE: 1155

Pro Gly Met Val Val
1               5
```

<210> SEQ ID NO 1156
<211> LENGTH: 5
<212> TYPE: PRT
<213> ORGANISM: Homo sapiens

<400> SEQUENCE: 1156

Gly Met Val Val Asp
1               5

<210> SEQ ID NO 1157
<211> LENGTH: 5
<212> TYPE: PRT
<213> ORGANISM: Homo sapiens

<400> SEQUENCE: 1157

Met Val Val Asp Arg
1               5

<210> SEQ ID NO 1158
<211> LENGTH: 5
<212> TYPE: PRT
<213> ORGANISM: Homo sapiens

<400> SEQUENCE: 1158

Val Val Asp Arg Cys
1               5

<210> SEQ ID NO 1159
<211> LENGTH: 5
<212> TYPE: PRT
<213> ORGANISM: Homo sapiens

<400> SEQUENCE: 1159

Val Asp Arg Cys Gly
1               5

<210> SEQ ID NO 1160
<211> LENGTH: 5
<212> TYPE: PRT
<213> ORGANISM: Homo sapiens

<400> SEQUENCE: 1160

Asp Arg Cys Gly Cys
1               5

<210> SEQ ID NO 1161
<211> LENGTH: 5
<212> TYPE: PRT
<213> ORGANISM: Homo sapiens

<400> SEQUENCE: 1161

Arg Cys Gly Cys Ser
1               5

<210> SEQ ID NO 1162
<211> LENGTH: 6
<212> TYPE: PRT
<213> ORGANISM: Homo sapiens

<400> SEQUENCE: 1162

Met Val Leu Ala Ala Pro
1               5

```
<210> SEQ ID NO 1163
<211> LENGTH: 6
<212> TYPE: PRT
<213> ORGANISM: Homo sapiens

<400> SEQUENCE: 1163

Val Leu Ala Ala Pro Leu
1               5

<210> SEQ ID NO 1164
<211> LENGTH: 6
<212> TYPE: PRT
<213> ORGANISM: Homo sapiens

<400> SEQUENCE: 1164

Leu Ala Ala Pro Leu Leu
1               5

<210> SEQ ID NO 1165
<211> LENGTH: 6
<212> TYPE: PRT
<213> ORGANISM: Homo sapiens

<400> SEQUENCE: 1165

Ala Ala Pro Leu Leu Leu
1               5

<210> SEQ ID NO 1166
<211> LENGTH: 6
<212> TYPE: PRT
<213> ORGANISM: Homo sapiens

<400> SEQUENCE: 1166

Ala Pro Leu Leu Leu Gly
1               5

<210> SEQ ID NO 1167
<211> LENGTH: 6
<212> TYPE: PRT
<213> ORGANISM: Homo sapiens

<400> SEQUENCE: 1167

Pro Leu Leu Leu Gly Phe
1               5

<210> SEQ ID NO 1168
<211> LENGTH: 6
<212> TYPE: PRT
<213> ORGANISM: Homo sapiens

<400> SEQUENCE: 1168

Leu Leu Leu Gly Phe Leu
1               5

<210> SEQ ID NO 1169
<211> LENGTH: 6
<212> TYPE: PRT
<213> ORGANISM: Homo sapiens

<400> SEQUENCE: 1169

Leu Leu Gly Phe Leu Leu
1               5

<210> SEQ ID NO 1170
<211> LENGTH: 6
```

<212> TYPE: PRT
<213> ORGANISM: Homo sapiens

<400> SEQUENCE: 1170

Leu Gly Phe Leu Leu Leu
1               5

<210> SEQ ID NO 1171
<211> LENGTH: 6
<212> TYPE: PRT
<213> ORGANISM: Homo sapiens

<400> SEQUENCE: 1171

Gly Phe Leu Leu Leu Ala
1               5

<210> SEQ ID NO 1172
<211> LENGTH: 6
<212> TYPE: PRT
<213> ORGANISM: Homo sapiens

<400> SEQUENCE: 1172

Phe Leu Leu Leu Ala Leu
1               5

<210> SEQ ID NO 1173
<211> LENGTH: 6
<212> TYPE: PRT
<213> ORGANISM: Homo sapiens

<400> SEQUENCE: 1173

Leu Leu Leu Ala Leu Glu
1               5

<210> SEQ ID NO 1174
<211> LENGTH: 6
<212> TYPE: PRT
<213> ORGANISM: Homo sapiens

<400> SEQUENCE: 1174

Leu Leu Ala Leu Glu Leu
1               5

<210> SEQ ID NO 1175
<211> LENGTH: 6
<212> TYPE: PRT
<213> ORGANISM: Homo sapiens

<400> SEQUENCE: 1175

Leu Ala Leu Glu Leu Arg
1               5

<210> SEQ ID NO 1176
<211> LENGTH: 6
<212> TYPE: PRT
<213> ORGANISM: Homo sapiens

<400> SEQUENCE: 1176

Ala Leu Glu Leu Arg Pro
1               5

<210> SEQ ID NO 1177
<211> LENGTH: 6
<212> TYPE: PRT
<213> ORGANISM: Homo sapiens

<400> SEQUENCE: 1177

Leu Glu Leu Arg Pro Arg
1               5

<210> SEQ ID NO 1178
<211> LENGTH: 6
<212> TYPE: PRT
<213> ORGANISM: Homo sapiens

<400> SEQUENCE: 1178

Glu Leu Arg Pro Arg Gly
1               5

<210> SEQ ID NO 1179
<211> LENGTH: 6
<212> TYPE: PRT
<213> ORGANISM: Homo sapiens

<400> SEQUENCE: 1179

Leu Arg Pro Arg Gly Glu
1               5

<210> SEQ ID NO 1180
<211> LENGTH: 6
<212> TYPE: PRT
<213> ORGANISM: Homo sapiens

<400> SEQUENCE: 1180

Arg Pro Arg Gly Glu Ala
1               5

<210> SEQ ID NO 1181
<211> LENGTH: 6
<212> TYPE: PRT
<213> ORGANISM: Homo sapiens

<400> SEQUENCE: 1181

Pro Arg Gly Glu Ala Ala
1               5

<210> SEQ ID NO 1182
<211> LENGTH: 6
<212> TYPE: PRT
<213> ORGANISM: Homo sapiens

<400> SEQUENCE: 1182

Arg Gly Glu Ala Ala Glu
1               5

<210> SEQ ID NO 1183
<211> LENGTH: 6
<212> TYPE: PRT
<213> ORGANISM: Homo sapiens

<400> SEQUENCE: 1183

Gly Glu Ala Ala Glu Gly
1               5

<210> SEQ ID NO 1184
<211> LENGTH: 6
<212> TYPE: PRT
<213> ORGANISM: Homo sapiens

<400> SEQUENCE: 1184

```
Glu Ala Ala Glu Gly Pro
1               5

<210> SEQ ID NO 1185
<211> LENGTH: 6
<212> TYPE: PRT
<213> ORGANISM: Homo sapiens

<400> SEQUENCE: 1185

Ala Ala Glu Gly Pro Ala
1               5

<210> SEQ ID NO 1186
<211> LENGTH: 6
<212> TYPE: PRT
<213> ORGANISM: Homo sapiens

<400> SEQUENCE: 1186

Ala Glu Gly Pro Ala Ala
1               5

<210> SEQ ID NO 1187
<211> LENGTH: 6
<212> TYPE: PRT
<213> ORGANISM: Homo sapiens

<400> SEQUENCE: 1187

Glu Gly Pro Ala Ala Ala
1               5

<210> SEQ ID NO 1188
<211> LENGTH: 6
<212> TYPE: PRT
<213> ORGANISM: Homo sapiens

<400> SEQUENCE: 1188

Gly Pro Ala Ala Ala Ala
1               5

<210> SEQ ID NO 1189
<211> LENGTH: 6
<212> TYPE: PRT
<213> ORGANISM: Homo sapiens

<400> SEQUENCE: 1189

Pro Ala Ala Ala Ala Ala
1               5

<210> SEQ ID NO 1190
<211> LENGTH: 6
<212> TYPE: PRT
<213> ORGANISM: Homo sapiens

<400> SEQUENCE: 1190

Ala Ala Ala Ala Ala Ala
1               5

<210> SEQ ID NO 1191
<211> LENGTH: 6
<212> TYPE: PRT
<213> ORGANISM: Homo sapiens

<400> SEQUENCE: 1191

Ala Ala Ala Ala Ala Gly
```

```
1               5

<210> SEQ ID NO 1192
<211> LENGTH: 6
<212> TYPE: PRT
<213> ORGANISM: Homo sapiens

<400> SEQUENCE: 1192

Ala Ala Ala Ala Gly Val
1               5

<210> SEQ ID NO 1193
<211> LENGTH: 6
<212> TYPE: PRT
<213> ORGANISM: Homo sapiens

<400> SEQUENCE: 1193

Ala Ala Ala Gly Val Gly
1               5

<210> SEQ ID NO 1194
<211> LENGTH: 6
<212> TYPE: PRT
<213> ORGANISM: Homo sapiens

<400> SEQUENCE: 1194

Ala Ala Gly Val Gly Gly
1               5

<210> SEQ ID NO 1195
<211> LENGTH: 6
<212> TYPE: PRT
<213> ORGANISM: Homo sapiens

<400> SEQUENCE: 1195

Ala Gly Val Gly Gly Glu
1               5

<210> SEQ ID NO 1196
<211> LENGTH: 6
<212> TYPE: PRT
<213> ORGANISM: Homo sapiens

<400> SEQUENCE: 1196

Gly Val Gly Gly Glu Arg
1               5

<210> SEQ ID NO 1197
<211> LENGTH: 6
<212> TYPE: PRT
<213> ORGANISM: Homo sapiens

<400> SEQUENCE: 1197

Val Gly Gly Glu Arg Ser
1               5

<210> SEQ ID NO 1198
<211> LENGTH: 6
<212> TYPE: PRT
<213> ORGANISM: Homo sapiens

<400> SEQUENCE: 1198

Gly Gly Glu Arg Ser Ser
1               5
```

<210> SEQ ID NO 1199
<211> LENGTH: 6
<212> TYPE: PRT
<213> ORGANISM: Homo sapiens

<400> SEQUENCE: 1199

Gly Glu Arg Ser Ser Arg
1               5

<210> SEQ ID NO 1200
<211> LENGTH: 6
<212> TYPE: PRT
<213> ORGANISM: Homo sapiens

<400> SEQUENCE: 1200

Glu Arg Ser Ser Arg Pro
1               5

<210> SEQ ID NO 1201
<211> LENGTH: 6
<212> TYPE: PRT
<213> ORGANISM: Homo sapiens

<400> SEQUENCE: 1201

Arg Ser Ser Arg Pro Ala
1               5

<210> SEQ ID NO 1202
<211> LENGTH: 6
<212> TYPE: PRT
<213> ORGANISM: Homo sapiens

<400> SEQUENCE: 1202

Ser Ser Arg Pro Ala Pro
1               5

<210> SEQ ID NO 1203
<211> LENGTH: 6
<212> TYPE: PRT
<213> ORGANISM: Homo sapiens

<400> SEQUENCE: 1203

Ser Arg Pro Ala Pro Ser
1               5

<210> SEQ ID NO 1204
<211> LENGTH: 6
<212> TYPE: PRT
<213> ORGANISM: Homo sapiens

<400> SEQUENCE: 1204

Arg Pro Ala Pro Ser Val
1               5

<210> SEQ ID NO 1205
<211> LENGTH: 6
<212> TYPE: PRT
<213> ORGANISM: Homo sapiens

<400> SEQUENCE: 1205

Pro Ala Pro Ser Val Ala
1               5

<210> SEQ ID NO 1206

```
<211> LENGTH: 6
<212> TYPE: PRT
<213> ORGANISM: Homo sapiens

<400> SEQUENCE: 1206

Ala Pro Ser Val Ala Pro
1               5

<210> SEQ ID NO 1207
<211> LENGTH: 6
<212> TYPE: PRT
<213> ORGANISM: Homo sapiens

<400> SEQUENCE: 1207

Pro Ser Val Ala Pro Glu
1               5

<210> SEQ ID NO 1208
<211> LENGTH: 6
<212> TYPE: PRT
<213> ORGANISM: Homo sapiens

<400> SEQUENCE: 1208

Ser Val Ala Pro Glu Pro
1               5

<210> SEQ ID NO 1209
<211> LENGTH: 6
<212> TYPE: PRT
<213> ORGANISM: Homo sapiens

<400> SEQUENCE: 1209

Val Ala Pro Glu Pro Asp
1               5

<210> SEQ ID NO 1210
<211> LENGTH: 6
<212> TYPE: PRT
<213> ORGANISM: Homo sapiens

<400> SEQUENCE: 1210

Ala Pro Glu Pro Asp Gly
1               5

<210> SEQ ID NO 1211
<211> LENGTH: 6
<212> TYPE: PRT
<213> ORGANISM: Homo sapiens

<400> SEQUENCE: 1211

Pro Glu Pro Asp Gly Cys
1               5

<210> SEQ ID NO 1212
<211> LENGTH: 6
<212> TYPE: PRT
<213> ORGANISM: Homo sapiens

<400> SEQUENCE: 1212

Glu Pro Asp Gly Cys Pro
1               5

<210> SEQ ID NO 1213
<211> LENGTH: 6
<212> TYPE: PRT
```

<213> ORGANISM: Homo sapiens

<400> SEQUENCE: 1213

Pro Asp Gly Cys Pro Val
1               5

<210> SEQ ID NO 1214
<211> LENGTH: 6
<212> TYPE: PRT
<213> ORGANISM: Homo sapiens

<400> SEQUENCE: 1214

Asp Gly Cys Pro Val Cys
1               5

<210> SEQ ID NO 1215
<211> LENGTH: 6
<212> TYPE: PRT
<213> ORGANISM: Homo sapiens

<400> SEQUENCE: 1215

Gly Cys Pro Val Cys Val
1               5

<210> SEQ ID NO 1216
<211> LENGTH: 6
<212> TYPE: PRT
<213> ORGANISM: Homo sapiens

<400> SEQUENCE: 1216

Cys Pro Val Cys Val Trp
1               5

<210> SEQ ID NO 1217
<211> LENGTH: 6
<212> TYPE: PRT
<213> ORGANISM: Homo sapiens

<400> SEQUENCE: 1217

Pro Val Cys Val Trp Arg
1               5

<210> SEQ ID NO 1218
<211> LENGTH: 6
<212> TYPE: PRT
<213> ORGANISM: Homo sapiens

<400> SEQUENCE: 1218

Val Cys Val Trp Arg Gln
1               5

<210> SEQ ID NO 1219
<211> LENGTH: 6
<212> TYPE: PRT
<213> ORGANISM: Homo sapiens

<400> SEQUENCE: 1219

Cys Val Trp Arg Gln His
1               5

<210> SEQ ID NO 1220
<211> LENGTH: 6
<212> TYPE: PRT
<213> ORGANISM: Homo sapiens

<400> SEQUENCE: 1220

Val Trp Arg Gln His Ser
1               5

<210> SEQ ID NO 1221
<211> LENGTH: 6
<212> TYPE: PRT
<213> ORGANISM: Homo sapiens

<400> SEQUENCE: 1221

Trp Arg Gln His Ser Arg
1               5

<210> SEQ ID NO 1222
<211> LENGTH: 6
<212> TYPE: PRT
<213> ORGANISM: Homo sapiens

<400> SEQUENCE: 1222

Arg Gln His Ser Arg Glu
1               5

<210> SEQ ID NO 1223
<211> LENGTH: 6
<212> TYPE: PRT
<213> ORGANISM: Homo sapiens

<400> SEQUENCE: 1223

Gln His Ser Arg Glu Leu
1               5

<210> SEQ ID NO 1224
<211> LENGTH: 6
<212> TYPE: PRT
<213> ORGANISM: Homo sapiens

<400> SEQUENCE: 1224

His Ser Arg Glu Leu Arg
1               5

<210> SEQ ID NO 1225
<211> LENGTH: 6
<212> TYPE: PRT
<213> ORGANISM: Homo sapiens

<400> SEQUENCE: 1225

Ser Arg Glu Leu Arg Leu
1               5

<210> SEQ ID NO 1226
<211> LENGTH: 6
<212> TYPE: PRT
<213> ORGANISM: Homo sapiens

<400> SEQUENCE: 1226

Arg Glu Leu Arg Leu Glu
1               5

<210> SEQ ID NO 1227
<211> LENGTH: 6
<212> TYPE: PRT
<213> ORGANISM: Homo sapiens

<400> SEQUENCE: 1227

Glu Leu Arg Leu Glu Ser
1               5

<210> SEQ ID NO 1228
<211> LENGTH: 6
<212> TYPE: PRT
<213> ORGANISM: Homo sapiens

<400> SEQUENCE: 1228

Leu Arg Leu Glu Ser Ile
1               5

<210> SEQ ID NO 1229
<211> LENGTH: 6
<212> TYPE: PRT
<213> ORGANISM: Homo sapiens

<400> SEQUENCE: 1229

Arg Leu Glu Ser Ile Lys
1               5

<210> SEQ ID NO 1230
<211> LENGTH: 6
<212> TYPE: PRT
<213> ORGANISM: Homo sapiens

<400> SEQUENCE: 1230

Leu Glu Ser Ile Lys Ser
1               5

<210> SEQ ID NO 1231
<211> LENGTH: 6
<212> TYPE: PRT
<213> ORGANISM: Homo sapiens

<400> SEQUENCE: 1231

Glu Ser Ile Lys Ser Gln
1               5

<210> SEQ ID NO 1232
<211> LENGTH: 6
<212> TYPE: PRT
<213> ORGANISM: Homo sapiens

<400> SEQUENCE: 1232

Ser Ile Lys Ser Gln Ile
1               5

<210> SEQ ID NO 1233
<211> LENGTH: 6
<212> TYPE: PRT
<213> ORGANISM: Homo sapiens

<400> SEQUENCE: 1233

Ile Lys Ser Gln Ile Leu
1               5

<210> SEQ ID NO 1234
<211> LENGTH: 6
<212> TYPE: PRT
<213> ORGANISM: Homo sapiens

<400> SEQUENCE: 1234

Lys Ser Gln Ile Leu Ser
1               5

<210> SEQ ID NO 1235
<211> LENGTH: 6
<212> TYPE: PRT
<213> ORGANISM: Homo sapiens

<400> SEQUENCE: 1235

Ser Gln Ile Leu Ser Lys
1               5

<210> SEQ ID NO 1236
<211> LENGTH: 6
<212> TYPE: PRT
<213> ORGANISM: Homo sapiens

<400> SEQUENCE: 1236

Gln Ile Leu Ser Lys Leu
1               5

<210> SEQ ID NO 1237
<211> LENGTH: 6
<212> TYPE: PRT
<213> ORGANISM: Homo sapiens

<400> SEQUENCE: 1237

Ile Leu Ser Lys Leu Arg
1               5

<210> SEQ ID NO 1238
<211> LENGTH: 6
<212> TYPE: PRT
<213> ORGANISM: Homo sapiens

<400> SEQUENCE: 1238

Leu Ser Lys Leu Arg Leu
1               5

<210> SEQ ID NO 1239
<211> LENGTH: 6
<212> TYPE: PRT
<213> ORGANISM: Homo sapiens

<400> SEQUENCE: 1239

Ser Lys Leu Arg Leu Lys
1               5

<210> SEQ ID NO 1240
<211> LENGTH: 6
<212> TYPE: PRT
<213> ORGANISM: Homo sapiens

<400> SEQUENCE: 1240

Lys Leu Arg Leu Lys Glu
1               5

<210> SEQ ID NO 1241
<211> LENGTH: 6
<212> TYPE: PRT
<213> ORGANISM: Homo sapiens

<400> SEQUENCE: 1241

Leu Arg Leu Lys Glu Ala
1               5

```
<210> SEQ ID NO 1242
<211> LENGTH: 6
<212> TYPE: PRT
<213> ORGANISM: Homo sapiens

<400> SEQUENCE: 1242

Arg Leu Lys Glu Ala Pro
1               5

<210> SEQ ID NO 1243
<211> LENGTH: 6
<212> TYPE: PRT
<213> ORGANISM: Homo sapiens

<400> SEQUENCE: 1243

Leu Lys Glu Ala Pro Asn
1               5

<210> SEQ ID NO 1244
<211> LENGTH: 6
<212> TYPE: PRT
<213> ORGANISM: Homo sapiens

<400> SEQUENCE: 1244

Lys Glu Ala Pro Asn Ile
1               5

<210> SEQ ID NO 1245
<211> LENGTH: 6
<212> TYPE: PRT
<213> ORGANISM: Homo sapiens

<400> SEQUENCE: 1245

Glu Ala Pro Asn Ile Ser
1               5

<210> SEQ ID NO 1246
<211> LENGTH: 6
<212> TYPE: PRT
<213> ORGANISM: Homo sapiens

<400> SEQUENCE: 1246

Ala Pro Asn Ile Ser Arg
1               5

<210> SEQ ID NO 1247
<211> LENGTH: 6
<212> TYPE: PRT
<213> ORGANISM: Homo sapiens

<400> SEQUENCE: 1247

Pro Asn Ile Ser Arg Glu
1               5

<210> SEQ ID NO 1248
<211> LENGTH: 6
<212> TYPE: PRT
<213> ORGANISM: Homo sapiens

<400> SEQUENCE: 1248

Asn Ile Ser Arg Glu Val
1               5

<210> SEQ ID NO 1249
<211> LENGTH: 6
```

<212> TYPE: PRT
<213> ORGANISM: Homo sapiens

<400> SEQUENCE: 1249

Ile Ser Arg Glu Val Val
1               5

<210> SEQ ID NO 1250
<211> LENGTH: 6
<212> TYPE: PRT
<213> ORGANISM: Homo sapiens

<400> SEQUENCE: 1250

Ser Arg Glu Val Val Lys
1               5

<210> SEQ ID NO 1251
<211> LENGTH: 6
<212> TYPE: PRT
<213> ORGANISM: Homo sapiens

<400> SEQUENCE: 1251

Arg Glu Val Val Lys Gln
1               5

<210> SEQ ID NO 1252
<211> LENGTH: 6
<212> TYPE: PRT
<213> ORGANISM: Homo sapiens

<400> SEQUENCE: 1252

Glu Val Val Lys Gln Leu
1               5

<210> SEQ ID NO 1253
<211> LENGTH: 6
<212> TYPE: PRT
<213> ORGANISM: Homo sapiens

<400> SEQUENCE: 1253

Val Val Lys Gln Leu Leu
1               5

<210> SEQ ID NO 1254
<211> LENGTH: 6
<212> TYPE: PRT
<213> ORGANISM: Homo sapiens

<400> SEQUENCE: 1254

Val Lys Gln Leu Leu Pro
1               5

<210> SEQ ID NO 1255
<211> LENGTH: 6
<212> TYPE: PRT
<213> ORGANISM: Homo sapiens

<400> SEQUENCE: 1255

Lys Gln Leu Leu Pro Lys
1               5

<210> SEQ ID NO 1256
<211> LENGTH: 6
<212> TYPE: PRT
<213> ORGANISM: Homo sapiens

<400> SEQUENCE: 1256

Gln Leu Leu Pro Lys Ala
1               5

<210> SEQ ID NO 1257
<211> LENGTH: 6
<212> TYPE: PRT
<213> ORGANISM: Homo sapiens

<400> SEQUENCE: 1257

Leu Leu Pro Lys Ala Pro
1               5

<210> SEQ ID NO 1258
<211> LENGTH: 6
<212> TYPE: PRT
<213> ORGANISM: Homo sapiens

<400> SEQUENCE: 1258

Leu Pro Lys Ala Pro Pro
1               5

<210> SEQ ID NO 1259
<211> LENGTH: 6
<212> TYPE: PRT
<213> ORGANISM: Homo sapiens

<400> SEQUENCE: 1259

Pro Lys Ala Pro Pro Leu
1               5

<210> SEQ ID NO 1260
<211> LENGTH: 6
<212> TYPE: PRT
<213> ORGANISM: Homo sapiens

<400> SEQUENCE: 1260

Lys Ala Pro Pro Leu Gln
1               5

<210> SEQ ID NO 1261
<211> LENGTH: 6
<212> TYPE: PRT
<213> ORGANISM: Homo sapiens

<400> SEQUENCE: 1261

Ala Pro Pro Leu Gln Gln
1               5

<210> SEQ ID NO 1262
<211> LENGTH: 6
<212> TYPE: PRT
<213> ORGANISM: Homo sapiens

<400> SEQUENCE: 1262

Pro Pro Leu Gln Gln Ile
1               5

<210> SEQ ID NO 1263
<211> LENGTH: 6
<212> TYPE: PRT
<213> ORGANISM: Homo sapiens

<400> SEQUENCE: 1263

```
Pro Leu Gln Gln Ile Leu
1               5

<210> SEQ ID NO 1264
<211> LENGTH: 6
<212> TYPE: PRT
<213> ORGANISM: Homo sapiens

<400> SEQUENCE: 1264

Leu Gln Gln Ile Leu Asp
1               5

<210> SEQ ID NO 1265
<211> LENGTH: 6
<212> TYPE: PRT
<213> ORGANISM: Homo sapiens

<400> SEQUENCE: 1265

Gln Gln Ile Leu Asp Leu
1               5

<210> SEQ ID NO 1266
<211> LENGTH: 6
<212> TYPE: PRT
<213> ORGANISM: Homo sapiens

<400> SEQUENCE: 1266

Gln Ile Leu Asp Leu His
1               5

<210> SEQ ID NO 1267
<211> LENGTH: 6
<212> TYPE: PRT
<213> ORGANISM: Homo sapiens

<400> SEQUENCE: 1267

Ile Leu Asp Leu His Asp
1               5

<210> SEQ ID NO 1268
<211> LENGTH: 6
<212> TYPE: PRT
<213> ORGANISM: Homo sapiens

<400> SEQUENCE: 1268

Leu Asp Leu His Asp Phe
1               5

<210> SEQ ID NO 1269
<211> LENGTH: 6
<212> TYPE: PRT
<213> ORGANISM: Homo sapiens

<400> SEQUENCE: 1269

Asp Leu His Asp Phe Gln
1               5

<210> SEQ ID NO 1270
<211> LENGTH: 6
<212> TYPE: PRT
<213> ORGANISM: Homo sapiens

<400> SEQUENCE: 1270

Leu His Asp Phe Gln Gly
```

```
1               5

<210> SEQ ID NO 1271
<211> LENGTH: 6
<212> TYPE: PRT
<213> ORGANISM: Homo sapiens

<400> SEQUENCE: 1271

His Asp Phe Gln Gly Asp
1               5

<210> SEQ ID NO 1272
<211> LENGTH: 6
<212> TYPE: PRT
<213> ORGANISM: Homo sapiens

<400> SEQUENCE: 1272

Asp Phe Gln Gly Asp Ala
1               5

<210> SEQ ID NO 1273
<211> LENGTH: 6
<212> TYPE: PRT
<213> ORGANISM: Homo sapiens

<400> SEQUENCE: 1273

Phe Gln Gly Asp Ala Leu
1               5

<210> SEQ ID NO 1274
<211> LENGTH: 6
<212> TYPE: PRT
<213> ORGANISM: Homo sapiens

<400> SEQUENCE: 1274

Gln Gly Asp Ala Leu Gln
1               5

<210> SEQ ID NO 1275
<211> LENGTH: 6
<212> TYPE: PRT
<213> ORGANISM: Homo sapiens

<400> SEQUENCE: 1275

Gly Asp Ala Leu Gln Pro
1               5

<210> SEQ ID NO 1276
<211> LENGTH: 6
<212> TYPE: PRT
<213> ORGANISM: Homo sapiens

<400> SEQUENCE: 1276

Asp Ala Leu Gln Pro Glu
1               5

<210> SEQ ID NO 1277
<211> LENGTH: 6
<212> TYPE: PRT
<213> ORGANISM: Homo sapiens

<400> SEQUENCE: 1277

Ala Leu Gln Pro Glu Asp
1               5
```

<210> SEQ ID NO 1278
<211> LENGTH: 6
<212> TYPE: PRT
<213> ORGANISM: Homo sapiens

<400> SEQUENCE: 1278

Leu Gln Pro Glu Asp Phe
1               5

<210> SEQ ID NO 1279
<211> LENGTH: 6
<212> TYPE: PRT
<213> ORGANISM: Homo sapiens

<400> SEQUENCE: 1279

Gln Pro Glu Asp Phe Leu
1               5

<210> SEQ ID NO 1280
<211> LENGTH: 6
<212> TYPE: PRT
<213> ORGANISM: Homo sapiens

<400> SEQUENCE: 1280

Pro Glu Asp Phe Leu Glu
1               5

<210> SEQ ID NO 1281
<211> LENGTH: 6
<212> TYPE: PRT
<213> ORGANISM: Homo sapiens

<400> SEQUENCE: 1281

Glu Asp Phe Leu Glu Glu
1               5

<210> SEQ ID NO 1282
<211> LENGTH: 6
<212> TYPE: PRT
<213> ORGANISM: Homo sapiens

<400> SEQUENCE: 1282

Asp Phe Leu Glu Glu Asp
1               5

<210> SEQ ID NO 1283
<211> LENGTH: 6
<212> TYPE: PRT
<213> ORGANISM: Homo sapiens

<400> SEQUENCE: 1283

Phe Leu Glu Glu Asp Glu
1               5

<210> SEQ ID NO 1284
<211> LENGTH: 6
<212> TYPE: PRT
<213> ORGANISM: Homo sapiens

<400> SEQUENCE: 1284

Leu Glu Glu Asp Glu Tyr
1               5

<210> SEQ ID NO 1285

```
<211> LENGTH: 6
<212> TYPE: PRT
<213> ORGANISM: Homo sapiens

<400> SEQUENCE: 1285

Glu Glu Asp Glu Tyr His
1               5

<210> SEQ ID NO 1286
<211> LENGTH: 6
<212> TYPE: PRT
<213> ORGANISM: Homo sapiens

<400> SEQUENCE: 1286

Glu Asp Glu Tyr His Ala
1               5

<210> SEQ ID NO 1287
<211> LENGTH: 6
<212> TYPE: PRT
<213> ORGANISM: Homo sapiens

<400> SEQUENCE: 1287

Asp Glu Tyr His Ala Thr
1               5

<210> SEQ ID NO 1288
<211> LENGTH: 6
<212> TYPE: PRT
<213> ORGANISM: Homo sapiens

<400> SEQUENCE: 1288

Glu Tyr His Ala Thr Thr
1               5

<210> SEQ ID NO 1289
<211> LENGTH: 6
<212> TYPE: PRT
<213> ORGANISM: Homo sapiens

<400> SEQUENCE: 1289

Tyr His Ala Thr Thr Glu
1               5

<210> SEQ ID NO 1290
<211> LENGTH: 6
<212> TYPE: PRT
<213> ORGANISM: Homo sapiens

<400> SEQUENCE: 1290

His Ala Thr Thr Glu Thr
1               5

<210> SEQ ID NO 1291
<211> LENGTH: 6
<212> TYPE: PRT
<213> ORGANISM: Homo sapiens

<400> SEQUENCE: 1291

Ala Thr Thr Glu Thr Val
1               5

<210> SEQ ID NO 1292
<211> LENGTH: 6
<212> TYPE: PRT
```

<213> ORGANISM: Homo sapiens

<400> SEQUENCE: 1292

Thr Thr Glu Thr Val Ile
1               5

<210> SEQ ID NO 1293
<211> LENGTH: 6
<212> TYPE: PRT
<213> ORGANISM: Homo sapiens

<400> SEQUENCE: 1293

Thr Glu Thr Val Ile Ser
1               5

<210> SEQ ID NO 1294
<211> LENGTH: 6
<212> TYPE: PRT
<213> ORGANISM: Homo sapiens

<400> SEQUENCE: 1294

Glu Thr Val Ile Ser Met
1               5

<210> SEQ ID NO 1295
<211> LENGTH: 6
<212> TYPE: PRT
<213> ORGANISM: Homo sapiens

<400> SEQUENCE: 1295

Thr Val Ile Ser Met Ala
1               5

<210> SEQ ID NO 1296
<211> LENGTH: 6
<212> TYPE: PRT
<213> ORGANISM: Homo sapiens

<400> SEQUENCE: 1296

Val Ile Ser Met Ala Gln
1               5

<210> SEQ ID NO 1297
<211> LENGTH: 6
<212> TYPE: PRT
<213> ORGANISM: Homo sapiens

<400> SEQUENCE: 1297

Ile Ser Met Ala Gln Glu
1               5

<210> SEQ ID NO 1298
<211> LENGTH: 6
<212> TYPE: PRT
<213> ORGANISM: Homo sapiens

<400> SEQUENCE: 1298

Ser Met Ala Gln Glu Thr
1               5

<210> SEQ ID NO 1299
<211> LENGTH: 6
<212> TYPE: PRT
<213> ORGANISM: Homo sapiens

```
<400> SEQUENCE: 1299

Met Ala Gln Glu Thr Asp
 1               5

<210> SEQ ID NO 1300
<211> LENGTH: 6
<212> TYPE: PRT
<213> ORGANISM: Homo sapiens

<400> SEQUENCE: 1300

Ala Gln Glu Thr Asp Pro
 1               5

<210> SEQ ID NO 1301
<211> LENGTH: 6
<212> TYPE: PRT
<213> ORGANISM: Homo sapiens

<400> SEQUENCE: 1301

Gln Glu Thr Asp Pro Ala
 1               5

<210> SEQ ID NO 1302
<211> LENGTH: 6
<212> TYPE: PRT
<213> ORGANISM: Homo sapiens

<400> SEQUENCE: 1302

Glu Thr Asp Pro Ala Val
 1               5

<210> SEQ ID NO 1303
<211> LENGTH: 6
<212> TYPE: PRT
<213> ORGANISM: Homo sapiens

<400> SEQUENCE: 1303

Thr Asp Pro Ala Val Gln
 1               5

<210> SEQ ID NO 1304
<211> LENGTH: 6
<212> TYPE: PRT
<213> ORGANISM: Homo sapiens

<400> SEQUENCE: 1304

Asp Pro Ala Val Gln Thr
 1               5

<210> SEQ ID NO 1305
<211> LENGTH: 6
<212> TYPE: PRT
<213> ORGANISM: Homo sapiens

<400> SEQUENCE: 1305

Pro Ala Val Gln Thr Asp
 1               5

<210> SEQ ID NO 1306
<211> LENGTH: 6
<212> TYPE: PRT
<213> ORGANISM: Homo sapiens

<400> SEQUENCE: 1306
```

Ala Val Gln Thr Asp Gly
1               5

<210> SEQ ID NO 1307
<211> LENGTH: 6
<212> TYPE: PRT
<213> ORGANISM: Homo sapiens

<400> SEQUENCE: 1307

Val Gln Thr Asp Gly Ser
1               5

<210> SEQ ID NO 1308
<211> LENGTH: 6
<212> TYPE: PRT
<213> ORGANISM: Homo sapiens

<400> SEQUENCE: 1308

Gln Thr Asp Gly Ser Pro
1               5

<210> SEQ ID NO 1309
<211> LENGTH: 6
<212> TYPE: PRT
<213> ORGANISM: Homo sapiens

<400> SEQUENCE: 1309

Thr Asp Gly Ser Pro Leu
1               5

<210> SEQ ID NO 1310
<211> LENGTH: 6
<212> TYPE: PRT
<213> ORGANISM: Homo sapiens

<400> SEQUENCE: 1310

Asp Gly Ser Pro Leu Cys
1               5

<210> SEQ ID NO 1311
<211> LENGTH: 6
<212> TYPE: PRT
<213> ORGANISM: Homo sapiens

<400> SEQUENCE: 1311

Gly Ser Pro Leu Cys Cys
1               5

<210> SEQ ID NO 1312
<211> LENGTH: 6
<212> TYPE: PRT
<213> ORGANISM: Homo sapiens

<400> SEQUENCE: 1312

Ser Pro Leu Cys Cys His
1               5

<210> SEQ ID NO 1313
<211> LENGTH: 6
<212> TYPE: PRT
<213> ORGANISM: Homo sapiens

<400> SEQUENCE: 1313

Pro Leu Cys Cys His Phe
1               5

```
<210> SEQ ID NO 1314
<211> LENGTH: 6
<212> TYPE: PRT
<213> ORGANISM: Homo sapiens

<400> SEQUENCE: 1314

Leu Cys Cys His Phe His
1               5

<210> SEQ ID NO 1315
<211> LENGTH: 6
<212> TYPE: PRT
<213> ORGANISM: Homo sapiens

<400> SEQUENCE: 1315

Cys Cys His Phe His Phe
1               5

<210> SEQ ID NO 1316
<211> LENGTH: 6
<212> TYPE: PRT
<213> ORGANISM: Homo sapiens

<400> SEQUENCE: 1316

Cys His Phe His Phe Ser
1               5

<210> SEQ ID NO 1317
<211> LENGTH: 6
<212> TYPE: PRT
<213> ORGANISM: Homo sapiens

<400> SEQUENCE: 1317

His Phe His Phe Ser Pro
1               5

<210> SEQ ID NO 1318
<211> LENGTH: 6
<212> TYPE: PRT
<213> ORGANISM: Homo sapiens

<400> SEQUENCE: 1318

Phe His Phe Ser Pro Lys
1               5

<210> SEQ ID NO 1319
<211> LENGTH: 6
<212> TYPE: PRT
<213> ORGANISM: Homo sapiens

<400> SEQUENCE: 1319

His Phe Ser Pro Lys Val
1               5

<210> SEQ ID NO 1320
<211> LENGTH: 6
<212> TYPE: PRT
<213> ORGANISM: Homo sapiens

<400> SEQUENCE: 1320

Phe Ser Pro Lys Val Met
1               5
```

```
<210> SEQ ID NO 1321
<211> LENGTH: 6
<212> TYPE: PRT
<213> ORGANISM: Homo sapiens

<400> SEQUENCE: 1321

Ser Pro Lys Val Met Phe
1               5

<210> SEQ ID NO 1322
<211> LENGTH: 6
<212> TYPE: PRT
<213> ORGANISM: Homo sapiens

<400> SEQUENCE: 1322

Pro Lys Val Met Phe Thr
1               5

<210> SEQ ID NO 1323
<211> LENGTH: 6
<212> TYPE: PRT
<213> ORGANISM: Homo sapiens

<400> SEQUENCE: 1323

Lys Val Met Phe Thr Lys
1               5

<210> SEQ ID NO 1324
<211> LENGTH: 6
<212> TYPE: PRT
<213> ORGANISM: Homo sapiens

<400> SEQUENCE: 1324

Val Met Phe Thr Lys Val
1               5

<210> SEQ ID NO 1325
<211> LENGTH: 6
<212> TYPE: PRT
<213> ORGANISM: Homo sapiens

<400> SEQUENCE: 1325

Met Phe Thr Lys Val Leu
1               5

<210> SEQ ID NO 1326
<211> LENGTH: 6
<212> TYPE: PRT
<213> ORGANISM: Homo sapiens

<400> SEQUENCE: 1326

Phe Thr Lys Val Leu Lys
1               5

<210> SEQ ID NO 1327
<211> LENGTH: 6
<212> TYPE: PRT
<213> ORGANISM: Homo sapiens

<400> SEQUENCE: 1327

Thr Lys Val Leu Lys Ala
1               5

<210> SEQ ID NO 1328
<211> LENGTH: 6
```

```
<212> TYPE: PRT
<213> ORGANISM: Homo sapiens

<400> SEQUENCE: 1328

Lys Val Leu Lys Ala Gln
1               5

<210> SEQ ID NO 1329
<211> LENGTH: 6
<212> TYPE: PRT
<213> ORGANISM: Homo sapiens

<400> SEQUENCE: 1329

Val Leu Lys Ala Gln Leu
1               5

<210> SEQ ID NO 1330
<211> LENGTH: 6
<212> TYPE: PRT
<213> ORGANISM: Homo sapiens

<400> SEQUENCE: 1330

Leu Lys Ala Gln Leu Trp
1               5

<210> SEQ ID NO 1331
<211> LENGTH: 6
<212> TYPE: PRT
<213> ORGANISM: Homo sapiens

<400> SEQUENCE: 1331

Lys Ala Gln Leu Trp Val
1               5

<210> SEQ ID NO 1332
<211> LENGTH: 6
<212> TYPE: PRT
<213> ORGANISM: Homo sapiens

<400> SEQUENCE: 1332

Ala Gln Leu Trp Val Tyr
1               5

<210> SEQ ID NO 1333
<211> LENGTH: 6
<212> TYPE: PRT
<213> ORGANISM: Homo sapiens

<400> SEQUENCE: 1333

Gln Leu Trp Val Tyr Leu
1               5

<210> SEQ ID NO 1334
<211> LENGTH: 6
<212> TYPE: PRT
<213> ORGANISM: Homo sapiens

<400> SEQUENCE: 1334

Leu Trp Val Tyr Leu Arg
1               5

<210> SEQ ID NO 1335
<211> LENGTH: 6
<212> TYPE: PRT
<213> ORGANISM: Homo sapiens
```

```
<400> SEQUENCE: 1335

Trp Val Tyr Leu Arg Pro
1               5

<210> SEQ ID NO 1336
<211> LENGTH: 6
<212> TYPE: PRT
<213> ORGANISM: Homo sapiens

<400> SEQUENCE: 1336

Val Tyr Leu Arg Pro Val
1               5

<210> SEQ ID NO 1337
<211> LENGTH: 6
<212> TYPE: PRT
<213> ORGANISM: Homo sapiens

<400> SEQUENCE: 1337

Tyr Leu Arg Pro Val Pro
1               5

<210> SEQ ID NO 1338
<211> LENGTH: 6
<212> TYPE: PRT
<213> ORGANISM: Homo sapiens

<400> SEQUENCE: 1338

Leu Arg Pro Val Pro Arg
1               5

<210> SEQ ID NO 1339
<211> LENGTH: 6
<212> TYPE: PRT
<213> ORGANISM: Homo sapiens

<400> SEQUENCE: 1339

Arg Pro Val Pro Arg Pro
1               5

<210> SEQ ID NO 1340
<211> LENGTH: 6
<212> TYPE: PRT
<213> ORGANISM: Homo sapiens

<400> SEQUENCE: 1340

Pro Val Pro Arg Pro Ala
1               5

<210> SEQ ID NO 1341
<211> LENGTH: 6
<212> TYPE: PRT
<213> ORGANISM: Homo sapiens

<400> SEQUENCE: 1341

Val Pro Arg Pro Ala Thr
1               5

<210> SEQ ID NO 1342
<211> LENGTH: 6
<212> TYPE: PRT
<213> ORGANISM: Homo sapiens

<400> SEQUENCE: 1342
```

Pro Arg Pro Ala Thr Val
1               5

<210> SEQ ID NO 1343
<211> LENGTH: 6
<212> TYPE: PRT
<213> ORGANISM: Homo sapiens

<400> SEQUENCE: 1343

Arg Pro Ala Thr Val Tyr
1               5

<210> SEQ ID NO 1344
<211> LENGTH: 6
<212> TYPE: PRT
<213> ORGANISM: Homo sapiens

<400> SEQUENCE: 1344

Pro Ala Thr Val Tyr Leu
1               5

<210> SEQ ID NO 1345
<211> LENGTH: 6
<212> TYPE: PRT
<213> ORGANISM: Homo sapiens

<400> SEQUENCE: 1345

Ala Thr Val Tyr Leu Gln
1               5

<210> SEQ ID NO 1346
<211> LENGTH: 6
<212> TYPE: PRT
<213> ORGANISM: Homo sapiens

<400> SEQUENCE: 1346

Thr Val Tyr Leu Gln Ile
1               5

<210> SEQ ID NO 1347
<211> LENGTH: 6
<212> TYPE: PRT
<213> ORGANISM: Homo sapiens

<400> SEQUENCE: 1347

Val Tyr Leu Gln Ile Leu
1               5

<210> SEQ ID NO 1348
<211> LENGTH: 6
<212> TYPE: PRT
<213> ORGANISM: Homo sapiens

<400> SEQUENCE: 1348

Tyr Leu Gln Ile Leu Arg
1               5

<210> SEQ ID NO 1349
<211> LENGTH: 6
<212> TYPE: PRT
<213> ORGANISM: Homo sapiens

<400> SEQUENCE: 1349

Leu Gln Ile Leu Arg Leu

```
1               5

<210> SEQ ID NO 1350
<211> LENGTH: 6
<212> TYPE: PRT
<213> ORGANISM: Homo sapiens

<400> SEQUENCE: 1350

Gln Ile Leu Arg Leu Lys
1               5

<210> SEQ ID NO 1351
<211> LENGTH: 6
<212> TYPE: PRT
<213> ORGANISM: Homo sapiens

<400> SEQUENCE: 1351

Ile Leu Arg Leu Lys Pro
1               5

<210> SEQ ID NO 1352
<211> LENGTH: 6
<212> TYPE: PRT
<213> ORGANISM: Homo sapiens

<400> SEQUENCE: 1352

Leu Arg Leu Lys Pro Leu
1               5

<210> SEQ ID NO 1353
<211> LENGTH: 6
<212> TYPE: PRT
<213> ORGANISM: Homo sapiens

<400> SEQUENCE: 1353

Arg Leu Lys Pro Leu Thr
1               5

<210> SEQ ID NO 1354
<211> LENGTH: 6
<212> TYPE: PRT
<213> ORGANISM: Homo sapiens

<400> SEQUENCE: 1354

Leu Lys Pro Leu Thr Gly
1               5

<210> SEQ ID NO 1355
<211> LENGTH: 6
<212> TYPE: PRT
<213> ORGANISM: Homo sapiens

<400> SEQUENCE: 1355

Lys Pro Leu Thr Gly Glu
1               5

<210> SEQ ID NO 1356
<211> LENGTH: 6
<212> TYPE: PRT
<213> ORGANISM: Homo sapiens

<400> SEQUENCE: 1356

Pro Leu Thr Gly Glu Gly
1               5
```

<210> SEQ ID NO 1357
<211> LENGTH: 6
<212> TYPE: PRT
<213> ORGANISM: Homo sapiens

<400> SEQUENCE: 1357

Leu Thr Gly Glu Gly Thr
1               5

<210> SEQ ID NO 1358
<211> LENGTH: 6
<212> TYPE: PRT
<213> ORGANISM: Homo sapiens

<400> SEQUENCE: 1358

Thr Gly Glu Gly Thr Ala
1               5

<210> SEQ ID NO 1359
<211> LENGTH: 6
<212> TYPE: PRT
<213> ORGANISM: Homo sapiens

<400> SEQUENCE: 1359

Gly Glu Gly Thr Ala Gly
1               5

<210> SEQ ID NO 1360
<211> LENGTH: 6
<212> TYPE: PRT
<213> ORGANISM: Homo sapiens

<400> SEQUENCE: 1360

Glu Gly Thr Ala Gly Gly
1               5

<210> SEQ ID NO 1361
<211> LENGTH: 6
<212> TYPE: PRT
<213> ORGANISM: Homo sapiens

<400> SEQUENCE: 1361

Gly Thr Ala Gly Gly Gly
1               5

<210> SEQ ID NO 1362
<211> LENGTH: 6
<212> TYPE: PRT
<213> ORGANISM: Homo sapiens

<400> SEQUENCE: 1362

Thr Ala Gly Gly Gly Gly
1               5

<210> SEQ ID NO 1363
<211> LENGTH: 6
<212> TYPE: PRT
<213> ORGANISM: Homo sapiens

<400> SEQUENCE: 1363

Ala Gly Gly Gly Gly Gly
1               5

<210> SEQ ID NO 1364

```
<211> LENGTH: 6
<212> TYPE: PRT
<213> ORGANISM: Homo sapiens

<400> SEQUENCE: 1364

Gly Gly Gly Gly Gly Gly
1               5

<210> SEQ ID NO 1365
<211> LENGTH: 6
<212> TYPE: PRT
<213> ORGANISM: Homo sapiens

<400> SEQUENCE: 1365

Gly Gly Gly Gly Gly Arg
1               5

<210> SEQ ID NO 1366
<211> LENGTH: 6
<212> TYPE: PRT
<213> ORGANISM: Homo sapiens

<400> SEQUENCE: 1366

Gly Gly Gly Gly Arg Arg
1               5

<210> SEQ ID NO 1367
<211> LENGTH: 6
<212> TYPE: PRT
<213> ORGANISM: Homo sapiens

<400> SEQUENCE: 1367

Gly Gly Gly Arg Arg His
1               5

<210> SEQ ID NO 1368
<211> LENGTH: 6
<212> TYPE: PRT
<213> ORGANISM: Homo sapiens

<400> SEQUENCE: 1368

Gly Gly Arg Arg His Ile
1               5

<210> SEQ ID NO 1369
<211> LENGTH: 6
<212> TYPE: PRT
<213> ORGANISM: Homo sapiens

<400> SEQUENCE: 1369

Gly Arg Arg His Ile Arg
1               5

<210> SEQ ID NO 1370
<211> LENGTH: 6
<212> TYPE: PRT
<213> ORGANISM: Homo sapiens

<400> SEQUENCE: 1370

Arg Arg His Ile Arg Ile
1               5

<210> SEQ ID NO 1371
<211> LENGTH: 6
<212> TYPE: PRT
```

```
<213> ORGANISM: Homo sapiens

<400> SEQUENCE: 1371

Arg His Ile Arg Ile Arg
1               5

<210> SEQ ID NO 1372
<211> LENGTH: 6
<212> TYPE: PRT
<213> ORGANISM: Homo sapiens

<400> SEQUENCE: 1372

His Ile Arg Ile Arg Ser
1               5

<210> SEQ ID NO 1373
<211> LENGTH: 6
<212> TYPE: PRT
<213> ORGANISM: Homo sapiens

<400> SEQUENCE: 1373

Ile Arg Ile Arg Ser Leu
1               5

<210> SEQ ID NO 1374
<211> LENGTH: 6
<212> TYPE: PRT
<213> ORGANISM: Homo sapiens

<400> SEQUENCE: 1374

Arg Ile Arg Ser Leu Lys
1               5

<210> SEQ ID NO 1375
<211> LENGTH: 6
<212> TYPE: PRT
<213> ORGANISM: Homo sapiens

<400> SEQUENCE: 1375

Ile Arg Ser Leu Lys Ile
1               5

<210> SEQ ID NO 1376
<211> LENGTH: 6
<212> TYPE: PRT
<213> ORGANISM: Homo sapiens

<400> SEQUENCE: 1376

Arg Ser Leu Lys Ile Glu
1               5

<210> SEQ ID NO 1377
<211> LENGTH: 6
<212> TYPE: PRT
<213> ORGANISM: Homo sapiens

<400> SEQUENCE: 1377

Ser Leu Lys Ile Glu Leu
1               5

<210> SEQ ID NO 1378
<211> LENGTH: 6
<212> TYPE: PRT
<213> ORGANISM: Homo sapiens
```

<400> SEQUENCE: 1378

Leu Lys Ile Glu Leu His
1               5

<210> SEQ ID NO 1379
<211> LENGTH: 6
<212> TYPE: PRT
<213> ORGANISM: Homo sapiens

<400> SEQUENCE: 1379

Lys Ile Glu Leu His Ser
1               5

<210> SEQ ID NO 1380
<211> LENGTH: 6
<212> TYPE: PRT
<213> ORGANISM: Homo sapiens

<400> SEQUENCE: 1380

Ile Glu Leu His Ser Arg
1               5

<210> SEQ ID NO 1381
<211> LENGTH: 6
<212> TYPE: PRT
<213> ORGANISM: Homo sapiens

<400> SEQUENCE: 1381

Glu Leu His Ser Arg Ser
1               5

<210> SEQ ID NO 1382
<211> LENGTH: 6
<212> TYPE: PRT
<213> ORGANISM: Homo sapiens

<400> SEQUENCE: 1382

Leu His Ser Arg Ser Gly
1               5

<210> SEQ ID NO 1383
<211> LENGTH: 6
<212> TYPE: PRT
<213> ORGANISM: Homo sapiens

<400> SEQUENCE: 1383

His Ser Arg Ser Gly His
1               5

<210> SEQ ID NO 1384
<211> LENGTH: 6
<212> TYPE: PRT
<213> ORGANISM: Homo sapiens

<400> SEQUENCE: 1384

Ser Arg Ser Gly His Trp
1               5

<210> SEQ ID NO 1385
<211> LENGTH: 6
<212> TYPE: PRT
<213> ORGANISM: Homo sapiens

<400> SEQUENCE: 1385

Arg Ser Gly His Trp Gln
1               5

<210> SEQ ID NO 1386
<211> LENGTH: 6
<212> TYPE: PRT
<213> ORGANISM: Homo sapiens

<400> SEQUENCE: 1386

Ser Gly His Trp Gln Ser
1               5

<210> SEQ ID NO 1387
<211> LENGTH: 6
<212> TYPE: PRT
<213> ORGANISM: Homo sapiens

<400> SEQUENCE: 1387

Gly His Trp Gln Ser Ile
1               5

<210> SEQ ID NO 1388
<211> LENGTH: 6
<212> TYPE: PRT
<213> ORGANISM: Homo sapiens

<400> SEQUENCE: 1388

His Trp Gln Ser Ile Asp
1               5

<210> SEQ ID NO 1389
<211> LENGTH: 6
<212> TYPE: PRT
<213> ORGANISM: Homo sapiens

<400> SEQUENCE: 1389

Trp Gln Ser Ile Asp Phe
1               5

<210> SEQ ID NO 1390
<211> LENGTH: 6
<212> TYPE: PRT
<213> ORGANISM: Homo sapiens

<400> SEQUENCE: 1390

Gln Ser Ile Asp Phe Lys
1               5

<210> SEQ ID NO 1391
<211> LENGTH: 6
<212> TYPE: PRT
<213> ORGANISM: Homo sapiens

<400> SEQUENCE: 1391

Ser Ile Asp Phe Lys Gln
1               5

<210> SEQ ID NO 1392
<211> LENGTH: 6
<212> TYPE: PRT
<213> ORGANISM: Homo sapiens

<400> SEQUENCE: 1392

Ile Asp Phe Lys Gln Val
1               5

<210> SEQ ID NO 1393
<211> LENGTH: 6
<212> TYPE: PRT
<213> ORGANISM: Homo sapiens

<400> SEQUENCE: 1393

Asp Phe Lys Gln Val Leu
1               5

<210> SEQ ID NO 1394
<211> LENGTH: 6
<212> TYPE: PRT
<213> ORGANISM: Homo sapiens

<400> SEQUENCE: 1394

Phe Lys Gln Val Leu His
1               5

<210> SEQ ID NO 1395
<211> LENGTH: 6
<212> TYPE: PRT
<213> ORGANISM: Homo sapiens

<400> SEQUENCE: 1395

Lys Gln Val Leu His Ser
1               5

<210> SEQ ID NO 1396
<211> LENGTH: 6
<212> TYPE: PRT
<213> ORGANISM: Homo sapiens

<400> SEQUENCE: 1396

Gln Val Leu His Ser Trp
1               5

<210> SEQ ID NO 1397
<211> LENGTH: 6
<212> TYPE: PRT
<213> ORGANISM: Homo sapiens

<400> SEQUENCE: 1397

Val Leu His Ser Trp Phe
1               5

<210> SEQ ID NO 1398
<211> LENGTH: 6
<212> TYPE: PRT
<213> ORGANISM: Homo sapiens

<400> SEQUENCE: 1398

Leu His Ser Trp Phe Arg
1               5

<210> SEQ ID NO 1399
<211> LENGTH: 6
<212> TYPE: PRT
<213> ORGANISM: Homo sapiens

<400> SEQUENCE: 1399

His Ser Trp Phe Arg Gln
1               5

```
<210> SEQ ID NO 1400
<211> LENGTH: 6
<212> TYPE: PRT
<213> ORGANISM: Homo sapiens

<400> SEQUENCE: 1400

Ser Trp Phe Arg Gln Pro
1               5

<210> SEQ ID NO 1401
<211> LENGTH: 6
<212> TYPE: PRT
<213> ORGANISM: Homo sapiens

<400> SEQUENCE: 1401

Trp Phe Arg Gln Pro Gln
1               5

<210> SEQ ID NO 1402
<211> LENGTH: 6
<212> TYPE: PRT
<213> ORGANISM: Homo sapiens

<400> SEQUENCE: 1402

Phe Arg Gln Pro Gln Ser
1               5

<210> SEQ ID NO 1403
<211> LENGTH: 6
<212> TYPE: PRT
<213> ORGANISM: Homo sapiens

<400> SEQUENCE: 1403

Arg Gln Pro Gln Ser Asn
1               5

<210> SEQ ID NO 1404
<211> LENGTH: 6
<212> TYPE: PRT
<213> ORGANISM: Homo sapiens

<400> SEQUENCE: 1404

Gln Pro Gln Ser Asn Trp
1               5

<210> SEQ ID NO 1405
<211> LENGTH: 6
<212> TYPE: PRT
<213> ORGANISM: Homo sapiens

<400> SEQUENCE: 1405

Pro Gln Ser Asn Trp Gly
1               5

<210> SEQ ID NO 1406
<211> LENGTH: 6
<212> TYPE: PRT
<213> ORGANISM: Homo sapiens

<400> SEQUENCE: 1406

Gln Ser Asn Trp Gly Ile
1               5

<210> SEQ ID NO 1407
<211> LENGTH: 6
```

```
<212> TYPE: PRT
<213> ORGANISM: Homo sapiens

<400> SEQUENCE: 1407

Ser Asn Trp Gly Ile Glu
1               5

<210> SEQ ID NO 1408
<211> LENGTH: 6
<212> TYPE: PRT
<213> ORGANISM: Homo sapiens

<400> SEQUENCE: 1408

Asn Trp Gly Ile Glu Ile
1               5

<210> SEQ ID NO 1409
<211> LENGTH: 6
<212> TYPE: PRT
<213> ORGANISM: Homo sapiens

<400> SEQUENCE: 1409

Trp Gly Ile Glu Ile Asn
1               5

<210> SEQ ID NO 1410
<211> LENGTH: 6
<212> TYPE: PRT
<213> ORGANISM: Homo sapiens

<400> SEQUENCE: 1410

Gly Ile Glu Ile Asn Ala
1               5

<210> SEQ ID NO 1411
<211> LENGTH: 6
<212> TYPE: PRT
<213> ORGANISM: Homo sapiens

<400> SEQUENCE: 1411

Ile Glu Ile Asn Ala Phe
1               5

<210> SEQ ID NO 1412
<211> LENGTH: 6
<212> TYPE: PRT
<213> ORGANISM: Homo sapiens

<400> SEQUENCE: 1412

Glu Ile Asn Ala Phe Asp
1               5

<210> SEQ ID NO 1413
<211> LENGTH: 6
<212> TYPE: PRT
<213> ORGANISM: Homo sapiens

<400> SEQUENCE: 1413

Ile Asn Ala Phe Asp Pro
1               5

<210> SEQ ID NO 1414
<211> LENGTH: 6
<212> TYPE: PRT
<213> ORGANISM: Homo sapiens
```

```
<400> SEQUENCE: 1414

Asn Ala Phe Asp Pro Ser
1               5

<210> SEQ ID NO 1415
<211> LENGTH: 6
<212> TYPE: PRT
<213> ORGANISM: Homo sapiens

<400> SEQUENCE: 1415

Ala Phe Asp Pro Ser Gly
1               5

<210> SEQ ID NO 1416
<211> LENGTH: 6
<212> TYPE: PRT
<213> ORGANISM: Homo sapiens

<400> SEQUENCE: 1416

Phe Asp Pro Ser Gly Thr
1               5

<210> SEQ ID NO 1417
<211> LENGTH: 6
<212> TYPE: PRT
<213> ORGANISM: Homo sapiens

<400> SEQUENCE: 1417

Asp Pro Ser Gly Thr Asp
1               5

<210> SEQ ID NO 1418
<211> LENGTH: 6
<212> TYPE: PRT
<213> ORGANISM: Homo sapiens

<400> SEQUENCE: 1418

Pro Ser Gly Thr Asp Leu
1               5

<210> SEQ ID NO 1419
<211> LENGTH: 6
<212> TYPE: PRT
<213> ORGANISM: Homo sapiens

<400> SEQUENCE: 1419

Ser Gly Thr Asp Leu Ala
1               5

<210> SEQ ID NO 1420
<211> LENGTH: 6
<212> TYPE: PRT
<213> ORGANISM: Homo sapiens

<400> SEQUENCE: 1420

Gly Thr Asp Leu Ala Val
1               5

<210> SEQ ID NO 1421
<211> LENGTH: 6
<212> TYPE: PRT
<213> ORGANISM: Homo sapiens

<400> SEQUENCE: 1421
```

Thr Asp Leu Ala Val Thr
1               5

<210> SEQ ID NO 1422
<211> LENGTH: 6
<212> TYPE: PRT
<213> ORGANISM: Homo sapiens

<400> SEQUENCE: 1422

Asp Leu Ala Val Thr Ser
1               5

<210> SEQ ID NO 1423
<211> LENGTH: 6
<212> TYPE: PRT
<213> ORGANISM: Homo sapiens

<400> SEQUENCE: 1423

Leu Ala Val Thr Ser Leu
1               5

<210> SEQ ID NO 1424
<211> LENGTH: 6
<212> TYPE: PRT
<213> ORGANISM: Homo sapiens

<400> SEQUENCE: 1424

Ala Val Thr Ser Leu Gly
1               5

<210> SEQ ID NO 1425
<211> LENGTH: 6
<212> TYPE: PRT
<213> ORGANISM: Homo sapiens

<400> SEQUENCE: 1425

Val Thr Ser Leu Gly Pro
1               5

<210> SEQ ID NO 1426
<211> LENGTH: 6
<212> TYPE: PRT
<213> ORGANISM: Homo sapiens

<400> SEQUENCE: 1426

Thr Ser Leu Gly Pro Gly
1               5

<210> SEQ ID NO 1427
<211> LENGTH: 6
<212> TYPE: PRT
<213> ORGANISM: Homo sapiens

<400> SEQUENCE: 1427

Ser Leu Gly Pro Gly Ala
1               5

<210> SEQ ID NO 1428
<211> LENGTH: 6
<212> TYPE: PRT
<213> ORGANISM: Homo sapiens

<400> SEQUENCE: 1428

Leu Gly Pro Gly Ala Glu 1               5

<210> SEQ ID NO 1429
<211> LENGTH: 6
<212> TYPE: PRT
<213> ORGANISM: Homo sapiens

<400> SEQUENCE: 1429

Gly Pro Gly Ala Glu Gly
1               5

<210> SEQ ID NO 1430
<211> LENGTH: 6
<212> TYPE: PRT
<213> ORGANISM: Homo sapiens

<400> SEQUENCE: 1430

Pro Gly Ala Glu Gly Leu
1               5

<210> SEQ ID NO 1431
<211> LENGTH: 6
<212> TYPE: PRT
<213> ORGANISM: Homo sapiens

<400> SEQUENCE: 1431

Gly Ala Glu Gly Leu His
1               5

<210> SEQ ID NO 1432
<211> LENGTH: 6
<212> TYPE: PRT
<213> ORGANISM: Homo sapiens

<400> SEQUENCE: 1432

Ala Glu Gly Leu His Pro
1               5

<210> SEQ ID NO 1433
<211> LENGTH: 6
<212> TYPE: PRT
<213> ORGANISM: Homo sapiens

<400> SEQUENCE: 1433

Glu Gly Leu His Pro Phe
1               5

<210> SEQ ID NO 1434
<211> LENGTH: 6
<212> TYPE: PRT
<213> ORGANISM: Homo sapiens

<400> SEQUENCE: 1434

Gly Leu His Pro Phe Met
1               5

<210> SEQ ID NO 1435
<211> LENGTH: 6
<212> TYPE: PRT
<213> ORGANISM: Homo sapiens

<400> SEQUENCE: 1435

Leu His Pro Phe Met Glu
1               5

```
<210> SEQ ID NO 1436
<211> LENGTH: 6
<212> TYPE: PRT
<213> ORGANISM: Homo sapiens

<400> SEQUENCE: 1436

His Pro Phe Met Glu Leu
1               5

<210> SEQ ID NO 1437
<211> LENGTH: 6
<212> TYPE: PRT
<213> ORGANISM: Homo sapiens

<400> SEQUENCE: 1437

Pro Phe Met Glu Leu Arg
1               5

<210> SEQ ID NO 1438
<211> LENGTH: 6
<212> TYPE: PRT
<213> ORGANISM: Homo sapiens

<400> SEQUENCE: 1438

Phe Met Glu Leu Arg Val
1               5

<210> SEQ ID NO 1439
<211> LENGTH: 6
<212> TYPE: PRT
<213> ORGANISM: Homo sapiens

<400> SEQUENCE: 1439

Met Glu Leu Arg Val Leu
1               5

<210> SEQ ID NO 1440
<211> LENGTH: 6
<212> TYPE: PRT
<213> ORGANISM: Homo sapiens

<400> SEQUENCE: 1440

Glu Leu Arg Val Leu Glu
1               5

<210> SEQ ID NO 1441
<211> LENGTH: 6
<212> TYPE: PRT
<213> ORGANISM: Homo sapiens

<400> SEQUENCE: 1441

Leu Arg Val Leu Glu Asn
1               5

<210> SEQ ID NO 1442
<211> LENGTH: 6
<212> TYPE: PRT
<213> ORGANISM: Homo sapiens

<400> SEQUENCE: 1442

Arg Val Leu Glu Asn Thr
1               5

<210> SEQ ID NO 1443
```

```
<211> LENGTH: 6
<212> TYPE: PRT
<213> ORGANISM: Homo sapiens

<400> SEQUENCE: 1443

Val Leu Glu Asn Thr Lys
1               5

<210> SEQ ID NO 1444
<211> LENGTH: 6
<212> TYPE: PRT
<213> ORGANISM: Homo sapiens

<400> SEQUENCE: 1444

Leu Glu Asn Thr Lys Arg
1               5

<210> SEQ ID NO 1445
<211> LENGTH: 6
<212> TYPE: PRT
<213> ORGANISM: Homo sapiens

<400> SEQUENCE: 1445

Glu Asn Thr Lys Arg Ser
1               5

<210> SEQ ID NO 1446
<211> LENGTH: 6
<212> TYPE: PRT
<213> ORGANISM: Homo sapiens

<400> SEQUENCE: 1446

Asn Thr Lys Arg Ser Arg
1               5

<210> SEQ ID NO 1447
<211> LENGTH: 6
<212> TYPE: PRT
<213> ORGANISM: Homo sapiens

<400> SEQUENCE: 1447

Thr Lys Arg Ser Arg Arg
1               5

<210> SEQ ID NO 1448
<211> LENGTH: 6
<212> TYPE: PRT
<213> ORGANISM: Homo sapiens

<400> SEQUENCE: 1448

Lys Arg Ser Arg Arg Asn
1               5

<210> SEQ ID NO 1449
<211> LENGTH: 6
<212> TYPE: PRT
<213> ORGANISM: Homo sapiens

<400> SEQUENCE: 1449

Arg Ser Arg Arg Asn Leu
1               5

<210> SEQ ID NO 1450
<211> LENGTH: 6
<212> TYPE: PRT
```

<213> ORGANISM: Homo sapiens

<400> SEQUENCE: 1450

Ser Arg Arg Asn Leu Gly
1               5

<210> SEQ ID NO 1451
<211> LENGTH: 6
<212> TYPE: PRT
<213> ORGANISM: Homo sapiens

<400> SEQUENCE: 1451

Arg Arg Asn Leu Gly Leu
1               5

<210> SEQ ID NO 1452
<211> LENGTH: 6
<212> TYPE: PRT
<213> ORGANISM: Homo sapiens

<400> SEQUENCE: 1452

Arg Asn Leu Gly Leu Asp
1               5

<210> SEQ ID NO 1453
<211> LENGTH: 6
<212> TYPE: PRT
<213> ORGANISM: Homo sapiens

<400> SEQUENCE: 1453

Asn Leu Gly Leu Asp Cys
1               5

<210> SEQ ID NO 1454
<211> LENGTH: 6
<212> TYPE: PRT
<213> ORGANISM: Homo sapiens

<400> SEQUENCE: 1454

Leu Gly Leu Asp Cys Asp
1               5

<210> SEQ ID NO 1455
<211> LENGTH: 6
<212> TYPE: PRT
<213> ORGANISM: Homo sapiens

<400> SEQUENCE: 1455

Gly Leu Asp Cys Asp Glu
1               5

<210> SEQ ID NO 1456
<211> LENGTH: 6
<212> TYPE: PRT
<213> ORGANISM: Homo sapiens

<400> SEQUENCE: 1456

Leu Asp Cys Asp Glu His
1               5

<210> SEQ ID NO 1457
<211> LENGTH: 6
<212> TYPE: PRT
<213> ORGANISM: Homo sapiens

```
<400> SEQUENCE: 1457

Asp Cys Asp Glu His Ser
1               5

<210> SEQ ID NO 1458
<211> LENGTH: 6
<212> TYPE: PRT
<213> ORGANISM: Homo sapiens

<400> SEQUENCE: 1458

Cys Asp Glu His Ser Ser
1               5

<210> SEQ ID NO 1459
<211> LENGTH: 6
<212> TYPE: PRT
<213> ORGANISM: Homo sapiens

<400> SEQUENCE: 1459

Asp Glu His Ser Ser Glu
1               5

<210> SEQ ID NO 1460
<211> LENGTH: 6
<212> TYPE: PRT
<213> ORGANISM: Homo sapiens

<400> SEQUENCE: 1460

Glu His Ser Ser Glu Ser
1               5

<210> SEQ ID NO 1461
<211> LENGTH: 6
<212> TYPE: PRT
<213> ORGANISM: Homo sapiens

<400> SEQUENCE: 1461

His Ser Ser Glu Ser Arg
1               5

<210> SEQ ID NO 1462
<211> LENGTH: 6
<212> TYPE: PRT
<213> ORGANISM: Homo sapiens

<400> SEQUENCE: 1462

Ser Ser Glu Ser Arg Cys
1               5

<210> SEQ ID NO 1463
<211> LENGTH: 6
<212> TYPE: PRT
<213> ORGANISM: Homo sapiens

<400> SEQUENCE: 1463

Ser Glu Ser Arg Cys Cys
1               5

<210> SEQ ID NO 1464
<211> LENGTH: 6
<212> TYPE: PRT
<213> ORGANISM: Homo sapiens

<400> SEQUENCE: 1464
```

Glu Ser Arg Cys Cys Arg
1               5

<210> SEQ ID NO 1465
<211> LENGTH: 6
<212> TYPE: PRT
<213> ORGANISM: Homo sapiens

<400> SEQUENCE: 1465

Ser Arg Cys Cys Arg Tyr
1               5

<210> SEQ ID NO 1466
<211> LENGTH: 6
<212> TYPE: PRT
<213> ORGANISM: Homo sapiens

<400> SEQUENCE: 1466

Arg Cys Cys Arg Tyr Pro
1               5

<210> SEQ ID NO 1467
<211> LENGTH: 6
<212> TYPE: PRT
<213> ORGANISM: Homo sapiens

<400> SEQUENCE: 1467

Cys Cys Arg Tyr Pro Leu
1               5

<210> SEQ ID NO 1468
<211> LENGTH: 6
<212> TYPE: PRT
<213> ORGANISM: Homo sapiens

<400> SEQUENCE: 1468

Cys Arg Tyr Pro Leu Thr
1               5

<210> SEQ ID NO 1469
<211> LENGTH: 6
<212> TYPE: PRT
<213> ORGANISM: Homo sapiens

<400> SEQUENCE: 1469

Arg Tyr Pro Leu Thr Val
1               5

<210> SEQ ID NO 1470
<211> LENGTH: 6
<212> TYPE: PRT
<213> ORGANISM: Homo sapiens

<400> SEQUENCE: 1470

Tyr Pro Leu Thr Val Asp
1               5

<210> SEQ ID NO 1471
<211> LENGTH: 6
<212> TYPE: PRT
<213> ORGANISM: Homo sapiens

<400> SEQUENCE: 1471

Pro Leu Thr Val Asp Phe
1               5

```
<210> SEQ ID NO 1472
<211> LENGTH: 6
<212> TYPE: PRT
<213> ORGANISM: Homo sapiens

<400> SEQUENCE: 1472

Leu Thr Val Asp Phe Glu
1               5

<210> SEQ ID NO 1473
<211> LENGTH: 6
<212> TYPE: PRT
<213> ORGANISM: Homo sapiens

<400> SEQUENCE: 1473

Thr Val Asp Phe Glu Ala
1               5

<210> SEQ ID NO 1474
<211> LENGTH: 6
<212> TYPE: PRT
<213> ORGANISM: Homo sapiens

<400> SEQUENCE: 1474

Val Asp Phe Glu Ala Phe
1               5

<210> SEQ ID NO 1475
<211> LENGTH: 6
<212> TYPE: PRT
<213> ORGANISM: Homo sapiens

<400> SEQUENCE: 1475

Asp Phe Glu Ala Phe Gly
1               5

<210> SEQ ID NO 1476
<211> LENGTH: 6
<212> TYPE: PRT
<213> ORGANISM: Homo sapiens

<400> SEQUENCE: 1476

Phe Glu Ala Phe Gly Trp
1               5

<210> SEQ ID NO 1477
<211> LENGTH: 6
<212> TYPE: PRT
<213> ORGANISM: Homo sapiens

<400> SEQUENCE: 1477

Glu Ala Phe Gly Trp Asp
1               5

<210> SEQ ID NO 1478
<211> LENGTH: 6
<212> TYPE: PRT
<213> ORGANISM: Homo sapiens

<400> SEQUENCE: 1478

Ala Phe Gly Trp Asp Trp
1               5
```

```
<210> SEQ ID NO 1479
<211> LENGTH: 6
<212> TYPE: PRT
<213> ORGANISM: Homo sapiens

<400> SEQUENCE: 1479

Phe Gly Trp Asp Trp Ile
1               5

<210> SEQ ID NO 1480
<211> LENGTH: 6
<212> TYPE: PRT
<213> ORGANISM: Homo sapiens

<400> SEQUENCE: 1480

Gly Trp Asp Trp Ile Ile
1               5

<210> SEQ ID NO 1481
<211> LENGTH: 6
<212> TYPE: PRT
<213> ORGANISM: Homo sapiens

<400> SEQUENCE: 1481

Trp Asp Trp Ile Ile Ala
1               5

<210> SEQ ID NO 1482
<211> LENGTH: 6
<212> TYPE: PRT
<213> ORGANISM: Homo sapiens

<400> SEQUENCE: 1482

Asp Trp Ile Ile Ala Pro
1               5

<210> SEQ ID NO 1483
<211> LENGTH: 6
<212> TYPE: PRT
<213> ORGANISM: Homo sapiens

<400> SEQUENCE: 1483

Trp Ile Ile Ala Pro Lys
1               5

<210> SEQ ID NO 1484
<211> LENGTH: 6
<212> TYPE: PRT
<213> ORGANISM: Homo sapiens

<400> SEQUENCE: 1484

Ile Ile Ala Pro Lys Arg
1               5

<210> SEQ ID NO 1485
<211> LENGTH: 6
<212> TYPE: PRT
<213> ORGANISM: Homo sapiens

<400> SEQUENCE: 1485

Ile Ala Pro Lys Arg Tyr
1               5

<210> SEQ ID NO 1486
<211> LENGTH: 6
```

```
<212> TYPE: PRT
<213> ORGANISM: Homo sapiens

<400> SEQUENCE: 1486

Ala Pro Lys Arg Tyr Lys
1               5

<210> SEQ ID NO 1487
<211> LENGTH: 6
<212> TYPE: PRT
<213> ORGANISM: Homo sapiens

<400> SEQUENCE: 1487

Pro Lys Arg Tyr Lys Ala
1               5

<210> SEQ ID NO 1488
<211> LENGTH: 6
<212> TYPE: PRT
<213> ORGANISM: Homo sapiens

<400> SEQUENCE: 1488

Lys Arg Tyr Lys Ala Asn
1               5

<210> SEQ ID NO 1489
<211> LENGTH: 6
<212> TYPE: PRT
<213> ORGANISM: Homo sapiens

<400> SEQUENCE: 1489

Arg Tyr Lys Ala Asn Tyr
1               5

<210> SEQ ID NO 1490
<211> LENGTH: 6
<212> TYPE: PRT
<213> ORGANISM: Homo sapiens

<400> SEQUENCE: 1490

Tyr Lys Ala Asn Tyr Cys
1               5

<210> SEQ ID NO 1491
<211> LENGTH: 6
<212> TYPE: PRT
<213> ORGANISM: Homo sapiens

<400> SEQUENCE: 1491

Lys Ala Asn Tyr Cys Ser
1               5

<210> SEQ ID NO 1492
<211> LENGTH: 6
<212> TYPE: PRT
<213> ORGANISM: Homo sapiens

<400> SEQUENCE: 1492

Ala Asn Tyr Cys Ser Gly
1               5

<210> SEQ ID NO 1493
<211> LENGTH: 6
<212> TYPE: PRT
<213> ORGANISM: Homo sapiens
```

```
<400> SEQUENCE: 1493

Asn Tyr Cys Ser Gly Gln
1               5

<210> SEQ ID NO 1494
<211> LENGTH: 6
<212> TYPE: PRT
<213> ORGANISM: Homo sapiens

<400> SEQUENCE: 1494

Tyr Cys Ser Gly Gln Cys
1               5

<210> SEQ ID NO 1495
<211> LENGTH: 6
<212> TYPE: PRT
<213> ORGANISM: Homo sapiens

<400> SEQUENCE: 1495

Cys Ser Gly Gln Cys Glu
1               5

<210> SEQ ID NO 1496
<211> LENGTH: 6
<212> TYPE: PRT
<213> ORGANISM: Homo sapiens

<400> SEQUENCE: 1496

Ser Gly Gln Cys Glu Tyr
1               5

<210> SEQ ID NO 1497
<211> LENGTH: 6
<212> TYPE: PRT
<213> ORGANISM: Homo sapiens

<400> SEQUENCE: 1497

Gly Gln Cys Glu Tyr Met
1               5

<210> SEQ ID NO 1498
<211> LENGTH: 6
<212> TYPE: PRT
<213> ORGANISM: Homo sapiens

<400> SEQUENCE: 1498

Gln Cys Glu Tyr Met Phe
1               5

<210> SEQ ID NO 1499
<211> LENGTH: 6
<212> TYPE: PRT
<213> ORGANISM: Homo sapiens

<400> SEQUENCE: 1499

Cys Glu Tyr Met Phe Met
1               5

<210> SEQ ID NO 1500
<211> LENGTH: 6
<212> TYPE: PRT
<213> ORGANISM: Homo sapiens

<400> SEQUENCE: 1500
```

Glu Tyr Met Phe Met Gln
1               5

<210> SEQ ID NO 1501
<211> LENGTH: 6
<212> TYPE: PRT
<213> ORGANISM: Homo sapiens

<400> SEQUENCE: 1501

Tyr Met Phe Met Gln Lys
1               5

<210> SEQ ID NO 1502
<211> LENGTH: 6
<212> TYPE: PRT
<213> ORGANISM: Homo sapiens

<400> SEQUENCE: 1502

Met Phe Met Gln Lys Tyr
1               5

<210> SEQ ID NO 1503
<211> LENGTH: 6
<212> TYPE: PRT
<213> ORGANISM: Homo sapiens

<400> SEQUENCE: 1503

Phe Met Gln Lys Tyr Pro
1               5

<210> SEQ ID NO 1504
<211> LENGTH: 6
<212> TYPE: PRT
<213> ORGANISM: Homo sapiens

<400> SEQUENCE: 1504

Met Gln Lys Tyr Pro His
1               5

<210> SEQ ID NO 1505
<211> LENGTH: 6
<212> TYPE: PRT
<213> ORGANISM: Homo sapiens

<400> SEQUENCE: 1505

Gln Lys Tyr Pro His Thr
1               5

<210> SEQ ID NO 1506
<211> LENGTH: 6
<212> TYPE: PRT
<213> ORGANISM: Homo sapiens

<400> SEQUENCE: 1506

Lys Tyr Pro His Thr His
1               5

<210> SEQ ID NO 1507
<211> LENGTH: 6
<212> TYPE: PRT
<213> ORGANISM: Homo sapiens

<400> SEQUENCE: 1507

Tyr Pro His Thr His Leu

```
<210> SEQ ID NO 1508
<211> LENGTH: 6
<212> TYPE: PRT
<213> ORGANISM: Homo sapiens

<400> SEQUENCE: 1508

Pro His Thr His Leu Val
1               5

<210> SEQ ID NO 1509
<211> LENGTH: 6
<212> TYPE: PRT
<213> ORGANISM: Homo sapiens

<400> SEQUENCE: 1509

His Thr His Leu Val Gln
1               5

<210> SEQ ID NO 1510
<211> LENGTH: 6
<212> TYPE: PRT
<213> ORGANISM: Homo sapiens

<400> SEQUENCE: 1510

Thr His Leu Val Gln Gln
1               5

<210> SEQ ID NO 1511
<211> LENGTH: 6
<212> TYPE: PRT
<213> ORGANISM: Homo sapiens

<400> SEQUENCE: 1511

His Leu Val Gln Gln Ala
1               5

<210> SEQ ID NO 1512
<211> LENGTH: 6
<212> TYPE: PRT
<213> ORGANISM: Homo sapiens

<400> SEQUENCE: 1512

Leu Val Gln Gln Ala Asn
1               5

<210> SEQ ID NO 1513
<211> LENGTH: 6
<212> TYPE: PRT
<213> ORGANISM: Homo sapiens

<400> SEQUENCE: 1513

Val Gln Gln Ala Asn Pro
1               5

<210> SEQ ID NO 1514
<211> LENGTH: 6
<212> TYPE: PRT
<213> ORGANISM: Homo sapiens

<400> SEQUENCE: 1514

Gln Gln Ala Asn Pro Arg
1               5
```

```
<210> SEQ ID NO 1515
<211> LENGTH: 6
<212> TYPE: PRT
<213> ORGANISM: Homo sapiens

<400> SEQUENCE: 1515

Gln Ala Asn Pro Arg Gly
1               5

<210> SEQ ID NO 1516
<211> LENGTH: 6
<212> TYPE: PRT
<213> ORGANISM: Homo sapiens

<400> SEQUENCE: 1516

Ala Asn Pro Arg Gly Ser
1               5

<210> SEQ ID NO 1517
<211> LENGTH: 6
<212> TYPE: PRT
<213> ORGANISM: Homo sapiens

<400> SEQUENCE: 1517

Asn Pro Arg Gly Ser Ala
1               5

<210> SEQ ID NO 1518
<211> LENGTH: 6
<212> TYPE: PRT
<213> ORGANISM: Homo sapiens

<400> SEQUENCE: 1518

Pro Arg Gly Ser Ala Gly
1               5

<210> SEQ ID NO 1519
<211> LENGTH: 6
<212> TYPE: PRT
<213> ORGANISM: Homo sapiens

<400> SEQUENCE: 1519

Arg Gly Ser Ala Gly Pro
1               5

<210> SEQ ID NO 1520
<211> LENGTH: 6
<212> TYPE: PRT
<213> ORGANISM: Homo sapiens

<400> SEQUENCE: 1520

Gly Ser Ala Gly Pro Cys
1               5

<210> SEQ ID NO 1521
<211> LENGTH: 6
<212> TYPE: PRT
<213> ORGANISM: Homo sapiens

<400> SEQUENCE: 1521

Ser Ala Gly Pro Cys Cys
1               5

<210> SEQ ID NO 1522
```

```
<211> LENGTH: 6
<212> TYPE: PRT
<213> ORGANISM: Homo sapiens

<400> SEQUENCE: 1522

Ala Gly Pro Cys Cys Thr
1               5

<210> SEQ ID NO 1523
<211> LENGTH: 6
<212> TYPE: PRT
<213> ORGANISM: Homo sapiens

<400> SEQUENCE: 1523

Gly Pro Cys Cys Thr Pro
1               5

<210> SEQ ID NO 1524
<211> LENGTH: 6
<212> TYPE: PRT
<213> ORGANISM: Homo sapiens

<400> SEQUENCE: 1524

Pro Cys Cys Thr Pro Thr
1               5

<210> SEQ ID NO 1525
<211> LENGTH: 6
<212> TYPE: PRT
<213> ORGANISM: Homo sapiens

<400> SEQUENCE: 1525

Cys Cys Thr Pro Thr Lys
1               5

<210> SEQ ID NO 1526
<211> LENGTH: 6
<212> TYPE: PRT
<213> ORGANISM: Homo sapiens

<400> SEQUENCE: 1526

Cys Thr Pro Thr Lys Met
1               5

<210> SEQ ID NO 1527
<211> LENGTH: 6
<212> TYPE: PRT
<213> ORGANISM: Homo sapiens

<400> SEQUENCE: 1527

Thr Pro Thr Lys Met Ser
1               5

<210> SEQ ID NO 1528
<211> LENGTH: 6
<212> TYPE: PRT
<213> ORGANISM: Homo sapiens

<400> SEQUENCE: 1528

Pro Thr Lys Met Ser Pro
1               5

<210> SEQ ID NO 1529
<211> LENGTH: 6
<212> TYPE: PRT
```

```
<213> ORGANISM: Homo sapiens

<400> SEQUENCE: 1529

Thr Lys Met Ser Pro Ile
1               5

<210> SEQ ID NO 1530
<211> LENGTH: 6
<212> TYPE: PRT
<213> ORGANISM: Homo sapiens

<400> SEQUENCE: 1530

Lys Met Ser Pro Ile Asn
1               5

<210> SEQ ID NO 1531
<211> LENGTH: 6
<212> TYPE: PRT
<213> ORGANISM: Homo sapiens

<400> SEQUENCE: 1531

Met Ser Pro Ile Asn Met
1               5

<210> SEQ ID NO 1532
<211> LENGTH: 6
<212> TYPE: PRT
<213> ORGANISM: Homo sapiens

<400> SEQUENCE: 1532

Ser Pro Ile Asn Met Leu
1               5

<210> SEQ ID NO 1533
<211> LENGTH: 6
<212> TYPE: PRT
<213> ORGANISM: Homo sapiens

<400> SEQUENCE: 1533

Pro Ile Asn Met Leu Tyr
1               5

<210> SEQ ID NO 1534
<211> LENGTH: 6
<212> TYPE: PRT
<213> ORGANISM: Homo sapiens

<400> SEQUENCE: 1534

Ile Asn Met Leu Tyr Phe
1               5

<210> SEQ ID NO 1535
<211> LENGTH: 6
<212> TYPE: PRT
<213> ORGANISM: Homo sapiens

<400> SEQUENCE: 1535

Asn Met Leu Tyr Phe Asn
1               5

<210> SEQ ID NO 1536
<211> LENGTH: 6
<212> TYPE: PRT
<213> ORGANISM: Homo sapiens
```

<400> SEQUENCE: 1536

Met Leu Tyr Phe Asn Asp
1               5

<210> SEQ ID NO 1537
<211> LENGTH: 6
<212> TYPE: PRT
<213> ORGANISM: Homo sapiens

<400> SEQUENCE: 1537

Leu Tyr Phe Asn Asp Lys
1               5

<210> SEQ ID NO 1538
<211> LENGTH: 6
<212> TYPE: PRT
<213> ORGANISM: Homo sapiens

<400> SEQUENCE: 1538

Tyr Phe Asn Asp Lys Gln
1               5

<210> SEQ ID NO 1539
<211> LENGTH: 6
<212> TYPE: PRT
<213> ORGANISM: Homo sapiens

<400> SEQUENCE: 1539

Phe Asn Asp Lys Gln Gln
1               5

<210> SEQ ID NO 1540
<211> LENGTH: 6
<212> TYPE: PRT
<213> ORGANISM: Homo sapiens

<400> SEQUENCE: 1540

Asn Asp Lys Gln Gln Ile
1               5

<210> SEQ ID NO 1541
<211> LENGTH: 6
<212> TYPE: PRT
<213> ORGANISM: Homo sapiens

<400> SEQUENCE: 1541

Asp Lys Gln Gln Ile Ile
1               5

<210> SEQ ID NO 1542
<211> LENGTH: 6
<212> TYPE: PRT
<213> ORGANISM: Homo sapiens

<400> SEQUENCE: 1542

Lys Gln Gln Ile Ile Tyr
1               5

<210> SEQ ID NO 1543
<211> LENGTH: 6
<212> TYPE: PRT
<213> ORGANISM: Homo sapiens

<400> SEQUENCE: 1543

Gln Gln Ile Ile Tyr Gly
1               5

<210> SEQ ID NO 1544
<211> LENGTH: 6
<212> TYPE: PRT
<213> ORGANISM: Homo sapiens

<400> SEQUENCE: 1544

Gln Ile Ile Tyr Gly Lys
1               5

<210> SEQ ID NO 1545
<211> LENGTH: 6
<212> TYPE: PRT
<213> ORGANISM: Homo sapiens

<400> SEQUENCE: 1545

Ile Ile Tyr Gly Lys Ile
1               5

<210> SEQ ID NO 1546
<211> LENGTH: 6
<212> TYPE: PRT
<213> ORGANISM: Homo sapiens

<400> SEQUENCE: 1546

Ile Tyr Gly Lys Ile Pro
1               5

<210> SEQ ID NO 1547
<211> LENGTH: 6
<212> TYPE: PRT
<213> ORGANISM: Homo sapiens

<400> SEQUENCE: 1547

Tyr Gly Lys Ile Pro Gly
1               5

<210> SEQ ID NO 1548
<211> LENGTH: 6
<212> TYPE: PRT
<213> ORGANISM: Homo sapiens

<400> SEQUENCE: 1548

Gly Lys Ile Pro Gly Met
1               5

<210> SEQ ID NO 1549
<211> LENGTH: 6
<212> TYPE: PRT
<213> ORGANISM: Homo sapiens

<400> SEQUENCE: 1549

Lys Ile Pro Gly Met Val
1               5

<210> SEQ ID NO 1550
<211> LENGTH: 6
<212> TYPE: PRT
<213> ORGANISM: Homo sapiens

<400> SEQUENCE: 1550

Ile Pro Gly Met Val Val
1               5

<210> SEQ ID NO 1551
<211> LENGTH: 6
<212> TYPE: PRT
<213> ORGANISM: Homo sapiens

<400> SEQUENCE: 1551

Pro Gly Met Val Val Asp
1               5

<210> SEQ ID NO 1552
<211> LENGTH: 6
<212> TYPE: PRT
<213> ORGANISM: Homo sapiens

<400> SEQUENCE: 1552

Gly Met Val Val Asp Arg
1               5

<210> SEQ ID NO 1553
<211> LENGTH: 6
<212> TYPE: PRT
<213> ORGANISM: Homo sapiens

<400> SEQUENCE: 1553

Met Val Val Asp Arg Cys
1               5

<210> SEQ ID NO 1554
<211> LENGTH: 6
<212> TYPE: PRT
<213> ORGANISM: Homo sapiens

<400> SEQUENCE: 1554

Val Val Asp Arg Cys Gly
1               5

<210> SEQ ID NO 1555
<211> LENGTH: 6
<212> TYPE: PRT
<213> ORGANISM: Homo sapiens

<400> SEQUENCE: 1555

Val Asp Arg Cys Gly Cys
1               5

<210> SEQ ID NO 1556
<211> LENGTH: 6
<212> TYPE: PRT
<213> ORGANISM: Homo sapiens

<400> SEQUENCE: 1556

Asp Arg Cys Gly Cys Ser
1               5

<210> SEQ ID NO 1557
<211> LENGTH: 7
<212> TYPE: PRT
<213> ORGANISM: Homo sapiens

<400> SEQUENCE: 1557

Met Val Leu Ala Ala Pro Leu
1               5

```
<210> SEQ ID NO 1558
<211> LENGTH: 7
<212> TYPE: PRT
<213> ORGANISM: Homo sapiens

<400> SEQUENCE: 1558

Val Leu Ala Ala Pro Leu Leu
1               5

<210> SEQ ID NO 1559
<211> LENGTH: 7
<212> TYPE: PRT
<213> ORGANISM: Homo sapiens

<400> SEQUENCE: 1559

Leu Ala Ala Pro Leu Leu Leu
1               5

<210> SEQ ID NO 1560
<211> LENGTH: 7
<212> TYPE: PRT
<213> ORGANISM: Homo sapiens

<400> SEQUENCE: 1560

Ala Ala Pro Leu Leu Leu Gly
1               5

<210> SEQ ID NO 1561
<211> LENGTH: 7
<212> TYPE: PRT
<213> ORGANISM: Homo sapiens

<400> SEQUENCE: 1561

Ala Pro Leu Leu Leu Gly Phe
1               5

<210> SEQ ID NO 1562
<211> LENGTH: 7
<212> TYPE: PRT
<213> ORGANISM: Homo sapiens

<400> SEQUENCE: 1562

Pro Leu Leu Leu Gly Phe Leu
1               5

<210> SEQ ID NO 1563
<211> LENGTH: 7
<212> TYPE: PRT
<213> ORGANISM: Homo sapiens

<400> SEQUENCE: 1563

Leu Leu Leu Gly Phe Leu Leu
1               5

<210> SEQ ID NO 1564
<211> LENGTH: 7
<212> TYPE: PRT
<213> ORGANISM: Homo sapiens

<400> SEQUENCE: 1564

Leu Leu Gly Phe Leu Leu Leu
1               5

<210> SEQ ID NO 1565
<211> LENGTH: 7
```

<212> TYPE: PRT
<213> ORGANISM: Homo sapiens

<400> SEQUENCE: 1565

Leu Gly Phe Leu Leu Leu Ala
1               5

<210> SEQ ID NO 1566
<211> LENGTH: 7
<212> TYPE: PRT
<213> ORGANISM: Homo sapiens

<400> SEQUENCE: 1566

Gly Phe Leu Leu Leu Ala Leu
1               5

<210> SEQ ID NO 1567
<211> LENGTH: 7
<212> TYPE: PRT
<213> ORGANISM: Homo sapiens

<400> SEQUENCE: 1567

Phe Leu Leu Leu Ala Leu Glu
1               5

<210> SEQ ID NO 1568
<211> LENGTH: 7
<212> TYPE: PRT
<213> ORGANISM: Homo sapiens

<400> SEQUENCE: 1568

Leu Leu Leu Ala Leu Glu Leu
1               5

<210> SEQ ID NO 1569
<211> LENGTH: 7
<212> TYPE: PRT
<213> ORGANISM: Homo sapiens

<400> SEQUENCE: 1569

Leu Leu Ala Leu Glu Leu Arg
1               5

<210> SEQ ID NO 1570
<211> LENGTH: 7
<212> TYPE: PRT
<213> ORGANISM: Homo sapiens

<400> SEQUENCE: 1570

Leu Ala Leu Glu Leu Arg Pro
1               5

<210> SEQ ID NO 1571
<211> LENGTH: 7
<212> TYPE: PRT
<213> ORGANISM: Homo sapiens

<400> SEQUENCE: 1571

Ala Leu Glu Leu Arg Pro Arg
1               5

<210> SEQ ID NO 1572
<211> LENGTH: 7
<212> TYPE: PRT
<213> ORGANISM: Homo sapiens

<400> SEQUENCE: 1572

Leu Glu Leu Arg Pro Arg Gly
1               5

<210> SEQ ID NO 1573
<211> LENGTH: 7
<212> TYPE: PRT
<213> ORGANISM: Homo sapiens

<400> SEQUENCE: 1573

Glu Leu Arg Pro Arg Gly Glu
1               5

<210> SEQ ID NO 1574
<211> LENGTH: 7
<212> TYPE: PRT
<213> ORGANISM: Homo sapiens

<400> SEQUENCE: 1574

Leu Arg Pro Arg Gly Glu Ala
1               5

<210> SEQ ID NO 1575
<211> LENGTH: 7
<212> TYPE: PRT
<213> ORGANISM: Homo sapiens

<400> SEQUENCE: 1575

Arg Pro Arg Gly Glu Ala Ala
1               5

<210> SEQ ID NO 1576
<211> LENGTH: 7
<212> TYPE: PRT
<213> ORGANISM: Homo sapiens

<400> SEQUENCE: 1576

Pro Arg Gly Glu Ala Ala Glu
1               5

<210> SEQ ID NO 1577
<211> LENGTH: 7
<212> TYPE: PRT
<213> ORGANISM: Homo sapiens

<400> SEQUENCE: 1577

Arg Gly Glu Ala Ala Glu Gly
1               5

<210> SEQ ID NO 1578
<211> LENGTH: 7
<212> TYPE: PRT
<213> ORGANISM: Homo sapiens

<400> SEQUENCE: 1578

Gly Glu Ala Ala Glu Gly Pro
1               5

<210> SEQ ID NO 1579
<211> LENGTH: 7
<212> TYPE: PRT
<213> ORGANISM: Homo sapiens

<400> SEQUENCE: 1579

Glu Ala Ala Glu Gly Pro Ala
1               5

<210> SEQ ID NO 1580
<211> LENGTH: 7
<212> TYPE: PRT
<213> ORGANISM: Homo sapiens

<400> SEQUENCE: 1580

Ala Ala Glu Gly Pro Ala Ala
1               5

<210> SEQ ID NO 1581
<211> LENGTH: 7
<212> TYPE: PRT
<213> ORGANISM: Homo sapiens

<400> SEQUENCE: 1581

Ala Glu Gly Pro Ala Ala Ala
1               5

<210> SEQ ID NO 1582
<211> LENGTH: 7
<212> TYPE: PRT
<213> ORGANISM: Homo sapiens

<400> SEQUENCE: 1582

Glu Gly Pro Ala Ala Ala Ala
1               5

<210> SEQ ID NO 1583
<211> LENGTH: 7
<212> TYPE: PRT
<213> ORGANISM: Homo sapiens

<400> SEQUENCE: 1583

Gly Pro Ala Ala Ala Ala Ala
1               5

<210> SEQ ID NO 1584
<211> LENGTH: 7
<212> TYPE: PRT
<213> ORGANISM: Homo sapiens

<400> SEQUENCE: 1584

Pro Ala Ala Ala Ala Ala Ala
1               5

<210> SEQ ID NO 1585
<211> LENGTH: 7
<212> TYPE: PRT
<213> ORGANISM: Homo sapiens

<400> SEQUENCE: 1585

Ala Ala Ala Ala Ala Ala Ala
1               5

<210> SEQ ID NO 1586
<211> LENGTH: 7
<212> TYPE: PRT
<213> ORGANISM: Homo sapiens

<400> SEQUENCE: 1586

Ala Ala Ala Ala Ala Ala Gly

```
1               5

<210> SEQ ID NO 1587
<211> LENGTH: 7
<212> TYPE: PRT
<213> ORGANISM: Homo sapiens

<400> SEQUENCE: 1587

Ala Ala Ala Ala Ala Gly Val
1               5

<210> SEQ ID NO 1588
<211> LENGTH: 7
<212> TYPE: PRT
<213> ORGANISM: Homo sapiens

<400> SEQUENCE: 1588

Ala Ala Ala Ala Gly Val Gly
1               5

<210> SEQ ID NO 1589
<211> LENGTH: 7
<212> TYPE: PRT
<213> ORGANISM: Homo sapiens

<400> SEQUENCE: 1589

Ala Ala Ala Gly Val Gly Gly
1               5

<210> SEQ ID NO 1590
<211> LENGTH: 7
<212> TYPE: PRT
<213> ORGANISM: Homo sapiens

<400> SEQUENCE: 1590

Ala Ala Gly Val Gly Gly Glu
1               5

<210> SEQ ID NO 1591
<211> LENGTH: 7
<212> TYPE: PRT
<213> ORGANISM: Homo sapiens

<400> SEQUENCE: 1591

Ala Gly Val Gly Gly Glu Arg
1               5

<210> SEQ ID NO 1592
<211> LENGTH: 7
<212> TYPE: PRT
<213> ORGANISM: Homo sapiens

<400> SEQUENCE: 1592

Gly Val Gly Gly Glu Arg Ser
1               5

<210> SEQ ID NO 1593
<211> LENGTH: 7
<212> TYPE: PRT
<213> ORGANISM: Homo sapiens

<400> SEQUENCE: 1593

Val Gly Gly Glu Arg Ser Ser
1               5
```

<210> SEQ ID NO 1594
<211> LENGTH: 7
<212> TYPE: PRT
<213> ORGANISM: Homo sapiens

<400> SEQUENCE: 1594

Gly Gly Glu Arg Ser Ser Arg
1               5

<210> SEQ ID NO 1595
<211> LENGTH: 7
<212> TYPE: PRT
<213> ORGANISM: Homo sapiens

<400> SEQUENCE: 1595

Gly Glu Arg Ser Ser Arg Pro
1               5

<210> SEQ ID NO 1596
<211> LENGTH: 7
<212> TYPE: PRT
<213> ORGANISM: Homo sapiens

<400> SEQUENCE: 1596

Glu Arg Ser Ser Arg Pro Ala
1               5

<210> SEQ ID NO 1597
<211> LENGTH: 7
<212> TYPE: PRT
<213> ORGANISM: Homo sapiens

<400> SEQUENCE: 1597

Arg Ser Ser Arg Pro Ala Pro
1               5

<210> SEQ ID NO 1598
<211> LENGTH: 7
<212> TYPE: PRT
<213> ORGANISM: Homo sapiens

<400> SEQUENCE: 1598

Ser Ser Arg Pro Ala Pro Ser
1               5

<210> SEQ ID NO 1599
<211> LENGTH: 7
<212> TYPE: PRT
<213> ORGANISM: Homo sapiens

<400> SEQUENCE: 1599

Ser Arg Pro Ala Pro Ser Val
1               5

<210> SEQ ID NO 1600
<211> LENGTH: 7
<212> TYPE: PRT
<213> ORGANISM: Homo sapiens

<400> SEQUENCE: 1600

Arg Pro Ala Pro Ser Val Ala
1               5

<210> SEQ ID NO 1601

```
<211> LENGTH: 7
<212> TYPE: PRT
<213> ORGANISM: Homo sapiens

<400> SEQUENCE: 1601

Pro Ala Pro Ser Val Ala Pro
1               5

<210> SEQ ID NO 1602
<211> LENGTH: 7
<212> TYPE: PRT
<213> ORGANISM: Homo sapiens

<400> SEQUENCE: 1602

Ala Pro Ser Val Ala Pro Glu
1               5

<210> SEQ ID NO 1603
<211> LENGTH: 7
<212> TYPE: PRT
<213> ORGANISM: Homo sapiens

<400> SEQUENCE: 1603

Pro Ser Val Ala Pro Glu Pro
1               5

<210> SEQ ID NO 1604
<211> LENGTH: 7
<212> TYPE: PRT
<213> ORGANISM: Homo sapiens

<400> SEQUENCE: 1604

Ser Val Ala Pro Glu Pro Asp
1               5

<210> SEQ ID NO 1605
<211> LENGTH: 7
<212> TYPE: PRT
<213> ORGANISM: Homo sapiens

<400> SEQUENCE: 1605

Val Ala Pro Glu Pro Asp Gly
1               5

<210> SEQ ID NO 1606
<211> LENGTH: 7
<212> TYPE: PRT
<213> ORGANISM: Homo sapiens

<400> SEQUENCE: 1606

Ala Pro Glu Pro Asp Gly Cys
1               5

<210> SEQ ID NO 1607
<211> LENGTH: 7
<212> TYPE: PRT
<213> ORGANISM: Homo sapiens

<400> SEQUENCE: 1607

Pro Glu Pro Asp Gly Cys Pro
1               5

<210> SEQ ID NO 1608
<211> LENGTH: 7
<212> TYPE: PRT
```

```
<213> ORGANISM: Homo sapiens

<400> SEQUENCE: 1608

Glu Pro Asp Gly Cys Pro Val
1               5

<210> SEQ ID NO 1609
<211> LENGTH: 7
<212> TYPE: PRT
<213> ORGANISM: Homo sapiens

<400> SEQUENCE: 1609

Pro Asp Gly Cys Pro Val Cys
1               5

<210> SEQ ID NO 1610
<211> LENGTH: 7
<212> TYPE: PRT
<213> ORGANISM: Homo sapiens

<400> SEQUENCE: 1610

Asp Gly Cys Pro Val Cys Val
1               5

<210> SEQ ID NO 1611
<211> LENGTH: 7
<212> TYPE: PRT
<213> ORGANISM: Homo sapiens

<400> SEQUENCE: 1611

Gly Cys Pro Val Cys Val Trp
1               5

<210> SEQ ID NO 1612
<211> LENGTH: 7
<212> TYPE: PRT
<213> ORGANISM: Homo sapiens

<400> SEQUENCE: 1612

Cys Pro Val Cys Val Trp Arg
1               5

<210> SEQ ID NO 1613
<211> LENGTH: 7
<212> TYPE: PRT
<213> ORGANISM: Homo sapiens

<400> SEQUENCE: 1613

Pro Val Cys Val Trp Arg Gln
1               5

<210> SEQ ID NO 1614
<211> LENGTH: 7
<212> TYPE: PRT
<213> ORGANISM: Homo sapiens

<400> SEQUENCE: 1614

Val Cys Val Trp Arg Gln His
1               5

<210> SEQ ID NO 1615
<211> LENGTH: 7
<212> TYPE: PRT
<213> ORGANISM: Homo sapiens
```

```
<400> SEQUENCE: 1615

Cys Val Trp Arg Gln His Ser
1               5

<210> SEQ ID NO 1616
<211> LENGTH: 7
<212> TYPE: PRT
<213> ORGANISM: Homo sapiens

<400> SEQUENCE: 1616

Val Trp Arg Gln His Ser Arg
1               5

<210> SEQ ID NO 1617
<211> LENGTH: 7
<212> TYPE: PRT
<213> ORGANISM: Homo sapiens

<400> SEQUENCE: 1617

Trp Arg Gln His Ser Arg Glu
1               5

<210> SEQ ID NO 1618
<211> LENGTH: 7
<212> TYPE: PRT
<213> ORGANISM: Homo sapiens

<400> SEQUENCE: 1618

Arg Gln His Ser Arg Glu Leu
1               5

<210> SEQ ID NO 1619
<211> LENGTH: 7
<212> TYPE: PRT
<213> ORGANISM: Homo sapiens

<400> SEQUENCE: 1619

Gln His Ser Arg Glu Leu Arg
1               5

<210> SEQ ID NO 1620
<211> LENGTH: 7
<212> TYPE: PRT
<213> ORGANISM: Homo sapiens

<400> SEQUENCE: 1620

His Ser Arg Glu Leu Arg Leu
1               5

<210> SEQ ID NO 1621
<211> LENGTH: 7
<212> TYPE: PRT
<213> ORGANISM: Homo sapiens

<400> SEQUENCE: 1621

Ser Arg Glu Leu Arg Leu Glu
1               5

<210> SEQ ID NO 1622
<211> LENGTH: 7
<212> TYPE: PRT
<213> ORGANISM: Homo sapiens

<400> SEQUENCE: 1622
```

Arg Glu Leu Arg Leu Glu Ser
1               5

<210> SEQ ID NO 1623
<211> LENGTH: 7
<212> TYPE: PRT
<213> ORGANISM: Homo sapiens

<400> SEQUENCE: 1623

Glu Leu Arg Leu Glu Ser Ile
1               5

<210> SEQ ID NO 1624
<211> LENGTH: 7
<212> TYPE: PRT
<213> ORGANISM: Homo sapiens

<400> SEQUENCE: 1624

Leu Arg Leu Glu Ser Ile Lys
1               5

<210> SEQ ID NO 1625
<211> LENGTH: 7
<212> TYPE: PRT
<213> ORGANISM: Homo sapiens

<400> SEQUENCE: 1625

Arg Leu Glu Ser Ile Lys Ser
1               5

<210> SEQ ID NO 1626
<211> LENGTH: 7
<212> TYPE: PRT
<213> ORGANISM: Homo sapiens

<400> SEQUENCE: 1626

Leu Glu Ser Ile Lys Ser Gln
1               5

<210> SEQ ID NO 1627
<211> LENGTH: 7
<212> TYPE: PRT
<213> ORGANISM: Homo sapiens

<400> SEQUENCE: 1627

Glu Ser Ile Lys Ser Gln Ile
1               5

<210> SEQ ID NO 1628
<211> LENGTH: 7
<212> TYPE: PRT
<213> ORGANISM: Homo sapiens

<400> SEQUENCE: 1628

Ser Ile Lys Ser Gln Ile Leu
1               5

<210> SEQ ID NO 1629
<211> LENGTH: 7
<212> TYPE: PRT
<213> ORGANISM: Homo sapiens

<400> SEQUENCE: 1629

Ile Lys Ser Gln Ile Leu Ser
1               5

<210> SEQ ID NO 1630
<211> LENGTH: 7
<212> TYPE: PRT
<213> ORGANISM: Homo sapiens

<400> SEQUENCE: 1630

Lys Ser Gln Ile Leu Ser Lys
1               5

<210> SEQ ID NO 1631
<211> LENGTH: 7
<212> TYPE: PRT
<213> ORGANISM: Homo sapiens

<400> SEQUENCE: 1631

Ser Gln Ile Leu Ser Lys Leu
1               5

<210> SEQ ID NO 1632
<211> LENGTH: 7
<212> TYPE: PRT
<213> ORGANISM: Homo sapiens

<400> SEQUENCE: 1632

Gln Ile Leu Ser Lys Leu Arg
1               5

<210> SEQ ID NO 1633
<211> LENGTH: 7
<212> TYPE: PRT
<213> ORGANISM: Homo sapiens

<400> SEQUENCE: 1633

Ile Leu Ser Lys Leu Arg Leu
1               5

<210> SEQ ID NO 1634
<211> LENGTH: 7
<212> TYPE: PRT
<213> ORGANISM: Homo sapiens

<400> SEQUENCE: 1634

Leu Ser Lys Leu Arg Leu Lys
1               5

<210> SEQ ID NO 1635
<211> LENGTH: 7
<212> TYPE: PRT
<213> ORGANISM: Homo sapiens

<400> SEQUENCE: 1635

Ser Lys Leu Arg Leu Lys Glu
1               5

<210> SEQ ID NO 1636
<211> LENGTH: 7
<212> TYPE: PRT
<213> ORGANISM: Homo sapiens

<400> SEQUENCE: 1636

Lys Leu Arg Leu Lys Glu Ala
1               5

```
<210> SEQ ID NO 1637
<211> LENGTH: 7
<212> TYPE: PRT
<213> ORGANISM: Homo sapiens

<400> SEQUENCE: 1637

Leu Arg Leu Lys Glu Ala Pro
1               5

<210> SEQ ID NO 1638
<211> LENGTH: 7
<212> TYPE: PRT
<213> ORGANISM: Homo sapiens

<400> SEQUENCE: 1638

Arg Leu Lys Glu Ala Pro Asn
1               5

<210> SEQ ID NO 1639
<211> LENGTH: 7
<212> TYPE: PRT
<213> ORGANISM: Homo sapiens

<400> SEQUENCE: 1639

Leu Lys Glu Ala Pro Asn Ile
1               5

<210> SEQ ID NO 1640
<211> LENGTH: 7
<212> TYPE: PRT
<213> ORGANISM: Homo sapiens

<400> SEQUENCE: 1640

Lys Glu Ala Pro Asn Ile Ser
1               5

<210> SEQ ID NO 1641
<211> LENGTH: 7
<212> TYPE: PRT
<213> ORGANISM: Homo sapiens

<400> SEQUENCE: 1641

Glu Ala Pro Asn Ile Ser Arg
1               5

<210> SEQ ID NO 1642
<211> LENGTH: 7
<212> TYPE: PRT
<213> ORGANISM: Homo sapiens

<400> SEQUENCE: 1642

Ala Pro Asn Ile Ser Arg Glu
1               5

<210> SEQ ID NO 1643
<211> LENGTH: 7
<212> TYPE: PRT
<213> ORGANISM: Homo sapiens

<400> SEQUENCE: 1643

Pro Asn Ile Ser Arg Glu Val
1               5

<210> SEQ ID NO 1644
<211> LENGTH: 7
```

```
<212> TYPE: PRT
<213> ORGANISM: Homo sapiens

<400> SEQUENCE: 1644

Asn Ile Ser Arg Glu Val Val
1               5

<210> SEQ ID NO 1645
<211> LENGTH: 7
<212> TYPE: PRT
<213> ORGANISM: Homo sapiens

<400> SEQUENCE: 1645

Ile Ser Arg Glu Val Val Lys
1               5

<210> SEQ ID NO 1646
<211> LENGTH: 7
<212> TYPE: PRT
<213> ORGANISM: Homo sapiens

<400> SEQUENCE: 1646

Ser Arg Glu Val Val Lys Gln
1               5

<210> SEQ ID NO 1647
<211> LENGTH: 7
<212> TYPE: PRT
<213> ORGANISM: Homo sapiens

<400> SEQUENCE: 1647

Arg Glu Val Val Lys Gln Leu
1               5

<210> SEQ ID NO 1648
<211> LENGTH: 7
<212> TYPE: PRT
<213> ORGANISM: Homo sapiens

<400> SEQUENCE: 1648

Glu Val Val Lys Gln Leu Leu
1               5

<210> SEQ ID NO 1649
<211> LENGTH: 7
<212> TYPE: PRT
<213> ORGANISM: Homo sapiens

<400> SEQUENCE: 1649

Val Val Lys Gln Leu Leu Pro
1               5

<210> SEQ ID NO 1650
<211> LENGTH: 7
<212> TYPE: PRT
<213> ORGANISM: Homo sapiens

<400> SEQUENCE: 1650

Val Lys Gln Leu Leu Pro Lys
1               5

<210> SEQ ID NO 1651
<211> LENGTH: 7
<212> TYPE: PRT
<213> ORGANISM: Homo sapiens
```

<400> SEQUENCE: 1651

Lys Gln Leu Leu Pro Lys Ala
1               5

<210> SEQ ID NO 1652
<211> LENGTH: 7
<212> TYPE: PRT
<213> ORGANISM: Homo sapiens

<400> SEQUENCE: 1652

Gln Leu Leu Pro Lys Ala Pro
1               5

<210> SEQ ID NO 1653
<211> LENGTH: 7
<212> TYPE: PRT
<213> ORGANISM: Homo sapiens

<400> SEQUENCE: 1653

Leu Leu Pro Lys Ala Pro Pro
1               5

<210> SEQ ID NO 1654
<211> LENGTH: 7
<212> TYPE: PRT
<213> ORGANISM: Homo sapiens

<400> SEQUENCE: 1654

Leu Pro Lys Ala Pro Pro Leu
1               5

<210> SEQ ID NO 1655
<211> LENGTH: 7
<212> TYPE: PRT
<213> ORGANISM: Homo sapiens

<400> SEQUENCE: 1655

Pro Lys Ala Pro Pro Leu Gln
1               5

<210> SEQ ID NO 1656
<211> LENGTH: 7
<212> TYPE: PRT
<213> ORGANISM: Homo sapiens

<400> SEQUENCE: 1656

Lys Ala Pro Pro Leu Gln Gln
1               5

<210> SEQ ID NO 1657
<211> LENGTH: 7
<212> TYPE: PRT
<213> ORGANISM: Homo sapiens

<400> SEQUENCE: 1657

Ala Pro Pro Leu Gln Gln Ile
1               5

<210> SEQ ID NO 1658
<211> LENGTH: 7
<212> TYPE: PRT
<213> ORGANISM: Homo sapiens

<400> SEQUENCE: 1658

```
Pro Pro Leu Gln Gln Ile Leu
1               5

<210> SEQ ID NO 1659
<211> LENGTH: 7
<212> TYPE: PRT
<213> ORGANISM: Homo sapiens

<400> SEQUENCE: 1659

Pro Leu Gln Gln Ile Leu Asp
1               5

<210> SEQ ID NO 1660
<211> LENGTH: 7
<212> TYPE: PRT
<213> ORGANISM: Homo sapiens

<400> SEQUENCE: 1660

Leu Gln Gln Ile Leu Asp Leu
1               5

<210> SEQ ID NO 1661
<211> LENGTH: 7
<212> TYPE: PRT
<213> ORGANISM: Homo sapiens

<400> SEQUENCE: 1661

Gln Gln Ile Leu Asp Leu His
1               5

<210> SEQ ID NO 1662
<211> LENGTH: 7
<212> TYPE: PRT
<213> ORGANISM: Homo sapiens

<400> SEQUENCE: 1662

Gln Ile Leu Asp Leu His Asp
1               5

<210> SEQ ID NO 1663
<211> LENGTH: 7
<212> TYPE: PRT
<213> ORGANISM: Homo sapiens

<400> SEQUENCE: 1663

Ile Leu Asp Leu His Asp Phe
1               5

<210> SEQ ID NO 1664
<211> LENGTH: 7
<212> TYPE: PRT
<213> ORGANISM: Homo sapiens

<400> SEQUENCE: 1664

Leu Asp Leu His Asp Phe Gln
1               5

<210> SEQ ID NO 1665
<211> LENGTH: 7
<212> TYPE: PRT
<213> ORGANISM: Homo sapiens

<400> SEQUENCE: 1665

Asp Leu His Asp Phe Gln Gly
```

```
1               5

<210> SEQ ID NO 1666
<211> LENGTH: 7
<212> TYPE: PRT
<213> ORGANISM: Homo sapiens

<400> SEQUENCE: 1666

Leu His Asp Phe Gln Gly Asp
1               5

<210> SEQ ID NO 1667
<211> LENGTH: 7
<212> TYPE: PRT
<213> ORGANISM: Homo sapiens

<400> SEQUENCE: 1667

His Asp Phe Gln Gly Asp Ala
1               5

<210> SEQ ID NO 1668
<211> LENGTH: 7
<212> TYPE: PRT
<213> ORGANISM: Homo sapiens

<400> SEQUENCE: 1668

Asp Phe Gln Gly Asp Ala Leu
1               5

<210> SEQ ID NO 1669
<211> LENGTH: 7
<212> TYPE: PRT
<213> ORGANISM: Homo sapiens

<400> SEQUENCE: 1669

Phe Gln Gly Asp Ala Leu Gln
1               5

<210> SEQ ID NO 1670
<211> LENGTH: 7
<212> TYPE: PRT
<213> ORGANISM: Homo sapiens

<400> SEQUENCE: 1670

Gln Gly Asp Ala Leu Gln Pro
1               5

<210> SEQ ID NO 1671
<211> LENGTH: 7
<212> TYPE: PRT
<213> ORGANISM: Homo sapiens

<400> SEQUENCE: 1671

Gly Asp Ala Leu Gln Pro Glu
1               5

<210> SEQ ID NO 1672
<211> LENGTH: 7
<212> TYPE: PRT
<213> ORGANISM: Homo sapiens

<400> SEQUENCE: 1672

Asp Ala Leu Gln Pro Glu Asp
1               5
```

<210> SEQ ID NO 1673
<211> LENGTH: 7
<212> TYPE: PRT
<213> ORGANISM: Homo sapiens

<400> SEQUENCE: 1673

Ala Leu Gln Pro Glu Asp Phe
1               5

<210> SEQ ID NO 1674
<211> LENGTH: 7
<212> TYPE: PRT
<213> ORGANISM: Homo sapiens

<400> SEQUENCE: 1674

Leu Gln Pro Glu Asp Phe Leu
1               5

<210> SEQ ID NO 1675
<211> LENGTH: 7
<212> TYPE: PRT
<213> ORGANISM: Homo sapiens

<400> SEQUENCE: 1675

Gln Pro Glu Asp Phe Leu Glu
1               5

<210> SEQ ID NO 1676
<211> LENGTH: 7
<212> TYPE: PRT
<213> ORGANISM: Homo sapiens

<400> SEQUENCE: 1676

Pro Glu Asp Phe Leu Glu Glu
1               5

<210> SEQ ID NO 1677
<211> LENGTH: 7
<212> TYPE: PRT
<213> ORGANISM: Homo sapiens

<400> SEQUENCE: 1677

Glu Asp Phe Leu Glu Glu Asp
1               5

<210> SEQ ID NO 1678
<211> LENGTH: 7
<212> TYPE: PRT
<213> ORGANISM: Homo sapiens

<400> SEQUENCE: 1678

Asp Phe Leu Glu Glu Asp Glu
1               5

<210> SEQ ID NO 1679
<211> LENGTH: 7
<212> TYPE: PRT
<213> ORGANISM: Homo sapiens

<400> SEQUENCE: 1679

Phe Leu Glu Glu Asp Glu Tyr
1               5

<210> SEQ ID NO 1680

<210> SEQ ID NO 1680
<211> LENGTH: 7
<212> TYPE: PRT
<213> ORGANISM: Homo sapiens

<400> SEQUENCE: 1680

Leu Glu Glu Asp Glu Tyr His
1               5

<210> SEQ ID NO 1681
<211> LENGTH: 7
<212> TYPE: PRT
<213> ORGANISM: Homo sapiens

<400> SEQUENCE: 1681

Glu Glu Asp Glu Tyr His Ala
1               5

<210> SEQ ID NO 1682
<211> LENGTH: 7
<212> TYPE: PRT
<213> ORGANISM: Homo sapiens

<400> SEQUENCE: 1682

Glu Asp Glu Tyr His Ala Thr
1               5

<210> SEQ ID NO 1683
<211> LENGTH: 7
<212> TYPE: PRT
<213> ORGANISM: Homo sapiens

<400> SEQUENCE: 1683

Asp Glu Tyr His Ala Thr Thr
1               5

<210> SEQ ID NO 1684
<211> LENGTH: 7
<212> TYPE: PRT
<213> ORGANISM: Homo sapiens

<400> SEQUENCE: 1684

Glu Tyr His Ala Thr Thr Glu
1               5

<210> SEQ ID NO 1685
<211> LENGTH: 7
<212> TYPE: PRT
<213> ORGANISM: Homo sapiens

<400> SEQUENCE: 1685

Tyr His Ala Thr Thr Glu Thr
1               5

<210> SEQ ID NO 1686
<211> LENGTH: 7
<212> TYPE: PRT
<213> ORGANISM: Homo sapiens

<400> SEQUENCE: 1686

His Ala Thr Thr Glu Thr Val
1               5

<210> SEQ ID NO 1687
<211> LENGTH: 7
<212> TYPE: PRT

```
<213> ORGANISM: Homo sapiens

<400> SEQUENCE: 1687

Ala Thr Thr Glu Thr Val Ile
1               5

<210> SEQ ID NO 1688
<211> LENGTH: 7
<212> TYPE: PRT
<213> ORGANISM: Homo sapiens

<400> SEQUENCE: 1688

Thr Thr Glu Thr Val Ile Ser
1               5

<210> SEQ ID NO 1689
<211> LENGTH: 7
<212> TYPE: PRT
<213> ORGANISM: Homo sapiens

<400> SEQUENCE: 1689

Thr Glu Thr Val Ile Ser Met
1               5

<210> SEQ ID NO 1690
<211> LENGTH: 7
<212> TYPE: PRT
<213> ORGANISM: Homo sapiens

<400> SEQUENCE: 1690

Glu Thr Val Ile Ser Met Ala
1               5

<210> SEQ ID NO 1691
<211> LENGTH: 7
<212> TYPE: PRT
<213> ORGANISM: Homo sapiens

<400> SEQUENCE: 1691

Thr Val Ile Ser Met Ala Gln
1               5

<210> SEQ ID NO 1692
<211> LENGTH: 7
<212> TYPE: PRT
<213> ORGANISM: Homo sapiens

<400> SEQUENCE: 1692

Val Ile Ser Met Ala Gln Glu
1               5

<210> SEQ ID NO 1693
<211> LENGTH: 7
<212> TYPE: PRT
<213> ORGANISM: Homo sapiens

<400> SEQUENCE: 1693

Ile Ser Met Ala Gln Glu Thr
1               5

<210> SEQ ID NO 1694
<211> LENGTH: 7
<212> TYPE: PRT
<213> ORGANISM: Homo sapiens
```

```
<400> SEQUENCE: 1694

Ser Met Ala Gln Glu Thr Asp
1               5

<210> SEQ ID NO 1695
<211> LENGTH: 7
<212> TYPE: PRT
<213> ORGANISM: Homo sapiens

<400> SEQUENCE: 1695

Met Ala Gln Glu Thr Asp Pro
1               5

<210> SEQ ID NO 1696
<211> LENGTH: 7
<212> TYPE: PRT
<213> ORGANISM: Homo sapiens

<400> SEQUENCE: 1696

Ala Gln Glu Thr Asp Pro Ala
1               5

<210> SEQ ID NO 1697
<211> LENGTH: 7
<212> TYPE: PRT
<213> ORGANISM: Homo sapiens

<400> SEQUENCE: 1697

Gln Glu Thr Asp Pro Ala Val
1               5

<210> SEQ ID NO 1698
<211> LENGTH: 7
<212> TYPE: PRT
<213> ORGANISM: Homo sapiens

<400> SEQUENCE: 1698

Glu Thr Asp Pro Ala Val Gln
1               5

<210> SEQ ID NO 1699
<211> LENGTH: 7
<212> TYPE: PRT
<213> ORGANISM: Homo sapiens

<400> SEQUENCE: 1699

Thr Asp Pro Ala Val Gln Thr
1               5

<210> SEQ ID NO 1700
<211> LENGTH: 7
<212> TYPE: PRT
<213> ORGANISM: Homo sapiens

<400> SEQUENCE: 1700

Asp Pro Ala Val Gln Thr Asp
1               5

<210> SEQ ID NO 1701
<211> LENGTH: 7
<212> TYPE: PRT
<213> ORGANISM: Homo sapiens

<400> SEQUENCE: 1701
```

```
Pro Ala Val Gln Thr Asp Gly
1               5

<210> SEQ ID NO 1702
<211> LENGTH: 7
<212> TYPE: PRT
<213> ORGANISM: Homo sapiens

<400> SEQUENCE: 1702

Ala Val Gln Thr Asp Gly Ser
1               5

<210> SEQ ID NO 1703
<211> LENGTH: 7
<212> TYPE: PRT
<213> ORGANISM: Homo sapiens

<400> SEQUENCE: 1703

Val Gln Thr Asp Gly Ser Pro
1               5

<210> SEQ ID NO 1704
<211> LENGTH: 7
<212> TYPE: PRT
<213> ORGANISM: Homo sapiens

<400> SEQUENCE: 1704

Gln Thr Asp Gly Ser Pro Leu
1               5

<210> SEQ ID NO 1705
<211> LENGTH: 7
<212> TYPE: PRT
<213> ORGANISM: Homo sapiens

<400> SEQUENCE: 1705

Thr Asp Gly Ser Pro Leu Cys
1               5

<210> SEQ ID NO 1706
<211> LENGTH: 7
<212> TYPE: PRT
<213> ORGANISM: Homo sapiens

<400> SEQUENCE: 1706

Asp Gly Ser Pro Leu Cys Cys
1               5

<210> SEQ ID NO 1707
<211> LENGTH: 7
<212> TYPE: PRT
<213> ORGANISM: Homo sapiens

<400> SEQUENCE: 1707

Gly Ser Pro Leu Cys Cys His
1               5

<210> SEQ ID NO 1708
<211> LENGTH: 7
<212> TYPE: PRT
<213> ORGANISM: Homo sapiens

<400> SEQUENCE: 1708

Ser Pro Leu Cys Cys His Phe
1               5
```

```
<210> SEQ ID NO 1709
<211> LENGTH: 7
<212> TYPE: PRT
<213> ORGANISM: Homo sapiens

<400> SEQUENCE: 1709

Pro Leu Cys Cys His Phe His
1               5

<210> SEQ ID NO 1710
<211> LENGTH: 7
<212> TYPE: PRT
<213> ORGANISM: Homo sapiens

<400> SEQUENCE: 1710

Leu Cys Cys His Phe His Phe
1               5

<210> SEQ ID NO 1711
<211> LENGTH: 7
<212> TYPE: PRT
<213> ORGANISM: Homo sapiens

<400> SEQUENCE: 1711

Cys Cys His Phe His Phe Ser
1               5

<210> SEQ ID NO 1712
<211> LENGTH: 7
<212> TYPE: PRT
<213> ORGANISM: Homo sapiens

<400> SEQUENCE: 1712

Cys His Phe His Phe Ser Pro
1               5

<210> SEQ ID NO 1713
<211> LENGTH: 7
<212> TYPE: PRT
<213> ORGANISM: Homo sapiens

<400> SEQUENCE: 1713

His Phe His Phe Ser Pro Lys
1               5

<210> SEQ ID NO 1714
<211> LENGTH: 7
<212> TYPE: PRT
<213> ORGANISM: Homo sapiens

<400> SEQUENCE: 1714

Phe His Phe Ser Pro Lys Val
1               5

<210> SEQ ID NO 1715
<211> LENGTH: 7
<212> TYPE: PRT
<213> ORGANISM: Homo sapiens

<400> SEQUENCE: 1715

His Phe Ser Pro Lys Val Met
1               5
```

```
<210> SEQ ID NO 1716
<211> LENGTH: 7
<212> TYPE: PRT
<213> ORGANISM: Homo sapiens

<400> SEQUENCE: 1716

Phe Ser Pro Lys Val Met Phe
1               5

<210> SEQ ID NO 1717
<211> LENGTH: 7
<212> TYPE: PRT
<213> ORGANISM: Homo sapiens

<400> SEQUENCE: 1717

Ser Pro Lys Val Met Phe Thr
1               5

<210> SEQ ID NO 1718
<211> LENGTH: 7
<212> TYPE: PRT
<213> ORGANISM: Homo sapiens

<400> SEQUENCE: 1718

Pro Lys Val Met Phe Thr Lys
1               5

<210> SEQ ID NO 1719
<211> LENGTH: 7
<212> TYPE: PRT
<213> ORGANISM: Homo sapiens

<400> SEQUENCE: 1719

Lys Val Met Phe Thr Lys Val
1               5

<210> SEQ ID NO 1720
<211> LENGTH: 7
<212> TYPE: PRT
<213> ORGANISM: Homo sapiens

<400> SEQUENCE: 1720

Val Met Phe Thr Lys Val Leu
1               5

<210> SEQ ID NO 1721
<211> LENGTH: 7
<212> TYPE: PRT
<213> ORGANISM: Homo sapiens

<400> SEQUENCE: 1721

Met Phe Thr Lys Val Leu Lys
1               5

<210> SEQ ID NO 1722
<211> LENGTH: 7
<212> TYPE: PRT
<213> ORGANISM: Homo sapiens

<400> SEQUENCE: 1722

Phe Thr Lys Val Leu Lys Ala
1               5

<210> SEQ ID NO 1723
<211> LENGTH: 7
```

<212> TYPE: PRT
<213> ORGANISM: Homo sapiens

<400> SEQUENCE: 1723

Thr Lys Val Leu Lys Ala Gln
1               5

<210> SEQ ID NO 1724
<211> LENGTH: 7
<212> TYPE: PRT
<213> ORGANISM: Homo sapiens

<400> SEQUENCE: 1724

Lys Val Leu Lys Ala Gln Leu
1               5

<210> SEQ ID NO 1725
<211> LENGTH: 7
<212> TYPE: PRT
<213> ORGANISM: Homo sapiens

<400> SEQUENCE: 1725

Val Leu Lys Ala Gln Leu Trp
1               5

<210> SEQ ID NO 1726
<211> LENGTH: 7
<212> TYPE: PRT
<213> ORGANISM: Homo sapiens

<400> SEQUENCE: 1726

Leu Lys Ala Gln Leu Trp Val
1               5

<210> SEQ ID NO 1727
<211> LENGTH: 7
<212> TYPE: PRT
<213> ORGANISM: Homo sapiens

<400> SEQUENCE: 1727

Lys Ala Gln Leu Trp Val Tyr
1               5

<210> SEQ ID NO 1728
<211> LENGTH: 7
<212> TYPE: PRT
<213> ORGANISM: Homo sapiens

<400> SEQUENCE: 1728

Ala Gln Leu Trp Val Tyr Leu
1               5

<210> SEQ ID NO 1729
<211> LENGTH: 7
<212> TYPE: PRT
<213> ORGANISM: Homo sapiens

<400> SEQUENCE: 1729

Gln Leu Trp Val Tyr Leu Arg
1               5

<210> SEQ ID NO 1730
<211> LENGTH: 7
<212> TYPE: PRT
<213> ORGANISM: Homo sapiens

<400> SEQUENCE: 1730

Leu Trp Val Tyr Leu Arg Pro
1               5

<210> SEQ ID NO 1731
<211> LENGTH: 7
<212> TYPE: PRT
<213> ORGANISM: Homo sapiens

<400> SEQUENCE: 1731

Trp Val Tyr Leu Arg Pro Val
1               5

<210> SEQ ID NO 1732
<211> LENGTH: 7
<212> TYPE: PRT
<213> ORGANISM: Homo sapiens

<400> SEQUENCE: 1732

Val Tyr Leu Arg Pro Val Pro
1               5

<210> SEQ ID NO 1733
<211> LENGTH: 7
<212> TYPE: PRT
<213> ORGANISM: Homo sapiens

<400> SEQUENCE: 1733

Tyr Leu Arg Pro Val Pro Arg
1               5

<210> SEQ ID NO 1734
<211> LENGTH: 7
<212> TYPE: PRT
<213> ORGANISM: Homo sapiens

<400> SEQUENCE: 1734

Leu Arg Pro Val Pro Arg Pro
1               5

<210> SEQ ID NO 1735
<211> LENGTH: 7
<212> TYPE: PRT
<213> ORGANISM: Homo sapiens

<400> SEQUENCE: 1735

Arg Pro Val Pro Arg Pro Ala
1               5

<210> SEQ ID NO 1736
<211> LENGTH: 7
<212> TYPE: PRT
<213> ORGANISM: Homo sapiens

<400> SEQUENCE: 1736

Pro Val Pro Arg Pro Ala Thr
1               5

<210> SEQ ID NO 1737
<211> LENGTH: 7
<212> TYPE: PRT
<213> ORGANISM: Homo sapiens

<400> SEQUENCE: 1737

Val Pro Arg Pro Ala Thr Val
1               5

<210> SEQ ID NO 1738
<211> LENGTH: 7
<212> TYPE: PRT
<213> ORGANISM: Homo sapiens

<400> SEQUENCE: 1738

Pro Arg Pro Ala Thr Val Tyr
1               5

<210> SEQ ID NO 1739
<211> LENGTH: 7
<212> TYPE: PRT
<213> ORGANISM: Homo sapiens

<400> SEQUENCE: 1739

Arg Pro Ala Thr Val Tyr Leu
1               5

<210> SEQ ID NO 1740
<211> LENGTH: 7
<212> TYPE: PRT
<213> ORGANISM: Homo sapiens

<400> SEQUENCE: 1740

Pro Ala Thr Val Tyr Leu Gln
1               5

<210> SEQ ID NO 1741
<211> LENGTH: 7
<212> TYPE: PRT
<213> ORGANISM: Homo sapiens

<400> SEQUENCE: 1741

Ala Thr Val Tyr Leu Gln Ile
1               5

<210> SEQ ID NO 1742
<211> LENGTH: 7
<212> TYPE: PRT
<213> ORGANISM: Homo sapiens

<400> SEQUENCE: 1742

Thr Val Tyr Leu Gln Ile Leu
1               5

<210> SEQ ID NO 1743
<211> LENGTH: 7
<212> TYPE: PRT
<213> ORGANISM: Homo sapiens

<400> SEQUENCE: 1743

Val Tyr Leu Gln Ile Leu Arg
1               5

<210> SEQ ID NO 1744
<211> LENGTH: 7
<212> TYPE: PRT
<213> ORGANISM: Homo sapiens

<400> SEQUENCE: 1744

Tyr Leu Gln Ile Leu Arg Leu

```
1               5

<210> SEQ ID NO 1745
<211> LENGTH: 7
<212> TYPE: PRT
<213> ORGANISM: Homo sapiens

<400> SEQUENCE: 1745

Leu Gln Ile Leu Arg Leu Lys
1               5

<210> SEQ ID NO 1746
<211> LENGTH: 7
<212> TYPE: PRT
<213> ORGANISM: Homo sapiens

<400> SEQUENCE: 1746

Gln Ile Leu Arg Leu Lys Pro
1               5

<210> SEQ ID NO 1747
<211> LENGTH: 7
<212> TYPE: PRT
<213> ORGANISM: Homo sapiens

<400> SEQUENCE: 1747

Ile Leu Arg Leu Lys Pro Leu
1               5

<210> SEQ ID NO 1748
<211> LENGTH: 7
<212> TYPE: PRT
<213> ORGANISM: Homo sapiens

<400> SEQUENCE: 1748

Leu Arg Leu Lys Pro Leu Thr
1               5

<210> SEQ ID NO 1749
<211> LENGTH: 7
<212> TYPE: PRT
<213> ORGANISM: Homo sapiens

<400> SEQUENCE: 1749

Arg Leu Lys Pro Leu Thr Gly
1               5

<210> SEQ ID NO 1750
<211> LENGTH: 7
<212> TYPE: PRT
<213> ORGANISM: Homo sapiens

<400> SEQUENCE: 1750

Leu Lys Pro Leu Thr Gly Glu
1               5

<210> SEQ ID NO 1751
<211> LENGTH: 7
<212> TYPE: PRT
<213> ORGANISM: Homo sapiens

<400> SEQUENCE: 1751

Lys Pro Leu Thr Gly Glu Gly
1               5
```

<210> SEQ ID NO 1752
<211> LENGTH: 7
<212> TYPE: PRT
<213> ORGANISM: Homo sapiens

<400> SEQUENCE: 1752

Pro Leu Thr Gly Glu Gly Thr
1               5

<210> SEQ ID NO 1753
<211> LENGTH: 7
<212> TYPE: PRT
<213> ORGANISM: Homo sapiens

<400> SEQUENCE: 1753

Leu Thr Gly Glu Gly Thr Ala
1               5

<210> SEQ ID NO 1754
<211> LENGTH: 7
<212> TYPE: PRT
<213> ORGANISM: Homo sapiens

<400> SEQUENCE: 1754

Thr Gly Glu Gly Thr Ala Gly
1               5

<210> SEQ ID NO 1755
<211> LENGTH: 7
<212> TYPE: PRT
<213> ORGANISM: Homo sapiens

<400> SEQUENCE: 1755

Gly Glu Gly Thr Ala Gly Gly
1               5

<210> SEQ ID NO 1756
<211> LENGTH: 7
<212> TYPE: PRT
<213> ORGANISM: Homo sapiens

<400> SEQUENCE: 1756

Glu Gly Thr Ala Gly Gly Gly
1               5

<210> SEQ ID NO 1757
<211> LENGTH: 7
<212> TYPE: PRT
<213> ORGANISM: Homo sapiens

<400> SEQUENCE: 1757

Gly Thr Ala Gly Gly Gly Gly
1               5

<210> SEQ ID NO 1758
<211> LENGTH: 7
<212> TYPE: PRT
<213> ORGANISM: Homo sapiens

<400> SEQUENCE: 1758

Thr Ala Gly Gly Gly Gly Gly
1               5

<210> SEQ ID NO 1759

```
<211> LENGTH: 7
<212> TYPE: PRT
<213> ORGANISM: Homo sapiens

<400> SEQUENCE: 1759

Ala Gly Gly Gly Gly Gly Gly
1               5

<210> SEQ ID NO 1760
<211> LENGTH: 7
<212> TYPE: PRT
<213> ORGANISM: Homo sapiens

<400> SEQUENCE: 1760

Gly Gly Gly Gly Gly Gly Arg
1               5

<210> SEQ ID NO 1761
<211> LENGTH: 7
<212> TYPE: PRT
<213> ORGANISM: Homo sapiens

<400> SEQUENCE: 1761

Gly Gly Gly Gly Gly Arg Arg
1               5

<210> SEQ ID NO 1762
<211> LENGTH: 7
<212> TYPE: PRT
<213> ORGANISM: Homo sapiens

<400> SEQUENCE: 1762

Gly Gly Gly Gly Arg Arg His
1               5

<210> SEQ ID NO 1763
<211> LENGTH: 7
<212> TYPE: PRT
<213> ORGANISM: Homo sapiens

<400> SEQUENCE: 1763

Gly Gly Gly Arg Arg His Ile
1               5

<210> SEQ ID NO 1764
<211> LENGTH: 7
<212> TYPE: PRT
<213> ORGANISM: Homo sapiens

<400> SEQUENCE: 1764

Gly Gly Arg Arg His Ile Arg
1               5

<210> SEQ ID NO 1765
<211> LENGTH: 7
<212> TYPE: PRT
<213> ORGANISM: Homo sapiens

<400> SEQUENCE: 1765

Gly Arg Arg His Ile Arg Ile
1               5

<210> SEQ ID NO 1766
<211> LENGTH: 7
<212> TYPE: PRT
```

<213> ORGANISM: Homo sapiens

<400> SEQUENCE: 1766

Arg Arg His Ile Arg Ile Arg
1               5

<210> SEQ ID NO 1767
<211> LENGTH: 7
<212> TYPE: PRT
<213> ORGANISM: Homo sapiens

<400> SEQUENCE: 1767

Arg His Ile Arg Ile Arg Ser
1               5

<210> SEQ ID NO 1768
<211> LENGTH: 7
<212> TYPE: PRT
<213> ORGANISM: Homo sapiens

<400> SEQUENCE: 1768

His Ile Arg Ile Arg Ser Leu
1               5

<210> SEQ ID NO 1769
<211> LENGTH: 7
<212> TYPE: PRT
<213> ORGANISM: Homo sapiens

<400> SEQUENCE: 1769

Ile Arg Ile Arg Ser Leu Lys
1               5

<210> SEQ ID NO 1770
<211> LENGTH: 7
<212> TYPE: PRT
<213> ORGANISM: Homo sapiens

<400> SEQUENCE: 1770

Arg Ile Arg Ser Leu Lys Ile
1               5

<210> SEQ ID NO 1771
<211> LENGTH: 7
<212> TYPE: PRT
<213> ORGANISM: Homo sapiens

<400> SEQUENCE: 1771

Ile Arg Ser Leu Lys Ile Glu
1               5

<210> SEQ ID NO 1772
<211> LENGTH: 7
<212> TYPE: PRT
<213> ORGANISM: Homo sapiens

<400> SEQUENCE: 1772

Arg Ser Leu Lys Ile Glu Leu
1               5

<210> SEQ ID NO 1773
<211> LENGTH: 7
<212> TYPE: PRT
<213> ORGANISM: Homo sapiens

```
<400> SEQUENCE: 1773

Ser Leu Lys Ile Glu Leu His
1               5

<210> SEQ ID NO 1774
<211> LENGTH: 7
<212> TYPE: PRT
<213> ORGANISM: Homo sapiens

<400> SEQUENCE: 1774

Leu Lys Ile Glu Leu His Ser
1               5

<210> SEQ ID NO 1775
<211> LENGTH: 7
<212> TYPE: PRT
<213> ORGANISM: Homo sapiens

<400> SEQUENCE: 1775

Lys Ile Glu Leu His Ser Arg
1               5

<210> SEQ ID NO 1776
<211> LENGTH: 7
<212> TYPE: PRT
<213> ORGANISM: Homo sapiens

<400> SEQUENCE: 1776

Ile Glu Leu His Ser Arg Ser
1               5

<210> SEQ ID NO 1777
<211> LENGTH: 7
<212> TYPE: PRT
<213> ORGANISM: Homo sapiens

<400> SEQUENCE: 1777

Glu Leu His Ser Arg Ser Gly
1               5

<210> SEQ ID NO 1778
<211> LENGTH: 7
<212> TYPE: PRT
<213> ORGANISM: Homo sapiens

<400> SEQUENCE: 1778

Leu His Ser Arg Ser Gly His
1               5

<210> SEQ ID NO 1779
<211> LENGTH: 7
<212> TYPE: PRT
<213> ORGANISM: Homo sapiens

<400> SEQUENCE: 1779

His Ser Arg Ser Gly His Trp
1               5

<210> SEQ ID NO 1780
<211> LENGTH: 7
<212> TYPE: PRT
<213> ORGANISM: Homo sapiens

<400> SEQUENCE: 1780
```

Ser Arg Ser Gly His Trp Gln
1               5

<210> SEQ ID NO 1781
<211> LENGTH: 7
<212> TYPE: PRT
<213> ORGANISM: Homo sapiens

<400> SEQUENCE: 1781

Arg Ser Gly His Trp Gln Ser
1               5

<210> SEQ ID NO 1782
<211> LENGTH: 7
<212> TYPE: PRT
<213> ORGANISM: Homo sapiens

<400> SEQUENCE: 1782

Ser Gly His Trp Gln Ser Ile
1               5

<210> SEQ ID NO 1783
<211> LENGTH: 7
<212> TYPE: PRT
<213> ORGANISM: Homo sapiens

<400> SEQUENCE: 1783

Gly His Trp Gln Ser Ile Asp
1               5

<210> SEQ ID NO 1784
<211> LENGTH: 7
<212> TYPE: PRT
<213> ORGANISM: Homo sapiens

<400> SEQUENCE: 1784

His Trp Gln Ser Ile Asp Phe
1               5

<210> SEQ ID NO 1785
<211> LENGTH: 7
<212> TYPE: PRT
<213> ORGANISM: Homo sapiens

<400> SEQUENCE: 1785

Trp Gln Ser Ile Asp Phe Lys
1               5

<210> SEQ ID NO 1786
<211> LENGTH: 7
<212> TYPE: PRT
<213> ORGANISM: Homo sapiens

<400> SEQUENCE: 1786

Gln Ser Ile Asp Phe Lys Gln
1               5

<210> SEQ ID NO 1787
<211> LENGTH: 7
<212> TYPE: PRT
<213> ORGANISM: Homo sapiens

<400> SEQUENCE: 1787

Ser Ile Asp Phe Lys Gln Val
1               5

```
<210> SEQ ID NO 1788
<211> LENGTH: 7
<212> TYPE: PRT
<213> ORGANISM: Homo sapiens

<400> SEQUENCE: 1788

Ile Asp Phe Lys Gln Val Leu
1               5

<210> SEQ ID NO 1789
<211> LENGTH: 7
<212> TYPE: PRT
<213> ORGANISM: Homo sapiens

<400> SEQUENCE: 1789

Asp Phe Lys Gln Val Leu His
1               5

<210> SEQ ID NO 1790
<211> LENGTH: 7
<212> TYPE: PRT
<213> ORGANISM: Homo sapiens

<400> SEQUENCE: 1790

Phe Lys Gln Val Leu His Ser
1               5

<210> SEQ ID NO 1791
<211> LENGTH: 7
<212> TYPE: PRT
<213> ORGANISM: Homo sapiens

<400> SEQUENCE: 1791

Lys Gln Val Leu His Ser Trp
1               5

<210> SEQ ID NO 1792
<211> LENGTH: 7
<212> TYPE: PRT
<213> ORGANISM: Homo sapiens

<400> SEQUENCE: 1792

Gln Val Leu His Ser Trp Phe
1               5

<210> SEQ ID NO 1793
<211> LENGTH: 7
<212> TYPE: PRT
<213> ORGANISM: Homo sapiens

<400> SEQUENCE: 1793

Val Leu His Ser Trp Phe Arg
1               5

<210> SEQ ID NO 1794
<211> LENGTH: 7
<212> TYPE: PRT
<213> ORGANISM: Homo sapiens

<400> SEQUENCE: 1794

Leu His Ser Trp Phe Arg Gln
1               5
```

<210> SEQ ID NO 1795
<211> LENGTH: 7
<212> TYPE: PRT
<213> ORGANISM: Homo sapiens

<400> SEQUENCE: 1795

His Ser Trp Phe Arg Gln Pro
1               5

<210> SEQ ID NO 1796
<211> LENGTH: 7
<212> TYPE: PRT
<213> ORGANISM: Homo sapiens

<400> SEQUENCE: 1796

Ser Trp Phe Arg Gln Pro Gln
1               5

<210> SEQ ID NO 1797
<211> LENGTH: 7
<212> TYPE: PRT
<213> ORGANISM: Homo sapiens

<400> SEQUENCE: 1797

Trp Phe Arg Gln Pro Gln Ser
1               5

<210> SEQ ID NO 1798
<211> LENGTH: 7
<212> TYPE: PRT
<213> ORGANISM: Homo sapiens

<400> SEQUENCE: 1798

Phe Arg Gln Pro Gln Ser Asn
1               5

<210> SEQ ID NO 1799
<211> LENGTH: 7
<212> TYPE: PRT
<213> ORGANISM: Homo sapiens

<400> SEQUENCE: 1799

Arg Gln Pro Gln Ser Asn Trp
1               5

<210> SEQ ID NO 1800
<211> LENGTH: 7
<212> TYPE: PRT
<213> ORGANISM: Homo sapiens

<400> SEQUENCE: 1800

Gln Pro Gln Ser Asn Trp Gly
1               5

<210> SEQ ID NO 1801
<211> LENGTH: 7
<212> TYPE: PRT
<213> ORGANISM: Homo sapiens

<400> SEQUENCE: 1801

Pro Gln Ser Asn Trp Gly Ile
1               5

<210> SEQ ID NO 1802
<211> LENGTH: 7

```
<212> TYPE: PRT
<213> ORGANISM: Homo sapiens

<400> SEQUENCE: 1802

Gln Ser Asn Trp Gly Ile Glu
1               5

<210> SEQ ID NO 1803
<211> LENGTH: 7
<212> TYPE: PRT
<213> ORGANISM: Homo sapiens

<400> SEQUENCE: 1803

Ser Asn Trp Gly Ile Glu Ile
1               5

<210> SEQ ID NO 1804
<211> LENGTH: 7
<212> TYPE: PRT
<213> ORGANISM: Homo sapiens

<400> SEQUENCE: 1804

Asn Trp Gly Ile Glu Ile Asn
1               5

<210> SEQ ID NO 1805
<211> LENGTH: 7
<212> TYPE: PRT
<213> ORGANISM: Homo sapiens

<400> SEQUENCE: 1805

Trp Gly Ile Glu Ile Asn Ala
1               5

<210> SEQ ID NO 1806
<211> LENGTH: 7
<212> TYPE: PRT
<213> ORGANISM: Homo sapiens

<400> SEQUENCE: 1806

Gly Ile Glu Ile Asn Ala Phe
1               5

<210> SEQ ID NO 1807
<211> LENGTH: 7
<212> TYPE: PRT
<213> ORGANISM: Homo sapiens

<400> SEQUENCE: 1807

Ile Glu Ile Asn Ala Phe Asp
1               5

<210> SEQ ID NO 1808
<211> LENGTH: 7
<212> TYPE: PRT
<213> ORGANISM: Homo sapiens

<400> SEQUENCE: 1808

Glu Ile Asn Ala Phe Asp Pro
1               5

<210> SEQ ID NO 1809
<211> LENGTH: 7
<212> TYPE: PRT
<213> ORGANISM: Homo sapiens
```

```
<400> SEQUENCE: 1809

Ile Asn Ala Phe Asp Pro Ser
1               5

<210> SEQ ID NO 1810
<211> LENGTH: 7
<212> TYPE: PRT
<213> ORGANISM: Homo sapiens

<400> SEQUENCE: 1810

Asn Ala Phe Asp Pro Ser Gly
1               5

<210> SEQ ID NO 1811
<211> LENGTH: 7
<212> TYPE: PRT
<213> ORGANISM: Homo sapiens

<400> SEQUENCE: 1811

Ala Phe Asp Pro Ser Gly Thr
1               5

<210> SEQ ID NO 1812
<211> LENGTH: 7
<212> TYPE: PRT
<213> ORGANISM: Homo sapiens

<400> SEQUENCE: 1812

Phe Asp Pro Ser Gly Thr Asp
1               5

<210> SEQ ID NO 1813
<211> LENGTH: 7
<212> TYPE: PRT
<213> ORGANISM: Homo sapiens

<400> SEQUENCE: 1813

Asp Pro Ser Gly Thr Asp Leu
1               5

<210> SEQ ID NO 1814
<211> LENGTH: 7
<212> TYPE: PRT
<213> ORGANISM: Homo sapiens

<400> SEQUENCE: 1814

Pro Ser Gly Thr Asp Leu Ala
1               5

<210> SEQ ID NO 1815
<211> LENGTH: 7
<212> TYPE: PRT
<213> ORGANISM: Homo sapiens

<400> SEQUENCE: 1815

Ser Gly Thr Asp Leu Ala Val
1               5

<210> SEQ ID NO 1816
<211> LENGTH: 7
<212> TYPE: PRT
<213> ORGANISM: Homo sapiens

<400> SEQUENCE: 1816
```

Gly Thr Asp Leu Ala Val Thr
1               5

<210> SEQ ID NO 1817
<211> LENGTH: 7
<212> TYPE: PRT
<213> ORGANISM: Homo sapiens

<400> SEQUENCE: 1817

Thr Asp Leu Ala Val Thr Ser
1               5

<210> SEQ ID NO 1818
<211> LENGTH: 7
<212> TYPE: PRT
<213> ORGANISM: Homo sapiens

<400> SEQUENCE: 1818

Asp Leu Ala Val Thr Ser Leu
1               5

<210> SEQ ID NO 1819
<211> LENGTH: 7
<212> TYPE: PRT
<213> ORGANISM: Homo sapiens

<400> SEQUENCE: 1819

Leu Ala Val Thr Ser Leu Gly
1               5

<210> SEQ ID NO 1820
<211> LENGTH: 7
<212> TYPE: PRT
<213> ORGANISM: Homo sapiens

<400> SEQUENCE: 1820

Ala Val Thr Ser Leu Gly Pro
1               5

<210> SEQ ID NO 1821
<211> LENGTH: 7
<212> TYPE: PRT
<213> ORGANISM: Homo sapiens

<400> SEQUENCE: 1821

Val Thr Ser Leu Gly Pro Gly
1               5

<210> SEQ ID NO 1822
<211> LENGTH: 7
<212> TYPE: PRT
<213> ORGANISM: Homo sapiens

<400> SEQUENCE: 1822

Thr Ser Leu Gly Pro Gly Ala
1               5

<210> SEQ ID NO 1823
<211> LENGTH: 7
<212> TYPE: PRT
<213> ORGANISM: Homo sapiens

<400> SEQUENCE: 1823

Ser Leu Gly Pro Gly Ala Glu

```
<210> SEQ ID NO 1824
<211> LENGTH: 7
<212> TYPE: PRT
<213> ORGANISM: Homo sapiens

<400> SEQUENCE: 1824

Leu Gly Pro Gly Ala Glu Gly
1               5

<210> SEQ ID NO 1825
<211> LENGTH: 7
<212> TYPE: PRT
<213> ORGANISM: Homo sapiens

<400> SEQUENCE: 1825

Gly Pro Gly Ala Glu Gly Leu
1               5

<210> SEQ ID NO 1826
<211> LENGTH: 7
<212> TYPE: PRT
<213> ORGANISM: Homo sapiens

<400> SEQUENCE: 1826

Pro Gly Ala Glu Gly Leu His
1               5

<210> SEQ ID NO 1827
<211> LENGTH: 7
<212> TYPE: PRT
<213> ORGANISM: Homo sapiens

<400> SEQUENCE: 1827

Gly Ala Glu Gly Leu His Pro
1               5

<210> SEQ ID NO 1828
<211> LENGTH: 7
<212> TYPE: PRT
<213> ORGANISM: Homo sapiens

<400> SEQUENCE: 1828

Ala Glu Gly Leu His Pro Phe
1               5

<210> SEQ ID NO 1829
<211> LENGTH: 7
<212> TYPE: PRT
<213> ORGANISM: Homo sapiens

<400> SEQUENCE: 1829

Glu Gly Leu His Pro Phe Met
1               5

<210> SEQ ID NO 1830
<211> LENGTH: 7
<212> TYPE: PRT
<213> ORGANISM: Homo sapiens

<400> SEQUENCE: 1830

Gly Leu His Pro Phe Met Glu
1               5
```

<210> SEQ ID NO 1831
<211> LENGTH: 7
<212> TYPE: PRT
<213> ORGANISM: Homo sapiens

<400> SEQUENCE: 1831

Leu His Pro Phe Met Glu Leu
1               5

<210> SEQ ID NO 1832
<211> LENGTH: 7
<212> TYPE: PRT
<213> ORGANISM: Homo sapiens

<400> SEQUENCE: 1832

His Pro Phe Met Glu Leu Arg
1               5

<210> SEQ ID NO 1833
<211> LENGTH: 7
<212> TYPE: PRT
<213> ORGANISM: Homo sapiens

<400> SEQUENCE: 1833

Pro Phe Met Glu Leu Arg Val
1               5

<210> SEQ ID NO 1834
<211> LENGTH: 7
<212> TYPE: PRT
<213> ORGANISM: Homo sapiens

<400> SEQUENCE: 1834

Phe Met Glu Leu Arg Val Leu
1               5

<210> SEQ ID NO 1835
<211> LENGTH: 7
<212> TYPE: PRT
<213> ORGANISM: Homo sapiens

<400> SEQUENCE: 1835

Met Glu Leu Arg Val Leu Glu
1               5

<210> SEQ ID NO 1836
<211> LENGTH: 7
<212> TYPE: PRT
<213> ORGANISM: Homo sapiens

<400> SEQUENCE: 1836

Glu Leu Arg Val Leu Glu Asn
1               5

<210> SEQ ID NO 1837
<211> LENGTH: 7
<212> TYPE: PRT
<213> ORGANISM: Homo sapiens

<400> SEQUENCE: 1837

Leu Arg Val Leu Glu Asn Thr
1               5

<210> SEQ ID NO 1838

```
<211> LENGTH: 7
<212> TYPE: PRT
<213> ORGANISM: Homo sapiens

<400> SEQUENCE: 1838

Arg Val Leu Glu Asn Thr Lys
1               5

<210> SEQ ID NO 1839
<211> LENGTH: 7
<212> TYPE: PRT
<213> ORGANISM: Homo sapiens

<400> SEQUENCE: 1839

Val Leu Glu Asn Thr Lys Arg
1               5

<210> SEQ ID NO 1840
<211> LENGTH: 7
<212> TYPE: PRT
<213> ORGANISM: Homo sapiens

<400> SEQUENCE: 1840

Leu Glu Asn Thr Lys Arg Ser
1               5

<210> SEQ ID NO 1841
<211> LENGTH: 7
<212> TYPE: PRT
<213> ORGANISM: Homo sapiens

<400> SEQUENCE: 1841

Glu Asn Thr Lys Arg Ser Arg
1               5

<210> SEQ ID NO 1842
<211> LENGTH: 7
<212> TYPE: PRT
<213> ORGANISM: Homo sapiens

<400> SEQUENCE: 1842

Asn Thr Lys Arg Ser Arg Arg
1               5

<210> SEQ ID NO 1843
<211> LENGTH: 7
<212> TYPE: PRT
<213> ORGANISM: Homo sapiens

<400> SEQUENCE: 1843

Thr Lys Arg Ser Arg Arg Asn
1               5

<210> SEQ ID NO 1844
<211> LENGTH: 7
<212> TYPE: PRT
<213> ORGANISM: Homo sapiens

<400> SEQUENCE: 1844

Lys Arg Ser Arg Arg Asn Leu
1               5

<210> SEQ ID NO 1845
<211> LENGTH: 7
<212> TYPE: PRT
```

<213> ORGANISM: Homo sapiens

<400> SEQUENCE: 1845

Arg Ser Arg Arg Asn Leu Gly
1               5

<210> SEQ ID NO 1846
<211> LENGTH: 7
<212> TYPE: PRT
<213> ORGANISM: Homo sapiens

<400> SEQUENCE: 1846

Ser Arg Arg Asn Leu Gly Leu
1               5

<210> SEQ ID NO 1847
<211> LENGTH: 7
<212> TYPE: PRT
<213> ORGANISM: Homo sapiens

<400> SEQUENCE: 1847

Arg Arg Asn Leu Gly Leu Asp
1               5

<210> SEQ ID NO 1848
<211> LENGTH: 7
<212> TYPE: PRT
<213> ORGANISM: Homo sapiens

<400> SEQUENCE: 1848

Arg Asn Leu Gly Leu Asp Cys
1               5

<210> SEQ ID NO 1849
<211> LENGTH: 7
<212> TYPE: PRT
<213> ORGANISM: Homo sapiens

<400> SEQUENCE: 1849

Asn Leu Gly Leu Asp Cys Asp
1               5

<210> SEQ ID NO 1850
<211> LENGTH: 7
<212> TYPE: PRT
<213> ORGANISM: Homo sapiens

<400> SEQUENCE: 1850

Leu Gly Leu Asp Cys Asp Glu
1               5

<210> SEQ ID NO 1851
<211> LENGTH: 7
<212> TYPE: PRT
<213> ORGANISM: Homo sapiens

<400> SEQUENCE: 1851

Gly Leu Asp Cys Asp Glu His
1               5

<210> SEQ ID NO 1852
<211> LENGTH: 7
<212> TYPE: PRT
<213> ORGANISM: Homo sapiens

<400> SEQUENCE: 1852

Leu Asp Cys Asp Glu His Ser
1               5

<210> SEQ ID NO 1853
<211> LENGTH: 7
<212> TYPE: PRT
<213> ORGANISM: Homo sapiens

<400> SEQUENCE: 1853

Asp Cys Asp Glu His Ser Ser
1               5

<210> SEQ ID NO 1854
<211> LENGTH: 7
<212> TYPE: PRT
<213> ORGANISM: Homo sapiens

<400> SEQUENCE: 1854

Cys Asp Glu His Ser Ser Glu
1               5

<210> SEQ ID NO 1855
<211> LENGTH: 7
<212> TYPE: PRT
<213> ORGANISM: Homo sapiens

<400> SEQUENCE: 1855

Asp Glu His Ser Ser Glu Ser
1               5

<210> SEQ ID NO 1856
<211> LENGTH: 7
<212> TYPE: PRT
<213> ORGANISM: Homo sapiens

<400> SEQUENCE: 1856

Glu His Ser Ser Glu Ser Arg
1               5

<210> SEQ ID NO 1857
<211> LENGTH: 7
<212> TYPE: PRT
<213> ORGANISM: Homo sapiens

<400> SEQUENCE: 1857

His Ser Ser Glu Ser Arg Cys
1               5

<210> SEQ ID NO 1858
<211> LENGTH: 7
<212> TYPE: PRT
<213> ORGANISM: Homo sapiens

<400> SEQUENCE: 1858

Ser Ser Glu Ser Arg Cys Cys
1               5

<210> SEQ ID NO 1859
<211> LENGTH: 7
<212> TYPE: PRT
<213> ORGANISM: Homo sapiens

<400> SEQUENCE: 1859

Ser Glu Ser Arg Cys Cys Arg
1               5

<210> SEQ ID NO 1860
<211> LENGTH: 7
<212> TYPE: PRT
<213> ORGANISM: Homo sapiens

<400> SEQUENCE: 1860

Glu Ser Arg Cys Cys Arg Tyr
1               5

<210> SEQ ID NO 1861
<211> LENGTH: 7
<212> TYPE: PRT
<213> ORGANISM: Homo sapiens

<400> SEQUENCE: 1861

Ser Arg Cys Cys Arg Tyr Pro
1               5

<210> SEQ ID NO 1862
<211> LENGTH: 7
<212> TYPE: PRT
<213> ORGANISM: Homo sapiens

<400> SEQUENCE: 1862

Arg Cys Cys Arg Tyr Pro Leu
1               5

<210> SEQ ID NO 1863
<211> LENGTH: 7
<212> TYPE: PRT
<213> ORGANISM: Homo sapiens

<400> SEQUENCE: 1863

Cys Cys Arg Tyr Pro Leu Thr
1               5

<210> SEQ ID NO 1864
<211> LENGTH: 7
<212> TYPE: PRT
<213> ORGANISM: Homo sapiens

<400> SEQUENCE: 1864

Cys Arg Tyr Pro Leu Thr Val
1               5

<210> SEQ ID NO 1865
<211> LENGTH: 7
<212> TYPE: PRT
<213> ORGANISM: Homo sapiens

<400> SEQUENCE: 1865

Arg Tyr Pro Leu Thr Val Asp
1               5

<210> SEQ ID NO 1866
<211> LENGTH: 7
<212> TYPE: PRT
<213> ORGANISM: Homo sapiens

<400> SEQUENCE: 1866

Tyr Pro Leu Thr Val Asp Phe
1               5

<210> SEQ ID NO 1867
<211> LENGTH: 7
<212> TYPE: PRT
<213> ORGANISM: Homo sapiens

<400> SEQUENCE: 1867

Pro Leu Thr Val Asp Phe Glu
1               5

<210> SEQ ID NO 1868
<211> LENGTH: 7
<212> TYPE: PRT
<213> ORGANISM: Homo sapiens

<400> SEQUENCE: 1868

Leu Thr Val Asp Phe Glu Ala
1               5

<210> SEQ ID NO 1869
<211> LENGTH: 7
<212> TYPE: PRT
<213> ORGANISM: Homo sapiens

<400> SEQUENCE: 1869

Thr Val Asp Phe Glu Ala Phe
1               5

<210> SEQ ID NO 1870
<211> LENGTH: 7
<212> TYPE: PRT
<213> ORGANISM: Homo sapiens

<400> SEQUENCE: 1870

Val Asp Phe Glu Ala Phe Gly
1               5

<210> SEQ ID NO 1871
<211> LENGTH: 7
<212> TYPE: PRT
<213> ORGANISM: Homo sapiens

<400> SEQUENCE: 1871

Asp Phe Glu Ala Phe Gly Trp
1               5

<210> SEQ ID NO 1872
<211> LENGTH: 7
<212> TYPE: PRT
<213> ORGANISM: Homo sapiens

<400> SEQUENCE: 1872

Phe Glu Ala Phe Gly Trp Asp
1               5

<210> SEQ ID NO 1873
<211> LENGTH: 7
<212> TYPE: PRT
<213> ORGANISM: Homo sapiens

<400> SEQUENCE: 1873

Glu Ala Phe Gly Trp Asp Trp
1               5

-continued

```
<210> SEQ ID NO 1874
<211> LENGTH: 7
<212> TYPE: PRT
<213> ORGANISM: Homo sapiens

<400> SEQUENCE: 1874

Ala Phe Gly Trp Asp Trp Ile
1               5

<210> SEQ ID NO 1875
<211> LENGTH: 7
<212> TYPE: PRT
<213> ORGANISM: Homo sapiens

<400> SEQUENCE: 1875

Phe Gly Trp Asp Trp Ile Ile
1               5

<210> SEQ ID NO 1876
<211> LENGTH: 7
<212> TYPE: PRT
<213> ORGANISM: Homo sapiens

<400> SEQUENCE: 1876

Gly Trp Asp Trp Ile Ile Ala
1               5

<210> SEQ ID NO 1877
<211> LENGTH: 7
<212> TYPE: PRT
<213> ORGANISM: Homo sapiens

<400> SEQUENCE: 1877

Trp Asp Trp Ile Ile Ala Pro
1               5

<210> SEQ ID NO 1878
<211> LENGTH: 7
<212> TYPE: PRT
<213> ORGANISM: Homo sapiens

<400> SEQUENCE: 1878

Asp Trp Ile Ile Ala Pro Lys
1               5

<210> SEQ ID NO 1879
<211> LENGTH: 7
<212> TYPE: PRT
<213> ORGANISM: Homo sapiens

<400> SEQUENCE: 1879

Trp Ile Ile Ala Pro Lys Arg
1               5

<210> SEQ ID NO 1880
<211> LENGTH: 7
<212> TYPE: PRT
<213> ORGANISM: Homo sapiens

<400> SEQUENCE: 1880

Ile Ile Ala Pro Lys Arg Tyr
1               5

<210> SEQ ID NO 1881
<211> LENGTH: 7
```

<212> TYPE: PRT
<213> ORGANISM: Homo sapiens

<400> SEQUENCE: 1881

Ile Ala Pro Lys Arg Tyr Lys
1               5

<210> SEQ ID NO 1882
<211> LENGTH: 7
<212> TYPE: PRT
<213> ORGANISM: Homo sapiens

<400> SEQUENCE: 1882

Ala Pro Lys Arg Tyr Lys Ala
1               5

<210> SEQ ID NO 1883
<211> LENGTH: 7
<212> TYPE: PRT
<213> ORGANISM: Homo sapiens

<400> SEQUENCE: 1883

Pro Lys Arg Tyr Lys Ala Asn
1               5

<210> SEQ ID NO 1884
<211> LENGTH: 7
<212> TYPE: PRT
<213> ORGANISM: Homo sapiens

<400> SEQUENCE: 1884

Lys Arg Tyr Lys Ala Asn Tyr
1               5

<210> SEQ ID NO 1885
<211> LENGTH: 7
<212> TYPE: PRT
<213> ORGANISM: Homo sapiens

<400> SEQUENCE: 1885

Arg Tyr Lys Ala Asn Tyr Cys
1               5

<210> SEQ ID NO 1886
<211> LENGTH: 7
<212> TYPE: PRT
<213> ORGANISM: Homo sapiens

<400> SEQUENCE: 1886

Tyr Lys Ala Asn Tyr Cys Ser
1               5

<210> SEQ ID NO 1887
<211> LENGTH: 7
<212> TYPE: PRT
<213> ORGANISM: Homo sapiens

<400> SEQUENCE: 1887

Lys Ala Asn Tyr Cys Ser Gly
1               5

<210> SEQ ID NO 1888
<211> LENGTH: 7
<212> TYPE: PRT
<213> ORGANISM: Homo sapiens

<400> SEQUENCE: 1888

Ala Asn Tyr Cys Ser Gly Gln
1               5

<210> SEQ ID NO 1889
<211> LENGTH: 7
<212> TYPE: PRT
<213> ORGANISM: Homo sapiens

<400> SEQUENCE: 1889

Asn Tyr Cys Ser Gly Gln Cys
1               5

<210> SEQ ID NO 1890
<211> LENGTH: 7
<212> TYPE: PRT
<213> ORGANISM: Homo sapiens

<400> SEQUENCE: 1890

Tyr Cys Ser Gly Gln Cys Glu
1               5

<210> SEQ ID NO 1891
<211> LENGTH: 7
<212> TYPE: PRT
<213> ORGANISM: Homo sapiens

<400> SEQUENCE: 1891

Cys Ser Gly Gln Cys Glu Tyr
1               5

<210> SEQ ID NO 1892
<211> LENGTH: 7
<212> TYPE: PRT
<213> ORGANISM: Homo sapiens

<400> SEQUENCE: 1892

Ser Gly Gln Cys Glu Tyr Met
1               5

<210> SEQ ID NO 1893
<211> LENGTH: 7
<212> TYPE: PRT
<213> ORGANISM: Homo sapiens

<400> SEQUENCE: 1893

Gly Gln Cys Glu Tyr Met Phe
1               5

<210> SEQ ID NO 1894
<211> LENGTH: 7
<212> TYPE: PRT
<213> ORGANISM: Homo sapiens

<400> SEQUENCE: 1894

Gln Cys Glu Tyr Met Phe Met
1               5

<210> SEQ ID NO 1895
<211> LENGTH: 7
<212> TYPE: PRT
<213> ORGANISM: Homo sapiens

<400> SEQUENCE: 1895

Cys Glu Tyr Met Phe Met Gln
1               5

<210> SEQ ID NO 1896
<211> LENGTH: 7
<212> TYPE: PRT
<213> ORGANISM: Homo sapiens

<400> SEQUENCE: 1896

Glu Tyr Met Phe Met Gln Lys
1               5

<210> SEQ ID NO 1897
<211> LENGTH: 7
<212> TYPE: PRT
<213> ORGANISM: Homo sapiens

<400> SEQUENCE: 1897

Tyr Met Phe Met Gln Lys Tyr
1               5

<210> SEQ ID NO 1898
<211> LENGTH: 7
<212> TYPE: PRT
<213> ORGANISM: Homo sapiens

<400> SEQUENCE: 1898

Met Phe Met Gln Lys Tyr Pro
1               5

<210> SEQ ID NO 1899
<211> LENGTH: 7
<212> TYPE: PRT
<213> ORGANISM: Homo sapiens

<400> SEQUENCE: 1899

Phe Met Gln Lys Tyr Pro His
1               5

<210> SEQ ID NO 1900
<211> LENGTH: 7
<212> TYPE: PRT
<213> ORGANISM: Homo sapiens

<400> SEQUENCE: 1900

Met Gln Lys Tyr Pro His Thr
1               5

<210> SEQ ID NO 1901
<211> LENGTH: 7
<212> TYPE: PRT
<213> ORGANISM: Homo sapiens

<400> SEQUENCE: 1901

Gln Lys Tyr Pro His Thr His
1               5

<210> SEQ ID NO 1902
<211> LENGTH: 7
<212> TYPE: PRT
<213> ORGANISM: Homo sapiens

<400> SEQUENCE: 1902

Lys Tyr Pro His Thr His Leu

```
<210> SEQ ID NO 1903
<211> LENGTH: 7
<212> TYPE: PRT
<213> ORGANISM: Homo sapiens

<400> SEQUENCE: 1903

Tyr Pro His Thr His Leu Val
1               5

<210> SEQ ID NO 1904
<211> LENGTH: 7
<212> TYPE: PRT
<213> ORGANISM: Homo sapiens

<400> SEQUENCE: 1904

Pro His Thr His Leu Val Gln
1               5

<210> SEQ ID NO 1905
<211> LENGTH: 7
<212> TYPE: PRT
<213> ORGANISM: Homo sapiens

<400> SEQUENCE: 1905

His Thr His Leu Val Gln Gln
1               5

<210> SEQ ID NO 1906
<211> LENGTH: 7
<212> TYPE: PRT
<213> ORGANISM: Homo sapiens

<400> SEQUENCE: 1906

Thr His Leu Val Gln Gln Ala
1               5

<210> SEQ ID NO 1907
<211> LENGTH: 7
<212> TYPE: PRT
<213> ORGANISM: Homo sapiens

<400> SEQUENCE: 1907

His Leu Val Gln Gln Ala Asn
1               5

<210> SEQ ID NO 1908
<211> LENGTH: 7
<212> TYPE: PRT
<213> ORGANISM: Homo sapiens

<400> SEQUENCE: 1908

Leu Val Gln Gln Ala Asn Pro
1               5

<210> SEQ ID NO 1909
<211> LENGTH: 7
<212> TYPE: PRT
<213> ORGANISM: Homo sapiens

<400> SEQUENCE: 1909

Val Gln Gln Ala Asn Pro Arg
1               5
```

<210> SEQ ID NO 1910
<211> LENGTH: 7
<212> TYPE: PRT
<213> ORGANISM: Homo sapiens

<400> SEQUENCE: 1910

Gln Gln Ala Asn Pro Arg Gly
1               5

<210> SEQ ID NO 1911
<211> LENGTH: 7
<212> TYPE: PRT
<213> ORGANISM: Homo sapiens

<400> SEQUENCE: 1911

Gln Ala Asn Pro Arg Gly Ser
1               5

<210> SEQ ID NO 1912
<211> LENGTH: 7
<212> TYPE: PRT
<213> ORGANISM: Homo sapiens

<400> SEQUENCE: 1912

Ala Asn Pro Arg Gly Ser Ala
1               5

<210> SEQ ID NO 1913
<211> LENGTH: 7
<212> TYPE: PRT
<213> ORGANISM: Homo sapiens

<400> SEQUENCE: 1913

Asn Pro Arg Gly Ser Ala Gly
1               5

<210> SEQ ID NO 1914
<211> LENGTH: 7
<212> TYPE: PRT
<213> ORGANISM: Homo sapiens

<400> SEQUENCE: 1914

Pro Arg Gly Ser Ala Gly Pro
1               5

<210> SEQ ID NO 1915
<211> LENGTH: 7
<212> TYPE: PRT
<213> ORGANISM: Homo sapiens

<400> SEQUENCE: 1915

Arg Gly Ser Ala Gly Pro Cys
1               5

<210> SEQ ID NO 1916
<211> LENGTH: 7
<212> TYPE: PRT
<213> ORGANISM: Homo sapiens

<400> SEQUENCE: 1916

Gly Ser Ala Gly Pro Cys Cys
1               5

<210> SEQ ID NO 1917

```
<211> LENGTH: 7
<212> TYPE: PRT
<213> ORGANISM: Homo sapiens

<400> SEQUENCE: 1917

Ser Ala Gly Pro Cys Cys Thr
1               5

<210> SEQ ID NO 1918
<211> LENGTH: 7
<212> TYPE: PRT
<213> ORGANISM: Homo sapiens

<400> SEQUENCE: 1918

Ala Gly Pro Cys Cys Thr Pro
1               5

<210> SEQ ID NO 1919
<211> LENGTH: 7
<212> TYPE: PRT
<213> ORGANISM: Homo sapiens

<400> SEQUENCE: 1919

Gly Pro Cys Cys Thr Pro Thr
1               5

<210> SEQ ID NO 1920
<211> LENGTH: 7
<212> TYPE: PRT
<213> ORGANISM: Homo sapiens

<400> SEQUENCE: 1920

Pro Cys Cys Thr Pro Thr Lys
1               5

<210> SEQ ID NO 1921
<211> LENGTH: 7
<212> TYPE: PRT
<213> ORGANISM: Homo sapiens

<400> SEQUENCE: 1921

Cys Cys Thr Pro Thr Lys Met
1               5

<210> SEQ ID NO 1922
<211> LENGTH: 7
<212> TYPE: PRT
<213> ORGANISM: Homo sapiens

<400> SEQUENCE: 1922

Cys Thr Pro Thr Lys Met Ser
1               5

<210> SEQ ID NO 1923
<211> LENGTH: 7
<212> TYPE: PRT
<213> ORGANISM: Homo sapiens

<400> SEQUENCE: 1923

Thr Pro Thr Lys Met Ser Pro
1               5

<210> SEQ ID NO 1924
<211> LENGTH: 7
<212> TYPE: PRT
```

<213> ORGANISM: Homo sapiens

<400> SEQUENCE: 1924

Pro Thr Lys Met Ser Pro Ile
1               5

<210> SEQ ID NO 1925
<211> LENGTH: 7
<212> TYPE: PRT
<213> ORGANISM: Homo sapiens

<400> SEQUENCE: 1925

Thr Lys Met Ser Pro Ile Asn
1               5

<210> SEQ ID NO 1926
<211> LENGTH: 7
<212> TYPE: PRT
<213> ORGANISM: Homo sapiens

<400> SEQUENCE: 1926

Lys Met Ser Pro Ile Asn Met
1               5

<210> SEQ ID NO 1927
<211> LENGTH: 7
<212> TYPE: PRT
<213> ORGANISM: Homo sapiens

<400> SEQUENCE: 1927

Met Ser Pro Ile Asn Met Leu
1               5

<210> SEQ ID NO 1928
<211> LENGTH: 7
<212> TYPE: PRT
<213> ORGANISM: Homo sapiens

<400> SEQUENCE: 1928

Ser Pro Ile Asn Met Leu Tyr
1               5

<210> SEQ ID NO 1929
<211> LENGTH: 7
<212> TYPE: PRT
<213> ORGANISM: Homo sapiens

<400> SEQUENCE: 1929

Pro Ile Asn Met Leu Tyr Phe
1               5

<210> SEQ ID NO 1930
<211> LENGTH: 7
<212> TYPE: PRT
<213> ORGANISM: Homo sapiens

<400> SEQUENCE: 1930

Ile Asn Met Leu Tyr Phe Asn
1               5

<210> SEQ ID NO 1931
<211> LENGTH: 7
<212> TYPE: PRT
<213> ORGANISM: Homo sapiens

```
<400> SEQUENCE: 1931

Asn Met Leu Tyr Phe Asn Asp
1               5

<210> SEQ ID NO 1932
<211> LENGTH: 7
<212> TYPE: PRT
<213> ORGANISM: Homo sapiens

<400> SEQUENCE: 1932

Met Leu Tyr Phe Asn Asp Lys
1               5

<210> SEQ ID NO 1933
<211> LENGTH: 7
<212> TYPE: PRT
<213> ORGANISM: Homo sapiens

<400> SEQUENCE: 1933

Leu Tyr Phe Asn Asp Lys Gln
1               5

<210> SEQ ID NO 1934
<211> LENGTH: 7
<212> TYPE: PRT
<213> ORGANISM: Homo sapiens

<400> SEQUENCE: 1934

Tyr Phe Asn Asp Lys Gln Gln
1               5

<210> SEQ ID NO 1935
<211> LENGTH: 7
<212> TYPE: PRT
<213> ORGANISM: Homo sapiens

<400> SEQUENCE: 1935

Phe Asn Asp Lys Gln Gln Ile
1               5

<210> SEQ ID NO 1936
<211> LENGTH: 7
<212> TYPE: PRT
<213> ORGANISM: Homo sapiens

<400> SEQUENCE: 1936

Asn Asp Lys Gln Gln Ile Ile
1               5

<210> SEQ ID NO 1937
<211> LENGTH: 7
<212> TYPE: PRT
<213> ORGANISM: Homo sapiens

<400> SEQUENCE: 1937

Asp Lys Gln Gln Ile Ile Tyr
1               5

<210> SEQ ID NO 1938
<211> LENGTH: 7
<212> TYPE: PRT
<213> ORGANISM: Homo sapiens

<400> SEQUENCE: 1938
```

```
Lys Gln Gln Ile Ile Tyr Gly
1               5

<210> SEQ ID NO 1939
<211> LENGTH: 7
<212> TYPE: PRT
<213> ORGANISM: Homo sapiens

<400> SEQUENCE: 1939

Gln Gln Ile Ile Tyr Gly Lys
1               5

<210> SEQ ID NO 1940
<211> LENGTH: 7
<212> TYPE: PRT
<213> ORGANISM: Homo sapiens

<400> SEQUENCE: 1940

Gln Ile Ile Tyr Gly Lys Ile
1               5

<210> SEQ ID NO 1941
<211> LENGTH: 7
<212> TYPE: PRT
<213> ORGANISM: Homo sapiens

<400> SEQUENCE: 1941

Ile Ile Tyr Gly Lys Ile Pro
1               5

<210> SEQ ID NO 1942
<211> LENGTH: 7
<212> TYPE: PRT
<213> ORGANISM: Homo sapiens

<400> SEQUENCE: 1942

Ile Tyr Gly Lys Ile Pro Gly
1               5

<210> SEQ ID NO 1943
<211> LENGTH: 7
<212> TYPE: PRT
<213> ORGANISM: Homo sapiens

<400> SEQUENCE: 1943

Tyr Gly Lys Ile Pro Gly Met
1               5

<210> SEQ ID NO 1944
<211> LENGTH: 7
<212> TYPE: PRT
<213> ORGANISM: Homo sapiens

<400> SEQUENCE: 1944

Gly Lys Ile Pro Gly Met Val
1               5

<210> SEQ ID NO 1945
<211> LENGTH: 7
<212> TYPE: PRT
<213> ORGANISM: Homo sapiens

<400> SEQUENCE: 1945

Lys Ile Pro Gly Met Val Val
1               5
```

<210> SEQ ID NO 1946
<211> LENGTH: 7
<212> TYPE: PRT
<213> ORGANISM: Homo sapiens

<400> SEQUENCE: 1946

Ile Pro Gly Met Val Val Asp
1               5

<210> SEQ ID NO 1947
<211> LENGTH: 7
<212> TYPE: PRT
<213> ORGANISM: Homo sapiens

<400> SEQUENCE: 1947

Pro Gly Met Val Val Asp Arg
1               5

<210> SEQ ID NO 1948
<211> LENGTH: 7
<212> TYPE: PRT
<213> ORGANISM: Homo sapiens

<400> SEQUENCE: 1948

Gly Met Val Val Asp Arg Cys
1               5

<210> SEQ ID NO 1949
<211> LENGTH: 7
<212> TYPE: PRT
<213> ORGANISM: Homo sapiens

<400> SEQUENCE: 1949

Met Val Val Asp Arg Cys Gly
1               5

<210> SEQ ID NO 1950
<211> LENGTH: 7
<212> TYPE: PRT
<213> ORGANISM: Homo sapiens

<400> SEQUENCE: 1950

Val Val Asp Arg Cys Gly Cys
1               5

<210> SEQ ID NO 1951
<211> LENGTH: 7
<212> TYPE: PRT
<213> ORGANISM: Homo sapiens

<400> SEQUENCE: 1951

Val Asp Arg Cys Gly Cys Ser
1               5

<210> SEQ ID NO 1952
<211> LENGTH: 8
<212> TYPE: PRT
<213> ORGANISM: Homo sapiens

<400> SEQUENCE: 1952

Met Val Leu Ala Ala Pro Leu Leu
1               5

<210> SEQ ID NO 1953
<211> LENGTH: 8
<212> TYPE: PRT
<213> ORGANISM: Homo sapiens

<400> SEQUENCE: 1953

Val Leu Ala Ala Pro Leu Leu Leu
1               5

<210> SEQ ID NO 1954
<211> LENGTH: 8
<212> TYPE: PRT
<213> ORGANISM: Homo sapiens

<400> SEQUENCE: 1954

Leu Ala Ala Pro Leu Leu Leu Gly
1               5

<210> SEQ ID NO 1955
<211> LENGTH: 8
<212> TYPE: PRT
<213> ORGANISM: Homo sapiens

<400> SEQUENCE: 1955

Ala Ala Pro Leu Leu Leu Gly Phe
1               5

<210> SEQ ID NO 1956
<211> LENGTH: 8
<212> TYPE: PRT
<213> ORGANISM: Homo sapiens

<400> SEQUENCE: 1956

Ala Pro Leu Leu Leu Gly Phe Leu
1               5

<210> SEQ ID NO 1957
<211> LENGTH: 8
<212> TYPE: PRT
<213> ORGANISM: Homo sapiens

<400> SEQUENCE: 1957

Pro Leu Leu Leu Gly Phe Leu Leu
1               5

<210> SEQ ID NO 1958
<211> LENGTH: 8
<212> TYPE: PRT
<213> ORGANISM: Homo sapiens

<400> SEQUENCE: 1958

Leu Leu Leu Gly Phe Leu Leu Leu
1               5

<210> SEQ ID NO 1959
<211> LENGTH: 8
<212> TYPE: PRT
<213> ORGANISM: Homo sapiens

<400> SEQUENCE: 1959

Leu Leu Gly Phe Leu Leu Leu Ala
1               5

<210> SEQ ID NO 1960
<211> LENGTH: 8

```
<212> TYPE: PRT
<213> ORGANISM: Homo sapiens

<400> SEQUENCE: 1960

Leu Gly Phe Leu Leu Leu Ala Leu
1               5

<210> SEQ ID NO 1961
<211> LENGTH: 8
<212> TYPE: PRT
<213> ORGANISM: Homo sapiens

<400> SEQUENCE: 1961

Gly Phe Leu Leu Leu Ala Leu Glu
1               5

<210> SEQ ID NO 1962
<211> LENGTH: 8
<212> TYPE: PRT
<213> ORGANISM: Homo sapiens

<400> SEQUENCE: 1962

Phe Leu Leu Leu Ala Leu Glu Leu
1               5

<210> SEQ ID NO 1963
<211> LENGTH: 8
<212> TYPE: PRT
<213> ORGANISM: Homo sapiens

<400> SEQUENCE: 1963

Leu Leu Leu Ala Leu Glu Leu Arg
1               5

<210> SEQ ID NO 1964
<211> LENGTH: 8
<212> TYPE: PRT
<213> ORGANISM: Homo sapiens

<400> SEQUENCE: 1964

Leu Leu Ala Leu Glu Leu Arg Pro
1               5

<210> SEQ ID NO 1965
<211> LENGTH: 8
<212> TYPE: PRT
<213> ORGANISM: Homo sapiens

<400> SEQUENCE: 1965

Leu Ala Leu Glu Leu Arg Pro Arg
1               5

<210> SEQ ID NO 1966
<211> LENGTH: 8
<212> TYPE: PRT
<213> ORGANISM: Homo sapiens

<400> SEQUENCE: 1966

Ala Leu Glu Leu Arg Pro Arg Gly
1               5

<210> SEQ ID NO 1967
<211> LENGTH: 8
<212> TYPE: PRT
<213> ORGANISM: Homo sapiens
```

<400> SEQUENCE: 1967

Leu Glu Leu Arg Pro Arg Gly Glu
1               5

<210> SEQ ID NO 1968
<211> LENGTH: 8
<212> TYPE: PRT
<213> ORGANISM: Homo sapiens

<400> SEQUENCE: 1968

Glu Leu Arg Pro Arg Gly Glu Ala
1               5

<210> SEQ ID NO 1969
<211> LENGTH: 8
<212> TYPE: PRT
<213> ORGANISM: Homo sapiens

<400> SEQUENCE: 1969

Leu Arg Pro Arg Gly Glu Ala Ala
1               5

<210> SEQ ID NO 1970
<211> LENGTH: 8
<212> TYPE: PRT
<213> ORGANISM: Homo sapiens

<400> SEQUENCE: 1970

Arg Pro Arg Gly Glu Ala Ala Glu
1               5

<210> SEQ ID NO 1971
<211> LENGTH: 8
<212> TYPE: PRT
<213> ORGANISM: Homo sapiens

<400> SEQUENCE: 1971

Pro Arg Gly Glu Ala Ala Glu Gly
1               5

<210> SEQ ID NO 1972
<211> LENGTH: 8
<212> TYPE: PRT
<213> ORGANISM: Homo sapiens

<400> SEQUENCE: 1972

Arg Gly Glu Ala Ala Glu Gly Pro
1               5

<210> SEQ ID NO 1973
<211> LENGTH: 8
<212> TYPE: PRT
<213> ORGANISM: Homo sapiens

<400> SEQUENCE: 1973

Gly Glu Ala Ala Glu Gly Pro Ala
1               5

<210> SEQ ID NO 1974
<211> LENGTH: 8
<212> TYPE: PRT
<213> ORGANISM: Homo sapiens

<400> SEQUENCE: 1974

Glu Ala Ala Glu Gly Pro Ala Ala
1               5

<210> SEQ ID NO 1975
<211> LENGTH: 8
<212> TYPE: PRT
<213> ORGANISM: Homo sapiens

<400> SEQUENCE: 1975

Ala Ala Glu Gly Pro Ala Ala Ala
1               5

<210> SEQ ID NO 1976
<211> LENGTH: 8
<212> TYPE: PRT
<213> ORGANISM: Homo sapiens

<400> SEQUENCE: 1976

Ala Glu Gly Pro Ala Ala Ala Ala
1               5

<210> SEQ ID NO 1977
<211> LENGTH: 8
<212> TYPE: PRT
<213> ORGANISM: Homo sapiens

<400> SEQUENCE: 1977

Glu Gly Pro Ala Ala Ala Ala Ala
1               5

<210> SEQ ID NO 1978
<211> LENGTH: 8
<212> TYPE: PRT
<213> ORGANISM: Homo sapiens

<400> SEQUENCE: 1978

Gly Pro Ala Ala Ala Ala Ala Ala
1               5

<210> SEQ ID NO 1979
<211> LENGTH: 8
<212> TYPE: PRT
<213> ORGANISM: Homo sapiens

<400> SEQUENCE: 1979

Pro Ala Ala Ala Ala Ala Ala Ala
1               5

<210> SEQ ID NO 1980
<211> LENGTH: 8
<212> TYPE: PRT
<213> ORGANISM: Homo sapiens

<400> SEQUENCE: 1980

Ala Ala Ala Ala Ala Ala Ala Ala
1               5

<210> SEQ ID NO 1981
<211> LENGTH: 8
<212> TYPE: PRT
<213> ORGANISM: Homo sapiens

<400> SEQUENCE: 1981

Ala Ala Ala Ala Ala Ala Ala Gly 1               5

<210> SEQ ID NO 1982
<211> LENGTH: 8
<212> TYPE: PRT
<213> ORGANISM: Homo sapiens

<400> SEQUENCE: 1982

Ala Ala Ala Ala Ala Ala Gly Val
1               5

<210> SEQ ID NO 1983
<211> LENGTH: 8
<212> TYPE: PRT
<213> ORGANISM: Homo sapiens

<400> SEQUENCE: 1983

Ala Ala Ala Ala Ala Gly Val Gly
1               5

<210> SEQ ID NO 1984
<211> LENGTH: 8
<212> TYPE: PRT
<213> ORGANISM: Homo sapiens

<400> SEQUENCE: 1984

Ala Ala Ala Ala Gly Val Gly Gly
1               5

<210> SEQ ID NO 1985
<211> LENGTH: 8
<212> TYPE: PRT
<213> ORGANISM: Homo sapiens

<400> SEQUENCE: 1985

Ala Ala Ala Gly Val Gly Gly Glu
1               5

<210> SEQ ID NO 1986
<211> LENGTH: 8
<212> TYPE: PRT
<213> ORGANISM: Homo sapiens

<400> SEQUENCE: 1986

Ala Ala Gly Val Gly Gly Glu Arg
1               5

<210> SEQ ID NO 1987
<211> LENGTH: 8
<212> TYPE: PRT
<213> ORGANISM: Homo sapiens

<400> SEQUENCE: 1987

Ala Gly Val Gly Gly Glu Arg Ser
1               5

<210> SEQ ID NO 1988
<211> LENGTH: 8
<212> TYPE: PRT
<213> ORGANISM: Homo sapiens

<400> SEQUENCE: 1988

Gly Val Gly Gly Glu Arg Ser Ser
1               5

<210> SEQ ID NO 1989
<211> LENGTH: 8
<212> TYPE: PRT
<213> ORGANISM: Homo sapiens

<400> SEQUENCE: 1989

Val Gly Gly Glu Arg Ser Ser Arg
1               5

<210> SEQ ID NO 1990
<211> LENGTH: 8
<212> TYPE: PRT
<213> ORGANISM: Homo sapiens

<400> SEQUENCE: 1990

Gly Gly Glu Arg Ser Ser Arg Pro
1               5

<210> SEQ ID NO 1991
<211> LENGTH: 8
<212> TYPE: PRT
<213> ORGANISM: Homo sapiens

<400> SEQUENCE: 1991

Gly Glu Arg Ser Ser Arg Pro Ala
1               5

<210> SEQ ID NO 1992
<211> LENGTH: 8
<212> TYPE: PRT
<213> ORGANISM: Homo sapiens

<400> SEQUENCE: 1992

Glu Arg Ser Ser Arg Pro Ala Pro
1               5

<210> SEQ ID NO 1993
<211> LENGTH: 8
<212> TYPE: PRT
<213> ORGANISM: Homo sapiens

<400> SEQUENCE: 1993

Arg Ser Ser Arg Pro Ala Pro Ser
1               5

<210> SEQ ID NO 1994
<211> LENGTH: 8
<212> TYPE: PRT
<213> ORGANISM: Homo sapiens

<400> SEQUENCE: 1994

Ser Ser Arg Pro Ala Pro Ser Val
1               5

<210> SEQ ID NO 1995
<211> LENGTH: 8
<212> TYPE: PRT
<213> ORGANISM: Homo sapiens

<400> SEQUENCE: 1995

Ser Arg Pro Ala Pro Ser Val Ala
1               5

<210> SEQ ID NO 1996

```
<211> LENGTH: 8
<212> TYPE: PRT
<213> ORGANISM: Homo sapiens

<400> SEQUENCE: 1996

Arg Pro Ala Pro Ser Val Ala Pro
1               5

<210> SEQ ID NO 1997
<211> LENGTH: 8
<212> TYPE: PRT
<213> ORGANISM: Homo sapiens

<400> SEQUENCE: 1997

Pro Ala Pro Ser Val Ala Pro Glu
1               5

<210> SEQ ID NO 1998
<211> LENGTH: 8
<212> TYPE: PRT
<213> ORGANISM: Homo sapiens

<400> SEQUENCE: 1998

Ala Pro Ser Val Ala Pro Glu Pro
1               5

<210> SEQ ID NO 1999
<211> LENGTH: 8
<212> TYPE: PRT
<213> ORGANISM: Homo sapiens

<400> SEQUENCE: 1999

Pro Ser Val Ala Pro Glu Pro Asp
1               5

<210> SEQ ID NO 2000
<211> LENGTH: 8
<212> TYPE: PRT
<213> ORGANISM: Homo sapiens

<400> SEQUENCE: 2000

Ser Val Ala Pro Glu Pro Asp Gly
1               5

<210> SEQ ID NO 2001
<211> LENGTH: 8
<212> TYPE: PRT
<213> ORGANISM: Homo sapiens

<400> SEQUENCE: 2001

Val Ala Pro Glu Pro Asp Gly Cys
1               5

<210> SEQ ID NO 2002
<211> LENGTH: 8
<212> TYPE: PRT
<213> ORGANISM: Homo sapiens

<400> SEQUENCE: 2002

Ala Pro Glu Pro Asp Gly Cys Pro
1               5

<210> SEQ ID NO 2003
<211> LENGTH: 8
<212> TYPE: PRT
```

```
<213> ORGANISM: Homo sapiens

<400> SEQUENCE: 2003

Pro Glu Pro Asp Gly Cys Pro Val
1               5

<210> SEQ ID NO 2004
<211> LENGTH: 8
<212> TYPE: PRT
<213> ORGANISM: Homo sapiens

<400> SEQUENCE: 2004

Glu Pro Asp Gly Cys Pro Val Cys
1               5

<210> SEQ ID NO 2005
<211> LENGTH: 8
<212> TYPE: PRT
<213> ORGANISM: Homo sapiens

<400> SEQUENCE: 2005

Pro Asp Gly Cys Pro Val Cys Val
1               5

<210> SEQ ID NO 2006
<211> LENGTH: 8
<212> TYPE: PRT
<213> ORGANISM: Homo sapiens

<400> SEQUENCE: 2006

Asp Gly Cys Pro Val Cys Val Trp
1               5

<210> SEQ ID NO 2007
<211> LENGTH: 8
<212> TYPE: PRT
<213> ORGANISM: Homo sapiens

<400> SEQUENCE: 2007

Gly Cys Pro Val Cys Val Trp Arg
1               5

<210> SEQ ID NO 2008
<211> LENGTH: 8
<212> TYPE: PRT
<213> ORGANISM: Homo sapiens

<400> SEQUENCE: 2008

Cys Pro Val Cys Val Trp Arg Gln
1               5

<210> SEQ ID NO 2009
<211> LENGTH: 8
<212> TYPE: PRT
<213> ORGANISM: Homo sapiens

<400> SEQUENCE: 2009

Pro Val Cys Val Trp Arg Gln His
1               5

<210> SEQ ID NO 2010
<211> LENGTH: 8
<212> TYPE: PRT
<213> ORGANISM: Homo sapiens
```

<400> SEQUENCE: 2010

Val Cys Val Trp Arg Gln His Ser
1               5

<210> SEQ ID NO 2011
<211> LENGTH: 8
<212> TYPE: PRT
<213> ORGANISM: Homo sapiens

<400> SEQUENCE: 2011

Cys Val Trp Arg Gln His Ser Arg
1               5

<210> SEQ ID NO 2012
<211> LENGTH: 8
<212> TYPE: PRT
<213> ORGANISM: Homo sapiens

<400> SEQUENCE: 2012

Val Trp Arg Gln His Ser Arg Glu
1               5

<210> SEQ ID NO 2013
<211> LENGTH: 8
<212> TYPE: PRT
<213> ORGANISM: Homo sapiens

<400> SEQUENCE: 2013

Trp Arg Gln His Ser Arg Glu Leu
1               5

<210> SEQ ID NO 2014
<211> LENGTH: 8
<212> TYPE: PRT
<213> ORGANISM: Homo sapiens

<400> SEQUENCE: 2014

Arg Gln His Ser Arg Glu Leu Arg
1               5

<210> SEQ ID NO 2015
<211> LENGTH: 8
<212> TYPE: PRT
<213> ORGANISM: Homo sapiens

<400> SEQUENCE: 2015

Gln His Ser Arg Glu Leu Arg Leu
1               5

<210> SEQ ID NO 2016
<211> LENGTH: 8
<212> TYPE: PRT
<213> ORGANISM: Homo sapiens

<400> SEQUENCE: 2016

His Ser Arg Glu Leu Arg Leu Glu
1               5

<210> SEQ ID NO 2017
<211> LENGTH: 8
<212> TYPE: PRT
<213> ORGANISM: Homo sapiens

<400> SEQUENCE: 2017

Ser Arg Glu Leu Arg Leu Glu Ser
1               5

<210> SEQ ID NO 2018
<211> LENGTH: 8
<212> TYPE: PRT
<213> ORGANISM: Homo sapiens

<400> SEQUENCE: 2018

Arg Glu Leu Arg Leu Glu Ser Ile
1               5

<210> SEQ ID NO 2019
<211> LENGTH: 8
<212> TYPE: PRT
<213> ORGANISM: Homo sapiens

<400> SEQUENCE: 2019

Glu Leu Arg Leu Glu Ser Ile Lys
1               5

<210> SEQ ID NO 2020
<211> LENGTH: 8
<212> TYPE: PRT
<213> ORGANISM: Homo sapiens

<400> SEQUENCE: 2020

Leu Arg Leu Glu Ser Ile Lys Ser
1               5

<210> SEQ ID NO 2021
<211> LENGTH: 8
<212> TYPE: PRT
<213> ORGANISM: Homo sapiens

<400> SEQUENCE: 2021

Arg Leu Glu Ser Ile Lys Ser Gln
1               5

<210> SEQ ID NO 2022
<211> LENGTH: 8
<212> TYPE: PRT
<213> ORGANISM: Homo sapiens

<400> SEQUENCE: 2022

Leu Glu Ser Ile Lys Ser Gln Ile
1               5

<210> SEQ ID NO 2023
<211> LENGTH: 8
<212> TYPE: PRT
<213> ORGANISM: Homo sapiens

<400> SEQUENCE: 2023

Glu Ser Ile Lys Ser Gln Ile Leu
1               5

<210> SEQ ID NO 2024
<211> LENGTH: 8
<212> TYPE: PRT
<213> ORGANISM: Homo sapiens

<400> SEQUENCE: 2024

Ser Ile Lys Ser Gln Ile Leu Ser
1               5

<210> SEQ ID NO 2025
<211> LENGTH: 8
<212> TYPE: PRT
<213> ORGANISM: Homo sapiens

<400> SEQUENCE: 2025

Ile Lys Ser Gln Ile Leu Ser Lys
1               5

<210> SEQ ID NO 2026
<211> LENGTH: 8
<212> TYPE: PRT
<213> ORGANISM: Homo sapiens

<400> SEQUENCE: 2026

Lys Ser Gln Ile Leu Ser Lys Leu
1               5

<210> SEQ ID NO 2027
<211> LENGTH: 8
<212> TYPE: PRT
<213> ORGANISM: Homo sapiens

<400> SEQUENCE: 2027

Ser Gln Ile Leu Ser Lys Leu Arg
1               5

<210> SEQ ID NO 2028
<211> LENGTH: 8
<212> TYPE: PRT
<213> ORGANISM: Homo sapiens

<400> SEQUENCE: 2028

Gln Ile Leu Ser Lys Leu Arg Leu
1               5

<210> SEQ ID NO 2029
<211> LENGTH: 8
<212> TYPE: PRT
<213> ORGANISM: Homo sapiens

<400> SEQUENCE: 2029

Ile Leu Ser Lys Leu Arg Leu Lys
1               5

<210> SEQ ID NO 2030
<211> LENGTH: 8
<212> TYPE: PRT
<213> ORGANISM: Homo sapiens

<400> SEQUENCE: 2030

Leu Ser Lys Leu Arg Leu Lys Glu
1               5

<210> SEQ ID NO 2031
<211> LENGTH: 8
<212> TYPE: PRT
<213> ORGANISM: Homo sapiens

<400> SEQUENCE: 2031

Ser Lys Leu Arg Leu Lys Glu Ala
1               5

```
<210> SEQ ID NO 2032
<211> LENGTH: 8
<212> TYPE: PRT
<213> ORGANISM: Homo sapiens

<400> SEQUENCE: 2032

Lys Leu Arg Leu Lys Glu Ala Pro
1               5

<210> SEQ ID NO 2033
<211> LENGTH: 8
<212> TYPE: PRT
<213> ORGANISM: Homo sapiens

<400> SEQUENCE: 2033

Leu Arg Leu Lys Glu Ala Pro Asn
1               5

<210> SEQ ID NO 2034
<211> LENGTH: 8
<212> TYPE: PRT
<213> ORGANISM: Homo sapiens

<400> SEQUENCE: 2034

Arg Leu Lys Glu Ala Pro Asn Ile
1               5

<210> SEQ ID NO 2035
<211> LENGTH: 8
<212> TYPE: PRT
<213> ORGANISM: Homo sapiens

<400> SEQUENCE: 2035

Leu Lys Glu Ala Pro Asn Ile Ser
1               5

<210> SEQ ID NO 2036
<211> LENGTH: 8
<212> TYPE: PRT
<213> ORGANISM: Homo sapiens

<400> SEQUENCE: 2036

Lys Glu Ala Pro Asn Ile Ser Arg
1               5

<210> SEQ ID NO 2037
<211> LENGTH: 8
<212> TYPE: PRT
<213> ORGANISM: Homo sapiens

<400> SEQUENCE: 2037

Glu Ala Pro Asn Ile Ser Arg Glu
1               5

<210> SEQ ID NO 2038
<211> LENGTH: 8
<212> TYPE: PRT
<213> ORGANISM: Homo sapiens

<400> SEQUENCE: 2038

Ala Pro Asn Ile Ser Arg Glu Val
1               5

<210> SEQ ID NO 2039
<211> LENGTH: 8
```

<212> TYPE: PRT
<213> ORGANISM: Homo sapiens

<400> SEQUENCE: 2039

Pro Asn Ile Ser Arg Glu Val Val
1               5

<210> SEQ ID NO 2040
<211> LENGTH: 8
<212> TYPE: PRT
<213> ORGANISM: Homo sapiens

<400> SEQUENCE: 2040

Asn Ile Ser Arg Glu Val Val Lys
1               5

<210> SEQ ID NO 2041
<211> LENGTH: 8
<212> TYPE: PRT
<213> ORGANISM: Homo sapiens

<400> SEQUENCE: 2041

Ile Ser Arg Glu Val Val Lys Gln
1               5

<210> SEQ ID NO 2042
<211> LENGTH: 8
<212> TYPE: PRT
<213> ORGANISM: Homo sapiens

<400> SEQUENCE: 2042

Ser Arg Glu Val Val Lys Gln Leu
1               5

<210> SEQ ID NO 2043
<211> LENGTH: 8
<212> TYPE: PRT
<213> ORGANISM: Homo sapiens

<400> SEQUENCE: 2043

Arg Glu Val Val Lys Gln Leu Leu
1               5

<210> SEQ ID NO 2044
<211> LENGTH: 8
<212> TYPE: PRT
<213> ORGANISM: Homo sapiens

<400> SEQUENCE: 2044

Glu Val Val Lys Gln Leu Leu Pro
1               5

<210> SEQ ID NO 2045
<211> LENGTH: 8
<212> TYPE: PRT
<213> ORGANISM: Homo sapiens

<400> SEQUENCE: 2045

Val Val Lys Gln Leu Leu Pro Lys
1               5

<210> SEQ ID NO 2046
<211> LENGTH: 8
<212> TYPE: PRT
<213> ORGANISM: Homo sapiens

<400> SEQUENCE: 2046

Val Lys Gln Leu Leu Pro Lys Ala
1               5

<210> SEQ ID NO 2047
<211> LENGTH: 8
<212> TYPE: PRT
<213> ORGANISM: Homo sapiens

<400> SEQUENCE: 2047

Lys Gln Leu Leu Pro Lys Ala Pro
1               5

<210> SEQ ID NO 2048
<211> LENGTH: 8
<212> TYPE: PRT
<213> ORGANISM: Homo sapiens

<400> SEQUENCE: 2048

Gln Leu Leu Pro Lys Ala Pro Pro
1               5

<210> SEQ ID NO 2049
<211> LENGTH: 8
<212> TYPE: PRT
<213> ORGANISM: Homo sapiens

<400> SEQUENCE: 2049

Leu Leu Pro Lys Ala Pro Pro Leu
1               5

<210> SEQ ID NO 2050
<211> LENGTH: 8
<212> TYPE: PRT
<213> ORGANISM: Homo sapiens

<400> SEQUENCE: 2050

Leu Pro Lys Ala Pro Pro Leu Gln
1               5

<210> SEQ ID NO 2051
<211> LENGTH: 8
<212> TYPE: PRT
<213> ORGANISM: Homo sapiens

<400> SEQUENCE: 2051

Pro Lys Ala Pro Pro Leu Gln Gln
1               5

<210> SEQ ID NO 2052
<211> LENGTH: 8
<212> TYPE: PRT
<213> ORGANISM: Homo sapiens

<400> SEQUENCE: 2052

Lys Ala Pro Pro Leu Gln Gln Ile
1               5

<210> SEQ ID NO 2053
<211> LENGTH: 8
<212> TYPE: PRT
<213> ORGANISM: Homo sapiens

<400> SEQUENCE: 2053

Ala Pro Pro Leu Gln Gln Ile Leu
1               5

<210> SEQ ID NO 2054
<211> LENGTH: 8
<212> TYPE: PRT
<213> ORGANISM: Homo sapiens

<400> SEQUENCE: 2054

Pro Pro Leu Gln Gln Ile Leu Asp
1               5

<210> SEQ ID NO 2055
<211> LENGTH: 8
<212> TYPE: PRT
<213> ORGANISM: Homo sapiens

<400> SEQUENCE: 2055

Pro Leu Gln Gln Ile Leu Asp Leu
1               5

<210> SEQ ID NO 2056
<211> LENGTH: 8
<212> TYPE: PRT
<213> ORGANISM: Homo sapiens

<400> SEQUENCE: 2056

Leu Gln Gln Ile Leu Asp Leu His
1               5

<210> SEQ ID NO 2057
<211> LENGTH: 8
<212> TYPE: PRT
<213> ORGANISM: Homo sapiens

<400> SEQUENCE: 2057

Gln Gln Ile Leu Asp Leu His Asp
1               5

<210> SEQ ID NO 2058
<211> LENGTH: 8
<212> TYPE: PRT
<213> ORGANISM: Homo sapiens

<400> SEQUENCE: 2058

Gln Ile Leu Asp Leu His Asp Phe
1               5

<210> SEQ ID NO 2059
<211> LENGTH: 8
<212> TYPE: PRT
<213> ORGANISM: Homo sapiens

<400> SEQUENCE: 2059

Ile Leu Asp Leu His Asp Phe Gln
1               5

<210> SEQ ID NO 2060
<211> LENGTH: 8
<212> TYPE: PRT
<213> ORGANISM: Homo sapiens

<400> SEQUENCE: 2060

Leu Asp Leu His Asp Phe Gln Gly

```
1               5

<210> SEQ ID NO 2061
<211> LENGTH: 8
<212> TYPE: PRT
<213> ORGANISM: Homo sapiens

<400> SEQUENCE: 2061

Asp Leu His Asp Phe Gln Gly Asp
1               5

<210> SEQ ID NO 2062
<211> LENGTH: 8
<212> TYPE: PRT
<213> ORGANISM: Homo sapiens

<400> SEQUENCE: 2062

Leu His Asp Phe Gln Gly Asp Ala
1               5

<210> SEQ ID NO 2063
<211> LENGTH: 8
<212> TYPE: PRT
<213> ORGANISM: Homo sapiens

<400> SEQUENCE: 2063

His Asp Phe Gln Gly Asp Ala Leu
1               5

<210> SEQ ID NO 2064
<211> LENGTH: 8
<212> TYPE: PRT
<213> ORGANISM: Homo sapiens

<400> SEQUENCE: 2064

Asp Phe Gln Gly Asp Ala Leu Gln
1               5

<210> SEQ ID NO 2065
<211> LENGTH: 8
<212> TYPE: PRT
<213> ORGANISM: Homo sapiens

<400> SEQUENCE: 2065

Phe Gln Gly Asp Ala Leu Gln Pro
1               5

<210> SEQ ID NO 2066
<211> LENGTH: 8
<212> TYPE: PRT
<213> ORGANISM: Homo sapiens

<400> SEQUENCE: 2066

Gln Gly Asp Ala Leu Gln Pro Glu
1               5

<210> SEQ ID NO 2067
<211> LENGTH: 8
<212> TYPE: PRT
<213> ORGANISM: Homo sapiens

<400> SEQUENCE: 2067

Gly Asp Ala Leu Gln Pro Glu Asp
1               5
```

<210> SEQ ID NO 2068
<211> LENGTH: 8
<212> TYPE: PRT
<213> ORGANISM: Homo sapiens

<400> SEQUENCE: 2068

Asp Ala Leu Gln Pro Glu Asp Phe
1               5

<210> SEQ ID NO 2069
<211> LENGTH: 8
<212> TYPE: PRT
<213> ORGANISM: Homo sapiens

<400> SEQUENCE: 2069

Ala Leu Gln Pro Glu Asp Phe Leu
1               5

<210> SEQ ID NO 2070
<211> LENGTH: 8
<212> TYPE: PRT
<213> ORGANISM: Homo sapiens

<400> SEQUENCE: 2070

Leu Gln Pro Glu Asp Phe Leu Glu
1               5

<210> SEQ ID NO 2071
<211> LENGTH: 8
<212> TYPE: PRT
<213> ORGANISM: Homo sapiens

<400> SEQUENCE: 2071

Gln Pro Glu Asp Phe Leu Glu Glu
1               5

<210> SEQ ID NO 2072
<211> LENGTH: 8
<212> TYPE: PRT
<213> ORGANISM: Homo sapiens

<400> SEQUENCE: 2072

Pro Glu Asp Phe Leu Glu Glu Asp
1               5

<210> SEQ ID NO 2073
<211> LENGTH: 8
<212> TYPE: PRT
<213> ORGANISM: Homo sapiens

<400> SEQUENCE: 2073

Glu Asp Phe Leu Glu Glu Asp Glu
1               5

<210> SEQ ID NO 2074
<211> LENGTH: 8
<212> TYPE: PRT
<213> ORGANISM: Homo sapiens

<400> SEQUENCE: 2074

Asp Phe Leu Glu Glu Asp Glu Tyr
1               5

<210> SEQ ID NO 2075

```
<211> LENGTH: 8
<212> TYPE: PRT
<213> ORGANISM: Homo sapiens

<400> SEQUENCE: 2075

Phe Leu Glu Glu Asp Glu Tyr His
1               5

<210> SEQ ID NO 2076
<211> LENGTH: 8
<212> TYPE: PRT
<213> ORGANISM: Homo sapiens

<400> SEQUENCE: 2076

Leu Glu Glu Asp Glu Tyr His Ala
1               5

<210> SEQ ID NO 2077
<211> LENGTH: 8
<212> TYPE: PRT
<213> ORGANISM: Homo sapiens

<400> SEQUENCE: 2077

Glu Glu Asp Glu Tyr His Ala Thr
1               5

<210> SEQ ID NO 2078
<211> LENGTH: 8
<212> TYPE: PRT
<213> ORGANISM: Homo sapiens

<400> SEQUENCE: 2078

Glu Asp Glu Tyr His Ala Thr Thr
1               5

<210> SEQ ID NO 2079
<211> LENGTH: 8
<212> TYPE: PRT
<213> ORGANISM: Homo sapiens

<400> SEQUENCE: 2079

Asp Glu Tyr His Ala Thr Thr Glu
1               5

<210> SEQ ID NO 2080
<211> LENGTH: 8
<212> TYPE: PRT
<213> ORGANISM: Homo sapiens

<400> SEQUENCE: 2080

Glu Tyr His Ala Thr Thr Glu Thr
1               5

<210> SEQ ID NO 2081
<211> LENGTH: 8
<212> TYPE: PRT
<213> ORGANISM: Homo sapiens

<400> SEQUENCE: 2081

Tyr His Ala Thr Thr Glu Thr Val
1               5

<210> SEQ ID NO 2082
<211> LENGTH: 8
<212> TYPE: PRT
```

<213> ORGANISM: Homo sapiens

<400> SEQUENCE: 2082

His Ala Thr Thr Glu Thr Val Ile
1               5

<210> SEQ ID NO 2083
<211> LENGTH: 8
<212> TYPE: PRT
<213> ORGANISM: Homo sapiens

<400> SEQUENCE: 2083

Ala Thr Thr Glu Thr Val Ile Ser
1               5

<210> SEQ ID NO 2084
<211> LENGTH: 8
<212> TYPE: PRT
<213> ORGANISM: Homo sapiens

<400> SEQUENCE: 2084

Thr Thr Glu Thr Val Ile Ser Met
1               5

<210> SEQ ID NO 2085
<211> LENGTH: 8
<212> TYPE: PRT
<213> ORGANISM: Homo sapiens

<400> SEQUENCE: 2085

Thr Glu Thr Val Ile Ser Met Ala
1               5

<210> SEQ ID NO 2086
<211> LENGTH: 8
<212> TYPE: PRT
<213> ORGANISM: Homo sapiens

<400> SEQUENCE: 2086

Glu Thr Val Ile Ser Met Ala Gln
1               5

<210> SEQ ID NO 2087
<211> LENGTH: 8
<212> TYPE: PRT
<213> ORGANISM: Homo sapiens

<400> SEQUENCE: 2087

Thr Val Ile Ser Met Ala Gln Glu
1               5

<210> SEQ ID NO 2088
<211> LENGTH: 8
<212> TYPE: PRT
<213> ORGANISM: Homo sapiens

<400> SEQUENCE: 2088

Val Ile Ser Met Ala Gln Glu Thr
1               5

<210> SEQ ID NO 2089
<211> LENGTH: 8
<212> TYPE: PRT
<213> ORGANISM: Homo sapiens

<400> SEQUENCE: 2089

Ile Ser Met Ala Gln Glu Thr Asp
1               5

<210> SEQ ID NO 2090
<211> LENGTH: 8
<212> TYPE: PRT
<213> ORGANISM: Homo sapiens

<400> SEQUENCE: 2090

Ser Met Ala Gln Glu Thr Asp Pro
1               5

<210> SEQ ID NO 2091
<211> LENGTH: 8
<212> TYPE: PRT
<213> ORGANISM: Homo sapiens

<400> SEQUENCE: 2091

Met Ala Gln Glu Thr Asp Pro Ala
1               5

<210> SEQ ID NO 2092
<211> LENGTH: 8
<212> TYPE: PRT
<213> ORGANISM: Homo sapiens

<400> SEQUENCE: 2092

Ala Gln Glu Thr Asp Pro Ala Val
1               5

<210> SEQ ID NO 2093
<211> LENGTH: 8
<212> TYPE: PRT
<213> ORGANISM: Homo sapiens

<400> SEQUENCE: 2093

Gln Glu Thr Asp Pro Ala Val Gln
1               5

<210> SEQ ID NO 2094
<211> LENGTH: 8
<212> TYPE: PRT
<213> ORGANISM: Homo sapiens

<400> SEQUENCE: 2094

Glu Thr Asp Pro Ala Val Gln Thr
1               5

<210> SEQ ID NO 2095
<211> LENGTH: 8
<212> TYPE: PRT
<213> ORGANISM: Homo sapiens

<400> SEQUENCE: 2095

Thr Asp Pro Ala Val Gln Thr Asp
1               5

<210> SEQ ID NO 2096
<211> LENGTH: 8
<212> TYPE: PRT
<213> ORGANISM: Homo sapiens

<400> SEQUENCE: 2096

Asp Pro Ala Val Gln Thr Asp Gly
1               5

<210> SEQ ID NO 2097
<211> LENGTH: 8
<212> TYPE: PRT
<213> ORGANISM: Homo sapiens

<400> SEQUENCE: 2097

Pro Ala Val Gln Thr Asp Gly Ser
1               5

<210> SEQ ID NO 2098
<211> LENGTH: 8
<212> TYPE: PRT
<213> ORGANISM: Homo sapiens

<400> SEQUENCE: 2098

Ala Val Gln Thr Asp Gly Ser Pro
1               5

<210> SEQ ID NO 2099
<211> LENGTH: 8
<212> TYPE: PRT
<213> ORGANISM: Homo sapiens

<400> SEQUENCE: 2099

Val Gln Thr Asp Gly Ser Pro Leu
1               5

<210> SEQ ID NO 2100
<211> LENGTH: 8
<212> TYPE: PRT
<213> ORGANISM: Homo sapiens

<400> SEQUENCE: 2100

Gln Thr Asp Gly Ser Pro Leu Cys
1               5

<210> SEQ ID NO 2101
<211> LENGTH: 8
<212> TYPE: PRT
<213> ORGANISM: Homo sapiens

<400> SEQUENCE: 2101

Thr Asp Gly Ser Pro Leu Cys Cys
1               5

<210> SEQ ID NO 2102
<211> LENGTH: 8
<212> TYPE: PRT
<213> ORGANISM: Homo sapiens

<400> SEQUENCE: 2102

Asp Gly Ser Pro Leu Cys Cys His
1               5

<210> SEQ ID NO 2103
<211> LENGTH: 8
<212> TYPE: PRT
<213> ORGANISM: Homo sapiens

<400> SEQUENCE: 2103

Gly Ser Pro Leu Cys Cys His Phe
1               5

<210> SEQ ID NO 2104
<211> LENGTH: 8
<212> TYPE: PRT
<213> ORGANISM: Homo sapiens

<400> SEQUENCE: 2104

Ser Pro Leu Cys Cys His Phe His
1               5

<210> SEQ ID NO 2105
<211> LENGTH: 8
<212> TYPE: PRT
<213> ORGANISM: Homo sapiens

<400> SEQUENCE: 2105

Pro Leu Cys Cys His Phe His Phe
1               5

<210> SEQ ID NO 2106
<211> LENGTH: 8
<212> TYPE: PRT
<213> ORGANISM: Homo sapiens

<400> SEQUENCE: 2106

Leu Cys Cys His Phe His Phe Ser
1               5

<210> SEQ ID NO 2107
<211> LENGTH: 8
<212> TYPE: PRT
<213> ORGANISM: Homo sapiens

<400> SEQUENCE: 2107

Cys Cys His Phe His Phe Ser Pro
1               5

<210> SEQ ID NO 2108
<211> LENGTH: 8
<212> TYPE: PRT
<213> ORGANISM: Homo sapiens

<400> SEQUENCE: 2108

Cys His Phe His Phe Ser Pro Lys
1               5

<210> SEQ ID NO 2109
<211> LENGTH: 8
<212> TYPE: PRT
<213> ORGANISM: Homo sapiens

<400> SEQUENCE: 2109

His Phe His Phe Ser Pro Lys Val
1               5

<210> SEQ ID NO 2110
<211> LENGTH: 8
<212> TYPE: PRT
<213> ORGANISM: Homo sapiens

<400> SEQUENCE: 2110

Phe His Phe Ser Pro Lys Val Met
1               5

```
<210> SEQ ID NO 2111
<211> LENGTH: 8
<212> TYPE: PRT
<213> ORGANISM: Homo sapiens

<400> SEQUENCE: 2111

His Phe Ser Pro Lys Val Met Phe
1               5

<210> SEQ ID NO 2112
<211> LENGTH: 8
<212> TYPE: PRT
<213> ORGANISM: Homo sapiens

<400> SEQUENCE: 2112

Phe Ser Pro Lys Val Met Phe Thr
1               5

<210> SEQ ID NO 2113
<211> LENGTH: 8
<212> TYPE: PRT
<213> ORGANISM: Homo sapiens

<400> SEQUENCE: 2113

Ser Pro Lys Val Met Phe Thr Lys
1               5

<210> SEQ ID NO 2114
<211> LENGTH: 8
<212> TYPE: PRT
<213> ORGANISM: Homo sapiens

<400> SEQUENCE: 2114

Pro Lys Val Met Phe Thr Lys Val
1               5

<210> SEQ ID NO 2115
<211> LENGTH: 8
<212> TYPE: PRT
<213> ORGANISM: Homo sapiens

<400> SEQUENCE: 2115

Lys Val Met Phe Thr Lys Val Leu
1               5

<210> SEQ ID NO 2116
<211> LENGTH: 8
<212> TYPE: PRT
<213> ORGANISM: Homo sapiens

<400> SEQUENCE: 2116

Val Met Phe Thr Lys Val Leu Lys
1               5

<210> SEQ ID NO 2117
<211> LENGTH: 8
<212> TYPE: PRT
<213> ORGANISM: Homo sapiens

<400> SEQUENCE: 2117

Met Phe Thr Lys Val Leu Lys Ala
1               5

<210> SEQ ID NO 2118
<211> LENGTH: 8
```

```
<212> TYPE: PRT
<213> ORGANISM: Homo sapiens

<400> SEQUENCE: 2118

Phe Thr Lys Val Leu Lys Ala Gln
1               5

<210> SEQ ID NO 2119
<211> LENGTH: 8
<212> TYPE: PRT
<213> ORGANISM: Homo sapiens

<400> SEQUENCE: 2119

Thr Lys Val Leu Lys Ala Gln Leu
1               5

<210> SEQ ID NO 2120
<211> LENGTH: 8
<212> TYPE: PRT
<213> ORGANISM: Homo sapiens

<400> SEQUENCE: 2120

Lys Val Leu Lys Ala Gln Leu Trp
1               5

<210> SEQ ID NO 2121
<211> LENGTH: 8
<212> TYPE: PRT
<213> ORGANISM: Homo sapiens

<400> SEQUENCE: 2121

Val Leu Lys Ala Gln Leu Trp Val
1               5

<210> SEQ ID NO 2122
<211> LENGTH: 8
<212> TYPE: PRT
<213> ORGANISM: Homo sapiens

<400> SEQUENCE: 2122

Leu Lys Ala Gln Leu Trp Val Tyr
1               5

<210> SEQ ID NO 2123
<211> LENGTH: 8
<212> TYPE: PRT
<213> ORGANISM: Homo sapiens

<400> SEQUENCE: 2123

Lys Ala Gln Leu Trp Val Tyr Leu
1               5

<210> SEQ ID NO 2124
<211> LENGTH: 8
<212> TYPE: PRT
<213> ORGANISM: Homo sapiens

<400> SEQUENCE: 2124

Ala Gln Leu Trp Val Tyr Leu Arg
1               5

<210> SEQ ID NO 2125
<211> LENGTH: 8
<212> TYPE: PRT
<213> ORGANISM: Homo sapiens
```

<400> SEQUENCE: 2125

Gln Leu Trp Val Tyr Leu Arg Pro
1               5

<210> SEQ ID NO 2126
<211> LENGTH: 8
<212> TYPE: PRT
<213> ORGANISM: Homo sapiens

<400> SEQUENCE: 2126

Leu Trp Val Tyr Leu Arg Pro Val
1               5

<210> SEQ ID NO 2127
<211> LENGTH: 8
<212> TYPE: PRT
<213> ORGANISM: Homo sapiens

<400> SEQUENCE: 2127

Trp Val Tyr Leu Arg Pro Val Pro
1               5

<210> SEQ ID NO 2128
<211> LENGTH: 8
<212> TYPE: PRT
<213> ORGANISM: Homo sapiens

<400> SEQUENCE: 2128

Val Tyr Leu Arg Pro Val Pro Arg
1               5

<210> SEQ ID NO 2129
<211> LENGTH: 8
<212> TYPE: PRT
<213> ORGANISM: Homo sapiens

<400> SEQUENCE: 2129

Tyr Leu Arg Pro Val Pro Arg Pro
1               5

<210> SEQ ID NO 2130
<211> LENGTH: 8
<212> TYPE: PRT
<213> ORGANISM: Homo sapiens

<400> SEQUENCE: 2130

Leu Arg Pro Val Pro Arg Pro Ala
1               5

<210> SEQ ID NO 2131
<211> LENGTH: 8
<212> TYPE: PRT
<213> ORGANISM: Homo sapiens

<400> SEQUENCE: 2131

Arg Pro Val Pro Arg Pro Ala Thr
1               5

<210> SEQ ID NO 2132
<211> LENGTH: 8
<212> TYPE: PRT
<213> ORGANISM: Homo sapiens

<400> SEQUENCE: 2132

Pro Val Pro Arg Pro Ala Thr Val
1               5

<210> SEQ ID NO 2133
<211> LENGTH: 8
<212> TYPE: PRT
<213> ORGANISM: Homo sapiens

<400> SEQUENCE: 2133

Val Pro Arg Pro Ala Thr Val Tyr
1               5

<210> SEQ ID NO 2134
<211> LENGTH: 8
<212> TYPE: PRT
<213> ORGANISM: Homo sapiens

<400> SEQUENCE: 2134

Pro Arg Pro Ala Thr Val Tyr Leu
1               5

<210> SEQ ID NO 2135
<211> LENGTH: 8
<212> TYPE: PRT
<213> ORGANISM: Homo sapiens

<400> SEQUENCE: 2135

Arg Pro Ala Thr Val Tyr Leu Gln
1               5

<210> SEQ ID NO 2136
<211> LENGTH: 8
<212> TYPE: PRT
<213> ORGANISM: Homo sapiens

<400> SEQUENCE: 2136

Pro Ala Thr Val Tyr Leu Gln Ile
1               5

<210> SEQ ID NO 2137
<211> LENGTH: 8
<212> TYPE: PRT
<213> ORGANISM: Homo sapiens

<400> SEQUENCE: 2137

Ala Thr Val Tyr Leu Gln Ile Leu
1               5

<210> SEQ ID NO 2138
<211> LENGTH: 8
<212> TYPE: PRT
<213> ORGANISM: Homo sapiens

<400> SEQUENCE: 2138

Thr Val Tyr Leu Gln Ile Leu Arg
1               5

<210> SEQ ID NO 2139
<211> LENGTH: 8
<212> TYPE: PRT
<213> ORGANISM: Homo sapiens

<400> SEQUENCE: 2139

Val Tyr Leu Gln Ile Leu Arg Leu 1               5

<210> SEQ ID NO 2140
<211> LENGTH: 8
<212> TYPE: PRT
<213> ORGANISM: Homo sapiens

<400> SEQUENCE: 2140

Tyr Leu Gln Ile Leu Arg Leu Lys
1               5

<210> SEQ ID NO 2141
<211> LENGTH: 8
<212> TYPE: PRT
<213> ORGANISM: Homo sapiens

<400> SEQUENCE: 2141

Leu Gln Ile Leu Arg Leu Lys Pro
1               5

<210> SEQ ID NO 2142
<211> LENGTH: 8
<212> TYPE: PRT
<213> ORGANISM: Homo sapiens

<400> SEQUENCE: 2142

Gln Ile Leu Arg Leu Lys Pro Leu
1               5

<210> SEQ ID NO 2143
<211> LENGTH: 8
<212> TYPE: PRT
<213> ORGANISM: Homo sapiens

<400> SEQUENCE: 2143

Ile Leu Arg Leu Lys Pro Leu Thr
1               5

<210> SEQ ID NO 2144
<211> LENGTH: 8
<212> TYPE: PRT
<213> ORGANISM: Homo sapiens

<400> SEQUENCE: 2144

Leu Arg Leu Lys Pro Leu Thr Gly
1               5

<210> SEQ ID NO 2145
<211> LENGTH: 8
<212> TYPE: PRT
<213> ORGANISM: Homo sapiens

<400> SEQUENCE: 2145

Arg Leu Lys Pro Leu Thr Gly Glu
1               5

<210> SEQ ID NO 2146
<211> LENGTH: 8
<212> TYPE: PRT
<213> ORGANISM: Homo sapiens

<400> SEQUENCE: 2146

Leu Lys Pro Leu Thr Gly Glu Gly
1               5

<210> SEQ ID NO 2147
<211> LENGTH: 8
<212> TYPE: PRT
<213> ORGANISM: Homo sapiens

<400> SEQUENCE: 2147

Lys Pro Leu Thr Gly Glu Gly Thr
1               5

<210> SEQ ID NO 2148
<211> LENGTH: 8
<212> TYPE: PRT
<213> ORGANISM: Homo sapiens

<400> SEQUENCE: 2148

Pro Leu Thr Gly Glu Gly Thr Ala
1               5

<210> SEQ ID NO 2149
<211> LENGTH: 8
<212> TYPE: PRT
<213> ORGANISM: Homo sapiens

<400> SEQUENCE: 2149

Leu Thr Gly Glu Gly Thr Ala Gly
1               5

<210> SEQ ID NO 2150
<211> LENGTH: 8
<212> TYPE: PRT
<213> ORGANISM: Homo sapiens

<400> SEQUENCE: 2150

Thr Gly Glu Gly Thr Ala Gly Gly
1               5

<210> SEQ ID NO 2151
<211> LENGTH: 8
<212> TYPE: PRT
<213> ORGANISM: Homo sapiens

<400> SEQUENCE: 2151

Gly Glu Gly Thr Ala Gly Gly Gly
1               5

<210> SEQ ID NO 2152
<211> LENGTH: 8
<212> TYPE: PRT
<213> ORGANISM: Homo sapiens

<400> SEQUENCE: 2152

Glu Gly Thr Ala Gly Gly Gly Gly
1               5

<210> SEQ ID NO 2153
<211> LENGTH: 8
<212> TYPE: PRT
<213> ORGANISM: Homo sapiens

<400> SEQUENCE: 2153

Gly Thr Ala Gly Gly Gly Gly Gly
1               5

<210> SEQ ID NO 2154

```
<211> LENGTH: 8
<212> TYPE: PRT
<213> ORGANISM: Homo sapiens

<400> SEQUENCE: 2154

Thr Ala Gly Gly Gly Gly Gly Gly
1               5

<210> SEQ ID NO 2155
<211> LENGTH: 8
<212> TYPE: PRT
<213> ORGANISM: Homo sapiens

<400> SEQUENCE: 2155

Ala Gly Gly Gly Gly Gly Gly Arg
1               5

<210> SEQ ID NO 2156
<211> LENGTH: 8
<212> TYPE: PRT
<213> ORGANISM: Homo sapiens

<400> SEQUENCE: 2156

Gly Gly Gly Gly Gly Gly Arg Arg
1               5

<210> SEQ ID NO 2157
<211> LENGTH: 8
<212> TYPE: PRT
<213> ORGANISM: Homo sapiens

<400> SEQUENCE: 2157

Gly Gly Gly Gly Gly Arg Arg His
1               5

<210> SEQ ID NO 2158
<211> LENGTH: 8
<212> TYPE: PRT
<213> ORGANISM: Homo sapiens

<400> SEQUENCE: 2158

Gly Gly Gly Gly Arg Arg His Ile
1               5

<210> SEQ ID NO 2159
<211> LENGTH: 8
<212> TYPE: PRT
<213> ORGANISM: Homo sapiens

<400> SEQUENCE: 2159

Gly Gly Gly Arg Arg His Ile Arg
1               5

<210> SEQ ID NO 2160
<211> LENGTH: 8
<212> TYPE: PRT
<213> ORGANISM: Homo sapiens

<400> SEQUENCE: 2160

Gly Gly Arg Arg His Ile Arg Ile
1               5

<210> SEQ ID NO 2161
<211> LENGTH: 8
<212> TYPE: PRT
```

<213> ORGANISM: Homo sapiens

<400> SEQUENCE: 2161

Gly Arg Arg His Ile Arg Ile Arg
1               5

<210> SEQ ID NO 2162
<211> LENGTH: 8
<212> TYPE: PRT
<213> ORGANISM: Homo sapiens

<400> SEQUENCE: 2162

Arg Arg His Ile Arg Ile Arg Ser
1               5

<210> SEQ ID NO 2163
<211> LENGTH: 8
<212> TYPE: PRT
<213> ORGANISM: Homo sapiens

<400> SEQUENCE: 2163

Arg His Ile Arg Ile Arg Ser Leu
1               5

<210> SEQ ID NO 2164
<211> LENGTH: 8
<212> TYPE: PRT
<213> ORGANISM: Homo sapiens

<400> SEQUENCE: 2164

His Ile Arg Ile Arg Ser Leu Lys
1               5

<210> SEQ ID NO 2165
<211> LENGTH: 8
<212> TYPE: PRT
<213> ORGANISM: Homo sapiens

<400> SEQUENCE: 2165

Ile Arg Ile Arg Ser Leu Lys Ile
1               5

<210> SEQ ID NO 2166
<211> LENGTH: 8
<212> TYPE: PRT
<213> ORGANISM: Homo sapiens

<400> SEQUENCE: 2166

Arg Ile Arg Ser Leu Lys Ile Glu
1               5

<210> SEQ ID NO 2167
<211> LENGTH: 8
<212> TYPE: PRT
<213> ORGANISM: Homo sapiens

<400> SEQUENCE: 2167

Ile Arg Ser Leu Lys Ile Glu Leu
1               5

<210> SEQ ID NO 2168
<211> LENGTH: 8
<212> TYPE: PRT
<213> ORGANISM: Homo sapiens

<400> SEQUENCE: 2168

Arg Ser Leu Lys Ile Glu Leu His
1               5

<210> SEQ ID NO 2169
<211> LENGTH: 8
<212> TYPE: PRT
<213> ORGANISM: Homo sapiens

<400> SEQUENCE: 2169

Ser Leu Lys Ile Glu Leu His Ser
1               5

<210> SEQ ID NO 2170
<211> LENGTH: 8
<212> TYPE: PRT
<213> ORGANISM: Homo sapiens

<400> SEQUENCE: 2170

Leu Lys Ile Glu Leu His Ser Arg
1               5

<210> SEQ ID NO 2171
<211> LENGTH: 8
<212> TYPE: PRT
<213> ORGANISM: Homo sapiens

<400> SEQUENCE: 2171

Lys Ile Glu Leu His Ser Arg Ser
1               5

<210> SEQ ID NO 2172
<211> LENGTH: 8
<212> TYPE: PRT
<213> ORGANISM: Homo sapiens

<400> SEQUENCE: 2172

Ile Glu Leu His Ser Arg Ser Gly
1               5

<210> SEQ ID NO 2173
<211> LENGTH: 8
<212> TYPE: PRT
<213> ORGANISM: Homo sapiens

<400> SEQUENCE: 2173

Glu Leu His Ser Arg Ser Gly His
1               5

<210> SEQ ID NO 2174
<211> LENGTH: 8
<212> TYPE: PRT
<213> ORGANISM: Homo sapiens

<400> SEQUENCE: 2174

Leu His Ser Arg Ser Gly His Trp
1               5

<210> SEQ ID NO 2175
<211> LENGTH: 8
<212> TYPE: PRT
<213> ORGANISM: Homo sapiens

<400> SEQUENCE: 2175

His Ser Arg Ser Gly His Trp Gln
1               5

<210> SEQ ID NO 2176
<211> LENGTH: 8
<212> TYPE: PRT
<213> ORGANISM: Homo sapiens

<400> SEQUENCE: 2176

Ser Arg Ser Gly His Trp Gln Ser
1               5

<210> SEQ ID NO 2177
<211> LENGTH: 8
<212> TYPE: PRT
<213> ORGANISM: Homo sapiens

<400> SEQUENCE: 2177

Arg Ser Gly His Trp Gln Ser Ile
1               5

<210> SEQ ID NO 2178
<211> LENGTH: 8
<212> TYPE: PRT
<213> ORGANISM: Homo sapiens

<400> SEQUENCE: 2178

Ser Gly His Trp Gln Ser Ile Asp
1               5

<210> SEQ ID NO 2179
<211> LENGTH: 8
<212> TYPE: PRT
<213> ORGANISM: Homo sapiens

<400> SEQUENCE: 2179

Gly His Trp Gln Ser Ile Asp Phe
1               5

<210> SEQ ID NO 2180
<211> LENGTH: 8
<212> TYPE: PRT
<213> ORGANISM: Homo sapiens

<400> SEQUENCE: 2180

His Trp Gln Ser Ile Asp Phe Lys
1               5

<210> SEQ ID NO 2181
<211> LENGTH: 8
<212> TYPE: PRT
<213> ORGANISM: Homo sapiens

<400> SEQUENCE: 2181

Trp Gln Ser Ile Asp Phe Lys Gln
1               5

<210> SEQ ID NO 2182
<211> LENGTH: 8
<212> TYPE: PRT
<213> ORGANISM: Homo sapiens

<400> SEQUENCE: 2182

Gln Ser Ile Asp Phe Lys Gln Val
1               5

<210> SEQ ID NO 2183
<211> LENGTH: 8
<212> TYPE: PRT
<213> ORGANISM: Homo sapiens

<400> SEQUENCE: 2183

Ser Ile Asp Phe Lys Gln Val Leu
1               5

<210> SEQ ID NO 2184
<211> LENGTH: 8
<212> TYPE: PRT
<213> ORGANISM: Homo sapiens

<400> SEQUENCE: 2184

Ile Asp Phe Lys Gln Val Leu His
1               5

<210> SEQ ID NO 2185
<211> LENGTH: 8
<212> TYPE: PRT
<213> ORGANISM: Homo sapiens

<400> SEQUENCE: 2185

Asp Phe Lys Gln Val Leu His Ser
1               5

<210> SEQ ID NO 2186
<211> LENGTH: 8
<212> TYPE: PRT
<213> ORGANISM: Homo sapiens

<400> SEQUENCE: 2186

Phe Lys Gln Val Leu His Ser Trp
1               5

<210> SEQ ID NO 2187
<211> LENGTH: 8
<212> TYPE: PRT
<213> ORGANISM: Homo sapiens

<400> SEQUENCE: 2187

Lys Gln Val Leu His Ser Trp Phe
1               5

<210> SEQ ID NO 2188
<211> LENGTH: 8
<212> TYPE: PRT
<213> ORGANISM: Homo sapiens

<400> SEQUENCE: 2188

Gln Val Leu His Ser Trp Phe Arg
1               5

<210> SEQ ID NO 2189
<211> LENGTH: 8
<212> TYPE: PRT
<213> ORGANISM: Homo sapiens

<400> SEQUENCE: 2189

Val Leu His Ser Trp Phe Arg Gln
1               5

```
<210> SEQ ID NO 2190
<211> LENGTH: 8
<212> TYPE: PRT
<213> ORGANISM: Homo sapiens

<400> SEQUENCE: 2190

Leu His Ser Trp Phe Arg Gln Pro
1               5

<210> SEQ ID NO 2191
<211> LENGTH: 8
<212> TYPE: PRT
<213> ORGANISM: Homo sapiens

<400> SEQUENCE: 2191

His Ser Trp Phe Arg Gln Pro Gln
1               5

<210> SEQ ID NO 2192
<211> LENGTH: 8
<212> TYPE: PRT
<213> ORGANISM: Homo sapiens

<400> SEQUENCE: 2192

Ser Trp Phe Arg Gln Pro Gln Ser
1               5

<210> SEQ ID NO 2193
<211> LENGTH: 8
<212> TYPE: PRT
<213> ORGANISM: Homo sapiens

<400> SEQUENCE: 2193

Trp Phe Arg Gln Pro Gln Ser Asn
1               5

<210> SEQ ID NO 2194
<211> LENGTH: 8
<212> TYPE: PRT
<213> ORGANISM: Homo sapiens

<400> SEQUENCE: 2194

Phe Arg Gln Pro Gln Ser Asn Trp
1               5

<210> SEQ ID NO 2195
<211> LENGTH: 8
<212> TYPE: PRT
<213> ORGANISM: Homo sapiens

<400> SEQUENCE: 2195

Arg Gln Pro Gln Ser Asn Trp Gly
1               5

<210> SEQ ID NO 2196
<211> LENGTH: 8
<212> TYPE: PRT
<213> ORGANISM: Homo sapiens

<400> SEQUENCE: 2196

Gln Pro Gln Ser Asn Trp Gly Ile
1               5

<210> SEQ ID NO 2197
<211> LENGTH: 8
```

```
<212> TYPE: PRT
<213> ORGANISM: Homo sapiens

<400> SEQUENCE: 2197

Pro Gln Ser Asn Trp Gly Ile Glu
1               5

<210> SEQ ID NO 2198
<211> LENGTH: 8
<212> TYPE: PRT
<213> ORGANISM: Homo sapiens

<400> SEQUENCE: 2198

Gln Ser Asn Trp Gly Ile Glu Ile
1               5

<210> SEQ ID NO 2199
<211> LENGTH: 8
<212> TYPE: PRT
<213> ORGANISM: Homo sapiens

<400> SEQUENCE: 2199

Ser Asn Trp Gly Ile Glu Ile Asn
1               5

<210> SEQ ID NO 2200
<211> LENGTH: 8
<212> TYPE: PRT
<213> ORGANISM: Homo sapiens

<400> SEQUENCE: 2200

Asn Trp Gly Ile Glu Ile Asn Ala
1               5

<210> SEQ ID NO 2201
<211> LENGTH: 8
<212> TYPE: PRT
<213> ORGANISM: Homo sapiens

<400> SEQUENCE: 2201

Trp Gly Ile Glu Ile Asn Ala Phe
1               5

<210> SEQ ID NO 2202
<211> LENGTH: 8
<212> TYPE: PRT
<213> ORGANISM: Homo sapiens

<400> SEQUENCE: 2202

Gly Ile Glu Ile Asn Ala Phe Asp
1               5

<210> SEQ ID NO 2203
<211> LENGTH: 8
<212> TYPE: PRT
<213> ORGANISM: Homo sapiens

<400> SEQUENCE: 2203

Ile Glu Ile Asn Ala Phe Asp Pro
1               5

<210> SEQ ID NO 2204
<211> LENGTH: 8
<212> TYPE: PRT
<213> ORGANISM: Homo sapiens
```

```
<400> SEQUENCE: 2204

Glu Ile Asn Ala Phe Asp Pro Ser
1               5

<210> SEQ ID NO 2205
<211> LENGTH: 8
<212> TYPE: PRT
<213> ORGANISM: Homo sapiens

<400> SEQUENCE: 2205

Ile Asn Ala Phe Asp Pro Ser Gly
1               5

<210> SEQ ID NO 2206
<211> LENGTH: 8
<212> TYPE: PRT
<213> ORGANISM: Homo sapiens

<400> SEQUENCE: 2206

Asn Ala Phe Asp Pro Ser Gly Thr
1               5

<210> SEQ ID NO 2207
<211> LENGTH: 8
<212> TYPE: PRT
<213> ORGANISM: Homo sapiens

<400> SEQUENCE: 2207

Ala Phe Asp Pro Ser Gly Thr Asp
1               5

<210> SEQ ID NO 2208
<211> LENGTH: 8
<212> TYPE: PRT
<213> ORGANISM: Homo sapiens

<400> SEQUENCE: 2208

Phe Asp Pro Ser Gly Thr Asp Leu
1               5

<210> SEQ ID NO 2209
<211> LENGTH: 8
<212> TYPE: PRT
<213> ORGANISM: Homo sapiens

<400> SEQUENCE: 2209

Asp Pro Ser Gly Thr Asp Leu Ala
1               5

<210> SEQ ID NO 2210
<211> LENGTH: 8
<212> TYPE: PRT
<213> ORGANISM: Homo sapiens

<400> SEQUENCE: 2210

Pro Ser Gly Thr Asp Leu Ala Val
1               5

<210> SEQ ID NO 2211
<211> LENGTH: 8
<212> TYPE: PRT
<213> ORGANISM: Homo sapiens

<400> SEQUENCE: 2211
```

Ser Gly Thr Asp Leu Ala Val Thr
1               5

<210> SEQ ID NO 2212
<211> LENGTH: 8
<212> TYPE: PRT
<213> ORGANISM: Homo sapiens

<400> SEQUENCE: 2212

Gly Thr Asp Leu Ala Val Thr Ser
1               5

<210> SEQ ID NO 2213
<211> LENGTH: 8
<212> TYPE: PRT
<213> ORGANISM: Homo sapiens

<400> SEQUENCE: 2213

Thr Asp Leu Ala Val Thr Ser Leu
1               5

<210> SEQ ID NO 2214
<211> LENGTH: 8
<212> TYPE: PRT
<213> ORGANISM: Homo sapiens

<400> SEQUENCE: 2214

Asp Leu Ala Val Thr Ser Leu Gly
1               5

<210> SEQ ID NO 2215
<211> LENGTH: 8
<212> TYPE: PRT
<213> ORGANISM: Homo sapiens

<400> SEQUENCE: 2215

Leu Ala Val Thr Ser Leu Gly Pro
1               5

<210> SEQ ID NO 2216
<211> LENGTH: 8
<212> TYPE: PRT
<213> ORGANISM: Homo sapiens

<400> SEQUENCE: 2216

Ala Val Thr Ser Leu Gly Pro Gly
1               5

<210> SEQ ID NO 2217
<211> LENGTH: 8
<212> TYPE: PRT
<213> ORGANISM: Homo sapiens

<400> SEQUENCE: 2217

Val Thr Ser Leu Gly Pro Gly Ala
1               5

<210> SEQ ID NO 2218
<211> LENGTH: 8
<212> TYPE: PRT
<213> ORGANISM: Homo sapiens

<400> SEQUENCE: 2218

Thr Ser Leu Gly Pro Gly Ala Glu

```
1               5

<210> SEQ ID NO 2219
<211> LENGTH: 8
<212> TYPE: PRT
<213> ORGANISM: Homo sapiens

<400> SEQUENCE: 2219

Ser Leu Gly Pro Gly Ala Glu Gly
1               5

<210> SEQ ID NO 2220
<211> LENGTH: 8
<212> TYPE: PRT
<213> ORGANISM: Homo sapiens

<400> SEQUENCE: 2220

Leu Gly Pro Gly Ala Glu Gly Leu
1               5

<210> SEQ ID NO 2221
<211> LENGTH: 8
<212> TYPE: PRT
<213> ORGANISM: Homo sapiens

<400> SEQUENCE: 2221

Gly Pro Gly Ala Glu Gly Leu His
1               5

<210> SEQ ID NO 2222
<211> LENGTH: 8
<212> TYPE: PRT
<213> ORGANISM: Homo sapiens

<400> SEQUENCE: 2222

Pro Gly Ala Glu Gly Leu His Pro
1               5

<210> SEQ ID NO 2223
<211> LENGTH: 8
<212> TYPE: PRT
<213> ORGANISM: Homo sapiens

<400> SEQUENCE: 2223

Gly Ala Glu Gly Leu His Pro Phe
1               5

<210> SEQ ID NO 2224
<211> LENGTH: 8
<212> TYPE: PRT
<213> ORGANISM: Homo sapiens

<400> SEQUENCE: 2224

Ala Glu Gly Leu His Pro Phe Met
1               5

<210> SEQ ID NO 2225
<211> LENGTH: 8
<212> TYPE: PRT
<213> ORGANISM: Homo sapiens

<400> SEQUENCE: 2225

Glu Gly Leu His Pro Phe Met Glu
1               5
```

<210> SEQ ID NO 2226
<211> LENGTH: 8
<212> TYPE: PRT
<213> ORGANISM: Homo sapiens

<400> SEQUENCE: 2226

Gly Leu His Pro Phe Met Glu Leu
1               5

<210> SEQ ID NO 2227
<211> LENGTH: 8
<212> TYPE: PRT
<213> ORGANISM: Homo sapiens

<400> SEQUENCE: 2227

Leu His Pro Phe Met Glu Leu Arg
1               5

<210> SEQ ID NO 2228
<211> LENGTH: 8
<212> TYPE: PRT
<213> ORGANISM: Homo sapiens

<400> SEQUENCE: 2228

His Pro Phe Met Glu Leu Arg Val
1               5

<210> SEQ ID NO 2229
<211> LENGTH: 8
<212> TYPE: PRT
<213> ORGANISM: Homo sapiens

<400> SEQUENCE: 2229

Pro Phe Met Glu Leu Arg Val Leu
1               5

<210> SEQ ID NO 2230
<211> LENGTH: 8
<212> TYPE: PRT
<213> ORGANISM: Homo sapiens

<400> SEQUENCE: 2230

Phe Met Glu Leu Arg Val Leu Glu
1               5

<210> SEQ ID NO 2231
<211> LENGTH: 8
<212> TYPE: PRT
<213> ORGANISM: Homo sapiens

<400> SEQUENCE: 2231

Met Glu Leu Arg Val Leu Glu Asn
1               5

<210> SEQ ID NO 2232
<211> LENGTH: 8
<212> TYPE: PRT
<213> ORGANISM: Homo sapiens

<400> SEQUENCE: 2232

Glu Leu Arg Val Leu Glu Asn Thr
1               5

<210> SEQ ID NO 2233

```
<211> LENGTH: 8
<212> TYPE: PRT
<213> ORGANISM: Homo sapiens

<400> SEQUENCE: 2233

Leu Arg Val Leu Glu Asn Thr Lys
1               5

<210> SEQ ID NO 2234
<211> LENGTH: 8
<212> TYPE: PRT
<213> ORGANISM: Homo sapiens

<400> SEQUENCE: 2234

Arg Val Leu Glu Asn Thr Lys Arg
1               5

<210> SEQ ID NO 2235
<211> LENGTH: 8
<212> TYPE: PRT
<213> ORGANISM: Homo sapiens

<400> SEQUENCE: 2235

Val Leu Glu Asn Thr Lys Arg Ser
1               5

<210> SEQ ID NO 2236
<211> LENGTH: 8
<212> TYPE: PRT
<213> ORGANISM: Homo sapiens

<400> SEQUENCE: 2236

Leu Glu Asn Thr Lys Arg Ser Arg
1               5

<210> SEQ ID NO 2237
<211> LENGTH: 8
<212> TYPE: PRT
<213> ORGANISM: Homo sapiens

<400> SEQUENCE: 2237

Glu Asn Thr Lys Arg Ser Arg Arg
1               5

<210> SEQ ID NO 2238
<211> LENGTH: 8
<212> TYPE: PRT
<213> ORGANISM: Homo sapiens

<400> SEQUENCE: 2238

Asn Thr Lys Arg Ser Arg Arg Asn
1               5

<210> SEQ ID NO 2239
<211> LENGTH: 8
<212> TYPE: PRT
<213> ORGANISM: Homo sapiens

<400> SEQUENCE: 2239

Thr Lys Arg Ser Arg Arg Asn Leu
1               5

<210> SEQ ID NO 2240
<211> LENGTH: 8
<212> TYPE: PRT
```

<213> ORGANISM: Homo sapiens

<400> SEQUENCE: 2240

Lys Arg Ser Arg Arg Asn Leu Gly
1               5

<210> SEQ ID NO 2241
<211> LENGTH: 8
<212> TYPE: PRT
<213> ORGANISM: Homo sapiens

<400> SEQUENCE: 2241

Arg Ser Arg Arg Asn Leu Gly Leu
1               5

<210> SEQ ID NO 2242
<211> LENGTH: 8
<212> TYPE: PRT
<213> ORGANISM: Homo sapiens

<400> SEQUENCE: 2242

Ser Arg Arg Asn Leu Gly Leu Asp
1               5

<210> SEQ ID NO 2243
<211> LENGTH: 8
<212> TYPE: PRT
<213> ORGANISM: Homo sapiens

<400> SEQUENCE: 2243

Arg Arg Asn Leu Gly Leu Asp Cys
1               5

<210> SEQ ID NO 2244
<211> LENGTH: 8
<212> TYPE: PRT
<213> ORGANISM: Homo sapiens

<400> SEQUENCE: 2244

Arg Asn Leu Gly Leu Asp Cys Asp
1               5

<210> SEQ ID NO 2245
<211> LENGTH: 8
<212> TYPE: PRT
<213> ORGANISM: Homo sapiens

<400> SEQUENCE: 2245

Asn Leu Gly Leu Asp Cys Asp Glu
1               5

<210> SEQ ID NO 2246
<211> LENGTH: 8
<212> TYPE: PRT
<213> ORGANISM: Homo sapiens

<400> SEQUENCE: 2246

Leu Gly Leu Asp Cys Asp Glu His
1               5

<210> SEQ ID NO 2247
<211> LENGTH: 8
<212> TYPE: PRT
<213> ORGANISM: Homo sapiens

<400> SEQUENCE: 2247

Gly Leu Asp Cys Asp Glu His Ser
1               5

<210> SEQ ID NO 2248
<211> LENGTH: 8
<212> TYPE: PRT
<213> ORGANISM: Homo sapiens

<400> SEQUENCE: 2248

Leu Asp Cys Asp Glu His Ser Ser
1               5

<210> SEQ ID NO 2249
<211> LENGTH: 8
<212> TYPE: PRT
<213> ORGANISM: Homo sapiens

<400> SEQUENCE: 2249

Asp Cys Asp Glu His Ser Ser Glu
1               5

<210> SEQ ID NO 2250
<211> LENGTH: 8
<212> TYPE: PRT
<213> ORGANISM: Homo sapiens

<400> SEQUENCE: 2250

Cys Asp Glu His Ser Ser Glu Ser
1               5

<210> SEQ ID NO 2251
<211> LENGTH: 8
<212> TYPE: PRT
<213> ORGANISM: Homo sapiens

<400> SEQUENCE: 2251

Asp Glu His Ser Ser Glu Ser Arg
1               5

<210> SEQ ID NO 2252
<211> LENGTH: 8
<212> TYPE: PRT
<213> ORGANISM: Homo sapiens

<400> SEQUENCE: 2252

Glu His Ser Ser Glu Ser Arg Cys
1               5

<210> SEQ ID NO 2253
<211> LENGTH: 8
<212> TYPE: PRT
<213> ORGANISM: Homo sapiens

<400> SEQUENCE: 2253

His Ser Ser Glu Ser Arg Cys Cys
1               5

<210> SEQ ID NO 2254
<211> LENGTH: 8
<212> TYPE: PRT
<213> ORGANISM: Homo sapiens

<400> SEQUENCE: 2254

Ser Ser Glu Ser Arg Cys Cys Arg
1               5

<210> SEQ ID NO 2255
<211> LENGTH: 8
<212> TYPE: PRT
<213> ORGANISM: Homo sapiens

<400> SEQUENCE: 2255

Ser Glu Ser Arg Cys Cys Arg Tyr
1               5

<210> SEQ ID NO 2256
<211> LENGTH: 8
<212> TYPE: PRT
<213> ORGANISM: Homo sapiens

<400> SEQUENCE: 2256

Glu Ser Arg Cys Cys Arg Tyr Pro
1               5

<210> SEQ ID NO 2257
<211> LENGTH: 8
<212> TYPE: PRT
<213> ORGANISM: Homo sapiens

<400> SEQUENCE: 2257

Ser Arg Cys Cys Arg Tyr Pro Leu
1               5

<210> SEQ ID NO 2258
<211> LENGTH: 8
<212> TYPE: PRT
<213> ORGANISM: Homo sapiens

<400> SEQUENCE: 2258

Arg Cys Cys Arg Tyr Pro Leu Thr
1               5

<210> SEQ ID NO 2259
<211> LENGTH: 8
<212> TYPE: PRT
<213> ORGANISM: Homo sapiens

<400> SEQUENCE: 2259

Cys Cys Arg Tyr Pro Leu Thr Val
1               5

<210> SEQ ID NO 2260
<211> LENGTH: 8
<212> TYPE: PRT
<213> ORGANISM: Homo sapiens

<400> SEQUENCE: 2260

Cys Arg Tyr Pro Leu Thr Val Asp
1               5

<210> SEQ ID NO 2261
<211> LENGTH: 8
<212> TYPE: PRT
<213> ORGANISM: Homo sapiens

<400> SEQUENCE: 2261

Arg Tyr Pro Leu Thr Val Asp Phe
1               5

<210> SEQ ID NO 2262
<211> LENGTH: 8
<212> TYPE: PRT
<213> ORGANISM: Homo sapiens

<400> SEQUENCE: 2262

Tyr Pro Leu Thr Val Asp Phe Glu
1               5

<210> SEQ ID NO 2263
<211> LENGTH: 8
<212> TYPE: PRT
<213> ORGANISM: Homo sapiens

<400> SEQUENCE: 2263

Pro Leu Thr Val Asp Phe Glu Ala
1               5

<210> SEQ ID NO 2264
<211> LENGTH: 8
<212> TYPE: PRT
<213> ORGANISM: Homo sapiens

<400> SEQUENCE: 2264

Leu Thr Val Asp Phe Glu Ala Phe
1               5

<210> SEQ ID NO 2265
<211> LENGTH: 8
<212> TYPE: PRT
<213> ORGANISM: Homo sapiens

<400> SEQUENCE: 2265

Thr Val Asp Phe Glu Ala Phe Gly
1               5

<210> SEQ ID NO 2266
<211> LENGTH: 8
<212> TYPE: PRT
<213> ORGANISM: Homo sapiens

<400> SEQUENCE: 2266

Val Asp Phe Glu Ala Phe Gly Trp
1               5

<210> SEQ ID NO 2267
<211> LENGTH: 8
<212> TYPE: PRT
<213> ORGANISM: Homo sapiens

<400> SEQUENCE: 2267

Asp Phe Glu Ala Phe Gly Trp Asp
1               5

<210> SEQ ID NO 2268
<211> LENGTH: 8
<212> TYPE: PRT
<213> ORGANISM: Homo sapiens

<400> SEQUENCE: 2268

Phe Glu Ala Phe Gly Trp Asp Trp
1               5

```
<210> SEQ ID NO 2269
<211> LENGTH: 8
<212> TYPE: PRT
<213> ORGANISM: Homo sapiens

<400> SEQUENCE: 2269

Glu Ala Phe Gly Trp Asp Trp Ile
1               5

<210> SEQ ID NO 2270
<211> LENGTH: 8
<212> TYPE: PRT
<213> ORGANISM: Homo sapiens

<400> SEQUENCE: 2270

Ala Phe Gly Trp Asp Trp Ile Ile
1               5

<210> SEQ ID NO 2271
<211> LENGTH: 8
<212> TYPE: PRT
<213> ORGANISM: Homo sapiens

<400> SEQUENCE: 2271

Phe Gly Trp Asp Trp Ile Ile Ala
1               5

<210> SEQ ID NO 2272
<211> LENGTH: 8
<212> TYPE: PRT
<213> ORGANISM: Homo sapiens

<400> SEQUENCE: 2272

Gly Trp Asp Trp Ile Ile Ala Pro
1               5

<210> SEQ ID NO 2273
<211> LENGTH: 8
<212> TYPE: PRT
<213> ORGANISM: Homo sapiens

<400> SEQUENCE: 2273

Trp Asp Trp Ile Ile Ala Pro Lys
1               5

<210> SEQ ID NO 2274
<211> LENGTH: 8
<212> TYPE: PRT
<213> ORGANISM: Homo sapiens

<400> SEQUENCE: 2274

Asp Trp Ile Ile Ala Pro Lys Arg
1               5

<210> SEQ ID NO 2275
<211> LENGTH: 8
<212> TYPE: PRT
<213> ORGANISM: Homo sapiens

<400> SEQUENCE: 2275

Trp Ile Ile Ala Pro Lys Arg Tyr
1               5

<210> SEQ ID NO 2276
<211> LENGTH: 8
```

```
<212> TYPE: PRT
<213> ORGANISM: Homo sapiens

<400> SEQUENCE: 2276

Ile Ile Ala Pro Lys Arg Tyr Lys
1               5

<210> SEQ ID NO 2277
<211> LENGTH: 8
<212> TYPE: PRT
<213> ORGANISM: Homo sapiens

<400> SEQUENCE: 2277

Ile Ala Pro Lys Arg Tyr Lys Ala
1               5

<210> SEQ ID NO 2278
<211> LENGTH: 8
<212> TYPE: PRT
<213> ORGANISM: Homo sapiens

<400> SEQUENCE: 2278

Ala Pro Lys Arg Tyr Lys Ala Asn
1               5

<210> SEQ ID NO 2279
<211> LENGTH: 8
<212> TYPE: PRT
<213> ORGANISM: Homo sapiens

<400> SEQUENCE: 2279

Pro Lys Arg Tyr Lys Ala Asn Tyr
1               5

<210> SEQ ID NO 2280
<211> LENGTH: 8
<212> TYPE: PRT
<213> ORGANISM: Homo sapiens

<400> SEQUENCE: 2280

Lys Arg Tyr Lys Ala Asn Tyr Cys
1               5

<210> SEQ ID NO 2281
<211> LENGTH: 8
<212> TYPE: PRT
<213> ORGANISM: Homo sapiens

<400> SEQUENCE: 2281

Arg Tyr Lys Ala Asn Tyr Cys Ser
1               5

<210> SEQ ID NO 2282
<211> LENGTH: 8
<212> TYPE: PRT
<213> ORGANISM: Homo sapiens

<400> SEQUENCE: 2282

Tyr Lys Ala Asn Tyr Cys Ser Gly
1               5

<210> SEQ ID NO 2283
<211> LENGTH: 8
<212> TYPE: PRT
<213> ORGANISM: Homo sapiens
```

<400> SEQUENCE: 2283

Lys Ala Asn Tyr Cys Ser Gly Gln
1               5

<210> SEQ ID NO 2284
<211> LENGTH: 8
<212> TYPE: PRT
<213> ORGANISM: Homo sapiens

<400> SEQUENCE: 2284

Ala Asn Tyr Cys Ser Gly Gln Cys
1               5

<210> SEQ ID NO 2285
<211> LENGTH: 8
<212> TYPE: PRT
<213> ORGANISM: Homo sapiens

<400> SEQUENCE: 2285

Asn Tyr Cys Ser Gly Gln Cys Glu
1               5

<210> SEQ ID NO 2286
<211> LENGTH: 8
<212> TYPE: PRT
<213> ORGANISM: Homo sapiens

<400> SEQUENCE: 2286

Tyr Cys Ser Gly Gln Cys Glu Tyr
1               5

<210> SEQ ID NO 2287
<211> LENGTH: 8
<212> TYPE: PRT
<213> ORGANISM: Homo sapiens

<400> SEQUENCE: 2287

Cys Ser Gly Gln Cys Glu Tyr Met
1               5

<210> SEQ ID NO 2288
<211> LENGTH: 8
<212> TYPE: PRT
<213> ORGANISM: Homo sapiens

<400> SEQUENCE: 2288

Ser Gly Gln Cys Glu Tyr Met Phe
1               5

<210> SEQ ID NO 2289
<211> LENGTH: 8
<212> TYPE: PRT
<213> ORGANISM: Homo sapiens

<400> SEQUENCE: 2289

Gly Gln Cys Glu Tyr Met Phe Met
1               5

<210> SEQ ID NO 2290
<211> LENGTH: 8
<212> TYPE: PRT
<213> ORGANISM: Homo sapiens

<400> SEQUENCE: 2290

Gln Cys Glu Tyr Met Phe Met Gln
1               5

<210> SEQ ID NO 2291
<211> LENGTH: 8
<212> TYPE: PRT
<213> ORGANISM: Homo sapiens

<400> SEQUENCE: 2291

Cys Glu Tyr Met Phe Met Gln Lys
1               5

<210> SEQ ID NO 2292
<211> LENGTH: 8
<212> TYPE: PRT
<213> ORGANISM: Homo sapiens

<400> SEQUENCE: 2292

Glu Tyr Met Phe Met Gln Lys Tyr
1               5

<210> SEQ ID NO 2293
<211> LENGTH: 8
<212> TYPE: PRT
<213> ORGANISM: Homo sapiens

<400> SEQUENCE: 2293

Tyr Met Phe Met Gln Lys Tyr Pro
1               5

<210> SEQ ID NO 2294
<211> LENGTH: 8
<212> TYPE: PRT
<213> ORGANISM: Homo sapiens

<400> SEQUENCE: 2294

Met Phe Met Gln Lys Tyr Pro His
1               5

<210> SEQ ID NO 2295
<211> LENGTH: 8
<212> TYPE: PRT
<213> ORGANISM: Homo sapiens

<400> SEQUENCE: 2295

Phe Met Gln Lys Tyr Pro His Thr
1               5

<210> SEQ ID NO 2296
<211> LENGTH: 8
<212> TYPE: PRT
<213> ORGANISM: Homo sapiens

<400> SEQUENCE: 2296

Met Gln Lys Tyr Pro His Thr His
1               5

<210> SEQ ID NO 2297
<211> LENGTH: 8
<212> TYPE: PRT
<213> ORGANISM: Homo sapiens

<400> SEQUENCE: 2297

Gln Lys Tyr Pro His Thr His Leu

```
1               5

<210> SEQ ID NO 2298
<211> LENGTH: 8
<212> TYPE: PRT
<213> ORGANISM: Homo sapiens

<400> SEQUENCE: 2298

Lys Tyr Pro His Thr His Leu Val
1               5

<210> SEQ ID NO 2299
<211> LENGTH: 8
<212> TYPE: PRT
<213> ORGANISM: Homo sapiens

<400> SEQUENCE: 2299

Tyr Pro His Thr His Leu Val Gln
1               5

<210> SEQ ID NO 2300
<211> LENGTH: 8
<212> TYPE: PRT
<213> ORGANISM: Homo sapiens

<400> SEQUENCE: 2300

Pro His Thr His Leu Val Gln Gln
1               5

<210> SEQ ID NO 2301
<211> LENGTH: 8
<212> TYPE: PRT
<213> ORGANISM: Homo sapiens

<400> SEQUENCE: 2301

His Thr His Leu Val Gln Gln Ala
1               5

<210> SEQ ID NO 2302
<211> LENGTH: 8
<212> TYPE: PRT
<213> ORGANISM: Homo sapiens

<400> SEQUENCE: 2302

Thr His Leu Val Gln Gln Ala Asn
1               5

<210> SEQ ID NO 2303
<211> LENGTH: 8
<212> TYPE: PRT
<213> ORGANISM: Homo sapiens

<400> SEQUENCE: 2303

His Leu Val Gln Gln Ala Asn Pro
1               5

<210> SEQ ID NO 2304
<211> LENGTH: 8
<212> TYPE: PRT
<213> ORGANISM: Homo sapiens

<400> SEQUENCE: 2304

Leu Val Gln Gln Ala Asn Pro Arg
1               5
```

```
<210> SEQ ID NO 2305
<211> LENGTH: 8
<212> TYPE: PRT
<213> ORGANISM: Homo sapiens

<400> SEQUENCE: 2305

Val Gln Gln Ala Asn Pro Arg Gly
1               5

<210> SEQ ID NO 2306
<211> LENGTH: 8
<212> TYPE: PRT
<213> ORGANISM: Homo sapiens

<400> SEQUENCE: 2306

Gln Gln Ala Asn Pro Arg Gly Ser
1               5

<210> SEQ ID NO 2307
<211> LENGTH: 8
<212> TYPE: PRT
<213> ORGANISM: Homo sapiens

<400> SEQUENCE: 2307

Gln Ala Asn Pro Arg Gly Ser Ala
1               5

<210> SEQ ID NO 2308
<211> LENGTH: 8
<212> TYPE: PRT
<213> ORGANISM: Homo sapiens

<400> SEQUENCE: 2308

Ala Asn Pro Arg Gly Ser Ala Gly
1               5

<210> SEQ ID NO 2309
<211> LENGTH: 8
<212> TYPE: PRT
<213> ORGANISM: Homo sapiens

<400> SEQUENCE: 2309

Asn Pro Arg Gly Ser Ala Gly Pro
1               5

<210> SEQ ID NO 2310
<211> LENGTH: 8
<212> TYPE: PRT
<213> ORGANISM: Homo sapiens

<400> SEQUENCE: 2310

Pro Arg Gly Ser Ala Gly Pro Cys
1               5

<210> SEQ ID NO 2311
<211> LENGTH: 8
<212> TYPE: PRT
<213> ORGANISM: Homo sapiens

<400> SEQUENCE: 2311

Arg Gly Ser Ala Gly Pro Cys Cys
1               5

<210> SEQ ID NO 2312
```

```
<211> LENGTH: 8
<212> TYPE: PRT
<213> ORGANISM: Homo sapiens

<400> SEQUENCE: 2312

Gly Ser Ala Gly Pro Cys Cys Thr
1               5

<210> SEQ ID NO 2313
<211> LENGTH: 8
<212> TYPE: PRT
<213> ORGANISM: Homo sapiens

<400> SEQUENCE: 2313

Ser Ala Gly Pro Cys Cys Thr Pro
1               5

<210> SEQ ID NO 2314
<211> LENGTH: 8
<212> TYPE: PRT
<213> ORGANISM: Homo sapiens

<400> SEQUENCE: 2314

Ala Gly Pro Cys Cys Thr Pro Thr
1               5

<210> SEQ ID NO 2315
<211> LENGTH: 8
<212> TYPE: PRT
<213> ORGANISM: Homo sapiens

<400> SEQUENCE: 2315

Gly Pro Cys Cys Thr Pro Thr Lys
1               5

<210> SEQ ID NO 2316
<211> LENGTH: 8
<212> TYPE: PRT
<213> ORGANISM: Homo sapiens

<400> SEQUENCE: 2316

Pro Cys Cys Thr Pro Thr Lys Met
1               5

<210> SEQ ID NO 2317
<211> LENGTH: 8
<212> TYPE: PRT
<213> ORGANISM: Homo sapiens

<400> SEQUENCE: 2317

Cys Cys Thr Pro Thr Lys Met Ser
1               5

<210> SEQ ID NO 2318
<211> LENGTH: 8
<212> TYPE: PRT
<213> ORGANISM: Homo sapiens

<400> SEQUENCE: 2318

Cys Thr Pro Thr Lys Met Ser Pro
1               5

<210> SEQ ID NO 2319
<211> LENGTH: 8
<212> TYPE: PRT
```

<213> ORGANISM: Homo sapiens

<400> SEQUENCE: 2319

Thr Pro Thr Lys Met Ser Pro Ile
1               5

<210> SEQ ID NO 2320
<211> LENGTH: 8
<212> TYPE: PRT
<213> ORGANISM: Homo sapiens

<400> SEQUENCE: 2320

Pro Thr Lys Met Ser Pro Ile Asn
1               5

<210> SEQ ID NO 2321
<211> LENGTH: 8
<212> TYPE: PRT
<213> ORGANISM: Homo sapiens

<400> SEQUENCE: 2321

Thr Lys Met Ser Pro Ile Asn Met
1               5

<210> SEQ ID NO 2322
<211> LENGTH: 8
<212> TYPE: PRT
<213> ORGANISM: Homo sapiens

<400> SEQUENCE: 2322

Lys Met Ser Pro Ile Asn Met Leu
1               5

<210> SEQ ID NO 2323
<211> LENGTH: 8
<212> TYPE: PRT
<213> ORGANISM: Homo sapiens

<400> SEQUENCE: 2323

Met Ser Pro Ile Asn Met Leu Tyr
1               5

<210> SEQ ID NO 2324
<211> LENGTH: 8
<212> TYPE: PRT
<213> ORGANISM: Homo sapiens

<400> SEQUENCE: 2324

Ser Pro Ile Asn Met Leu Tyr Phe
1               5

<210> SEQ ID NO 2325
<211> LENGTH: 8
<212> TYPE: PRT
<213> ORGANISM: Homo sapiens

<400> SEQUENCE: 2325

Pro Ile Asn Met Leu Tyr Phe Asn
1               5

<210> SEQ ID NO 2326
<211> LENGTH: 8
<212> TYPE: PRT
<213> ORGANISM: Homo sapiens -continued

<400> SEQUENCE: 2326

Ile Asn Met Leu Tyr Phe Asn Asp
1               5

<210> SEQ ID NO 2327
<211> LENGTH: 8
<212> TYPE: PRT
<213> ORGANISM: Homo sapiens

<400> SEQUENCE: 2327

Asn Met Leu Tyr Phe Asn Asp Lys
1               5

<210> SEQ ID NO 2328
<211> LENGTH: 8
<212> TYPE: PRT
<213> ORGANISM: Homo sapiens

<400> SEQUENCE: 2328

Met Leu Tyr Phe Asn Asp Lys Gln
1               5

<210> SEQ ID NO 2329
<211> LENGTH: 8
<212> TYPE: PRT
<213> ORGANISM: Homo sapiens

<400> SEQUENCE: 2329

Leu Tyr Phe Asn Asp Lys Gln Gln
1               5

<210> SEQ ID NO 2330
<211> LENGTH: 8
<212> TYPE: PRT
<213> ORGANISM: Homo sapiens

<400> SEQUENCE: 2330

Tyr Phe Asn Asp Lys Gln Gln Ile
1               5

<210> SEQ ID NO 2331
<211> LENGTH: 8
<212> TYPE: PRT
<213> ORGANISM: Homo sapiens

<400> SEQUENCE: 2331

Phe Asn Asp Lys Gln Gln Ile Ile
1               5

<210> SEQ ID NO 2332
<211> LENGTH: 8
<212> TYPE: PRT
<213> ORGANISM: Homo sapiens

<400> SEQUENCE: 2332

Asn Asp Lys Gln Gln Ile Ile Tyr
1               5

<210> SEQ ID NO 2333
<211> LENGTH: 8
<212> TYPE: PRT
<213> ORGANISM: Homo sapiens

<400> SEQUENCE: 2333

Asp Lys Gln Gln Ile Ile Tyr Gly
1               5

<210> SEQ ID NO 2334
<211> LENGTH: 8
<212> TYPE: PRT
<213> ORGANISM: Homo sapiens

<400> SEQUENCE: 2334

Lys Gln Gln Ile Ile Tyr Gly Lys
1               5

<210> SEQ ID NO 2335
<211> LENGTH: 8
<212> TYPE: PRT
<213> ORGANISM: Homo sapiens

<400> SEQUENCE: 2335

Gln Gln Ile Ile Tyr Gly Lys Ile
1               5

<210> SEQ ID NO 2336
<211> LENGTH: 8
<212> TYPE: PRT
<213> ORGANISM: Homo sapiens

<400> SEQUENCE: 2336

Gln Ile Ile Tyr Gly Lys Ile Pro
1               5

<210> SEQ ID NO 2337
<211> LENGTH: 8
<212> TYPE: PRT
<213> ORGANISM: Homo sapiens

<400> SEQUENCE: 2337

Ile Ile Tyr Gly Lys Ile Pro Gly
1               5

<210> SEQ ID NO 2338
<211> LENGTH: 8
<212> TYPE: PRT
<213> ORGANISM: Homo sapiens

<400> SEQUENCE: 2338

Ile Tyr Gly Lys Ile Pro Gly Met
1               5

<210> SEQ ID NO 2339
<211> LENGTH: 8
<212> TYPE: PRT
<213> ORGANISM: Homo sapiens

<400> SEQUENCE: 2339

Tyr Gly Lys Ile Pro Gly Met Val
1               5

<210> SEQ ID NO 2340
<211> LENGTH: 8
<212> TYPE: PRT
<213> ORGANISM: Homo sapiens

<400> SEQUENCE: 2340

Gly Lys Ile Pro Gly Met Val Val
1               5

<210> SEQ ID NO 2341
<211> LENGTH: 8
<212> TYPE: PRT
<213> ORGANISM: Homo sapiens

<400> SEQUENCE: 2341

Lys Ile Pro Gly Met Val Val Asp
1               5

<210> SEQ ID NO 2342
<211> LENGTH: 8
<212> TYPE: PRT
<213> ORGANISM: Homo sapiens

<400> SEQUENCE: 2342

Ile Pro Gly Met Val Val Asp Arg
1               5

<210> SEQ ID NO 2343
<211> LENGTH: 8
<212> TYPE: PRT
<213> ORGANISM: Homo sapiens

<400> SEQUENCE: 2343

Pro Gly Met Val Val Asp Arg Cys
1               5

<210> SEQ ID NO 2344
<211> LENGTH: 8
<212> TYPE: PRT
<213> ORGANISM: Homo sapiens

<400> SEQUENCE: 2344

Gly Met Val Val Asp Arg Cys Gly
1               5

<210> SEQ ID NO 2345
<211> LENGTH: 8
<212> TYPE: PRT
<213> ORGANISM: Homo sapiens

<400> SEQUENCE: 2345

Met Val Val Asp Arg Cys Gly Cys
1               5

<210> SEQ ID NO 2346
<211> LENGTH: 8
<212> TYPE: PRT
<213> ORGANISM: Homo sapiens

<400> SEQUENCE: 2346

Val Val Asp Arg Cys Gly Cys Ser
1               5

<210> SEQ ID NO 2347
<211> LENGTH: 9
<212> TYPE: PRT
<213> ORGANISM: Homo sapiens

<400> SEQUENCE: 2347

Met Val Leu Ala Ala Pro Leu Leu Leu
1               5

```
<210> SEQ ID NO 2348
<211> LENGTH: 9
<212> TYPE: PRT
<213> ORGANISM: Homo sapiens

<400> SEQUENCE: 2348

Val Leu Ala Ala Pro Leu Leu Leu Gly
1               5

<210> SEQ ID NO 2349
<211> LENGTH: 9
<212> TYPE: PRT
<213> ORGANISM: Homo sapiens

<400> SEQUENCE: 2349

Leu Ala Ala Pro Leu Leu Leu Gly Phe
1               5

<210> SEQ ID NO 2350
<211> LENGTH: 9
<212> TYPE: PRT
<213> ORGANISM: Homo sapiens

<400> SEQUENCE: 2350

Ala Ala Pro Leu Leu Leu Gly Phe Leu
1               5

<210> SEQ ID NO 2351
<211> LENGTH: 9
<212> TYPE: PRT
<213> ORGANISM: Homo sapiens

<400> SEQUENCE: 2351

Ala Pro Leu Leu Leu Gly Phe Leu Leu
1               5

<210> SEQ ID NO 2352
<211> LENGTH: 9
<212> TYPE: PRT
<213> ORGANISM: Homo sapiens

<400> SEQUENCE: 2352

Pro Leu Leu Leu Gly Phe Leu Leu Leu
1               5

<210> SEQ ID NO 2353
<211> LENGTH: 9
<212> TYPE: PRT
<213> ORGANISM: Homo sapiens

<400> SEQUENCE: 2353

Leu Leu Leu Gly Phe Leu Leu Leu Ala
1               5

<210> SEQ ID NO 2354
<211> LENGTH: 9
<212> TYPE: PRT
<213> ORGANISM: Homo sapiens

<400> SEQUENCE: 2354

Leu Leu Gly Phe Leu Leu Leu Ala Leu
1               5

<210> SEQ ID NO 2355
<211> LENGTH: 9
```

```
<212> TYPE: PRT
<213> ORGANISM: Homo sapiens

<400> SEQUENCE: 2355

Leu Gly Phe Leu Leu Ala Leu Glu
1               5

<210> SEQ ID NO 2356
<211> LENGTH: 9
<212> TYPE: PRT
<213> ORGANISM: Homo sapiens

<400> SEQUENCE: 2356

Gly Phe Leu Leu Leu Ala Leu Glu Leu
1               5

<210> SEQ ID NO 2357
<211> LENGTH: 9
<212> TYPE: PRT
<213> ORGANISM: Homo sapiens

<400> SEQUENCE: 2357

Phe Leu Leu Leu Ala Leu Glu Leu Arg
1               5

<210> SEQ ID NO 2358
<211> LENGTH: 9
<212> TYPE: PRT
<213> ORGANISM: Homo sapiens

<400> SEQUENCE: 2358

Leu Leu Leu Ala Leu Glu Leu Arg Pro
1               5

<210> SEQ ID NO 2359
<211> LENGTH: 9
<212> TYPE: PRT
<213> ORGANISM: Homo sapiens

<400> SEQUENCE: 2359

Leu Leu Ala Leu Glu Leu Arg Pro Arg
1               5

<210> SEQ ID NO 2360
<211> LENGTH: 9
<212> TYPE: PRT
<213> ORGANISM: Homo sapiens

<400> SEQUENCE: 2360

Leu Ala Leu Glu Leu Arg Pro Arg Gly
1               5

<210> SEQ ID NO 2361
<211> LENGTH: 9
<212> TYPE: PRT
<213> ORGANISM: Homo sapiens

<400> SEQUENCE: 2361

Ala Leu Glu Leu Arg Pro Arg Gly Glu
1               5

<210> SEQ ID NO 2362
<211> LENGTH: 9
<212> TYPE: PRT
<213> ORGANISM: Homo sapiens
```

<400> SEQUENCE: 2362

Leu Glu Leu Arg Pro Arg Gly Glu Ala
1               5

<210> SEQ ID NO 2363
<211> LENGTH: 9
<212> TYPE: PRT
<213> ORGANISM: Homo sapiens

<400> SEQUENCE: 2363

Glu Leu Arg Pro Arg Gly Glu Ala Ala
1               5

<210> SEQ ID NO 2364
<211> LENGTH: 9
<212> TYPE: PRT
<213> ORGANISM: Homo sapiens

<400> SEQUENCE: 2364

Leu Arg Pro Arg Gly Glu Ala Ala Glu
1               5

<210> SEQ ID NO 2365
<211> LENGTH: 9
<212> TYPE: PRT
<213> ORGANISM: Homo sapiens

<400> SEQUENCE: 2365

Arg Pro Arg Gly Glu Ala Ala Glu Gly
1               5

<210> SEQ ID NO 2366
<211> LENGTH: 9
<212> TYPE: PRT
<213> ORGANISM: Homo sapiens

<400> SEQUENCE: 2366

Pro Arg Gly Glu Ala Ala Glu Gly Pro
1               5

<210> SEQ ID NO 2367
<211> LENGTH: 9
<212> TYPE: PRT
<213> ORGANISM: Homo sapiens

<400> SEQUENCE: 2367

Arg Gly Glu Ala Ala Glu Gly Pro Ala
1               5

<210> SEQ ID NO 2368
<211> LENGTH: 9
<212> TYPE: PRT
<213> ORGANISM: Homo sapiens

<400> SEQUENCE: 2368

Gly Glu Ala Ala Glu Gly Pro Ala Ala
1               5

<210> SEQ ID NO 2369
<211> LENGTH: 9
<212> TYPE: PRT
<213> ORGANISM: Homo sapiens

<400> SEQUENCE: 2369

Glu Ala Ala Glu Gly Pro Ala Ala Ala
1               5

<210> SEQ ID NO 2370
<211> LENGTH: 9
<212> TYPE: PRT
<213> ORGANISM: Homo sapiens

<400> SEQUENCE: 2370

Ala Ala Glu Gly Pro Ala Ala Ala Ala
1               5

<210> SEQ ID NO 2371
<211> LENGTH: 9
<212> TYPE: PRT
<213> ORGANISM: Homo sapiens

<400> SEQUENCE: 2371

Ala Glu Gly Pro Ala Ala Ala Ala Ala
1               5

<210> SEQ ID NO 2372
<211> LENGTH: 9
<212> TYPE: PRT
<213> ORGANISM: Homo sapiens

<400> SEQUENCE: 2372

Glu Gly Pro Ala Ala Ala Ala Ala Ala
1               5

<210> SEQ ID NO 2373
<211> LENGTH: 9
<212> TYPE: PRT
<213> ORGANISM: Homo sapiens

<400> SEQUENCE: 2373

Gly Pro Ala Ala Ala Ala Ala Ala Ala
1               5

<210> SEQ ID NO 2374
<211> LENGTH: 9
<212> TYPE: PRT
<213> ORGANISM: Homo sapiens

<400> SEQUENCE: 2374

Pro Ala Ala Ala Ala Ala Ala Ala Ala
1               5

<210> SEQ ID NO 2375
<211> LENGTH: 9
<212> TYPE: PRT
<213> ORGANISM: Homo sapiens

<400> SEQUENCE: 2375

Ala Ala Ala Ala Ala Ala Ala Ala Ala
1               5

<210> SEQ ID NO 2376
<211> LENGTH: 9
<212> TYPE: PRT
<213> ORGANISM: Homo sapiens

<400> SEQUENCE: 2376

Ala Ala Ala Ala Ala Ala Ala Ala Gly

```
1               5

<210> SEQ ID NO 2377
<211> LENGTH: 9
<212> TYPE: PRT
<213> ORGANISM: Homo sapiens

<400> SEQUENCE: 2377

Ala Ala Ala Ala Ala Ala Ala Gly Val
1               5

<210> SEQ ID NO 2378
<211> LENGTH: 9
<212> TYPE: PRT
<213> ORGANISM: Homo sapiens

<400> SEQUENCE: 2378

Ala Ala Ala Ala Ala Ala Gly Val Gly
1               5

<210> SEQ ID NO 2379
<211> LENGTH: 9
<212> TYPE: PRT
<213> ORGANISM: Homo sapiens

<400> SEQUENCE: 2379

Ala Ala Ala Ala Ala Gly Val Gly Gly
1               5

<210> SEQ ID NO 2380
<211> LENGTH: 9
<212> TYPE: PRT
<213> ORGANISM: Homo sapiens

<400> SEQUENCE: 2380

Ala Ala Ala Ala Gly Val Gly Gly Glu
1               5

<210> SEQ ID NO 2381
<211> LENGTH: 9
<212> TYPE: PRT
<213> ORGANISM: Homo sapiens

<400> SEQUENCE: 2381

Ala Ala Ala Gly Val Gly Gly Glu Arg
1               5

<210> SEQ ID NO 2382
<211> LENGTH: 9
<212> TYPE: PRT
<213> ORGANISM: Homo sapiens

<400> SEQUENCE: 2382

Ala Ala Gly Val Gly Gly Glu Arg Ser
1               5

<210> SEQ ID NO 2383
<211> LENGTH: 9
<212> TYPE: PRT
<213> ORGANISM: Homo sapiens

<400> SEQUENCE: 2383

Ala Gly Val Gly Gly Glu Arg Ser Ser
1               5
```

<210> SEQ ID NO 2384
<211> LENGTH: 9
<212> TYPE: PRT
<213> ORGANISM: Homo sapiens

<400> SEQUENCE: 2384

Gly Val Gly Gly Glu Arg Ser Ser Arg
1               5

<210> SEQ ID NO 2385
<211> LENGTH: 9
<212> TYPE: PRT
<213> ORGANISM: Homo sapiens

<400> SEQUENCE: 2385

Val Gly Gly Glu Arg Ser Ser Arg Pro
1               5

<210> SEQ ID NO 2386
<211> LENGTH: 9
<212> TYPE: PRT
<213> ORGANISM: Homo sapiens

<400> SEQUENCE: 2386

Gly Gly Glu Arg Ser Ser Arg Pro Ala
1               5

<210> SEQ ID NO 2387
<211> LENGTH: 9
<212> TYPE: PRT
<213> ORGANISM: Homo sapiens

<400> SEQUENCE: 2387

Gly Glu Arg Ser Ser Arg Pro Ala Pro
1               5

<210> SEQ ID NO 2388
<211> LENGTH: 9
<212> TYPE: PRT
<213> ORGANISM: Homo sapiens

<400> SEQUENCE: 2388

Glu Arg Ser Ser Arg Pro Ala Pro Ser
1               5

<210> SEQ ID NO 2389
<211> LENGTH: 9
<212> TYPE: PRT
<213> ORGANISM: Homo sapiens

<400> SEQUENCE: 2389

Arg Ser Ser Arg Pro Ala Pro Ser Val
1               5

<210> SEQ ID NO 2390
<211> LENGTH: 9
<212> TYPE: PRT
<213> ORGANISM: Homo sapiens

<400> SEQUENCE: 2390

Ser Ser Arg Pro Ala Pro Ser Val Ala
1               5

<210> SEQ ID NO 2391

```
<211> LENGTH: 9
<212> TYPE: PRT
<213> ORGANISM: Homo sapiens

<400> SEQUENCE: 2391

Ser Arg Pro Ala Pro Ser Val Ala Pro
1               5

<210> SEQ ID NO 2392
<211> LENGTH: 9
<212> TYPE: PRT
<213> ORGANISM: Homo sapiens

<400> SEQUENCE: 2392

Arg Pro Ala Pro Ser Val Ala Pro Glu
1               5

<210> SEQ ID NO 2393
<211> LENGTH: 9
<212> TYPE: PRT
<213> ORGANISM: Homo sapiens

<400> SEQUENCE: 2393

Pro Ala Pro Ser Val Ala Pro Glu Pro
1               5

<210> SEQ ID NO 2394
<211> LENGTH: 9
<212> TYPE: PRT
<213> ORGANISM: Homo sapiens

<400> SEQUENCE: 2394

Ala Pro Ser Val Ala Pro Glu Pro Asp
1               5

<210> SEQ ID NO 2395
<211> LENGTH: 9
<212> TYPE: PRT
<213> ORGANISM: Homo sapiens

<400> SEQUENCE: 2395

Pro Ser Val Ala Pro Glu Pro Asp Gly
1               5

<210> SEQ ID NO 2396
<211> LENGTH: 9
<212> TYPE: PRT
<213> ORGANISM: Homo sapiens

<400> SEQUENCE: 2396

Ser Val Ala Pro Glu Pro Asp Gly Cys
1               5

<210> SEQ ID NO 2397
<211> LENGTH: 9
<212> TYPE: PRT
<213> ORGANISM: Homo sapiens

<400> SEQUENCE: 2397

Val Ala Pro Glu Pro Asp Gly Cys Pro
1               5

<210> SEQ ID NO 2398
<211> LENGTH: 9
<212> TYPE: PRT
```

<213> ORGANISM: Homo sapiens

<400> SEQUENCE: 2398

Ala Pro Glu Pro Asp Gly Cys Pro Val
1               5

<210> SEQ ID NO 2399
<211> LENGTH: 9
<212> TYPE: PRT
<213> ORGANISM: Homo sapiens

<400> SEQUENCE: 2399

Pro Glu Pro Asp Gly Cys Pro Val Cys
1               5

<210> SEQ ID NO 2400
<211> LENGTH: 9
<212> TYPE: PRT
<213> ORGANISM: Homo sapiens

<400> SEQUENCE: 2400

Glu Pro Asp Gly Cys Pro Val Cys Val
1               5

<210> SEQ ID NO 2401
<211> LENGTH: 9
<212> TYPE: PRT
<213> ORGANISM: Homo sapiens

<400> SEQUENCE: 2401

Pro Asp Gly Cys Pro Val Cys Val Trp
1               5

<210> SEQ ID NO 2402
<211> LENGTH: 9
<212> TYPE: PRT
<213> ORGANISM: Homo sapiens

<400> SEQUENCE: 2402

Asp Gly Cys Pro Val Cys Val Trp Arg
1               5

<210> SEQ ID NO 2403
<211> LENGTH: 9
<212> TYPE: PRT
<213> ORGANISM: Homo sapiens

<400> SEQUENCE: 2403

Gly Cys Pro Val Cys Val Trp Arg Gln
1               5

<210> SEQ ID NO 2404
<211> LENGTH: 9
<212> TYPE: PRT
<213> ORGANISM: Homo sapiens

<400> SEQUENCE: 2404

Cys Pro Val Cys Val Trp Arg Gln His
1               5

<210> SEQ ID NO 2405
<211> LENGTH: 9
<212> TYPE: PRT
<213> ORGANISM: Homo sapiens

```
<400> SEQUENCE: 2405

Pro Val Cys Val Trp Arg Gln His Ser
1               5

<210> SEQ ID NO 2406
<211> LENGTH: 9
<212> TYPE: PRT
<213> ORGANISM: Homo sapiens

<400> SEQUENCE: 2406

Val Cys Val Trp Arg Gln His Ser Arg
1               5

<210> SEQ ID NO 2407
<211> LENGTH: 9
<212> TYPE: PRT
<213> ORGANISM: Homo sapiens

<400> SEQUENCE: 2407

Cys Val Trp Arg Gln His Ser Arg Glu
1               5

<210> SEQ ID NO 2408
<211> LENGTH: 9
<212> TYPE: PRT
<213> ORGANISM: Homo sapiens

<400> SEQUENCE: 2408

Val Trp Arg Gln His Ser Arg Glu Leu
1               5

<210> SEQ ID NO 2409
<211> LENGTH: 9
<212> TYPE: PRT
<213> ORGANISM: Homo sapiens

<400> SEQUENCE: 2409

Trp Arg Gln His Ser Arg Glu Leu Arg
1               5

<210> SEQ ID NO 2410
<211> LENGTH: 9
<212> TYPE: PRT
<213> ORGANISM: Homo sapiens

<400> SEQUENCE: 2410

Arg Gln His Ser Arg Glu Leu Arg Leu
1               5

<210> SEQ ID NO 2411
<211> LENGTH: 9
<212> TYPE: PRT
<213> ORGANISM: Homo sapiens

<400> SEQUENCE: 2411

Gln His Ser Arg Glu Leu Arg Leu Glu
1               5

<210> SEQ ID NO 2412
<211> LENGTH: 9
<212> TYPE: PRT
<213> ORGANISM: Homo sapiens

<400> SEQUENCE: 2412
```

His Ser Arg Glu Leu Arg Leu Glu Ser
1               5

<210> SEQ ID NO 2413
<211> LENGTH: 9
<212> TYPE: PRT
<213> ORGANISM: Homo sapiens

<400> SEQUENCE: 2413

Ser Arg Glu Leu Arg Leu Glu Ser Ile
1               5

<210> SEQ ID NO 2414
<211> LENGTH: 9
<212> TYPE: PRT
<213> ORGANISM: Homo sapiens

<400> SEQUENCE: 2414

Arg Glu Leu Arg Leu Glu Ser Ile Lys
1               5

<210> SEQ ID NO 2415
<211> LENGTH: 9
<212> TYPE: PRT
<213> ORGANISM: Homo sapiens

<400> SEQUENCE: 2415

Glu Leu Arg Leu Glu Ser Ile Lys Ser
1               5

<210> SEQ ID NO 2416
<211> LENGTH: 9
<212> TYPE: PRT
<213> ORGANISM: Homo sapiens

<400> SEQUENCE: 2416

Leu Arg Leu Glu Ser Ile Lys Ser Gln
1               5

<210> SEQ ID NO 2417
<211> LENGTH: 9
<212> TYPE: PRT
<213> ORGANISM: Homo sapiens

<400> SEQUENCE: 2417

Arg Leu Glu Ser Ile Lys Ser Gln Ile
1               5

<210> SEQ ID NO 2418
<211> LENGTH: 9
<212> TYPE: PRT
<213> ORGANISM: Homo sapiens

<400> SEQUENCE: 2418

Leu Glu Ser Ile Lys Ser Gln Ile Leu
1               5

<210> SEQ ID NO 2419
<211> LENGTH: 9
<212> TYPE: PRT
<213> ORGANISM: Homo sapiens

<400> SEQUENCE: 2419

Glu Ser Ile Lys Ser Gln Ile Leu Ser
1               5

<210> SEQ ID NO 2420
<211> LENGTH: 9
<212> TYPE: PRT
<213> ORGANISM: Homo sapiens

<400> SEQUENCE: 2420

Ser Ile Lys Ser Gln Ile Leu Ser Lys
1               5

<210> SEQ ID NO 2421
<211> LENGTH: 9
<212> TYPE: PRT
<213> ORGANISM: Homo sapiens

<400> SEQUENCE: 2421

Ile Lys Ser Gln Ile Leu Ser Lys Leu
1               5

<210> SEQ ID NO 2422
<211> LENGTH: 9
<212> TYPE: PRT
<213> ORGANISM: Homo sapiens

<400> SEQUENCE: 2422

Lys Ser Gln Ile Leu Ser Lys Leu Arg
1               5

<210> SEQ ID NO 2423
<211> LENGTH: 9
<212> TYPE: PRT
<213> ORGANISM: Homo sapiens

<400> SEQUENCE: 2423

Ser Gln Ile Leu Ser Lys Leu Arg Leu
1               5

<210> SEQ ID NO 2424
<211> LENGTH: 9
<212> TYPE: PRT
<213> ORGANISM: Homo sapiens

<400> SEQUENCE: 2424

Gln Ile Leu Ser Lys Leu Arg Leu Lys
1               5

<210> SEQ ID NO 2425
<211> LENGTH: 9
<212> TYPE: PRT
<213> ORGANISM: Homo sapiens

<400> SEQUENCE: 2425

Ile Leu Ser Lys Leu Arg Leu Lys Glu
1               5

<210> SEQ ID NO 2426
<211> LENGTH: 9
<212> TYPE: PRT
<213> ORGANISM: Homo sapiens

<400> SEQUENCE: 2426

Leu Ser Lys Leu Arg Leu Lys Glu Ala
1               5

```
<210> SEQ ID NO 2427
<211> LENGTH: 9
<212> TYPE: PRT
<213> ORGANISM: Homo sapiens

<400> SEQUENCE: 2427

Ser Lys Leu Arg Leu Lys Glu Ala Pro
1               5

<210> SEQ ID NO 2428
<211> LENGTH: 9
<212> TYPE: PRT
<213> ORGANISM: Homo sapiens

<400> SEQUENCE: 2428

Lys Leu Arg Leu Lys Glu Ala Pro Asn
1               5

<210> SEQ ID NO 2429
<211> LENGTH: 9
<212> TYPE: PRT
<213> ORGANISM: Homo sapiens

<400> SEQUENCE: 2429

Leu Arg Leu Lys Glu Ala Pro Asn Ile
1               5

<210> SEQ ID NO 2430
<211> LENGTH: 9
<212> TYPE: PRT
<213> ORGANISM: Homo sapiens

<400> SEQUENCE: 2430

Arg Leu Lys Glu Ala Pro Asn Ile Ser
1               5

<210> SEQ ID NO 2431
<211> LENGTH: 9
<212> TYPE: PRT
<213> ORGANISM: Homo sapiens

<400> SEQUENCE: 2431

Leu Lys Glu Ala Pro Asn Ile Ser Arg
1               5

<210> SEQ ID NO 2432
<211> LENGTH: 9
<212> TYPE: PRT
<213> ORGANISM: Homo sapiens

<400> SEQUENCE: 2432

Lys Glu Ala Pro Asn Ile Ser Arg Glu
1               5

<210> SEQ ID NO 2433
<211> LENGTH: 9
<212> TYPE: PRT
<213> ORGANISM: Homo sapiens

<400> SEQUENCE: 2433

Glu Ala Pro Asn Ile Ser Arg Glu Val
1               5

<210> SEQ ID NO 2434
<211> LENGTH: 9
```

```
<212> TYPE: PRT
<213> ORGANISM: Homo sapiens

<400> SEQUENCE: 2434

Ala Pro Asn Ile Ser Arg Glu Val Val
1               5

<210> SEQ ID NO 2435
<211> LENGTH: 9
<212> TYPE: PRT
<213> ORGANISM: Homo sapiens

<400> SEQUENCE: 2435

Pro Asn Ile Ser Arg Glu Val Val Lys
1               5

<210> SEQ ID NO 2436
<211> LENGTH: 9
<212> TYPE: PRT
<213> ORGANISM: Homo sapiens

<400> SEQUENCE: 2436

Asn Ile Ser Arg Glu Val Val Lys Gln
1               5

<210> SEQ ID NO 2437
<211> LENGTH: 9
<212> TYPE: PRT
<213> ORGANISM: Homo sapiens

<400> SEQUENCE: 2437

Ile Ser Arg Glu Val Val Lys Gln Leu
1               5

<210> SEQ ID NO 2438
<211> LENGTH: 9
<212> TYPE: PRT
<213> ORGANISM: Homo sapiens

<400> SEQUENCE: 2438

Ser Arg Glu Val Val Lys Gln Leu Leu
1               5

<210> SEQ ID NO 2439
<211> LENGTH: 9
<212> TYPE: PRT
<213> ORGANISM: Homo sapiens

<400> SEQUENCE: 2439

Arg Glu Val Val Lys Gln Leu Leu Pro
1               5

<210> SEQ ID NO 2440
<211> LENGTH: 9
<212> TYPE: PRT
<213> ORGANISM: Homo sapiens

<400> SEQUENCE: 2440

Glu Val Val Lys Gln Leu Leu Pro Lys
1               5

<210> SEQ ID NO 2441
<211> LENGTH: 9
<212> TYPE: PRT
<213> ORGANISM: Homo sapiens
```

<400> SEQUENCE: 2441

Val Val Lys Gln Leu Leu Pro Lys Ala
1               5

<210> SEQ ID NO 2442
<211> LENGTH: 9
<212> TYPE: PRT
<213> ORGANISM: Homo sapiens

<400> SEQUENCE: 2442

Val Lys Gln Leu Leu Pro Lys Ala Pro
1               5

<210> SEQ ID NO 2443
<211> LENGTH: 9
<212> TYPE: PRT
<213> ORGANISM: Homo sapiens

<400> SEQUENCE: 2443

Lys Gln Leu Leu Pro Lys Ala Pro Pro
1               5

<210> SEQ ID NO 2444
<211> LENGTH: 9
<212> TYPE: PRT
<213> ORGANISM: Homo sapiens

<400> SEQUENCE: 2444

Gln Leu Leu Pro Lys Ala Pro Pro Leu
1               5

<210> SEQ ID NO 2445
<211> LENGTH: 9
<212> TYPE: PRT
<213> ORGANISM: Homo sapiens

<400> SEQUENCE: 2445

Leu Leu Pro Lys Ala Pro Pro Leu Gln
1               5

<210> SEQ ID NO 2446
<211> LENGTH: 9
<212> TYPE: PRT
<213> ORGANISM: Homo sapiens

<400> SEQUENCE: 2446

Leu Pro Lys Ala Pro Pro Leu Gln Gln
1               5

<210> SEQ ID NO 2447
<211> LENGTH: 9
<212> TYPE: PRT
<213> ORGANISM: Homo sapiens

<400> SEQUENCE: 2447

Pro Lys Ala Pro Pro Leu Gln Gln Ile
1               5

<210> SEQ ID NO 2448
<211> LENGTH: 9
<212> TYPE: PRT
<213> ORGANISM: Homo sapiens

<400> SEQUENCE: 2448

```
Lys Ala Pro Pro Leu Gln Gln Ile Leu
1               5

<210> SEQ ID NO 2449
<211> LENGTH: 9
<212> TYPE: PRT
<213> ORGANISM: Homo sapiens

<400> SEQUENCE: 2449

Ala Pro Pro Leu Gln Gln Ile Leu Asp
1               5

<210> SEQ ID NO 2450
<211> LENGTH: 9
<212> TYPE: PRT
<213> ORGANISM: Homo sapiens

<400> SEQUENCE: 2450

Pro Pro Leu Gln Gln Ile Leu Asp Leu
1               5

<210> SEQ ID NO 2451
<211> LENGTH: 9
<212> TYPE: PRT
<213> ORGANISM: Homo sapiens

<400> SEQUENCE: 2451

Pro Leu Gln Gln Ile Leu Asp Leu His
1               5

<210> SEQ ID NO 2452
<211> LENGTH: 9
<212> TYPE: PRT
<213> ORGANISM: Homo sapiens

<400> SEQUENCE: 2452

Leu Gln Gln Ile Leu Asp Leu His Asp
1               5

<210> SEQ ID NO 2453
<211> LENGTH: 9
<212> TYPE: PRT
<213> ORGANISM: Homo sapiens

<400> SEQUENCE: 2453

Gln Gln Ile Leu Asp Leu His Asp Phe
1               5

<210> SEQ ID NO 2454
<211> LENGTH: 9
<212> TYPE: PRT
<213> ORGANISM: Homo sapiens

<400> SEQUENCE: 2454

Gln Ile Leu Asp Leu His Asp Phe Gln
1               5

<210> SEQ ID NO 2455
<211> LENGTH: 9
<212> TYPE: PRT
<213> ORGANISM: Homo sapiens

<400> SEQUENCE: 2455

Ile Leu Asp Leu His Asp Phe Gln Gly
```

```
1               5

<210> SEQ ID NO 2456
<211> LENGTH: 9
<212> TYPE: PRT
<213> ORGANISM: Homo sapiens

<400> SEQUENCE: 2456

Leu Asp Leu His Asp Phe Gln Gly Asp
1               5

<210> SEQ ID NO 2457
<211> LENGTH: 9
<212> TYPE: PRT
<213> ORGANISM: Homo sapiens

<400> SEQUENCE: 2457

Asp Leu His Asp Phe Gln Gly Asp Ala
1               5

<210> SEQ ID NO 2458
<211> LENGTH: 9
<212> TYPE: PRT
<213> ORGANISM: Homo sapiens

<400> SEQUENCE: 2458

Leu His Asp Phe Gln Gly Asp Ala Leu
1               5

<210> SEQ ID NO 2459
<211> LENGTH: 9
<212> TYPE: PRT
<213> ORGANISM: Homo sapiens

<400> SEQUENCE: 2459

His Asp Phe Gln Gly Asp Ala Leu Gln
1               5

<210> SEQ ID NO 2460
<211> LENGTH: 9
<212> TYPE: PRT
<213> ORGANISM: Homo sapiens

<400> SEQUENCE: 2460

Asp Phe Gln Gly Asp Ala Leu Gln Pro
1               5

<210> SEQ ID NO 2461
<211> LENGTH: 9
<212> TYPE: PRT
<213> ORGANISM: Homo sapiens

<400> SEQUENCE: 2461

Phe Gln Gly Asp Ala Leu Gln Pro Glu
1               5

<210> SEQ ID NO 2462
<211> LENGTH: 9
<212> TYPE: PRT
<213> ORGANISM: Homo sapiens

<400> SEQUENCE: 2462

Gln Gly Asp Ala Leu Gln Pro Glu Asp
1               5
```

<210> SEQ ID NO 2463
<211> LENGTH: 9
<212> TYPE: PRT
<213> ORGANISM: Homo sapiens

<400> SEQUENCE: 2463

Gly Asp Ala Leu Gln Pro Glu Asp Phe
1               5

<210> SEQ ID NO 2464
<211> LENGTH: 9
<212> TYPE: PRT
<213> ORGANISM: Homo sapiens

<400> SEQUENCE: 2464

Asp Ala Leu Gln Pro Glu Asp Phe Leu
1               5

<210> SEQ ID NO 2465
<211> LENGTH: 9
<212> TYPE: PRT
<213> ORGANISM: Homo sapiens

<400> SEQUENCE: 2465

Ala Leu Gln Pro Glu Asp Phe Leu Glu
1               5

<210> SEQ ID NO 2466
<211> LENGTH: 9
<212> TYPE: PRT
<213> ORGANISM: Homo sapiens

<400> SEQUENCE: 2466

Leu Gln Pro Glu Asp Phe Leu Glu Glu
1               5

<210> SEQ ID NO 2467
<211> LENGTH: 9
<212> TYPE: PRT
<213> ORGANISM: Homo sapiens

<400> SEQUENCE: 2467

Gln Pro Glu Asp Phe Leu Glu Glu Asp
1               5

<210> SEQ ID NO 2468
<211> LENGTH: 9
<212> TYPE: PRT
<213> ORGANISM: Homo sapiens

<400> SEQUENCE: 2468

Pro Glu Asp Phe Leu Glu Glu Asp Glu
1               5

<210> SEQ ID NO 2469
<211> LENGTH: 9
<212> TYPE: PRT
<213> ORGANISM: Homo sapiens

<400> SEQUENCE: 2469

Glu Asp Phe Leu Glu Glu Asp Glu Tyr
1               5

<210> SEQ ID NO 2470

<211> LENGTH: 9
<212> TYPE: PRT
<213> ORGANISM: Homo sapiens

<400> SEQUENCE: 2470

Asp Phe Leu Glu Glu Asp Glu Tyr His
1               5

<210> SEQ ID NO 2471
<211> LENGTH: 9
<212> TYPE: PRT
<213> ORGANISM: Homo sapiens

<400> SEQUENCE: 2471

Phe Leu Glu Glu Asp Glu Tyr His Ala
1               5

<210> SEQ ID NO 2472
<211> LENGTH: 9
<212> TYPE: PRT
<213> ORGANISM: Homo sapiens

<400> SEQUENCE: 2472

Leu Glu Glu Asp Glu Tyr His Ala Thr
1               5

<210> SEQ ID NO 2473
<211> LENGTH: 9
<212> TYPE: PRT
<213> ORGANISM: Homo sapiens

<400> SEQUENCE: 2473

Glu Glu Asp Glu Tyr His Ala Thr Thr
1               5

<210> SEQ ID NO 2474
<211> LENGTH: 9
<212> TYPE: PRT
<213> ORGANISM: Homo sapiens

<400> SEQUENCE: 2474

Glu Asp Glu Tyr His Ala Thr Thr Glu
1               5

<210> SEQ ID NO 2475
<211> LENGTH: 9
<212> TYPE: PRT
<213> ORGANISM: Homo sapiens

<400> SEQUENCE: 2475

Asp Glu Tyr His Ala Thr Thr Glu Thr
1               5

<210> SEQ ID NO 2476
<211> LENGTH: 9
<212> TYPE: PRT
<213> ORGANISM: Homo sapiens

<400> SEQUENCE: 2476

Glu Tyr His Ala Thr Thr Glu Thr Val
1               5

<210> SEQ ID NO 2477
<211> LENGTH: 9
<212> TYPE: PRT

```
<213> ORGANISM: Homo sapiens

<400> SEQUENCE: 2477

Tyr His Ala Thr Thr Glu Thr Val Ile
1               5

<210> SEQ ID NO 2478
<211> LENGTH: 9
<212> TYPE: PRT
<213> ORGANISM: Homo sapiens

<400> SEQUENCE: 2478

His Ala Thr Thr Glu Thr Val Ile Ser
1               5

<210> SEQ ID NO 2479
<211> LENGTH: 9
<212> TYPE: PRT
<213> ORGANISM: Homo sapiens

<400> SEQUENCE: 2479

Ala Thr Thr Glu Thr Val Ile Ser Met
1               5

<210> SEQ ID NO 2480
<211> LENGTH: 9
<212> TYPE: PRT
<213> ORGANISM: Homo sapiens

<400> SEQUENCE: 2480

Thr Thr Glu Thr Val Ile Ser Met Ala
1               5

<210> SEQ ID NO 2481
<211> LENGTH: 9
<212> TYPE: PRT
<213> ORGANISM: Homo sapiens

<400> SEQUENCE: 2481

Thr Glu Thr Val Ile Ser Met Ala Gln
1               5

<210> SEQ ID NO 2482
<211> LENGTH: 9
<212> TYPE: PRT
<213> ORGANISM: Homo sapiens

<400> SEQUENCE: 2482

Glu Thr Val Ile Ser Met Ala Gln Glu
1               5

<210> SEQ ID NO 2483
<211> LENGTH: 9
<212> TYPE: PRT
<213> ORGANISM: Homo sapiens

<400> SEQUENCE: 2483

Thr Val Ile Ser Met Ala Gln Glu Thr
1               5

<210> SEQ ID NO 2484
<211> LENGTH: 9
<212> TYPE: PRT
<213> ORGANISM: Homo sapiens
```

<400> SEQUENCE: 2484

Val Ile Ser Met Ala Gln Glu Thr Asp
1               5

<210> SEQ ID NO 2485
<211> LENGTH: 9
<212> TYPE: PRT
<213> ORGANISM: Homo sapiens

<400> SEQUENCE: 2485

Ile Ser Met Ala Gln Glu Thr Asp Pro
1               5

<210> SEQ ID NO 2486
<211> LENGTH: 9
<212> TYPE: PRT
<213> ORGANISM: Homo sapiens

<400> SEQUENCE: 2486

Ser Met Ala Gln Glu Thr Asp Pro Ala
1               5

<210> SEQ ID NO 2487
<211> LENGTH: 9
<212> TYPE: PRT
<213> ORGANISM: Homo sapiens

<400> SEQUENCE: 2487

Met Ala Gln Glu Thr Asp Pro Ala Val
1               5

<210> SEQ ID NO 2488
<211> LENGTH: 9
<212> TYPE: PRT
<213> ORGANISM: Homo sapiens

<400> SEQUENCE: 2488

Ala Gln Glu Thr Asp Pro Ala Val Gln
1               5

<210> SEQ ID NO 2489
<211> LENGTH: 9
<212> TYPE: PRT
<213> ORGANISM: Homo sapiens

<400> SEQUENCE: 2489

Gln Glu Thr Asp Pro Ala Val Gln Thr
1               5

<210> SEQ ID NO 2490
<211> LENGTH: 9
<212> TYPE: PRT
<213> ORGANISM: Homo sapiens

<400> SEQUENCE: 2490

Glu Thr Asp Pro Ala Val Gln Thr Asp
1               5

<210> SEQ ID NO 2491
<211> LENGTH: 9
<212> TYPE: PRT
<213> ORGANISM: Homo sapiens

<400> SEQUENCE: 2491

Thr Asp Pro Ala Val Gln Thr Asp Gly
1               5

<210> SEQ ID NO 2492
<211> LENGTH: 9
<212> TYPE: PRT
<213> ORGANISM: Homo sapiens

<400> SEQUENCE: 2492

Asp Pro Ala Val Gln Thr Asp Gly Ser
1               5

<210> SEQ ID NO 2493
<211> LENGTH: 9
<212> TYPE: PRT
<213> ORGANISM: Homo sapiens

<400> SEQUENCE: 2493

Pro Ala Val Gln Thr Asp Gly Ser Pro
1               5

<210> SEQ ID NO 2494
<211> LENGTH: 9
<212> TYPE: PRT
<213> ORGANISM: Homo sapiens

<400> SEQUENCE: 2494

Ala Val Gln Thr Asp Gly Ser Pro Leu
1               5

<210> SEQ ID NO 2495
<211> LENGTH: 9
<212> TYPE: PRT
<213> ORGANISM: Homo sapiens

<400> SEQUENCE: 2495

Val Gln Thr Asp Gly Ser Pro Leu Cys
1               5

<210> SEQ ID NO 2496
<211> LENGTH: 9
<212> TYPE: PRT
<213> ORGANISM: Homo sapiens

<400> SEQUENCE: 2496

Gln Thr Asp Gly Ser Pro Leu Cys Cys
1               5

<210> SEQ ID NO 2497
<211> LENGTH: 9
<212> TYPE: PRT
<213> ORGANISM: Homo sapiens

<400> SEQUENCE: 2497

Thr Asp Gly Ser Pro Leu Cys Cys His
1               5

<210> SEQ ID NO 2498
<211> LENGTH: 9
<212> TYPE: PRT
<213> ORGANISM: Homo sapiens

<400> SEQUENCE: 2498

Asp Gly Ser Pro Leu Cys Cys His Phe
1               5

<210> SEQ ID NO 2499
<211> LENGTH: 9
<212> TYPE: PRT
<213> ORGANISM: Homo sapiens

<400> SEQUENCE: 2499

Gly Ser Pro Leu Cys Cys His Phe His
1               5

<210> SEQ ID NO 2500
<211> LENGTH: 9
<212> TYPE: PRT
<213> ORGANISM: Homo sapiens

<400> SEQUENCE: 2500

Ser Pro Leu Cys Cys His Phe His Phe
1               5

<210> SEQ ID NO 2501
<211> LENGTH: 9
<212> TYPE: PRT
<213> ORGANISM: Homo sapiens

<400> SEQUENCE: 2501

Pro Leu Cys Cys His Phe His Phe Ser
1               5

<210> SEQ ID NO 2502
<211> LENGTH: 9
<212> TYPE: PRT
<213> ORGANISM: Homo sapiens

<400> SEQUENCE: 2502

Leu Cys Cys His Phe His Phe Ser Pro
1               5

<210> SEQ ID NO 2503
<211> LENGTH: 9
<212> TYPE: PRT
<213> ORGANISM: Homo sapiens

<400> SEQUENCE: 2503

Cys Cys His Phe His Phe Ser Pro Lys
1               5

<210> SEQ ID NO 2504
<211> LENGTH: 9
<212> TYPE: PRT
<213> ORGANISM: Homo sapiens

<400> SEQUENCE: 2504

Cys His Phe His Phe Ser Pro Lys Val
1               5

<210> SEQ ID NO 2505
<211> LENGTH: 9
<212> TYPE: PRT
<213> ORGANISM: Homo sapiens

<400> SEQUENCE: 2505

His Phe His Phe Ser Pro Lys Val Met
1               5

```
<210> SEQ ID NO 2506
<211> LENGTH: 9
<212> TYPE: PRT
<213> ORGANISM: Homo sapiens

<400> SEQUENCE: 2506

Phe His Phe Ser Pro Lys Val Met Phe
1               5

<210> SEQ ID NO 2507
<211> LENGTH: 9
<212> TYPE: PRT
<213> ORGANISM: Homo sapiens

<400> SEQUENCE: 2507

His Phe Ser Pro Lys Val Met Phe Thr
1               5

<210> SEQ ID NO 2508
<211> LENGTH: 9
<212> TYPE: PRT
<213> ORGANISM: Homo sapiens

<400> SEQUENCE: 2508

Phe Ser Pro Lys Val Met Phe Thr Lys
1               5

<210> SEQ ID NO 2509
<211> LENGTH: 9
<212> TYPE: PRT
<213> ORGANISM: Homo sapiens

<400> SEQUENCE: 2509

Ser Pro Lys Val Met Phe Thr Lys Val
1               5

<210> SEQ ID NO 2510
<211> LENGTH: 9
<212> TYPE: PRT
<213> ORGANISM: Homo sapiens

<400> SEQUENCE: 2510

Pro Lys Val Met Phe Thr Lys Val Leu
1               5

<210> SEQ ID NO 2511
<211> LENGTH: 9
<212> TYPE: PRT
<213> ORGANISM: Homo sapiens

<400> SEQUENCE: 2511

Lys Val Met Phe Thr Lys Val Leu Lys
1               5

<210> SEQ ID NO 2512
<211> LENGTH: 9
<212> TYPE: PRT
<213> ORGANISM: Homo sapiens

<400> SEQUENCE: 2512

Val Met Phe Thr Lys Val Leu Lys Ala
1               5

<210> SEQ ID NO 2513
<211> LENGTH: 9
```

<212> TYPE: PRT
<213> ORGANISM: Homo sapiens

<400> SEQUENCE: 2513

Met Phe Thr Lys Val Leu Lys Ala Gln
1               5

<210> SEQ ID NO 2514
<211> LENGTH: 9
<212> TYPE: PRT
<213> ORGANISM: Homo sapiens

<400> SEQUENCE: 2514

Phe Thr Lys Val Leu Lys Ala Gln Leu
1               5

<210> SEQ ID NO 2515
<211> LENGTH: 9
<212> TYPE: PRT
<213> ORGANISM: Homo sapiens

<400> SEQUENCE: 2515

Thr Lys Val Leu Lys Ala Gln Leu Trp
1               5

<210> SEQ ID NO 2516
<211> LENGTH: 9
<212> TYPE: PRT
<213> ORGANISM: Homo sapiens

<400> SEQUENCE: 2516

Lys Val Leu Lys Ala Gln Leu Trp Val
1               5

<210> SEQ ID NO 2517
<211> LENGTH: 9
<212> TYPE: PRT
<213> ORGANISM: Homo sapiens

<400> SEQUENCE: 2517

Val Leu Lys Ala Gln Leu Trp Val Tyr
1               5

<210> SEQ ID NO 2518
<211> LENGTH: 9
<212> TYPE: PRT
<213> ORGANISM: Homo sapiens

<400> SEQUENCE: 2518

Leu Lys Ala Gln Leu Trp Val Tyr Leu
1               5

<210> SEQ ID NO 2519
<211> LENGTH: 9
<212> TYPE: PRT
<213> ORGANISM: Homo sapiens

<400> SEQUENCE: 2519

Lys Ala Gln Leu Trp Val Tyr Leu Arg
1               5

<210> SEQ ID NO 2520
<211> LENGTH: 9
<212> TYPE: PRT
<213> ORGANISM: Homo sapiens

```
<400> SEQUENCE: 2520

Ala Gln Leu Trp Val Tyr Leu Arg Pro
1               5

<210> SEQ ID NO 2521
<211> LENGTH: 9
<212> TYPE: PRT
<213> ORGANISM: Homo sapiens

<400> SEQUENCE: 2521

Gln Leu Trp Val Tyr Leu Arg Pro Val
1               5

<210> SEQ ID NO 2522
<211> LENGTH: 9
<212> TYPE: PRT
<213> ORGANISM: Homo sapiens

<400> SEQUENCE: 2522

Leu Trp Val Tyr Leu Arg Pro Val Pro
1               5

<210> SEQ ID NO 2523
<211> LENGTH: 9
<212> TYPE: PRT
<213> ORGANISM: Homo sapiens

<400> SEQUENCE: 2523

Trp Val Tyr Leu Arg Pro Val Pro Arg
1               5

<210> SEQ ID NO 2524
<211> LENGTH: 9
<212> TYPE: PRT
<213> ORGANISM: Homo sapiens

<400> SEQUENCE: 2524

Val Tyr Leu Arg Pro Val Pro Arg Pro
1               5

<210> SEQ ID NO 2525
<211> LENGTH: 9
<212> TYPE: PRT
<213> ORGANISM: Homo sapiens

<400> SEQUENCE: 2525

Tyr Leu Arg Pro Val Pro Arg Pro Ala
1               5

<210> SEQ ID NO 2526
<211> LENGTH: 9
<212> TYPE: PRT
<213> ORGANISM: Homo sapiens

<400> SEQUENCE: 2526

Leu Arg Pro Val Pro Arg Pro Ala Thr
1               5

<210> SEQ ID NO 2527
<211> LENGTH: 9
<212> TYPE: PRT
<213> ORGANISM: Homo sapiens

<400> SEQUENCE: 2527
```

Arg Pro Val Pro Arg Pro Ala Thr Val
1               5

<210> SEQ ID NO 2528
<211> LENGTH: 9
<212> TYPE: PRT
<213> ORGANISM: Homo sapiens

<400> SEQUENCE: 2528

Pro Val Pro Arg Pro Ala Thr Val Tyr
1               5

<210> SEQ ID NO 2529
<211> LENGTH: 9
<212> TYPE: PRT
<213> ORGANISM: Homo sapiens

<400> SEQUENCE: 2529

Val Pro Arg Pro Ala Thr Val Tyr Leu
1               5

<210> SEQ ID NO 2530
<211> LENGTH: 9
<212> TYPE: PRT
<213> ORGANISM: Homo sapiens

<400> SEQUENCE: 2530

Pro Arg Pro Ala Thr Val Tyr Leu Gln
1               5

<210> SEQ ID NO 2531
<211> LENGTH: 9
<212> TYPE: PRT
<213> ORGANISM: Homo sapiens

<400> SEQUENCE: 2531

Arg Pro Ala Thr Val Tyr Leu Gln Ile
1               5

<210> SEQ ID NO 2532
<211> LENGTH: 9
<212> TYPE: PRT
<213> ORGANISM: Homo sapiens

<400> SEQUENCE: 2532

Pro Ala Thr Val Tyr Leu Gln Ile Leu
1               5

<210> SEQ ID NO 2533
<211> LENGTH: 9
<212> TYPE: PRT
<213> ORGANISM: Homo sapiens

<400> SEQUENCE: 2533

Ala Thr Val Tyr Leu Gln Ile Leu Arg
1               5

<210> SEQ ID NO 2534
<211> LENGTH: 9
<212> TYPE: PRT
<213> ORGANISM: Homo sapiens

<400> SEQUENCE: 2534

Thr Val Tyr Leu Gln Ile Leu Arg Leu

```
1               5

<210> SEQ ID NO 2535
<211> LENGTH: 9
<212> TYPE: PRT
<213> ORGANISM: Homo sapiens

<400> SEQUENCE: 2535

Val Tyr Leu Gln Ile Leu Arg Leu Lys
1               5

<210> SEQ ID NO 2536
<211> LENGTH: 9
<212> TYPE: PRT
<213> ORGANISM: Homo sapiens

<400> SEQUENCE: 2536

Tyr Leu Gln Ile Leu Arg Leu Lys Pro
1               5

<210> SEQ ID NO 2537
<211> LENGTH: 9
<212> TYPE: PRT
<213> ORGANISM: Homo sapiens

<400> SEQUENCE: 2537

Leu Gln Ile Leu Arg Leu Lys Pro Leu
1               5

<210> SEQ ID NO 2538
<211> LENGTH: 9
<212> TYPE: PRT
<213> ORGANISM: Homo sapiens

<400> SEQUENCE: 2538

Gln Ile Leu Arg Leu Lys Pro Leu Thr
1               5

<210> SEQ ID NO 2539
<211> LENGTH: 9
<212> TYPE: PRT
<213> ORGANISM: Homo sapiens

<400> SEQUENCE: 2539

Ile Leu Arg Leu Lys Pro Leu Thr Gly
1               5

<210> SEQ ID NO 2540
<211> LENGTH: 9
<212> TYPE: PRT
<213> ORGANISM: Homo sapiens

<400> SEQUENCE: 2540

Leu Arg Leu Lys Pro Leu Thr Gly Glu
1               5

<210> SEQ ID NO 2541
<211> LENGTH: 9
<212> TYPE: PRT
<213> ORGANISM: Homo sapiens

<400> SEQUENCE: 2541

Arg Leu Lys Pro Leu Thr Gly Glu Gly
1               5
```

<210> SEQ ID NO 2542
<211> LENGTH: 9
<212> TYPE: PRT
<213> ORGANISM: Homo sapiens

<400> SEQUENCE: 2542

Leu Lys Pro Leu Thr Gly Glu Gly Thr
1               5

<210> SEQ ID NO 2543
<211> LENGTH: 9
<212> TYPE: PRT
<213> ORGANISM: Homo sapiens

<400> SEQUENCE: 2543

Lys Pro Leu Thr Gly Glu Gly Thr Ala
1               5

<210> SEQ ID NO 2544
<211> LENGTH: 9
<212> TYPE: PRT
<213> ORGANISM: Homo sapiens

<400> SEQUENCE: 2544

Pro Leu Thr Gly Glu Gly Thr Ala Gly
1               5

<210> SEQ ID NO 2545
<211> LENGTH: 9
<212> TYPE: PRT
<213> ORGANISM: Homo sapiens

<400> SEQUENCE: 2545

Leu Thr Gly Glu Gly Thr Ala Gly Gly
1               5

<210> SEQ ID NO 2546
<211> LENGTH: 9
<212> TYPE: PRT
<213> ORGANISM: Homo sapiens

<400> SEQUENCE: 2546

Thr Gly Glu Gly Thr Ala Gly Gly Gly
1               5

<210> SEQ ID NO 2547
<211> LENGTH: 9
<212> TYPE: PRT
<213> ORGANISM: Homo sapiens

<400> SEQUENCE: 2547

Gly Glu Gly Thr Ala Gly Gly Gly Gly
1               5

<210> SEQ ID NO 2548
<211> LENGTH: 9
<212> TYPE: PRT
<213> ORGANISM: Homo sapiens

<400> SEQUENCE: 2548

Glu Gly Thr Ala Gly Gly Gly Gly Gly
1               5

<210> SEQ ID NO 2549

```
<211> LENGTH: 9
<212> TYPE: PRT
<213> ORGANISM: Homo sapiens

<400> SEQUENCE: 2549

Gly Thr Ala Gly Gly Gly Gly Gly Gly
1               5

<210> SEQ ID NO 2550
<211> LENGTH: 9
<212> TYPE: PRT
<213> ORGANISM: Homo sapiens

<400> SEQUENCE: 2550

Thr Ala Gly Gly Gly Gly Gly Gly Arg
1               5

<210> SEQ ID NO 2551
<211> LENGTH: 9
<212> TYPE: PRT
<213> ORGANISM: Homo sapiens

<400> SEQUENCE: 2551

Ala Gly Gly Gly Gly Gly Gly Arg Arg
1               5

<210> SEQ ID NO 2552
<211> LENGTH: 9
<212> TYPE: PRT
<213> ORGANISM: Homo sapiens

<400> SEQUENCE: 2552

Gly Gly Gly Gly Gly Gly Arg Arg His
1               5

<210> SEQ ID NO 2553
<211> LENGTH: 9
<212> TYPE: PRT
<213> ORGANISM: Homo sapiens

<400> SEQUENCE: 2553

Gly Gly Gly Gly Gly Arg Arg His Ile
1               5

<210> SEQ ID NO 2554
<211> LENGTH: 9
<212> TYPE: PRT
<213> ORGANISM: Homo sapiens

<400> SEQUENCE: 2554

Gly Gly Gly Gly Arg Arg His Ile Arg
1               5

<210> SEQ ID NO 2555
<211> LENGTH: 9
<212> TYPE: PRT
<213> ORGANISM: Homo sapiens

<400> SEQUENCE: 2555

Gly Gly Gly Arg Arg His Ile Arg Ile
1               5

<210> SEQ ID NO 2556
<211> LENGTH: 9
<212> TYPE: PRT
```

<213> ORGANISM: Homo sapiens

<400> SEQUENCE: 2556

Gly Gly Arg Arg His Ile Arg Ile Arg
1               5

<210> SEQ ID NO 2557
<211> LENGTH: 9
<212> TYPE: PRT
<213> ORGANISM: Homo sapiens

<400> SEQUENCE: 2557

Gly Arg Arg His Ile Arg Ile Arg Ser
1               5

<210> SEQ ID NO 2558
<211> LENGTH: 9
<212> TYPE: PRT
<213> ORGANISM: Homo sapiens

<400> SEQUENCE: 2558

Arg Arg His Ile Arg Ile Arg Ser Leu
1               5

<210> SEQ ID NO 2559
<211> LENGTH: 9
<212> TYPE: PRT
<213> ORGANISM: Homo sapiens

<400> SEQUENCE: 2559

Arg His Ile Arg Ile Arg Ser Leu Lys
1               5

<210> SEQ ID NO 2560
<211> LENGTH: 9
<212> TYPE: PRT
<213> ORGANISM: Homo sapiens

<400> SEQUENCE: 2560

His Ile Arg Ile Arg Ser Leu Lys Ile
1               5

<210> SEQ ID NO 2561
<211> LENGTH: 9
<212> TYPE: PRT
<213> ORGANISM: Homo sapiens

<400> SEQUENCE: 2561

Ile Arg Ile Arg Ser Leu Lys Ile Glu
1               5

<210> SEQ ID NO 2562
<211> LENGTH: 9
<212> TYPE: PRT
<213> ORGANISM: Homo sapiens

<400> SEQUENCE: 2562

Arg Ile Arg Ser Leu Lys Ile Glu Leu
1               5

<210> SEQ ID NO 2563
<211> LENGTH: 9
<212> TYPE: PRT
<213> ORGANISM: Homo sapiens

```
<400> SEQUENCE: 2563

Ile Arg Ser Leu Lys Ile Glu Leu His
1               5

<210> SEQ ID NO 2564
<211> LENGTH: 9
<212> TYPE: PRT
<213> ORGANISM: Homo sapiens

<400> SEQUENCE: 2564

Arg Ser Leu Lys Ile Glu Leu His Ser
1               5

<210> SEQ ID NO 2565
<211> LENGTH: 9
<212> TYPE: PRT
<213> ORGANISM: Homo sapiens

<400> SEQUENCE: 2565

Ser Leu Lys Ile Glu Leu His Ser Arg
1               5

<210> SEQ ID NO 2566
<211> LENGTH: 9
<212> TYPE: PRT
<213> ORGANISM: Homo sapiens

<400> SEQUENCE: 2566

Leu Lys Ile Glu Leu His Ser Arg Ser
1               5

<210> SEQ ID NO 2567
<211> LENGTH: 9
<212> TYPE: PRT
<213> ORGANISM: Homo sapiens

<400> SEQUENCE: 2567

Lys Ile Glu Leu His Ser Arg Ser Gly
1               5

<210> SEQ ID NO 2568
<211> LENGTH: 9
<212> TYPE: PRT
<213> ORGANISM: Homo sapiens

<400> SEQUENCE: 2568

Ile Glu Leu His Ser Arg Ser Gly His
1               5

<210> SEQ ID NO 2569
<211> LENGTH: 9
<212> TYPE: PRT
<213> ORGANISM: Homo sapiens

<400> SEQUENCE: 2569

Glu Leu His Ser Arg Ser Gly His Trp
1               5

<210> SEQ ID NO 2570
<211> LENGTH: 9
<212> TYPE: PRT
<213> ORGANISM: Homo sapiens

<400> SEQUENCE: 2570
```

Leu His Ser Arg Ser Gly His Trp Gln
1               5

<210> SEQ ID NO 2571
<211> LENGTH: 9
<212> TYPE: PRT
<213> ORGANISM: Homo sapiens

<400> SEQUENCE: 2571

His Ser Arg Ser Gly His Trp Gln Ser
1               5

<210> SEQ ID NO 2572
<211> LENGTH: 9
<212> TYPE: PRT
<213> ORGANISM: Homo sapiens

<400> SEQUENCE: 2572

Ser Arg Ser Gly His Trp Gln Ser Ile
1               5

<210> SEQ ID NO 2573
<211> LENGTH: 9
<212> TYPE: PRT
<213> ORGANISM: Homo sapiens

<400> SEQUENCE: 2573

Arg Ser Gly His Trp Gln Ser Ile Asp
1               5

<210> SEQ ID NO 2574
<211> LENGTH: 9
<212> TYPE: PRT
<213> ORGANISM: Homo sapiens

<400> SEQUENCE: 2574

Ser Gly His Trp Gln Ser Ile Asp Phe
1               5

<210> SEQ ID NO 2575
<211> LENGTH: 9
<212> TYPE: PRT
<213> ORGANISM: Homo sapiens

<400> SEQUENCE: 2575

Gly His Trp Gln Ser Ile Asp Phe Lys
1               5

<210> SEQ ID NO 2576
<211> LENGTH: 9
<212> TYPE: PRT
<213> ORGANISM: Homo sapiens

<400> SEQUENCE: 2576

His Trp Gln Ser Ile Asp Phe Lys Gln
1               5

<210> SEQ ID NO 2577
<211> LENGTH: 9
<212> TYPE: PRT
<213> ORGANISM: Homo sapiens

<400> SEQUENCE: 2577

Trp Gln Ser Ile Asp Phe Lys Gln Val
1               5

<210> SEQ ID NO 2578
<211> LENGTH: 9
<212> TYPE: PRT
<213> ORGANISM: Homo sapiens

<400> SEQUENCE: 2578

Gln Ser Ile Asp Phe Lys Gln Val Leu
1               5

<210> SEQ ID NO 2579
<211> LENGTH: 9
<212> TYPE: PRT
<213> ORGANISM: Homo sapiens

<400> SEQUENCE: 2579

Ser Ile Asp Phe Lys Gln Val Leu His
1               5

<210> SEQ ID NO 2580
<211> LENGTH: 9
<212> TYPE: PRT
<213> ORGANISM: Homo sapiens

<400> SEQUENCE: 2580

Ile Asp Phe Lys Gln Val Leu His Ser
1               5

<210> SEQ ID NO 2581
<211> LENGTH: 9
<212> TYPE: PRT
<213> ORGANISM: Homo sapiens

<400> SEQUENCE: 2581

Asp Phe Lys Gln Val Leu His Ser Trp
1               5

<210> SEQ ID NO 2582
<211> LENGTH: 9
<212> TYPE: PRT
<213> ORGANISM: Homo sapiens

<400> SEQUENCE: 2582

Phe Lys Gln Val Leu His Ser Trp Phe
1               5

<210> SEQ ID NO 2583
<211> LENGTH: 9
<212> TYPE: PRT
<213> ORGANISM: Homo sapiens

<400> SEQUENCE: 2583

Lys Gln Val Leu His Ser Trp Phe Arg
1               5

<210> SEQ ID NO 2584
<211> LENGTH: 9
<212> TYPE: PRT
<213> ORGANISM: Homo sapiens

<400> SEQUENCE: 2584

Gln Val Leu His Ser Trp Phe Arg Gln
1               5

<210> SEQ ID NO 2585
<211> LENGTH: 9
<212> TYPE: PRT
<213> ORGANISM: Homo sapiens

<400> SEQUENCE: 2585

Val Leu His Ser Trp Phe Arg Gln Pro
1               5

<210> SEQ ID NO 2586
<211> LENGTH: 9
<212> TYPE: PRT
<213> ORGANISM: Homo sapiens

<400> SEQUENCE: 2586

Leu His Ser Trp Phe Arg Gln Pro Gln
1               5

<210> SEQ ID NO 2587
<211> LENGTH: 9
<212> TYPE: PRT
<213> ORGANISM: Homo sapiens

<400> SEQUENCE: 2587

His Ser Trp Phe Arg Gln Pro Gln Ser
1               5

<210> SEQ ID NO 2588
<211> LENGTH: 9
<212> TYPE: PRT
<213> ORGANISM: Homo sapiens

<400> SEQUENCE: 2588

Ser Trp Phe Arg Gln Pro Gln Ser Asn
1               5

<210> SEQ ID NO 2589
<211> LENGTH: 9
<212> TYPE: PRT
<213> ORGANISM: Homo sapiens

<400> SEQUENCE: 2589

Trp Phe Arg Gln Pro Gln Ser Asn Trp
1               5

<210> SEQ ID NO 2590
<211> LENGTH: 9
<212> TYPE: PRT
<213> ORGANISM: Homo sapiens

<400> SEQUENCE: 2590

Phe Arg Gln Pro Gln Ser Asn Trp Gly
1               5

<210> SEQ ID NO 2591
<211> LENGTH: 9
<212> TYPE: PRT
<213> ORGANISM: Homo sapiens

<400> SEQUENCE: 2591

Arg Gln Pro Gln Ser Asn Trp Gly Ile
1               5

<210> SEQ ID NO 2592
<211> LENGTH: 9

<212> TYPE: PRT
<213> ORGANISM: Homo sapiens

<400> SEQUENCE: 2592

Gln Pro Gln Ser Asn Trp Gly Ile Glu
1               5

<210> SEQ ID NO 2593
<211> LENGTH: 9
<212> TYPE: PRT
<213> ORGANISM: Homo sapiens

<400> SEQUENCE: 2593

Pro Gln Ser Asn Trp Gly Ile Glu Ile
1               5

<210> SEQ ID NO 2594
<211> LENGTH: 9
<212> TYPE: PRT
<213> ORGANISM: Homo sapiens

<400> SEQUENCE: 2594

Gln Ser Asn Trp Gly Ile Glu Ile Asn
1               5

<210> SEQ ID NO 2595
<211> LENGTH: 9
<212> TYPE: PRT
<213> ORGANISM: Homo sapiens

<400> SEQUENCE: 2595

Ser Asn Trp Gly Ile Glu Ile Asn Ala
1               5

<210> SEQ ID NO 2596
<211> LENGTH: 9
<212> TYPE: PRT
<213> ORGANISM: Homo sapiens

<400> SEQUENCE: 2596

Asn Trp Gly Ile Glu Ile Asn Ala Phe
1               5

<210> SEQ ID NO 2597
<211> LENGTH: 9
<212> TYPE: PRT
<213> ORGANISM: Homo sapiens

<400> SEQUENCE: 2597

Trp Gly Ile Glu Ile Asn Ala Phe Asp
1               5

<210> SEQ ID NO 2598
<211> LENGTH: 9
<212> TYPE: PRT
<213> ORGANISM: Homo sapiens

<400> SEQUENCE: 2598

Gly Ile Glu Ile Asn Ala Phe Asp Pro
1               5

<210> SEQ ID NO 2599
<211> LENGTH: 9
<212> TYPE: PRT
<213> ORGANISM: Homo sapiens

<400> SEQUENCE: 2599

Ile Glu Ile Asn Ala Phe Asp Pro Ser
1               5

<210> SEQ ID NO 2600
<211> LENGTH: 9
<212> TYPE: PRT
<213> ORGANISM: Homo sapiens

<400> SEQUENCE: 2600

Glu Ile Asn Ala Phe Asp Pro Ser Gly
1               5

<210> SEQ ID NO 2601
<211> LENGTH: 9
<212> TYPE: PRT
<213> ORGANISM: Homo sapiens

<400> SEQUENCE: 2601

Ile Asn Ala Phe Asp Pro Ser Gly Thr
1               5

<210> SEQ ID NO 2602
<211> LENGTH: 9
<212> TYPE: PRT
<213> ORGANISM: Homo sapiens

<400> SEQUENCE: 2602

Asn Ala Phe Asp Pro Ser Gly Thr Asp
1               5

<210> SEQ ID NO 2603
<211> LENGTH: 9
<212> TYPE: PRT
<213> ORGANISM: Homo sapiens

<400> SEQUENCE: 2603

Ala Phe Asp Pro Ser Gly Thr Asp Leu
1               5

<210> SEQ ID NO 2604
<211> LENGTH: 9
<212> TYPE: PRT
<213> ORGANISM: Homo sapiens

<400> SEQUENCE: 2604

Phe Asp Pro Ser Gly Thr Asp Leu Ala
1               5

<210> SEQ ID NO 2605
<211> LENGTH: 9
<212> TYPE: PRT
<213> ORGANISM: Homo sapiens

<400> SEQUENCE: 2605

Asp Pro Ser Gly Thr Asp Leu Ala Val
1               5

<210> SEQ ID NO 2606
<211> LENGTH: 9
<212> TYPE: PRT
<213> ORGANISM: Homo sapiens

<400> SEQUENCE: 2606

Pro Ser Gly Thr Asp Leu Ala Val Thr
1               5

<210> SEQ ID NO 2607
<211> LENGTH: 9
<212> TYPE: PRT
<213> ORGANISM: Homo sapiens

<400> SEQUENCE: 2607

Ser Gly Thr Asp Leu Ala Val Thr Ser
1               5

<210> SEQ ID NO 2608
<211> LENGTH: 9
<212> TYPE: PRT
<213> ORGANISM: Homo sapiens

<400> SEQUENCE: 2608

Gly Thr Asp Leu Ala Val Thr Ser Leu
1               5

<210> SEQ ID NO 2609
<211> LENGTH: 9
<212> TYPE: PRT
<213> ORGANISM: Homo sapiens

<400> SEQUENCE: 2609

Thr Asp Leu Ala Val Thr Ser Leu Gly
1               5

<210> SEQ ID NO 2610
<211> LENGTH: 9
<212> TYPE: PRT
<213> ORGANISM: Homo sapiens

<400> SEQUENCE: 2610

Asp Leu Ala Val Thr Ser Leu Gly Pro
1               5

<210> SEQ ID NO 2611
<211> LENGTH: 9
<212> TYPE: PRT
<213> ORGANISM: Homo sapiens

<400> SEQUENCE: 2611

Leu Ala Val Thr Ser Leu Gly Pro Gly
1               5

<210> SEQ ID NO 2612
<211> LENGTH: 9
<212> TYPE: PRT
<213> ORGANISM: Homo sapiens

<400> SEQUENCE: 2612

Ala Val Thr Ser Leu Gly Pro Gly Ala
1               5

<210> SEQ ID NO 2613
<211> LENGTH: 9
<212> TYPE: PRT
<213> ORGANISM: Homo sapiens

<400> SEQUENCE: 2613

Val Thr Ser Leu Gly Pro Gly Ala Glu

```
1               5
```

<210> SEQ ID NO 2614
<211> LENGTH: 9
<212> TYPE: PRT
<213> ORGANISM: Homo sapiens

<400> SEQUENCE: 2614

```
Thr Ser Leu Gly Pro Gly Ala Glu Gly
1               5
```

<210> SEQ ID NO 2615
<211> LENGTH: 9
<212> TYPE: PRT
<213> ORGANISM: Homo sapiens

<400> SEQUENCE: 2615

```
Ser Leu Gly Pro Gly Ala Glu Gly Leu
1               5
```

<210> SEQ ID NO 2616
<211> LENGTH: 9
<212> TYPE: PRT
<213> ORGANISM: Homo sapiens

<400> SEQUENCE: 2616

```
Leu Gly Pro Gly Ala Glu Gly Leu His
1               5
```

<210> SEQ ID NO 2617
<211> LENGTH: 9
<212> TYPE: PRT
<213> ORGANISM: Homo sapiens

<400> SEQUENCE: 2617

```
Gly Pro Gly Ala Glu Gly Leu His Pro
1               5
```

<210> SEQ ID NO 2618
<211> LENGTH: 9
<212> TYPE: PRT
<213> ORGANISM: Homo sapiens

<400> SEQUENCE: 2618

```
Pro Gly Ala Glu Gly Leu His Pro Phe
1               5
```

<210> SEQ ID NO 2619
<211> LENGTH: 9
<212> TYPE: PRT
<213> ORGANISM: Homo sapiens

<400> SEQUENCE: 2619

```
Gly Ala Glu Gly Leu His Pro Phe Met
1               5
```

<210> SEQ ID NO 2620
<211> LENGTH: 9
<212> TYPE: PRT
<213> ORGANISM: Homo sapiens

<400> SEQUENCE: 2620

```
Ala Glu Gly Leu His Pro Phe Met Glu
1               5
```

<210> SEQ ID NO 2621
<211> LENGTH: 9
<212> TYPE: PRT
<213> ORGANISM: Homo sapiens

<400> SEQUENCE: 2621

Glu Gly Leu His Pro Phe Met Glu Leu
1               5

<210> SEQ ID NO 2622
<211> LENGTH: 9
<212> TYPE: PRT
<213> ORGANISM: Homo sapiens

<400> SEQUENCE: 2622

Gly Leu His Pro Phe Met Glu Leu Arg
1               5

<210> SEQ ID NO 2623
<211> LENGTH: 9
<212> TYPE: PRT
<213> ORGANISM: Homo sapiens

<400> SEQUENCE: 2623

Leu His Pro Phe Met Glu Leu Arg Val
1               5

<210> SEQ ID NO 2624
<211> LENGTH: 9
<212> TYPE: PRT
<213> ORGANISM: Homo sapiens

<400> SEQUENCE: 2624

His Pro Phe Met Glu Leu Arg Val Leu
1               5

<210> SEQ ID NO 2625
<211> LENGTH: 9
<212> TYPE: PRT
<213> ORGANISM: Homo sapiens

<400> SEQUENCE: 2625

Pro Phe Met Glu Leu Arg Val Leu Glu
1               5

<210> SEQ ID NO 2626
<211> LENGTH: 9
<212> TYPE: PRT
<213> ORGANISM: Homo sapiens

<400> SEQUENCE: 2626

Phe Met Glu Leu Arg Val Leu Glu Asn
1               5

<210> SEQ ID NO 2627
<211> LENGTH: 9
<212> TYPE: PRT
<213> ORGANISM: Homo sapiens

<400> SEQUENCE: 2627

Met Glu Leu Arg Val Leu Glu Asn Thr
1               5

<210> SEQ ID NO 2628

<210> SEQ ID NO 2628
<211> LENGTH: 9
<212> TYPE: PRT
<213> ORGANISM: Homo sapiens

<400> SEQUENCE: 2628

Glu Leu Arg Val Leu Glu Asn Thr Lys
1               5

<210> SEQ ID NO 2629
<211> LENGTH: 9
<212> TYPE: PRT
<213> ORGANISM: Homo sapiens

<400> SEQUENCE: 2629

Leu Arg Val Leu Glu Asn Thr Lys Arg
1               5

<210> SEQ ID NO 2630
<211> LENGTH: 9
<212> TYPE: PRT
<213> ORGANISM: Homo sapiens

<400> SEQUENCE: 2630

Arg Val Leu Glu Asn Thr Lys Arg Ser
1               5

<210> SEQ ID NO 2631
<211> LENGTH: 9
<212> TYPE: PRT
<213> ORGANISM: Homo sapiens

<400> SEQUENCE: 2631

Val Leu Glu Asn Thr Lys Arg Ser Arg
1               5

<210> SEQ ID NO 2632
<211> LENGTH: 9
<212> TYPE: PRT
<213> ORGANISM: Homo sapiens

<400> SEQUENCE: 2632

Leu Glu Asn Thr Lys Arg Ser Arg Arg
1               5

<210> SEQ ID NO 2633
<211> LENGTH: 9
<212> TYPE: PRT
<213> ORGANISM: Homo sapiens

<400> SEQUENCE: 2633

Glu Asn Thr Lys Arg Ser Arg Arg Asn
1               5

<210> SEQ ID NO 2634
<211> LENGTH: 9
<212> TYPE: PRT
<213> ORGANISM: Homo sapiens

<400> SEQUENCE: 2634

Asn Thr Lys Arg Ser Arg Arg Asn Leu
1               5

<210> SEQ ID NO 2635
<211> LENGTH: 9
<212> TYPE: PRT

<213> ORGANISM: Homo sapiens

<400> SEQUENCE: 2635

Thr Lys Arg Ser Arg Arg Asn Leu Gly
1               5

<210> SEQ ID NO 2636
<211> LENGTH: 9
<212> TYPE: PRT
<213> ORGANISM: Homo sapiens

<400> SEQUENCE: 2636

Lys Arg Ser Arg Arg Asn Leu Gly Leu
1               5

<210> SEQ ID NO 2637
<211> LENGTH: 9
<212> TYPE: PRT
<213> ORGANISM: Homo sapiens

<400> SEQUENCE: 2637

Arg Ser Arg Arg Asn Leu Gly Leu Asp
1               5

<210> SEQ ID NO 2638
<211> LENGTH: 9
<212> TYPE: PRT
<213> ORGANISM: Homo sapiens

<400> SEQUENCE: 2638

Ser Arg Arg Asn Leu Gly Leu Asp Cys
1               5

<210> SEQ ID NO 2639
<211> LENGTH: 9
<212> TYPE: PRT
<213> ORGANISM: Homo sapiens

<400> SEQUENCE: 2639

Arg Arg Asn Leu Gly Leu Asp Cys Asp
1               5

<210> SEQ ID NO 2640
<211> LENGTH: 9
<212> TYPE: PRT
<213> ORGANISM: Homo sapiens

<400> SEQUENCE: 2640

Arg Asn Leu Gly Leu Asp Cys Asp Glu
1               5

<210> SEQ ID NO 2641
<211> LENGTH: 9
<212> TYPE: PRT
<213> ORGANISM: Homo sapiens

<400> SEQUENCE: 2641

Asn Leu Gly Leu Asp Cys Asp Glu His
1               5

<210> SEQ ID NO 2642
<211> LENGTH: 9
<212> TYPE: PRT
<213> ORGANISM: Homo sapiens

<400> SEQUENCE: 2642

Leu Gly Leu Asp Cys Asp Glu His Ser
1               5

<210> SEQ ID NO 2643
<211> LENGTH: 9
<212> TYPE: PRT
<213> ORGANISM: Homo sapiens

<400> SEQUENCE: 2643

Gly Leu Asp Cys Asp Glu His Ser Ser
1               5

<210> SEQ ID NO 2644
<211> LENGTH: 9
<212> TYPE: PRT
<213> ORGANISM: Homo sapiens

<400> SEQUENCE: 2644

Leu Asp Cys Asp Glu His Ser Ser Glu
1               5

<210> SEQ ID NO 2645
<211> LENGTH: 9
<212> TYPE: PRT
<213> ORGANISM: Homo sapiens

<400> SEQUENCE: 2645

Asp Cys Asp Glu His Ser Ser Glu Ser
1               5

<210> SEQ ID NO 2646
<211> LENGTH: 9
<212> TYPE: PRT
<213> ORGANISM: Homo sapiens

<400> SEQUENCE: 2646

Cys Asp Glu His Ser Ser Glu Ser Arg
1               5

<210> SEQ ID NO 2647
<211> LENGTH: 9
<212> TYPE: PRT
<213> ORGANISM: Homo sapiens

<400> SEQUENCE: 2647

Asp Glu His Ser Ser Glu Ser Arg Cys
1               5

<210> SEQ ID NO 2648
<211> LENGTH: 9
<212> TYPE: PRT
<213> ORGANISM: Homo sapiens

<400> SEQUENCE: 2648

Glu His Ser Ser Glu Ser Arg Cys Cys
1               5

<210> SEQ ID NO 2649
<211> LENGTH: 9
<212> TYPE: PRT
<213> ORGANISM: Homo sapiens

<400> SEQUENCE: 2649

His Ser Ser Glu Ser Arg Cys Cys Arg
1               5

<210> SEQ ID NO 2650
<211> LENGTH: 9
<212> TYPE: PRT
<213> ORGANISM: Homo sapiens

<400> SEQUENCE: 2650

Ser Ser Glu Ser Arg Cys Cys Arg Tyr
1               5

<210> SEQ ID NO 2651
<211> LENGTH: 9
<212> TYPE: PRT
<213> ORGANISM: Homo sapiens

<400> SEQUENCE: 2651

Ser Glu Ser Arg Cys Cys Arg Tyr Pro
1               5

<210> SEQ ID NO 2652
<211> LENGTH: 9
<212> TYPE: PRT
<213> ORGANISM: Homo sapiens

<400> SEQUENCE: 2652

Glu Ser Arg Cys Cys Arg Tyr Pro Leu
1               5

<210> SEQ ID NO 2653
<211> LENGTH: 9
<212> TYPE: PRT
<213> ORGANISM: Homo sapiens

<400> SEQUENCE: 2653

Ser Arg Cys Cys Arg Tyr Pro Leu Thr
1               5

<210> SEQ ID NO 2654
<211> LENGTH: 9
<212> TYPE: PRT
<213> ORGANISM: Homo sapiens

<400> SEQUENCE: 2654

Arg Cys Cys Arg Tyr Pro Leu Thr Val
1               5

<210> SEQ ID NO 2655
<211> LENGTH: 9
<212> TYPE: PRT
<213> ORGANISM: Homo sapiens

<400> SEQUENCE: 2655

Cys Cys Arg Tyr Pro Leu Thr Val Asp
1               5

<210> SEQ ID NO 2656
<211> LENGTH: 9
<212> TYPE: PRT
<213> ORGANISM: Homo sapiens

<400> SEQUENCE: 2656

Cys Arg Tyr Pro Leu Thr Val Asp Phe
1               5

<210> SEQ ID NO 2657
<211> LENGTH: 9
<212> TYPE: PRT
<213> ORGANISM: Homo sapiens

<400> SEQUENCE: 2657

Arg Tyr Pro Leu Thr Val Asp Phe Glu
1               5

<210> SEQ ID NO 2658
<211> LENGTH: 9
<212> TYPE: PRT
<213> ORGANISM: Homo sapiens

<400> SEQUENCE: 2658

Tyr Pro Leu Thr Val Asp Phe Glu Ala
1               5

<210> SEQ ID NO 2659
<211> LENGTH: 9
<212> TYPE: PRT
<213> ORGANISM: Homo sapiens

<400> SEQUENCE: 2659

Pro Leu Thr Val Asp Phe Glu Ala Phe
1               5

<210> SEQ ID NO 2660
<211> LENGTH: 9
<212> TYPE: PRT
<213> ORGANISM: Homo sapiens

<400> SEQUENCE: 2660

Leu Thr Val Asp Phe Glu Ala Phe Gly
1               5

<210> SEQ ID NO 2661
<211> LENGTH: 9
<212> TYPE: PRT
<213> ORGANISM: Homo sapiens

<400> SEQUENCE: 2661

Thr Val Asp Phe Glu Ala Phe Gly Trp
1               5

<210> SEQ ID NO 2662
<211> LENGTH: 9
<212> TYPE: PRT
<213> ORGANISM: Homo sapiens

<400> SEQUENCE: 2662

Val Asp Phe Glu Ala Phe Gly Trp Asp
1               5

<210> SEQ ID NO 2663
<211> LENGTH: 9
<212> TYPE: PRT
<213> ORGANISM: Homo sapiens

<400> SEQUENCE: 2663

Asp Phe Glu Ala Phe Gly Trp Asp Trp
1               5

```
<210> SEQ ID NO 2664
<211> LENGTH: 9
<212> TYPE: PRT
<213> ORGANISM: Homo sapiens

<400> SEQUENCE: 2664

Phe Glu Ala Phe Gly Trp Asp Trp Ile
1               5

<210> SEQ ID NO 2665
<211> LENGTH: 9
<212> TYPE: PRT
<213> ORGANISM: Homo sapiens

<400> SEQUENCE: 2665

Glu Ala Phe Gly Trp Asp Trp Ile Ile
1               5

<210> SEQ ID NO 2666
<211> LENGTH: 9
<212> TYPE: PRT
<213> ORGANISM: Homo sapiens

<400> SEQUENCE: 2666

Ala Phe Gly Trp Asp Trp Ile Ile Ala
1               5

<210> SEQ ID NO 2667
<211> LENGTH: 9
<212> TYPE: PRT
<213> ORGANISM: Homo sapiens

<400> SEQUENCE: 2667

Phe Gly Trp Asp Trp Ile Ile Ala Pro
1               5

<210> SEQ ID NO 2668
<211> LENGTH: 9
<212> TYPE: PRT
<213> ORGANISM: Homo sapiens

<400> SEQUENCE: 2668

Gly Trp Asp Trp Ile Ile Ala Pro Lys
1               5

<210> SEQ ID NO 2669
<211> LENGTH: 9
<212> TYPE: PRT
<213> ORGANISM: Homo sapiens

<400> SEQUENCE: 2669

Trp Asp Trp Ile Ile Ala Pro Lys Arg
1               5

<210> SEQ ID NO 2670
<211> LENGTH: 9
<212> TYPE: PRT
<213> ORGANISM: Homo sapiens

<400> SEQUENCE: 2670

Asp Trp Ile Ile Ala Pro Lys Arg Tyr
1               5

<210> SEQ ID NO 2671
<211> LENGTH: 9
```

```
<212> TYPE: PRT
<213> ORGANISM: Homo sapiens

<400> SEQUENCE: 2671

Trp Ile Ile Ala Pro Lys Arg Tyr Lys
1               5

<210> SEQ ID NO 2672
<211> LENGTH: 9
<212> TYPE: PRT
<213> ORGANISM: Homo sapiens

<400> SEQUENCE: 2672

Ile Ile Ala Pro Lys Arg Tyr Lys Ala
1               5

<210> SEQ ID NO 2673
<211> LENGTH: 9
<212> TYPE: PRT
<213> ORGANISM: Homo sapiens

<400> SEQUENCE: 2673

Ile Ala Pro Lys Arg Tyr Lys Ala Asn
1               5

<210> SEQ ID NO 2674
<211> LENGTH: 9
<212> TYPE: PRT
<213> ORGANISM: Homo sapiens

<400> SEQUENCE: 2674

Ala Pro Lys Arg Tyr Lys Ala Asn Tyr
1               5

<210> SEQ ID NO 2675
<211> LENGTH: 9
<212> TYPE: PRT
<213> ORGANISM: Homo sapiens

<400> SEQUENCE: 2675

Pro Lys Arg Tyr Lys Ala Asn Tyr Cys
1               5

<210> SEQ ID NO 2676
<211> LENGTH: 9
<212> TYPE: PRT
<213> ORGANISM: Homo sapiens

<400> SEQUENCE: 2676

Lys Arg Tyr Lys Ala Asn Tyr Cys Ser
1               5

<210> SEQ ID NO 2677
<211> LENGTH: 9
<212> TYPE: PRT
<213> ORGANISM: Homo sapiens

<400> SEQUENCE: 2677

Arg Tyr Lys Ala Asn Tyr Cys Ser Gly
1               5

<210> SEQ ID NO 2678
<211> LENGTH: 9
<212> TYPE: PRT
<213> ORGANISM: Homo sapiens
```

<400> SEQUENCE: 2678

Tyr Lys Ala Asn Tyr Cys Ser Gly Gln
1               5

<210> SEQ ID NO 2679
<211> LENGTH: 9
<212> TYPE: PRT
<213> ORGANISM: Homo sapiens

<400> SEQUENCE: 2679

Lys Ala Asn Tyr Cys Ser Gly Gln Cys
1               5

<210> SEQ ID NO 2680
<211> LENGTH: 9
<212> TYPE: PRT
<213> ORGANISM: Homo sapiens

<400> SEQUENCE: 2680

Ala Asn Tyr Cys Ser Gly Gln Cys Glu
1               5

<210> SEQ ID NO 2681
<211> LENGTH: 9
<212> TYPE: PRT
<213> ORGANISM: Homo sapiens

<400> SEQUENCE: 2681

Asn Tyr Cys Ser Gly Gln Cys Glu Tyr
1               5

<210> SEQ ID NO 2682
<211> LENGTH: 9
<212> TYPE: PRT
<213> ORGANISM: Homo sapiens

<400> SEQUENCE: 2682

Tyr Cys Ser Gly Gln Cys Glu Tyr Met
1               5

<210> SEQ ID NO 2683
<211> LENGTH: 9
<212> TYPE: PRT
<213> ORGANISM: Homo sapiens

<400> SEQUENCE: 2683

Cys Ser Gly Gln Cys Glu Tyr Met Phe
1               5

<210> SEQ ID NO 2684
<211> LENGTH: 9
<212> TYPE: PRT
<213> ORGANISM: Homo sapiens

<400> SEQUENCE: 2684

Ser Gly Gln Cys Glu Tyr Met Phe Met
1               5

<210> SEQ ID NO 2685
<211> LENGTH: 9
<212> TYPE: PRT
<213> ORGANISM: Homo sapiens

<400> SEQUENCE: 2685

Gly Gln Cys Glu Tyr Met Phe Met Gln
1               5

<210> SEQ ID NO 2686
<211> LENGTH: 9
<212> TYPE: PRT
<213> ORGANISM: Homo sapiens

<400> SEQUENCE: 2686

Gln Cys Glu Tyr Met Phe Met Gln Lys
1               5

<210> SEQ ID NO 2687
<211> LENGTH: 9
<212> TYPE: PRT
<213> ORGANISM: Homo sapiens

<400> SEQUENCE: 2687

Cys Glu Tyr Met Phe Met Gln Lys Tyr
1               5

<210> SEQ ID NO 2688
<211> LENGTH: 9
<212> TYPE: PRT
<213> ORGANISM: Homo sapiens

<400> SEQUENCE: 2688

Glu Tyr Met Phe Met Gln Lys Tyr Pro
1               5

<210> SEQ ID NO 2689
<211> LENGTH: 9
<212> TYPE: PRT
<213> ORGANISM: Homo sapiens

<400> SEQUENCE: 2689

Tyr Met Phe Met Gln Lys Tyr Pro His
1               5

<210> SEQ ID NO 2690
<211> LENGTH: 9
<212> TYPE: PRT
<213> ORGANISM: Homo sapiens

<400> SEQUENCE: 2690

Met Phe Met Gln Lys Tyr Pro His Thr
1               5

<210> SEQ ID NO 2691
<211> LENGTH: 9
<212> TYPE: PRT
<213> ORGANISM: Homo sapiens

<400> SEQUENCE: 2691

Phe Met Gln Lys Tyr Pro His Thr His
1               5

<210> SEQ ID NO 2692
<211> LENGTH: 9
<212> TYPE: PRT
<213> ORGANISM: Homo sapiens

<400> SEQUENCE: 2692

Met Gln Lys Tyr Pro His Thr His Leu 1               5

<210> SEQ ID NO 2693
<211> LENGTH: 9
<212> TYPE: PRT
<213> ORGANISM: Homo sapiens

<400> SEQUENCE: 2693

Gln Lys Tyr Pro His Thr His Leu Val
1               5

<210> SEQ ID NO 2694
<211> LENGTH: 9
<212> TYPE: PRT
<213> ORGANISM: Homo sapiens

<400> SEQUENCE: 2694

Lys Tyr Pro His Thr His Leu Val Gln
1               5

<210> SEQ ID NO 2695
<211> LENGTH: 9
<212> TYPE: PRT
<213> ORGANISM: Homo sapiens

<400> SEQUENCE: 2695

Tyr Pro His Thr His Leu Val Gln Gln
1               5

<210> SEQ ID NO 2696
<211> LENGTH: 9
<212> TYPE: PRT
<213> ORGANISM: Homo sapiens

<400> SEQUENCE: 2696

Pro His Thr His Leu Val Gln Gln Ala
1               5

<210> SEQ ID NO 2697
<211> LENGTH: 9
<212> TYPE: PRT
<213> ORGANISM: Homo sapiens

<400> SEQUENCE: 2697

His Thr His Leu Val Gln Gln Ala Asn
1               5

<210> SEQ ID NO 2698
<211> LENGTH: 9
<212> TYPE: PRT
<213> ORGANISM: Homo sapiens

<400> SEQUENCE: 2698

Thr His Leu Val Gln Gln Ala Asn Pro
1               5

<210> SEQ ID NO 2699
<211> LENGTH: 9
<212> TYPE: PRT
<213> ORGANISM: Homo sapiens

<400> SEQUENCE: 2699

His Leu Val Gln Gln Ala Asn Pro Arg
1               5

<210> SEQ ID NO 2700
<211> LENGTH: 9
<212> TYPE: PRT
<213> ORGANISM: Homo sapiens

<400> SEQUENCE: 2700

Leu Val Gln Gln Ala Asn Pro Arg Gly
1               5

<210> SEQ ID NO 2701
<211> LENGTH: 9
<212> TYPE: PRT
<213> ORGANISM: Homo sapiens

<400> SEQUENCE: 2701

Val Gln Gln Ala Asn Pro Arg Gly Ser
1               5

<210> SEQ ID NO 2702
<211> LENGTH: 9
<212> TYPE: PRT
<213> ORGANISM: Homo sapiens

<400> SEQUENCE: 2702

Gln Gln Ala Asn Pro Arg Gly Ser Ala
1               5

<210> SEQ ID NO 2703
<211> LENGTH: 9
<212> TYPE: PRT
<213> ORGANISM: Homo sapiens

<400> SEQUENCE: 2703

Gln Ala Asn Pro Arg Gly Ser Ala Gly
1               5

<210> SEQ ID NO 2704
<211> LENGTH: 9
<212> TYPE: PRT
<213> ORGANISM: Homo sapiens

<400> SEQUENCE: 2704

Ala Asn Pro Arg Gly Ser Ala Gly Pro
1               5

<210> SEQ ID NO 2705
<211> LENGTH: 9
<212> TYPE: PRT
<213> ORGANISM: Homo sapiens

<400> SEQUENCE: 2705

Asn Pro Arg Gly Ser Ala Gly Pro Cys
1               5

<210> SEQ ID NO 2706
<211> LENGTH: 9
<212> TYPE: PRT
<213> ORGANISM: Homo sapiens

<400> SEQUENCE: 2706

Pro Arg Gly Ser Ala Gly Pro Cys Cys
1               5

<210> SEQ ID NO 2707

<211> LENGTH: 9
<212> TYPE: PRT
<213> ORGANISM: Homo sapiens

<400> SEQUENCE: 2707

Arg Gly Ser Ala Gly Pro Cys Cys Thr
1               5

<210> SEQ ID NO 2708
<211> LENGTH: 9
<212> TYPE: PRT
<213> ORGANISM: Homo sapiens

<400> SEQUENCE: 2708

Gly Ser Ala Gly Pro Cys Cys Thr Pro
1               5

<210> SEQ ID NO 2709
<211> LENGTH: 9
<212> TYPE: PRT
<213> ORGANISM: Homo sapiens

<400> SEQUENCE: 2709

Ser Ala Gly Pro Cys Cys Thr Pro Thr
1               5

<210> SEQ ID NO 2710
<211> LENGTH: 9
<212> TYPE: PRT
<213> ORGANISM: Homo sapiens

<400> SEQUENCE: 2710

Ala Gly Pro Cys Cys Thr Pro Thr Lys
1               5

<210> SEQ ID NO 2711
<211> LENGTH: 9
<212> TYPE: PRT
<213> ORGANISM: Homo sapiens

<400> SEQUENCE: 2711

Gly Pro Cys Cys Thr Pro Thr Lys Met
1               5

<210> SEQ ID NO 2712
<211> LENGTH: 9
<212> TYPE: PRT
<213> ORGANISM: Homo sapiens

<400> SEQUENCE: 2712

Pro Cys Cys Thr Pro Thr Lys Met Ser
1               5

<210> SEQ ID NO 2713
<211> LENGTH: 9
<212> TYPE: PRT
<213> ORGANISM: Homo sapiens

<400> SEQUENCE: 2713

Cys Cys Thr Pro Thr Lys Met Ser Pro
1               5

<210> SEQ ID NO 2714
<211> LENGTH: 9
<212> TYPE: PRT

<213> ORGANISM: Homo sapiens

<400> SEQUENCE: 2714

Cys Thr Pro Thr Lys Met Ser Pro Ile
1               5

<210> SEQ ID NO 2715
<211> LENGTH: 9
<212> TYPE: PRT
<213> ORGANISM: Homo sapiens

<400> SEQUENCE: 2715

Thr Pro Thr Lys Met Ser Pro Ile Asn
1               5

<210> SEQ ID NO 2716
<211> LENGTH: 9
<212> TYPE: PRT
<213> ORGANISM: Homo sapiens

<400> SEQUENCE: 2716

Pro Thr Lys Met Ser Pro Ile Asn Met
1               5

<210> SEQ ID NO 2717
<211> LENGTH: 9
<212> TYPE: PRT
<213> ORGANISM: Homo sapiens

<400> SEQUENCE: 2717

Thr Lys Met Ser Pro Ile Asn Met Leu
1               5

<210> SEQ ID NO 2718
<211> LENGTH: 9
<212> TYPE: PRT
<213> ORGANISM: Homo sapiens

<400> SEQUENCE: 2718

Lys Met Ser Pro Ile Asn Met Leu Tyr
1               5

<210> SEQ ID NO 2719
<211> LENGTH: 9
<212> TYPE: PRT
<213> ORGANISM: Homo sapiens

<400> SEQUENCE: 2719

Met Ser Pro Ile Asn Met Leu Tyr Phe
1               5

<210> SEQ ID NO 2720
<211> LENGTH: 9
<212> TYPE: PRT
<213> ORGANISM: Homo sapiens

<400> SEQUENCE: 2720

Ser Pro Ile Asn Met Leu Tyr Phe Asn
1               5

<210> SEQ ID NO 2721
<211> LENGTH: 9
<212> TYPE: PRT
<213> ORGANISM: Homo sapiens

<400> SEQUENCE: 2721

Pro Ile Asn Met Leu Tyr Phe Asn Asp
1               5

<210> SEQ ID NO 2722
<211> LENGTH: 9
<212> TYPE: PRT
<213> ORGANISM: Homo sapiens

<400> SEQUENCE: 2722

Ile Asn Met Leu Tyr Phe Asn Asp Lys
1               5

<210> SEQ ID NO 2723
<211> LENGTH: 9
<212> TYPE: PRT
<213> ORGANISM: Homo sapiens

<400> SEQUENCE: 2723

Asn Met Leu Tyr Phe Asn Asp Lys Gln
1               5

<210> SEQ ID NO 2724
<211> LENGTH: 9
<212> TYPE: PRT
<213> ORGANISM: Homo sapiens

<400> SEQUENCE: 2724

Met Leu Tyr Phe Asn Asp Lys Gln Gln
1               5

<210> SEQ ID NO 2725
<211> LENGTH: 9
<212> TYPE: PRT
<213> ORGANISM: Homo sapiens

<400> SEQUENCE: 2725

Leu Tyr Phe Asn Asp Lys Gln Gln Ile
1               5

<210> SEQ ID NO 2726
<211> LENGTH: 9
<212> TYPE: PRT
<213> ORGANISM: Homo sapiens

<400> SEQUENCE: 2726

Tyr Phe Asn Asp Lys Gln Gln Ile Ile
1               5

<210> SEQ ID NO 2727
<211> LENGTH: 9
<212> TYPE: PRT
<213> ORGANISM: Homo sapiens

<400> SEQUENCE: 2727

Phe Asn Asp Lys Gln Gln Ile Ile Tyr
1               5

<210> SEQ ID NO 2728
<211> LENGTH: 9
<212> TYPE: PRT
<213> ORGANISM: Homo sapiens

<400> SEQUENCE: 2728

Asn Asp Lys Gln Gln Ile Ile Tyr Gly
1               5

<210> SEQ ID NO 2729
<211> LENGTH: 9
<212> TYPE: PRT
<213> ORGANISM: Homo sapiens

<400> SEQUENCE: 2729

Asp Lys Gln Gln Ile Ile Tyr Gly Lys
1               5

<210> SEQ ID NO 2730
<211> LENGTH: 9
<212> TYPE: PRT
<213> ORGANISM: Homo sapiens

<400> SEQUENCE: 2730

Lys Gln Gln Ile Ile Tyr Gly Lys Ile
1               5

<210> SEQ ID NO 2731
<211> LENGTH: 9
<212> TYPE: PRT
<213> ORGANISM: Homo sapiens

<400> SEQUENCE: 2731

Gln Gln Ile Ile Tyr Gly Lys Ile Pro
1               5

<210> SEQ ID NO 2732
<211> LENGTH: 9
<212> TYPE: PRT
<213> ORGANISM: Homo sapiens

<400> SEQUENCE: 2732

Gln Ile Ile Tyr Gly Lys Ile Pro Gly
1               5

<210> SEQ ID NO 2733
<211> LENGTH: 9
<212> TYPE: PRT
<213> ORGANISM: Homo sapiens

<400> SEQUENCE: 2733

Ile Ile Tyr Gly Lys Ile Pro Gly Met
1               5

<210> SEQ ID NO 2734
<211> LENGTH: 9
<212> TYPE: PRT
<213> ORGANISM: Homo sapiens

<400> SEQUENCE: 2734

Ile Tyr Gly Lys Ile Pro Gly Met Val
1               5

<210> SEQ ID NO 2735
<211> LENGTH: 9
<212> TYPE: PRT
<213> ORGANISM: Homo sapiens

<400> SEQUENCE: 2735

Tyr Gly Lys Ile Pro Gly Met Val Val
1               5

<210> SEQ ID NO 2736
<211> LENGTH: 9
<212> TYPE: PRT
<213> ORGANISM: Homo sapiens

<400> SEQUENCE: 2736

Gly Lys Ile Pro Gly Met Val Val Asp
1               5

<210> SEQ ID NO 2737
<211> LENGTH: 9
<212> TYPE: PRT
<213> ORGANISM: Homo sapiens

<400> SEQUENCE: 2737

Lys Ile Pro Gly Met Val Val Asp Arg
1               5

<210> SEQ ID NO 2738
<211> LENGTH: 9
<212> TYPE: PRT
<213> ORGANISM: Homo sapiens

<400> SEQUENCE: 2738

Ile Pro Gly Met Val Val Asp Arg Cys
1               5

<210> SEQ ID NO 2739
<211> LENGTH: 9
<212> TYPE: PRT
<213> ORGANISM: Homo sapiens

<400> SEQUENCE: 2739

Pro Gly Met Val Val Asp Arg Cys Gly
1               5

<210> SEQ ID NO 2740
<211> LENGTH: 9
<212> TYPE: PRT
<213> ORGANISM: Homo sapiens

<400> SEQUENCE: 2740

Gly Met Val Val Asp Arg Cys Gly Cys
1               5

<210> SEQ ID NO 2741
<211> LENGTH: 9
<212> TYPE: PRT
<213> ORGANISM: Homo sapiens

<400> SEQUENCE: 2741

Met Val Val Asp Arg Cys Gly Cys Ser
1               5

<210> SEQ ID NO 2742
<211> LENGTH: 10
<212> TYPE: PRT
<213> ORGANISM: Homo sapiens

<400> SEQUENCE: 2742

Met Val Leu Ala Ala Pro Leu Leu Leu Gly
1               5                   10

<210> SEQ ID NO 2743
<211> LENGTH: 10
<212> TYPE: PRT
<213> ORGANISM: Homo sapiens

<400> SEQUENCE: 2743

Val Leu Ala Ala Pro Leu Leu Leu Gly Phe
1               5                   10

<210> SEQ ID NO 2744
<211> LENGTH: 10
<212> TYPE: PRT
<213> ORGANISM: Homo sapiens

<400> SEQUENCE: 2744

Leu Ala Ala Pro Leu Leu Leu Gly Phe Leu
1               5                   10

<210> SEQ ID NO 2745
<211> LENGTH: 10
<212> TYPE: PRT
<213> ORGANISM: Homo sapiens

<400> SEQUENCE: 2745

Ala Ala Pro Leu Leu Leu Gly Phe Leu Leu
1               5                   10

<210> SEQ ID NO 2746
<211> LENGTH: 10
<212> TYPE: PRT
<213> ORGANISM: Homo sapiens

<400> SEQUENCE: 2746

Ala Pro Leu Leu Leu Gly Phe Leu Leu Leu
1               5                   10

<210> SEQ ID NO 2747
<211> LENGTH: 10
<212> TYPE: PRT
<213> ORGANISM: Homo sapiens

<400> SEQUENCE: 2747

Pro Leu Leu Leu Gly Phe Leu Leu Leu Ala
1               5                   10

<210> SEQ ID NO 2748
<211> LENGTH: 10
<212> TYPE: PRT
<213> ORGANISM: Homo sapiens

<400> SEQUENCE: 2748

Leu Leu Leu Gly Phe Leu Leu Leu Ala Leu
1               5                   10

<210> SEQ ID NO 2749
<211> LENGTH: 10
<212> TYPE: PRT
<213> ORGANISM: Homo sapiens

<400> SEQUENCE: 2749

Leu Leu Gly Phe Leu Leu Leu Ala Leu Glu
1               5                   10

<210> SEQ ID NO 2750
<211> LENGTH: 10

-continued

<212> TYPE: PRT
<213> ORGANISM: Homo sapiens

<400> SEQUENCE: 2750

Leu Gly Phe Leu Leu Ala Leu Glu Leu
1               5                   10

<210> SEQ ID NO 2751
<211> LENGTH: 10
<212> TYPE: PRT
<213> ORGANISM: Homo sapiens

<400> SEQUENCE: 2751

Gly Phe Leu Leu Leu Ala Leu Glu Leu Arg
1               5                   10

<210> SEQ ID NO 2752
<211> LENGTH: 10
<212> TYPE: PRT
<213> ORGANISM: Homo sapiens

<400> SEQUENCE: 2752

Phe Leu Leu Leu Ala Leu Glu Leu Arg Pro
1               5                   10

<210> SEQ ID NO 2753
<211> LENGTH: 10
<212> TYPE: PRT
<213> ORGANISM: Homo sapiens

<400> SEQUENCE: 2753

Leu Leu Leu Ala Leu Glu Leu Arg Pro Arg
1               5                   10

<210> SEQ ID NO 2754
<211> LENGTH: 10
<212> TYPE: PRT
<213> ORGANISM: Homo sapiens

<400> SEQUENCE: 2754

Leu Leu Ala Leu Glu Leu Arg Pro Arg Gly
1               5                   10

<210> SEQ ID NO 2755
<211> LENGTH: 10
<212> TYPE: PRT
<213> ORGANISM: Homo sapiens

<400> SEQUENCE: 2755

Leu Ala Leu Glu Leu Arg Pro Arg Gly Glu
1               5                   10

<210> SEQ ID NO 2756
<211> LENGTH: 10
<212> TYPE: PRT
<213> ORGANISM: Homo sapiens

<400> SEQUENCE: 2756

Ala Leu Glu Leu Arg Pro Arg Gly Glu Ala
1               5                   10

<210> SEQ ID NO 2757
<211> LENGTH: 10
<212> TYPE: PRT
<213> ORGANISM: Homo sapiens

<400> SEQUENCE: 2757

Leu Glu Leu Arg Pro Arg Gly Glu Ala Ala
1               5                   10

<210> SEQ ID NO 2758
<211> LENGTH: 10
<212> TYPE: PRT
<213> ORGANISM: Homo sapiens

<400> SEQUENCE: 2758

Glu Leu Arg Pro Arg Gly Glu Ala Ala Glu
1               5                   10

<210> SEQ ID NO 2759
<211> LENGTH: 10
<212> TYPE: PRT
<213> ORGANISM: Homo sapiens

<400> SEQUENCE: 2759

Leu Arg Pro Arg Gly Glu Ala Ala Glu Gly
1               5                   10

<210> SEQ ID NO 2760
<211> LENGTH: 10
<212> TYPE: PRT
<213> ORGANISM: Homo sapiens

<400> SEQUENCE: 2760

Arg Pro Arg Gly Glu Ala Ala Glu Gly Pro
1               5                   10

<210> SEQ ID NO 2761
<211> LENGTH: 10
<212> TYPE: PRT
<213> ORGANISM: Homo sapiens

<400> SEQUENCE: 2761

Pro Arg Gly Glu Ala Ala Glu Gly Pro Ala
1               5                   10

<210> SEQ ID NO 2762
<211> LENGTH: 10
<212> TYPE: PRT
<213> ORGANISM: Homo sapiens

<400> SEQUENCE: 2762

Arg Gly Glu Ala Ala Glu Gly Pro Ala Ala
1               5                   10

<210> SEQ ID NO 2763
<211> LENGTH: 10
<212> TYPE: PRT
<213> ORGANISM: Homo sapiens

<400> SEQUENCE: 2763

Gly Glu Ala Ala Glu Gly Pro Ala Ala Ala
1               5                   10

<210> SEQ ID NO 2764
<211> LENGTH: 10
<212> TYPE: PRT
<213> ORGANISM: Homo sapiens

<400> SEQUENCE: 2764

Glu Ala Ala Glu Gly Pro Ala Ala Ala Ala
1               5                   10

<210> SEQ ID NO 2765
<211> LENGTH: 10
<212> TYPE: PRT
<213> ORGANISM: Homo sapiens

<400> SEQUENCE: 2765

Ala Ala Glu Gly Pro Ala Ala Ala Ala Ala
1               5                   10

<210> SEQ ID NO 2766
<211> LENGTH: 10
<212> TYPE: PRT
<213> ORGANISM: Homo sapiens

<400> SEQUENCE: 2766

Ala Glu Gly Pro Ala Ala Ala Ala Ala Ala
1               5                   10

<210> SEQ ID NO 2767
<211> LENGTH: 10
<212> TYPE: PRT
<213> ORGANISM: Homo sapiens

<400> SEQUENCE: 2767

Glu Gly Pro Ala Ala Ala Ala Ala Ala Ala
1               5                   10

<210> SEQ ID NO 2768
<211> LENGTH: 10
<212> TYPE: PRT
<213> ORGANISM: Homo sapiens

<400> SEQUENCE: 2768

Gly Pro Ala Ala Ala Ala Ala Ala Ala Ala
1               5                   10

<210> SEQ ID NO 2769
<211> LENGTH: 10
<212> TYPE: PRT
<213> ORGANISM: Homo sapiens

<400> SEQUENCE: 2769

Pro Ala Ala Ala Ala Ala Ala Ala Ala Ala
1               5                   10

<210> SEQ ID NO 2770
<211> LENGTH: 10
<212> TYPE: PRT
<213> ORGANISM: Homo sapiens

<400> SEQUENCE: 2770

Ala Ala Ala Ala Ala Ala Ala Ala Ala Ala
1               5                   10

<210> SEQ ID NO 2771
<211> LENGTH: 10
<212> TYPE: PRT
<213> ORGANISM: Homo sapiens

<400> SEQUENCE: 2771

Ala Ala Ala Ala Ala Ala Ala Ala Ala Gly

<210> SEQ ID NO 2772
<211> LENGTH: 10
<212> TYPE: PRT
<213> ORGANISM: Homo sapiens

<400> SEQUENCE: 2772

Ala Ala Ala Ala Ala Ala Ala Ala Gly Val
1               5                   10

<210> SEQ ID NO 2773
<211> LENGTH: 10
<212> TYPE: PRT
<213> ORGANISM: Homo sapiens

<400> SEQUENCE: 2773

Ala Ala Ala Ala Ala Ala Ala Gly Val Gly
1               5                   10

<210> SEQ ID NO 2774
<211> LENGTH: 10
<212> TYPE: PRT
<213> ORGANISM: Homo sapiens

<400> SEQUENCE: 2774

Ala Ala Ala Ala Ala Ala Gly Val Gly Gly
1               5                   10

<210> SEQ ID NO 2775
<211> LENGTH: 10
<212> TYPE: PRT
<213> ORGANISM: Homo sapiens

<400> SEQUENCE: 2775

Ala Ala Ala Ala Ala Gly Val Gly Gly Glu
1               5                   10

<210> SEQ ID NO 2776
<211> LENGTH: 10
<212> TYPE: PRT
<213> ORGANISM: Homo sapiens

<400> SEQUENCE: 2776

Ala Ala Ala Ala Gly Val Gly Gly Glu Arg
1               5                   10

<210> SEQ ID NO 2777
<211> LENGTH: 10
<212> TYPE: PRT
<213> ORGANISM: Homo sapiens

<400> SEQUENCE: 2777

Ala Ala Ala Gly Val Gly Gly Glu Arg Ser
1               5                   10

<210> SEQ ID NO 2778
<211> LENGTH: 10
<212> TYPE: PRT
<213> ORGANISM: Homo sapiens

<400> SEQUENCE: 2778

Ala Ala Gly Val Gly Gly Glu Arg Ser Ser
1               5                   10

<210> SEQ ID NO 2779
<211> LENGTH: 10
<212> TYPE: PRT
<213> ORGANISM: Homo sapiens

<400> SEQUENCE: 2779

Ala Gly Val Gly Gly Glu Arg Ser Ser Arg
1               5                   10

<210> SEQ ID NO 2780
<211> LENGTH: 10
<212> TYPE: PRT
<213> ORGANISM: Homo sapiens

<400> SEQUENCE: 2780

Gly Val Gly Gly Glu Arg Ser Ser Arg Pro
1               5                   10

<210> SEQ ID NO 2781
<211> LENGTH: 10
<212> TYPE: PRT
<213> ORGANISM: Homo sapiens

<400> SEQUENCE: 2781

Val Gly Gly Glu Arg Ser Ser Arg Pro Ala
1               5                   10

<210> SEQ ID NO 2782
<211> LENGTH: 10
<212> TYPE: PRT
<213> ORGANISM: Homo sapiens

<400> SEQUENCE: 2782

Gly Gly Glu Arg Ser Ser Arg Pro Ala Pro
1               5                   10

<210> SEQ ID NO 2783
<211> LENGTH: 10
<212> TYPE: PRT
<213> ORGANISM: Homo sapiens

<400> SEQUENCE: 2783

Gly Glu Arg Ser Ser Arg Pro Ala Pro Ser
1               5                   10

<210> SEQ ID NO 2784
<211> LENGTH: 10
<212> TYPE: PRT
<213> ORGANISM: Homo sapiens

<400> SEQUENCE: 2784

Glu Arg Ser Ser Arg Pro Ala Pro Ser Val
1               5                   10

<210> SEQ ID NO 2785
<211> LENGTH: 10
<212> TYPE: PRT
<213> ORGANISM: Homo sapiens

<400> SEQUENCE: 2785

Arg Ser Ser Arg Pro Ala Pro Ser Val Ala
1               5                   10

<210> SEQ ID NO 2786

```
<211> LENGTH: 10
<212> TYPE: PRT
<213> ORGANISM: Homo sapiens

<400> SEQUENCE: 2786

Ser Ser Arg Pro Ala Pro Ser Val Ala Pro
1               5                   10

<210> SEQ ID NO 2787
<211> LENGTH: 10
<212> TYPE: PRT
<213> ORGANISM: Homo sapiens

<400> SEQUENCE: 2787

Ser Arg Pro Ala Pro Ser Val Ala Pro Glu
1               5                   10

<210> SEQ ID NO 2788
<211> LENGTH: 10
<212> TYPE: PRT
<213> ORGANISM: Homo sapiens

<400> SEQUENCE: 2788

Arg Pro Ala Pro Ser Val Ala Pro Glu Pro
1               5                   10

<210> SEQ ID NO 2789
<211> LENGTH: 10
<212> TYPE: PRT
<213> ORGANISM: Homo sapiens

<400> SEQUENCE: 2789

Pro Ala Pro Ser Val Ala Pro Glu Pro Asp
1               5                   10

<210> SEQ ID NO 2790
<211> LENGTH: 10
<212> TYPE: PRT
<213> ORGANISM: Homo sapiens

<400> SEQUENCE: 2790

Ala Pro Ser Val Ala Pro Glu Pro Asp Gly
1               5                   10

<210> SEQ ID NO 2791
<211> LENGTH: 10
<212> TYPE: PRT
<213> ORGANISM: Homo sapiens

<400> SEQUENCE: 2791

Pro Ser Val Ala Pro Glu Pro Asp Gly Cys
1               5                   10

<210> SEQ ID NO 2792
<211> LENGTH: 10
<212> TYPE: PRT
<213> ORGANISM: Homo sapiens

<400> SEQUENCE: 2792

Ser Val Ala Pro Glu Pro Asp Gly Cys Pro
1               5                   10

<210> SEQ ID NO 2793
<211> LENGTH: 10
<212> TYPE: PRT
```

```
<213> ORGANISM: Homo sapiens

<400> SEQUENCE: 2793

Val Ala Pro Glu Pro Asp Gly Cys Pro Val
1               5                   10

<210> SEQ ID NO 2794
<211> LENGTH: 10
<212> TYPE: PRT
<213> ORGANISM: Homo sapiens

<400> SEQUENCE: 2794

Ala Pro Glu Pro Asp Gly Cys Pro Val Cys
1               5                   10

<210> SEQ ID NO 2795
<211> LENGTH: 10
<212> TYPE: PRT
<213> ORGANISM: Homo sapiens

<400> SEQUENCE: 2795

Pro Glu Pro Asp Gly Cys Pro Val Cys Val
1               5                   10

<210> SEQ ID NO 2796
<211> LENGTH: 10
<212> TYPE: PRT
<213> ORGANISM: Homo sapiens

<400> SEQUENCE: 2796

Glu Pro Asp Gly Cys Pro Val Cys Val Trp
1               5                   10

<210> SEQ ID NO 2797
<211> LENGTH: 10
<212> TYPE: PRT
<213> ORGANISM: Homo sapiens

<400> SEQUENCE: 2797

Pro Asp Gly Cys Pro Val Cys Val Trp Arg
1               5                   10

<210> SEQ ID NO 2798
<211> LENGTH: 10
<212> TYPE: PRT
<213> ORGANISM: Homo sapiens

<400> SEQUENCE: 2798

Asp Gly Cys Pro Val Cys Val Trp Arg Gln
1               5                   10

<210> SEQ ID NO 2799
<211> LENGTH: 10
<212> TYPE: PRT
<213> ORGANISM: Homo sapiens

<400> SEQUENCE: 2799

Gly Cys Pro Val Cys Val Trp Arg Gln His
1               5                   10

<210> SEQ ID NO 2800
<211> LENGTH: 10
<212> TYPE: PRT
<213> ORGANISM: Homo sapiens
```

```
<400> SEQUENCE: 2800

Cys Pro Val Cys Val Trp Arg Gln His Ser
1               5                   10

<210> SEQ ID NO 2801
<211> LENGTH: 10
<212> TYPE: PRT
<213> ORGANISM: Homo sapiens

<400> SEQUENCE: 2801

Pro Val Cys Val Trp Arg Gln His Ser Arg
1               5                   10

<210> SEQ ID NO 2802
<211> LENGTH: 10
<212> TYPE: PRT
<213> ORGANISM: Homo sapiens

<400> SEQUENCE: 2802

Val Cys Val Trp Arg Gln His Ser Arg Glu
1               5                   10

<210> SEQ ID NO 2803
<211> LENGTH: 10
<212> TYPE: PRT
<213> ORGANISM: Homo sapiens

<400> SEQUENCE: 2803

Cys Val Trp Arg Gln His Ser Arg Glu Leu
1               5                   10

<210> SEQ ID NO 2804
<211> LENGTH: 10
<212> TYPE: PRT
<213> ORGANISM: Homo sapiens

<400> SEQUENCE: 2804

Val Trp Arg Gln His Ser Arg Glu Leu Arg
1               5                   10

<210> SEQ ID NO 2805
<211> LENGTH: 10
<212> TYPE: PRT
<213> ORGANISM: Homo sapiens

<400> SEQUENCE: 2805

Trp Arg Gln His Ser Arg Glu Leu Arg Leu
1               5                   10

<210> SEQ ID NO 2806
<211> LENGTH: 10
<212> TYPE: PRT
<213> ORGANISM: Homo sapiens

<400> SEQUENCE: 2806

Arg Gln His Ser Arg Glu Leu Arg Leu Glu
1               5                   10

<210> SEQ ID NO 2807
<211> LENGTH: 10
<212> TYPE: PRT
<213> ORGANISM: Homo sapiens

<400> SEQUENCE: 2807
```

Gln His Ser Arg Glu Leu Arg Leu Glu Ser
1               5                   10

<210> SEQ ID NO 2808
<211> LENGTH: 10
<212> TYPE: PRT
<213> ORGANISM: Homo sapiens

<400> SEQUENCE: 2808

His Ser Arg Glu Leu Arg Leu Glu Ser Ile
1               5                   10

<210> SEQ ID NO 2809
<211> LENGTH: 10
<212> TYPE: PRT
<213> ORGANISM: Homo sapiens

<400> SEQUENCE: 2809

Ser Arg Glu Leu Arg Leu Glu Ser Ile Lys
1               5                   10

<210> SEQ ID NO 2810
<211> LENGTH: 10
<212> TYPE: PRT
<213> ORGANISM: Homo sapiens

<400> SEQUENCE: 2810

Arg Glu Leu Arg Leu Glu Ser Ile Lys Ser
1               5                   10

<210> SEQ ID NO 2811
<211> LENGTH: 10
<212> TYPE: PRT
<213> ORGANISM: Homo sapiens

<400> SEQUENCE: 2811

Glu Leu Arg Leu Glu Ser Ile Lys Ser Gln
1               5                   10

<210> SEQ ID NO 2812
<211> LENGTH: 10
<212> TYPE: PRT
<213> ORGANISM: Homo sapiens

<400> SEQUENCE: 2812

Leu Arg Leu Glu Ser Ile Lys Ser Gln Ile
1               5                   10

<210> SEQ ID NO 2813
<211> LENGTH: 10
<212> TYPE: PRT
<213> ORGANISM: Homo sapiens

<400> SEQUENCE: 2813

Arg Leu Glu Ser Ile Lys Ser Gln Ile Leu
1               5                   10

<210> SEQ ID NO 2814
<211> LENGTH: 10
<212> TYPE: PRT
<213> ORGANISM: Homo sapiens

<400> SEQUENCE: 2814

Leu Glu Ser Ile Lys Ser Gln Ile Leu Ser
1               5                   10

<210> SEQ ID NO 2815
<211> LENGTH: 10
<212> TYPE: PRT
<213> ORGANISM: Homo sapiens

<400> SEQUENCE: 2815

Glu Ser Ile Lys Ser Gln Ile Leu Ser Lys
1               5                   10

<210> SEQ ID NO 2816
<211> LENGTH: 10
<212> TYPE: PRT
<213> ORGANISM: Homo sapiens

<400> SEQUENCE: 2816

Ser Ile Lys Ser Gln Ile Leu Ser Lys Leu
1               5                   10

<210> SEQ ID NO 2817
<211> LENGTH: 10
<212> TYPE: PRT
<213> ORGANISM: Homo sapiens

<400> SEQUENCE: 2817

Ile Lys Ser Gln Ile Leu Ser Lys Leu Arg
1               5                   10

<210> SEQ ID NO 2818
<211> LENGTH: 10
<212> TYPE: PRT
<213> ORGANISM: Homo sapiens

<400> SEQUENCE: 2818

Lys Ser Gln Ile Leu Ser Lys Leu Arg Leu
1               5                   10

<210> SEQ ID NO 2819
<211> LENGTH: 10
<212> TYPE: PRT
<213> ORGANISM: Homo sapiens

<400> SEQUENCE: 2819

Ser Gln Ile Leu Ser Lys Leu Arg Leu Lys
1               5                   10

<210> SEQ ID NO 2820
<211> LENGTH: 10
<212> TYPE: PRT
<213> ORGANISM: Homo sapiens

<400> SEQUENCE: 2820

Gln Ile Leu Ser Lys Leu Arg Leu Lys Glu
1               5                   10

<210> SEQ ID NO 2821
<211> LENGTH: 10
<212> TYPE: PRT
<213> ORGANISM: Homo sapiens

<400> SEQUENCE: 2821

Ile Leu Ser Lys Leu Arg Leu Lys Glu Ala
1               5                   10

```
<210> SEQ ID NO 2822
<211> LENGTH: 10
<212> TYPE: PRT
<213> ORGANISM: Homo sapiens

<400> SEQUENCE: 2822

Leu Ser Lys Leu Arg Leu Lys Glu Ala Pro
1               5                   10

<210> SEQ ID NO 2823
<211> LENGTH: 10
<212> TYPE: PRT
<213> ORGANISM: Homo sapiens

<400> SEQUENCE: 2823

Ser Lys Leu Arg Leu Lys Glu Ala Pro Asn
1               5                   10

<210> SEQ ID NO 2824
<211> LENGTH: 10
<212> TYPE: PRT
<213> ORGANISM: Homo sapiens

<400> SEQUENCE: 2824

Lys Leu Arg Leu Lys Glu Ala Pro Asn Ile
1               5                   10

<210> SEQ ID NO 2825
<211> LENGTH: 10
<212> TYPE: PRT
<213> ORGANISM: Homo sapiens

<400> SEQUENCE: 2825

Leu Arg Leu Lys Glu Ala Pro Asn Ile Ser
1               5                   10

<210> SEQ ID NO 2826
<211> LENGTH: 10
<212> TYPE: PRT
<213> ORGANISM: Homo sapiens

<400> SEQUENCE: 2826

Arg Leu Lys Glu Ala Pro Asn Ile Ser Arg
1               5                   10

<210> SEQ ID NO 2827
<211> LENGTH: 10
<212> TYPE: PRT
<213> ORGANISM: Homo sapiens

<400> SEQUENCE: 2827

Leu Lys Glu Ala Pro Asn Ile Ser Arg Glu
1               5                   10

<210> SEQ ID NO 2828
<211> LENGTH: 10
<212> TYPE: PRT
<213> ORGANISM: Homo sapiens

<400> SEQUENCE: 2828

Lys Glu Ala Pro Asn Ile Ser Arg Glu Val
1               5                   10

<210> SEQ ID NO 2829
<211> LENGTH: 10
```

<212> TYPE: PRT
<213> ORGANISM: Homo sapiens

<400> SEQUENCE: 2829

Glu Ala Pro Asn Ile Ser Arg Glu Val Val
1               5                   10

<210> SEQ ID NO 2830
<211> LENGTH: 10
<212> TYPE: PRT
<213> ORGANISM: Homo sapiens

<400> SEQUENCE: 2830

Ala Pro Asn Ile Ser Arg Glu Val Val Lys
1               5                   10

<210> SEQ ID NO 2831
<211> LENGTH: 10
<212> TYPE: PRT
<213> ORGANISM: Homo sapiens

<400> SEQUENCE: 2831

Pro Asn Ile Ser Arg Glu Val Val Lys Gln
1               5                   10

<210> SEQ ID NO 2832
<211> LENGTH: 10
<212> TYPE: PRT
<213> ORGANISM: Homo sapiens

<400> SEQUENCE: 2832

Asn Ile Ser Arg Glu Val Val Lys Gln Leu
1               5                   10

<210> SEQ ID NO 2833
<211> LENGTH: 10
<212> TYPE: PRT
<213> ORGANISM: Homo sapiens

<400> SEQUENCE: 2833

Ile Ser Arg Glu Val Val Lys Gln Leu Leu
1               5                   10

<210> SEQ ID NO 2834
<211> LENGTH: 10
<212> TYPE: PRT
<213> ORGANISM: Homo sapiens

<400> SEQUENCE: 2834

Ser Arg Glu Val Val Lys Gln Leu Leu Pro
1               5                   10

<210> SEQ ID NO 2835
<211> LENGTH: 10
<212> TYPE: PRT
<213> ORGANISM: Homo sapiens

<400> SEQUENCE: 2835

Arg Glu Val Val Lys Gln Leu Leu Pro Lys
1               5                   10

<210> SEQ ID NO 2836
<211> LENGTH: 10
<212> TYPE: PRT
<213> ORGANISM: Homo sapiens

<400> SEQUENCE: 2836

Glu Val Val Lys Gln Leu Leu Pro Lys Ala
1               5                   10

<210> SEQ ID NO 2837
<211> LENGTH: 10
<212> TYPE: PRT
<213> ORGANISM: Homo sapiens

<400> SEQUENCE: 2837

Val Val Lys Gln Leu Leu Pro Lys Ala Pro
1               5                   10

<210> SEQ ID NO 2838
<211> LENGTH: 10
<212> TYPE: PRT
<213> ORGANISM: Homo sapiens

<400> SEQUENCE: 2838

Val Lys Gln Leu Leu Pro Lys Ala Pro Pro
1               5                   10

<210> SEQ ID NO 2839
<211> LENGTH: 10
<212> TYPE: PRT
<213> ORGANISM: Homo sapiens

<400> SEQUENCE: 2839

Lys Gln Leu Leu Pro Lys Ala Pro Pro Leu
1               5                   10

<210> SEQ ID NO 2840
<211> LENGTH: 10
<212> TYPE: PRT
<213> ORGANISM: Homo sapiens

<400> SEQUENCE: 2840

Gln Leu Leu Pro Lys Ala Pro Pro Leu Gln
1               5                   10

<210> SEQ ID NO 2841
<211> LENGTH: 10
<212> TYPE: PRT
<213> ORGANISM: Homo sapiens

<400> SEQUENCE: 2841

Leu Leu Pro Lys Ala Pro Pro Leu Gln Gln
1               5                   10

<210> SEQ ID NO 2842
<211> LENGTH: 10
<212> TYPE: PRT
<213> ORGANISM: Homo sapiens

<400> SEQUENCE: 2842

Leu Pro Lys Ala Pro Pro Leu Gln Gln Ile
1               5                   10

<210> SEQ ID NO 2843
<211> LENGTH: 10
<212> TYPE: PRT
<213> ORGANISM: Homo sapiens

<400> SEQUENCE: 2843

Pro Lys Ala Pro Pro Leu Gln Gln Ile Leu
1               5                   10

<210> SEQ ID NO 2844
<211> LENGTH: 10
<212> TYPE: PRT
<213> ORGANISM: Homo sapiens

<400> SEQUENCE: 2844

Lys Ala Pro Pro Leu Gln Gln Ile Leu Asp
1               5                   10

<210> SEQ ID NO 2845
<211> LENGTH: 10
<212> TYPE: PRT
<213> ORGANISM: Homo sapiens

<400> SEQUENCE: 2845

Ala Pro Pro Leu Gln Gln Ile Leu Asp Leu
1               5                   10

<210> SEQ ID NO 2846
<211> LENGTH: 10
<212> TYPE: PRT
<213> ORGANISM: Homo sapiens

<400> SEQUENCE: 2846

Pro Pro Leu Gln Gln Ile Leu Asp Leu His
1               5                   10

<210> SEQ ID NO 2847
<211> LENGTH: 10
<212> TYPE: PRT
<213> ORGANISM: Homo sapiens

<400> SEQUENCE: 2847

Pro Leu Gln Gln Ile Leu Asp Leu His Asp
1               5                   10

<210> SEQ ID NO 2848
<211> LENGTH: 10
<212> TYPE: PRT
<213> ORGANISM: Homo sapiens

<400> SEQUENCE: 2848

Leu Gln Gln Ile Leu Asp Leu His Asp Phe
1               5                   10

<210> SEQ ID NO 2849
<211> LENGTH: 10
<212> TYPE: PRT
<213> ORGANISM: Homo sapiens

<400> SEQUENCE: 2849

Gln Gln Ile Leu Asp Leu His Asp Phe Gln
1               5                   10

<210> SEQ ID NO 2850
<211> LENGTH: 10
<212> TYPE: PRT
<213> ORGANISM: Homo sapiens

<400> SEQUENCE: 2850

Gln Ile Leu Asp Leu His Asp Phe Gln Gly

```
                         1               5                   10

<210> SEQ ID NO 2851
<211> LENGTH: 10
<212> TYPE: PRT
<213> ORGANISM: Homo sapiens

<400> SEQUENCE: 2851

Ile Leu Asp Leu His Asp Phe Gln Gly Asp
1               5                   10

<210> SEQ ID NO 2852
<211> LENGTH: 10
<212> TYPE: PRT
<213> ORGANISM: Homo sapiens

<400> SEQUENCE: 2852

Leu Asp Leu His Asp Phe Gln Gly Asp Ala
1               5                   10

<210> SEQ ID NO 2853
<211> LENGTH: 10
<212> TYPE: PRT
<213> ORGANISM: Homo sapiens

<400> SEQUENCE: 2853

Asp Leu His Asp Phe Gln Gly Asp Ala Leu
1               5                   10

<210> SEQ ID NO 2854
<211> LENGTH: 10
<212> TYPE: PRT
<213> ORGANISM: Homo sapiens

<400> SEQUENCE: 2854

Leu His Asp Phe Gln Gly Asp Ala Leu Gln
1               5                   10

<210> SEQ ID NO 2855
<211> LENGTH: 10
<212> TYPE: PRT
<213> ORGANISM: Homo sapiens

<400> SEQUENCE: 2855

His Asp Phe Gln Gly Asp Ala Leu Gln Pro
1               5                   10

<210> SEQ ID NO 2856
<211> LENGTH: 10
<212> TYPE: PRT
<213> ORGANISM: Homo sapiens

<400> SEQUENCE: 2856

Asp Phe Gln Gly Asp Ala Leu Gln Pro Glu
1               5                   10

<210> SEQ ID NO 2857
<211> LENGTH: 10
<212> TYPE: PRT
<213> ORGANISM: Homo sapiens

<400> SEQUENCE: 2857

Phe Gln Gly Asp Ala Leu Gln Pro Glu Asp
1               5                   10
```

<210> SEQ ID NO 2858
<211> LENGTH: 10
<212> TYPE: PRT
<213> ORGANISM: Homo sapiens

<400> SEQUENCE: 2858

Gln Gly Asp Ala Leu Gln Pro Glu Asp Phe
1               5                   10

<210> SEQ ID NO 2859
<211> LENGTH: 10
<212> TYPE: PRT
<213> ORGANISM: Homo sapiens

<400> SEQUENCE: 2859

Gly Asp Ala Leu Gln Pro Glu Asp Phe Leu
1               5                   10

<210> SEQ ID NO 2860
<211> LENGTH: 10
<212> TYPE: PRT
<213> ORGANISM: Homo sapiens

<400> SEQUENCE: 2860

Asp Ala Leu Gln Pro Glu Asp Phe Leu Glu
1               5                   10

<210> SEQ ID NO 2861
<211> LENGTH: 10
<212> TYPE: PRT
<213> ORGANISM: Homo sapiens

<400> SEQUENCE: 2861

Ala Leu Gln Pro Glu Asp Phe Leu Glu Glu
1               5                   10

<210> SEQ ID NO 2862
<211> LENGTH: 10
<212> TYPE: PRT
<213> ORGANISM: Homo sapiens

<400> SEQUENCE: 2862

Leu Gln Pro Glu Asp Phe Leu Glu Glu Asp
1               5                   10

<210> SEQ ID NO 2863
<211> LENGTH: 10
<212> TYPE: PRT
<213> ORGANISM: Homo sapiens

<400> SEQUENCE: 2863

Gln Pro Glu Asp Phe Leu Glu Glu Asp Glu
1               5                   10

<210> SEQ ID NO 2864
<211> LENGTH: 10
<212> TYPE: PRT
<213> ORGANISM: Homo sapiens

<400> SEQUENCE: 2864

Pro Glu Asp Phe Leu Glu Glu Asp Glu Tyr
1               5                   10

<210> SEQ ID NO 2865

```
<211> LENGTH: 10
<212> TYPE: PRT
<213> ORGANISM: Homo sapiens

<400> SEQUENCE: 2865

Glu Asp Phe Leu Glu Glu Asp Glu Tyr His
1               5                   10

<210> SEQ ID NO 2866
<211> LENGTH: 10
<212> TYPE: PRT
<213> ORGANISM: Homo sapiens

<400> SEQUENCE: 2866

Asp Phe Leu Glu Glu Asp Glu Tyr His Ala
1               5                   10

<210> SEQ ID NO 2867
<211> LENGTH: 10
<212> TYPE: PRT
<213> ORGANISM: Homo sapiens

<400> SEQUENCE: 2867

Phe Leu Glu Glu Asp Glu Tyr His Ala Thr
1               5                   10

<210> SEQ ID NO 2868
<211> LENGTH: 10
<212> TYPE: PRT
<213> ORGANISM: Homo sapiens

<400> SEQUENCE: 2868

Leu Glu Glu Asp Glu Tyr His Ala Thr Thr
1               5                   10

<210> SEQ ID NO 2869
<211> LENGTH: 10
<212> TYPE: PRT
<213> ORGANISM: Homo sapiens

<400> SEQUENCE: 2869

Glu Glu Asp Glu Tyr His Ala Thr Thr Glu
1               5                   10

<210> SEQ ID NO 2870
<211> LENGTH: 10
<212> TYPE: PRT
<213> ORGANISM: Homo sapiens

<400> SEQUENCE: 2870

Glu Asp Glu Tyr His Ala Thr Thr Glu Thr
1               5                   10

<210> SEQ ID NO 2871
<211> LENGTH: 10
<212> TYPE: PRT
<213> ORGANISM: Homo sapiens

<400> SEQUENCE: 2871

Asp Glu Tyr His Ala Thr Thr Glu Thr Val
1               5                   10

<210> SEQ ID NO 2872
<211> LENGTH: 10
<212> TYPE: PRT
```

<213> ORGANISM: Homo sapiens

<400> SEQUENCE: 2872

Glu Tyr His Ala Thr Thr Glu Thr Val Ile
1               5                   10

<210> SEQ ID NO 2873
<211> LENGTH: 10
<212> TYPE: PRT
<213> ORGANISM: Homo sapiens

<400> SEQUENCE: 2873

Tyr His Ala Thr Thr Glu Thr Val Ile Ser
1               5                   10

<210> SEQ ID NO 2874
<211> LENGTH: 10
<212> TYPE: PRT
<213> ORGANISM: Homo sapiens

<400> SEQUENCE: 2874

His Ala Thr Thr Glu Thr Val Ile Ser Met
1               5                   10

<210> SEQ ID NO 2875
<211> LENGTH: 10
<212> TYPE: PRT
<213> ORGANISM: Homo sapiens

<400> SEQUENCE: 2875

Ala Thr Thr Glu Thr Val Ile Ser Met Ala
1               5                   10

<210> SEQ ID NO 2876
<211> LENGTH: 10
<212> TYPE: PRT
<213> ORGANISM: Homo sapiens

<400> SEQUENCE: 2876

Thr Thr Glu Thr Val Ile Ser Met Ala Gln
1               5                   10

<210> SEQ ID NO 2877
<211> LENGTH: 10
<212> TYPE: PRT
<213> ORGANISM: Homo sapiens

<400> SEQUENCE: 2877

Thr Glu Thr Val Ile Ser Met Ala Gln Glu
1               5                   10

<210> SEQ ID NO 2878
<211> LENGTH: 10
<212> TYPE: PRT
<213> ORGANISM: Homo sapiens

<400> SEQUENCE: 2878

Glu Thr Val Ile Ser Met Ala Gln Glu Thr
1               5                   10

<210> SEQ ID NO 2879
<211> LENGTH: 10
<212> TYPE: PRT
<213> ORGANISM: Homo sapiens

<400> SEQUENCE: 2879

Thr Val Ile Ser Met Ala Gln Glu Thr Asp
1               5                   10

<210> SEQ ID NO 2880
<211> LENGTH: 10
<212> TYPE: PRT
<213> ORGANISM: Homo sapiens

<400> SEQUENCE: 2880

Val Ile Ser Met Ala Gln Glu Thr Asp Pro
1               5                   10

<210> SEQ ID NO 2881
<211> LENGTH: 10
<212> TYPE: PRT
<213> ORGANISM: Homo sapiens

<400> SEQUENCE: 2881

Ile Ser Met Ala Gln Glu Thr Asp Pro Ala
1               5                   10

<210> SEQ ID NO 2882
<211> LENGTH: 10
<212> TYPE: PRT
<213> ORGANISM: Homo sapiens

<400> SEQUENCE: 2882

Ser Met Ala Gln Glu Thr Asp Pro Ala Val
1               5                   10

<210> SEQ ID NO 2883
<211> LENGTH: 10
<212> TYPE: PRT
<213> ORGANISM: Homo sapiens

<400> SEQUENCE: 2883

Met Ala Gln Glu Thr Asp Pro Ala Val Gln
1               5                   10

<210> SEQ ID NO 2884
<211> LENGTH: 10
<212> TYPE: PRT
<213> ORGANISM: Homo sapiens

<400> SEQUENCE: 2884

Ala Gln Glu Thr Asp Pro Ala Val Gln Thr
1               5                   10

<210> SEQ ID NO 2885
<211> LENGTH: 10
<212> TYPE: PRT
<213> ORGANISM: Homo sapiens

<400> SEQUENCE: 2885

Gln Glu Thr Asp Pro Ala Val Gln Thr Asp
1               5                   10

<210> SEQ ID NO 2886
<211> LENGTH: 10
<212> TYPE: PRT
<213> ORGANISM: Homo sapiens

<400> SEQUENCE: 2886

Glu Thr Asp Pro Ala Val Gln Thr Asp Gly
1               5                   10

<210> SEQ ID NO 2887
<211> LENGTH: 10
<212> TYPE: PRT
<213> ORGANISM: Homo sapiens

<400> SEQUENCE: 2887

Thr Asp Pro Ala Val Gln Thr Asp Gly Ser
1               5                   10

<210> SEQ ID NO 2888
<211> LENGTH: 10
<212> TYPE: PRT
<213> ORGANISM: Homo sapiens

<400> SEQUENCE: 2888

Asp Pro Ala Val Gln Thr Asp Gly Ser Pro
1               5                   10

<210> SEQ ID NO 2889
<211> LENGTH: 10
<212> TYPE: PRT
<213> ORGANISM: Homo sapiens

<400> SEQUENCE: 2889

Pro Ala Val Gln Thr Asp Gly Ser Pro Leu
1               5                   10

<210> SEQ ID NO 2890
<211> LENGTH: 10
<212> TYPE: PRT
<213> ORGANISM: Homo sapiens

<400> SEQUENCE: 2890

Ala Val Gln Thr Asp Gly Ser Pro Leu Cys
1               5                   10

<210> SEQ ID NO 2891
<211> LENGTH: 10
<212> TYPE: PRT
<213> ORGANISM: Homo sapiens

<400> SEQUENCE: 2891

Val Gln Thr Asp Gly Ser Pro Leu Cys Cys
1               5                   10

<210> SEQ ID NO 2892
<211> LENGTH: 10
<212> TYPE: PRT
<213> ORGANISM: Homo sapiens

<400> SEQUENCE: 2892

Gln Thr Asp Gly Ser Pro Leu Cys Cys His
1               5                   10

<210> SEQ ID NO 2893
<211> LENGTH: 10
<212> TYPE: PRT
<213> ORGANISM: Homo sapiens

<400> SEQUENCE: 2893

Thr Asp Gly Ser Pro Leu Cys Cys His Phe
1               5                   10

```
<210> SEQ ID NO 2894
<211> LENGTH: 10
<212> TYPE: PRT
<213> ORGANISM: Homo sapiens

<400> SEQUENCE: 2894

Asp Gly Ser Pro Leu Cys Cys His Phe His
1               5                   10

<210> SEQ ID NO 2895
<211> LENGTH: 10
<212> TYPE: PRT
<213> ORGANISM: Homo sapiens

<400> SEQUENCE: 2895

Gly Ser Pro Leu Cys Cys His Phe His Phe
1               5                   10

<210> SEQ ID NO 2896
<211> LENGTH: 10
<212> TYPE: PRT
<213> ORGANISM: Homo sapiens

<400> SEQUENCE: 2896

Ser Pro Leu Cys Cys His Phe His Phe Ser
1               5                   10

<210> SEQ ID NO 2897
<211> LENGTH: 10
<212> TYPE: PRT
<213> ORGANISM: Homo sapiens

<400> SEQUENCE: 2897

Pro Leu Cys Cys His Phe His Phe Ser Pro
1               5                   10

<210> SEQ ID NO 2898
<211> LENGTH: 10
<212> TYPE: PRT
<213> ORGANISM: Homo sapiens

<400> SEQUENCE: 2898

Leu Cys Cys His Phe His Phe Ser Pro Lys
1               5                   10

<210> SEQ ID NO 2899
<211> LENGTH: 10
<212> TYPE: PRT
<213> ORGANISM: Homo sapiens

<400> SEQUENCE: 2899

Cys Cys His Phe His Phe Ser Pro Lys Val
1               5                   10

<210> SEQ ID NO 2900
<211> LENGTH: 10
<212> TYPE: PRT
<213> ORGANISM: Homo sapiens

<400> SEQUENCE: 2900

Cys His Phe His Phe Ser Pro Lys Val Met
1               5                   10
```

-continued

```
<210> SEQ ID NO 2901
<211> LENGTH: 10
<212> TYPE: PRT
<213> ORGANISM: Homo sapiens

<400> SEQUENCE: 2901

His Phe His Phe Ser Pro Lys Val Met Phe
1               5                   10

<210> SEQ ID NO 2902
<211> LENGTH: 10
<212> TYPE: PRT
<213> ORGANISM: Homo sapiens

<400> SEQUENCE: 2902

Phe His Phe Ser Pro Lys Val Met Phe Thr
1               5                   10

<210> SEQ ID NO 2903
<211> LENGTH: 10
<212> TYPE: PRT
<213> ORGANISM: Homo sapiens

<400> SEQUENCE: 2903

His Phe Ser Pro Lys Val Met Phe Thr Lys
1               5                   10

<210> SEQ ID NO 2904
<211> LENGTH: 10
<212> TYPE: PRT
<213> ORGANISM: Homo sapiens

<400> SEQUENCE: 2904

Phe Ser Pro Lys Val Met Phe Thr Lys Val
1               5                   10

<210> SEQ ID NO 2905
<211> LENGTH: 10
<212> TYPE: PRT
<213> ORGANISM: Homo sapiens

<400> SEQUENCE: 2905

Ser Pro Lys Val Met Phe Thr Lys Val Leu
1               5                   10

<210> SEQ ID NO 2906
<211> LENGTH: 10
<212> TYPE: PRT
<213> ORGANISM: Homo sapiens

<400> SEQUENCE: 2906

Pro Lys Val Met Phe Thr Lys Val Leu Lys
1               5                   10

<210> SEQ ID NO 2907
<211> LENGTH: 10
<212> TYPE: PRT
<213> ORGANISM: Homo sapiens

<400> SEQUENCE: 2907

Lys Val Met Phe Thr Lys Val Leu Lys Ala
1               5                   10

<210> SEQ ID NO 2908
<211> LENGTH: 10
```

<212> TYPE: PRT
<213> ORGANISM: Homo sapiens

<400> SEQUENCE: 2908

Val Met Phe Thr Lys Val Leu Lys Ala Gln
1               5                   10

<210> SEQ ID NO 2909
<211> LENGTH: 10
<212> TYPE: PRT
<213> ORGANISM: Homo sapiens

<400> SEQUENCE: 2909

Met Phe Thr Lys Val Leu Lys Ala Gln Leu
1               5                   10

<210> SEQ ID NO 2910
<211> LENGTH: 10
<212> TYPE: PRT
<213> ORGANISM: Homo sapiens

<400> SEQUENCE: 2910

Phe Thr Lys Val Leu Lys Ala Gln Leu Trp
1               5                   10

<210> SEQ ID NO 2911
<211> LENGTH: 10
<212> TYPE: PRT
<213> ORGANISM: Homo sapiens

<400> SEQUENCE: 2911

Thr Lys Val Leu Lys Ala Gln Leu Trp Val
1               5                   10

<210> SEQ ID NO 2912
<211> LENGTH: 10
<212> TYPE: PRT
<213> ORGANISM: Homo sapiens

<400> SEQUENCE: 2912

Lys Val Leu Lys Ala Gln Leu Trp Val Tyr
1               5                   10

<210> SEQ ID NO 2913
<211> LENGTH: 10
<212> TYPE: PRT
<213> ORGANISM: Homo sapiens

<400> SEQUENCE: 2913

Val Leu Lys Ala Gln Leu Trp Val Tyr Leu
1               5                   10

<210> SEQ ID NO 2914
<211> LENGTH: 10
<212> TYPE: PRT
<213> ORGANISM: Homo sapiens

<400> SEQUENCE: 2914

Leu Lys Ala Gln Leu Trp Val Tyr Leu Arg
1               5                   10

<210> SEQ ID NO 2915
<211> LENGTH: 10
<212> TYPE: PRT
<213> ORGANISM: Homo sapiens

<400> SEQUENCE: 2915

Lys Ala Gln Leu Trp Val Tyr Leu Arg Pro
1               5                   10

<210> SEQ ID NO 2916
<211> LENGTH: 10
<212> TYPE: PRT
<213> ORGANISM: Homo sapiens

<400> SEQUENCE: 2916

Ala Gln Leu Trp Val Tyr Leu Arg Pro Val
1               5                   10

<210> SEQ ID NO 2917
<211> LENGTH: 10
<212> TYPE: PRT
<213> ORGANISM: Homo sapiens

<400> SEQUENCE: 2917

Gln Leu Trp Val Tyr Leu Arg Pro Val Pro
1               5                   10

<210> SEQ ID NO 2918
<211> LENGTH: 10
<212> TYPE: PRT
<213> ORGANISM: Homo sapiens

<400> SEQUENCE: 2918

Leu Trp Val Tyr Leu Arg Pro Val Pro Arg
1               5                   10

<210> SEQ ID NO 2919
<211> LENGTH: 10
<212> TYPE: PRT
<213> ORGANISM: Homo sapiens

<400> SEQUENCE: 2919

Trp Val Tyr Leu Arg Pro Val Pro Arg Pro
1               5                   10

<210> SEQ ID NO 2920
<211> LENGTH: 10
<212> TYPE: PRT
<213> ORGANISM: Homo sapiens

<400> SEQUENCE: 2920

Val Tyr Leu Arg Pro Val Pro Arg Pro Ala
1               5                   10

<210> SEQ ID NO 2921
<211> LENGTH: 10
<212> TYPE: PRT
<213> ORGANISM: Homo sapiens

<400> SEQUENCE: 2921

Tyr Leu Arg Pro Val Pro Arg Pro Ala Thr
1               5                   10

<210> SEQ ID NO 2922
<211> LENGTH: 10
<212> TYPE: PRT
<213> ORGANISM: Homo sapiens

<400> SEQUENCE: 2922

```
Leu Arg Pro Val Pro Arg Pro Ala Thr Val
1               5                   10

<210> SEQ ID NO 2923
<211> LENGTH: 10
<212> TYPE: PRT
<213> ORGANISM: Homo sapiens

<400> SEQUENCE: 2923

Arg Pro Val Pro Arg Pro Ala Thr Val Tyr
1               5                   10

<210> SEQ ID NO 2924
<211> LENGTH: 10
<212> TYPE: PRT
<213> ORGANISM: Homo sapiens

<400> SEQUENCE: 2924

Pro Val Pro Arg Pro Ala Thr Val Tyr Leu
1               5                   10

<210> SEQ ID NO 2925
<211> LENGTH: 10
<212> TYPE: PRT
<213> ORGANISM: Homo sapiens

<400> SEQUENCE: 2925

Val Pro Arg Pro Ala Thr Val Tyr Leu Gln
1               5                   10

<210> SEQ ID NO 2926
<211> LENGTH: 10
<212> TYPE: PRT
<213> ORGANISM: Homo sapiens

<400> SEQUENCE: 2926

Pro Arg Pro Ala Thr Val Tyr Leu Gln Ile
1               5                   10

<210> SEQ ID NO 2927
<211> LENGTH: 10
<212> TYPE: PRT
<213> ORGANISM: Homo sapiens

<400> SEQUENCE: 2927

Arg Pro Ala Thr Val Tyr Leu Gln Ile Leu
1               5                   10

<210> SEQ ID NO 2928
<211> LENGTH: 10
<212> TYPE: PRT
<213> ORGANISM: Homo sapiens

<400> SEQUENCE: 2928

Pro Ala Thr Val Tyr Leu Gln Ile Leu Arg
1               5                   10

<210> SEQ ID NO 2929
<211> LENGTH: 10
<212> TYPE: PRT
<213> ORGANISM: Homo sapiens

<400> SEQUENCE: 2929

Ala Thr Val Tyr Leu Gln Ile Leu Arg Leu
```

```
1               5                   10
```

<210> SEQ ID NO 2930
<211> LENGTH: 10
<212> TYPE: PRT
<213> ORGANISM: Homo sapiens

<400> SEQUENCE: 2930

```
Thr Val Tyr Leu Gln Ile Leu Arg Leu Lys
1               5                   10
```

<210> SEQ ID NO 2931
<211> LENGTH: 10
<212> TYPE: PRT
<213> ORGANISM: Homo sapiens

<400> SEQUENCE: 2931

```
Val Tyr Leu Gln Ile Leu Arg Leu Lys Pro
1               5                   10
```

<210> SEQ ID NO 2932
<211> LENGTH: 10
<212> TYPE: PRT
<213> ORGANISM: Homo sapiens

<400> SEQUENCE: 2932

```
Tyr Leu Gln Ile Leu Arg Leu Lys Pro Leu
1               5                   10
```

<210> SEQ ID NO 2933
<211> LENGTH: 10
<212> TYPE: PRT
<213> ORGANISM: Homo sapiens

<400> SEQUENCE: 2933

```
Leu Gln Ile Leu Arg Leu Lys Pro Leu Thr
1               5                   10
```

<210> SEQ ID NO 2934
<211> LENGTH: 10
<212> TYPE: PRT
<213> ORGANISM: Homo sapiens

<400> SEQUENCE: 2934

```
Gln Ile Leu Arg Leu Lys Pro Leu Thr Gly
1               5                   10
```

<210> SEQ ID NO 2935
<211> LENGTH: 10
<212> TYPE: PRT
<213> ORGANISM: Homo sapiens

<400> SEQUENCE: 2935

```
Ile Leu Arg Leu Lys Pro Leu Thr Gly Glu
1               5                   10
```

<210> SEQ ID NO 2936
<211> LENGTH: 10
<212> TYPE: PRT
<213> ORGANISM: Homo sapiens

<400> SEQUENCE: 2936

```
Leu Arg Leu Lys Pro Leu Thr Gly Glu Gly
1               5                   10
```

<210> SEQ ID NO 2937
<211> LENGTH: 10
<212> TYPE: PRT
<213> ORGANISM: Homo sapiens

<400> SEQUENCE: 2937

Arg Leu Lys Pro Leu Thr Gly Glu Gly Thr
1               5                   10

<210> SEQ ID NO 2938
<211> LENGTH: 10
<212> TYPE: PRT
<213> ORGANISM: Homo sapiens

<400> SEQUENCE: 2938

Leu Lys Pro Leu Thr Gly Glu Gly Thr Ala
1               5                   10

<210> SEQ ID NO 2939
<211> LENGTH: 10
<212> TYPE: PRT
<213> ORGANISM: Homo sapiens

<400> SEQUENCE: 2939

Lys Pro Leu Thr Gly Glu Gly Thr Ala Gly
1               5                   10

<210> SEQ ID NO 2940
<211> LENGTH: 10
<212> TYPE: PRT
<213> ORGANISM: Homo sapiens

<400> SEQUENCE: 2940

Pro Leu Thr Gly Glu Gly Thr Ala Gly Gly
1               5                   10

<210> SEQ ID NO 2941
<211> LENGTH: 10
<212> TYPE: PRT
<213> ORGANISM: Homo sapiens

<400> SEQUENCE: 2941

Leu Thr Gly Glu Gly Thr Ala Gly Gly Gly
1               5                   10

<210> SEQ ID NO 2942
<211> LENGTH: 10
<212> TYPE: PRT
<213> ORGANISM: Homo sapiens

<400> SEQUENCE: 2942

Thr Gly Glu Gly Thr Ala Gly Gly Gly Gly
1               5                   10

<210> SEQ ID NO 2943
<211> LENGTH: 10
<212> TYPE: PRT
<213> ORGANISM: Homo sapiens

<400> SEQUENCE: 2943

Gly Glu Gly Thr Ala Gly Gly Gly Gly Gly
1               5                   10

<210> SEQ ID NO 2944

```
<211> LENGTH: 10
<212> TYPE: PRT
<213> ORGANISM: Homo sapiens

<400> SEQUENCE: 2944

Glu Gly Thr Ala Gly Gly Gly Gly Gly Gly
1               5                   10

<210> SEQ ID NO 2945
<211> LENGTH: 10
<212> TYPE: PRT
<213> ORGANISM: Homo sapiens

<400> SEQUENCE: 2945

Gly Thr Ala Gly Gly Gly Gly Gly Gly Arg
1               5                   10

<210> SEQ ID NO 2946
<211> LENGTH: 10
<212> TYPE: PRT
<213> ORGANISM: Homo sapiens

<400> SEQUENCE: 2946

Thr Ala Gly Gly Gly Gly Gly Gly Arg Arg
1               5                   10

<210> SEQ ID NO 2947
<211> LENGTH: 10
<212> TYPE: PRT
<213> ORGANISM: Homo sapiens

<400> SEQUENCE: 2947

Ala Gly Gly Gly Gly Gly Gly Arg Arg His
1               5                   10

<210> SEQ ID NO 2948
<211> LENGTH: 10
<212> TYPE: PRT
<213> ORGANISM: Homo sapiens

<400> SEQUENCE: 2948

Gly Gly Gly Gly Gly Gly Arg Arg His Ile
1               5                   10

<210> SEQ ID NO 2949
<211> LENGTH: 10
<212> TYPE: PRT
<213> ORGANISM: Homo sapiens

<400> SEQUENCE: 2949

Gly Gly Gly Gly Gly Arg Arg His Ile Arg
1               5                   10

<210> SEQ ID NO 2950
<211> LENGTH: 10
<212> TYPE: PRT
<213> ORGANISM: Homo sapiens

<400> SEQUENCE: 2950

Gly Gly Gly Gly Arg Arg His Ile Arg Ile
1               5                   10

<210> SEQ ID NO 2951
<211> LENGTH: 10
<212> TYPE: PRT
```

<213> ORGANISM: Homo sapiens

<400> SEQUENCE: 2951

Gly Gly Gly Arg Arg His Ile Arg Ile Arg
1               5                   10

<210> SEQ ID NO 2952
<211> LENGTH: 10
<212> TYPE: PRT
<213> ORGANISM: Homo sapiens

<400> SEQUENCE: 2952

Gly Gly Arg Arg His Ile Arg Ile Arg Ser
1               5                   10

<210> SEQ ID NO 2953
<211> LENGTH: 10
<212> TYPE: PRT
<213> ORGANISM: Homo sapiens

<400> SEQUENCE: 2953

Gly Arg Arg His Ile Arg Ile Arg Ser Leu
1               5                   10

<210> SEQ ID NO 2954
<211> LENGTH: 10
<212> TYPE: PRT
<213> ORGANISM: Homo sapiens

<400> SEQUENCE: 2954

Arg Arg His Ile Arg Ile Arg Ser Leu Lys
1               5                   10

<210> SEQ ID NO 2955
<211> LENGTH: 10
<212> TYPE: PRT
<213> ORGANISM: Homo sapiens

<400> SEQUENCE: 2955

Arg His Ile Arg Ile Arg Ser Leu Lys Ile
1               5                   10

<210> SEQ ID NO 2956
<211> LENGTH: 10
<212> TYPE: PRT
<213> ORGANISM: Homo sapiens

<400> SEQUENCE: 2956

His Ile Arg Ile Arg Ser Leu Lys Ile Glu
1               5                   10

<210> SEQ ID NO 2957
<211> LENGTH: 10
<212> TYPE: PRT
<213> ORGANISM: Homo sapiens

<400> SEQUENCE: 2957

Ile Arg Ile Arg Ser Leu Lys Ile Glu Leu
1               5                   10

<210> SEQ ID NO 2958
<211> LENGTH: 10
<212> TYPE: PRT
<213> ORGANISM: Homo sapiens

```
<400> SEQUENCE: 2958

Arg Ile Arg Ser Leu Lys Ile Glu Leu His
1               5                   10

<210> SEQ ID NO 2959
<211> LENGTH: 10
<212> TYPE: PRT
<213> ORGANISM: Homo sapiens

<400> SEQUENCE: 2959

Ile Arg Ser Leu Lys Ile Glu Leu His Ser
1               5                   10

<210> SEQ ID NO 2960
<211> LENGTH: 10
<212> TYPE: PRT
<213> ORGANISM: Homo sapiens

<400> SEQUENCE: 2960

Arg Ser Leu Lys Ile Glu Leu His Ser Arg
1               5                   10

<210> SEQ ID NO 2961
<211> LENGTH: 10
<212> TYPE: PRT
<213> ORGANISM: Homo sapiens

<400> SEQUENCE: 2961

Ser Leu Lys Ile Glu Leu His Ser Arg Ser
1               5                   10

<210> SEQ ID NO 2962
<211> LENGTH: 10
<212> TYPE: PRT
<213> ORGANISM: Homo sapiens

<400> SEQUENCE: 2962

Leu Lys Ile Glu Leu His Ser Arg Ser Gly
1               5                   10

<210> SEQ ID NO 2963
<211> LENGTH: 10
<212> TYPE: PRT
<213> ORGANISM: Homo sapiens

<400> SEQUENCE: 2963

Lys Ile Glu Leu His Ser Arg Ser Gly His
1               5                   10

<210> SEQ ID NO 2964
<211> LENGTH: 10
<212> TYPE: PRT
<213> ORGANISM: Homo sapiens

<400> SEQUENCE: 2964

Ile Glu Leu His Ser Arg Ser Gly His Trp
1               5                   10

<210> SEQ ID NO 2965
<211> LENGTH: 10
<212> TYPE: PRT
<213> ORGANISM: Homo sapiens

<400> SEQUENCE: 2965
```

```
Glu Leu His Ser Arg Ser Gly His Trp Gln
1               5                   10
```

<210> SEQ ID NO 2966
<211> LENGTH: 10
<212> TYPE: PRT
<213> ORGANISM: Homo sapiens

<400> SEQUENCE: 2966

```
Leu His Ser Arg Ser Gly His Trp Gln Ser
1               5                   10
```

<210> SEQ ID NO 2967
<211> LENGTH: 10
<212> TYPE: PRT
<213> ORGANISM: Homo sapiens

<400> SEQUENCE: 2967

```
His Ser Arg Ser Gly His Trp Gln Ser Ile
1               5                   10
```

<210> SEQ ID NO 2968
<211> LENGTH: 10
<212> TYPE: PRT
<213> ORGANISM: Homo sapiens

<400> SEQUENCE: 2968

```
Ser Arg Ser Gly His Trp Gln Ser Ile Asp
1               5                   10
```

<210> SEQ ID NO 2969
<211> LENGTH: 10
<212> TYPE: PRT
<213> ORGANISM: Homo sapiens

<400> SEQUENCE: 2969

```
Arg Ser Gly His Trp Gln Ser Ile Asp Phe
1               5                   10
```

<210> SEQ ID NO 2970
<211> LENGTH: 10
<212> TYPE: PRT
<213> ORGANISM: Homo sapiens

<400> SEQUENCE: 2970

```
Ser Gly His Trp Gln Ser Ile Asp Phe Lys
1               5                   10
```

<210> SEQ ID NO 2971
<211> LENGTH: 10
<212> TYPE: PRT
<213> ORGANISM: Homo sapiens

<400> SEQUENCE: 2971

```
Gly His Trp Gln Ser Ile Asp Phe Lys Gln
1               5                   10
```

<210> SEQ ID NO 2972
<211> LENGTH: 10
<212> TYPE: PRT
<213> ORGANISM: Homo sapiens

<400> SEQUENCE: 2972

```
His Trp Gln Ser Ile Asp Phe Lys Gln Val
1               5                   10
```

<210> SEQ ID NO 2973
<211> LENGTH: 10
<212> TYPE: PRT
<213> ORGANISM: Homo sapiens

<400> SEQUENCE: 2973

Trp Gln Ser Ile Asp Phe Lys Gln Val Leu
1               5                   10

<210> SEQ ID NO 2974
<211> LENGTH: 10
<212> TYPE: PRT
<213> ORGANISM: Homo sapiens

<400> SEQUENCE: 2974

Gln Ser Ile Asp Phe Lys Gln Val Leu His
1               5                   10

<210> SEQ ID NO 2975
<211> LENGTH: 10
<212> TYPE: PRT
<213> ORGANISM: Homo sapiens

<400> SEQUENCE: 2975

Ser Ile Asp Phe Lys Gln Val Leu His Ser
1               5                   10

<210> SEQ ID NO 2976
<211> LENGTH: 10
<212> TYPE: PRT
<213> ORGANISM: Homo sapiens

<400> SEQUENCE: 2976

Ile Asp Phe Lys Gln Val Leu His Ser Trp
1               5                   10

<210> SEQ ID NO 2977
<211> LENGTH: 10
<212> TYPE: PRT
<213> ORGANISM: Homo sapiens

<400> SEQUENCE: 2977

Asp Phe Lys Gln Val Leu His Ser Trp Phe
1               5                   10

<210> SEQ ID NO 2978
<211> LENGTH: 10
<212> TYPE: PRT
<213> ORGANISM: Homo sapiens

<400> SEQUENCE: 2978

Phe Lys Gln Val Leu His Ser Trp Phe Arg
1               5                   10

<210> SEQ ID NO 2979
<211> LENGTH: 10
<212> TYPE: PRT
<213> ORGANISM: Homo sapiens

<400> SEQUENCE: 2979

Lys Gln Val Leu His Ser Trp Phe Arg Gln
1               5                   10

<210> SEQ ID NO 2980
<211> LENGTH: 10
<212> TYPE: PRT
<213> ORGANISM: Homo sapiens

<400> SEQUENCE: 2980

Gln Val Leu His Ser Trp Phe Arg Gln Pro
1               5                   10

<210> SEQ ID NO 2981
<211> LENGTH: 10
<212> TYPE: PRT
<213> ORGANISM: Homo sapiens

<400> SEQUENCE: 2981

Val Leu His Ser Trp Phe Arg Gln Pro Gln
1               5                   10

<210> SEQ ID NO 2982
<211> LENGTH: 10
<212> TYPE: PRT
<213> ORGANISM: Homo sapiens

<400> SEQUENCE: 2982

Leu His Ser Trp Phe Arg Gln Pro Gln Ser
1               5                   10

<210> SEQ ID NO 2983
<211> LENGTH: 10
<212> TYPE: PRT
<213> ORGANISM: Homo sapiens

<400> SEQUENCE: 2983

His Ser Trp Phe Arg Gln Pro Gln Ser Asn
1               5                   10

<210> SEQ ID NO 2984
<211> LENGTH: 10
<212> TYPE: PRT
<213> ORGANISM: Homo sapiens

<400> SEQUENCE: 2984

Ser Trp Phe Arg Gln Pro Gln Ser Asn Trp
1               5                   10

<210> SEQ ID NO 2985
<211> LENGTH: 10
<212> TYPE: PRT
<213> ORGANISM: Homo sapiens

<400> SEQUENCE: 2985

Trp Phe Arg Gln Pro Gln Ser Asn Trp Gly
1               5                   10

<210> SEQ ID NO 2986
<211> LENGTH: 10
<212> TYPE: PRT
<213> ORGANISM: Homo sapiens

<400> SEQUENCE: 2986

Phe Arg Gln Pro Gln Ser Asn Trp Gly Ile
1               5                   10

<210> SEQ ID NO 2987
<211> LENGTH: 10

<212> TYPE: PRT
<213> ORGANISM: Homo sapiens

<400> SEQUENCE: 2987

Arg Gln Pro Gln Ser Asn Trp Gly Ile Glu
1               5                   10

<210> SEQ ID NO 2988
<211> LENGTH: 10
<212> TYPE: PRT
<213> ORGANISM: Homo sapiens

<400> SEQUENCE: 2988

Gln Pro Gln Ser Asn Trp Gly Ile Glu Ile
1               5                   10

<210> SEQ ID NO 2989
<211> LENGTH: 10
<212> TYPE: PRT
<213> ORGANISM: Homo sapiens

<400> SEQUENCE: 2989

Pro Gln Ser Asn Trp Gly Ile Glu Ile Asn
1               5                   10

<210> SEQ ID NO 2990
<211> LENGTH: 10
<212> TYPE: PRT
<213> ORGANISM: Homo sapiens

<400> SEQUENCE: 2990

Gln Ser Asn Trp Gly Ile Glu Ile Asn Ala
1               5                   10

<210> SEQ ID NO 2991
<211> LENGTH: 10
<212> TYPE: PRT
<213> ORGANISM: Homo sapiens

<400> SEQUENCE: 2991

Ser Asn Trp Gly Ile Glu Ile Asn Ala Phe
1               5                   10

<210> SEQ ID NO 2992
<211> LENGTH: 10
<212> TYPE: PRT
<213> ORGANISM: Homo sapiens

<400> SEQUENCE: 2992

Asn Trp Gly Ile Glu Ile Asn Ala Phe Asp
1               5                   10

<210> SEQ ID NO 2993
<211> LENGTH: 10
<212> TYPE: PRT
<213> ORGANISM: Homo sapiens

<400> SEQUENCE: 2993

Trp Gly Ile Glu Ile Asn Ala Phe Asp Pro
1               5                   10

<210> SEQ ID NO 2994
<211> LENGTH: 10
<212> TYPE: PRT
<213> ORGANISM: Homo sapiens

```
<400> SEQUENCE: 2994

Gly Ile Glu Ile Asn Ala Phe Asp Pro Ser
1               5                   10

<210> SEQ ID NO 2995
<211> LENGTH: 10
<212> TYPE: PRT
<213> ORGANISM: Homo sapiens

<400> SEQUENCE: 2995

Ile Glu Ile Asn Ala Phe Asp Pro Ser Gly
1               5                   10

<210> SEQ ID NO 2996
<211> LENGTH: 10
<212> TYPE: PRT
<213> ORGANISM: Homo sapiens

<400> SEQUENCE: 2996

Glu Ile Asn Ala Phe Asp Pro Ser Gly Thr
1               5                   10

<210> SEQ ID NO 2997
<211> LENGTH: 10
<212> TYPE: PRT
<213> ORGANISM: Homo sapiens

<400> SEQUENCE: 2997

Ile Asn Ala Phe Asp Pro Ser Gly Thr Asp
1               5                   10

<210> SEQ ID NO 2998
<211> LENGTH: 10
<212> TYPE: PRT
<213> ORGANISM: Homo sapiens

<400> SEQUENCE: 2998

Asn Ala Phe Asp Pro Ser Gly Thr Asp Leu
1               5                   10

<210> SEQ ID NO 2999
<211> LENGTH: 10
<212> TYPE: PRT
<213> ORGANISM: Homo sapiens

<400> SEQUENCE: 2999

Ala Phe Asp Pro Ser Gly Thr Asp Leu Ala
1               5                   10

<210> SEQ ID NO 3000
<211> LENGTH: 10
<212> TYPE: PRT
<213> ORGANISM: Homo sapiens

<400> SEQUENCE: 3000

Phe Asp Pro Ser Gly Thr Asp Leu Ala Val
1               5                   10

<210> SEQ ID NO 3001
<211> LENGTH: 10
<212> TYPE: PRT
<213> ORGANISM: Homo sapiens

<400> SEQUENCE: 3001
```

Asp Pro Ser Gly Thr Asp Leu Ala Val Thr
1               5                   10

<210> SEQ ID NO 3002
<211> LENGTH: 10
<212> TYPE: PRT
<213> ORGANISM: Homo sapiens

<400> SEQUENCE: 3002

Pro Ser Gly Thr Asp Leu Ala Val Thr Ser
1               5                   10

<210> SEQ ID NO 3003
<211> LENGTH: 10
<212> TYPE: PRT
<213> ORGANISM: Homo sapiens

<400> SEQUENCE: 3003

Ser Gly Thr Asp Leu Ala Val Thr Ser Leu
1               5                   10

<210> SEQ ID NO 3004
<211> LENGTH: 10
<212> TYPE: PRT
<213> ORGANISM: Homo sapiens

<400> SEQUENCE: 3004

Gly Thr Asp Leu Ala Val Thr Ser Leu Gly
1               5                   10

<210> SEQ ID NO 3005
<211> LENGTH: 10
<212> TYPE: PRT
<213> ORGANISM: Homo sapiens

<400> SEQUENCE: 3005

Thr Asp Leu Ala Val Thr Ser Leu Gly Pro
1               5                   10

<210> SEQ ID NO 3006
<211> LENGTH: 10
<212> TYPE: PRT
<213> ORGANISM: Homo sapiens

<400> SEQUENCE: 3006

Asp Leu Ala Val Thr Ser Leu Gly Pro Gly
1               5                   10

<210> SEQ ID NO 3007
<211> LENGTH: 10
<212> TYPE: PRT
<213> ORGANISM: Homo sapiens

<400> SEQUENCE: 3007

Leu Ala Val Thr Ser Leu Gly Pro Gly Ala
1               5                   10

<210> SEQ ID NO 3008
<211> LENGTH: 10
<212> TYPE: PRT
<213> ORGANISM: Homo sapiens

<400> SEQUENCE: 3008

Ala Val Thr Ser Leu Gly Pro Gly Ala Glu 1               5                    10

<210> SEQ ID NO 3009
<211> LENGTH: 10
<212> TYPE: PRT
<213> ORGANISM: Homo sapiens

<400> SEQUENCE: 3009

Val Thr Ser Leu Gly Pro Gly Ala Glu Gly
1               5                   10

<210> SEQ ID NO 3010
<211> LENGTH: 10
<212> TYPE: PRT
<213> ORGANISM: Homo sapiens

<400> SEQUENCE: 3010

Thr Ser Leu Gly Pro Gly Ala Glu Gly Leu
1               5                   10

<210> SEQ ID NO 3011
<211> LENGTH: 10
<212> TYPE: PRT
<213> ORGANISM: Homo sapiens

<400> SEQUENCE: 3011

Ser Leu Gly Pro Gly Ala Glu Gly Leu His
1               5                   10

<210> SEQ ID NO 3012
<211> LENGTH: 10
<212> TYPE: PRT
<213> ORGANISM: Homo sapiens

<400> SEQUENCE: 3012

Leu Gly Pro Gly Ala Glu Gly Leu His Pro
1               5                   10

<210> SEQ ID NO 3013
<211> LENGTH: 10
<212> TYPE: PRT
<213> ORGANISM: Homo sapiens

<400> SEQUENCE: 3013

Gly Pro Gly Ala Glu Gly Leu His Pro Phe
1               5                   10

<210> SEQ ID NO 3014
<211> LENGTH: 10
<212> TYPE: PRT
<213> ORGANISM: Homo sapiens

<400> SEQUENCE: 3014

Pro Gly Ala Glu Gly Leu His Pro Phe Met
1               5                   10

<210> SEQ ID NO 3015
<211> LENGTH: 10
<212> TYPE: PRT
<213> ORGANISM: Homo sapiens

<400> SEQUENCE: 3015

Gly Ala Glu Gly Leu His Pro Phe Met Glu
1               5                   10

<210> SEQ ID NO 3016
<211> LENGTH: 10
<212> TYPE: PRT
<213> ORGANISM: Homo sapiens

<400> SEQUENCE: 3016

Ala Glu Gly Leu His Pro Phe Met Glu Leu
1               5                   10

<210> SEQ ID NO 3017
<211> LENGTH: 10
<212> TYPE: PRT
<213> ORGANISM: Homo sapiens

<400> SEQUENCE: 3017

Glu Gly Leu His Pro Phe Met Glu Leu Arg
1               5                   10

<210> SEQ ID NO 3018
<211> LENGTH: 10
<212> TYPE: PRT
<213> ORGANISM: Homo sapiens

<400> SEQUENCE: 3018

Gly Leu His Pro Phe Met Glu Leu Arg Val
1               5                   10

<210> SEQ ID NO 3019
<211> LENGTH: 10
<212> TYPE: PRT
<213> ORGANISM: Homo sapiens

<400> SEQUENCE: 3019

Leu His Pro Phe Met Glu Leu Arg Val Leu
1               5                   10

<210> SEQ ID NO 3020
<211> LENGTH: 10
<212> TYPE: PRT
<213> ORGANISM: Homo sapiens

<400> SEQUENCE: 3020

His Pro Phe Met Glu Leu Arg Val Leu Glu
1               5                   10

<210> SEQ ID NO 3021
<211> LENGTH: 10
<212> TYPE: PRT
<213> ORGANISM: Homo sapiens

<400> SEQUENCE: 3021

Pro Phe Met Glu Leu Arg Val Leu Glu Asn
1               5                   10

<210> SEQ ID NO 3022
<211> LENGTH: 10
<212> TYPE: PRT
<213> ORGANISM: Homo sapiens

<400> SEQUENCE: 3022

Phe Met Glu Leu Arg Val Leu Glu Asn Thr
1               5                   10

<210> SEQ ID NO 3023

```
<211> LENGTH: 10
<212> TYPE: PRT
<213> ORGANISM: Homo sapiens

<400> SEQUENCE: 3023

Met Glu Leu Arg Val Leu Glu Asn Thr Lys
1               5                   10

<210> SEQ ID NO 3024
<211> LENGTH: 10
<212> TYPE: PRT
<213> ORGANISM: Homo sapiens

<400> SEQUENCE: 3024

Glu Leu Arg Val Leu Glu Asn Thr Lys Arg
1               5                   10

<210> SEQ ID NO 3025
<211> LENGTH: 10
<212> TYPE: PRT
<213> ORGANISM: Homo sapiens

<400> SEQUENCE: 3025

Leu Arg Val Leu Glu Asn Thr Lys Arg Ser
1               5                   10

<210> SEQ ID NO 3026
<211> LENGTH: 10
<212> TYPE: PRT
<213> ORGANISM: Homo sapiens

<400> SEQUENCE: 3026

Arg Val Leu Glu Asn Thr Lys Arg Ser Arg
1               5                   10

<210> SEQ ID NO 3027
<211> LENGTH: 10
<212> TYPE: PRT
<213> ORGANISM: Homo sapiens

<400> SEQUENCE: 3027

Val Leu Glu Asn Thr Lys Arg Ser Arg Arg
1               5                   10

<210> SEQ ID NO 3028
<211> LENGTH: 10
<212> TYPE: PRT
<213> ORGANISM: Homo sapiens

<400> SEQUENCE: 3028

Leu Glu Asn Thr Lys Arg Ser Arg Arg Asn
1               5                   10

<210> SEQ ID NO 3029
<211> LENGTH: 10
<212> TYPE: PRT
<213> ORGANISM: Homo sapiens

<400> SEQUENCE: 3029

Glu Asn Thr Lys Arg Ser Arg Arg Asn Leu
1               5                   10

<210> SEQ ID NO 3030
<211> LENGTH: 10
<212> TYPE: PRT
```

-continued

<213> ORGANISM: Homo sapiens

<400> SEQUENCE: 3030

Asn Thr Lys Arg Ser Arg Arg Asn Leu Gly
1               5                   10

<210> SEQ ID NO 3031
<211> LENGTH: 10
<212> TYPE: PRT
<213> ORGANISM: Homo sapiens

<400> SEQUENCE: 3031

Thr Lys Arg Ser Arg Arg Asn Leu Gly Leu
1               5                   10

<210> SEQ ID NO 3032
<211> LENGTH: 10
<212> TYPE: PRT
<213> ORGANISM: Homo sapiens

<400> SEQUENCE: 3032

Lys Arg Ser Arg Arg Asn Leu Gly Leu Asp
1               5                   10

<210> SEQ ID NO 3033
<211> LENGTH: 10
<212> TYPE: PRT
<213> ORGANISM: Homo sapiens

<400> SEQUENCE: 3033

Arg Ser Arg Arg Asn Leu Gly Leu Asp Cys
1               5                   10

<210> SEQ ID NO 3034
<211> LENGTH: 10
<212> TYPE: PRT
<213> ORGANISM: Homo sapiens

<400> SEQUENCE: 3034

Ser Arg Arg Asn Leu Gly Leu Asp Cys Asp
1               5                   10

<210> SEQ ID NO 3035
<211> LENGTH: 10
<212> TYPE: PRT
<213> ORGANISM: Homo sapiens

<400> SEQUENCE: 3035

Arg Arg Asn Leu Gly Leu Asp Cys Asp Glu
1               5                   10

<210> SEQ ID NO 3036
<211> LENGTH: 10
<212> TYPE: PRT
<213> ORGANISM: Homo sapiens

<400> SEQUENCE: 3036

Arg Asn Leu Gly Leu Asp Cys Asp Glu His
1               5                   10

<210> SEQ ID NO 3037
<211> LENGTH: 10
<212> TYPE: PRT
<213> ORGANISM: Homo sapiens

<400> SEQUENCE: 3037

Asn Leu Gly Leu Asp Cys Asp Glu His Ser
1               5                   10

<210> SEQ ID NO 3038
<211> LENGTH: 10
<212> TYPE: PRT
<213> ORGANISM: Homo sapiens

<400> SEQUENCE: 3038

Leu Gly Leu Asp Cys Asp Glu His Ser Ser
1               5                   10

<210> SEQ ID NO 3039
<211> LENGTH: 10
<212> TYPE: PRT
<213> ORGANISM: Homo sapiens

<400> SEQUENCE: 3039

Gly Leu Asp Cys Asp Glu His Ser Ser Glu
1               5                   10

<210> SEQ ID NO 3040
<211> LENGTH: 10
<212> TYPE: PRT
<213> ORGANISM: Homo sapiens

<400> SEQUENCE: 3040

Leu Asp Cys Asp Glu His Ser Ser Glu Ser
1               5                   10

<210> SEQ ID NO 3041
<211> LENGTH: 10
<212> TYPE: PRT
<213> ORGANISM: Homo sapiens

<400> SEQUENCE: 3041

Asp Cys Asp Glu His Ser Ser Glu Ser Arg
1               5                   10

<210> SEQ ID NO 3042
<211> LENGTH: 10
<212> TYPE: PRT
<213> ORGANISM: Homo sapiens

<400> SEQUENCE: 3042

Cys Asp Glu His Ser Ser Glu Ser Arg Cys
1               5                   10

<210> SEQ ID NO 3043
<211> LENGTH: 10
<212> TYPE: PRT
<213> ORGANISM: Homo sapiens

<400> SEQUENCE: 3043

Asp Glu His Ser Ser Glu Ser Arg Cys Cys
1               5                   10

<210> SEQ ID NO 3044
<211> LENGTH: 10
<212> TYPE: PRT
<213> ORGANISM: Homo sapiens

<400> SEQUENCE: 3044

Glu His Ser Ser Glu Ser Arg Cys Cys Arg
1               5                   10

<210> SEQ ID NO 3045
<211> LENGTH: 10
<212> TYPE: PRT
<213> ORGANISM: Homo sapiens

<400> SEQUENCE: 3045

His Ser Ser Glu Ser Arg Cys Cys Arg Tyr
1               5                   10

<210> SEQ ID NO 3046
<211> LENGTH: 10
<212> TYPE: PRT
<213> ORGANISM: Homo sapiens

<400> SEQUENCE: 3046

Ser Ser Glu Ser Arg Cys Cys Arg Tyr Pro
1               5                   10

<210> SEQ ID NO 3047
<211> LENGTH: 10
<212> TYPE: PRT
<213> ORGANISM: Homo sapiens

<400> SEQUENCE: 3047

Ser Glu Ser Arg Cys Cys Arg Tyr Pro Leu
1               5                   10

<210> SEQ ID NO 3048
<211> LENGTH: 10
<212> TYPE: PRT
<213> ORGANISM: Homo sapiens

<400> SEQUENCE: 3048

Glu Ser Arg Cys Cys Arg Tyr Pro Leu Thr
1               5                   10

<210> SEQ ID NO 3049
<211> LENGTH: 10
<212> TYPE: PRT
<213> ORGANISM: Homo sapiens

<400> SEQUENCE: 3049

Ser Arg Cys Cys Arg Tyr Pro Leu Thr Val
1               5                   10

<210> SEQ ID NO 3050
<211> LENGTH: 10
<212> TYPE: PRT
<213> ORGANISM: Homo sapiens

<400> SEQUENCE: 3050

Arg Cys Cys Arg Tyr Pro Leu Thr Val Asp
1               5                   10

<210> SEQ ID NO 3051
<211> LENGTH: 10
<212> TYPE: PRT
<213> ORGANISM: Homo sapiens

<400> SEQUENCE: 3051

Cys Cys Arg Tyr Pro Leu Thr Val Asp Phe
1               5                   10

<210> SEQ ID NO 3052
<211> LENGTH: 10
<212> TYPE: PRT
<213> ORGANISM: Homo sapiens

<400> SEQUENCE: 3052

Cys Arg Tyr Pro Leu Thr Val Asp Phe Glu
1               5                   10

<210> SEQ ID NO 3053
<211> LENGTH: 10
<212> TYPE: PRT
<213> ORGANISM: Homo sapiens

<400> SEQUENCE: 3053

Arg Tyr Pro Leu Thr Val Asp Phe Glu Ala
1               5                   10

<210> SEQ ID NO 3054
<211> LENGTH: 10
<212> TYPE: PRT
<213> ORGANISM: Homo sapiens

<400> SEQUENCE: 3054

Tyr Pro Leu Thr Val Asp Phe Glu Ala Phe
1               5                   10

<210> SEQ ID NO 3055
<211> LENGTH: 10
<212> TYPE: PRT
<213> ORGANISM: Homo sapiens

<400> SEQUENCE: 3055

Pro Leu Thr Val Asp Phe Glu Ala Phe Gly
1               5                   10

<210> SEQ ID NO 3056
<211> LENGTH: 10
<212> TYPE: PRT
<213> ORGANISM: Homo sapiens

<400> SEQUENCE: 3056

Leu Thr Val Asp Phe Glu Ala Phe Gly Trp
1               5                   10

<210> SEQ ID NO 3057
<211> LENGTH: 10
<212> TYPE: PRT
<213> ORGANISM: Homo sapiens

<400> SEQUENCE: 3057

Thr Val Asp Phe Glu Ala Phe Gly Trp Asp
1               5                   10

<210> SEQ ID NO 3058
<211> LENGTH: 10
<212> TYPE: PRT
<213> ORGANISM: Homo sapiens

<400> SEQUENCE: 3058

Val Asp Phe Glu Ala Phe Gly Trp Asp Trp
1               5                   10

<210> SEQ ID NO 3059
<211> LENGTH: 10
<212> TYPE: PRT
<213> ORGANISM: Homo sapiens

<400> SEQUENCE: 3059

Asp Phe Glu Ala Phe Gly Trp Asp Trp Ile
1               5                   10

<210> SEQ ID NO 3060
<211> LENGTH: 10
<212> TYPE: PRT
<213> ORGANISM: Homo sapiens

<400> SEQUENCE: 3060

Phe Glu Ala Phe Gly Trp Asp Trp Ile Ile
1               5                   10

<210> SEQ ID NO 3061
<211> LENGTH: 10
<212> TYPE: PRT
<213> ORGANISM: Homo sapiens

<400> SEQUENCE: 3061

Glu Ala Phe Gly Trp Asp Trp Ile Ile Ala
1               5                   10

<210> SEQ ID NO 3062
<211> LENGTH: 10
<212> TYPE: PRT
<213> ORGANISM: Homo sapiens

<400> SEQUENCE: 3062

Ala Phe Gly Trp Asp Trp Ile Ile Ala Pro
1               5                   10

<210> SEQ ID NO 3063
<211> LENGTH: 10
<212> TYPE: PRT
<213> ORGANISM: Homo sapiens

<400> SEQUENCE: 3063

Phe Gly Trp Asp Trp Ile Ile Ala Pro Lys
1               5                   10

<210> SEQ ID NO 3064
<211> LENGTH: 10
<212> TYPE: PRT
<213> ORGANISM: Homo sapiens

<400> SEQUENCE: 3064

Gly Trp Asp Trp Ile Ile Ala Pro Lys Arg
1               5                   10

<210> SEQ ID NO 3065
<211> LENGTH: 10
<212> TYPE: PRT
<213> ORGANISM: Homo sapiens

<400> SEQUENCE: 3065

Trp Asp Trp Ile Ile Ala Pro Lys Arg Tyr
1               5                   10

<210> SEQ ID NO 3066
<211> LENGTH: 10

<212> TYPE: PRT
<213> ORGANISM: Homo sapiens

<400> SEQUENCE: 3066

Asp Trp Ile Ile Ala Pro Lys Arg Tyr Lys
1               5                   10

<210> SEQ ID NO 3067
<211> LENGTH: 10
<212> TYPE: PRT
<213> ORGANISM: Homo sapiens

<400> SEQUENCE: 3067

Trp Ile Ile Ala Pro Lys Arg Tyr Lys Ala
1               5                   10

<210> SEQ ID NO 3068
<211> LENGTH: 10
<212> TYPE: PRT
<213> ORGANISM: Homo sapiens

<400> SEQUENCE: 3068

Ile Ile Ala Pro Lys Arg Tyr Lys Ala Asn
1               5                   10

<210> SEQ ID NO 3069
<211> LENGTH: 10
<212> TYPE: PRT
<213> ORGANISM: Homo sapiens

<400> SEQUENCE: 3069

Ile Ala Pro Lys Arg Tyr Lys Ala Asn Tyr
1               5                   10

<210> SEQ ID NO 3070
<211> LENGTH: 10
<212> TYPE: PRT
<213> ORGANISM: Homo sapiens

<400> SEQUENCE: 3070

Ala Pro Lys Arg Tyr Lys Ala Asn Tyr Cys
1               5                   10

<210> SEQ ID NO 3071
<211> LENGTH: 10
<212> TYPE: PRT
<213> ORGANISM: Homo sapiens

<400> SEQUENCE: 3071

Pro Lys Arg Tyr Lys Ala Asn Tyr Cys Ser
1               5                   10

<210> SEQ ID NO 3072
<211> LENGTH: 10
<212> TYPE: PRT
<213> ORGANISM: Homo sapiens

<400> SEQUENCE: 3072

Lys Arg Tyr Lys Ala Asn Tyr Cys Ser Gly
1               5                   10

<210> SEQ ID NO 3073
<211> LENGTH: 10
<212> TYPE: PRT
<213> ORGANISM: Homo sapiens

<400> SEQUENCE: 3073

Arg Tyr Lys Ala Asn Tyr Cys Ser Gly Gln
1               5                   10

<210> SEQ ID NO 3074
<211> LENGTH: 10
<212> TYPE: PRT
<213> ORGANISM: Homo sapiens

<400> SEQUENCE: 3074

Tyr Lys Ala Asn Tyr Cys Ser Gly Gln Cys
1               5                   10

<210> SEQ ID NO 3075
<211> LENGTH: 10
<212> TYPE: PRT
<213> ORGANISM: Homo sapiens

<400> SEQUENCE: 3075

Lys Ala Asn Tyr Cys Ser Gly Gln Cys Glu
1               5                   10

<210> SEQ ID NO 3076
<211> LENGTH: 10
<212> TYPE: PRT
<213> ORGANISM: Homo sapiens

<400> SEQUENCE: 3076

Ala Asn Tyr Cys Ser Gly Gln Cys Glu Tyr
1               5                   10

<210> SEQ ID NO 3077
<211> LENGTH: 10
<212> TYPE: PRT
<213> ORGANISM: Homo sapiens

<400> SEQUENCE: 3077

Asn Tyr Cys Ser Gly Gln Cys Glu Tyr Met
1               5                   10

<210> SEQ ID NO 3078
<211> LENGTH: 10
<212> TYPE: PRT
<213> ORGANISM: Homo sapiens

<400> SEQUENCE: 3078

Tyr Cys Ser Gly Gln Cys Glu Tyr Met Phe
1               5                   10

<210> SEQ ID NO 3079
<211> LENGTH: 10
<212> TYPE: PRT
<213> ORGANISM: Homo sapiens

<400> SEQUENCE: 3079

Cys Ser Gly Gln Cys Glu Tyr Met Phe Met
1               5                   10

<210> SEQ ID NO 3080
<211> LENGTH: 10
<212> TYPE: PRT
<213> ORGANISM: Homo sapiens

<400> SEQUENCE: 3080

Ser Gly Gln Cys Glu Tyr Met Phe Met Gln
1               5                   10

<210> SEQ ID NO 3081
<211> LENGTH: 10
<212> TYPE: PRT
<213> ORGANISM: Homo sapiens

<400> SEQUENCE: 3081

Gly Gln Cys Glu Tyr Met Phe Met Gln Lys
1               5                   10

<210> SEQ ID NO 3082
<211> LENGTH: 10
<212> TYPE: PRT
<213> ORGANISM: Homo sapiens

<400> SEQUENCE: 3082

Gln Cys Glu Tyr Met Phe Met Gln Lys Tyr
1               5                   10

<210> SEQ ID NO 3083
<211> LENGTH: 10
<212> TYPE: PRT
<213> ORGANISM: Homo sapiens

<400> SEQUENCE: 3083

Cys Glu Tyr Met Phe Met Gln Lys Tyr Pro
1               5                   10

<210> SEQ ID NO 3084
<211> LENGTH: 10
<212> TYPE: PRT
<213> ORGANISM: Homo sapiens

<400> SEQUENCE: 3084

Glu Tyr Met Phe Met Gln Lys Tyr Pro His
1               5                   10

<210> SEQ ID NO 3085
<211> LENGTH: 10
<212> TYPE: PRT
<213> ORGANISM: Homo sapiens

<400> SEQUENCE: 3085

Tyr Met Phe Met Gln Lys Tyr Pro His Thr
1               5                   10

<210> SEQ ID NO 3086
<211> LENGTH: 10
<212> TYPE: PRT
<213> ORGANISM: Homo sapiens

<400> SEQUENCE: 3086

Met Phe Met Gln Lys Tyr Pro His Thr His
1               5                   10

<210> SEQ ID NO 3087
<211> LENGTH: 10
<212> TYPE: PRT
<213> ORGANISM: Homo sapiens

<400> SEQUENCE: 3087

Phe Met Gln Lys Tyr Pro His Thr His Leu

-continued

<210> SEQ ID NO 3088
<211> LENGTH: 10
<212> TYPE: PRT
<213> ORGANISM: Homo sapiens

<400> SEQUENCE: 3088

Met Gln Lys Tyr Pro His Thr His Leu Val
1               5                   10

<210> SEQ ID NO 3089
<211> LENGTH: 10
<212> TYPE: PRT
<213> ORGANISM: Homo sapiens

<400> SEQUENCE: 3089

Gln Lys Tyr Pro His Thr His Leu Val Gln
1               5                   10

<210> SEQ ID NO 3090
<211> LENGTH: 10
<212> TYPE: PRT
<213> ORGANISM: Homo sapiens

<400> SEQUENCE: 3090

Lys Tyr Pro His Thr His Leu Val Gln Gln
1               5                   10

<210> SEQ ID NO 3091
<211> LENGTH: 10
<212> TYPE: PRT
<213> ORGANISM: Homo sapiens

<400> SEQUENCE: 3091

Tyr Pro His Thr His Leu Val Gln Gln Ala
1               5                   10

<210> SEQ ID NO 3092
<211> LENGTH: 10
<212> TYPE: PRT
<213> ORGANISM: Homo sapiens

<400> SEQUENCE: 3092

Pro His Thr His Leu Val Gln Gln Ala Asn
1               5                   10

<210> SEQ ID NO 3093
<211> LENGTH: 10
<212> TYPE: PRT
<213> ORGANISM: Homo sapiens

<400> SEQUENCE: 3093

His Thr His Leu Val Gln Gln Ala Asn Pro
1               5                   10

<210> SEQ ID NO 3094
<211> LENGTH: 10
<212> TYPE: PRT
<213> ORGANISM: Homo sapiens

<400> SEQUENCE: 3094

Thr His Leu Val Gln Gln Ala Asn Pro Arg
1               5                   10

<210> SEQ ID NO 3095
<211> LENGTH: 10
<212> TYPE: PRT
<213> ORGANISM: Homo sapiens

<400> SEQUENCE: 3095

His Leu Val Gln Gln Ala Asn Pro Arg Gly
1               5                   10

<210> SEQ ID NO 3096
<211> LENGTH: 10
<212> TYPE: PRT
<213> ORGANISM: Homo sapiens

<400> SEQUENCE: 3096

Leu Val Gln Gln Ala Asn Pro Arg Gly Ser
1               5                   10

<210> SEQ ID NO 3097
<211> LENGTH: 10
<212> TYPE: PRT
<213> ORGANISM: Homo sapiens

<400> SEQUENCE: 3097

Val Gln Gln Ala Asn Pro Arg Gly Ser Ala
1               5                   10

<210> SEQ ID NO 3098
<211> LENGTH: 10
<212> TYPE: PRT
<213> ORGANISM: Homo sapiens

<400> SEQUENCE: 3098

Gln Gln Ala Asn Pro Arg Gly Ser Ala Gly
1               5                   10

<210> SEQ ID NO 3099
<211> LENGTH: 10
<212> TYPE: PRT
<213> ORGANISM: Homo sapiens

<400> SEQUENCE: 3099

Gln Ala Asn Pro Arg Gly Ser Ala Gly Pro
1               5                   10

<210> SEQ ID NO 3100
<211> LENGTH: 10
<212> TYPE: PRT
<213> ORGANISM: Homo sapiens

<400> SEQUENCE: 3100

Ala Asn Pro Arg Gly Ser Ala Gly Pro Cys
1               5                   10

<210> SEQ ID NO 3101
<211> LENGTH: 10
<212> TYPE: PRT
<213> ORGANISM: Homo sapiens

<400> SEQUENCE: 3101

Asn Pro Arg Gly Ser Ala Gly Pro Cys Cys
1               5                   10

<210> SEQ ID NO 3102

```
<211> LENGTH: 10
<212> TYPE: PRT
<213> ORGANISM: Homo sapiens

<400> SEQUENCE: 3102

Pro Arg Gly Ser Ala Gly Pro Cys Cys Thr
1               5                   10

<210> SEQ ID NO 3103
<211> LENGTH: 10
<212> TYPE: PRT
<213> ORGANISM: Homo sapiens

<400> SEQUENCE: 3103

Arg Gly Ser Ala Gly Pro Cys Cys Thr Pro
1               5                   10

<210> SEQ ID NO 3104
<211> LENGTH: 10
<212> TYPE: PRT
<213> ORGANISM: Homo sapiens

<400> SEQUENCE: 3104

Gly Ser Ala Gly Pro Cys Cys Thr Pro Thr
1               5                   10

<210> SEQ ID NO 3105
<211> LENGTH: 10
<212> TYPE: PRT
<213> ORGANISM: Homo sapiens

<400> SEQUENCE: 3105

Ser Ala Gly Pro Cys Cys Thr Pro Thr Lys
1               5                   10

<210> SEQ ID NO 3106
<211> LENGTH: 10
<212> TYPE: PRT
<213> ORGANISM: Homo sapiens

<400> SEQUENCE: 3106

Ala Gly Pro Cys Cys Thr Pro Thr Lys Met
1               5                   10

<210> SEQ ID NO 3107
<211> LENGTH: 10
<212> TYPE: PRT
<213> ORGANISM: Homo sapiens

<400> SEQUENCE: 3107

Gly Pro Cys Cys Thr Pro Thr Lys Met Ser
1               5                   10

<210> SEQ ID NO 3108
<211> LENGTH: 10
<212> TYPE: PRT
<213> ORGANISM: Homo sapiens

<400> SEQUENCE: 3108

Pro Cys Cys Thr Pro Thr Lys Met Ser Pro
1               5                   10

<210> SEQ ID NO 3109
<211> LENGTH: 10
<212> TYPE: PRT
```

<213> ORGANISM: Homo sapiens

<400> SEQUENCE: 3109

Cys Cys Thr Pro Thr Lys Met Ser Pro Ile
1               5                   10

<210> SEQ ID NO 3110
<211> LENGTH: 10
<212> TYPE: PRT
<213> ORGANISM: Homo sapiens

<400> SEQUENCE: 3110

Cys Thr Pro Thr Lys Met Ser Pro Ile Asn
1               5                   10

<210> SEQ ID NO 3111
<211> LENGTH: 10
<212> TYPE: PRT
<213> ORGANISM: Homo sapiens

<400> SEQUENCE: 3111

Thr Pro Thr Lys Met Ser Pro Ile Asn Met
1               5                   10

<210> SEQ ID NO 3112
<211> LENGTH: 10
<212> TYPE: PRT
<213> ORGANISM: Homo sapiens

<400> SEQUENCE: 3112

Pro Thr Lys Met Ser Pro Ile Asn Met Leu
1               5                   10

<210> SEQ ID NO 3113
<211> LENGTH: 10
<212> TYPE: PRT
<213> ORGANISM: Homo sapiens

<400> SEQUENCE: 3113

Thr Lys Met Ser Pro Ile Asn Met Leu Tyr
1               5                   10

<210> SEQ ID NO 3114
<211> LENGTH: 10
<212> TYPE: PRT
<213> ORGANISM: Homo sapiens

<400> SEQUENCE: 3114

Lys Met Ser Pro Ile Asn Met Leu Tyr Phe
1               5                   10

<210> SEQ ID NO 3115
<211> LENGTH: 10
<212> TYPE: PRT
<213> ORGANISM: Homo sapiens

<400> SEQUENCE: 3115

Met Ser Pro Ile Asn Met Leu Tyr Phe Asn
1               5                   10

<210> SEQ ID NO 3116
<211> LENGTH: 10
<212> TYPE: PRT
<213> ORGANISM: Homo sapiens

<400> SEQUENCE: 3116

Ser Pro Ile Asn Met Leu Tyr Phe Asn Asp
1               5                   10

<210> SEQ ID NO 3117
<211> LENGTH: 10
<212> TYPE: PRT
<213> ORGANISM: Homo sapiens

<400> SEQUENCE: 3117

Pro Ile Asn Met Leu Tyr Phe Asn Asp Lys
1               5                   10

<210> SEQ ID NO 3118
<211> LENGTH: 10
<212> TYPE: PRT
<213> ORGANISM: Homo sapiens

<400> SEQUENCE: 3118

Ile Asn Met Leu Tyr Phe Asn Asp Lys Gln
1               5                   10

<210> SEQ ID NO 3119
<211> LENGTH: 10
<212> TYPE: PRT
<213> ORGANISM: Homo sapiens

<400> SEQUENCE: 3119

Asn Met Leu Tyr Phe Asn Asp Lys Gln Gln
1               5                   10

<210> SEQ ID NO 3120
<211> LENGTH: 10
<212> TYPE: PRT
<213> ORGANISM: Homo sapiens

<400> SEQUENCE: 3120

Met Leu Tyr Phe Asn Asp Lys Gln Gln Ile
1               5                   10

<210> SEQ ID NO 3121
<211> LENGTH: 10
<212> TYPE: PRT
<213> ORGANISM: Homo sapiens

<400> SEQUENCE: 3121

Leu Tyr Phe Asn Asp Lys Gln Gln Ile Ile
1               5                   10

<210> SEQ ID NO 3122
<211> LENGTH: 10
<212> TYPE: PRT
<213> ORGANISM: Homo sapiens

<400> SEQUENCE: 3122

Tyr Phe Asn Asp Lys Gln Gln Ile Ile Tyr
1               5                   10

<210> SEQ ID NO 3123
<211> LENGTH: 10
<212> TYPE: PRT
<213> ORGANISM: Homo sapiens

<400> SEQUENCE: 3123

```
Phe Asn Asp Lys Gln Gln Ile Ile Tyr Gly
1               5                   10
```

<210> SEQ ID NO 3124
<211> LENGTH: 10
<212> TYPE: PRT
<213> ORGANISM: Homo sapiens

<400> SEQUENCE: 3124

```
Asn Asp Lys Gln Gln Ile Ile Tyr Gly Lys
1               5                   10
```

<210> SEQ ID NO 3125
<211> LENGTH: 10
<212> TYPE: PRT
<213> ORGANISM: Homo sapiens

<400> SEQUENCE: 3125

```
Asp Lys Gln Gln Ile Ile Tyr Gly Lys Ile
1               5                   10
```

<210> SEQ ID NO 3126
<211> LENGTH: 10
<212> TYPE: PRT
<213> ORGANISM: Homo sapiens

<400> SEQUENCE: 3126

```
Lys Gln Gln Ile Ile Tyr Gly Lys Ile Pro
1               5                   10
```

<210> SEQ ID NO 3127
<211> LENGTH: 10
<212> TYPE: PRT
<213> ORGANISM: Homo sapiens

<400> SEQUENCE: 3127

```
Gln Gln Ile Ile Tyr Gly Lys Ile Pro Gly
1               5                   10
```

<210> SEQ ID NO 3128
<211> LENGTH: 10
<212> TYPE: PRT
<213> ORGANISM: Homo sapiens

<400> SEQUENCE: 3128

```
Gln Ile Ile Tyr Gly Lys Ile Pro Gly Met
1               5                   10
```

<210> SEQ ID NO 3129
<211> LENGTH: 10
<212> TYPE: PRT
<213> ORGANISM: Homo sapiens

<400> SEQUENCE: 3129

```
Ile Ile Tyr Gly Lys Ile Pro Gly Met Val
1               5                   10
```

<210> SEQ ID NO 3130
<211> LENGTH: 10
<212> TYPE: PRT
<213> ORGANISM: Homo sapiens

<400> SEQUENCE: 3130

```
Ile Tyr Gly Lys Ile Pro Gly Met Val Val
1               5                   10
```

<210> SEQ ID NO 3131
<211> LENGTH: 10
<212> TYPE: PRT
<213> ORGANISM: Homo sapiens

<400> SEQUENCE: 3131

Tyr Gly Lys Ile Pro Gly Met Val Val Asp
1               5                   10

<210> SEQ ID NO 3132
<211> LENGTH: 10
<212> TYPE: PRT
<213> ORGANISM: Homo sapiens

<400> SEQUENCE: 3132

Gly Lys Ile Pro Gly Met Val Val Asp Arg
1               5                   10

<210> SEQ ID NO 3133
<211> LENGTH: 10
<212> TYPE: PRT
<213> ORGANISM: Homo sapiens

<400> SEQUENCE: 3133

Lys Ile Pro Gly Met Val Val Asp Arg Cys
1               5                   10

<210> SEQ ID NO 3134
<211> LENGTH: 10
<212> TYPE: PRT
<213> ORGANISM: Homo sapiens

<400> SEQUENCE: 3134

Ile Pro Gly Met Val Val Asp Arg Cys Gly
1               5                   10

<210> SEQ ID NO 3135
<211> LENGTH: 10
<212> TYPE: PRT
<213> ORGANISM: Homo sapiens

<400> SEQUENCE: 3135

Pro Gly Met Val Val Asp Arg Cys Gly Cys
1               5                   10

<210> SEQ ID NO 3136
<211> LENGTH: 10
<212> TYPE: PRT
<213> ORGANISM: Homo sapiens

<400> SEQUENCE: 3136

Gly Met Val Val Asp Arg Cys Gly Cys Ser
1               5                   10

<210> SEQ ID NO 3137
<211> LENGTH: 11
<212> TYPE: PRT
<213> ORGANISM: Homo sapiens

<400> SEQUENCE: 3137

Met Val Leu Ala Ala Pro Leu Leu Leu Gly Phe
1               5                   10

<210> SEQ ID NO 3138
<211> LENGTH: 11
<212> TYPE: PRT
<213> ORGANISM: Homo sapiens

<400> SEQUENCE: 3138

Val Leu Ala Ala Pro Leu Leu Leu Gly Phe Leu
1               5                   10

<210> SEQ ID NO 3139
<211> LENGTH: 11
<212> TYPE: PRT
<213> ORGANISM: Homo sapiens

<400> SEQUENCE: 3139

Leu Ala Ala Pro Leu Leu Leu Gly Phe Leu Leu
1               5                   10

<210> SEQ ID NO 3140
<211> LENGTH: 11
<212> TYPE: PRT
<213> ORGANISM: Homo sapiens

<400> SEQUENCE: 3140

Ala Ala Pro Leu Leu Leu Gly Phe Leu Leu Leu
1               5                   10

<210> SEQ ID NO 3141
<211> LENGTH: 11
<212> TYPE: PRT
<213> ORGANISM: Homo sapiens

<400> SEQUENCE: 3141

Ala Pro Leu Leu Leu Gly Phe Leu Leu Leu Ala
1               5                   10

<210> SEQ ID NO 3142
<211> LENGTH: 11
<212> TYPE: PRT
<213> ORGANISM: Homo sapiens

<400> SEQUENCE: 3142

Pro Leu Leu Leu Gly Phe Leu Leu Leu Ala Leu
1               5                   10

<210> SEQ ID NO 3143
<211> LENGTH: 11
<212> TYPE: PRT
<213> ORGANISM: Homo sapiens

<400> SEQUENCE: 3143

Leu Leu Leu Gly Phe Leu Leu Leu Ala Leu Glu
1               5                   10

<210> SEQ ID NO 3144
<211> LENGTH: 11
<212> TYPE: PRT
<213> ORGANISM: Homo sapiens

<400> SEQUENCE: 3144

Leu Leu Gly Phe Leu Leu Leu Ala Leu Glu Leu
1               5                   10

<210> SEQ ID NO 3145
<211> LENGTH: 11

<212> TYPE: PRT
<213> ORGANISM: Homo sapiens

<400> SEQUENCE: 3145

Leu Gly Phe Leu Leu Ala Leu Glu Leu Arg
1               5                   10

<210> SEQ ID NO 3146
<211> LENGTH: 11
<212> TYPE: PRT
<213> ORGANISM: Homo sapiens

<400> SEQUENCE: 3146

Gly Phe Leu Leu Leu Ala Leu Glu Leu Arg Pro
1               5                   10

<210> SEQ ID NO 3147
<211> LENGTH: 11
<212> TYPE: PRT
<213> ORGANISM: Homo sapiens

<400> SEQUENCE: 3147

Phe Leu Leu Leu Ala Leu Glu Leu Arg Pro Arg
1               5                   10

<210> SEQ ID NO 3148
<211> LENGTH: 11
<212> TYPE: PRT
<213> ORGANISM: Homo sapiens

<400> SEQUENCE: 3148

Leu Leu Leu Ala Leu Glu Leu Arg Pro Arg Gly
1               5                   10

<210> SEQ ID NO 3149
<211> LENGTH: 11
<212> TYPE: PRT
<213> ORGANISM: Homo sapiens

<400> SEQUENCE: 3149

Leu Leu Ala Leu Glu Leu Arg Pro Arg Gly Glu
1               5                   10

<210> SEQ ID NO 3150
<211> LENGTH: 11
<212> TYPE: PRT
<213> ORGANISM: Homo sapiens

<400> SEQUENCE: 3150

Leu Ala Leu Glu Leu Arg Pro Arg Gly Glu Ala
1               5                   10

<210> SEQ ID NO 3151
<211> LENGTH: 11
<212> TYPE: PRT
<213> ORGANISM: Homo sapiens

<400> SEQUENCE: 3151

Ala Leu Glu Leu Arg Pro Arg Gly Glu Ala Ala
1               5                   10

<210> SEQ ID NO 3152
<211> LENGTH: 11
<212> TYPE: PRT
<213> ORGANISM: Homo sapiens

<400> SEQUENCE: 3152

Leu Glu Leu Arg Pro Arg Gly Glu Ala Ala Glu
1               5                   10

<210> SEQ ID NO 3153
<211> LENGTH: 11
<212> TYPE: PRT
<213> ORGANISM: Homo sapiens

<400> SEQUENCE: 3153

Glu Leu Arg Pro Arg Gly Glu Ala Ala Glu Gly
1               5                   10

<210> SEQ ID NO 3154
<211> LENGTH: 11
<212> TYPE: PRT
<213> ORGANISM: Homo sapiens

<400> SEQUENCE: 3154

Leu Arg Pro Arg Gly Glu Ala Ala Glu Gly Pro
1               5                   10

<210> SEQ ID NO 3155
<211> LENGTH: 11
<212> TYPE: PRT
<213> ORGANISM: Homo sapiens

<400> SEQUENCE: 3155

Arg Pro Arg Gly Glu Ala Ala Glu Gly Pro Ala
1               5                   10

<210> SEQ ID NO 3156
<211> LENGTH: 11
<212> TYPE: PRT
<213> ORGANISM: Homo sapiens

<400> SEQUENCE: 3156

Pro Arg Gly Glu Ala Ala Glu Gly Pro Ala Ala
1               5                   10

<210> SEQ ID NO 3157
<211> LENGTH: 11
<212> TYPE: PRT
<213> ORGANISM: Homo sapiens

<400> SEQUENCE: 3157

Arg Gly Glu Ala Ala Glu Gly Pro Ala Ala Ala
1               5                   10

<210> SEQ ID NO 3158
<211> LENGTH: 11
<212> TYPE: PRT
<213> ORGANISM: Homo sapiens

<400> SEQUENCE: 3158

Gly Glu Ala Ala Glu Gly Pro Ala Ala Ala Ala
1               5                   10

<210> SEQ ID NO 3159
<211> LENGTH: 11
<212> TYPE: PRT
<213> ORGANISM: Homo sapiens

<400> SEQUENCE: 3159

Glu Ala Ala Glu Gly Pro Ala Ala Ala Ala
1               5                   10

<210> SEQ ID NO 3160
<211> LENGTH: 11
<212> TYPE: PRT
<213> ORGANISM: Homo sapiens

<400> SEQUENCE: 3160

Ala Ala Glu Gly Pro Ala Ala Ala Ala Ala
1               5                   10

<210> SEQ ID NO 3161
<211> LENGTH: 11
<212> TYPE: PRT
<213> ORGANISM: Homo sapiens

<400> SEQUENCE: 3161

Ala Glu Gly Pro Ala Ala Ala Ala Ala Ala
1               5                   10

<210> SEQ ID NO 3162
<211> LENGTH: 11
<212> TYPE: PRT
<213> ORGANISM: Homo sapiens

<400> SEQUENCE: 3162

Glu Gly Pro Ala Ala Ala Ala Ala Ala Ala
1               5                   10

<210> SEQ ID NO 3163
<211> LENGTH: 11
<212> TYPE: PRT
<213> ORGANISM: Homo sapiens

<400> SEQUENCE: 3163

Gly Pro Ala Ala Ala Ala Ala Ala Ala Ala
1               5                   10

<210> SEQ ID NO 3164
<211> LENGTH: 11
<212> TYPE: PRT
<213> ORGANISM: Homo sapiens

<400> SEQUENCE: 3164

Pro Ala Ala Ala Ala Ala Ala Ala Ala Ala
1               5                   10

<210> SEQ ID NO 3165
<211> LENGTH: 11
<212> TYPE: PRT
<213> ORGANISM: Homo sapiens

<400> SEQUENCE: 3165

Ala Ala Ala Ala Ala Ala Ala Ala Ala Ala
1               5                   10

<210> SEQ ID NO 3166
<211> LENGTH: 11
<212> TYPE: PRT
<213> ORGANISM: Homo sapiens

<400> SEQUENCE: 3166

Ala Ala Ala Ala Ala Ala Ala Ala Ala Ala Gly

```
1               5                   10
```

<210> SEQ ID NO 3167
<211> LENGTH: 11
<212> TYPE: PRT
<213> ORGANISM: Homo sapiens

<400> SEQUENCE: 3167

```
Ala Ala Ala Ala Ala Ala Ala Ala Ala Gly Val
1               5                   10
```

<210> SEQ ID NO 3168
<211> LENGTH: 11
<212> TYPE: PRT
<213> ORGANISM: Homo sapiens

<400> SEQUENCE: 3168

```
Ala Ala Ala Ala Ala Ala Ala Ala Gly Val Gly
1               5                   10
```

<210> SEQ ID NO 3169
<211> LENGTH: 11
<212> TYPE: PRT
<213> ORGANISM: Homo sapiens

<400> SEQUENCE: 3169

```
Ala Ala Ala Ala Ala Ala Ala Gly Val Gly Gly
1               5                   10
```

<210> SEQ ID NO 3170
<211> LENGTH: 11
<212> TYPE: PRT
<213> ORGANISM: Homo sapiens

<400> SEQUENCE: 3170

```
Ala Ala Ala Ala Ala Ala Gly Val Gly Gly Glu
1               5                   10
```

<210> SEQ ID NO 3171
<211> LENGTH: 11
<212> TYPE: PRT
<213> ORGANISM: Homo sapiens

<400> SEQUENCE: 3171

```
Ala Ala Ala Ala Ala Gly Val Gly Gly Glu Arg
1               5                   10
```

<210> SEQ ID NO 3172
<211> LENGTH: 11
<212> TYPE: PRT
<213> ORGANISM: Homo sapiens

<400> SEQUENCE: 3172

```
Ala Ala Ala Ala Gly Val Gly Gly Glu Arg Ser
1               5                   10
```

<210> SEQ ID NO 3173
<211> LENGTH: 11
<212> TYPE: PRT
<213> ORGANISM: Homo sapiens

<400> SEQUENCE: 3173

```
Ala Ala Ala Gly Val Gly Gly Glu Arg Ser Ser
1               5                   10
```

<210> SEQ ID NO 3174
<211> LENGTH: 11
<212> TYPE: PRT
<213> ORGANISM: Homo sapiens

<400> SEQUENCE: 3174

Ala Ala Gly Val Gly Gly Glu Arg Ser Ser Arg
1               5                   10

<210> SEQ ID NO 3175
<211> LENGTH: 11
<212> TYPE: PRT
<213> ORGANISM: Homo sapiens

<400> SEQUENCE: 3175

Ala Gly Val Gly Gly Glu Arg Ser Ser Arg Pro
1               5                   10

<210> SEQ ID NO 3176
<211> LENGTH: 11
<212> TYPE: PRT
<213> ORGANISM: Homo sapiens

<400> SEQUENCE: 3176

Gly Val Gly Gly Glu Arg Ser Ser Arg Pro Ala
1               5                   10

<210> SEQ ID NO 3177
<211> LENGTH: 11
<212> TYPE: PRT
<213> ORGANISM: Homo sapiens

<400> SEQUENCE: 3177

Val Gly Gly Glu Arg Ser Ser Arg Pro Ala Pro
1               5                   10

<210> SEQ ID NO 3178
<211> LENGTH: 11
<212> TYPE: PRT
<213> ORGANISM: Homo sapiens

<400> SEQUENCE: 3178

Gly Gly Glu Arg Ser Ser Arg Pro Ala Pro Ser
1               5                   10

<210> SEQ ID NO 3179
<211> LENGTH: 11
<212> TYPE: PRT
<213> ORGANISM: Homo sapiens

<400> SEQUENCE: 3179

Gly Glu Arg Ser Ser Arg Pro Ala Pro Ser Val
1               5                   10

<210> SEQ ID NO 3180
<211> LENGTH: 11
<212> TYPE: PRT
<213> ORGANISM: Homo sapiens

<400> SEQUENCE: 3180

Glu Arg Ser Ser Arg Pro Ala Pro Ser Val Ala
1               5                   10

<210> SEQ ID NO 3181

<211> LENGTH: 11
<212> TYPE: PRT
<213> ORGANISM: Homo sapiens

<400> SEQUENCE: 3181

Arg Ser Ser Arg Pro Ala Pro Ser Val Ala Pro
1               5                   10

<210> SEQ ID NO 3182
<211> LENGTH: 11
<212> TYPE: PRT
<213> ORGANISM: Homo sapiens

<400> SEQUENCE: 3182

Ser Ser Arg Pro Ala Pro Ser Val Ala Pro Glu
1               5                   10

<210> SEQ ID NO 3183
<211> LENGTH: 11
<212> TYPE: PRT
<213> ORGANISM: Homo sapiens

<400> SEQUENCE: 3183

Ser Arg Pro Ala Pro Ser Val Ala Pro Glu Pro
1               5                   10

<210> SEQ ID NO 3184
<211> LENGTH: 11
<212> TYPE: PRT
<213> ORGANISM: Homo sapiens

<400> SEQUENCE: 3184

Arg Pro Ala Pro Ser Val Ala Pro Glu Pro Asp
1               5                   10

<210> SEQ ID NO 3185
<211> LENGTH: 11
<212> TYPE: PRT
<213> ORGANISM: Homo sapiens

<400> SEQUENCE: 3185

Pro Ala Pro Ser Val Ala Pro Glu Pro Asp Gly
1               5                   10

<210> SEQ ID NO 3186
<211> LENGTH: 11
<212> TYPE: PRT
<213> ORGANISM: Homo sapiens

<400> SEQUENCE: 3186

Ala Pro Ser Val Ala Pro Glu Pro Asp Gly Cys
1               5                   10

<210> SEQ ID NO 3187
<211> LENGTH: 11
<212> TYPE: PRT
<213> ORGANISM: Homo sapiens

<400> SEQUENCE: 3187

Pro Ser Val Ala Pro Glu Pro Asp Gly Cys Pro
1               5                   10

<210> SEQ ID NO 3188
<211> LENGTH: 11
<212> TYPE: PRT

<213> ORGANISM: Homo sapiens

<400> SEQUENCE: 3188

Ser Val Ala Pro Glu Pro Asp Gly Cys Pro Val
1               5                   10

<210> SEQ ID NO 3189
<211> LENGTH: 11
<212> TYPE: PRT
<213> ORGANISM: Homo sapiens

<400> SEQUENCE: 3189

Val Ala Pro Glu Pro Asp Gly Cys Pro Val Cys
1               5                   10

<210> SEQ ID NO 3190
<211> LENGTH: 11
<212> TYPE: PRT
<213> ORGANISM: Homo sapiens

<400> SEQUENCE: 3190

Ala Pro Glu Pro Asp Gly Cys Pro Val Cys Val
1               5                   10

<210> SEQ ID NO 3191
<211> LENGTH: 11
<212> TYPE: PRT
<213> ORGANISM: Homo sapiens

<400> SEQUENCE: 3191

Pro Glu Pro Asp Gly Cys Pro Val Cys Val Trp
1               5                   10

<210> SEQ ID NO 3192
<211> LENGTH: 11
<212> TYPE: PRT
<213> ORGANISM: Homo sapiens

<400> SEQUENCE: 3192

Glu Pro Asp Gly Cys Pro Val Cys Val Trp Arg
1               5                   10

<210> SEQ ID NO 3193
<211> LENGTH: 11
<212> TYPE: PRT
<213> ORGANISM: Homo sapiens

<400> SEQUENCE: 3193

Pro Asp Gly Cys Pro Val Cys Val Trp Arg Gln
1               5                   10

<210> SEQ ID NO 3194
<211> LENGTH: 11
<212> TYPE: PRT
<213> ORGANISM: Homo sapiens

<400> SEQUENCE: 3194

Asp Gly Cys Pro Val Cys Val Trp Arg Gln His
1               5                   10

<210> SEQ ID NO 3195
<211> LENGTH: 11
<212> TYPE: PRT
<213> ORGANISM: Homo sapiens

<400> SEQUENCE: 3195

Gly Cys Pro Val Cys Val Trp Arg Gln His Ser
1               5                   10

<210> SEQ ID NO 3196
<211> LENGTH: 11
<212> TYPE: PRT
<213> ORGANISM: Homo sapiens

<400> SEQUENCE: 3196

Cys Pro Val Cys Val Trp Arg Gln His Ser Arg
1               5                   10

<210> SEQ ID NO 3197
<211> LENGTH: 11
<212> TYPE: PRT
<213> ORGANISM: Homo sapiens

<400> SEQUENCE: 3197

Pro Val Cys Val Trp Arg Gln His Ser Arg Glu
1               5                   10

<210> SEQ ID NO 3198
<211> LENGTH: 11
<212> TYPE: PRT
<213> ORGANISM: Homo sapiens

<400> SEQUENCE: 3198

Val Cys Val Trp Arg Gln His Ser Arg Glu Leu
1               5                   10

<210> SEQ ID NO 3199
<211> LENGTH: 11
<212> TYPE: PRT
<213> ORGANISM: Homo sapiens

<400> SEQUENCE: 3199

Cys Val Trp Arg Gln His Ser Arg Glu Leu Arg
1               5                   10

<210> SEQ ID NO 3200
<211> LENGTH: 11
<212> TYPE: PRT
<213> ORGANISM: Homo sapiens

<400> SEQUENCE: 3200

Val Trp Arg Gln His Ser Arg Glu Leu Arg Leu
1               5                   10

<210> SEQ ID NO 3201
<211> LENGTH: 11
<212> TYPE: PRT
<213> ORGANISM: Homo sapiens

<400> SEQUENCE: 3201

Trp Arg Gln His Ser Arg Glu Leu Arg Leu Glu
1               5                   10

<210> SEQ ID NO 3202
<211> LENGTH: 11
<212> TYPE: PRT
<213> ORGANISM: Homo sapiens

<400> SEQUENCE: 3202

```
Arg Gln His Ser Arg Glu Leu Arg Leu Glu Ser
1               5                   10

<210> SEQ ID NO 3203
<211> LENGTH: 11
<212> TYPE: PRT
<213> ORGANISM: Homo sapiens

<400> SEQUENCE: 3203

Gln His Ser Arg Glu Leu Arg Leu Glu Ser Ile
1               5                   10

<210> SEQ ID NO 3204
<211> LENGTH: 11
<212> TYPE: PRT
<213> ORGANISM: Homo sapiens

<400> SEQUENCE: 3204

His Ser Arg Glu Leu Arg Leu Glu Ser Ile Lys
1               5                   10

<210> SEQ ID NO 3205
<211> LENGTH: 11
<212> TYPE: PRT
<213> ORGANISM: Homo sapiens

<400> SEQUENCE: 3205

Ser Arg Glu Leu Arg Leu Glu Ser Ile Lys Ser
1               5                   10

<210> SEQ ID NO 3206
<211> LENGTH: 11
<212> TYPE: PRT
<213> ORGANISM: Homo sapiens

<400> SEQUENCE: 3206

Arg Glu Leu Arg Leu Glu Ser Ile Lys Ser Gln
1               5                   10

<210> SEQ ID NO 3207
<211> LENGTH: 11
<212> TYPE: PRT
<213> ORGANISM: Homo sapiens

<400> SEQUENCE: 3207

Glu Leu Arg Leu Glu Ser Ile Lys Ser Gln Ile
1               5                   10

<210> SEQ ID NO 3208
<211> LENGTH: 11
<212> TYPE: PRT
<213> ORGANISM: Homo sapiens

<400> SEQUENCE: 3208

Leu Arg Leu Glu Ser Ile Lys Ser Gln Ile Leu
1               5                   10

<210> SEQ ID NO 3209
<211> LENGTH: 11
<212> TYPE: PRT
<213> ORGANISM: Homo sapiens

<400> SEQUENCE: 3209

Arg Leu Glu Ser Ile Lys Ser Gln Ile Leu Ser
1               5                   10
```

```
<210> SEQ ID NO 3210
<211> LENGTH: 11
<212> TYPE: PRT
<213> ORGANISM: Homo sapiens

<400> SEQUENCE: 3210

Leu Glu Ser Ile Lys Ser Gln Ile Leu Ser Lys
1               5                   10

<210> SEQ ID NO 3211
<211> LENGTH: 11
<212> TYPE: PRT
<213> ORGANISM: Homo sapiens

<400> SEQUENCE: 3211

Glu Ser Ile Lys Ser Gln Ile Leu Ser Lys Leu
1               5                   10

<210> SEQ ID NO 3212
<211> LENGTH: 11
<212> TYPE: PRT
<213> ORGANISM: Homo sapiens

<400> SEQUENCE: 3212

Ser Ile Lys Ser Gln Ile Leu Ser Lys Leu Arg
1               5                   10

<210> SEQ ID NO 3213
<211> LENGTH: 11
<212> TYPE: PRT
<213> ORGANISM: Homo sapiens

<400> SEQUENCE: 3213

Ile Lys Ser Gln Ile Leu Ser Lys Leu Arg Leu
1               5                   10

<210> SEQ ID NO 3214
<211> LENGTH: 11
<212> TYPE: PRT
<213> ORGANISM: Homo sapiens

<400> SEQUENCE: 3214

Lys Ser Gln Ile Leu Ser Lys Leu Arg Leu Lys
1               5                   10

<210> SEQ ID NO 3215
<211> LENGTH: 11
<212> TYPE: PRT
<213> ORGANISM: Homo sapiens

<400> SEQUENCE: 3215

Ser Gln Ile Leu Ser Lys Leu Arg Leu Lys Glu
1               5                   10

<210> SEQ ID NO 3216
<211> LENGTH: 11
<212> TYPE: PRT
<213> ORGANISM: Homo sapiens

<400> SEQUENCE: 3216

Gln Ile Leu Ser Lys Leu Arg Leu Lys Glu Ala
1               5                   10
```

<210> SEQ ID NO 3217
<211> LENGTH: 11
<212> TYPE: PRT
<213> ORGANISM: Homo sapiens

<400> SEQUENCE: 3217

Ile Leu Ser Lys Leu Arg Leu Lys Glu Ala Pro
1               5                   10

<210> SEQ ID NO 3218
<211> LENGTH: 11
<212> TYPE: PRT
<213> ORGANISM: Homo sapiens

<400> SEQUENCE: 3218

Leu Ser Lys Leu Arg Leu Lys Glu Ala Pro Asn
1               5                   10

<210> SEQ ID NO 3219
<211> LENGTH: 11
<212> TYPE: PRT
<213> ORGANISM: Homo sapiens

<400> SEQUENCE: 3219

Ser Lys Leu Arg Leu Lys Glu Ala Pro Asn Ile
1               5                   10

<210> SEQ ID NO 3220
<211> LENGTH: 11
<212> TYPE: PRT
<213> ORGANISM: Homo sapiens

<400> SEQUENCE: 3220

Lys Leu Arg Leu Lys Glu Ala Pro Asn Ile Ser
1               5                   10

<210> SEQ ID NO 3221
<211> LENGTH: 11
<212> TYPE: PRT
<213> ORGANISM: Homo sapiens

<400> SEQUENCE: 3221

Leu Arg Leu Lys Glu Ala Pro Asn Ile Ser Arg
1               5                   10

<210> SEQ ID NO 3222
<211> LENGTH: 11
<212> TYPE: PRT
<213> ORGANISM: Homo sapiens

<400> SEQUENCE: 3222

Arg Leu Lys Glu Ala Pro Asn Ile Ser Arg Glu
1               5                   10

<210> SEQ ID NO 3223
<211> LENGTH: 11
<212> TYPE: PRT
<213> ORGANISM: Homo sapiens

<400> SEQUENCE: 3223

Leu Lys Glu Ala Pro Asn Ile Ser Arg Glu Val
1               5                   10

<210> SEQ ID NO 3224
<211> LENGTH: 11

```
<212> TYPE: PRT
<213> ORGANISM: Homo sapiens

<400> SEQUENCE: 3224

Lys Glu Ala Pro Asn Ile Ser Arg Glu Val Val
1               5                   10

<210> SEQ ID NO 3225
<211> LENGTH: 11
<212> TYPE: PRT
<213> ORGANISM: Homo sapiens

<400> SEQUENCE: 3225

Glu Ala Pro Asn Ile Ser Arg Glu Val Val Lys
1               5                   10

<210> SEQ ID NO 3226
<211> LENGTH: 11
<212> TYPE: PRT
<213> ORGANISM: Homo sapiens

<400> SEQUENCE: 3226

Ala Pro Asn Ile Ser Arg Glu Val Val Lys Gln
1               5                   10

<210> SEQ ID NO 3227
<211> LENGTH: 11
<212> TYPE: PRT
<213> ORGANISM: Homo sapiens

<400> SEQUENCE: 3227

Pro Asn Ile Ser Arg Glu Val Val Lys Gln Leu
1               5                   10

<210> SEQ ID NO 3228
<211> LENGTH: 11
<212> TYPE: PRT
<213> ORGANISM: Homo sapiens

<400> SEQUENCE: 3228

Asn Ile Ser Arg Glu Val Val Lys Gln Leu Leu
1               5                   10

<210> SEQ ID NO 3229
<211> LENGTH: 11
<212> TYPE: PRT
<213> ORGANISM: Homo sapiens

<400> SEQUENCE: 3229

Ile Ser Arg Glu Val Val Lys Gln Leu Leu Pro
1               5                   10

<210> SEQ ID NO 3230
<211> LENGTH: 11
<212> TYPE: PRT
<213> ORGANISM: Homo sapiens

<400> SEQUENCE: 3230

Ser Arg Glu Val Val Lys Gln Leu Leu Pro Lys
1               5                   10

<210> SEQ ID NO 3231
<211> LENGTH: 11
<212> TYPE: PRT
<213> ORGANISM: Homo sapiens
```

<400> SEQUENCE: 3231

Arg Glu Val Val Lys Gln Leu Leu Pro Lys Ala
1               5                   10

<210> SEQ ID NO 3232
<211> LENGTH: 11
<212> TYPE: PRT
<213> ORGANISM: Homo sapiens

<400> SEQUENCE: 3232

Glu Val Val Lys Gln Leu Leu Pro Lys Ala Pro
1               5                   10

<210> SEQ ID NO 3233
<211> LENGTH: 11
<212> TYPE: PRT
<213> ORGANISM: Homo sapiens

<400> SEQUENCE: 3233

Val Val Lys Gln Leu Leu Pro Lys Ala Pro Pro
1               5                   10

<210> SEQ ID NO 3234
<211> LENGTH: 11
<212> TYPE: PRT
<213> ORGANISM: Homo sapiens

<400> SEQUENCE: 3234

Val Lys Gln Leu Leu Pro Lys Ala Pro Pro Leu
1               5                   10

<210> SEQ ID NO 3235
<211> LENGTH: 11
<212> TYPE: PRT
<213> ORGANISM: Homo sapiens

<400> SEQUENCE: 3235

Lys Gln Leu Leu Pro Lys Ala Pro Pro Leu Gln
1               5                   10

<210> SEQ ID NO 3236
<211> LENGTH: 11
<212> TYPE: PRT
<213> ORGANISM: Homo sapiens

<400> SEQUENCE: 3236

Gln Leu Leu Pro Lys Ala Pro Pro Leu Gln Gln
1               5                   10

<210> SEQ ID NO 3237
<211> LENGTH: 11
<212> TYPE: PRT
<213> ORGANISM: Homo sapiens

<400> SEQUENCE: 3237

Leu Leu Pro Lys Ala Pro Pro Leu Gln Gln Ile
1               5                   10

<210> SEQ ID NO 3238
<211> LENGTH: 11
<212> TYPE: PRT
<213> ORGANISM: Homo sapiens

<400> SEQUENCE: 3238

```
Leu Pro Lys Ala Pro Pro Leu Gln Gln Ile Leu
1               5                   10
```

<210> SEQ ID NO 3239
<211> LENGTH: 11
<212> TYPE: PRT
<213> ORGANISM: Homo sapiens

<400> SEQUENCE: 3239

```
Pro Lys Ala Pro Pro Leu Gln Gln Ile Leu Asp
1               5                   10
```

<210> SEQ ID NO 3240
<211> LENGTH: 11
<212> TYPE: PRT
<213> ORGANISM: Homo sapiens

<400> SEQUENCE: 3240

```
Lys Ala Pro Pro Leu Gln Gln Ile Leu Asp Leu
1               5                   10
```

<210> SEQ ID NO 3241
<211> LENGTH: 11
<212> TYPE: PRT
<213> ORGANISM: Homo sapiens

<400> SEQUENCE: 3241

```
Ala Pro Pro Leu Gln Gln Ile Leu Asp Leu His
1               5                   10
```

<210> SEQ ID NO 3242
<211> LENGTH: 11
<212> TYPE: PRT
<213> ORGANISM: Homo sapiens

<400> SEQUENCE: 3242

```
Pro Pro Leu Gln Gln Ile Leu Asp Leu His Asp
1               5                   10
```

<210> SEQ ID NO 3243
<211> LENGTH: 11
<212> TYPE: PRT
<213> ORGANISM: Homo sapiens

<400> SEQUENCE: 3243

```
Pro Leu Gln Gln Ile Leu Asp Leu His Asp Phe
1               5                   10
```

<210> SEQ ID NO 3244
<211> LENGTH: 11
<212> TYPE: PRT
<213> ORGANISM: Homo sapiens

<400> SEQUENCE: 3244

```
Leu Gln Gln Ile Leu Asp Leu His Asp Phe Gln
1               5                   10
```

<210> SEQ ID NO 3245
<211> LENGTH: 11
<212> TYPE: PRT
<213> ORGANISM: Homo sapiens

<400> SEQUENCE: 3245

```
Gln Gln Ile Leu Asp Leu His Asp Phe Gln Gly
```

```
1               5                   10

<210> SEQ ID NO 3246
<211> LENGTH: 11
<212> TYPE: PRT
<213> ORGANISM: Homo sapiens

<400> SEQUENCE: 3246

Gln Ile Leu Asp Leu His Asp Phe Gln Gly Asp
1               5                   10

<210> SEQ ID NO 3247
<211> LENGTH: 11
<212> TYPE: PRT
<213> ORGANISM: Homo sapiens

<400> SEQUENCE: 3247

Ile Leu Asp Leu His Asp Phe Gln Gly Asp Ala
1               5                   10

<210> SEQ ID NO 3248
<211> LENGTH: 11
<212> TYPE: PRT
<213> ORGANISM: Homo sapiens

<400> SEQUENCE: 3248

Leu Asp Leu His Asp Phe Gln Gly Asp Ala Leu
1               5                   10

<210> SEQ ID NO 3249
<211> LENGTH: 11
<212> TYPE: PRT
<213> ORGANISM: Homo sapiens

<400> SEQUENCE: 3249

Asp Leu His Asp Phe Gln Gly Asp Ala Leu Gln
1               5                   10

<210> SEQ ID NO 3250
<211> LENGTH: 11
<212> TYPE: PRT
<213> ORGANISM: Homo sapiens

<400> SEQUENCE: 3250

Leu His Asp Phe Gln Gly Asp Ala Leu Gln Pro
1               5                   10

<210> SEQ ID NO 3251
<211> LENGTH: 11
<212> TYPE: PRT
<213> ORGANISM: Homo sapiens

<400> SEQUENCE: 3251

His Asp Phe Gln Gly Asp Ala Leu Gln Pro Glu
1               5                   10

<210> SEQ ID NO 3252
<211> LENGTH: 11
<212> TYPE: PRT
<213> ORGANISM: Homo sapiens

<400> SEQUENCE: 3252

Asp Phe Gln Gly Asp Ala Leu Gln Pro Glu Asp
1               5                   10
```

<210> SEQ ID NO 3253
<211> LENGTH: 11
<212> TYPE: PRT
<213> ORGANISM: Homo sapiens

<400> SEQUENCE: 3253

Phe Gln Gly Asp Ala Leu Gln Pro Glu Asp Phe
1               5                   10

<210> SEQ ID NO 3254
<211> LENGTH: 11
<212> TYPE: PRT
<213> ORGANISM: Homo sapiens

<400> SEQUENCE: 3254

Gln Gly Asp Ala Leu Gln Pro Glu Asp Phe Leu
1               5                   10

<210> SEQ ID NO 3255
<211> LENGTH: 11
<212> TYPE: PRT
<213> ORGANISM: Homo sapiens

<400> SEQUENCE: 3255

Gly Asp Ala Leu Gln Pro Glu Asp Phe Leu Glu
1               5                   10

<210> SEQ ID NO 3256
<211> LENGTH: 11
<212> TYPE: PRT
<213> ORGANISM: Homo sapiens

<400> SEQUENCE: 3256

Asp Ala Leu Gln Pro Glu Asp Phe Leu Glu Glu
1               5                   10

<210> SEQ ID NO 3257
<211> LENGTH: 11
<212> TYPE: PRT
<213> ORGANISM: Homo sapiens

<400> SEQUENCE: 3257

Ala Leu Gln Pro Glu Asp Phe Leu Glu Glu Asp
1               5                   10

<210> SEQ ID NO 3258
<211> LENGTH: 11
<212> TYPE: PRT
<213> ORGANISM: Homo sapiens

<400> SEQUENCE: 3258

Leu Gln Pro Glu Asp Phe Leu Glu Glu Asp Glu
1               5                   10

<210> SEQ ID NO 3259
<211> LENGTH: 11
<212> TYPE: PRT
<213> ORGANISM: Homo sapiens

<400> SEQUENCE: 3259

Gln Pro Glu Asp Phe Leu Glu Glu Asp Glu Tyr
1               5                   10

<210> SEQ ID NO 3260

```
<211> LENGTH: 11
<212> TYPE: PRT
<213> ORGANISM: Homo sapiens

<400> SEQUENCE: 3260

Pro Glu Asp Phe Leu Glu Glu Asp Glu Tyr His
1               5                   10

<210> SEQ ID NO 3261
<211> LENGTH: 11
<212> TYPE: PRT
<213> ORGANISM: Homo sapiens

<400> SEQUENCE: 3261

Glu Asp Phe Leu Glu Glu Asp Glu Tyr His Ala
1               5                   10

<210> SEQ ID NO 3262
<211> LENGTH: 11
<212> TYPE: PRT
<213> ORGANISM: Homo sapiens

<400> SEQUENCE: 3262

Asp Phe Leu Glu Glu Asp Glu Tyr His Ala Thr
1               5                   10

<210> SEQ ID NO 3263
<211> LENGTH: 11
<212> TYPE: PRT
<213> ORGANISM: Homo sapiens

<400> SEQUENCE: 3263

Phe Leu Glu Glu Asp Glu Tyr His Ala Thr Thr
1               5                   10

<210> SEQ ID NO 3264
<211> LENGTH: 11
<212> TYPE: PRT
<213> ORGANISM: Homo sapiens

<400> SEQUENCE: 3264

Leu Glu Glu Asp Glu Tyr His Ala Thr Thr Glu
1               5                   10

<210> SEQ ID NO 3265
<211> LENGTH: 11
<212> TYPE: PRT
<213> ORGANISM: Homo sapiens

<400> SEQUENCE: 3265

Glu Glu Asp Glu Tyr His Ala Thr Thr Glu Thr
1               5                   10

<210> SEQ ID NO 3266
<211> LENGTH: 11
<212> TYPE: PRT
<213> ORGANISM: Homo sapiens

<400> SEQUENCE: 3266

Glu Asp Glu Tyr His Ala Thr Thr Glu Thr Val
1               5                   10

<210> SEQ ID NO 3267
<211> LENGTH: 11
<212> TYPE: PRT
```

<213> ORGANISM: Homo sapiens

<400> SEQUENCE: 3267

Asp Glu Tyr His Ala Thr Thr Glu Thr Val Ile
1               5                   10

<210> SEQ ID NO 3268
<211> LENGTH: 11
<212> TYPE: PRT
<213> ORGANISM: Homo sapiens

<400> SEQUENCE: 3268

Glu Tyr His Ala Thr Thr Glu Thr Val Ile Ser
1               5                   10

<210> SEQ ID NO 3269
<211> LENGTH: 11
<212> TYPE: PRT
<213> ORGANISM: Homo sapiens

<400> SEQUENCE: 3269

Tyr His Ala Thr Thr Glu Thr Val Ile Ser Met
1               5                   10

<210> SEQ ID NO 3270
<211> LENGTH: 11
<212> TYPE: PRT
<213> ORGANISM: Homo sapiens

<400> SEQUENCE: 3270

His Ala Thr Thr Glu Thr Val Ile Ser Met Ala
1               5                   10

<210> SEQ ID NO 3271
<211> LENGTH: 11
<212> TYPE: PRT
<213> ORGANISM: Homo sapiens

<400> SEQUENCE: 3271

Ala Thr Thr Glu Thr Val Ile Ser Met Ala Gln
1               5                   10

<210> SEQ ID NO 3272
<211> LENGTH: 11
<212> TYPE: PRT
<213> ORGANISM: Homo sapiens

<400> SEQUENCE: 3272

Thr Thr Glu Thr Val Ile Ser Met Ala Gln Glu
1               5                   10

<210> SEQ ID NO 3273
<211> LENGTH: 11
<212> TYPE: PRT
<213> ORGANISM: Homo sapiens

<400> SEQUENCE: 3273

Thr Glu Thr Val Ile Ser Met Ala Gln Glu Thr
1               5                   10

<210> SEQ ID NO 3274
<211> LENGTH: 11
<212> TYPE: PRT
<213> ORGANISM: Homo sapiens

<400> SEQUENCE: 3274

Glu Thr Val Ile Ser Met Ala Gln Glu Thr Asp
1               5                   10

<210> SEQ ID NO 3275
<211> LENGTH: 11
<212> TYPE: PRT
<213> ORGANISM: Homo sapiens

<400> SEQUENCE: 3275

Thr Val Ile Ser Met Ala Gln Glu Thr Asp Pro
1               5                   10

<210> SEQ ID NO 3276
<211> LENGTH: 11
<212> TYPE: PRT
<213> ORGANISM: Homo sapiens

<400> SEQUENCE: 3276

Val Ile Ser Met Ala Gln Glu Thr Asp Pro Ala
1               5                   10

<210> SEQ ID NO 3277
<211> LENGTH: 11
<212> TYPE: PRT
<213> ORGANISM: Homo sapiens

<400> SEQUENCE: 3277

Ile Ser Met Ala Gln Glu Thr Asp Pro Ala Val
1               5                   10

<210> SEQ ID NO 3278
<211> LENGTH: 11
<212> TYPE: PRT
<213> ORGANISM: Homo sapiens

<400> SEQUENCE: 3278

Ser Met Ala Gln Glu Thr Asp Pro Ala Val Gln
1               5                   10

<210> SEQ ID NO 3279
<211> LENGTH: 11
<212> TYPE: PRT
<213> ORGANISM: Homo sapiens

<400> SEQUENCE: 3279

Met Ala Gln Glu Thr Asp Pro Ala Val Gln Thr
1               5                   10

<210> SEQ ID NO 3280
<211> LENGTH: 11
<212> TYPE: PRT
<213> ORGANISM: Homo sapiens

<400> SEQUENCE: 3280

Ala Gln Glu Thr Asp Pro Ala Val Gln Thr Asp
1               5                   10

<210> SEQ ID NO 3281
<211> LENGTH: 11
<212> TYPE: PRT
<213> ORGANISM: Homo sapiens

<400> SEQUENCE: 3281

Gln Glu Thr Asp Pro Ala Val Gln Thr Asp Gly
1               5                   10

<210> SEQ ID NO 3282
<211> LENGTH: 11
<212> TYPE: PRT
<213> ORGANISM: Homo sapiens

<400> SEQUENCE: 3282

Glu Thr Asp Pro Ala Val Gln Thr Asp Gly Ser
1               5                   10

<210> SEQ ID NO 3283
<211> LENGTH: 11
<212> TYPE: PRT
<213> ORGANISM: Homo sapiens

<400> SEQUENCE: 3283

Thr Asp Pro Ala Val Gln Thr Asp Gly Ser Pro
1               5                   10

<210> SEQ ID NO 3284
<211> LENGTH: 11
<212> TYPE: PRT
<213> ORGANISM: Homo sapiens

<400> SEQUENCE: 3284

Asp Pro Ala Val Gln Thr Asp Gly Ser Pro Leu
1               5                   10

<210> SEQ ID NO 3285
<211> LENGTH: 11
<212> TYPE: PRT
<213> ORGANISM: Homo sapiens

<400> SEQUENCE: 3285

Pro Ala Val Gln Thr Asp Gly Ser Pro Leu Cys
1               5                   10

<210> SEQ ID NO 3286
<211> LENGTH: 11
<212> TYPE: PRT
<213> ORGANISM: Homo sapiens

<400> SEQUENCE: 3286

Ala Val Gln Thr Asp Gly Ser Pro Leu Cys Cys
1               5                   10

<210> SEQ ID NO 3287
<211> LENGTH: 11
<212> TYPE: PRT
<213> ORGANISM: Homo sapiens

<400> SEQUENCE: 3287

Val Gln Thr Asp Gly Ser Pro Leu Cys Cys His
1               5                   10

<210> SEQ ID NO 3288
<211> LENGTH: 11
<212> TYPE: PRT
<213> ORGANISM: Homo sapiens

<400> SEQUENCE: 3288

Gln Thr Asp Gly Ser Pro Leu Cys Cys His Phe
1               5                   10

<210> SEQ ID NO 3289
<211> LENGTH: 11
<212> TYPE: PRT
<213> ORGANISM: Homo sapiens

<400> SEQUENCE: 3289

Thr Asp Gly Ser Pro Leu Cys Cys His Phe His
1               5                   10

<210> SEQ ID NO 3290
<211> LENGTH: 11
<212> TYPE: PRT
<213> ORGANISM: Homo sapiens

<400> SEQUENCE: 3290

Asp Gly Ser Pro Leu Cys Cys His Phe His Phe
1               5                   10

<210> SEQ ID NO 3291
<211> LENGTH: 11
<212> TYPE: PRT
<213> ORGANISM: Homo sapiens

<400> SEQUENCE: 3291

Gly Ser Pro Leu Cys Cys His Phe His Phe Ser
1               5                   10

<210> SEQ ID NO 3292
<211> LENGTH: 11
<212> TYPE: PRT
<213> ORGANISM: Homo sapiens

<400> SEQUENCE: 3292

Ser Pro Leu Cys Cys His Phe His Phe Ser Pro
1               5                   10

<210> SEQ ID NO 3293
<211> LENGTH: 11
<212> TYPE: PRT
<213> ORGANISM: Homo sapiens

<400> SEQUENCE: 3293

Pro Leu Cys Cys His Phe His Phe Ser Pro Lys
1               5                   10

<210> SEQ ID NO 3294
<211> LENGTH: 11
<212> TYPE: PRT
<213> ORGANISM: Homo sapiens

<400> SEQUENCE: 3294

Leu Cys Cys His Phe His Phe Ser Pro Lys Val
1               5                   10

<210> SEQ ID NO 3295
<211> LENGTH: 11
<212> TYPE: PRT
<213> ORGANISM: Homo sapiens

<400> SEQUENCE: 3295

Cys Cys His Phe His Phe Ser Pro Lys Val Met
1               5                   10

```
<210> SEQ ID NO 3296
<211> LENGTH: 11
<212> TYPE: PRT
<213> ORGANISM: Homo sapiens

<400> SEQUENCE: 3296

Cys His Phe His Phe Ser Pro Lys Val Met Phe
1               5                   10

<210> SEQ ID NO 3297
<211> LENGTH: 11
<212> TYPE: PRT
<213> ORGANISM: Homo sapiens

<400> SEQUENCE: 3297

His Phe His Phe Ser Pro Lys Val Met Phe Thr
1               5                   10

<210> SEQ ID NO 3298
<211> LENGTH: 11
<212> TYPE: PRT
<213> ORGANISM: Homo sapiens

<400> SEQUENCE: 3298

Phe His Phe Ser Pro Lys Val Met Phe Thr Lys
1               5                   10

<210> SEQ ID NO 3299
<211> LENGTH: 11
<212> TYPE: PRT
<213> ORGANISM: Homo sapiens

<400> SEQUENCE: 3299

His Phe Ser Pro Lys Val Met Phe Thr Lys Val
1               5                   10

<210> SEQ ID NO 3300
<211> LENGTH: 11
<212> TYPE: PRT
<213> ORGANISM: Homo sapiens

<400> SEQUENCE: 3300

Phe Ser Pro Lys Val Met Phe Thr Lys Val Leu
1               5                   10

<210> SEQ ID NO 3301
<211> LENGTH: 11
<212> TYPE: PRT
<213> ORGANISM: Homo sapiens

<400> SEQUENCE: 3301

Ser Pro Lys Val Met Phe Thr Lys Val Leu Lys
1               5                   10

<210> SEQ ID NO 3302
<211> LENGTH: 11
<212> TYPE: PRT
<213> ORGANISM: Homo sapiens

<400> SEQUENCE: 3302

Pro Lys Val Met Phe Thr Lys Val Leu Lys Ala
1               5                   10

<210> SEQ ID NO 3303
<211> LENGTH: 11
```

```
<212> TYPE: PRT
<213> ORGANISM: Homo sapiens

<400> SEQUENCE: 3303

Lys Val Met Phe Thr Lys Val Leu Lys Ala Gln
1               5                   10

<210> SEQ ID NO 3304
<211> LENGTH: 11
<212> TYPE: PRT
<213> ORGANISM: Homo sapiens

<400> SEQUENCE: 3304

Val Met Phe Thr Lys Val Leu Lys Ala Gln Leu
1               5                   10

<210> SEQ ID NO 3305
<211> LENGTH: 11
<212> TYPE: PRT
<213> ORGANISM: Homo sapiens

<400> SEQUENCE: 3305

Met Phe Thr Lys Val Leu Lys Ala Gln Leu Trp
1               5                   10

<210> SEQ ID NO 3306
<211> LENGTH: 11
<212> TYPE: PRT
<213> ORGANISM: Homo sapiens

<400> SEQUENCE: 3306

Phe Thr Lys Val Leu Lys Ala Gln Leu Trp Val
1               5                   10

<210> SEQ ID NO 3307
<211> LENGTH: 11
<212> TYPE: PRT
<213> ORGANISM: Homo sapiens

<400> SEQUENCE: 3307

Thr Lys Val Leu Lys Ala Gln Leu Trp Val Tyr
1               5                   10

<210> SEQ ID NO 3308
<211> LENGTH: 11
<212> TYPE: PRT
<213> ORGANISM: Homo sapiens

<400> SEQUENCE: 3308

Lys Val Leu Lys Ala Gln Leu Trp Val Tyr Leu
1               5                   10

<210> SEQ ID NO 3309
<211> LENGTH: 11
<212> TYPE: PRT
<213> ORGANISM: Homo sapiens

<400> SEQUENCE: 3309

Val Leu Lys Ala Gln Leu Trp Val Tyr Leu Arg
1               5                   10

<210> SEQ ID NO 3310
<211> LENGTH: 11
<212> TYPE: PRT
<213> ORGANISM: Homo sapiens
```

```
<400> SEQUENCE: 3310

Leu Lys Ala Gln Leu Trp Val Tyr Leu Arg Pro
1               5                   10

<210> SEQ ID NO 3311
<211> LENGTH: 11
<212> TYPE: PRT
<213> ORGANISM: Homo sapiens

<400> SEQUENCE: 3311

Lys Ala Gln Leu Trp Val Tyr Leu Arg Pro Val
1               5                   10

<210> SEQ ID NO 3312
<211> LENGTH: 11
<212> TYPE: PRT
<213> ORGANISM: Homo sapiens

<400> SEQUENCE: 3312

Ala Gln Leu Trp Val Tyr Leu Arg Pro Val Pro
1               5                   10

<210> SEQ ID NO 3313
<211> LENGTH: 11
<212> TYPE: PRT
<213> ORGANISM: Homo sapiens

<400> SEQUENCE: 3313

Gln Leu Trp Val Tyr Leu Arg Pro Val Pro Arg
1               5                   10

<210> SEQ ID NO 3314
<211> LENGTH: 11
<212> TYPE: PRT
<213> ORGANISM: Homo sapiens

<400> SEQUENCE: 3314

Leu Trp Val Tyr Leu Arg Pro Val Pro Arg Pro
1               5                   10

<210> SEQ ID NO 3315
<211> LENGTH: 11
<212> TYPE: PRT
<213> ORGANISM: Homo sapiens

<400> SEQUENCE: 3315

Trp Val Tyr Leu Arg Pro Val Pro Arg Pro Ala
1               5                   10

<210> SEQ ID NO 3316
<211> LENGTH: 11
<212> TYPE: PRT
<213> ORGANISM: Homo sapiens

<400> SEQUENCE: 3316

Val Tyr Leu Arg Pro Val Pro Arg Pro Ala Thr
1               5                   10

<210> SEQ ID NO 3317
<211> LENGTH: 11
<212> TYPE: PRT
<213> ORGANISM: Homo sapiens

<400> SEQUENCE: 3317
```

Tyr Leu Arg Pro Val Pro Arg Pro Ala Thr Val
1               5                   10

<210> SEQ ID NO 3318
<211> LENGTH: 11
<212> TYPE: PRT
<213> ORGANISM: Homo sapiens

<400> SEQUENCE: 3318

Leu Arg Pro Val Pro Arg Pro Ala Thr Val Tyr
1               5                   10

<210> SEQ ID NO 3319
<211> LENGTH: 11
<212> TYPE: PRT
<213> ORGANISM: Homo sapiens

<400> SEQUENCE: 3319

Arg Pro Val Pro Arg Pro Ala Thr Val Tyr Leu
1               5                   10

<210> SEQ ID NO 3320
<211> LENGTH: 11
<212> TYPE: PRT
<213> ORGANISM: Homo sapiens

<400> SEQUENCE: 3320

Pro Val Pro Arg Pro Ala Thr Val Tyr Leu Gln
1               5                   10

<210> SEQ ID NO 3321
<211> LENGTH: 11
<212> TYPE: PRT
<213> ORGANISM: Homo sapiens

<400> SEQUENCE: 3321

Val Pro Arg Pro Ala Thr Val Tyr Leu Gln Ile
1               5                   10

<210> SEQ ID NO 3322
<211> LENGTH: 11
<212> TYPE: PRT
<213> ORGANISM: Homo sapiens

<400> SEQUENCE: 3322

Pro Arg Pro Ala Thr Val Tyr Leu Gln Ile Leu
1               5                   10

<210> SEQ ID NO 3323
<211> LENGTH: 11
<212> TYPE: PRT
<213> ORGANISM: Homo sapiens

<400> SEQUENCE: 3323

Arg Pro Ala Thr Val Tyr Leu Gln Ile Leu Arg
1               5                   10

<210> SEQ ID NO 3324
<211> LENGTH: 11
<212> TYPE: PRT
<213> ORGANISM: Homo sapiens

<400> SEQUENCE: 3324

Pro Ala Thr Val Tyr Leu Gln Ile Leu Arg Leu 1    5    10

<210> SEQ ID NO 3325
<211> LENGTH: 11
<212> TYPE: PRT
<213> ORGANISM: Homo sapiens

<400> SEQUENCE: 3325

Ala Thr Val Tyr Leu Gln Ile Leu Arg Leu Lys
1               5                   10

<210> SEQ ID NO 3326
<211> LENGTH: 11
<212> TYPE: PRT
<213> ORGANISM: Homo sapiens

<400> SEQUENCE: 3326

Thr Val Tyr Leu Gln Ile Leu Arg Leu Lys Pro
1               5                   10

<210> SEQ ID NO 3327
<211> LENGTH: 11
<212> TYPE: PRT
<213> ORGANISM: Homo sapiens

<400> SEQUENCE: 3327

Val Tyr Leu Gln Ile Leu Arg Leu Lys Pro Leu
1               5                   10

<210> SEQ ID NO 3328
<211> LENGTH: 11
<212> TYPE: PRT
<213> ORGANISM: Homo sapiens

<400> SEQUENCE: 3328

Tyr Leu Gln Ile Leu Arg Leu Lys Pro Leu Thr
1               5                   10

<210> SEQ ID NO 3329
<211> LENGTH: 11
<212> TYPE: PRT
<213> ORGANISM: Homo sapiens

<400> SEQUENCE: 3329

Leu Gln Ile Leu Arg Leu Lys Pro Leu Thr Gly
1               5                   10

<210> SEQ ID NO 3330
<211> LENGTH: 11
<212> TYPE: PRT
<213> ORGANISM: Homo sapiens

<400> SEQUENCE: 3330

Gln Ile Leu Arg Leu Lys Pro Leu Thr Gly Glu
1               5                   10

<210> SEQ ID NO 3331
<211> LENGTH: 11
<212> TYPE: PRT
<213> ORGANISM: Homo sapiens

<400> SEQUENCE: 3331

Ile Leu Arg Leu Lys Pro Leu Thr Gly Glu Gly
1               5                   10

<210> SEQ ID NO 3332
<211> LENGTH: 11
<212> TYPE: PRT
<213> ORGANISM: Homo sapiens

<400> SEQUENCE: 3332

Leu Arg Leu Lys Pro Leu Thr Gly Glu Gly Thr
1               5                   10

<210> SEQ ID NO 3333
<211> LENGTH: 11
<212> TYPE: PRT
<213> ORGANISM: Homo sapiens

<400> SEQUENCE: 3333

Arg Leu Lys Pro Leu Thr Gly Glu Gly Thr Ala
1               5                   10

<210> SEQ ID NO 3334
<211> LENGTH: 11
<212> TYPE: PRT
<213> ORGANISM: Homo sapiens

<400> SEQUENCE: 3334

Leu Lys Pro Leu Thr Gly Glu Gly Thr Ala Gly
1               5                   10

<210> SEQ ID NO 3335
<211> LENGTH: 11
<212> TYPE: PRT
<213> ORGANISM: Homo sapiens

<400> SEQUENCE: 3335

Lys Pro Leu Thr Gly Glu Gly Thr Ala Gly Gly
1               5                   10

<210> SEQ ID NO 3336
<211> LENGTH: 11
<212> TYPE: PRT
<213> ORGANISM: Homo sapiens

<400> SEQUENCE: 3336

Pro Leu Thr Gly Glu Gly Thr Ala Gly Gly Gly
1               5                   10

<210> SEQ ID NO 3337
<211> LENGTH: 11
<212> TYPE: PRT
<213> ORGANISM: Homo sapiens

<400> SEQUENCE: 3337

Leu Thr Gly Glu Gly Thr Ala Gly Gly Gly Gly
1               5                   10

<210> SEQ ID NO 3338
<211> LENGTH: 11
<212> TYPE: PRT
<213> ORGANISM: Homo sapiens

<400> SEQUENCE: 3338

Thr Gly Glu Gly Thr Ala Gly Gly Gly Gly Gly
1               5                   10

<210> SEQ ID NO 3339

<211> LENGTH: 11
<212> TYPE: PRT
<213> ORGANISM: Homo sapiens

<400> SEQUENCE: 3339

Gly Glu Gly Thr Ala Gly Gly Gly Gly Gly Gly
1               5                   10

<210> SEQ ID NO 3340
<211> LENGTH: 11
<212> TYPE: PRT
<213> ORGANISM: Homo sapiens

<400> SEQUENCE: 3340

Glu Gly Thr Ala Gly Gly Gly Gly Gly Gly Arg
1               5                   10

<210> SEQ ID NO 3341
<211> LENGTH: 11
<212> TYPE: PRT
<213> ORGANISM: Homo sapiens

<400> SEQUENCE: 3341

Gly Thr Ala Gly Gly Gly Gly Gly Gly Arg Arg
1               5                   10

<210> SEQ ID NO 3342
<211> LENGTH: 11
<212> TYPE: PRT
<213> ORGANISM: Homo sapiens

<400> SEQUENCE: 3342

Thr Ala Gly Gly Gly Gly Gly Gly Arg Arg His
1               5                   10

<210> SEQ ID NO 3343
<211> LENGTH: 11
<212> TYPE: PRT
<213> ORGANISM: Homo sapiens

<400> SEQUENCE: 3343

Ala Gly Gly Gly Gly Gly Gly Arg Arg His Ile
1               5                   10

<210> SEQ ID NO 3344
<211> LENGTH: 11
<212> TYPE: PRT
<213> ORGANISM: Homo sapiens

<400> SEQUENCE: 3344

Gly Gly Gly Gly Gly Gly Arg Arg His Ile Arg
1               5                   10

<210> SEQ ID NO 3345
<211> LENGTH: 11
<212> TYPE: PRT
<213> ORGANISM: Homo sapiens

<400> SEQUENCE: 3345

Gly Gly Gly Gly Gly Arg Arg His Ile Arg Ile
1               5                   10

<210> SEQ ID NO 3346
<211> LENGTH: 11
<212> TYPE: PRT

<213> ORGANISM: Homo sapiens

<400> SEQUENCE: 3346

Gly Gly Gly Gly Arg Arg His Ile Arg Ile Arg
1               5                   10

<210> SEQ ID NO 3347
<211> LENGTH: 11
<212> TYPE: PRT
<213> ORGANISM: Homo sapiens

<400> SEQUENCE: 3347

Gly Gly Gly Arg Arg His Ile Arg Ile Arg Ser
1               5                   10

<210> SEQ ID NO 3348
<211> LENGTH: 11
<212> TYPE: PRT
<213> ORGANISM: Homo sapiens

<400> SEQUENCE: 3348

Gly Gly Arg Arg His Ile Arg Ile Arg Ser Leu
1               5                   10

<210> SEQ ID NO 3349
<211> LENGTH: 11
<212> TYPE: PRT
<213> ORGANISM: Homo sapiens

<400> SEQUENCE: 3349

Gly Arg Arg His Ile Arg Ile Arg Ser Leu Lys
1               5                   10

<210> SEQ ID NO 3350
<211> LENGTH: 11
<212> TYPE: PRT
<213> ORGANISM: Homo sapiens

<400> SEQUENCE: 3350

Arg Arg His Ile Arg Ile Arg Ser Leu Lys Ile
1               5                   10

<210> SEQ ID NO 3351
<211> LENGTH: 11
<212> TYPE: PRT
<213> ORGANISM: Homo sapiens

<400> SEQUENCE: 3351

Arg His Ile Arg Ile Arg Ser Leu Lys Ile Glu
1               5                   10

<210> SEQ ID NO 3352
<211> LENGTH: 11
<212> TYPE: PRT
<213> ORGANISM: Homo sapiens

<400> SEQUENCE: 3352

His Ile Arg Ile Arg Ser Leu Lys Ile Glu Leu
1               5                   10

<210> SEQ ID NO 3353
<211> LENGTH: 11
<212> TYPE: PRT
<213> ORGANISM: Homo sapiens

<400> SEQUENCE: 3353

Ile Arg Ile Arg Ser Leu Lys Ile Glu Leu His
1               5                   10

<210> SEQ ID NO 3354
<211> LENGTH: 11
<212> TYPE: PRT
<213> ORGANISM: Homo sapiens

<400> SEQUENCE: 3354

Arg Ile Arg Ser Leu Lys Ile Glu Leu His Ser
1               5                   10

<210> SEQ ID NO 3355
<211> LENGTH: 11
<212> TYPE: PRT
<213> ORGANISM: Homo sapiens

<400> SEQUENCE: 3355

Ile Arg Ser Leu Lys Ile Glu Leu His Ser Arg
1               5                   10

<210> SEQ ID NO 3356
<211> LENGTH: 11
<212> TYPE: PRT
<213> ORGANISM: Homo sapiens

<400> SEQUENCE: 3356

Arg Ser Leu Lys Ile Glu Leu His Ser Arg Ser
1               5                   10

<210> SEQ ID NO 3357
<211> LENGTH: 11
<212> TYPE: PRT
<213> ORGANISM: Homo sapiens

<400> SEQUENCE: 3357

Ser Leu Lys Ile Glu Leu His Ser Arg Ser Gly
1               5                   10

<210> SEQ ID NO 3358
<211> LENGTH: 11
<212> TYPE: PRT
<213> ORGANISM: Homo sapiens

<400> SEQUENCE: 3358

Leu Lys Ile Glu Leu His Ser Arg Ser Gly His
1               5                   10

<210> SEQ ID NO 3359
<211> LENGTH: 11
<212> TYPE: PRT
<213> ORGANISM: Homo sapiens

<400> SEQUENCE: 3359

Lys Ile Glu Leu His Ser Arg Ser Gly His Trp
1               5                   10

<210> SEQ ID NO 3360
<211> LENGTH: 11
<212> TYPE: PRT
<213> ORGANISM: Homo sapiens

<400> SEQUENCE: 3360

Ile Glu Leu His Ser Arg Ser Gly His Trp Gln
1               5                   10

<210> SEQ ID NO 3361
<211> LENGTH: 11
<212> TYPE: PRT
<213> ORGANISM: Homo sapiens

<400> SEQUENCE: 3361

Glu Leu His Ser Arg Ser Gly His Trp Gln Ser
1               5                   10

<210> SEQ ID NO 3362
<211> LENGTH: 11
<212> TYPE: PRT
<213> ORGANISM: Homo sapiens

<400> SEQUENCE: 3362

Leu His Ser Arg Ser Gly His Trp Gln Ser Ile
1               5                   10

<210> SEQ ID NO 3363
<211> LENGTH: 11
<212> TYPE: PRT
<213> ORGANISM: Homo sapiens

<400> SEQUENCE: 3363

His Ser Arg Ser Gly His Trp Gln Ser Ile Asp
1               5                   10

<210> SEQ ID NO 3364
<211> LENGTH: 11
<212> TYPE: PRT
<213> ORGANISM: Homo sapiens

<400> SEQUENCE: 3364

Ser Arg Ser Gly His Trp Gln Ser Ile Asp Phe
1               5                   10

<210> SEQ ID NO 3365
<211> LENGTH: 11
<212> TYPE: PRT
<213> ORGANISM: Homo sapiens

<400> SEQUENCE: 3365

Arg Ser Gly His Trp Gln Ser Ile Asp Phe Lys
1               5                   10

<210> SEQ ID NO 3366
<211> LENGTH: 11
<212> TYPE: PRT
<213> ORGANISM: Homo sapiens

<400> SEQUENCE: 3366

Ser Gly His Trp Gln Ser Ile Asp Phe Lys Gln
1               5                   10

<210> SEQ ID NO 3367
<211> LENGTH: 11
<212> TYPE: PRT
<213> ORGANISM: Homo sapiens

<400> SEQUENCE: 3367

Gly His Trp Gln Ser Ile Asp Phe Lys Gln Val
1               5                   10

```
<210> SEQ ID NO 3368
<211> LENGTH: 11
<212> TYPE: PRT
<213> ORGANISM: Homo sapiens

<400> SEQUENCE: 3368

His Trp Gln Ser Ile Asp Phe Lys Gln Val Leu
1               5                   10

<210> SEQ ID NO 3369
<211> LENGTH: 11
<212> TYPE: PRT
<213> ORGANISM: Homo sapiens

<400> SEQUENCE: 3369

Trp Gln Ser Ile Asp Phe Lys Gln Val Leu His
1               5                   10

<210> SEQ ID NO 3370
<211> LENGTH: 11
<212> TYPE: PRT
<213> ORGANISM: Homo sapiens

<400> SEQUENCE: 3370

Gln Ser Ile Asp Phe Lys Gln Val Leu His Ser
1               5                   10

<210> SEQ ID NO 3371
<211> LENGTH: 11
<212> TYPE: PRT
<213> ORGANISM: Homo sapiens

<400> SEQUENCE: 3371

Ser Ile Asp Phe Lys Gln Val Leu His Ser Trp
1               5                   10

<210> SEQ ID NO 3372
<211> LENGTH: 11
<212> TYPE: PRT
<213> ORGANISM: Homo sapiens

<400> SEQUENCE: 3372

Ile Asp Phe Lys Gln Val Leu His Ser Trp Phe
1               5                   10

<210> SEQ ID NO 3373
<211> LENGTH: 11
<212> TYPE: PRT
<213> ORGANISM: Homo sapiens

<400> SEQUENCE: 3373

Asp Phe Lys Gln Val Leu His Ser Trp Phe Arg
1               5                   10

<210> SEQ ID NO 3374
<211> LENGTH: 11
<212> TYPE: PRT
<213> ORGANISM: Homo sapiens

<400> SEQUENCE: 3374

Phe Lys Gln Val Leu His Ser Trp Phe Arg Gln
1               5                   10
```

<210> SEQ ID NO 3375
<211> LENGTH: 11
<212> TYPE: PRT
<213> ORGANISM: Homo sapiens

<400> SEQUENCE: 3375

Lys Gln Val Leu His Ser Trp Phe Arg Gln Pro
1               5                   10

<210> SEQ ID NO 3376
<211> LENGTH: 11
<212> TYPE: PRT
<213> ORGANISM: Homo sapiens

<400> SEQUENCE: 3376

Gln Val Leu His Ser Trp Phe Arg Gln Pro Gln
1               5                   10

<210> SEQ ID NO 3377
<211> LENGTH: 11
<212> TYPE: PRT
<213> ORGANISM: Homo sapiens

<400> SEQUENCE: 3377

Val Leu His Ser Trp Phe Arg Gln Pro Gln Ser
1               5                   10

<210> SEQ ID NO 3378
<211> LENGTH: 11
<212> TYPE: PRT
<213> ORGANISM: Homo sapiens

<400> SEQUENCE: 3378

Leu His Ser Trp Phe Arg Gln Pro Gln Ser Asn
1               5                   10

<210> SEQ ID NO 3379
<211> LENGTH: 11
<212> TYPE: PRT
<213> ORGANISM: Homo sapiens

<400> SEQUENCE: 3379

His Ser Trp Phe Arg Gln Pro Gln Ser Asn Trp
1               5                   10

<210> SEQ ID NO 3380
<211> LENGTH: 11
<212> TYPE: PRT
<213> ORGANISM: Homo sapiens

<400> SEQUENCE: 3380

Ser Trp Phe Arg Gln Pro Gln Ser Asn Trp Gly
1               5                   10

<210> SEQ ID NO 3381
<211> LENGTH: 11
<212> TYPE: PRT
<213> ORGANISM: Homo sapiens

<400> SEQUENCE: 3381

Trp Phe Arg Gln Pro Gln Ser Asn Trp Gly Ile
1               5                   10

<210> SEQ ID NO 3382
<211> LENGTH: 11

```
<212> TYPE: PRT
<213> ORGANISM: Homo sapiens

<400> SEQUENCE: 3382

Phe Arg Gln Pro Gln Ser Asn Trp Gly Ile Glu
1               5                   10

<210> SEQ ID NO 3383
<211> LENGTH: 11
<212> TYPE: PRT
<213> ORGANISM: Homo sapiens

<400> SEQUENCE: 3383

Arg Gln Pro Gln Ser Asn Trp Gly Ile Glu Ile
1               5                   10

<210> SEQ ID NO 3384
<211> LENGTH: 11
<212> TYPE: PRT
<213> ORGANISM: Homo sapiens

<400> SEQUENCE: 3384

Gln Pro Gln Ser Asn Trp Gly Ile Glu Ile Asn
1               5                   10

<210> SEQ ID NO 3385
<211> LENGTH: 11
<212> TYPE: PRT
<213> ORGANISM: Homo sapiens

<400> SEQUENCE: 3385

Pro Gln Ser Asn Trp Gly Ile Glu Ile Asn Ala
1               5                   10

<210> SEQ ID NO 3386
<211> LENGTH: 11
<212> TYPE: PRT
<213> ORGANISM: Homo sapiens

<400> SEQUENCE: 3386

Gln Ser Asn Trp Gly Ile Glu Ile Asn Ala Phe
1               5                   10

<210> SEQ ID NO 3387
<211> LENGTH: 11
<212> TYPE: PRT
<213> ORGANISM: Homo sapiens

<400> SEQUENCE: 3387

Ser Asn Trp Gly Ile Glu Ile Asn Ala Phe Asp
1               5                   10

<210> SEQ ID NO 3388
<211> LENGTH: 11
<212> TYPE: PRT
<213> ORGANISM: Homo sapiens

<400> SEQUENCE: 3388

Asn Trp Gly Ile Glu Ile Asn Ala Phe Asp Pro
1               5                   10

<210> SEQ ID NO 3389
<211> LENGTH: 11
<212> TYPE: PRT
<213> ORGANISM: Homo sapiens
```

<400> SEQUENCE: 3389

Trp Gly Ile Glu Ile Asn Ala Phe Asp Pro Ser
1               5                   10

<210> SEQ ID NO 3390
<211> LENGTH: 11
<212> TYPE: PRT
<213> ORGANISM: Homo sapiens

<400> SEQUENCE: 3390

Gly Ile Glu Ile Asn Ala Phe Asp Pro Ser Gly
1               5                   10

<210> SEQ ID NO 3391
<211> LENGTH: 11
<212> TYPE: PRT
<213> ORGANISM: Homo sapiens

<400> SEQUENCE: 3391

Ile Glu Ile Asn Ala Phe Asp Pro Ser Gly Thr
1               5                   10

<210> SEQ ID NO 3392
<211> LENGTH: 11
<212> TYPE: PRT
<213> ORGANISM: Homo sapiens

<400> SEQUENCE: 3392

Glu Ile Asn Ala Phe Asp Pro Ser Gly Thr Asp
1               5                   10

<210> SEQ ID NO 3393
<211> LENGTH: 11
<212> TYPE: PRT
<213> ORGANISM: Homo sapiens

<400> SEQUENCE: 3393

Ile Asn Ala Phe Asp Pro Ser Gly Thr Asp Leu
1               5                   10

<210> SEQ ID NO 3394
<211> LENGTH: 11
<212> TYPE: PRT
<213> ORGANISM: Homo sapiens

<400> SEQUENCE: 3394

Asn Ala Phe Asp Pro Ser Gly Thr Asp Leu Ala
1               5                   10

<210> SEQ ID NO 3395
<211> LENGTH: 11
<212> TYPE: PRT
<213> ORGANISM: Homo sapiens

<400> SEQUENCE: 3395

Ala Phe Asp Pro Ser Gly Thr Asp Leu Ala Val
1               5                   10

<210> SEQ ID NO 3396
<211> LENGTH: 11
<212> TYPE: PRT
<213> ORGANISM: Homo sapiens

<400> SEQUENCE: 3396

Phe Asp Pro Ser Gly Thr Asp Leu Ala Val Thr
1               5                   10

<210> SEQ ID NO 3397
<211> LENGTH: 11
<212> TYPE: PRT
<213> ORGANISM: Homo sapiens

<400> SEQUENCE: 3397

Asp Pro Ser Gly Thr Asp Leu Ala Val Thr Ser
1               5                   10

<210> SEQ ID NO 3398
<211> LENGTH: 11
<212> TYPE: PRT
<213> ORGANISM: Homo sapiens

<400> SEQUENCE: 3398

Pro Ser Gly Thr Asp Leu Ala Val Thr Ser Leu
1               5                   10

<210> SEQ ID NO 3399
<211> LENGTH: 11
<212> TYPE: PRT
<213> ORGANISM: Homo sapiens

<400> SEQUENCE: 3399

Ser Gly Thr Asp Leu Ala Val Thr Ser Leu Gly
1               5                   10

<210> SEQ ID NO 3400
<211> LENGTH: 11
<212> TYPE: PRT
<213> ORGANISM: Homo sapiens

<400> SEQUENCE: 3400

Gly Thr Asp Leu Ala Val Thr Ser Leu Gly Pro
1               5                   10

<210> SEQ ID NO 3401
<211> LENGTH: 11
<212> TYPE: PRT
<213> ORGANISM: Homo sapiens

<400> SEQUENCE: 3401

Thr Asp Leu Ala Val Thr Ser Leu Gly Pro Gly
1               5                   10

<210> SEQ ID NO 3402
<211> LENGTH: 11
<212> TYPE: PRT
<213> ORGANISM: Homo sapiens

<400> SEQUENCE: 3402

Asp Leu Ala Val Thr Ser Leu Gly Pro Gly Ala
1               5                   10

<210> SEQ ID NO 3403
<211> LENGTH: 11
<212> TYPE: PRT
<213> ORGANISM: Homo sapiens

<400> SEQUENCE: 3403

Leu Ala Val Thr Ser Leu Gly Pro Gly Ala Glu

```
1                 5                   10
```

<210> SEQ ID NO 3404
<211> LENGTH: 11
<212> TYPE: PRT
<213> ORGANISM: Homo sapiens

<400> SEQUENCE: 3404

```
Ala Val Thr Ser Leu Gly Pro Gly Ala Glu Gly
1                 5                   10
```

<210> SEQ ID NO 3405
<211> LENGTH: 11
<212> TYPE: PRT
<213> ORGANISM: Homo sapiens

<400> SEQUENCE: 3405

```
Val Thr Ser Leu Gly Pro Gly Ala Glu Gly Leu
1                 5                   10
```

<210> SEQ ID NO 3406
<211> LENGTH: 11
<212> TYPE: PRT
<213> ORGANISM: Homo sapiens

<400> SEQUENCE: 3406

```
Thr Ser Leu Gly Pro Gly Ala Glu Gly Leu His
1                 5                   10
```

<210> SEQ ID NO 3407
<211> LENGTH: 11
<212> TYPE: PRT
<213> ORGANISM: Homo sapiens

<400> SEQUENCE: 3407

```
Ser Leu Gly Pro Gly Ala Glu Gly Leu His Pro
1                 5                   10
```

<210> SEQ ID NO 3408
<211> LENGTH: 11
<212> TYPE: PRT
<213> ORGANISM: Homo sapiens

<400> SEQUENCE: 3408

```
Leu Gly Pro Gly Ala Glu Gly Leu His Pro Phe
1                 5                   10
```

<210> SEQ ID NO 3409
<211> LENGTH: 11
<212> TYPE: PRT
<213> ORGANISM: Homo sapiens

<400> SEQUENCE: 3409

```
Gly Pro Gly Ala Glu Gly Leu His Pro Phe Met
1                 5                   10
```

<210> SEQ ID NO 3410
<211> LENGTH: 11
<212> TYPE: PRT
<213> ORGANISM: Homo sapiens

<400> SEQUENCE: 3410

```
Pro Gly Ala Glu Gly Leu His Pro Phe Met Glu
1                 5                   10
```

<210> SEQ ID NO 3411
<211> LENGTH: 11
<212> TYPE: PRT
<213> ORGANISM: Homo sapiens

<400> SEQUENCE: 3411

Gly Ala Glu Gly Leu His Pro Phe Met Glu Leu
1               5                   10

<210> SEQ ID NO 3412
<211> LENGTH: 11
<212> TYPE: PRT
<213> ORGANISM: Homo sapiens

<400> SEQUENCE: 3412

Ala Glu Gly Leu His Pro Phe Met Glu Leu Arg
1               5                   10

<210> SEQ ID NO 3413
<211> LENGTH: 11
<212> TYPE: PRT
<213> ORGANISM: Homo sapiens

<400> SEQUENCE: 3413

Glu Gly Leu His Pro Phe Met Glu Leu Arg Val
1               5                   10

<210> SEQ ID NO 3414
<211> LENGTH: 11
<212> TYPE: PRT
<213> ORGANISM: Homo sapiens

<400> SEQUENCE: 3414

Gly Leu His Pro Phe Met Glu Leu Arg Val Leu
1               5                   10

<210> SEQ ID NO 3415
<211> LENGTH: 11
<212> TYPE: PRT
<213> ORGANISM: Homo sapiens

<400> SEQUENCE: 3415

Leu His Pro Phe Met Glu Leu Arg Val Leu Glu
1               5                   10

<210> SEQ ID NO 3416
<211> LENGTH: 11
<212> TYPE: PRT
<213> ORGANISM: Homo sapiens

<400> SEQUENCE: 3416

His Pro Phe Met Glu Leu Arg Val Leu Glu Asn
1               5                   10

<210> SEQ ID NO 3417
<211> LENGTH: 11
<212> TYPE: PRT
<213> ORGANISM: Homo sapiens

<400> SEQUENCE: 3417

Pro Phe Met Glu Leu Arg Val Leu Glu Asn Thr
1               5                   10

<210> SEQ ID NO 3418

<211> LENGTH: 11
<212> TYPE: PRT
<213> ORGANISM: Homo sapiens

<400> SEQUENCE: 3418

Phe Met Glu Leu Arg Val Leu Glu Asn Thr Lys
1               5                   10

<210> SEQ ID NO 3419
<211> LENGTH: 11
<212> TYPE: PRT
<213> ORGANISM: Homo sapiens

<400> SEQUENCE: 3419

Met Glu Leu Arg Val Leu Glu Asn Thr Lys Arg
1               5                   10

<210> SEQ ID NO 3420
<211> LENGTH: 11
<212> TYPE: PRT
<213> ORGANISM: Homo sapiens

<400> SEQUENCE: 3420

Glu Leu Arg Val Leu Glu Asn Thr Lys Arg Ser
1               5                   10

<210> SEQ ID NO 3421
<211> LENGTH: 11
<212> TYPE: PRT
<213> ORGANISM: Homo sapiens

<400> SEQUENCE: 3421

Leu Arg Val Leu Glu Asn Thr Lys Arg Ser Arg
1               5                   10

<210> SEQ ID NO 3422
<211> LENGTH: 11
<212> TYPE: PRT
<213> ORGANISM: Homo sapiens

<400> SEQUENCE: 3422

Arg Val Leu Glu Asn Thr Lys Arg Ser Arg Arg
1               5                   10

<210> SEQ ID NO 3423
<211> LENGTH: 11
<212> TYPE: PRT
<213> ORGANISM: Homo sapiens

<400> SEQUENCE: 3423

Val Leu Glu Asn Thr Lys Arg Ser Arg Arg Asn
1               5                   10

<210> SEQ ID NO 3424
<211> LENGTH: 11
<212> TYPE: PRT
<213> ORGANISM: Homo sapiens

<400> SEQUENCE: 3424

Leu Glu Asn Thr Lys Arg Ser Arg Arg Asn Leu
1               5                   10

<210> SEQ ID NO 3425
<211> LENGTH: 11
<212> TYPE: PRT

-continued

<213> ORGANISM: Homo sapiens

<400> SEQUENCE: 3425

Glu Asn Thr Lys Arg Ser Arg Arg Asn Leu Gly
1               5                   10

<210> SEQ ID NO 3426
<211> LENGTH: 11
<212> TYPE: PRT
<213> ORGANISM: Homo sapiens

<400> SEQUENCE: 3426

Asn Thr Lys Arg Ser Arg Arg Asn Leu Gly Leu
1               5                   10

<210> SEQ ID NO 3427
<211> LENGTH: 11
<212> TYPE: PRT
<213> ORGANISM: Homo sapiens

<400> SEQUENCE: 3427

Thr Lys Arg Ser Arg Arg Asn Leu Gly Leu Asp
1               5                   10

<210> SEQ ID NO 3428
<211> LENGTH: 11
<212> TYPE: PRT
<213> ORGANISM: Homo sapiens

<400> SEQUENCE: 3428

Lys Arg Ser Arg Arg Asn Leu Gly Leu Asp Cys
1               5                   10

<210> SEQ ID NO 3429
<211> LENGTH: 11
<212> TYPE: PRT
<213> ORGANISM: Homo sapiens

<400> SEQUENCE: 3429

Arg Ser Arg Arg Asn Leu Gly Leu Asp Cys Asp
1               5                   10

<210> SEQ ID NO 3430
<211> LENGTH: 11
<212> TYPE: PRT
<213> ORGANISM: Homo sapiens

<400> SEQUENCE: 3430

Ser Arg Arg Asn Leu Gly Leu Asp Cys Asp Glu
1               5                   10

<210> SEQ ID NO 3431
<211> LENGTH: 11
<212> TYPE: PRT
<213> ORGANISM: Homo sapiens

<400> SEQUENCE: 3431

Arg Arg Asn Leu Gly Leu Asp Cys Asp Glu His
1               5                   10

<210> SEQ ID NO 3432
<211> LENGTH: 11
<212> TYPE: PRT
<213> ORGANISM: Homo sapiens

<400> SEQUENCE: 3432

Arg Asn Leu Gly Leu Asp Cys Asp Glu His Ser
1               5                   10

<210> SEQ ID NO 3433
<211> LENGTH: 11
<212> TYPE: PRT
<213> ORGANISM: Homo sapiens

<400> SEQUENCE: 3433

Asn Leu Gly Leu Asp Cys Asp Glu His Ser Ser
1               5                   10

<210> SEQ ID NO 3434
<211> LENGTH: 11
<212> TYPE: PRT
<213> ORGANISM: Homo sapiens

<400> SEQUENCE: 3434

Leu Gly Leu Asp Cys Asp Glu His Ser Ser Glu
1               5                   10

<210> SEQ ID NO 3435
<211> LENGTH: 11
<212> TYPE: PRT
<213> ORGANISM: Homo sapiens

<400> SEQUENCE: 3435

Gly Leu Asp Cys Asp Glu His Ser Ser Glu Ser
1               5                   10

<210> SEQ ID NO 3436
<211> LENGTH: 11
<212> TYPE: PRT
<213> ORGANISM: Homo sapiens

<400> SEQUENCE: 3436

Leu Asp Cys Asp Glu His Ser Ser Glu Ser Arg
1               5                   10

<210> SEQ ID NO 3437
<211> LENGTH: 11
<212> TYPE: PRT
<213> ORGANISM: Homo sapiens

<400> SEQUENCE: 3437

Asp Cys Asp Glu His Ser Ser Glu Ser Arg Cys
1               5                   10

<210> SEQ ID NO 3438
<211> LENGTH: 11
<212> TYPE: PRT
<213> ORGANISM: Homo sapiens

<400> SEQUENCE: 3438

Cys Asp Glu His Ser Ser Glu Ser Arg Cys Cys
1               5                   10

<210> SEQ ID NO 3439
<211> LENGTH: 11
<212> TYPE: PRT
<213> ORGANISM: Homo sapiens

<400> SEQUENCE: 3439

```
Asp His Ser Ser Glu Ser Arg Cys Cys Arg
1               5                   10
```

<210> SEQ ID NO 3440
<211> LENGTH: 11
<212> TYPE: PRT
<213> ORGANISM: Homo sapiens

<400> SEQUENCE: 3440

```
Glu His Ser Ser Glu Ser Arg Cys Cys Arg Tyr
1               5                   10
```

<210> SEQ ID NO 3441
<211> LENGTH: 11
<212> TYPE: PRT
<213> ORGANISM: Homo sapiens

<400> SEQUENCE: 3441

```
His Ser Ser Glu Ser Arg Cys Cys Arg Tyr Pro
1               5                   10
```

<210> SEQ ID NO 3442
<211> LENGTH: 11
<212> TYPE: PRT
<213> ORGANISM: Homo sapiens

<400> SEQUENCE: 3442

```
Ser Ser Glu Ser Arg Cys Cys Arg Tyr Pro Leu
1               5                   10
```

<210> SEQ ID NO 3443
<211> LENGTH: 11
<212> TYPE: PRT
<213> ORGANISM: Homo sapiens

<400> SEQUENCE: 3443

```
Ser Glu Ser Arg Cys Cys Arg Tyr Pro Leu Thr
1               5                   10
```

<210> SEQ ID NO 3444
<211> LENGTH: 11
<212> TYPE: PRT
<213> ORGANISM: Homo sapiens

<400> SEQUENCE: 3444

```
Glu Ser Arg Cys Cys Arg Tyr Pro Leu Thr Val
1               5                   10
```

<210> SEQ ID NO 3445
<211> LENGTH: 11
<212> TYPE: PRT
<213> ORGANISM: Homo sapiens

<400> SEQUENCE: 3445

```
Ser Arg Cys Cys Arg Tyr Pro Leu Thr Val Asp
1               5                   10
```

<210> SEQ ID NO 3446
<211> LENGTH: 11
<212> TYPE: PRT
<213> ORGANISM: Homo sapiens

<400> SEQUENCE: 3446

```
Arg Cys Cys Arg Tyr Pro Leu Thr Val Asp Phe
1               5                   10
```

<210> SEQ ID NO 3447
<211> LENGTH: 11
<212> TYPE: PRT
<213> ORGANISM: Homo sapiens

<400> SEQUENCE: 3447

Cys Cys Arg Tyr Pro Leu Thr Val Asp Phe Glu
1               5                   10

<210> SEQ ID NO 3448
<211> LENGTH: 11
<212> TYPE: PRT
<213> ORGANISM: Homo sapiens

<400> SEQUENCE: 3448

Cys Arg Tyr Pro Leu Thr Val Asp Phe Glu Ala
1               5                   10

<210> SEQ ID NO 3449
<211> LENGTH: 11
<212> TYPE: PRT
<213> ORGANISM: Homo sapiens

<400> SEQUENCE: 3449

Arg Tyr Pro Leu Thr Val Asp Phe Glu Ala Phe
1               5                   10

<210> SEQ ID NO 3450
<211> LENGTH: 11
<212> TYPE: PRT
<213> ORGANISM: Homo sapiens

<400> SEQUENCE: 3450

Tyr Pro Leu Thr Val Asp Phe Glu Ala Phe Gly
1               5                   10

<210> SEQ ID NO 3451
<211> LENGTH: 11
<212> TYPE: PRT
<213> ORGANISM: Homo sapiens

<400> SEQUENCE: 3451

Pro Leu Thr Val Asp Phe Glu Ala Phe Gly Trp
1               5                   10

<210> SEQ ID NO 3452
<211> LENGTH: 11
<212> TYPE: PRT
<213> ORGANISM: Homo sapiens

<400> SEQUENCE: 3452

Leu Thr Val Asp Phe Glu Ala Phe Gly Trp Asp
1               5                   10

<210> SEQ ID NO 3453
<211> LENGTH: 11
<212> TYPE: PRT
<213> ORGANISM: Homo sapiens

<400> SEQUENCE: 3453

Thr Val Asp Phe Glu Ala Phe Gly Trp Asp Trp
1               5                   10

```
<210> SEQ ID NO 3454
<211> LENGTH: 11
<212> TYPE: PRT
<213> ORGANISM: Homo sapiens

<400> SEQUENCE: 3454

Val Asp Phe Glu Ala Phe Gly Trp Asp Trp Ile
1               5                   10

<210> SEQ ID NO 3455
<211> LENGTH: 11
<212> TYPE: PRT
<213> ORGANISM: Homo sapiens

<400> SEQUENCE: 3455

Asp Phe Glu Ala Phe Gly Trp Asp Trp Ile Ile
1               5                   10

<210> SEQ ID NO 3456
<211> LENGTH: 11
<212> TYPE: PRT
<213> ORGANISM: Homo sapiens

<400> SEQUENCE: 3456

Phe Glu Ala Phe Gly Trp Asp Trp Ile Ile Ala
1               5                   10

<210> SEQ ID NO 3457
<211> LENGTH: 11
<212> TYPE: PRT
<213> ORGANISM: Homo sapiens

<400> SEQUENCE: 3457

Glu Ala Phe Gly Trp Asp Trp Ile Ile Ala Pro
1               5                   10

<210> SEQ ID NO 3458
<211> LENGTH: 11
<212> TYPE: PRT
<213> ORGANISM: Homo sapiens

<400> SEQUENCE: 3458

Ala Phe Gly Trp Asp Trp Ile Ile Ala Pro Lys
1               5                   10

<210> SEQ ID NO 3459
<211> LENGTH: 11
<212> TYPE: PRT
<213> ORGANISM: Homo sapiens

<400> SEQUENCE: 3459

Phe Gly Trp Asp Trp Ile Ile Ala Pro Lys Arg
1               5                   10

<210> SEQ ID NO 3460
<211> LENGTH: 11
<212> TYPE: PRT
<213> ORGANISM: Homo sapiens

<400> SEQUENCE: 3460

Gly Trp Asp Trp Ile Ile Ala Pro Lys Arg Tyr
1               5                   10

<210> SEQ ID NO 3461
<211> LENGTH: 11
```

-continued

<212> TYPE: PRT
<213> ORGANISM: Homo sapiens

<400> SEQUENCE: 3461

Trp Asp Trp Ile Ile Ala Pro Lys Arg Tyr Lys
1               5                   10

<210> SEQ ID NO 3462
<211> LENGTH: 11
<212> TYPE: PRT
<213> ORGANISM: Homo sapiens

<400> SEQUENCE: 3462

Asp Trp Ile Ile Ala Pro Lys Arg Tyr Lys Ala
1               5                   10

<210> SEQ ID NO 3463
<211> LENGTH: 11
<212> TYPE: PRT
<213> ORGANISM: Homo sapiens

<400> SEQUENCE: 3463

Trp Ile Ile Ala Pro Lys Arg Tyr Lys Ala Asn
1               5                   10

<210> SEQ ID NO 3464
<211> LENGTH: 11
<212> TYPE: PRT
<213> ORGANISM: Homo sapiens

<400> SEQUENCE: 3464

Ile Ile Ala Pro Lys Arg Tyr Lys Ala Asn Tyr
1               5                   10

<210> SEQ ID NO 3465
<211> LENGTH: 11
<212> TYPE: PRT
<213> ORGANISM: Homo sapiens

<400> SEQUENCE: 3465

Ile Ala Pro Lys Arg Tyr Lys Ala Asn Tyr Cys
1               5                   10

<210> SEQ ID NO 3466
<211> LENGTH: 11
<212> TYPE: PRT
<213> ORGANISM: Homo sapiens

<400> SEQUENCE: 3466

Ala Pro Lys Arg Tyr Lys Ala Asn Tyr Cys Ser
1               5                   10

<210> SEQ ID NO 3467
<211> LENGTH: 11
<212> TYPE: PRT
<213> ORGANISM: Homo sapiens

<400> SEQUENCE: 3467

Pro Lys Arg Tyr Lys Ala Asn Tyr Cys Ser Gly
1               5                   10

<210> SEQ ID NO 3468
<211> LENGTH: 11
<212> TYPE: PRT
<213> ORGANISM: Homo sapiens

<400> SEQUENCE: 3468

Lys Arg Tyr Lys Ala Asn Tyr Cys Ser Gly Gln
1               5                   10

<210> SEQ ID NO 3469
<211> LENGTH: 11
<212> TYPE: PRT
<213> ORGANISM: Homo sapiens

<400> SEQUENCE: 3469

Arg Tyr Lys Ala Asn Tyr Cys Ser Gly Gln Cys
1               5                   10

<210> SEQ ID NO 3470
<211> LENGTH: 11
<212> TYPE: PRT
<213> ORGANISM: Homo sapiens

<400> SEQUENCE: 3470

Tyr Lys Ala Asn Tyr Cys Ser Gly Gln Cys Glu
1               5                   10

<210> SEQ ID NO 3471
<211> LENGTH: 11
<212> TYPE: PRT
<213> ORGANISM: Homo sapiens

<400> SEQUENCE: 3471

Lys Ala Asn Tyr Cys Ser Gly Gln Cys Glu Tyr
1               5                   10

<210> SEQ ID NO 3472
<211> LENGTH: 11
<212> TYPE: PRT
<213> ORGANISM: Homo sapiens

<400> SEQUENCE: 3472

Ala Asn Tyr Cys Ser Gly Gln Cys Glu Tyr Met
1               5                   10

<210> SEQ ID NO 3473
<211> LENGTH: 11
<212> TYPE: PRT
<213> ORGANISM: Homo sapiens

<400> SEQUENCE: 3473

Asn Tyr Cys Ser Gly Gln Cys Glu Tyr Met Phe
1               5                   10

<210> SEQ ID NO 3474
<211> LENGTH: 11
<212> TYPE: PRT
<213> ORGANISM: Homo sapiens

<400> SEQUENCE: 3474

Tyr Cys Ser Gly Gln Cys Glu Tyr Met Phe Met
1               5                   10

<210> SEQ ID NO 3475
<211> LENGTH: 11
<212> TYPE: PRT
<213> ORGANISM: Homo sapiens

<400> SEQUENCE: 3475

Cys Ser Gly Gln Cys Glu Tyr Met Phe Met Gln
1               5                   10

<210> SEQ ID NO 3476
<211> LENGTH: 11
<212> TYPE: PRT
<213> ORGANISM: Homo sapiens

<400> SEQUENCE: 3476

Ser Gly Gln Cys Glu Tyr Met Phe Met Gln Lys
1               5                   10

<210> SEQ ID NO 3477
<211> LENGTH: 11
<212> TYPE: PRT
<213> ORGANISM: Homo sapiens

<400> SEQUENCE: 3477

Gly Gln Cys Glu Tyr Met Phe Met Gln Lys Tyr
1               5                   10

<210> SEQ ID NO 3478
<211> LENGTH: 11
<212> TYPE: PRT
<213> ORGANISM: Homo sapiens

<400> SEQUENCE: 3478

Gln Cys Glu Tyr Met Phe Met Gln Lys Tyr Pro
1               5                   10

<210> SEQ ID NO 3479
<211> LENGTH: 11
<212> TYPE: PRT
<213> ORGANISM: Homo sapiens

<400> SEQUENCE: 3479

Cys Glu Tyr Met Phe Met Gln Lys Tyr Pro His
1               5                   10

<210> SEQ ID NO 3480
<211> LENGTH: 11
<212> TYPE: PRT
<213> ORGANISM: Homo sapiens

<400> SEQUENCE: 3480

Glu Tyr Met Phe Met Gln Lys Tyr Pro His Thr
1               5                   10

<210> SEQ ID NO 3481
<211> LENGTH: 11
<212> TYPE: PRT
<213> ORGANISM: Homo sapiens

<400> SEQUENCE: 3481

Tyr Met Phe Met Gln Lys Tyr Pro His Thr His
1               5                   10

<210> SEQ ID NO 3482
<211> LENGTH: 11
<212> TYPE: PRT
<213> ORGANISM: Homo sapiens

<400> SEQUENCE: 3482

Met Phe Met Gln Lys Tyr Pro His Thr His Leu

```
1               5                   10

<210> SEQ ID NO 3483
<211> LENGTH: 11
<212> TYPE: PRT
<213> ORGANISM: Homo sapiens

<400> SEQUENCE: 3483

Phe Met Gln Lys Tyr Pro His Thr His Leu Val
1               5                   10

<210> SEQ ID NO 3484
<211> LENGTH: 11
<212> TYPE: PRT
<213> ORGANISM: Homo sapiens

<400> SEQUENCE: 3484

Met Gln Lys Tyr Pro His Thr His Leu Val Gln
1               5                   10

<210> SEQ ID NO 3485
<211> LENGTH: 11
<212> TYPE: PRT
<213> ORGANISM: Homo sapiens

<400> SEQUENCE: 3485

Gln Lys Tyr Pro His Thr His Leu Val Gln Gln
1               5                   10

<210> SEQ ID NO 3486
<211> LENGTH: 11
<212> TYPE: PRT
<213> ORGANISM: Homo sapiens

<400> SEQUENCE: 3486

Lys Tyr Pro His Thr His Leu Val Gln Gln Ala
1               5                   10

<210> SEQ ID NO 3487
<211> LENGTH: 11
<212> TYPE: PRT
<213> ORGANISM: Homo sapiens

<400> SEQUENCE: 3487

Tyr Pro His Thr His Leu Val Gln Gln Ala Asn
1               5                   10

<210> SEQ ID NO 3488
<211> LENGTH: 11
<212> TYPE: PRT
<213> ORGANISM: Homo sapiens

<400> SEQUENCE: 3488

Pro His Thr His Leu Val Gln Gln Ala Asn Pro
1               5                   10

<210> SEQ ID NO 3489
<211> LENGTH: 11
<212> TYPE: PRT
<213> ORGANISM: Homo sapiens

<400> SEQUENCE: 3489

His Thr His Leu Val Gln Gln Ala Asn Pro Arg
1               5                   10
```

<210> SEQ ID NO 3490
<211> LENGTH: 11
<212> TYPE: PRT
<213> ORGANISM: Homo sapiens

<400> SEQUENCE: 3490

Thr His Leu Val Gln Gln Ala Asn Pro Arg Gly
1               5                   10

<210> SEQ ID NO 3491
<211> LENGTH: 11
<212> TYPE: PRT
<213> ORGANISM: Homo sapiens

<400> SEQUENCE: 3491

His Leu Val Gln Gln Ala Asn Pro Arg Gly Ser
1               5                   10

<210> SEQ ID NO 3492
<211> LENGTH: 11
<212> TYPE: PRT
<213> ORGANISM: Homo sapiens

<400> SEQUENCE: 3492

Leu Val Gln Gln Ala Asn Pro Arg Gly Ser Ala
1               5                   10

<210> SEQ ID NO 3493
<211> LENGTH: 11
<212> TYPE: PRT
<213> ORGANISM: Homo sapiens

<400> SEQUENCE: 3493

Val Gln Gln Ala Asn Pro Arg Gly Ser Ala Gly
1               5                   10

<210> SEQ ID NO 3494
<211> LENGTH: 11
<212> TYPE: PRT
<213> ORGANISM: Homo sapiens

<400> SEQUENCE: 3494

Gln Gln Ala Asn Pro Arg Gly Ser Ala Gly Pro
1               5                   10

<210> SEQ ID NO 3495
<211> LENGTH: 11
<212> TYPE: PRT
<213> ORGANISM: Homo sapiens

<400> SEQUENCE: 3495

Gln Ala Asn Pro Arg Gly Ser Ala Gly Pro Cys
1               5                   10

<210> SEQ ID NO 3496
<211> LENGTH: 11
<212> TYPE: PRT
<213> ORGANISM: Homo sapiens

<400> SEQUENCE: 3496

Ala Asn Pro Arg Gly Ser Ala Gly Pro Cys Cys
1               5                   10

<210> SEQ ID NO 3497

```
<211> LENGTH: 11
<212> TYPE: PRT
<213> ORGANISM: Homo sapiens

<400> SEQUENCE: 3497

Asn Pro Arg Gly Ser Ala Gly Pro Cys Cys Thr
1               5                   10

<210> SEQ ID NO 3498
<211> LENGTH: 11
<212> TYPE: PRT
<213> ORGANISM: Homo sapiens

<400> SEQUENCE: 3498

Pro Arg Gly Ser Ala Gly Pro Cys Cys Thr Pro
1               5                   10

<210> SEQ ID NO 3499
<211> LENGTH: 11
<212> TYPE: PRT
<213> ORGANISM: Homo sapiens

<400> SEQUENCE: 3499

Arg Gly Ser Ala Gly Pro Cys Cys Thr Pro Thr
1               5                   10

<210> SEQ ID NO 3500
<211> LENGTH: 11
<212> TYPE: PRT
<213> ORGANISM: Homo sapiens

<400> SEQUENCE: 3500

Gly Ser Ala Gly Pro Cys Cys Thr Pro Thr Lys
1               5                   10

<210> SEQ ID NO 3501
<211> LENGTH: 11
<212> TYPE: PRT
<213> ORGANISM: Homo sapiens

<400> SEQUENCE: 3501

Ser Ala Gly Pro Cys Cys Thr Pro Thr Lys Met
1               5                   10

<210> SEQ ID NO 3502
<211> LENGTH: 11
<212> TYPE: PRT
<213> ORGANISM: Homo sapiens

<400> SEQUENCE: 3502

Ala Gly Pro Cys Cys Thr Pro Thr Lys Met Ser
1               5                   10

<210> SEQ ID NO 3503
<211> LENGTH: 11
<212> TYPE: PRT
<213> ORGANISM: Homo sapiens

<400> SEQUENCE: 3503

Gly Pro Cys Cys Thr Pro Thr Lys Met Ser Pro
1               5                   10

<210> SEQ ID NO 3504
<211> LENGTH: 11
<212> TYPE: PRT
```

<213> ORGANISM: Homo sapiens

<400> SEQUENCE: 3504

Pro Cys Cys Thr Pro Thr Lys Met Ser Pro Ile
1               5                   10

<210> SEQ ID NO 3505
<211> LENGTH: 11
<212> TYPE: PRT
<213> ORGANISM: Homo sapiens

<400> SEQUENCE: 3505

Cys Cys Thr Pro Thr Lys Met Ser Pro Ile Asn
1               5                   10

<210> SEQ ID NO 3506
<211> LENGTH: 11
<212> TYPE: PRT
<213> ORGANISM: Homo sapiens

<400> SEQUENCE: 3506

Cys Thr Pro Thr Lys Met Ser Pro Ile Asn Met
1               5                   10

<210> SEQ ID NO 3507
<211> LENGTH: 11
<212> TYPE: PRT
<213> ORGANISM: Homo sapiens

<400> SEQUENCE: 3507

Thr Pro Thr Lys Met Ser Pro Ile Asn Met Leu
1               5                   10

<210> SEQ ID NO 3508
<211> LENGTH: 11
<212> TYPE: PRT
<213> ORGANISM: Homo sapiens

<400> SEQUENCE: 3508

Pro Thr Lys Met Ser Pro Ile Asn Met Leu Tyr
1               5                   10

<210> SEQ ID NO 3509
<211> LENGTH: 11
<212> TYPE: PRT
<213> ORGANISM: Homo sapiens

<400> SEQUENCE: 3509

Thr Lys Met Ser Pro Ile Asn Met Leu Tyr Phe
1               5                   10

<210> SEQ ID NO 3510
<211> LENGTH: 11
<212> TYPE: PRT
<213> ORGANISM: Homo sapiens

<400> SEQUENCE: 3510

Lys Met Ser Pro Ile Asn Met Leu Tyr Phe Asn
1               5                   10

<210> SEQ ID NO 3511
<211> LENGTH: 11
<212> TYPE: PRT
<213> ORGANISM: Homo sapiens

<400> SEQUENCE: 3511

Met Ser Pro Ile Asn Met Leu Tyr Phe Asn Asp
1               5                   10

<210> SEQ ID NO 3512
<211> LENGTH: 11
<212> TYPE: PRT
<213> ORGANISM: Homo sapiens

<400> SEQUENCE: 3512

Ser Pro Ile Asn Met Leu Tyr Phe Asn Asp Lys
1               5                   10

<210> SEQ ID NO 3513
<211> LENGTH: 11
<212> TYPE: PRT
<213> ORGANISM: Homo sapiens

<400> SEQUENCE: 3513

Pro Ile Asn Met Leu Tyr Phe Asn Asp Lys Gln
1               5                   10

<210> SEQ ID NO 3514
<211> LENGTH: 11
<212> TYPE: PRT
<213> ORGANISM: Homo sapiens

<400> SEQUENCE: 3514

Ile Asn Met Leu Tyr Phe Asn Asp Lys Gln Gln
1               5                   10

<210> SEQ ID NO 3515
<211> LENGTH: 11
<212> TYPE: PRT
<213> ORGANISM: Homo sapiens

<400> SEQUENCE: 3515

Asn Met Leu Tyr Phe Asn Asp Lys Gln Gln Ile
1               5                   10

<210> SEQ ID NO 3516
<211> LENGTH: 11
<212> TYPE: PRT
<213> ORGANISM: Homo sapiens

<400> SEQUENCE: 3516

Met Leu Tyr Phe Asn Asp Lys Gln Gln Ile Ile
1               5                   10

<210> SEQ ID NO 3517
<211> LENGTH: 11
<212> TYPE: PRT
<213> ORGANISM: Homo sapiens

<400> SEQUENCE: 3517

Leu Tyr Phe Asn Asp Lys Gln Gln Ile Ile Tyr
1               5                   10

<210> SEQ ID NO 3518
<211> LENGTH: 11
<212> TYPE: PRT
<213> ORGANISM: Homo sapiens

<400> SEQUENCE: 3518

Tyr Phe Asn Asp Lys Gln Gln Ile Ile Tyr Gly
1               5                   10

<210> SEQ ID NO 3519
<211> LENGTH: 11
<212> TYPE: PRT
<213> ORGANISM: Homo sapiens

<400> SEQUENCE: 3519

Phe Asn Asp Lys Gln Gln Ile Ile Tyr Gly Lys
1               5                   10

<210> SEQ ID NO 3520
<211> LENGTH: 11
<212> TYPE: PRT
<213> ORGANISM: Homo sapiens

<400> SEQUENCE: 3520

Asn Asp Lys Gln Gln Ile Ile Tyr Gly Lys Ile
1               5                   10

<210> SEQ ID NO 3521
<211> LENGTH: 11
<212> TYPE: PRT
<213> ORGANISM: Homo sapiens

<400> SEQUENCE: 3521

Asp Lys Gln Gln Ile Ile Tyr Gly Lys Ile Pro
1               5                   10

<210> SEQ ID NO 3522
<211> LENGTH: 11
<212> TYPE: PRT
<213> ORGANISM: Homo sapiens

<400> SEQUENCE: 3522

Lys Gln Gln Ile Ile Tyr Gly Lys Ile Pro Gly
1               5                   10

<210> SEQ ID NO 3523
<211> LENGTH: 11
<212> TYPE: PRT
<213> ORGANISM: Homo sapiens

<400> SEQUENCE: 3523

Gln Gln Ile Ile Tyr Gly Lys Ile Pro Gly Met
1               5                   10

<210> SEQ ID NO 3524
<211> LENGTH: 11
<212> TYPE: PRT
<213> ORGANISM: Homo sapiens

<400> SEQUENCE: 3524

Gln Ile Ile Tyr Gly Lys Ile Pro Gly Met Val
1               5                   10

<210> SEQ ID NO 3525
<211> LENGTH: 11
<212> TYPE: PRT
<213> ORGANISM: Homo sapiens

<400> SEQUENCE: 3525

Ile Ile Tyr Gly Lys Ile Pro Gly Met Val Val
1               5                   10

```
<210> SEQ ID NO 3526
<211> LENGTH: 11
<212> TYPE: PRT
<213> ORGANISM: Homo sapiens

<400> SEQUENCE: 3526

Ile Tyr Gly Lys Ile Pro Gly Met Val Val Asp
1               5                   10

<210> SEQ ID NO 3527
<211> LENGTH: 11
<212> TYPE: PRT
<213> ORGANISM: Homo sapiens

<400> SEQUENCE: 3527

Tyr Gly Lys Ile Pro Gly Met Val Val Asp Arg
1               5                   10

<210> SEQ ID NO 3528
<211> LENGTH: 11
<212> TYPE: PRT
<213> ORGANISM: Homo sapiens

<400> SEQUENCE: 3528

Gly Lys Ile Pro Gly Met Val Val Asp Arg Cys
1               5                   10

<210> SEQ ID NO 3529
<211> LENGTH: 11
<212> TYPE: PRT
<213> ORGANISM: Homo sapiens

<400> SEQUENCE: 3529

Lys Ile Pro Gly Met Val Val Asp Arg Cys Gly
1               5                   10

<210> SEQ ID NO 3530
<211> LENGTH: 11
<212> TYPE: PRT
<213> ORGANISM: Homo sapiens

<400> SEQUENCE: 3530

Ile Pro Gly Met Val Val Asp Arg Cys Gly Cys
1               5                   10

<210> SEQ ID NO 3531
<211> LENGTH: 11
<212> TYPE: PRT
<213> ORGANISM: Homo sapiens

<400> SEQUENCE: 3531

Pro Gly Met Val Val Asp Arg Cys Gly Cys Ser
1               5                   10
```